(12) United States Patent
Ma et al.

(10) Patent No.: US 11,618,754 B2
(45) Date of Patent: Apr. 4, 2023

(54) NITROGEN-CONTAINING COMPOUND, ELECTRONIC COMPONENT AND ELECTRONIC DEVICE INCLUDING SAME

(71) Applicant: Shaanxi Lighte Optoelectronics Material Co., Ltd., Xi'an (CN)

(72) Inventors: Tiantian Ma, Xi'an (CN); Kongyan Zhang, Xi'an (CN); Xinxuan Li, Xi'an (CN); Yiyi Zheng, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/763,869

(22) PCT Filed: Aug. 12, 2021

(86) PCT No.: PCT/CN2021/112354
§ 371 (c)(1),
(2) Date: Mar. 25, 2022

(87) PCT Pub. No.: WO2022/160661
PCT Pub. Date: Aug. 4, 2022

(65) Prior Publication Data
US 2023/0008185 A1    Jan. 12, 2023

(30) Foreign Application Priority Data

Jan. 28, 2021 (CN) .......................... 202110122427.9
Apr. 8, 2021 (CN) .......................... 202110380418.X

(51) Int. Cl.
| | | |
|---|---|---|
| H01L 51/00 | (2006.01) | |
| C07D 487/04 | (2006.01) | |
| C07D 519/00 | (2006.01) | |
| H01L 51/50 | (2006.01) | |

(52) U.S. Cl.
CPC ......... *C07D 487/04* (2013.01); *C07D 519/00* (2013.01); *H01L 51/0052* (2013.01); *H01L 51/0054* (2013.01); *H01L 51/0056* (2013.01); *H01L 51/0067* (2013.01); *H01L 51/0069* (2013.01); *H01L 51/0072* (2013.01); *H01L 51/0073* (2013.01); *H01L 51/0074* (2013.01); *H01L 51/5012* (2013.01); *C07B 2200/05* (2013.01)

(58) Field of Classification Search
CPC ............. H01L 51/0052; H01L 51/0054; H01L 51/0056; H01L 51/0067; H01L 51/0069; H01L 51/0072; H01L 51/0073; H01L 51/0074; H01L 51/5012
See application file for complete search history.

(56) References Cited

U.S. PATENT DOCUMENTS

| | | |
|---|---|---|
| 2014/0326984 A1 | 11/2014 | Park |
| 2015/0295189 A1 | 10/2015 | Brooks |
| 2015/0318510 A1 | 11/2015 | Ito et al. |
| 2016/0225992 A1 | 8/2016 | Ito et al. |
| 2019/0207125 A1 | 7/2019 | Ahn et al. |

FOREIGN PATENT DOCUMENTS

| | | |
|---|---|---|
| CN | 107382992 A | 11/2017 |
| CN | 107880058 A | 4/2018 |
| CN | 111018843 A | 4/2020 |
| CN | 113024566 B | 11/2021 |
| KR | 1020150136033 A | 12/2015 |
| KR | 10-2020-0018324 A | 2/2020 |
| WO | 2017078403 A1 | 5/2017 |
| WO | 2020050576 A1 | 3/2020 |

OTHER PUBLICATIONS

Jiang He et al., "Thermally Activated Delayed Fluorescence Materials Based on Donor-Acceptor Structures," Progress in Chemistry, DOI: 10.7536/PC160520, dated 2016; 13 pages (original) followed by 13 pages of machine translation.

*Primary Examiner* — Victor A Mandala
*Assistant Examiner* — Colleen E Snow
(74) *Attorney, Agent, or Firm* — Tucker Ellis LLP

(57) ABSTRACT

The present disclosure provides a nitrogen-containing compound, and an electronic component and an electronic device including the same, and belongs to the technical field of organic electroluminescence. The nitrogen-containing compound provided by the present disclosure has polycyclic conjugation properties, the compound has a core structure of fused indolocarbazole. The bond energy between the atoms is high, thus the compound has a good thermal stability, and facilitates solid state accumulation between the molecules. The electroluminescence device with the compound as a luminescent layer material has a long service life. According to the nitrogen-containing compound provided by the present disclosure with an indolocarbazole structure connecting with a nitrogen-containing group (triazine, pyridine and pyrimidine) and a benzoxazole or benzothiazole group respectively has a high dipole moment, thereby improving the polarity of the material. Using the nitrogen-containing compound of the present disclosure as the luminescent layer material of the organic electroluminescence device, the electron transport performance of the device can be improved, and the luminous efficiency and service life of the device can be improved.

17 Claims, 1 Drawing Sheet

NITROGEN-CONTAINING COMPOUND, ELECTRONIC COMPONENT AND ELECTRONIC DEVICE INCLUDING SAME

CROSS REFERENCE TO RELATED APPLICATIONS

The application claims priority to Chinese Patent Application No. CN202110122427.9 filed on Jan. 28, 2021 and Chinese Patent Application No. CN202110380418.X filed on Apr. 8, 2021, the contents of which are incorporated herein by reference in their entirety as a part of the application.

TECHNICAL FIELD

The present disclosure relates to the technical field of organic electroluminescence, in particular to a nitrogen-containing compound, an electronic component and an electronic device including the same.

BACKGROUND

An organic electroluminescence material (OLED), as a new generation of display technology, has advantages such as being ultrathin, self-illumination, wide viewing angle, fast response, high luminous efficiency, good temperature adaptability, simple production process, low driving voltage and low energy consumption, and thus the organic electroluminescence material has been widely used in industries such as panel display, flexible display, solid state lighting and vehicle-mounted display.

An organic luminescence phenomenon refers to a phenomenon of converting electrical energy into light energy by using organic materials. An organic light-emitting device utilizing the organic luminescence phenomenon usually has a structure including an anode, a cathode and an organic material layer between the anode and the cathode. The organic material layer is usually formed by a multilayered structure consisting of different materials to increase the brightness, efficiency and service life of an organic electroluminescence device, the organic material layer may consist of a hole injection layer, a hole transport layer, a luminescent layer, an electron transport layer and an electron injection layer. In a structure of the organic light-emitting device, when a voltage is applied between two electrodes, holes and electrons are respectively injected into the organic material layer from the anode and the cathode, when the injected holes and electrons meet, excitons are formed, and when these excitons return to a ground state, light is emitted. In the existing organic electroluminescence device, the major problem is the service life and the efficiency, with an enlargement in area of a display, a driving voltage also increases, and the luminous efficiency and electrical efficiency also need to increase, and it is needed to ensure a certain service life, hence, the organic material must solve these issues on efficiency or service life, and it is required to continually develop new materials for the organic light-emitting device having high efficiency and long service life, and being suitable for mass production.

It should be noted that, the information disclosed in the above background section is only used to enhance the understanding of background of the present disclosure, hence the present disclosure can include information not constituting the prior art known by those of ordinary skill in the art.

SUMMARY

The purpose of the present disclosure is to overcome the above shortcomings in the prior art, and provide a nitrogen-containing compound, and an electronic component and an electronic device including the same, which can increase the luminous efficiency and prolong the service life of the device.

In order to realize the above purpose, the present disclosure adopts the following technical solution:

According to the first aspect of the present disclosure, provided is a nitrogen-containing compound, and the structural general formula of the nitrogen-containing is as shown in a Formula 1:

Formula 1

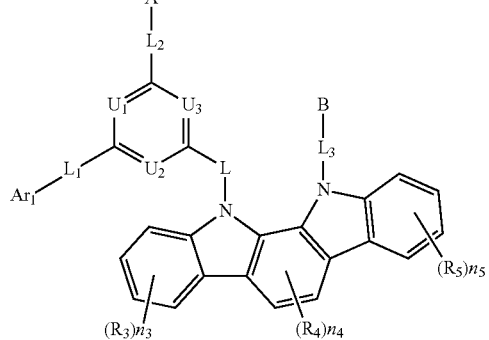

Formula 2-1

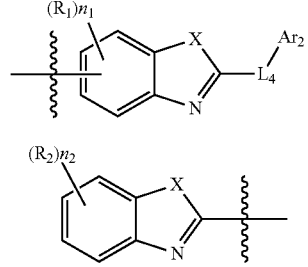

Formula 2-2 wherein,

represents a chemical bond, A and B are the same or different, and are each independently selected from substituted or unsubstituted aryl with 6 to 30 carbon atoms, substituted or unsubstituted heteroaryl with 3 to 30 carbon atoms, a structure shown in a Formula 2-1 or a structure shown in a Formula 2-2, and at least one of A and B is selected from the Formula 2-1 or the Formula 2-2;

$U_1$, $U_2$ and $U_3$ are the same or different, and are each independently selected from N or C(R), and at least one of $U_1$, $U_2$ and $U_3$ is N;

each of R, $R_1$, $R_2$, $R_3$, $R_4$ and $R_5$ is respectively and independently selected from hydrogen, deuterium, a halogen group, cyano, aryl with 6 to 12 carbon atoms, heteroaryl with 5 to 12 carbon atoms, alkyl with 1 to 5 carbon atoms, haloalkyl with 1 to 5 carbon atoms, and cycloalkyl with 3 to 10 carbon atoms;

$n_1$ represents the number of a substituent $R_1$, $n_1$ is selected from 1, 2 or 3, and when $n_1$ is greater than 1, any two $R_1$ are the same or different;

$n_2$ represents the number of a substituent $R_2$, $n_2$ is selected from 1, 2, 3 or 4, when $n_2$ is greater than 1, any two $R_2$ are the same or different, and alternatively, any two adjacent $R_2$ form a ring;

$n_3$ represents the number of a substituent $R_3$, $n_3$ is selected from 1, 2, 3 or 4, and when $n_3$ is greater than 1, any two $R_3$ are the same or different;

$n_4$ represents the number of a substituent $R_4$, $n_4$ is selected from 1 or 2, and when $n_4$ is greater than 1, any two $R_4$ are the same or different;

$n_5$ represents the number of a substituent $R_5$, $n_5$ is selected from 1, 2, 3 or 4, and when $n_5$ is greater than 1, any two $R_5$ are the same or different;

X is selected from S or O;

L, $L_1$, $L_2$, $L_3$ and $L_4$ are the same or different, and are each independently selected from a single bond, substituted or unsubstituted arylene with 6 to 30 carbon atoms, and substituted or unsubstituted heteroarylene with 3 to 30 carbon atoms;

$Ar_1$ and $Ar_2$ are the same or different, and are each independently selected from substituted or unsubstituted aryl with 6 to 30 carbon atoms, and substituted or unsubstituted heteroaryl with 3 to 30 carbon atoms;

substituents in the A, B, L, $L_1$, $L_2$, $L_3$, $L_4$, $Ar_1$ and $Ar_2$ are the same or different, and are each independently selected from deuterium, a halogen group, cyano, heteroaryl with 3 to 20 carbon atoms, aryl with 6 to 20 carbon atoms, trialkylsilyl with 3 to 12 carbon atoms, alkyl with 1 to 10 carbon atoms, haloalkyl with 1 to 10, cycloalkyl with 3 to 10 carbon atoms, heterocycloalkyl with 2 to 10 carbon atoms, and alkoxy with 1 to 10 carbon atoms;

alternatively, in $Ar_1$ and $Ar_2$, any two adjacent substituents form a ring.

The nitrogen-containing compound provided by the present disclosure has polycyclic conjugation properties, this compound has a core structure of fused indolocarbazole, the bond energy between atoms is high, thus the compound has a good thermal stability, and facilitates solid state accumulation between molecules, and as a luminescent layer material in an organic electroluminescence device which is manifested as a long service life. The nitrogen-containing compound provided by the present disclosure with an indolocarbazole structure connecting with a nitrogen-containing group (triazine, pyridine and pyrimidine) and a benzoxazole or benzothiazole group respectively has a high dipole moment, thereby improving the polarity of the material.

The nitrogen-containing compound provided by the present disclosure has a high $T_1$ energy, and the compound of the present disclosure is suitable to be used as a host material, particularly a green light host material, of the luminescent layer in an OLED device. When the compound of the present disclosure is used as the luminescent layer material of the organic electroluminescence device, the compound of the present disclosure will effectively improve the electron transport performance of the device, thereby enhancing the balance degree of hole and electron transport, and improve the luminous efficiency and service life of the device.

According to the second aspect of the present disclosure, provided is an electronic component comprising an anode, a cathode and at least one functional layer between the anode and the cathode, wherein the functional layer includes the above-mentioned nitrogen-containing compound.

According to the third aspect of the present disclosure, provided is an electronic device comprising the above-mentioned electronic component.

It should be understood that the above general description and the detailed description below are merely exemplary and illustrative, and do not limit the present disclosure.

BRIEF DESCRIPTION OF THE DRAWINGS

The accompanying drawings are used to provide a further understanding of the present disclosure, and constitute a part of the specification, together with the following specific embodiments, are intended to explain the present disclosure, but not to constitute a restriction on the present disclosure.

In the accompanying drawings.

DESCRIPTION OF REFERENCE SIGNS

Figure 1:
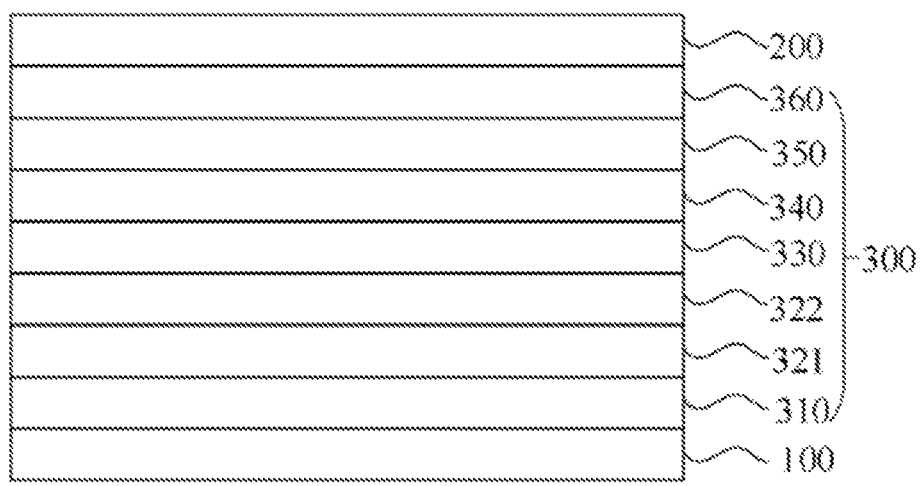
FIG. 1 is a structural schematic diagram of one embodiment of an organic electroluminescence device according to the present disclosure.

100: anode; 200: cathode; 300: functional layer; 310: hole injection layer; 321: first hole transport layer; 322: second hole transport layer; 330: organic electroluminescence layer; 340: hole blocking layer; 350: electron transport layer; 360: electron injection layer; and 400: first electronic device.

DETAILED DESCRIPTION

Now the exemplary embodiments will be described more fully with reference to the accompanying drawings. However, the exemplary embodiments can be implemented in various forms, and should not be understood to be limited to the examples set forth herein; on the contrary, these embodiments are provided to make the present disclosure more comprehensive and complete, and the concept of the exemplary embodiments is fully conveyed to those skilled in the art. The described features, structures or properties can be incorporated into one or more embodiments in any suitable way. In the following description, many details are provided so as to fully understand the embodiments of the present disclosure.

In the accompanying drawings, for clarity, the thickness of a region and a layer may be exaggerated. In the accompanying drawings, a same reference sign represents a same or similar structure, thus the detailed description thereof will be omitted.

The present disclosure provides a nitrogen-containing compound, and the structural general formula of the nitrogen-containing compound is as shown in a Formula 1:

Formula 1

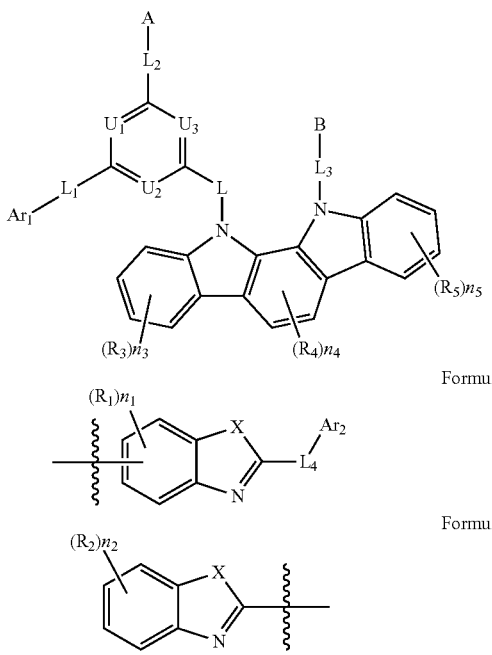

Formula 2-1

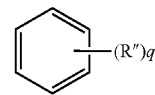

Formula 2-2

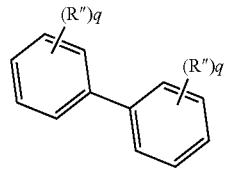

where,

represents a chemical bond, A and B are the same or different, and are each independently selected from substituted or unsubstituted aryl with 6 to 30 carbon atoms, substituted or unsubstituted heteroaryl with 3 to 30 carbon atoms, a structure shown in a Formula 2-1 or a structure shown in a Formula 2-2, and at least one of A and B is selected from the structure shown in the Formula 2-1 or the structure shown in the Formula 2-2;

$U_1$, $U_2$ and $U_3$ are the same or different, and are each independently selected from N or C(R), and at least one of $U_1$, $U_2$ and $U_3$ is N;

each of R, $R_1$, $R_2$, $R_3$, $R_4$ and $R_5$ is respectively and independently selected from hydrogen, deuterium, a halogen group, cyano, aryl with 6 to 12 carbon atoms, heteroaryl with 5 to 12 carbon atoms, alkyl with 1 to 5 carbon atoms, haloalkyl with 1 to 5 carbon atoms, and cycloalkyl with 3 to 10 carbon atoms;

$n_1$ represents the number of a substituent $R_1$, $n_1$ is selected from 1, 2 or 3, and when $n_1$ is greater than 1, any two $R_1$ are the same or different;

$n_2$ represents the number of a substituent $R_2$, $n_2$ is selected from 1, 2, 3 or 4, when $n_2$ is greater than 1, any two $R_2$ are the same or different, and alternatively, any two adjacent $R_2$ form a ring;

$n_3$ represents the number of a substituent $R_3$, $n_3$ is selected from 1, 2, 3 or 4, and when $n_3$ is greater than 1, any two $R_3$ are the same or different;

$n_4$ represents the number of a substituent $R_4$, $n_4$ is selected from 1 or 2, and when $n_4$ is greater than 1, any two $R_4$ are the same or different;

$n_5$ represents the number of a substituent $R_5$, $n_5$ is selected from 1, 2, 3 or 4, and when $n_5$ is greater than 1, any two $R_5$ are the same or different; X is selected from S or O;

L, $L_1$, $L_2$, $L_3$ and $L_4$ are the same or different, and are each independently selected from a single bond, substituted or unsubstituted arylene with 6 to 30 carbon atoms, and substituted or unsubstituted heteroarylene with 3 to 30 carbon atoms;

$Ar_1$ and $Ar_2$ are the same or different, and are each independently selected from substituted or unsubstituted aryl with 6 to 30 carbon atoms, and substituted or unsubstituted heteroaryl with 3 to 30 carbon atoms;

substituents in the A, B, L, $L_1$, $L_2$, $L_3$, $L_4$, $Ar_1$ and $Ar_2$ are the same or different, and are each independently selected from deuterium, a halogen group, cyano, heteroaryl with 3 to 20 carbon atoms, aryl with 6 to 20 carbon atoms, trialkylsilyl with 3 to 12 carbon atoms, alkyl with 1 to 10 carbon atoms, haloalkyl with 1 to 10, cycloalkyl with 3 to 10 carbon atoms, heterocycloalkyl with 2 to 10 carbon atoms, and alkoxy with 1 to 10 carbon atoms;

alternatively, in $Ar_1$ and $Ar_2$, any two adjacent substituents form a ring.

In the present disclosure, the description of "each independently selected from" and "respectively and independently selected from" can be exchanged, and both should be understood in a broad sense, which can mean that in different groups, the specific options expressed between the same signs do not affect each other, and can also mean that in the same group, the specific options expressed between the same signs do not affect each other. For example,

Q-1

Q-2 where, each q is independently 0, 1, 2 or 3, each R" is independently selected from hydrogen, deuterium, fluorine, and chlorine", their meanings are: a formula Q-1 indicates that a benzene ring has q substituents R", each R" can be the same or different, and the options of each R" do not affect each other; a formula Q-2 indicates that every benzene ring of biphenyl has q substituents R", the number q of the substituents R" on the two benzene ring can be the same or different, each R" can be the same or different, and the options of each R" do not affect each other.

In the present disclosure, a term such as "substituted or unsubstituted" means that, a functional group defined by the term can has or has no substituent (hereinafter, for ease of description, the substituent is collectively known as Rc). For example, "substituted or unsubstituted aryl" refers to aryl having a substituent Rc or unsubstituted aryl. The above-mentioned substituent namely Rc can be, for example, deuterium, a halogen group, cyano, heteroaryl with 3 to 20 carbon atoms, aryl with 6 to 20 carbon atoms, trialkylsilyl with 3 to 12 carbon atoms, alkyl with 1 to 10 carbon atoms, haloalkyl with 1 to 10 carbon atoms, cycloalkyl with 3 to 10 carbon atoms, heterocycloalkyl having a carbon number of 2 to 10 carbon atoms, or alkoxy with 1 to 10 carbon atoms. In the present disclosure, a "substituted" functional group can be substituted with one or two or more substituent in the above-mentioned Rc; when one atom is connect with two substituents Rc, these two substituents Rc can be independently present or connected with each other to form a ring with the atom; when there are two adjacent substituents Rc on the functional group, the two adjacent substituents Rc can be independently present or fused with the functional group to which they are connected to form a ring.

In the present disclosure, the terms "alternative" or "alternatively" mean that a subsequently described event or circumstance can occur but need not to occur, this description includes the situation in which the event or circumstance occurs or does not occur. For example, "alternatively, two adjacent substituents xx form a ring" mean that these two substituents can form a ring but not have to form a ring, including a situation in which two adjacent substituents form a ring and a situation in which two adjacent substituents do not form a ring.

In the present disclosure, in the case that "any two adjacent substituents form a ring", "any two adjacent substituents" can include a situation in which a same atom has two substituents, and also can include a situation in which two adjacent atoms respectively have one substituent; where, when the same atom have two substituents, the two substituents can form a saturated or unsaturated ring with the atom to which they are jointly connected; when the two adjacent atoms respectively have one substituent, these two substituents can be fused to form a ring. For instance, when $Ar_2$ has two or more substituents and any adjacent substituents form a ring, they can form a saturated or unsaturated ring with 5 to 13 carbon atoms, for example: a benzene ring, a naphthalene ring, cyclopentane, cyclohexane, adamantane, a fluorene ring and the like.

In the present disclosure, "alternatively, any two adjacent $R_2$ are connected with each other to form a ring" means that any two adjacent $R_2$ may form a ring or may not form a ring. For instance, when two adjacent $R_2$ form a ring, the carbon number of the ring is 5 to 14, and the ring can be saturated or unsaturated. For example: cyclohexane, cyclopentane, adamantane, a benzene ring, a naphthalene ring, a phenanthrene ring, etc., but are not limited thereto.

In the present disclosure, the carbon number of a substituted or unsubstituted functional group refers to all carbon number. For instance, if L is selected from substituted arylene with 12 carbon atoms, all carbon number of arylene and its substituents is 12. For example: if $Ar_1$ is

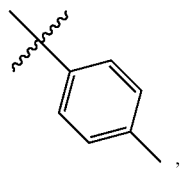 [SMILES: *c1ccc(C)cc1]

its carbon number is 7; if L is

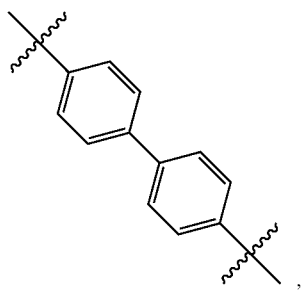 [SMILES: *c1ccc(-c2ccc(*)cc2)cc1]

its carbon number is 12.

In the present disclosure, if no additional specific definition is provided, "hetero" means that one functional group includes at least one heteroatom selected from B, N, O, S, P, Si or Se, etc., and the remaining atoms are carbon and hydrogen. The unsubstituted alkyl can be a "saturated alkyl group" without any double bond or triple bond.

In the present disclosure, "alkyl" can include linear alkyl or branched alkyl. The alkyl may have 1 to 10 carbon atoms. In the present disclosure, a numeric range such as "1 to 10" refers to each integer within a given range; for example, "1 to 10 carbon atoms" refers to alkyl that may include one carbon atom, two carbon atoms, three carbon atoms, four carbon atoms, five carbon atoms, six carbon atoms, seven carbon atoms, eight carbon atoms, nine carbon atoms or ten carbon atoms. Optionally, the alkyl is selected from alkyl with 1 to 5, and specific examples include, but are not limited to, methyl, ethyl, propyl, isopropyl, n-butyl, isobutyl, sec-butyl, tert-butyl and pentyl.

In the present disclosure, cycloalkyl refers to a saturated hydrocarbon including an alicyclic structure, including a monocyclic ring structure and a fused ring structure. Cycloalkyl may have 3-10 carbon atoms, a numeric range such as "3 to 10" refers to each integer within a given range; for example, "3 to 10 carbon atoms" refer to cycloalkyl that may include three carbon atoms, four carbon atoms, five carbon atoms, six carbon atoms, seven carbon atoms, eight carbon atoms, nine carbon atoms or ten carbon atoms. Cycloalkyl may be substituted or unsubstituted. Examples of cycloalkyl are such as cyclopentyl and cyclohexyl.

In the present disclosure, aryl refers to any optional functional group or substituent group derived from an aromatic carbon ring. Aryl can be monocyclic aryl (e.g. phenyl) or polycyclic aryl, in other words, aryl can be monocyclic aryl, fused aryl, two or more monocyclic aryl conjugatedly connected by a carbon-carbon bond, monocyclic aryl and fused aryl conjugatedly connected by a carbon-carbon bond or two or more fused aryl conjugatedly connected by a carbon-carbon bond. That is to say, unless otherwise noted, two or more aromatic groups conjugatedly connected by a carbon-carbon bond can also be regarded as the aryl of the present disclosure. The fused aryl can include, for example, bicyclic fused aryl (e.g. naphthyl), tricyclic fused aryl (e.g., phenanthryl, fluorenyl, anthryl), etc. The aryl has no heteroatom such as B, N, O, S, P, Se, Si, etc. The examples of aryl can include, but are not limited to, phenyl, naphthyl, fluorenyl, anthryl, phenanthryl, biphenyl, terphenyl, quaterphenyl, quinquephenyl, benzo[9,10]phenanthryl, pyrenyl, benzofluoranthyl, chrysenyl, etc. The "substituted or unsubstituted aryl" of the present disclosure contains 6 to 30 carbon atoms, in some embodiments, the carbon number in the substituted or unsubstituted aryl is 6 to 25, in some embodiments, the carbon number in the substituted or unsubstituted aryl is 6 to 20, in some other embodiments, the carbon number in the substituted or unsubstituted aryl is 6 to 18, and in some other embodiments, the carbon number in the substituted or unsubstituted aryl 6 to 12. For instance, in the present disclosure, the carbon number in the substituted or unsubstituted aryl is 6, 12, 13, 14, 15, 18, 20, 24, 25 or 30. Of course, the carbon number can also be other number, which is not enumerated here. In the present disclosure, biphenyl can be construed as aryl substituted with phenyl, and can also be construed as unsubstituted aryl.

In the present disclosure, the related arylene refers to a bivalent group which is formed by further loss of one hydrogen atom from the aryl.

In the present disclosure, the substituted aryl can be aryl in which one or two or more hydrogen atoms are substituted with a group such as a deuterium atom, a halogen group, cyano, aryl, heteroaryl, trialkylsilyl, alkyl, cycloalkyl, alkoxy, etc. It should be understood that, the carbon number of the substituted aryl refers to the total carbon number of substituents on aryl and aryl, for example, substituted aryl with 18 carbon atoms means that the total carbon number of aryl and its substituent is 18.

In the present disclosure, the specific examples of aryl as a substituent include but are not limited to: phenyl, naphthyl, anthryl, phenanthryl, dimethylfluorenyl, biphenyl and the like.

In the present disclosure, heteroaryl refer to a monovalent aromatic ring or its derivative in which the ring includes 1, 2, 3, 4, 5 or 6 heteroatoms, the heteroatom can be at least one of B, O, N, P, Si, Se and S. The heteroaryl can be monocyclic heteroaryl or polycyclic heteroaryl, in other words, the heteroaryl can be a single aromatic ring system, and can also be multiple aromatic ring systems conjugatedly connected by a carbon-carbon bond, where any one of the aromatic ring system is an aromatic monocyclic ring or an aromatic fused ring. For example, the heteroaryl can include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, benzoxazolyl, benzoimidazolyl, benzothiazolyl, benzocarbazolyl, benzothienyl, dibenzothienyl, thienothienyl, benzofuryl, phenanthrolinyl, isooxazolyl, thiadiazolyl, benzothiazolyl, phenothiazinyl, silafluorenyl, dibenzofuranyl and N-arylcarbazolyl (such as N-phenylcarbazolyl), N-heteroarylcarbazolyl (such as N-pyridylcarbazolyl), N-alkylcarbazolyl (such as N-methylcarbazolyl), etc., but is not limited thereto. Where, thienyl, furyl, phenanthrolinyl, etc. is heteroaryl of single aromatic ring system type, and N-phenylcarbazolyl or N-pyridylcarbazolyl is heteroaryl of polycyclic system type conjugatedly connected by a carbon-carbon bond. The "substituted or unsubstituted heteroaryl" of the present disclosure contains 3 to 30 carbon atoms, in some embodiments, the carbon number in the substituted or unsubstituted heteroaryl is 3 to 25, in some embodiments, the carbon number in the substituted or unsubstituted heteroaryl is 5 to 25, in some other embodiments, the carbon number in the substituted or unsubstituted heteroaryl is 5 to 20, and in some other embodiments, the carbon number in the substituted or unsubstituted heteroaryl is 5 to 12. For instance, the carbon number in the substituted or unsubstituted heteroaryl is 3, 4, 5, 7, 12, 13, 18, 20, 24, 25 or 30, and of course, the carbon number can also be other number, which is not be enumerated here.

In the present disclosure, the related heteroarylene refers to a bivalent group formed by further loss of one hydrogen atom from the heteroaryl.

In the present disclosure, the substituted heteroaryl can be heteroaryl in which one or more hydrogen atoms are substituted with a group such as a deuterium atom, a halogen group, cyano, aryl, heteroaryl, trialkylsilyl, alkyl, cycloalkyl, alkoxy, etc. It should be understood that, the carbon number of the substituted heteroaryl refers to the total carbon number of the heteroaryl and substituents on the heteroaryl.

In the present disclosure, the specific examples of the heteroaryl as a substituent include but are not limited to: pyridyl, carbazolyl, dibenzofuranyl, and dibenzothienyl.

In the present disclosure, the halogen group can include fluorine, iodine, bromine, chlorine, etc.

In the present disclosure, specific examples of the trialkylsilyl with 3 to 12 carbon atoms include, but are not limited to, trimethylsilyl, triethylsilyl, etc.

In the present disclosure, the specific examples of the haloalkyl with 1 to 10 carbon atoms include, but are not limited to, trifluoromethyl.

In the present disclosure, an unpositioned connecting bond refers to a single bond "

" extending from a ring system, which indicates that one end of the connecting bond can be linked to any position in the ring system through which the bond passes, and the other end is linked to the rest of a compound molecule.

For example, as shown in the following formula (f), naphthyl represented by the formula (f) is linked to other positions in the molecule through two unpositioned connecting bonds which pass through a dicyclic ring, and its meaning includes any possible connecting way shown in formulae (f-1) to (f-10).

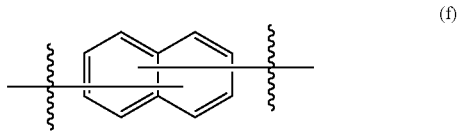 (f)

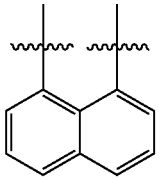 (f-1)

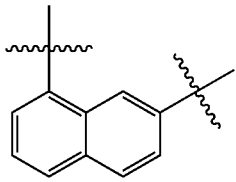 (f-2)

(f-3) 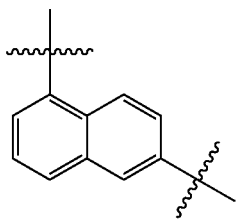

(f-4) 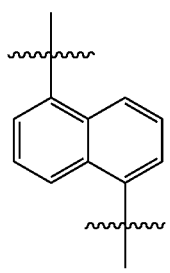

(f-5) 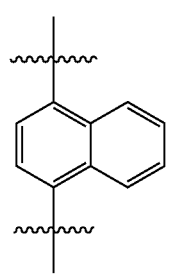

(f-6) 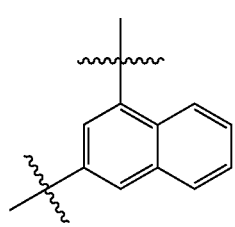

(f-7) 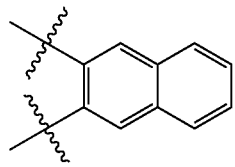

(f-8)

(f-9) 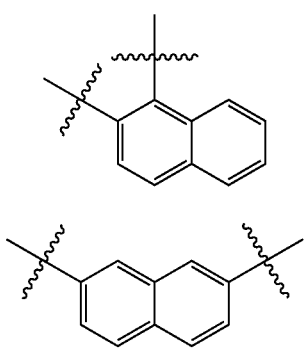

(f-10) 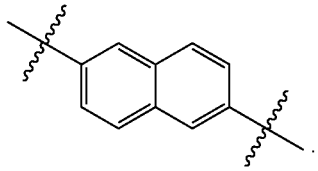

For instance again, as shown in the following formula (X'), dibenzofuranyl represented by the formula (X') is linked to other positions of the molecule through one unpositioned connecting bond extending from one side of the benzene ring, and its meaning includes any possible connecting way shown as in formulae (X'-1) to (X'-4).

(X') 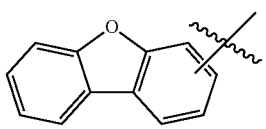

(X'-1) 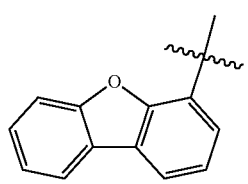

(X'-2) 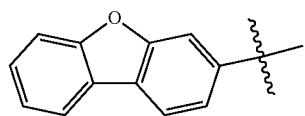

(X'-3) 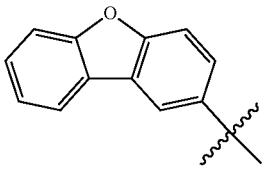

(X'-4) 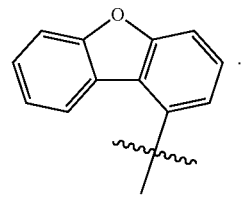

Hereinafter, the meaning of unpositioned connection or unpositioned substitution are the same as here, and no further details will be given.

In one embodiment of the present disclosure, two of $U_1$, $U_2$ and $U_3$ are N, the other one is C(R); or $U_1$, $U_2$ and $U_3$ are all N.

In some embodiments of the present disclosure, each of R, $R_1$, $R_2$, $R_3$, $R_4$ and $R_5$ is independently selected from hydrogen, deuterium, fluorine, cyano, methyl, ethyl, n-propyl, isopropyl, tert-butyl, phenyl, pyridyl, trifluoromethyl, biphenyl, alternatively, any two adjacent $R_2$ form a benzene ring, a naphthalene ring or a phenanthrene ring.

Optionally, each of R, $R_1$, $R_3$, $R_4$ and $R_5$ is hydrogen.

Optionally, each $R_2$ is selected from hydrogen, deuterium, fluorine, cyano, methyl, ethyl, n-propyl, isopropyl, tert-butyl, phenyl, naphthyl, pyridyl, trifluoromethyl, biphenyl, or any two adjacent $R_2$ are linked with each other to form a benzene ring, a naphthalene ring or a phenanthrene ring.

In the present disclosure, the group shown in Formula 2-1

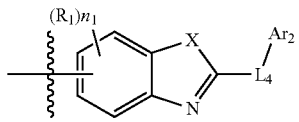

is selected from the following structures:

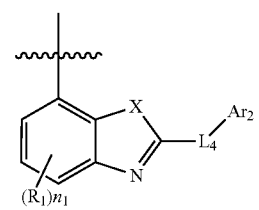

Formula 2-1-1

Formula 2-1-2

Formula 2-1-3

Formula 2-1-4

In some embodiments of the present disclosure, the L, $L_1$, $L_2$, $L_3$ and $L_4$ are the same or different, and are each independently selected from a single bond, substituted or unsubstituted arylene with 6 to 20 carbon atoms, or substituted or unsubstituted heteroarylene with 5 to 20 carbon atoms.

Optionally, the substituents in the L, $L_1$, $L_2$, $L_3$ and $L_4$ are the same or different, and are each independently selected from deuterium, a halogen group, cyano, aryl with 6 to 12 carbon atoms, and alkyl with 1 to 5 carbon atoms.

Specifically, the specific examples of substituents in the L, $L_1$, $L_2$, $L_3$ and $L_4$ include but are not limited to: deuterium, fluorine, cyano, methyl, ethyl, n-propyl, isopropyl, tert-butyl, and phenyl.

In some embodiments of the present disclosure, the L, $L_1$, $L_2$, $L_3$ and $L_4$ are the same or different, and are each independently selected from a single bond, substituted or unsubstituted phenylene, substituted or unsubstituted naphthylene, substituted or unsubstituted biphenylene, substituted or unsubstituted pyridylidene, substituted or unsubstituted dibenzofurylidene, substituted or unsubstituted dibenzothienylene, substituted or unsubstituted fluorenylidene, substituted or unsubstituted carbazolylene, and substituted or unsubstituted anthrylene.

In some embodiments of the present disclosure, the L, $L_1$, $L_2$, $L_3$ and $L_4$ are the same or different, and are each independently selected from a single bond or a substituted or unsubstituted group V, and the unsubstituted group V is selected from a group consisting of the following groups:

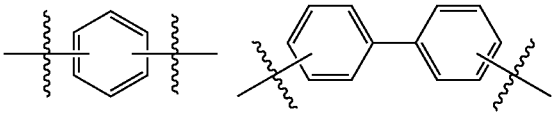

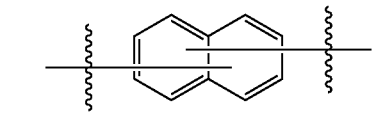

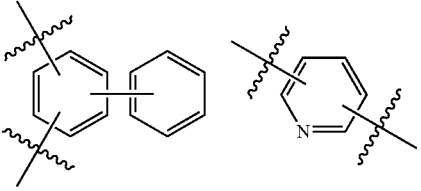

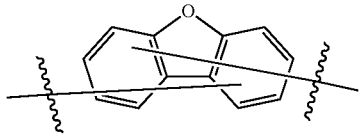

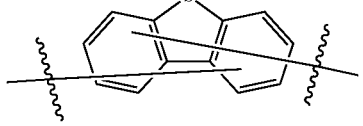

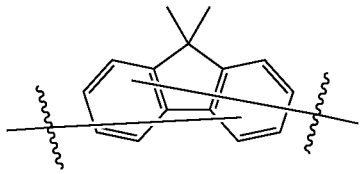

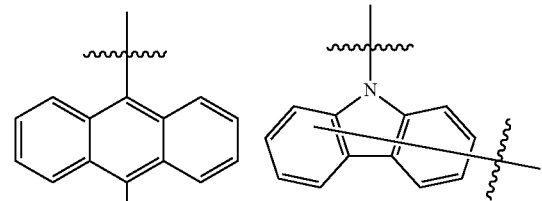

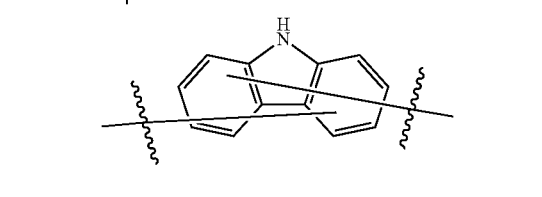

-continued

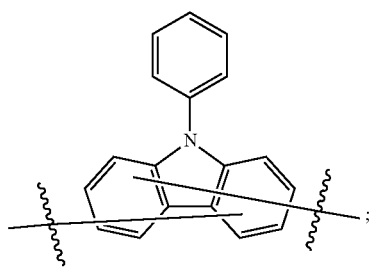

where,

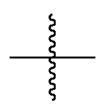

represents a chemical bond; the substituted group V has one or more substituent(s), the substituents are each independently selected from deuterium, cyano, fluorine, methyl, ethyl, n-propyl, isopropyl, tert-butyl or phenyl; when the number of the substituents in V is greater than 1, the substituents are the same or different.

Optionally, L, $L_1$, $L_2$, $L_3$ and $L_4$ are each independently selected from a single bond or a group consisting of the following groups:

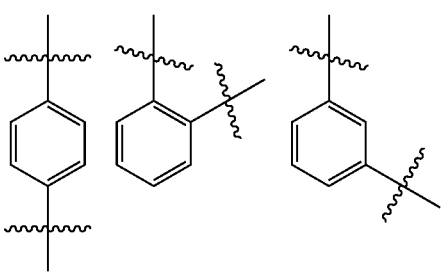

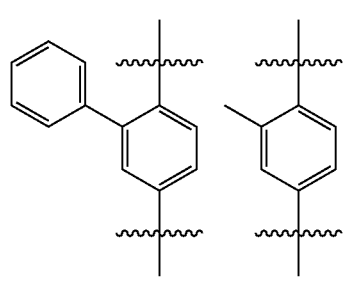

-continued

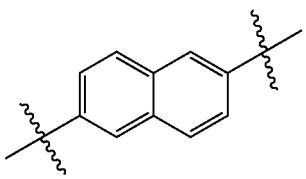

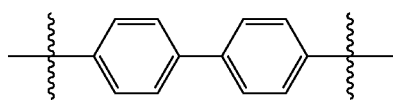

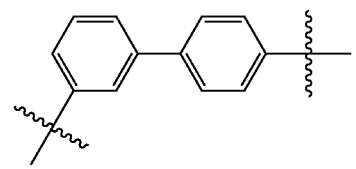

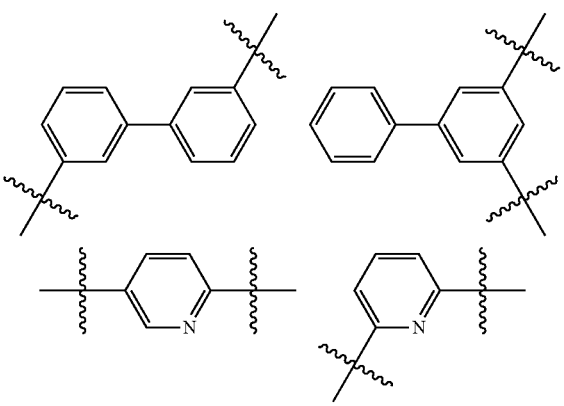

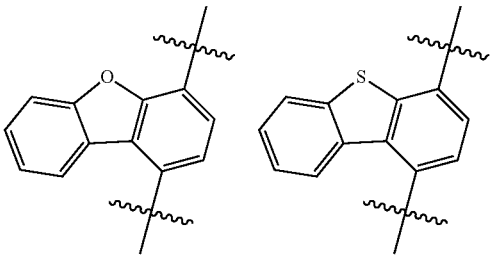

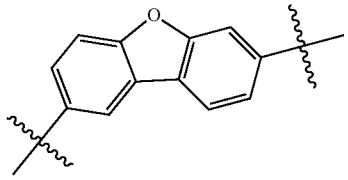

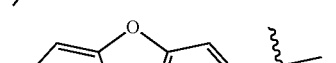

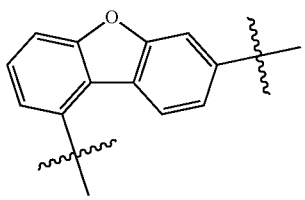

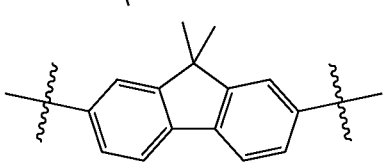

-continued

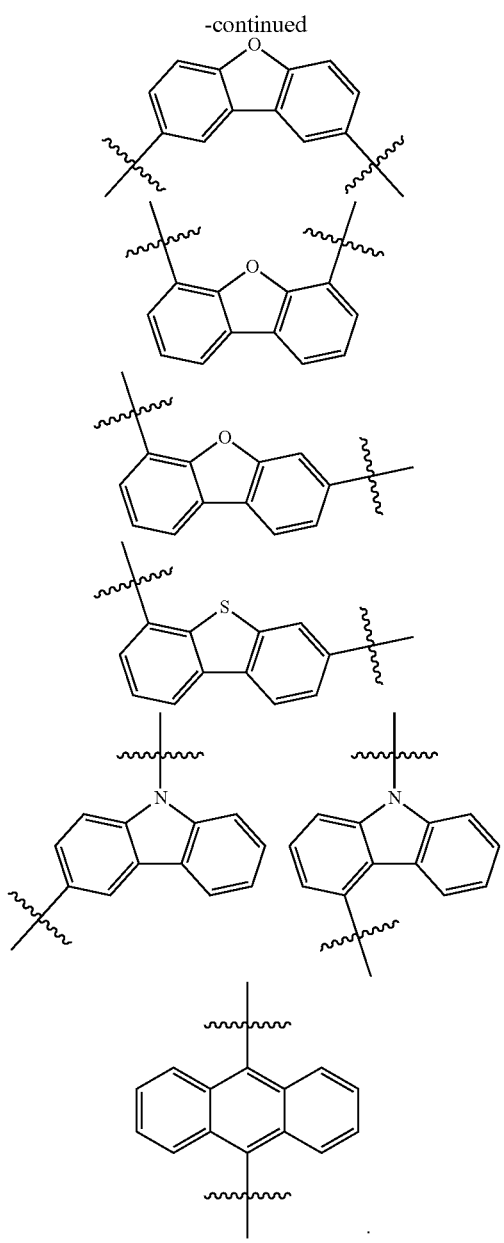

In some embodiments of the present disclosure, the $Ar_1$ and $Ar_2$ are each independently selected from substituted or unsubstituted aryl with 6 to 25 carbon atoms, or substituted or unsubstituted heteroaryl with 4 to 20 carbon atoms.

Optionally, the substituents in the $Ar_1$ are each independently selected from deuterium, a halogen group, cyano, aryl with 6 to 12 carbons atoms, heteroaryl with 5 to 12 carbons atoms, alkyl with 1 to 5 carbons atoms or cycloalkyl with 3 to 10 carbons atoms.

Specifically, substituents in the $Ar_1$ are each independently selected from: deuterium, cyano, fluorine, methyl, ethyl, n-propyl, isopropyl, tert-butyl, phenyl, naphthyl, biphenyl or carbazolyl.

Alternatively, any two adjacent substituents in the $Ar_1$ form a saturated or unsaturated ring with 5 to 13 carbons atoms. For instance, any two adjacent substituents form cyclopentane, cyclohexane, a fluorene ring, etc.

Further optionally, the $Ar_1$ is selected from substituted or unsubstituted aryl with 6 to 20 carbons atoms, or substituted or unsubstituted heteroaryl with 5 to 12 carbon atoms.

Alternatively, any two adjacent substituents in the $Ar_1$ form cyclopentane, cyclohexane or a fluorene ring.

In some embodiments of the present disclosure, $Ar_1$ is selected from substituted or unsubstituted phenyl, substituted or unsubstituted naphthyl, substituted or unsubstituted biphenyl, substituted or unsubstituted phenanthryl, substituted or unsubstituted anthryl, substituted or unsubstituted pyridyl, substituted or unsubstituted benzophenanthryl, substituted or unsubstituted spirobifluorenyl, substituted or unsubstituted quinolyl, substituted or unsubstituted isoquinolyl, substituted or unsubstituted dibenzofuranyl, substituted or unsubstituted carbazolyl, substituted or unsubstituted dibenzothienyl, substituted or unsubstituted pyrenyl, and substituted or unsubstituted phenanthrolinyl.

In some embodiments of the present disclosure, the $Ar_2$ is selected from substituted or unsubstituted aryl with 6 to 25 carbon atoms, or substituted or unsubstituted heteroaryl with 4 to 20 carbon atoms;

Optionally, substituents in the $Ar_2$ are each independently selected from deuterium, a halogen group, cyano, aryl with 6 to 12 carbon atoms, heteroaryl with 5 to 12 carbon atoms, alkyl with 1 to 5 carbon atoms, haloalkyl with 1 to 5 carbon atoms or cycloalkyl with 3 to 10 carbon atoms, and alternatively, any two adjacent substituents in the $Ar_2$ form a saturated or unsaturated ring with 5 to 13 carbon atoms.

Specifically, substituents in the $Ar_2$ are each independently selected from: deuterium, cyano, fluorine, methyl, ethyl, n-propyl, isopropyl, tert-butyl, phenyl, naphthyl, biphenyl, and carbazolyl, and alternatively, any two adjacent substituents form a 5-13-membered ring. For instance, any two adjacent substituents form cyclopentyl, cyclohexyl, etc.

In some other embodiments of the present disclosure, the $Ar_2$ is selected from substituted or unsubstituted phenyl, substituted or unsubstituted biphenyl, substituted or unsubstituted naphthyl, substituted or unsubstituted dibenzofuranyl, substituted or unsubstituted dibenzothienyl, substituted or unsubstituted fluorenyl, substituted or unsubstituted N-phenylcarbazolyl, substituted or unsubstituted carbazolyl, substituted or unsubstituted phenanthryl, substituted or unsubstituted anthryl, substituted or unsubstituted terphenyl, substituted or unsubstituted pyridyl, substituted or unsubstituted pyrenyl, substituted or unsubstituted quinolyl, substituted or unsubstituted isoquinolyl, substituted or unsubstituted phenanthrolinyl, substituted or unsubstituted benzophenanthryl, substituted or unsubstituted furyl, substituted or unsubstituted thienyl or the following substituted or unsubstituted group:

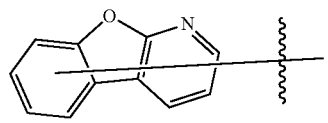

(benzofuro[2,3-b]pyridine).

In some embodiments of the present disclosure, the $Ar_1$, and $Ar_2$ are each independently selected from substituted or unsubstituted group $W_1$, and the unsubstituted group $W_1$ is selected from a group consisting of the following groups:

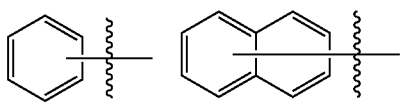

-continued

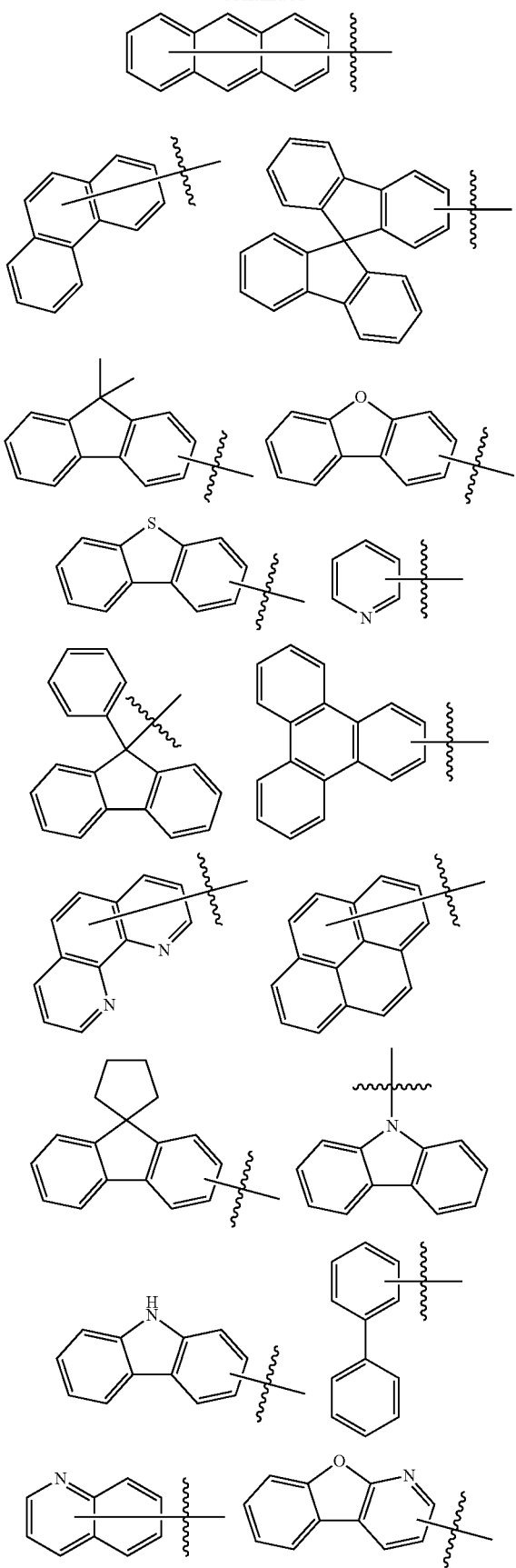

-continued

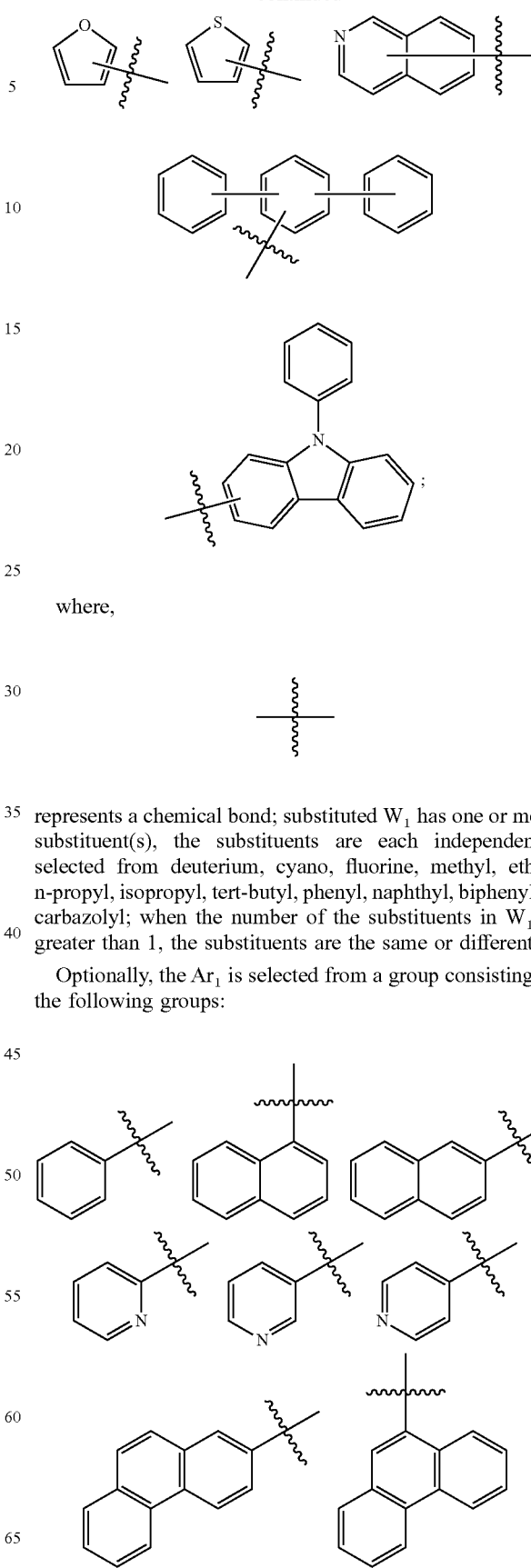

where,

represents a chemical bond; substituted $W_1$ has one or more substituent(s), the substituents are each independently selected from deuterium, cyano, fluorine, methyl, ethyl, n-propyl, isopropyl, tert-butyl, phenyl, naphthyl, biphenyl or carbazolyl; when the number of the substituents in $W_1$ is greater than 1, the substituents are the same or different.

Optionally, the $Ar_1$ is selected from a group consisting of the following groups:

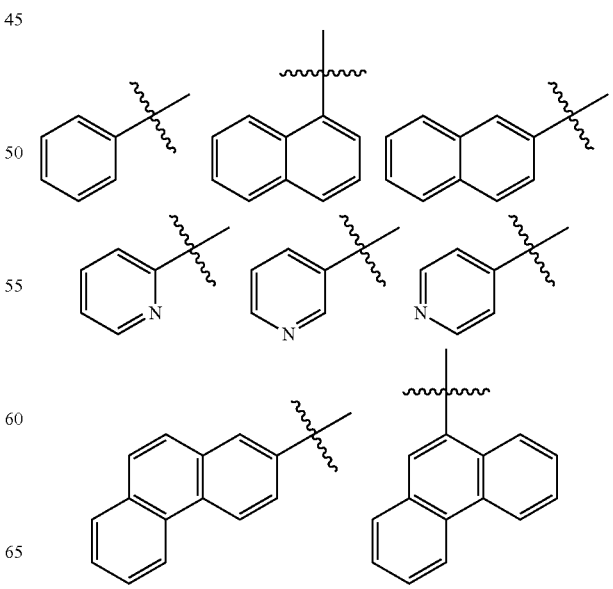

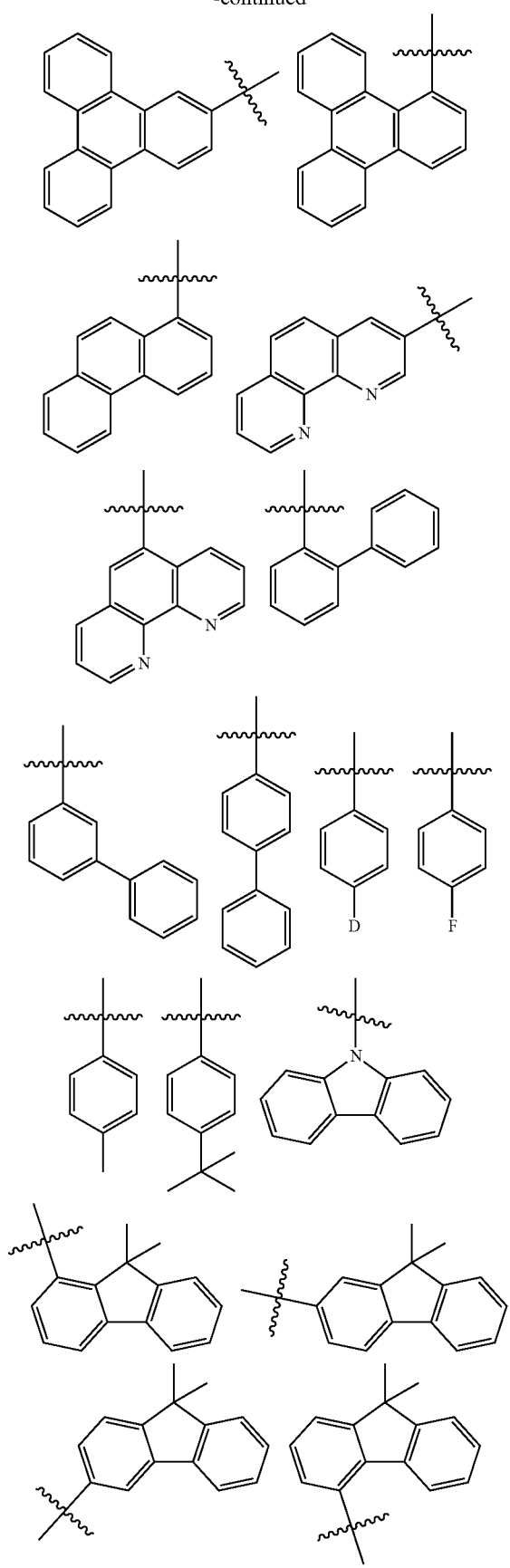

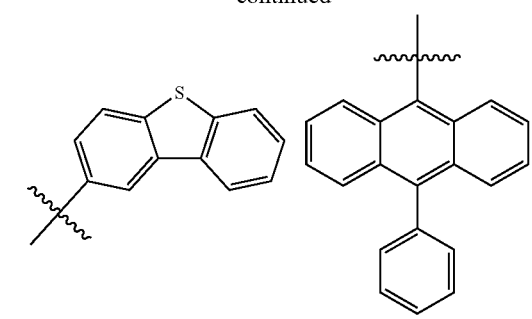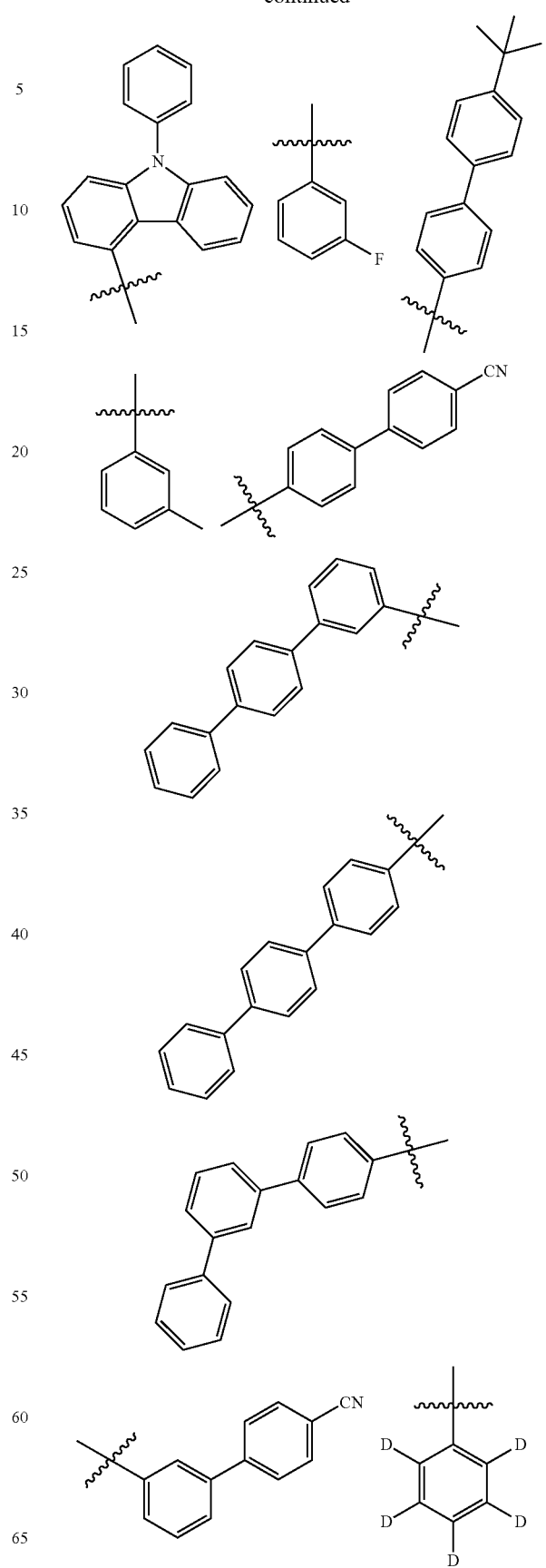

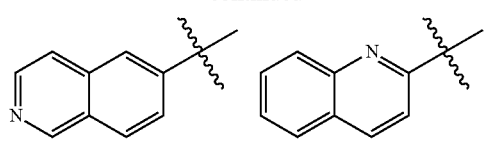
Optionally, the Ar₂ is selected from a group consisting of the following groups:
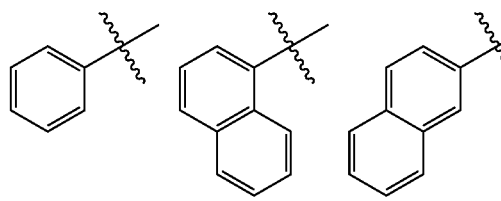
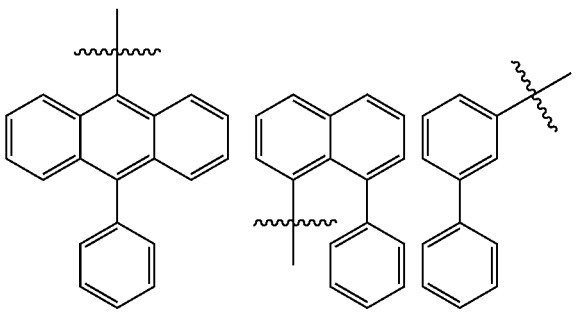
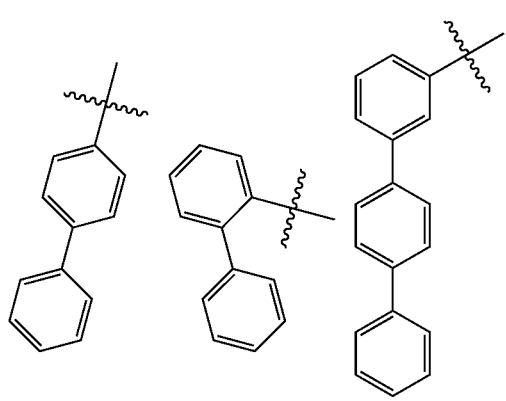
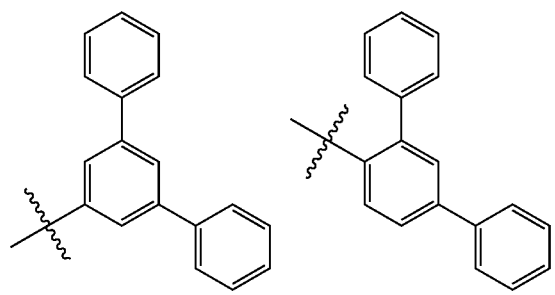
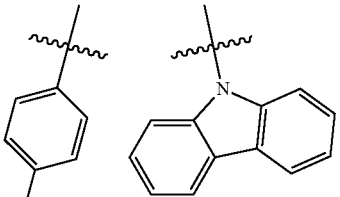
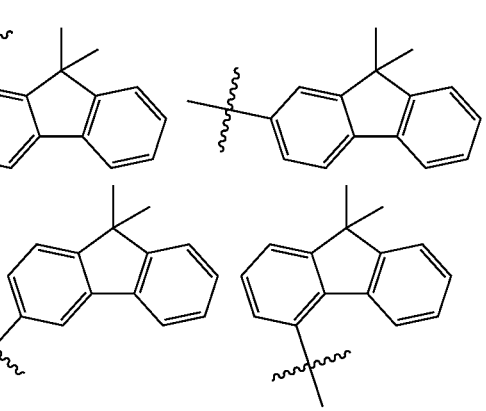
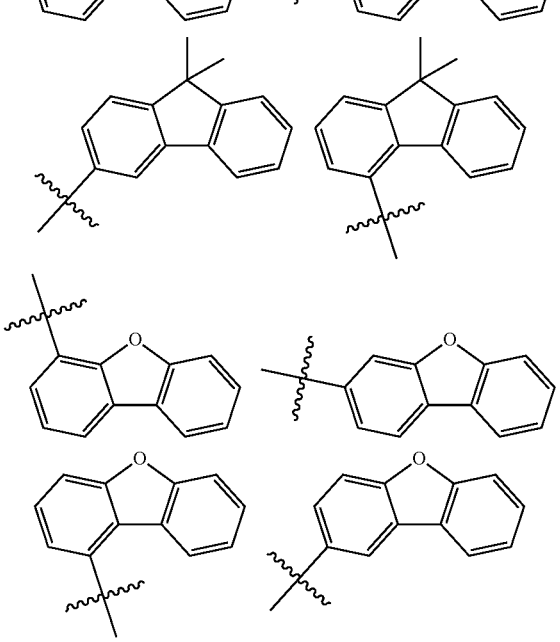
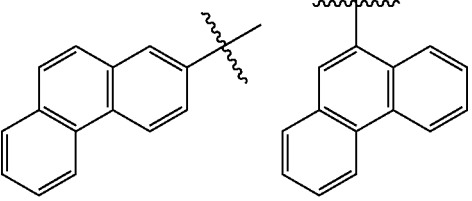
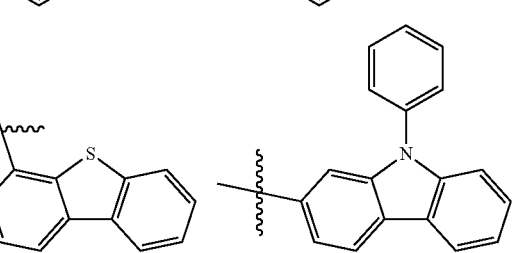

-continued
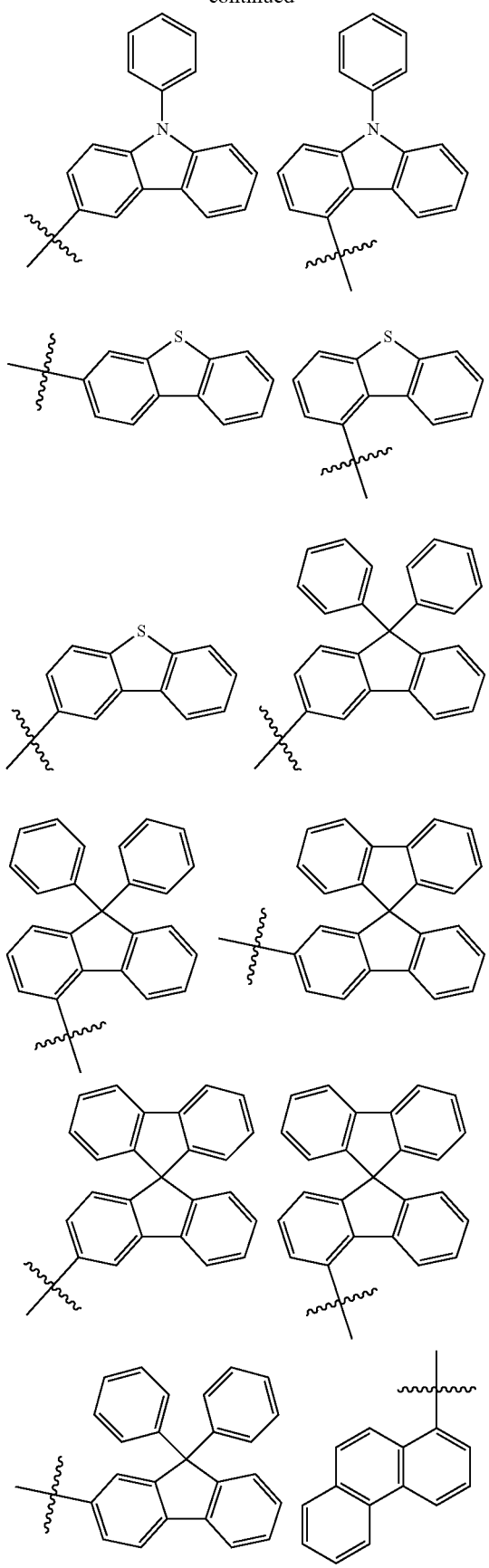
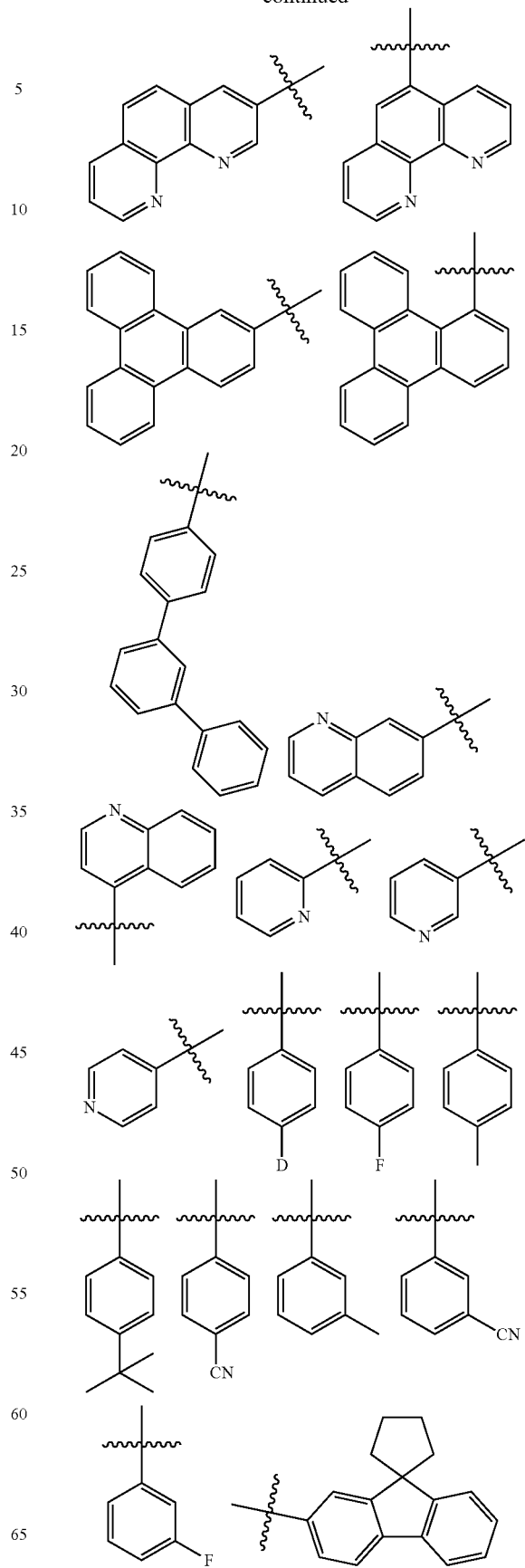

-continued

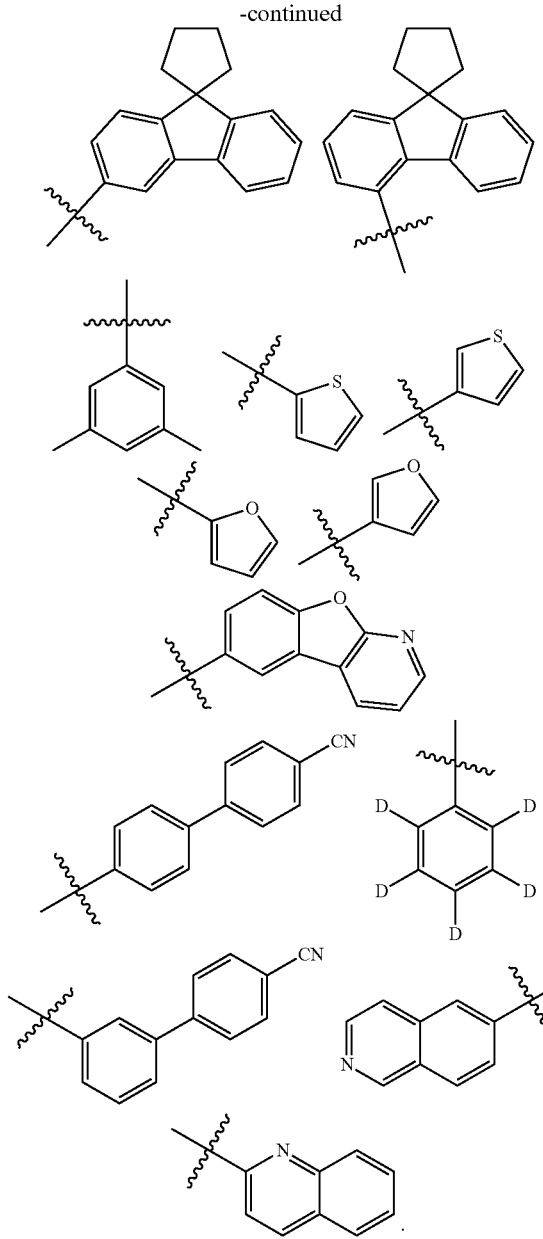

In some embodiments of the present disclosure, the A and B are each independently selected from substituted or unsubstituted aryl with 6 to 25 carbon atoms, substituted or unsubstituted heteroaryl with 5 to 20 carbon atoms, the structure shown in the Formula 2-1 or the structure shown in the Formula 2-2, and only one of A and B is selected from the structure shown in the Formula 2-1 or the structure shown in the Formula 2-2. That is, A is the structure shown in the Formula 2-1 or the structure shown in the Formula 2-2, B is selected from substituted or unsubstituted aryl with 6 to 25 carbon atoms, and substituted or unsubstituted heteroary with 5 to 20 carbon atoms, and B is not the structure shown in the Formula 2-1 or the Formula 2-2; or B is the structure shown in the Formula 2-1 or the structure shown in the Formula 2-2, A is selected from substituted or unsubstituted aryl with 6 to 25 carbon atoms, and substituted or unsubstituted heteroaryl with 5 to 20 carbon atoms, and A is not the structure shown in the Formula 2-1 or the Formula 2-2.

Optionally, substituents in the A and B are each independently selected from deuterium, a halogen group, cyano, aryl with 6 to 12 carbon atoms, heteroaryl with 5 to 12 carbon atoms, alkyl with 1 to 5 carbon atoms, and cycloalkyl with 3 to 10 carbon atoms.

Specifically, substituents in the A and B are each independently selected from: deuterium, fluorine, cyano, methyl, ethyl, n-propyl, isopropyl, tert-butyl, phenyl, naphthyl, biphenyl, pyridyl, carbazolyl, dibenzofuranyl, dibenzothienyl, cyclopentyl or cyclohexyl.

In some embodiments of the present disclosure, when the A or B is selected from substituted or unsubstituted aryl with 6 to 25 carbon atoms, and substituted or unsubstituted heteroaryl with 5 to 20 carbon atoms, the A or B is each independently selected from: substituted or unsubstituted phenyl, substituted or unsubstituted naphthyl, substituted or unsubstituted biphenyl, substituted or unsubstituted phenanthryl, substituted or unsubstituted anthryl, substituted or unsubstituted pyridyl, substituted or unsubstituted benzophenanthryl, substituted or unsubstituted spirobifluorenyl, substituted or unsubstituted quinolyl, substituted or unsubstituted isoquinolyl, substituted or unsubstituted dibenzofuranyl, substituted or unsubstituted carbazolyl, substituted or unsubstituted dibenzothienyl, substituted or unsubstituted fluorenyl, substituted or unsubstituted pyrenyl, and substituted or unsubstituted phenanthrolinyl.

In some other embodiments of the present disclosure, when the A or B is selected from substituted or unsubstituted aryl with 6 to 25 carbon atoms, and substituted or unsubstituted heteroaryl with 5 to 20 carbon atoms, the A and B are each independently selected from following groups:

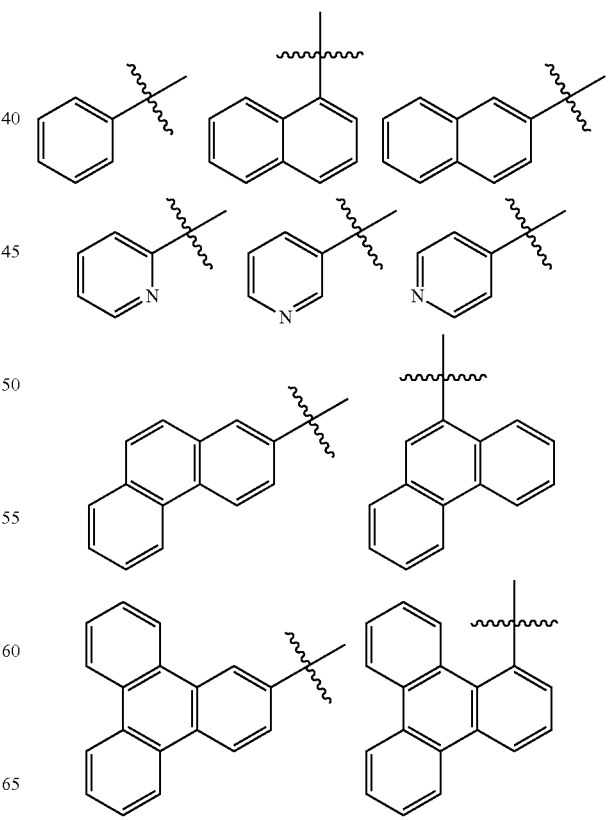

-continued
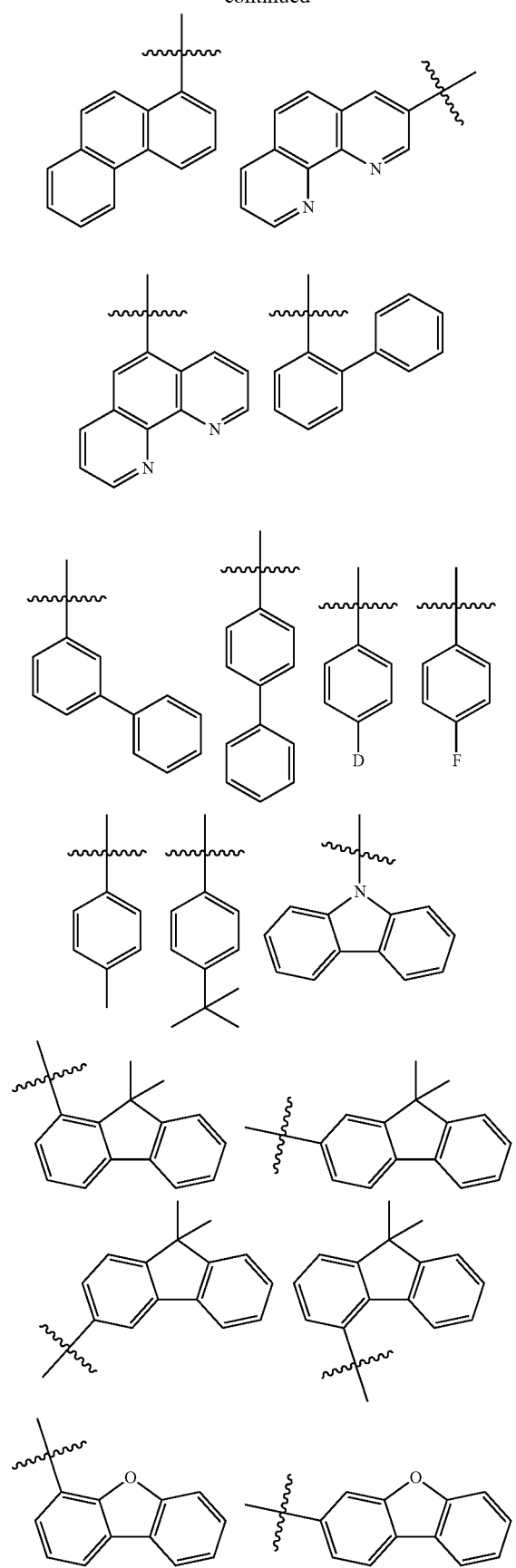
-continued
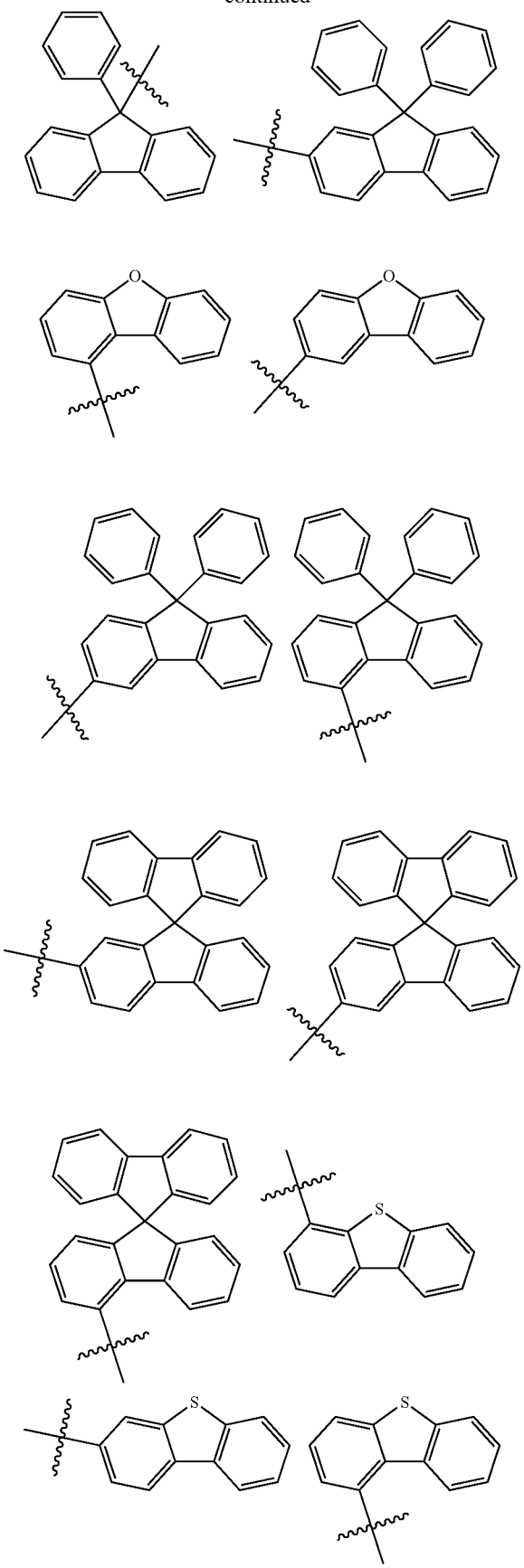

33
-continued
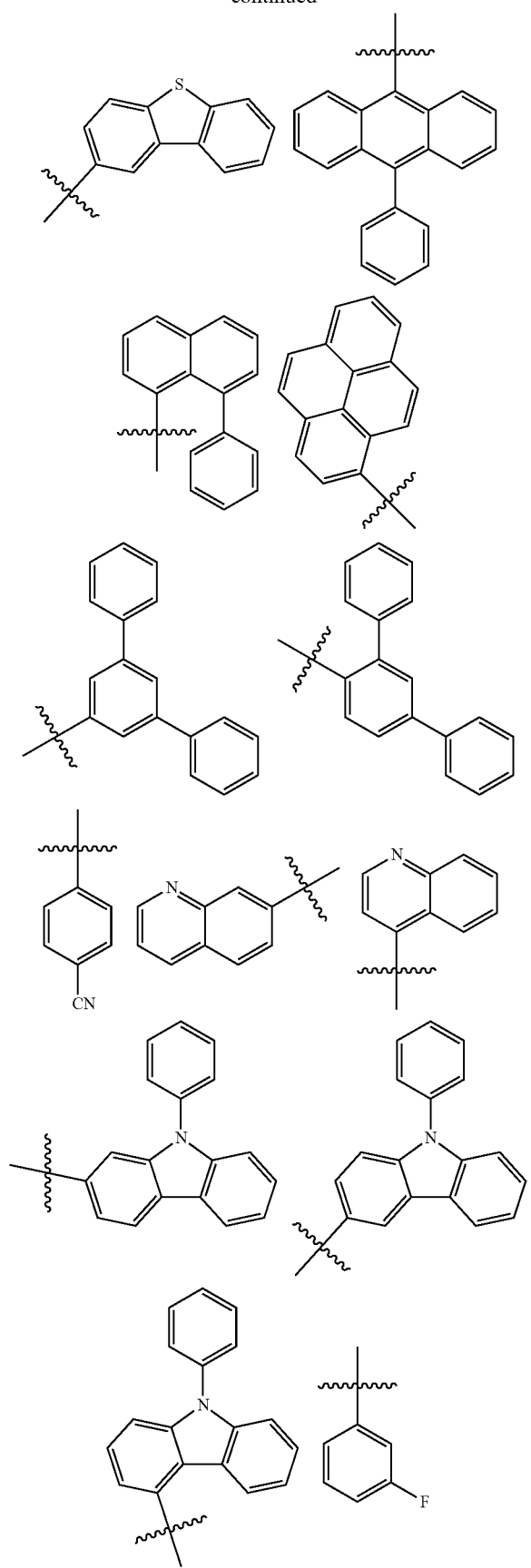
34
-continued
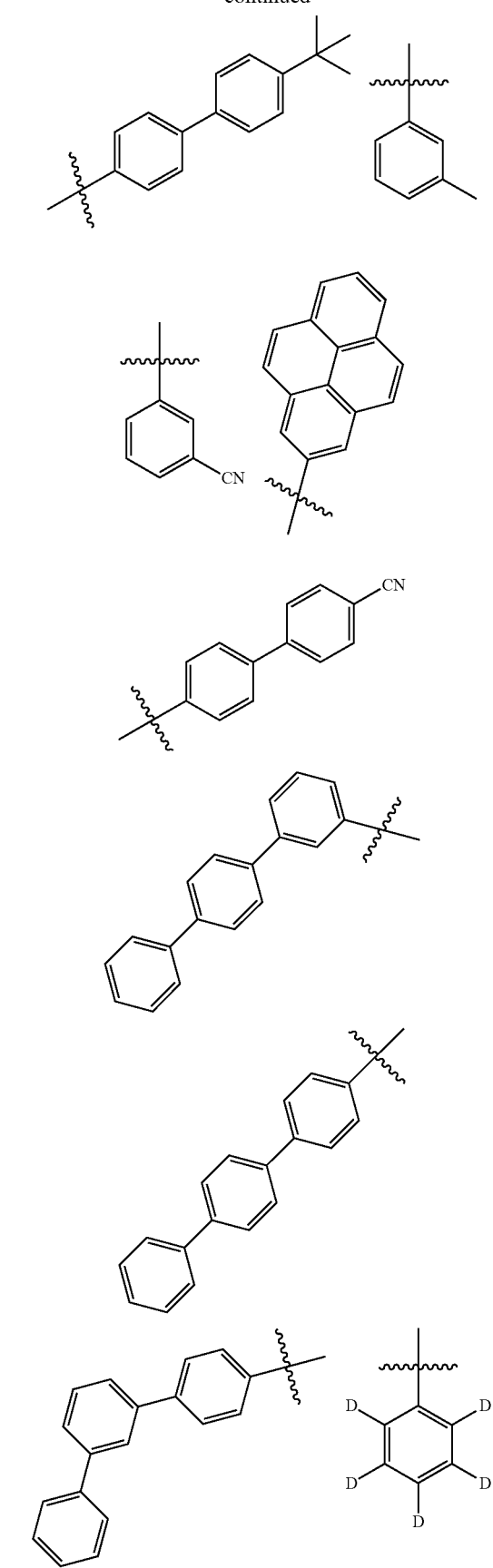

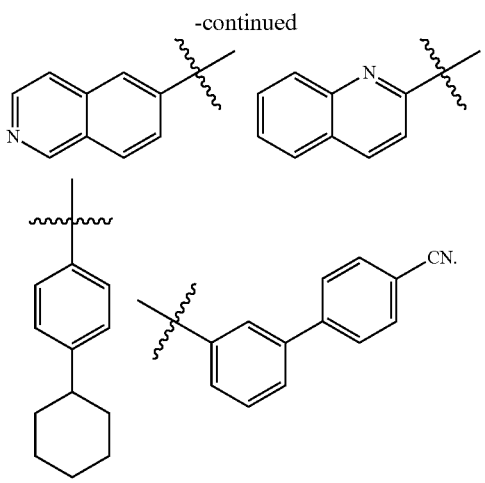

In some embodiments of the present disclosure, A is the structure shown in the Formula 2-1, B is selected from a group consisting of substituted or unsubstituted phenyl, substituted or unsubstituted naphthyl, substituted or unsubstituted biphenyl, substituted or unsubstituted phenanthryl, substituted or unsubstituted anthryl, substituted or unsubstituted benzophenanthryl, substituted or unsubstituted spirobifluorenyl, substituted or unsubstituted pyridyl, substituted or unsubstituted quinolyl, substituted or unsubstituted isoquinolyl, substituted or unsubstituted dibenzofuranyl, substituted or unsubstituted carbazolyl, substituted or unsubstituted dibenzothienyl, substituted or unsubstituted fluorenyl, substituted or unsubstituted pyrenyl, and substituted or unsubstituted phenanthrolinyl.

In some embodiments of the present disclosure, A is the structure shown in the Formula 2-2, B is selected from a group consisting of substituted or unsubstituted phenyl, substituted or unsubstituted naphthyl, substituted or unsubstituted biphenyl, substituted or unsubstituted phenanthryl, substituted or unsubstituted anthryl, substituted or unsubstituted benzophenanthryl, substituted or unsubstituted spirobifluorenyl, substituted or unsubstituted pyridyl, substituted or unsubstituted quinolyl, substituted or unsubstituted isoquinolyl, substituted or unsubstituted dibenzofuranyl, substituted or unsubstituted carbazolyl, substituted or unsubstituted dibenzothienyl, substituted or unsubstituted fluorenyl, substituted or unsubstituted pyrenyl, and substituted or unsubstituted phenanthrolinyl.

In some embodiments of the present disclosure, substituent in B is selected from a group consisting of deuterium, a halogen group, cyano, aryl with 6 to 12 carbon atoms, heteroaryl having a carbon number of 5 to 12 carbon atoms, alkyl with 1 to 5 carbon atoms, and cycloalkyl with 3 to 10 carbon atoms, and substituent in B is further selected from a group consisting of deuterium, fluorine, cyano, methyl, ethyl, n-propyl, isopropyl, tert-butyl, phenyl, naphthyl, biphenyl, pyridyl, carbazolyl, dibenzofuranyl, dibenzothienyl, cyclopentyl, and cyclohexyl.

In some embodiments of the present disclosure, B is the structure shown in the Formula 2-1, A is selected from a group consisting of substituted or unsubstituted phenyl, substituted or unsubstituted naphthyl, substituted or unsubstituted biphenyl, substituted or unsubstituted phenanthryl, substituted or unsubstituted anthryl, substituted or unsubstituted benzophenanthryl, substituted or unsubstituted spirobifluorenyl, substituted or unsubstituted pyridyl, substituted or unsubstituted quinolyl, substituted or unsubstituted isoquinolyl, substituted or unsubstituted dibenzofuranyl, substituted or unsubstituted carbazolyl, substituted or unsubstituted dibenzothienyl, substituted or unsubstituted fluorenyl, substituted or unsubstituted pyrenyl, and substituted or unsubstituted phenanthrolinyl.

In some embodiments of the present disclosure, B is the structure shown in the Formula 2-2, A is selected from a group consisting of substituted or unsubstituted phenyl, substituted or unsubstituted naphthyl, substituted or unsubstituted biphenyl, substituted or unsubstituted phenanthryl, substituted or unsubstituted anthryl, substituted or unsubstituted benzophenanthryl, substituted or unsubstituted spirobifluorenyl, substituted or unsubstituted pyridyl, substituted or unsubstituted quinolyl, substituted or unsubstituted isoquinolyl, substituted or unsubstituted dibenzofuranyl, substituted or unsubstituted carbazolyl, substituted or unsubstituted dibenzothienyl, substituted or unsubstituted fluorenyl, substituted or unsubstituted pyrenyl, and substituted or unsubstituted phenanthrolinyl.

In some embodiments of the present disclosure, substituent in A is selected from a group consisting of deuterium, a halogen group, cyano, aryl with 6 to 12 carbon atoms, heteroaryl with 5 to 12 carbon atoms, alkyl with 1 to 5 carbon atoms, and cycloalkyl with 3 to 10 carbon atoms, and substituent in A is further selected from the group consisting of deuterium, fluorine, cyano, methyl, ethyl, n-propyl, isopropyl, tert-butyl, phenyl, naphthyl, biphenyl, pyridyl, carbazolyl, dibenzofuranyl, dibenzothienyl, cyclopentyl, and cyclohexyl.

In some embodiments of the present disclosure, when A is selected from the structure shown in the Formula 2-1 or the structure shown in the Formula 2-2, X is O.

Optionally, the nitrogen-containing compound is selected from a group consisting of the following compounds:

1

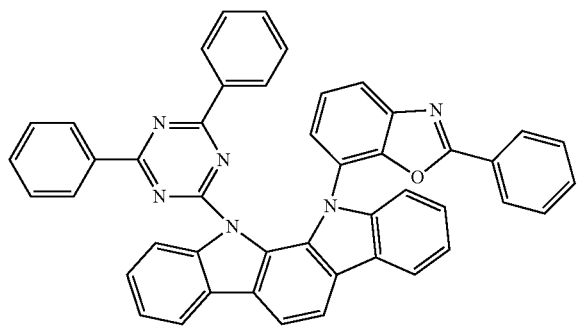

2

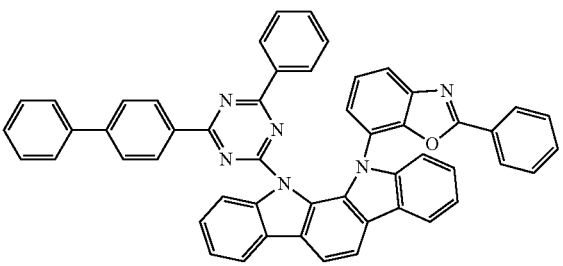

-continued
3
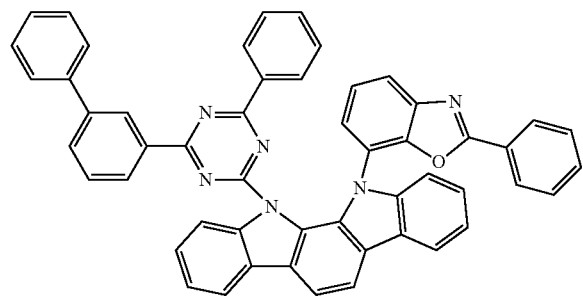
4
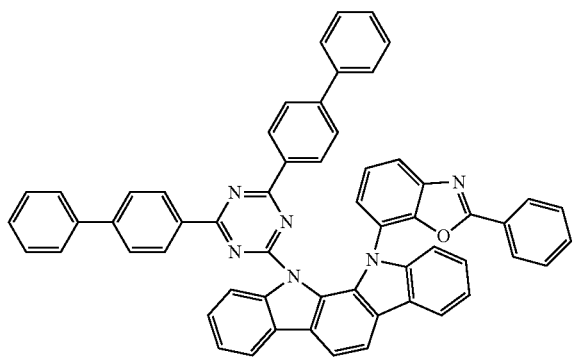
5
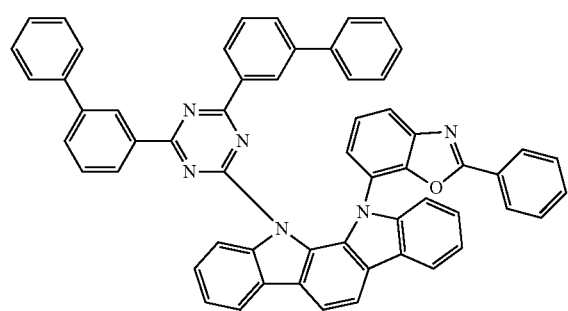
6
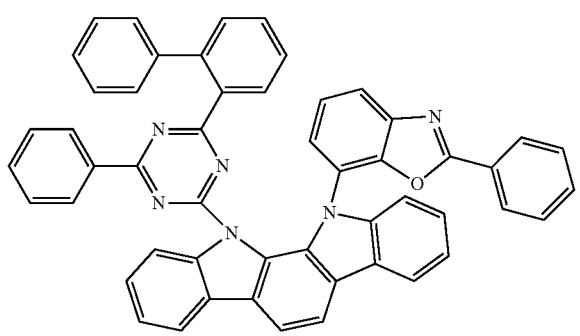
7
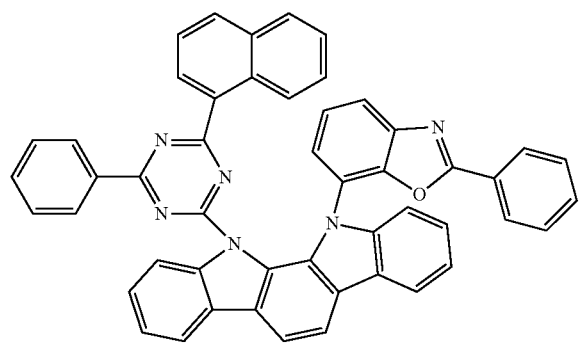
8
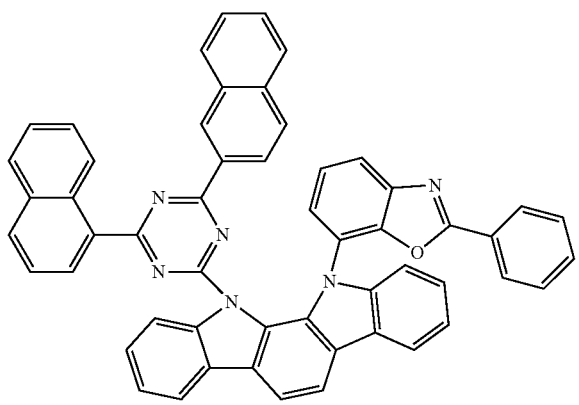
9
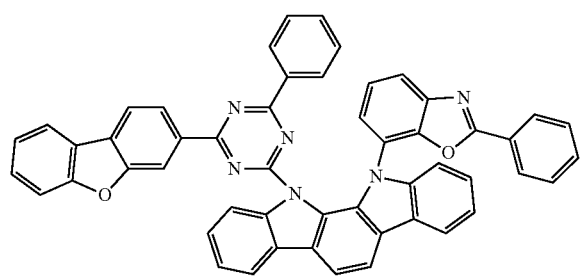
10
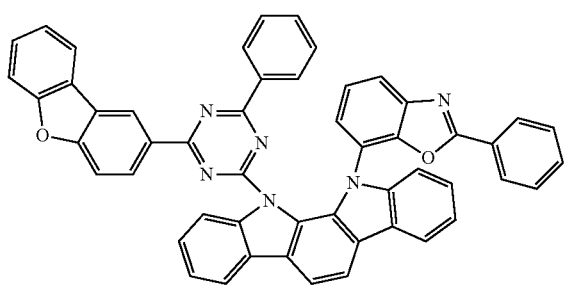

-continued
11
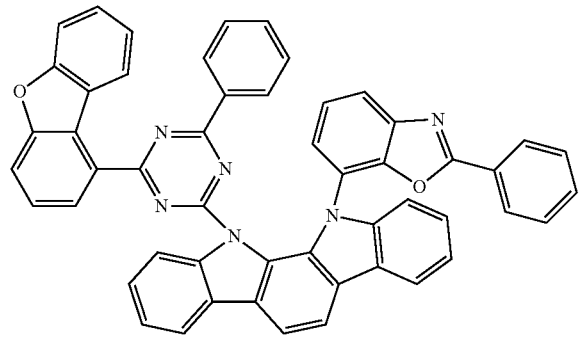
12
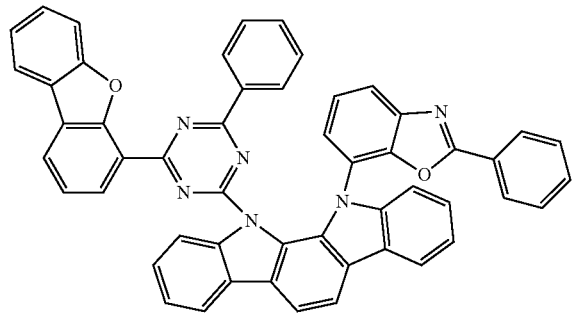
13
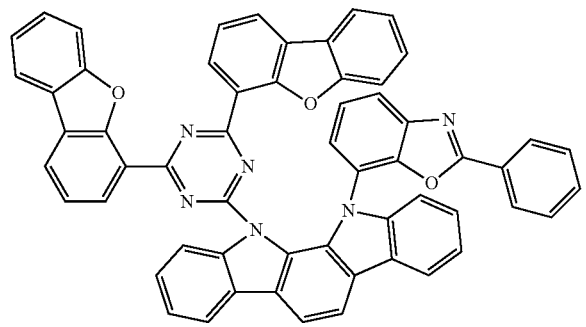
14
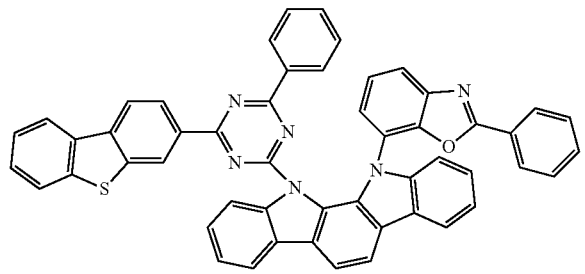
15
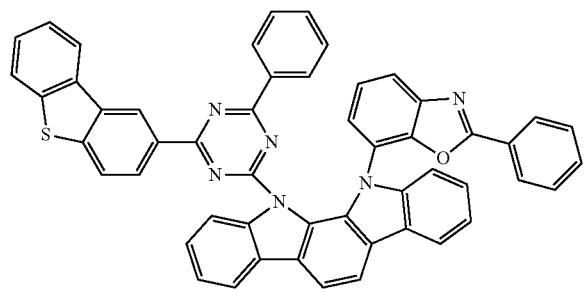
16
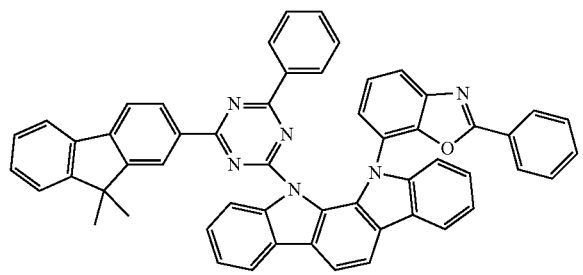
17
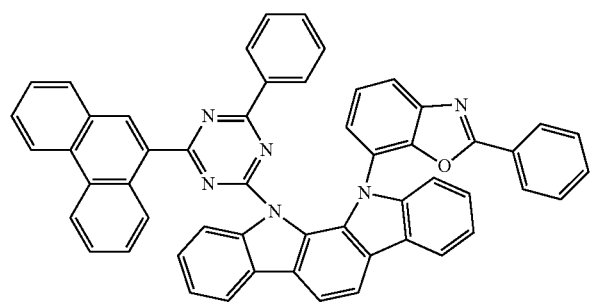
18
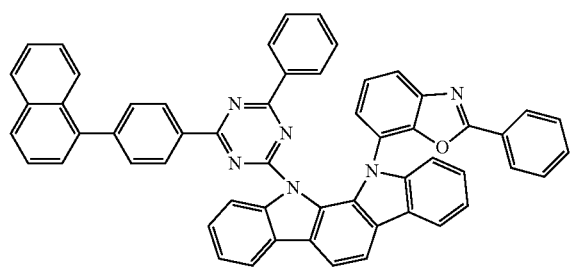
19
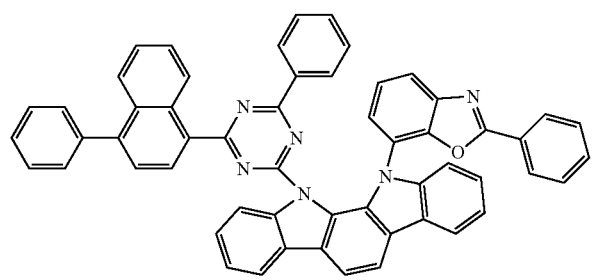
20
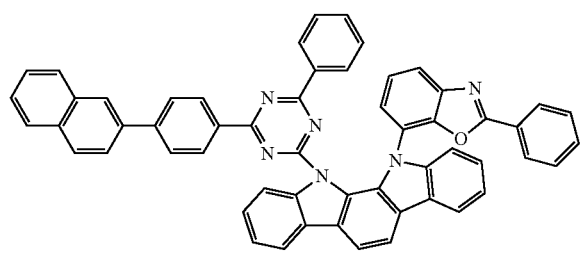

-continued
21
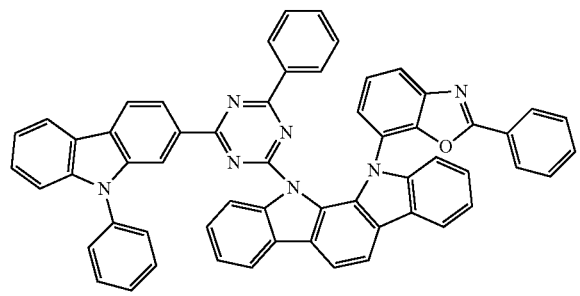
22
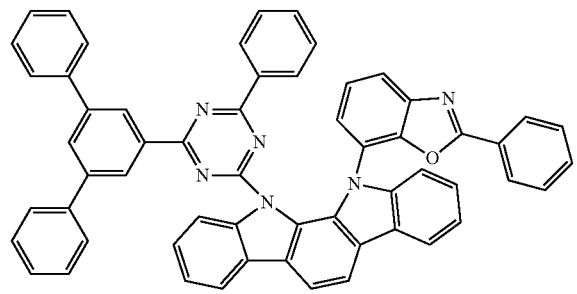
23
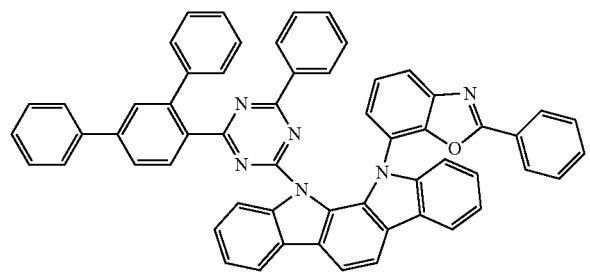
24
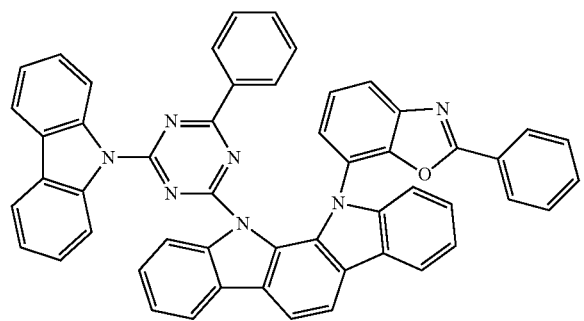
25
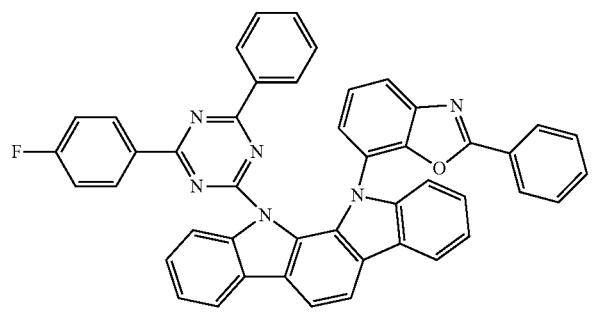
26
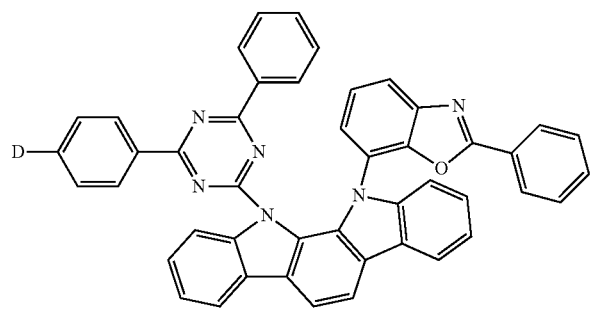
27
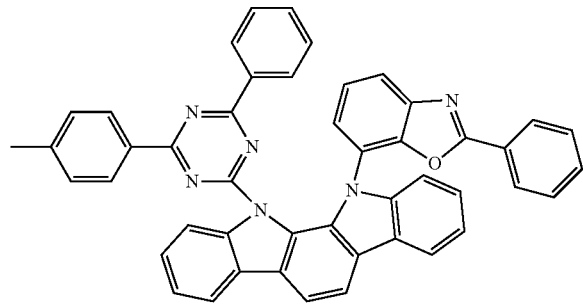
28
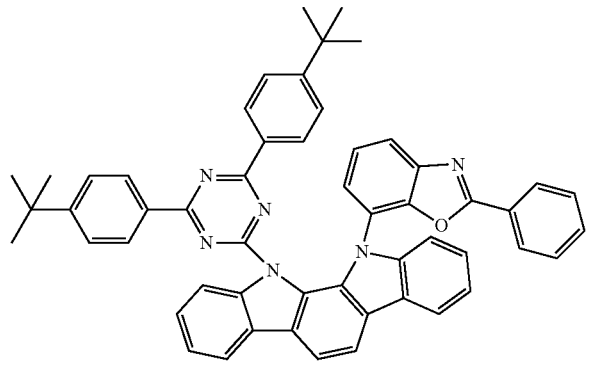

-continued
29
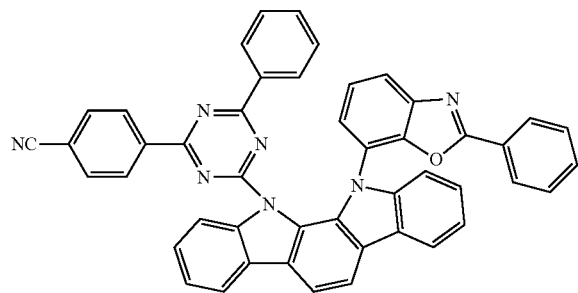
30
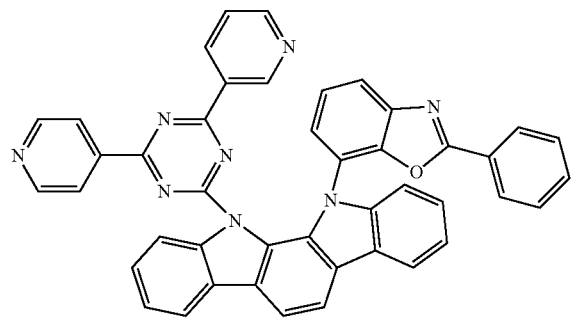
31
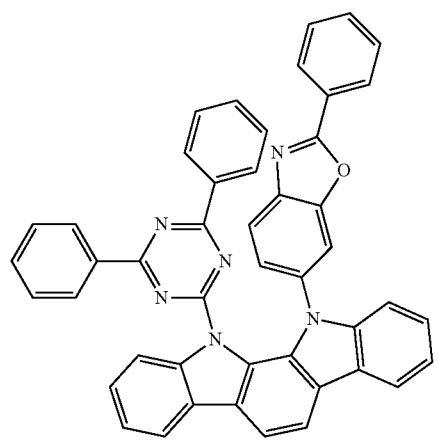
32
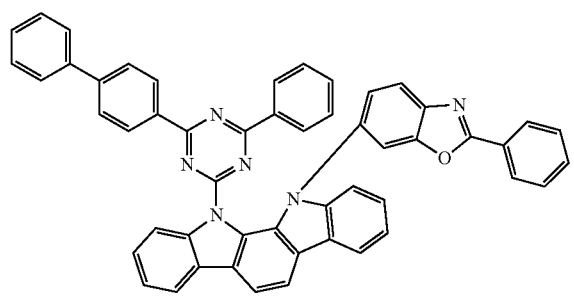
33
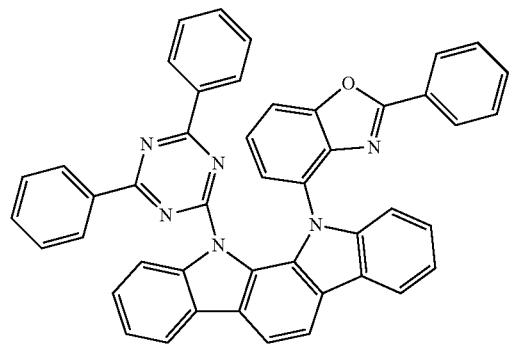
34
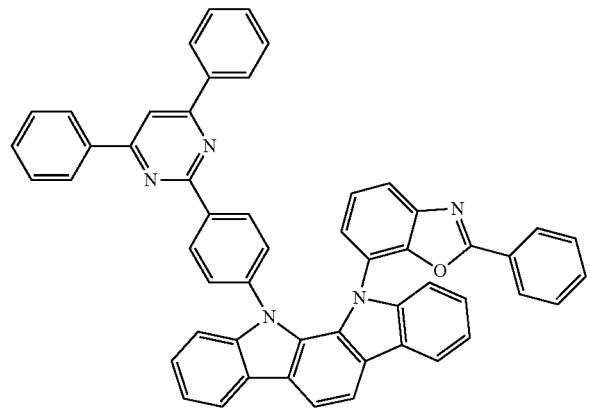
35
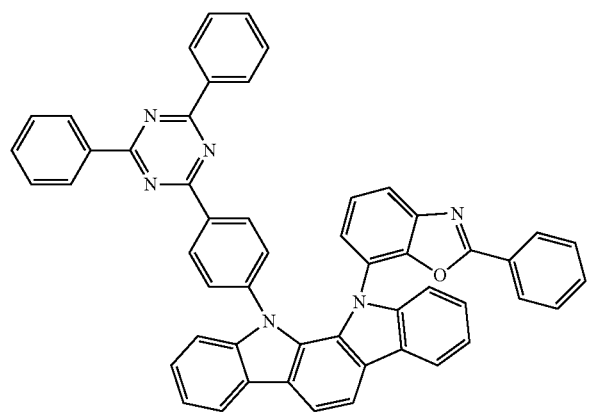
36
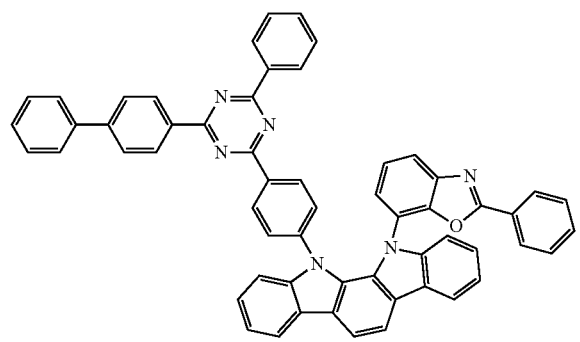

-continued
37
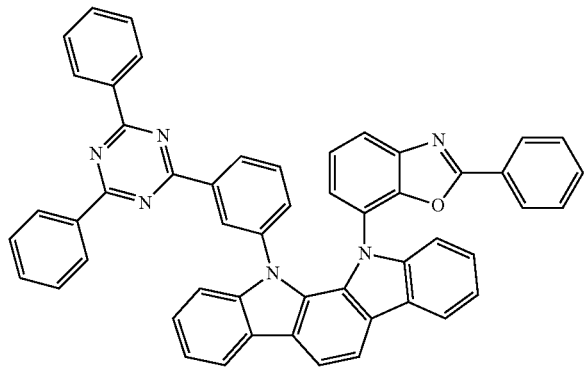
38
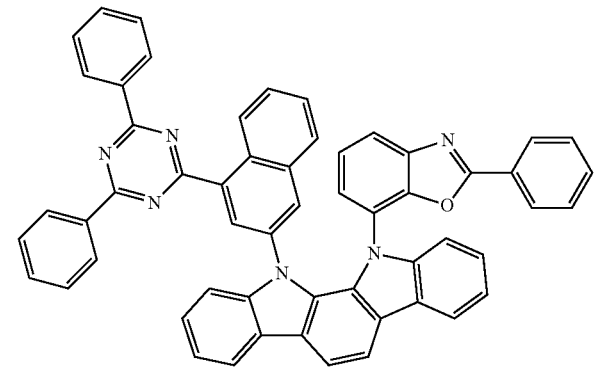
39
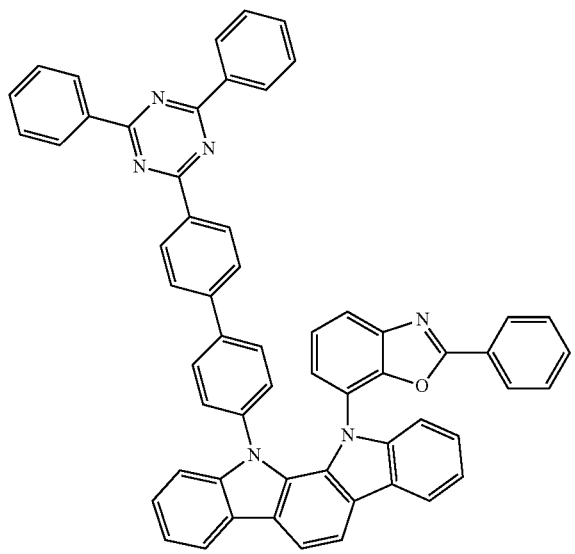
40
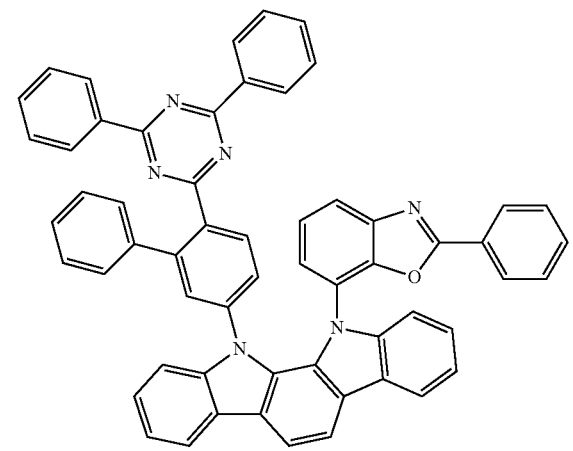
41
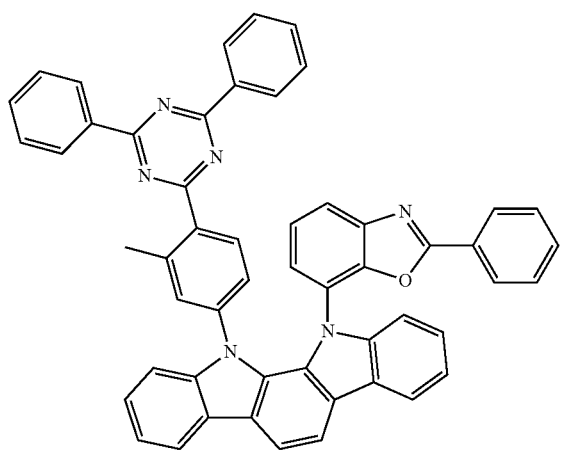
42
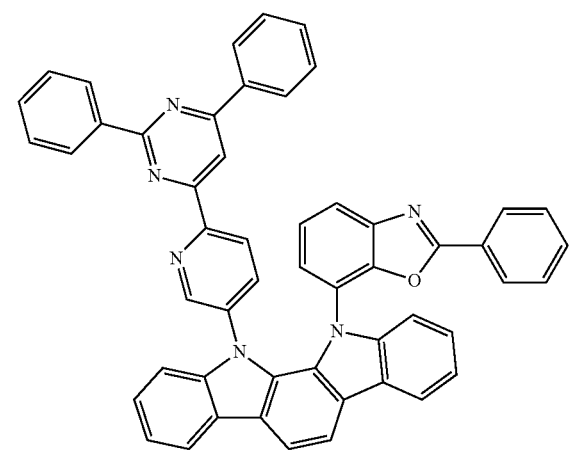

-continued
43
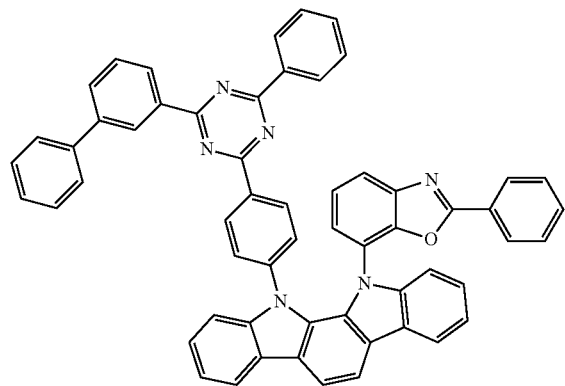
44
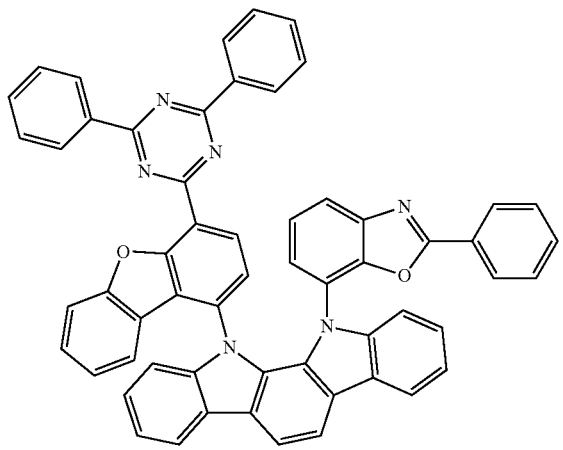
45
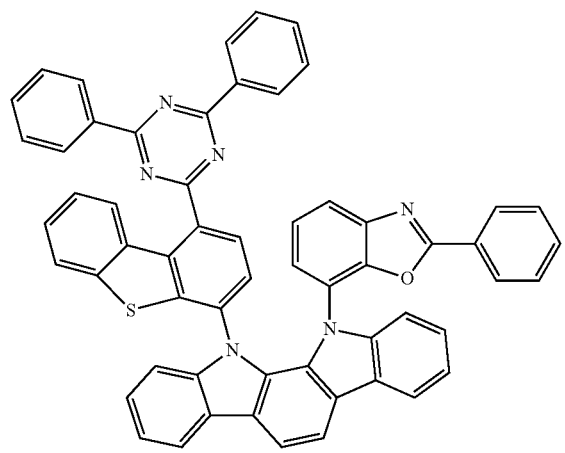
46
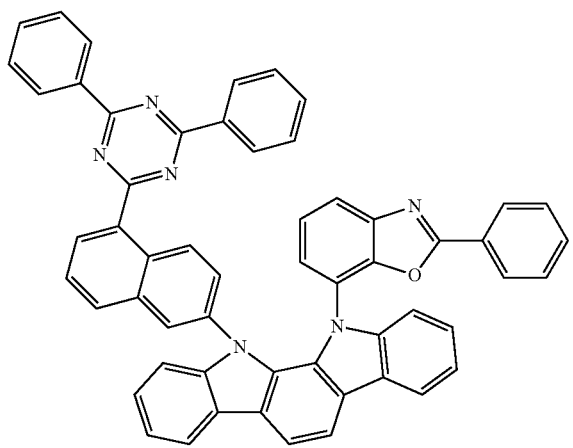
47
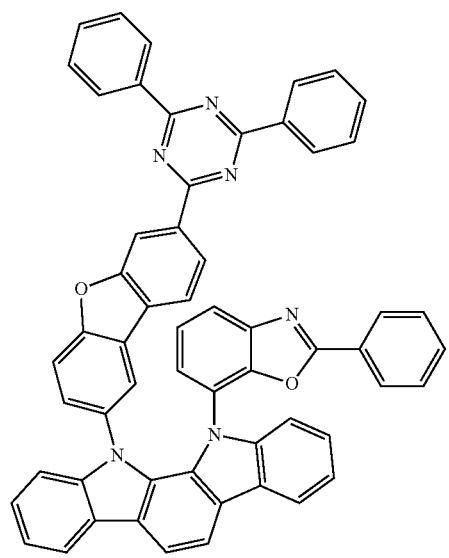
48
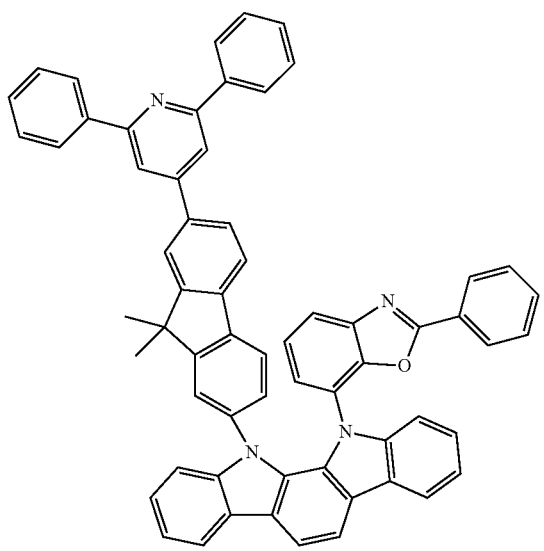

-continued
49
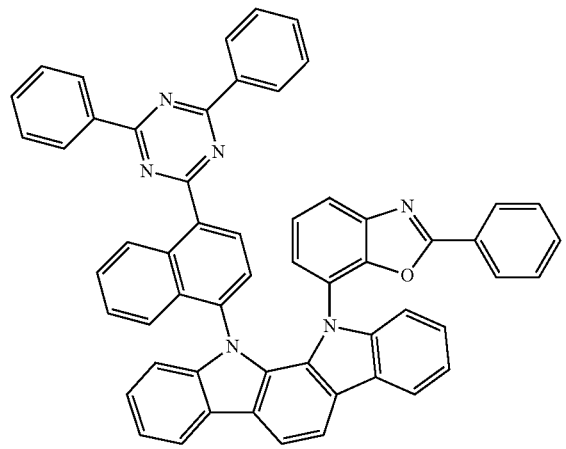
50
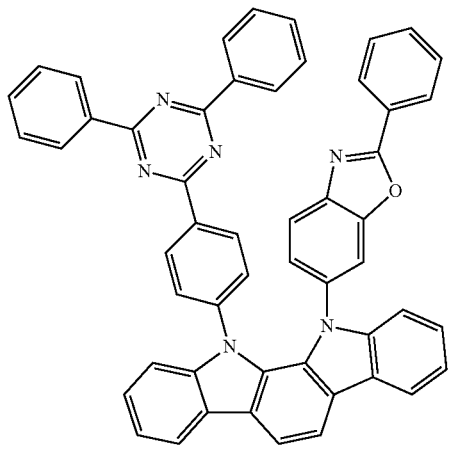
51
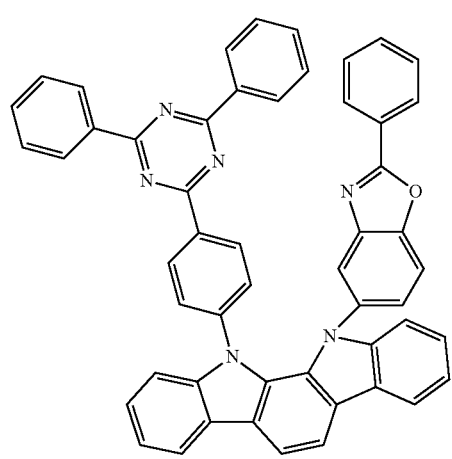
52
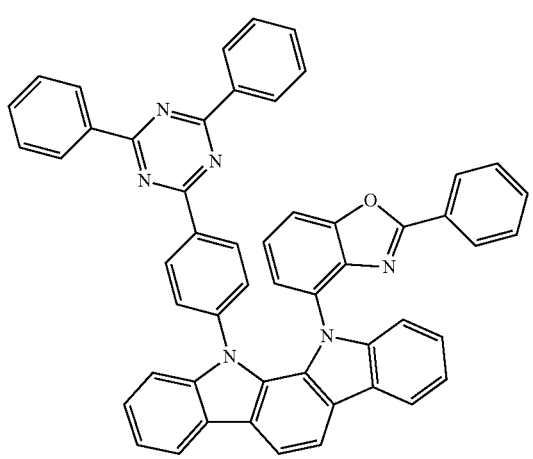
53
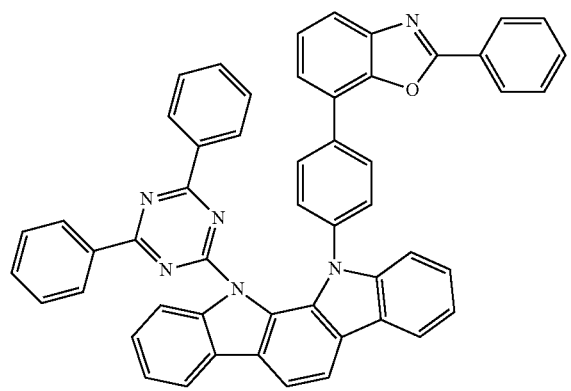
54
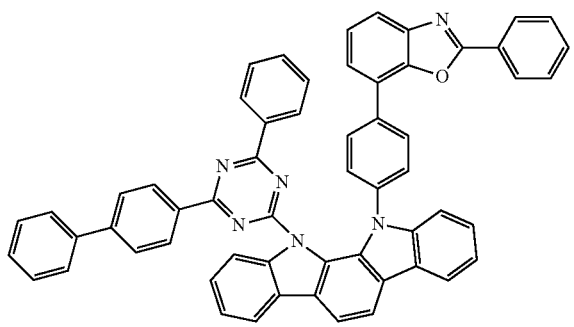

-continued
55
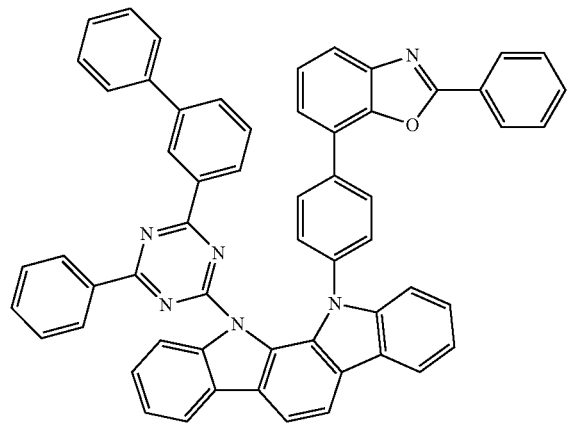
56
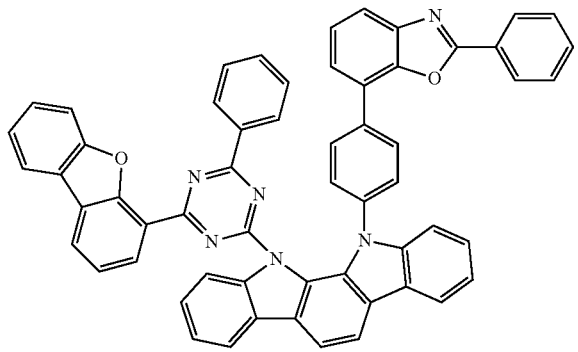
57
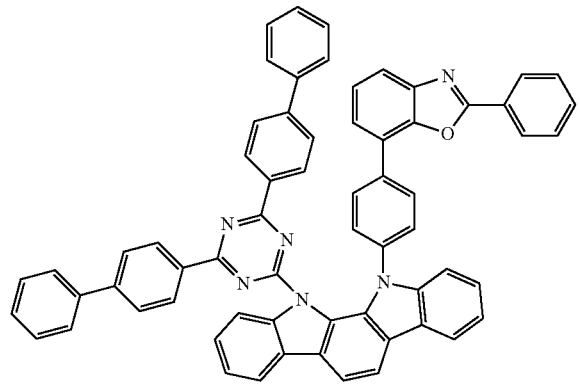
58
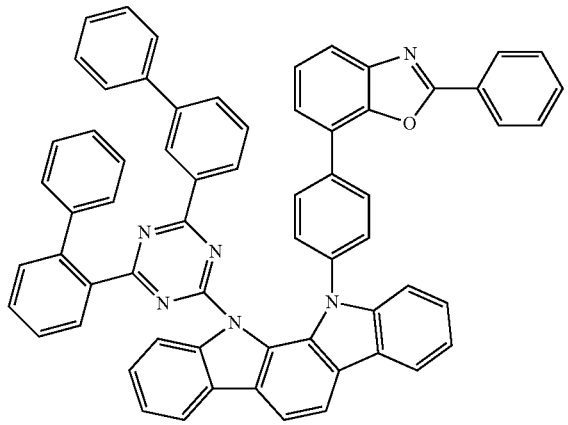
59
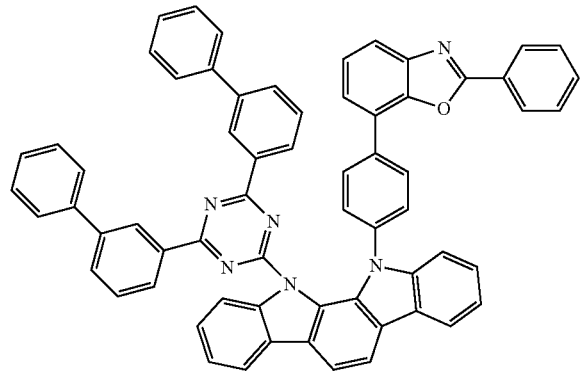
60
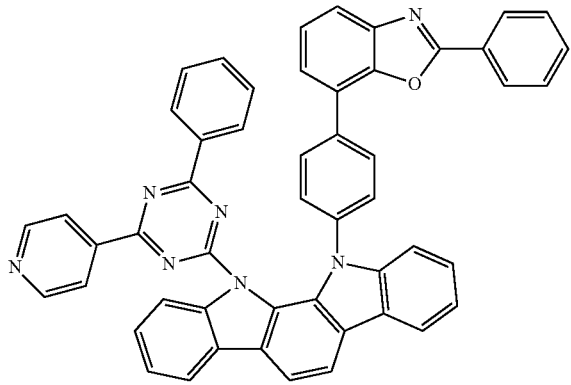

-continued
61
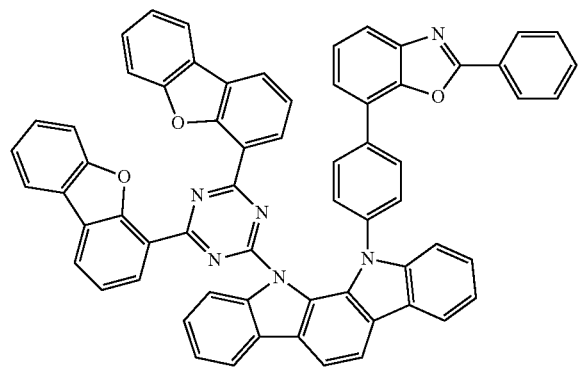
62
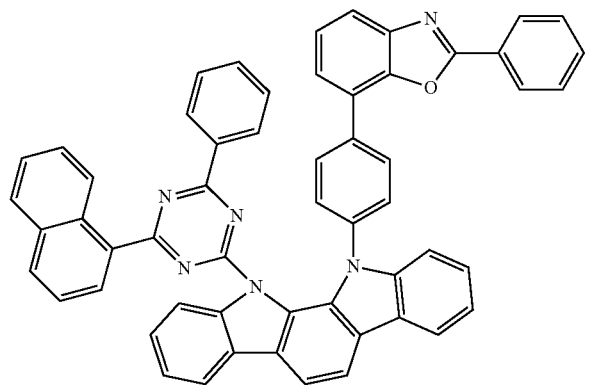
63
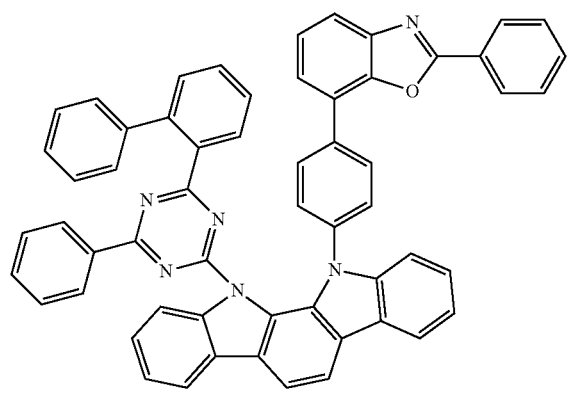
64
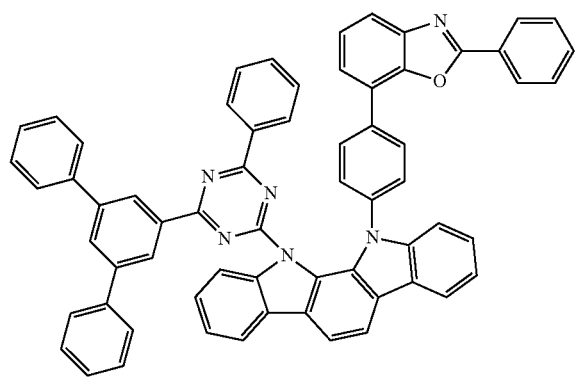
65
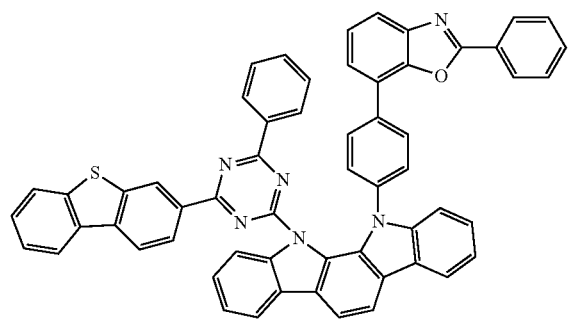
66
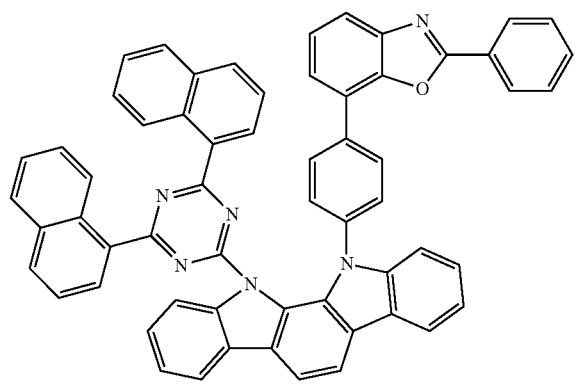

67
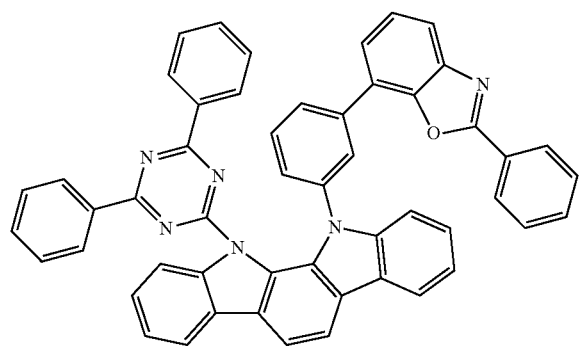
68
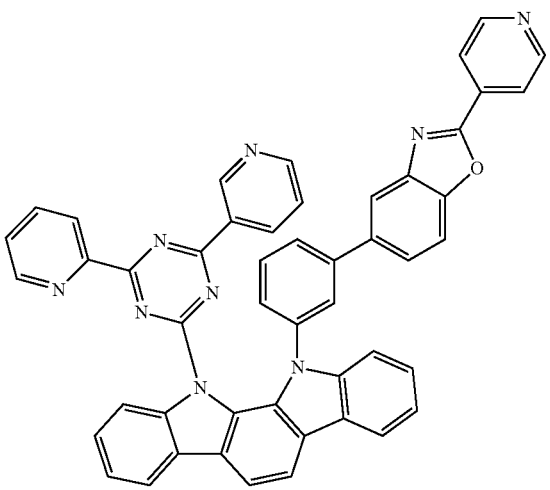
69
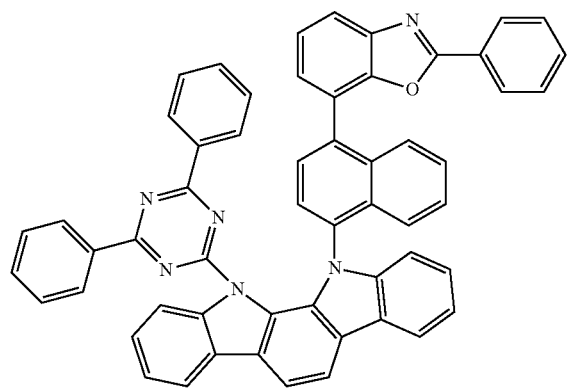
70
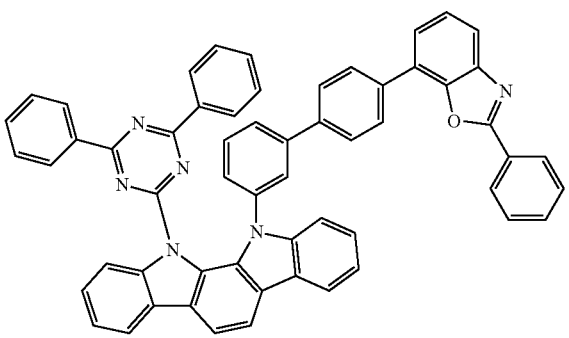
71
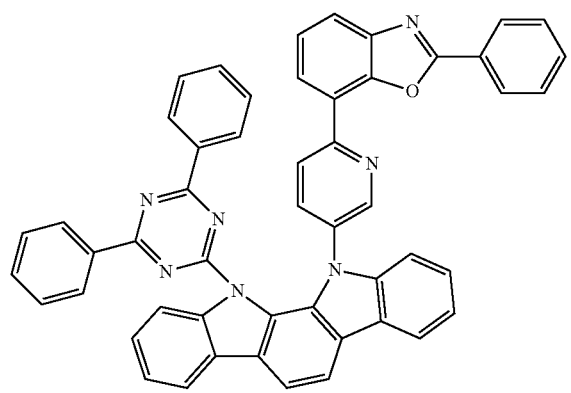
72
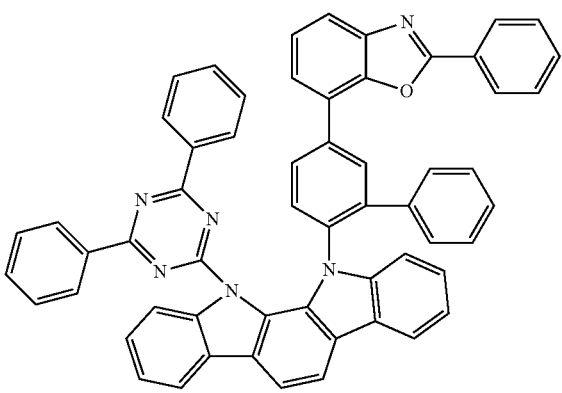

-continued
73
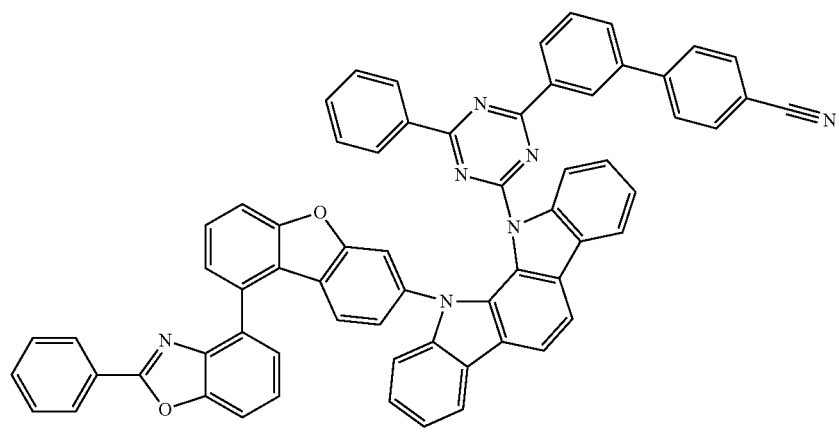
74
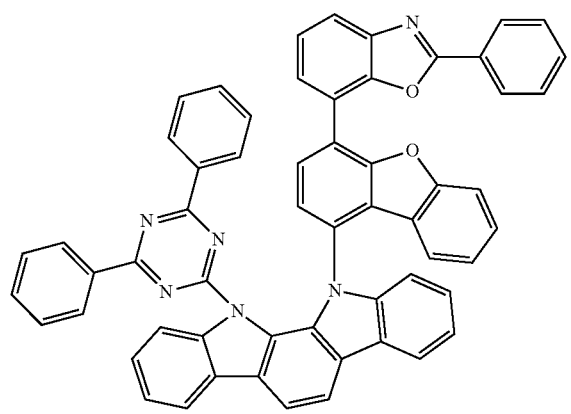
75
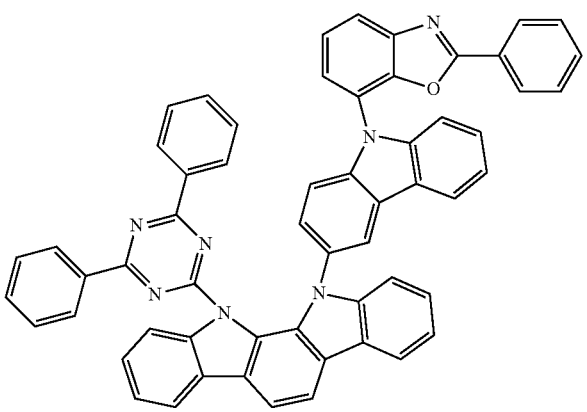
76
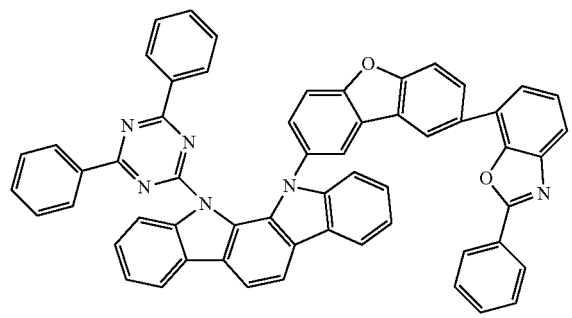
77
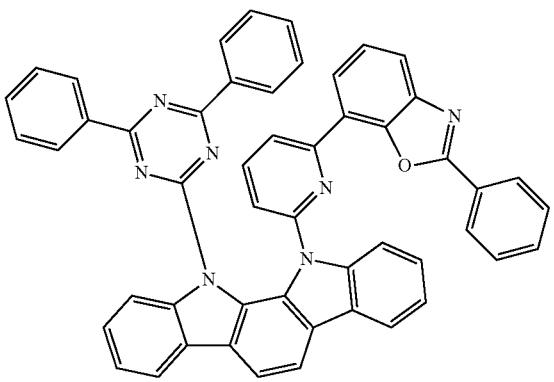
78
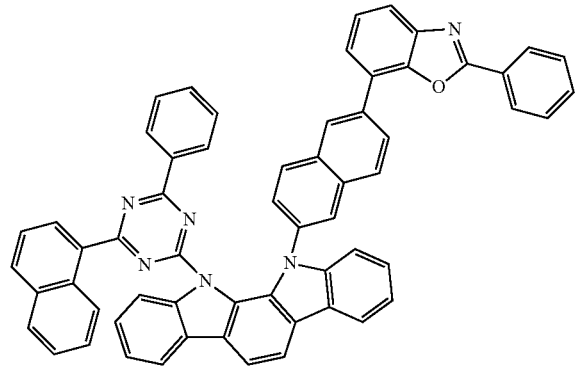
79
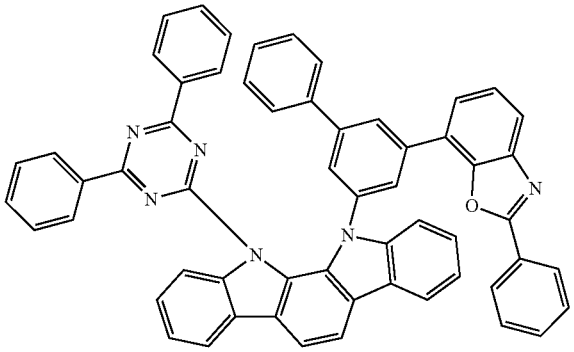

-continued
80
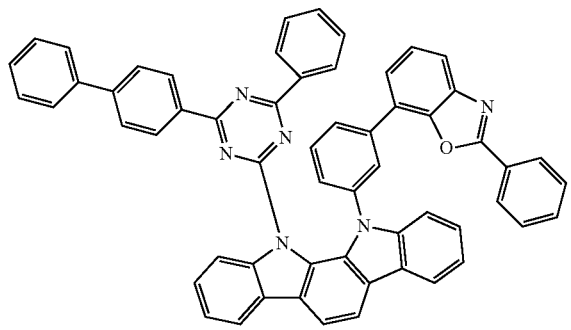
81
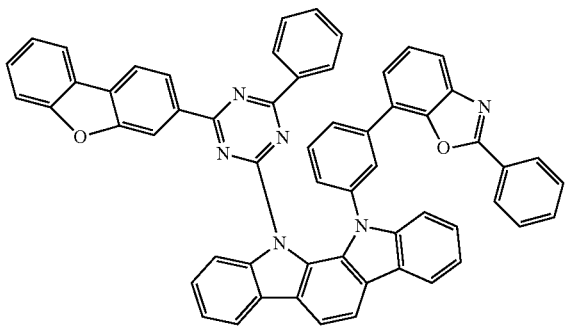
82
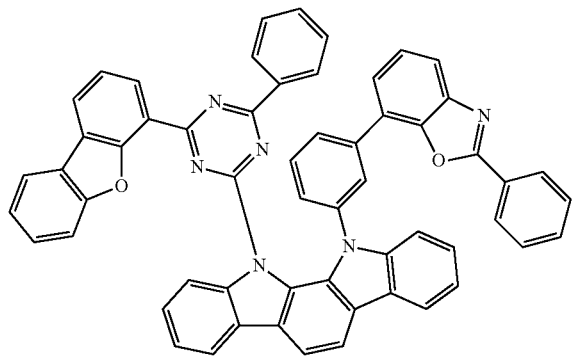
83
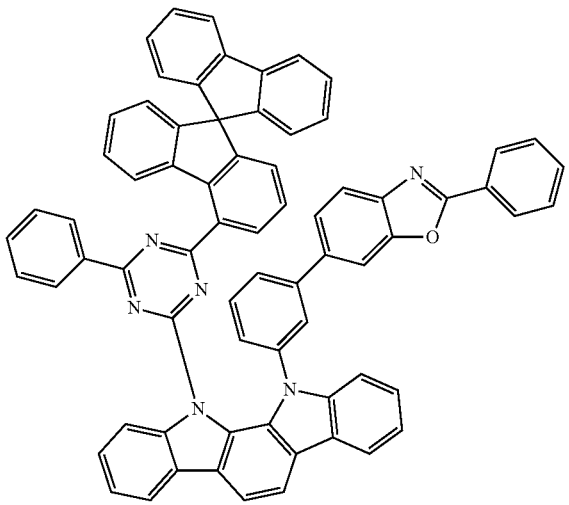
84
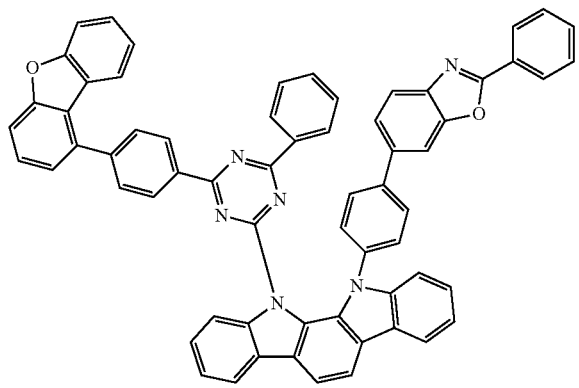
85
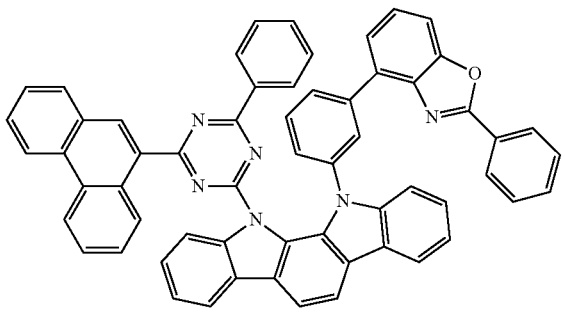
86
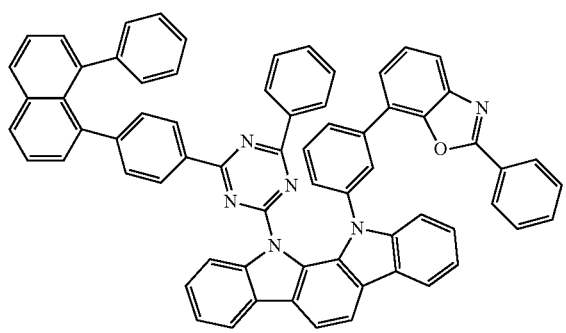
87
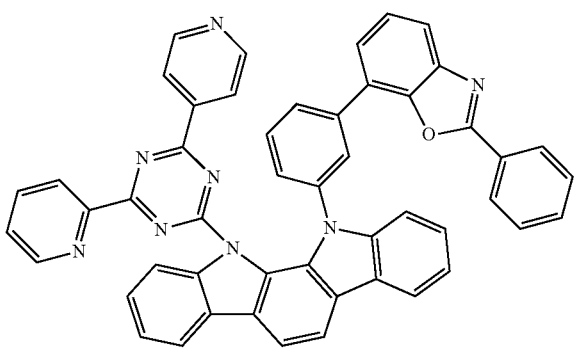

-continued
88
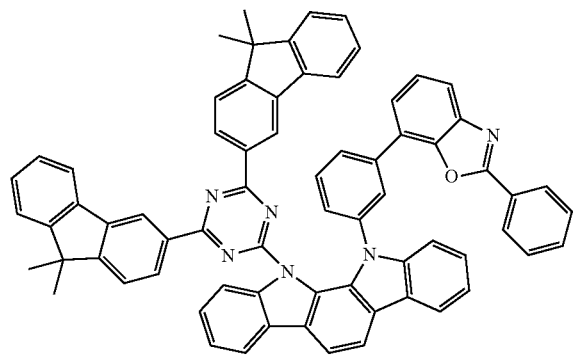
89
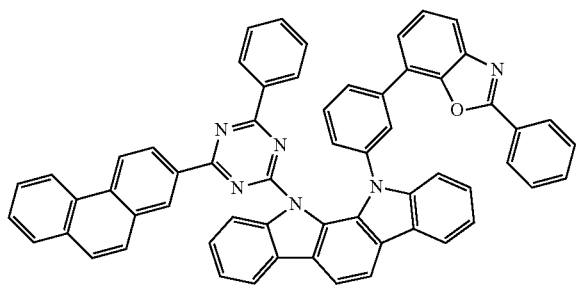
90
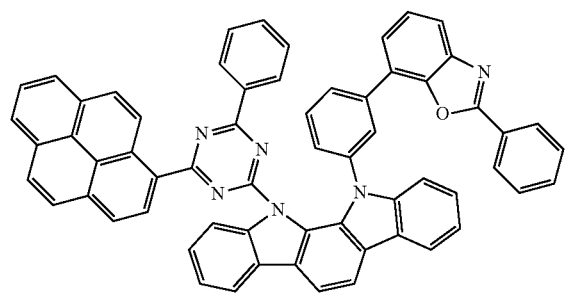
91
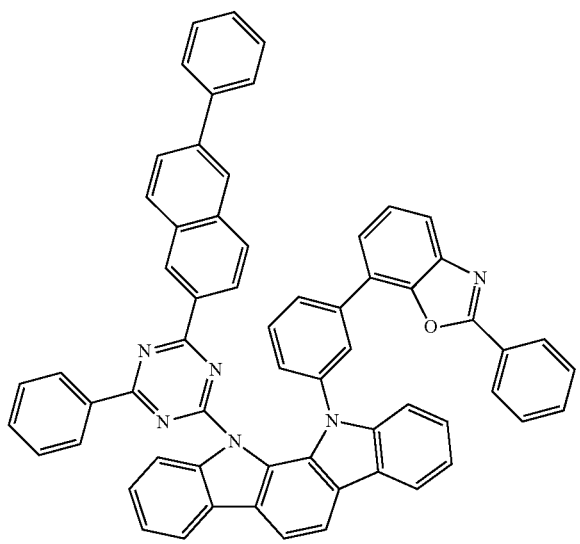
92
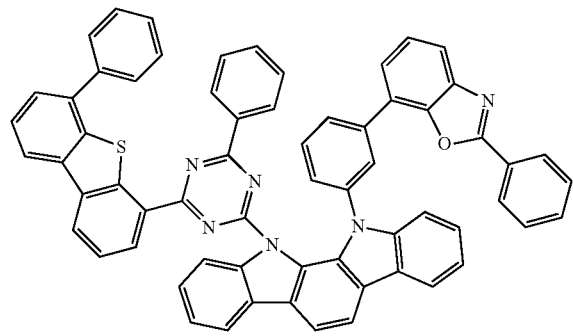
93
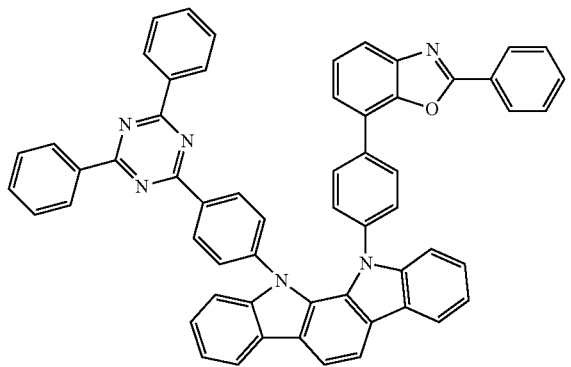

94
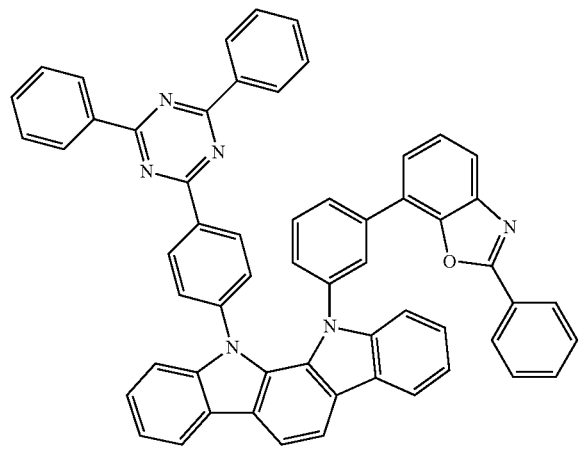
95
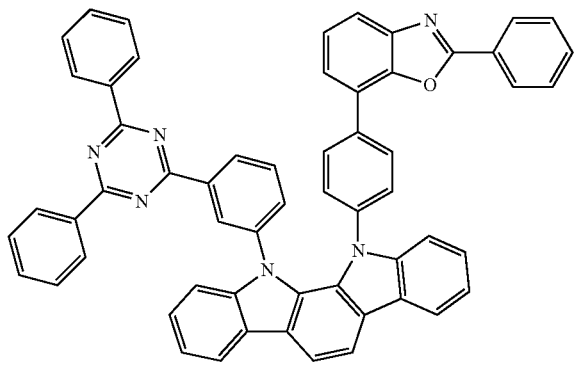
96
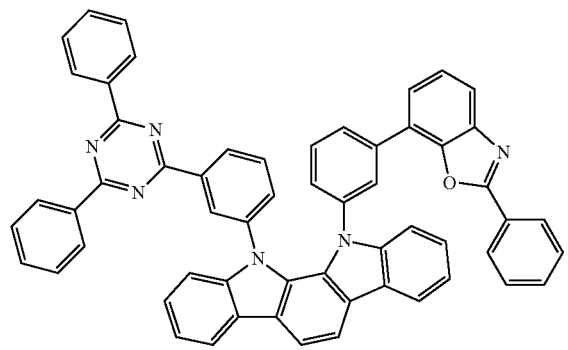
97
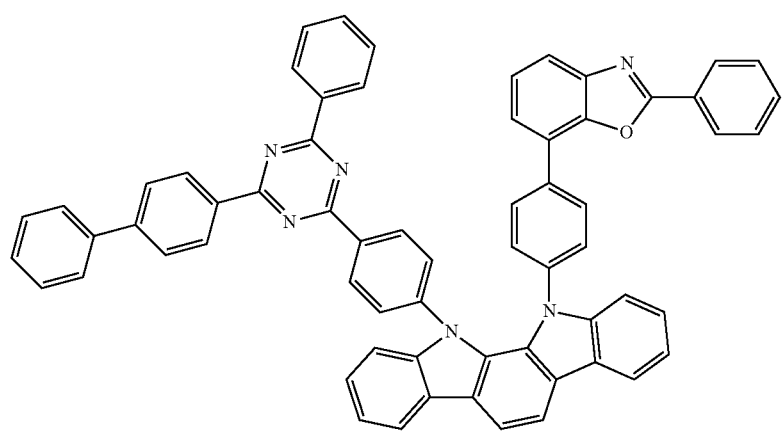

98
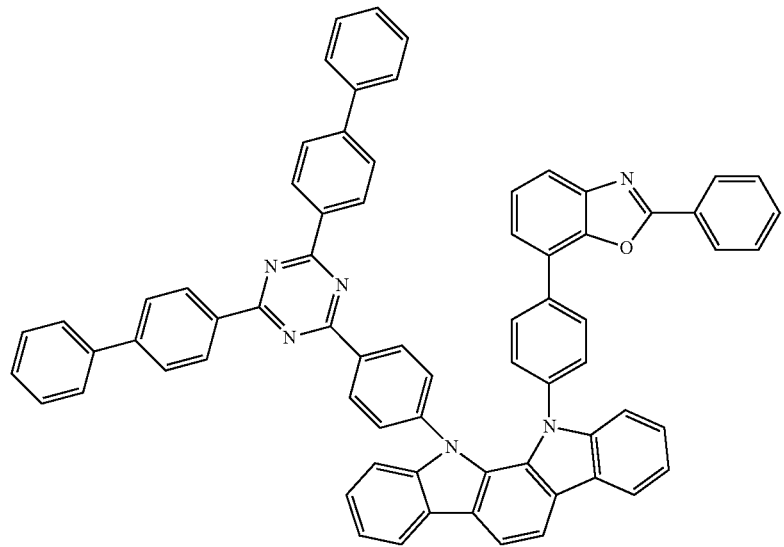
99 100
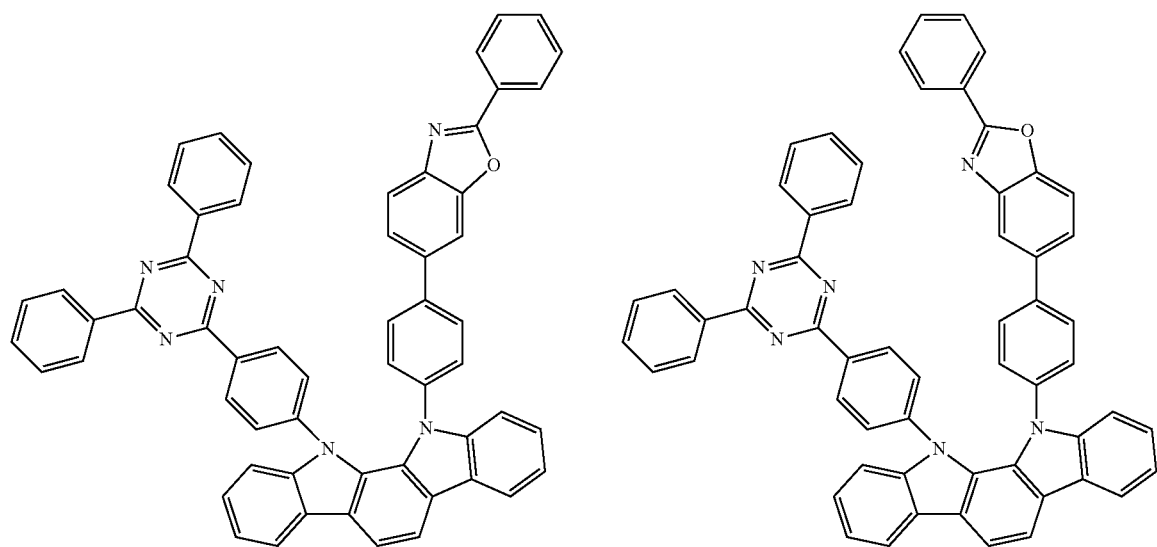
101 102
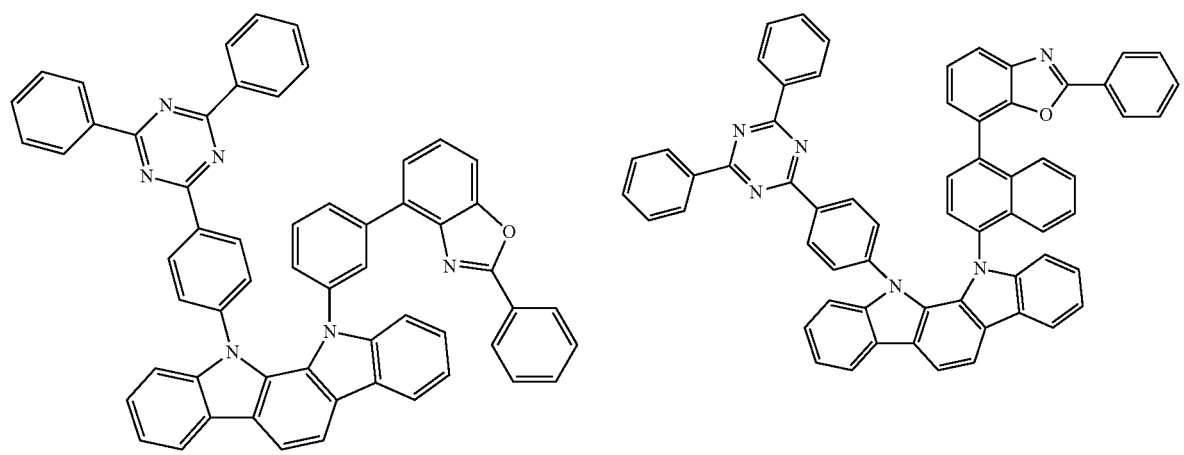

-continued
103
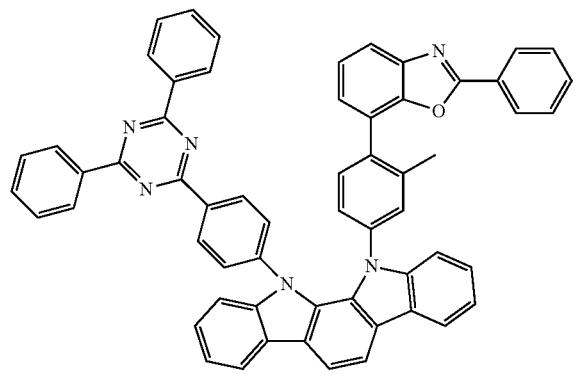
104
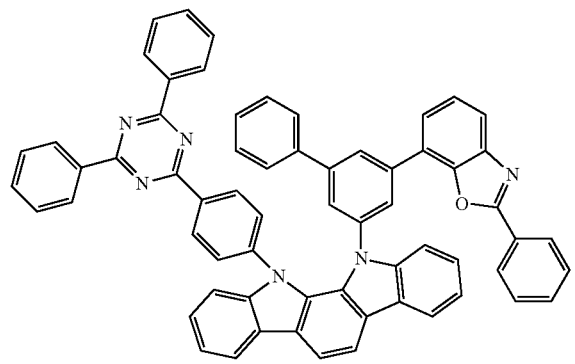
105
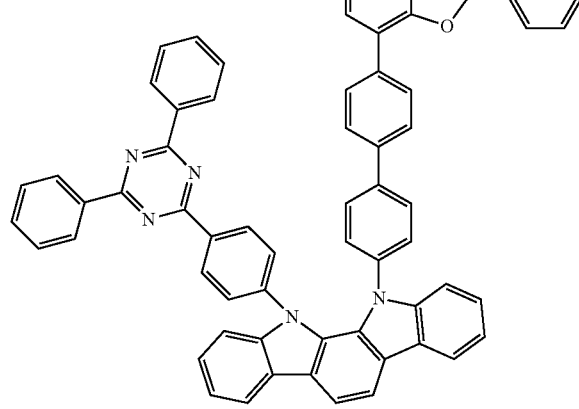
106
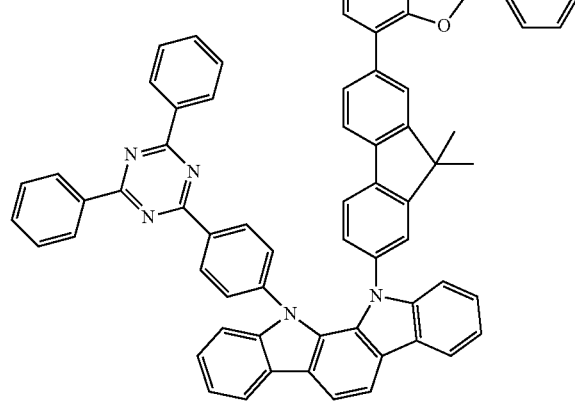
107
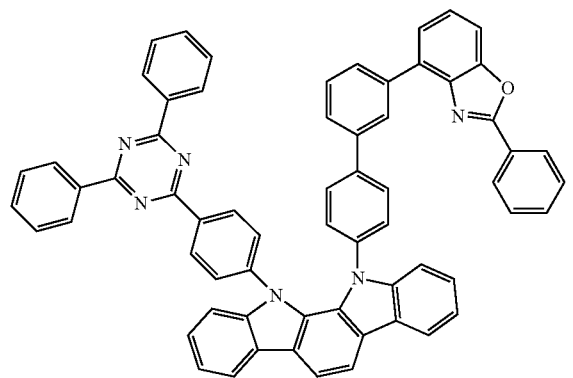
108
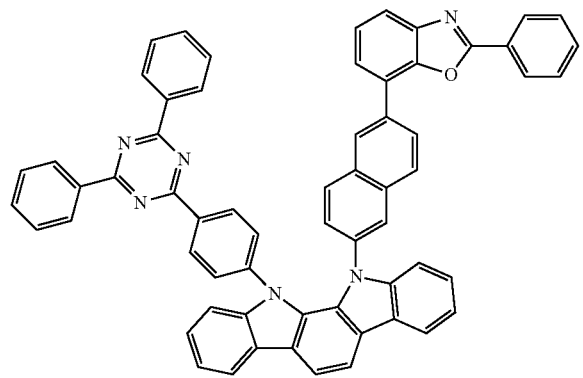

-continued
109
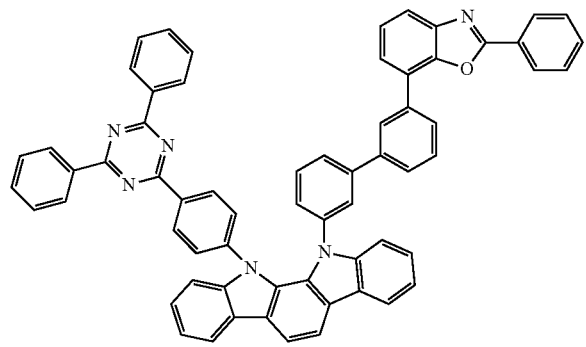
110
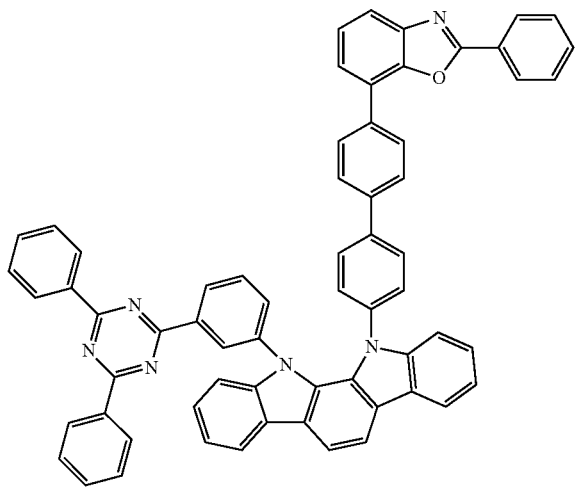
111
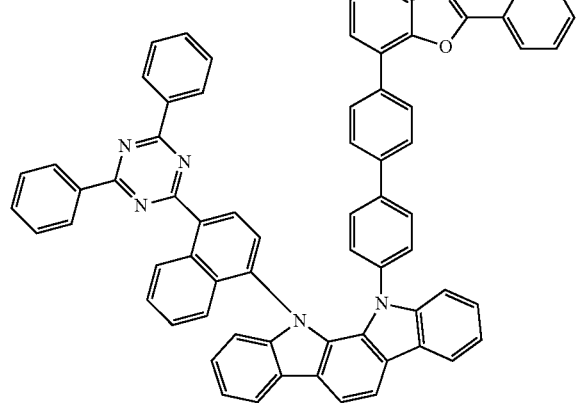
112
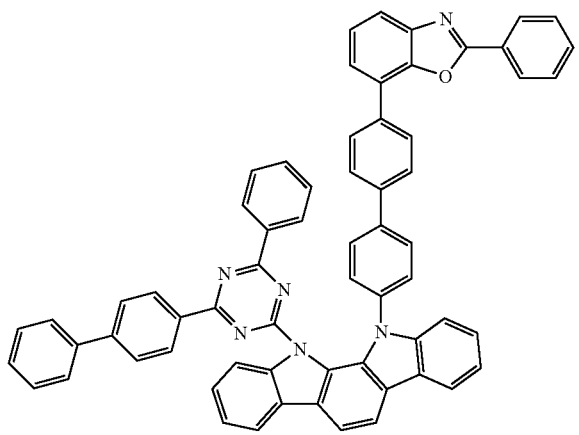
113
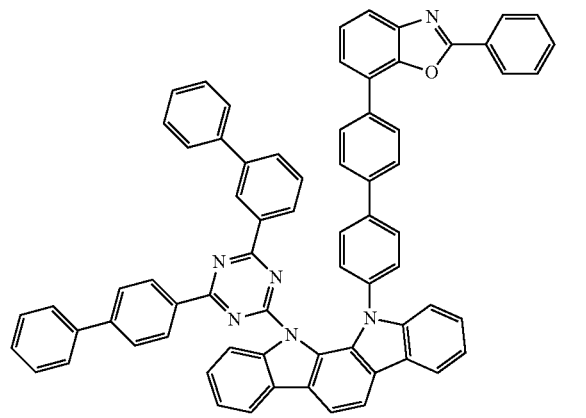
114
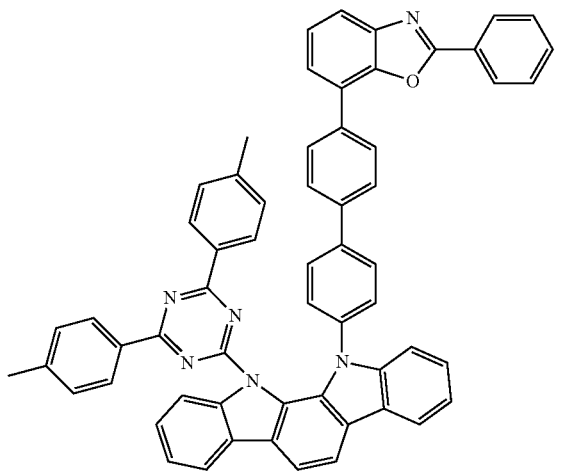

-continued
115
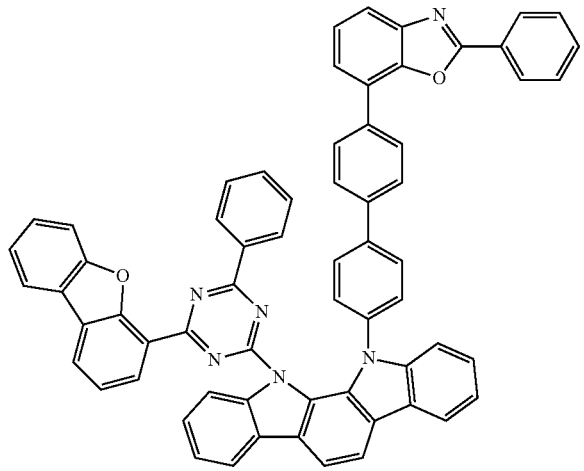
116
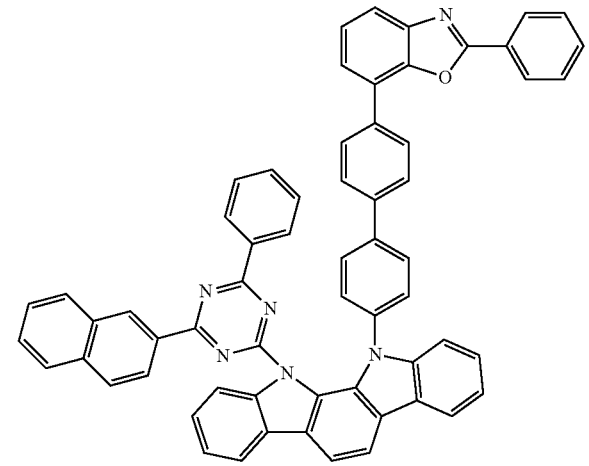
117
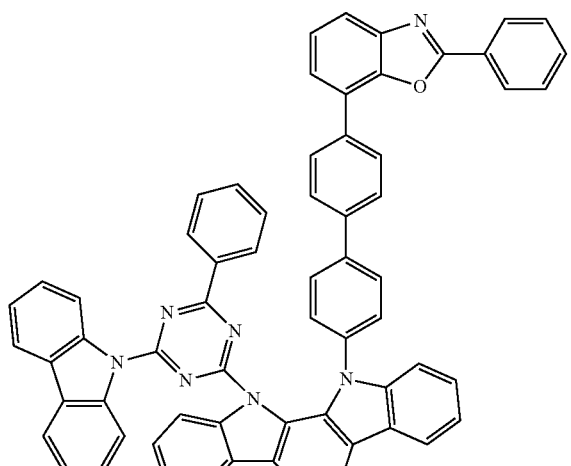
118
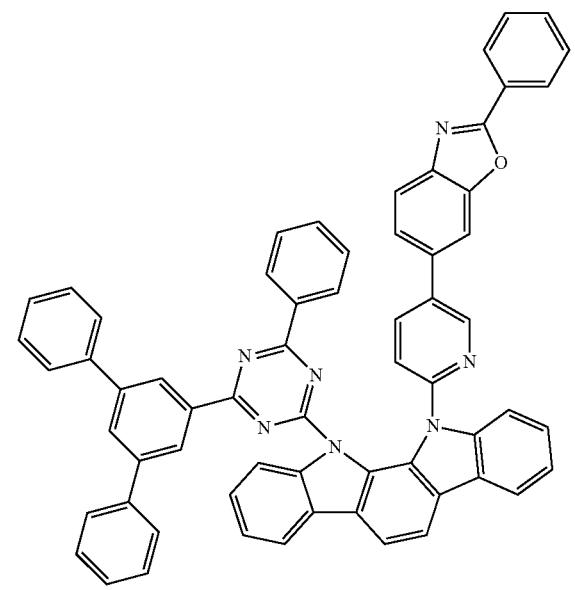
119
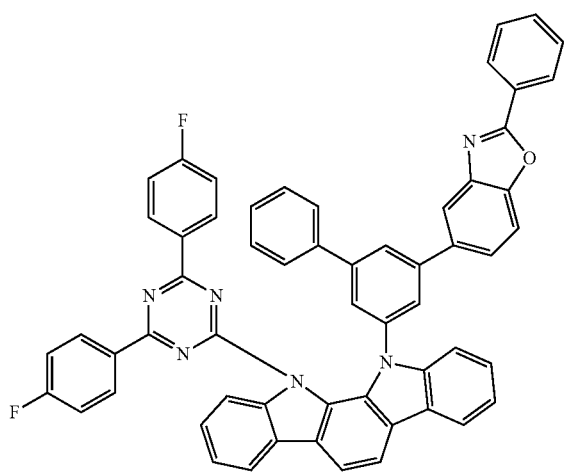
120
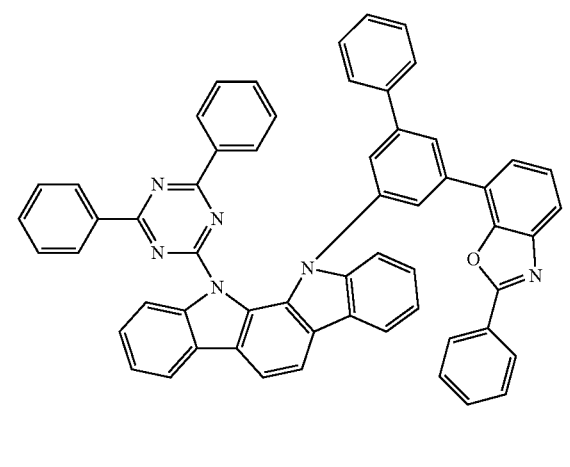

-continued
121
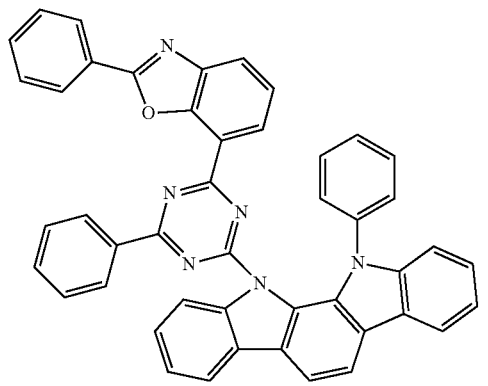
122
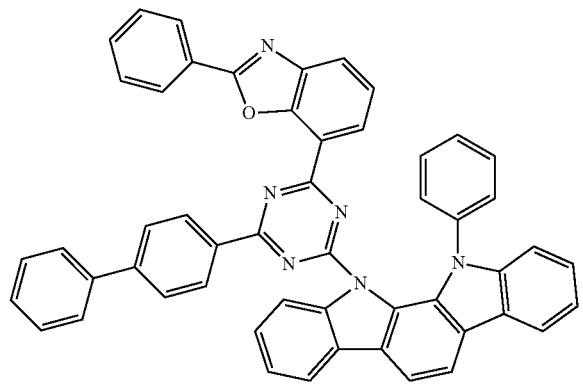
123
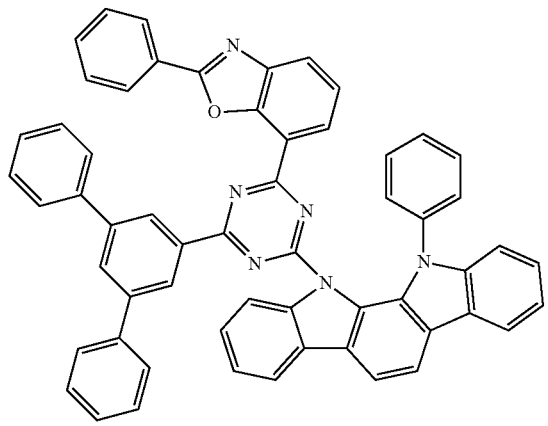
124
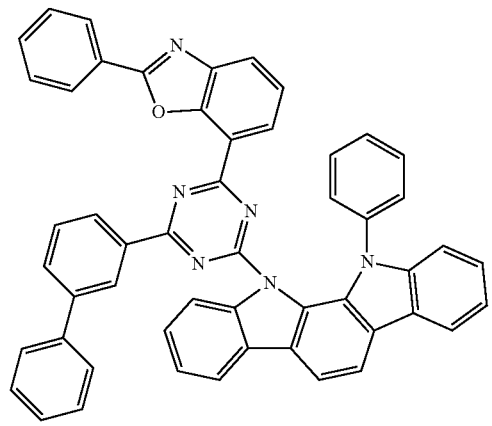
125
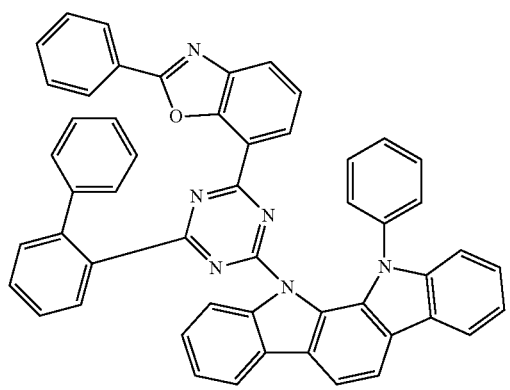
126
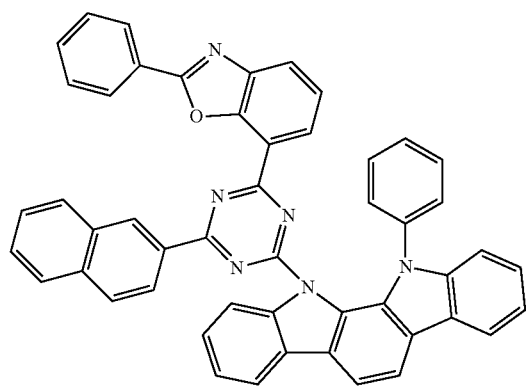
127
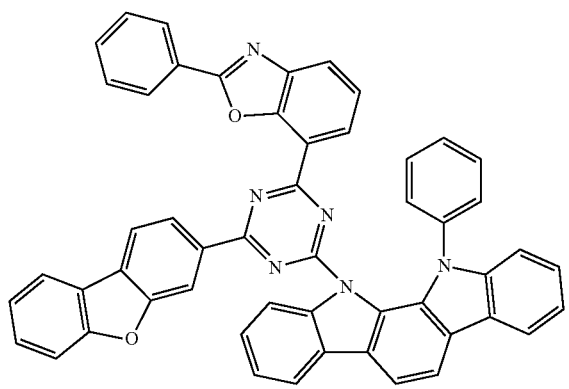
128
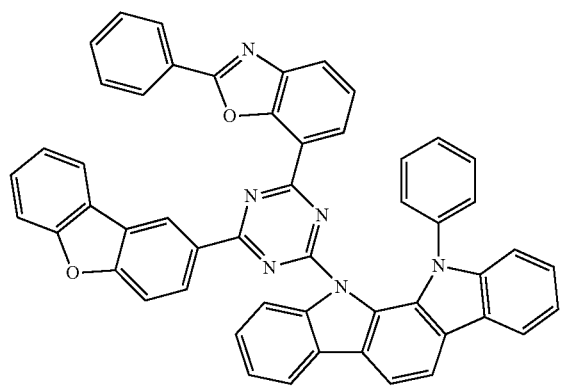

-continued
129
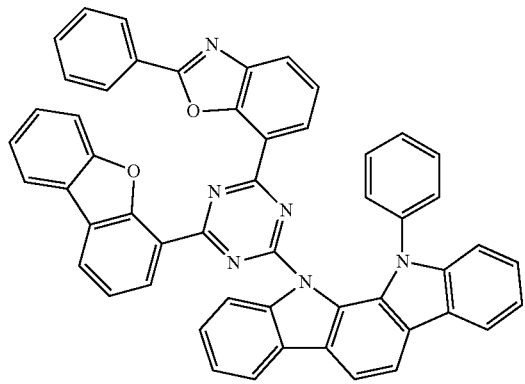
130
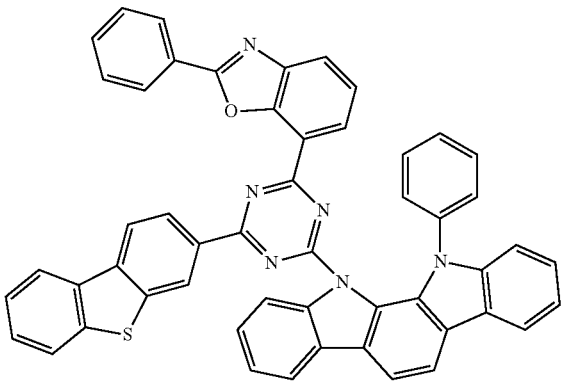
131
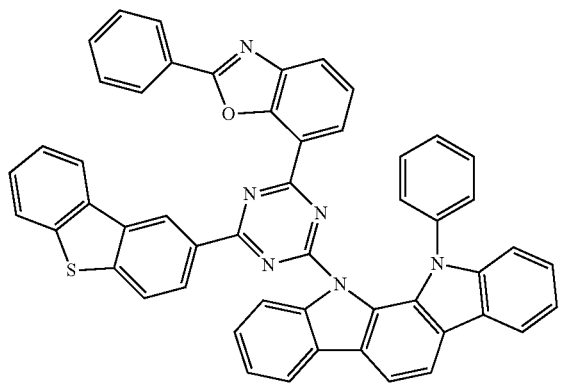
132
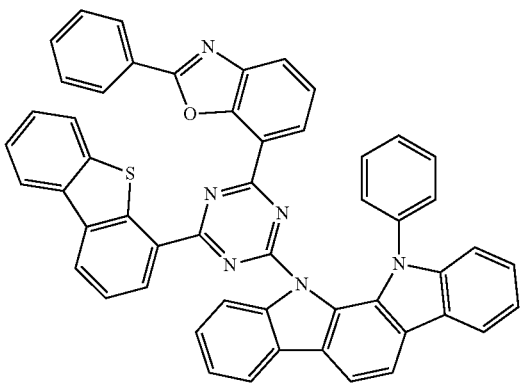
133
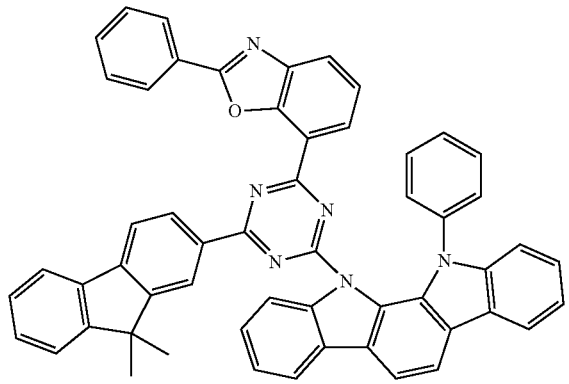
134
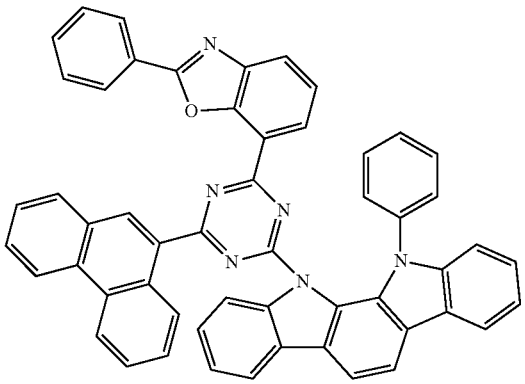
135
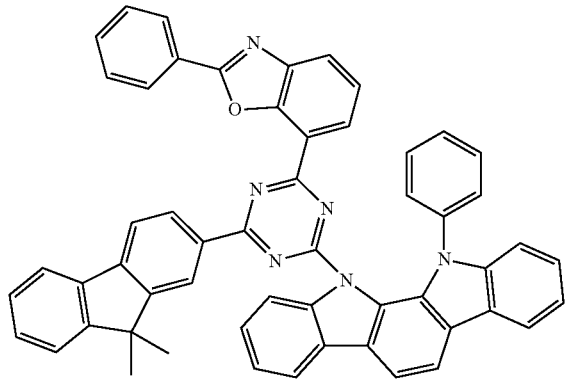
136
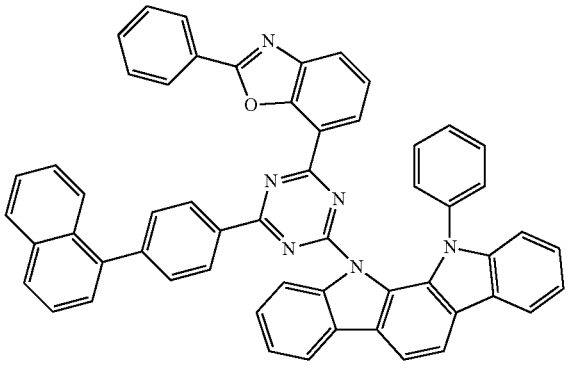

137
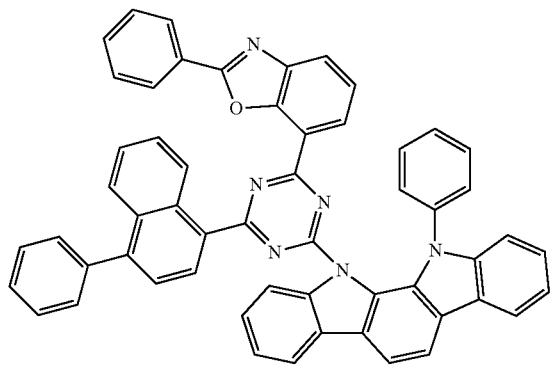
138
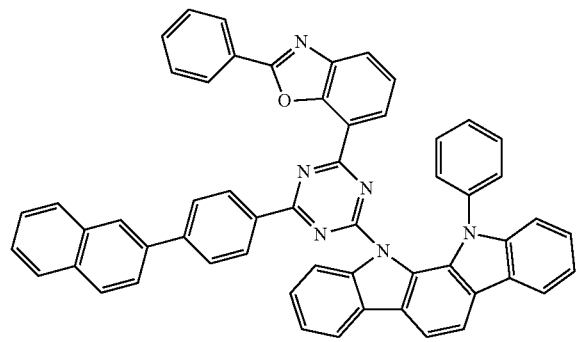
139
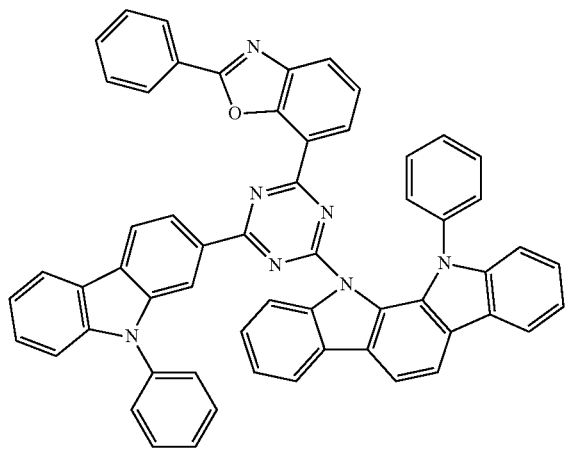
140
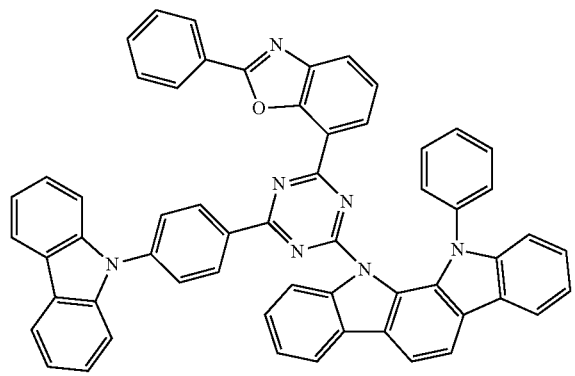
145
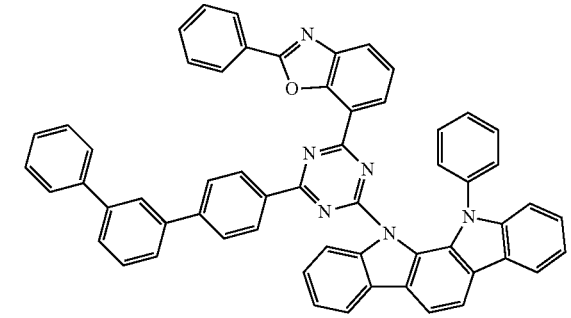
146
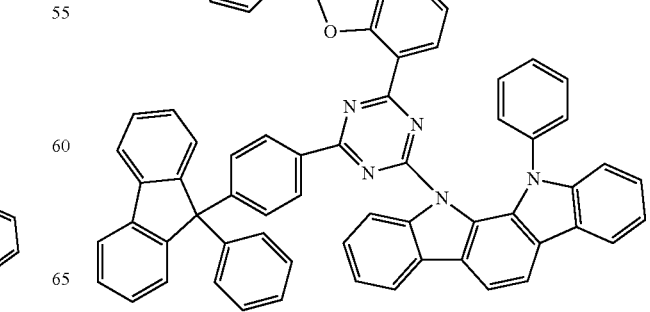

147
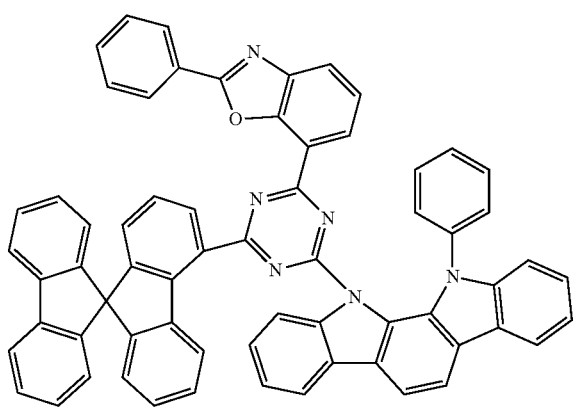
148
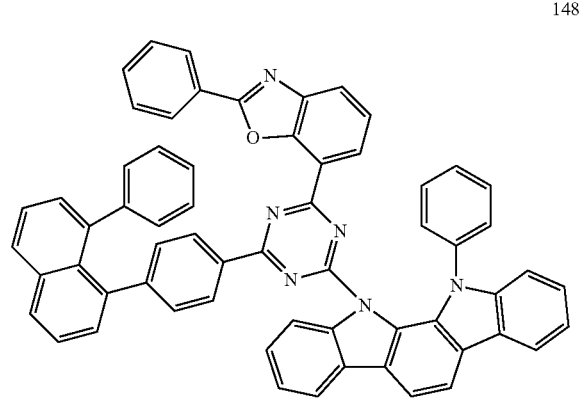
149
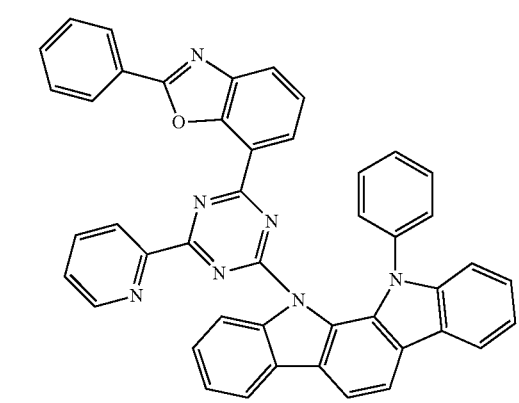
150
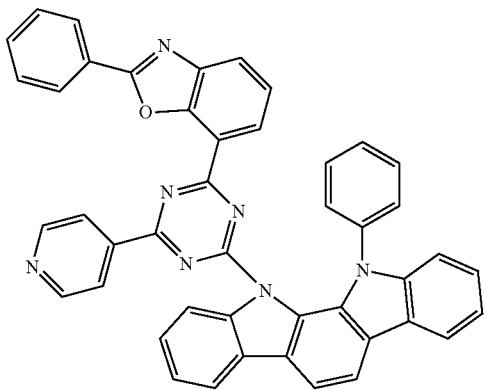
151
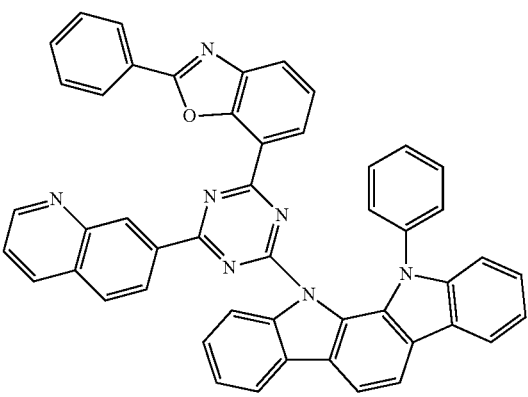
152
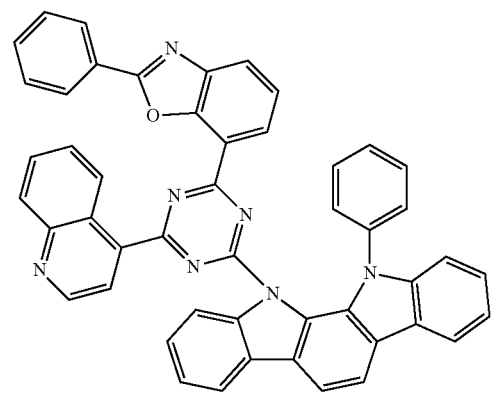
153
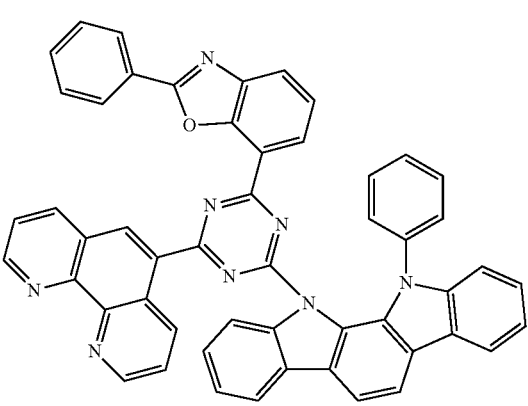
154
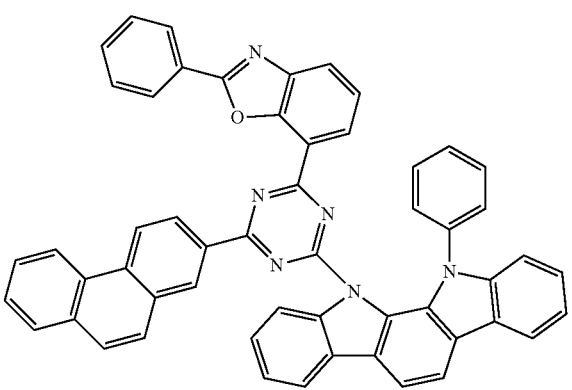

155
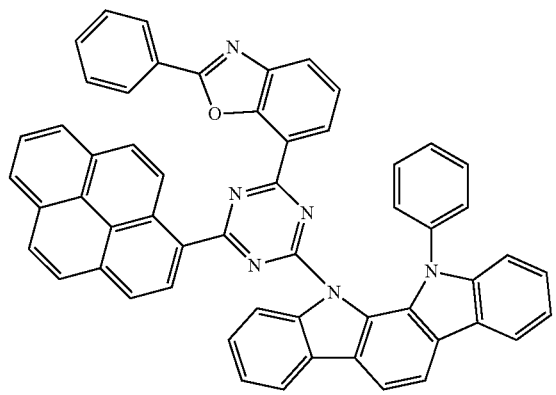
156
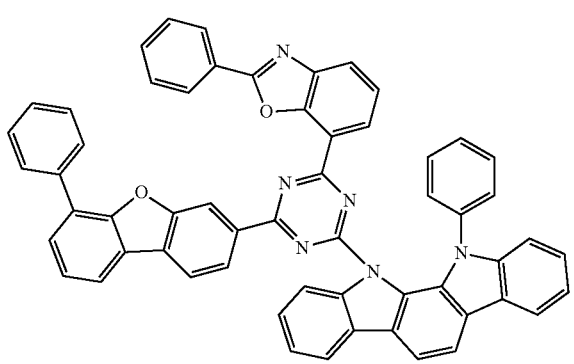
157
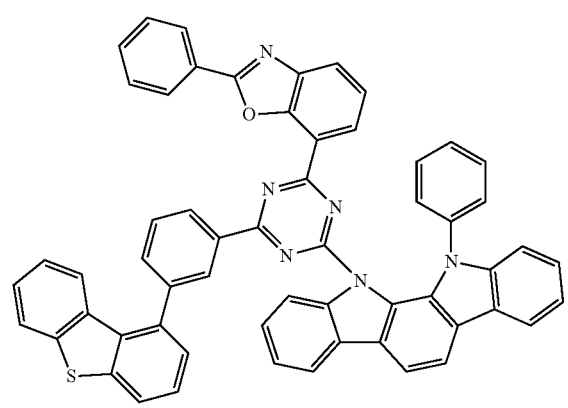
158
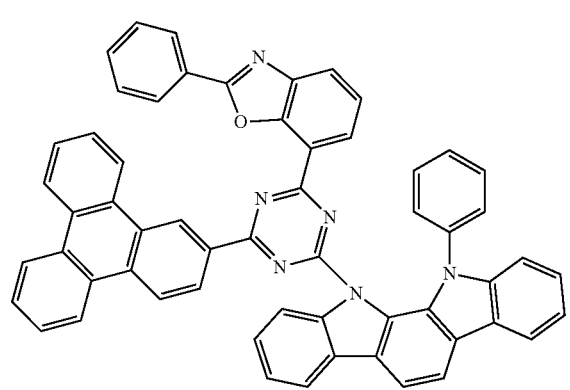
159
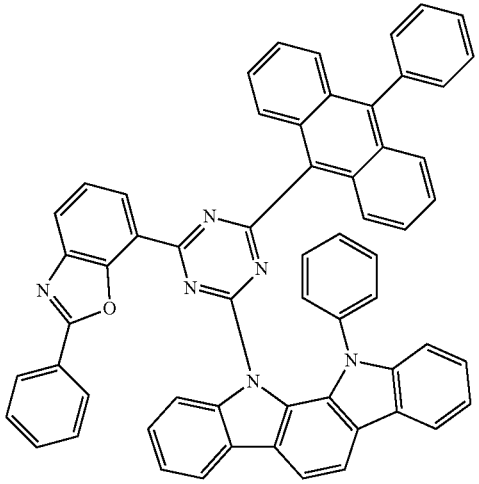
160
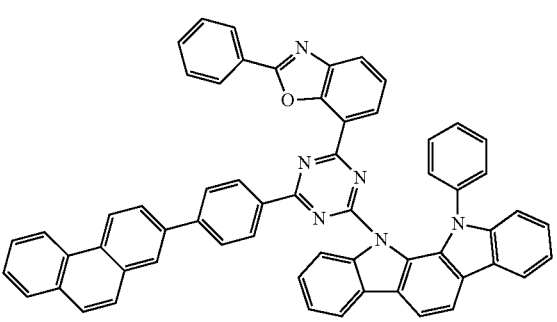
161
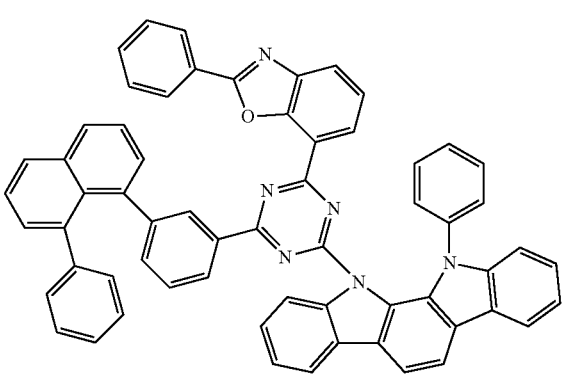
162
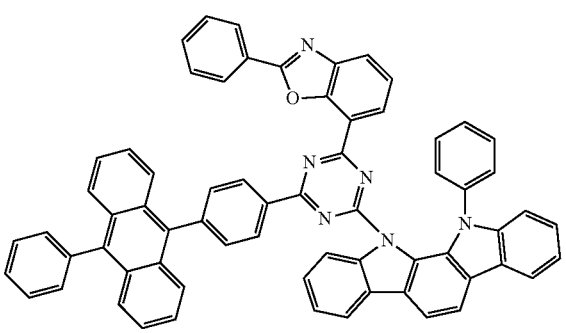

163
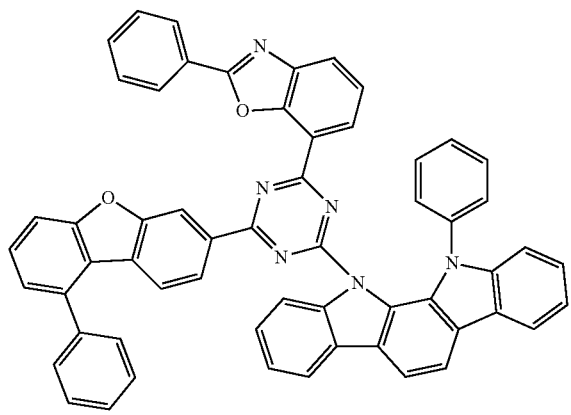
167
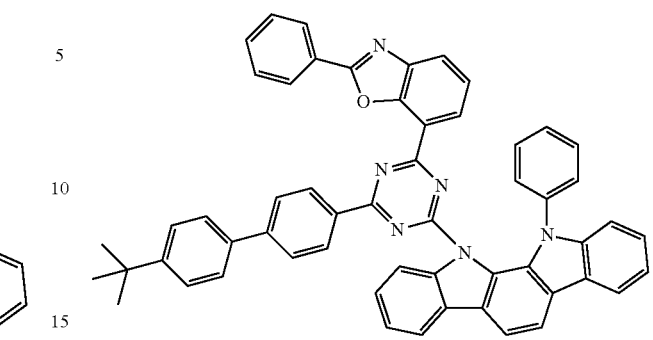
164
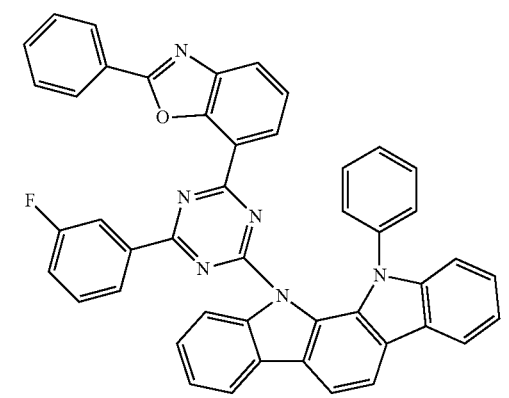
168
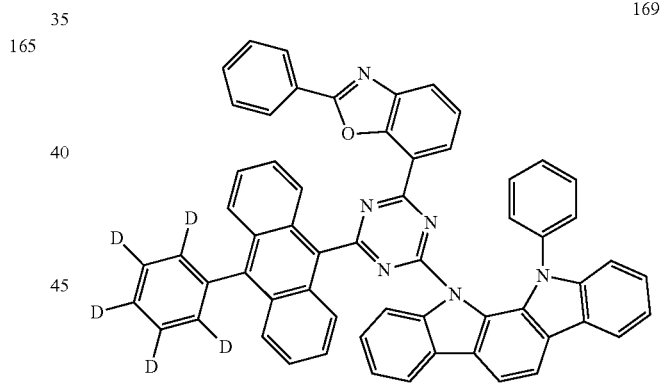
165
166
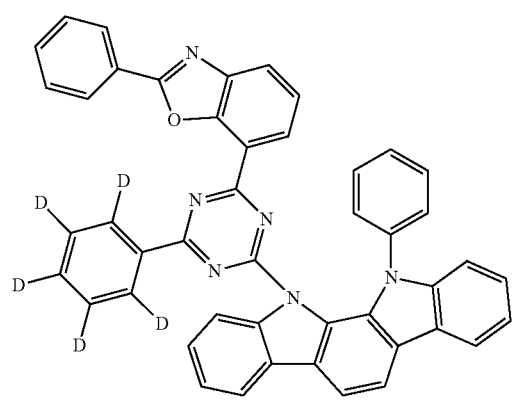
169
170

171
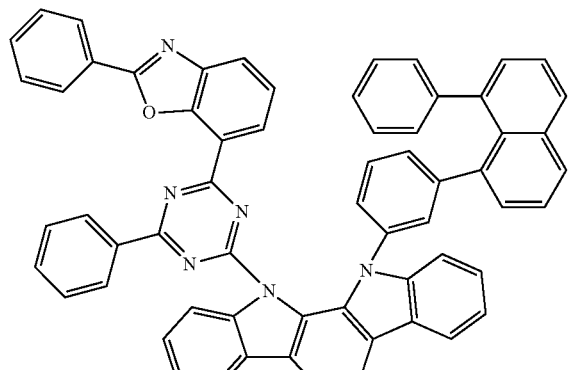
172
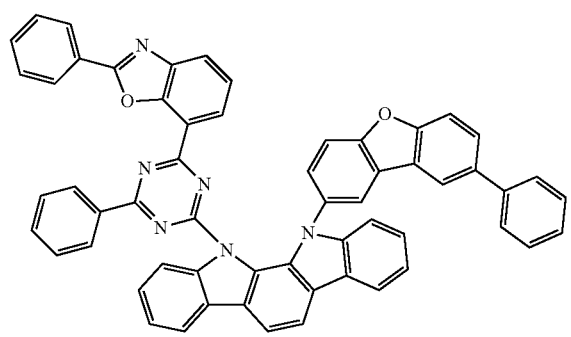
173
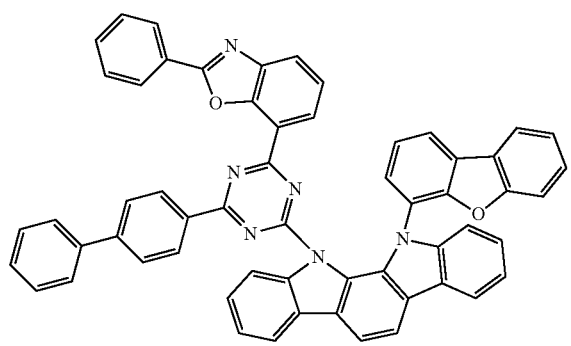
174
175
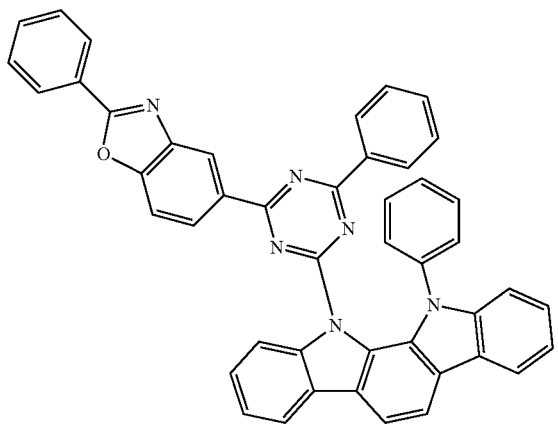
176
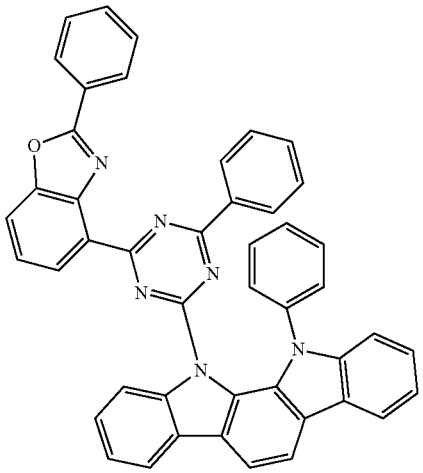
177
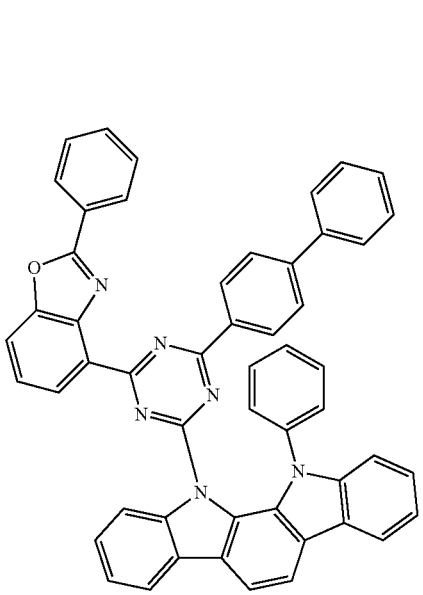

-continued
178
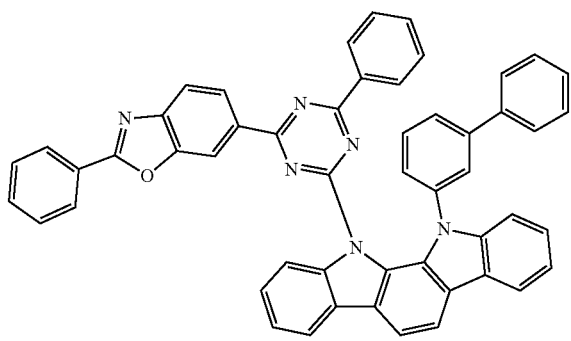
179
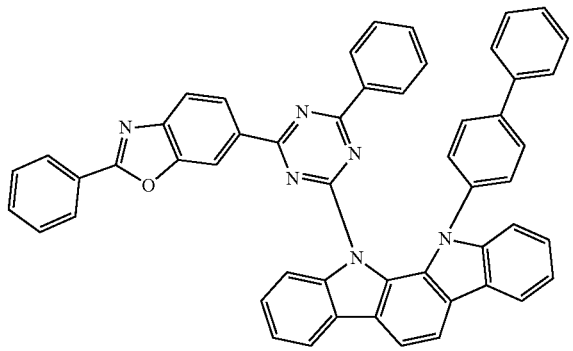
180
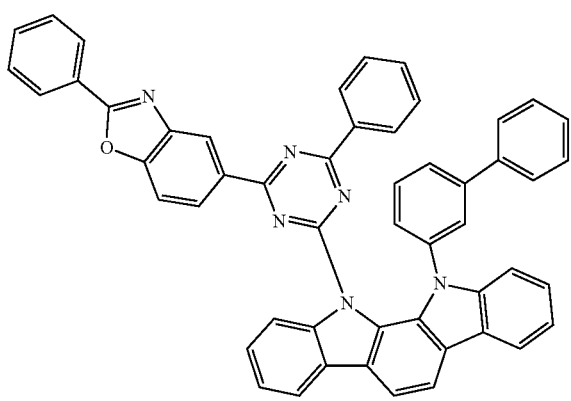
181
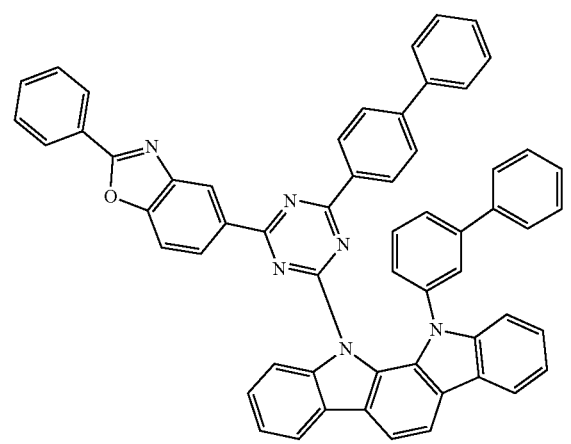
182
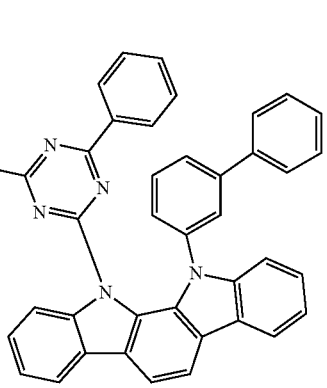
183
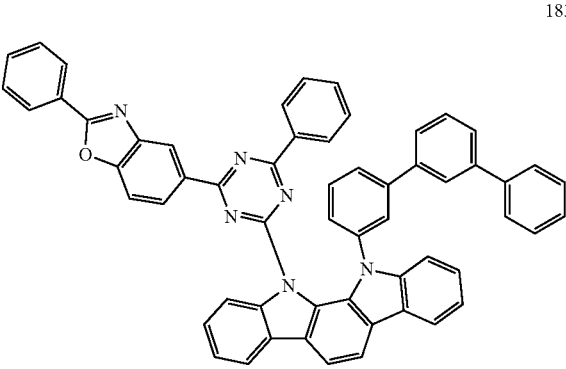
184
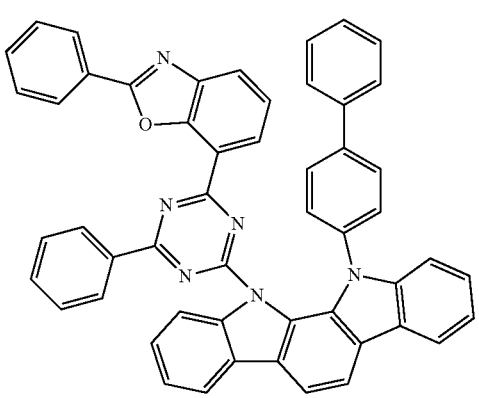
185
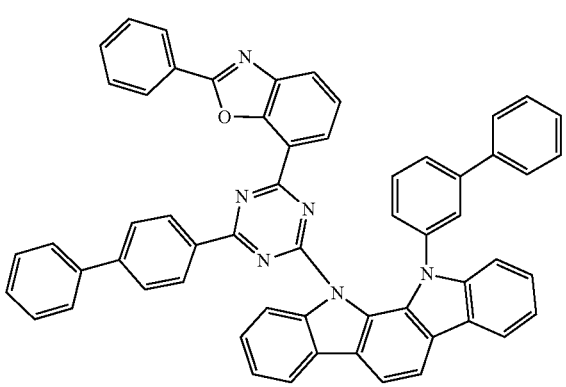

89
-continued
186
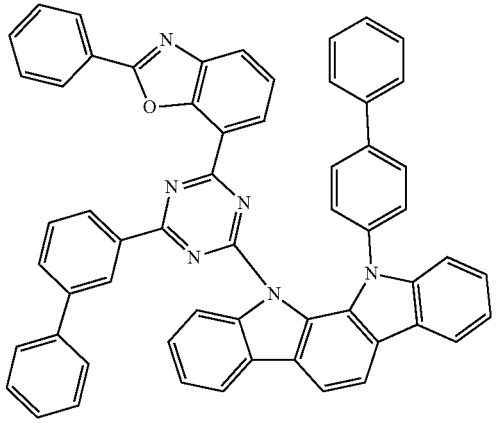
187
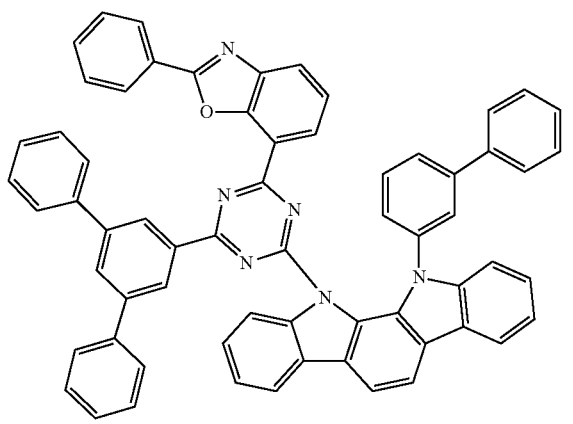
188
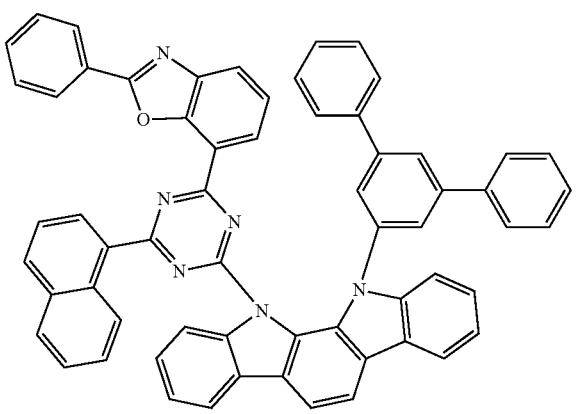
90
-continued
189
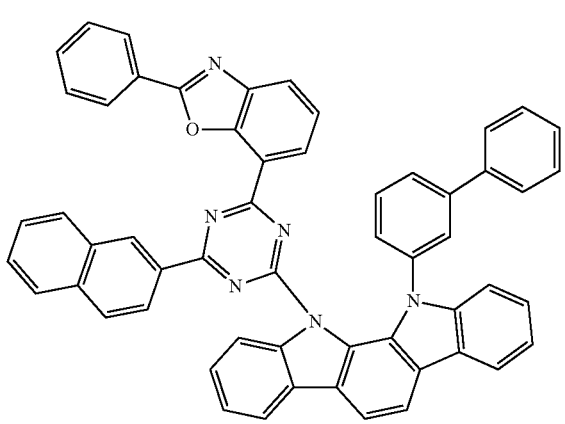
190
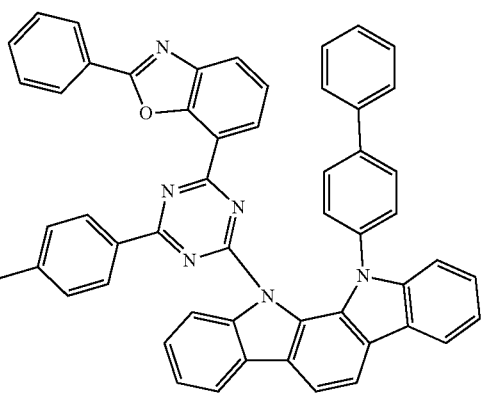
191
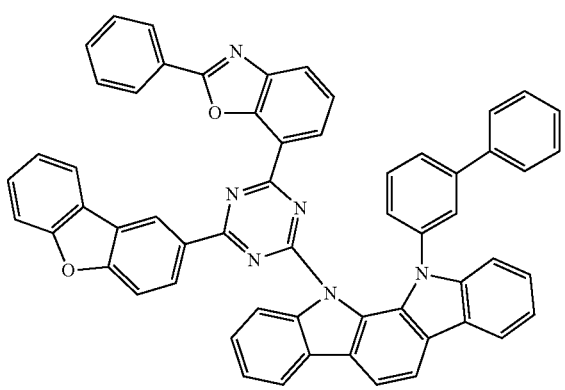

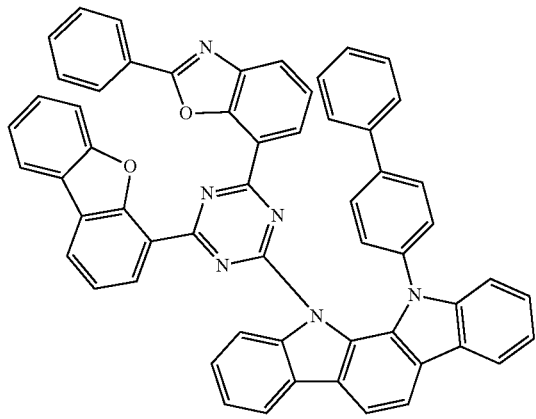
192
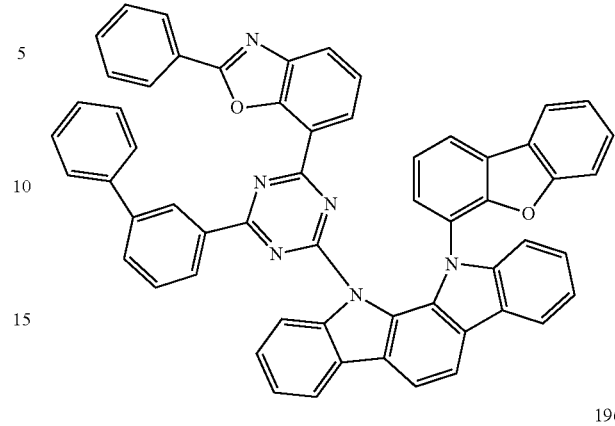
195
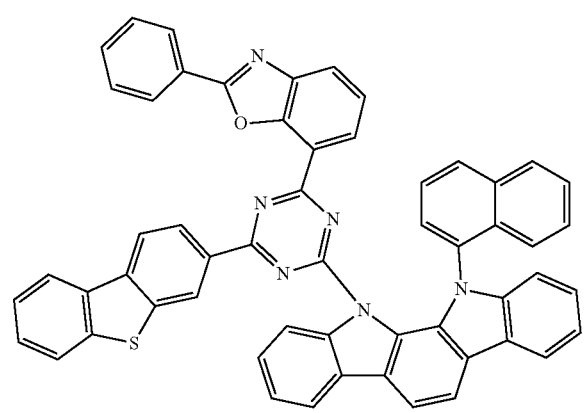
193
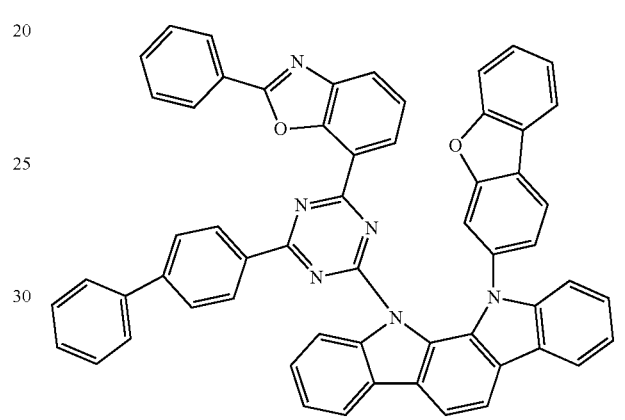
196
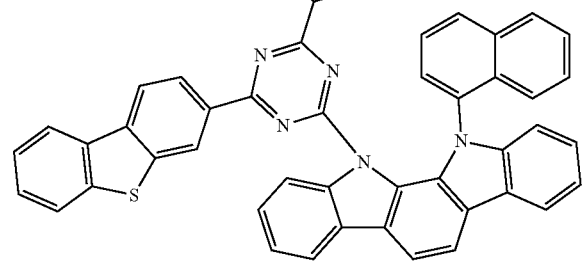
194
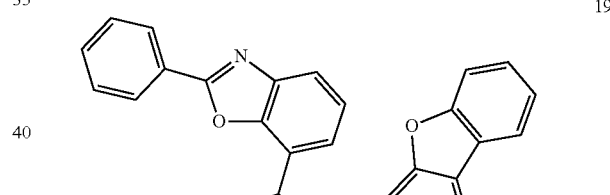
197
198

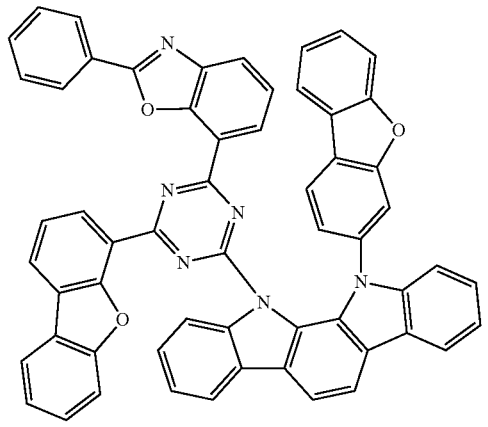
199
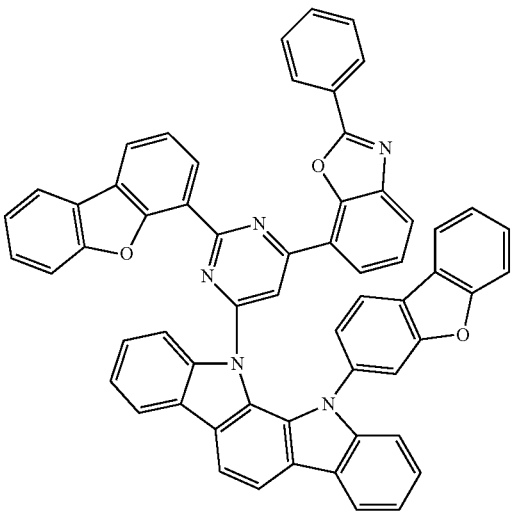
199
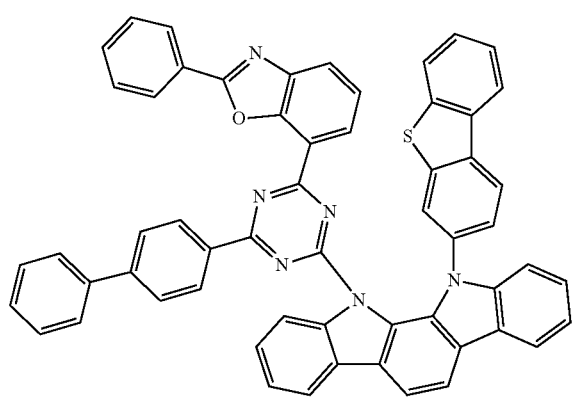
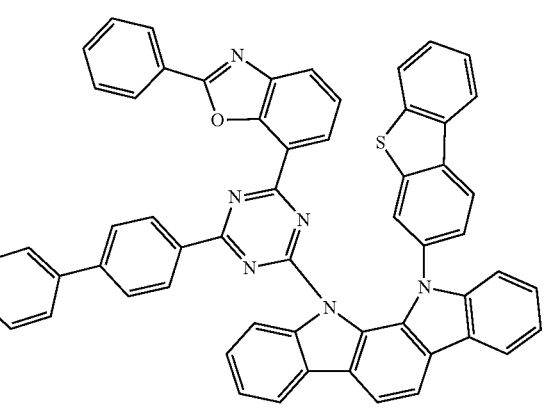
200
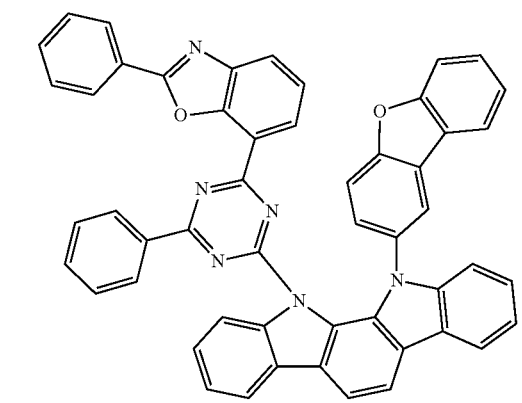
197
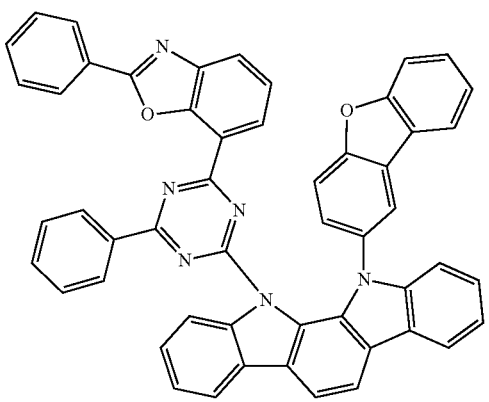
198
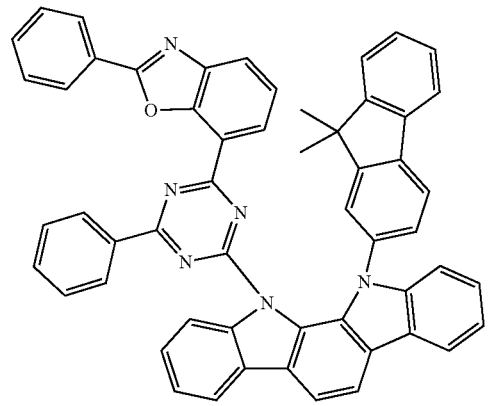
201

95
-continued
202
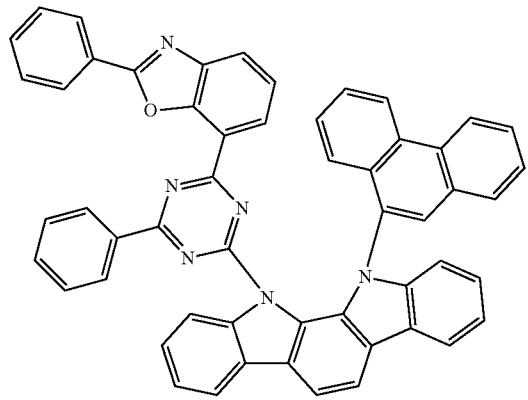
203
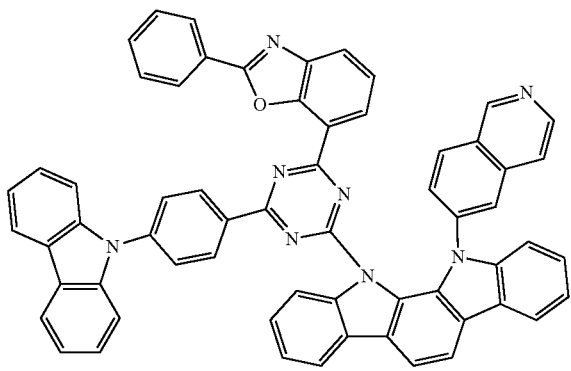
204
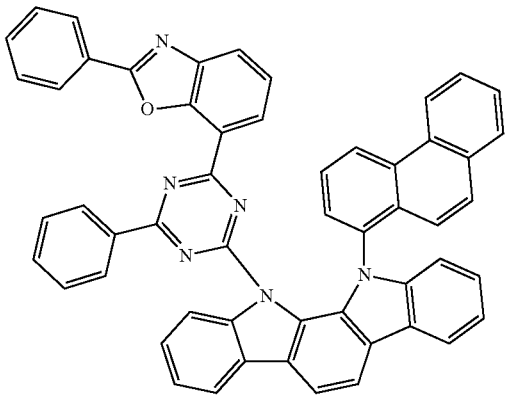
205
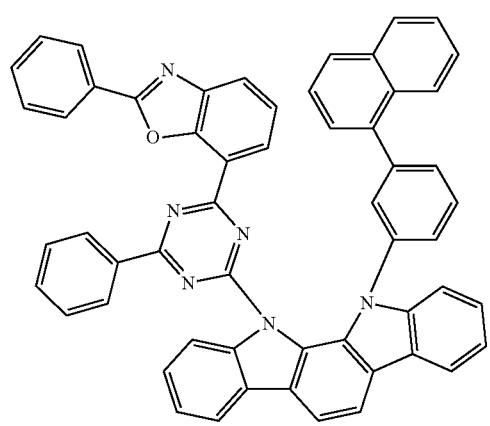
96
-continued
206
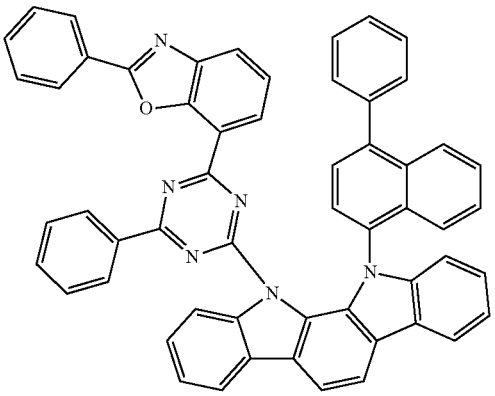
207
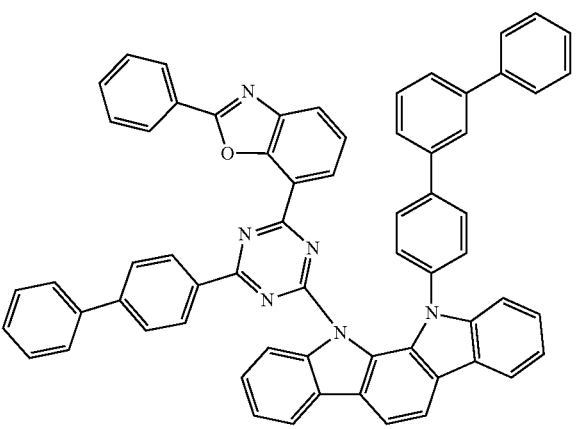
211
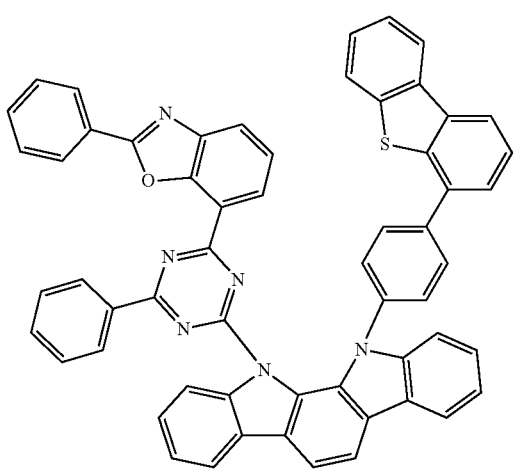

97
-continued
212
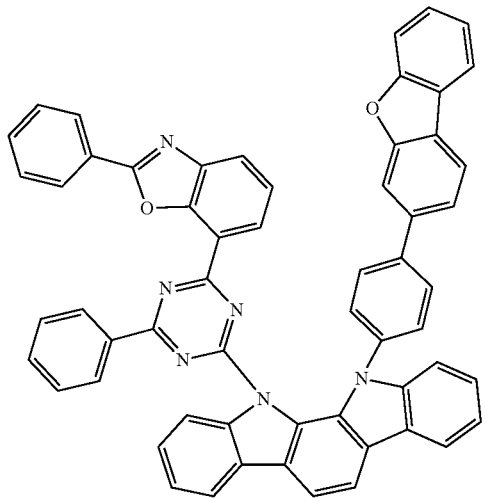
213
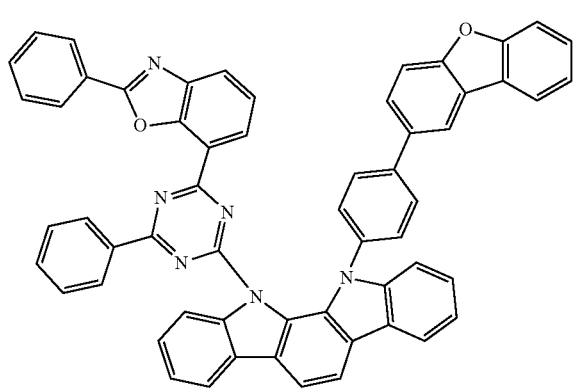
214
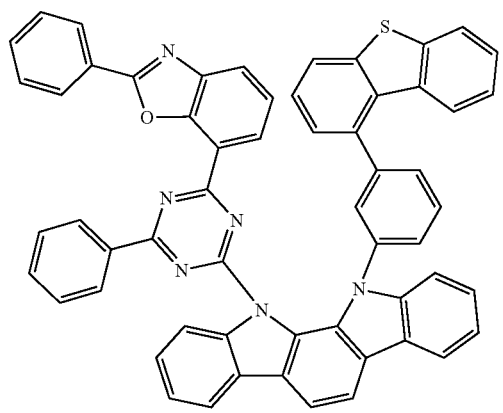
98
-continued
215
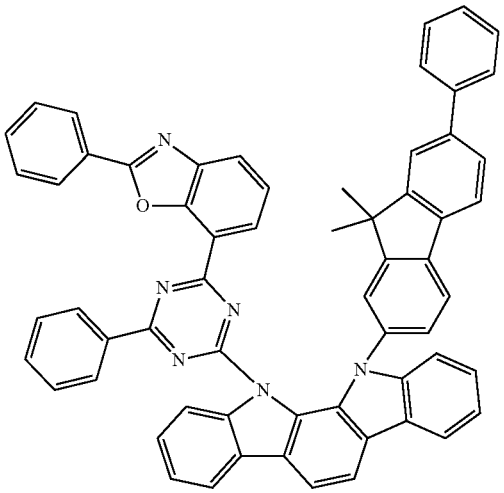
216
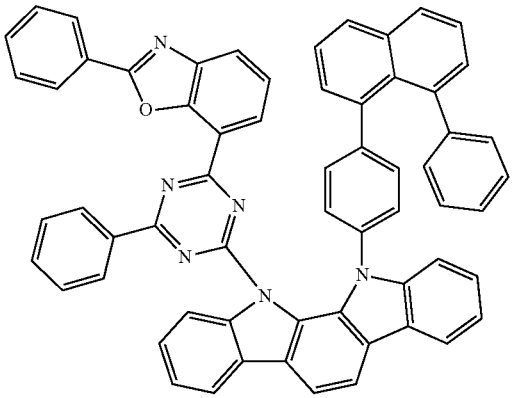
217
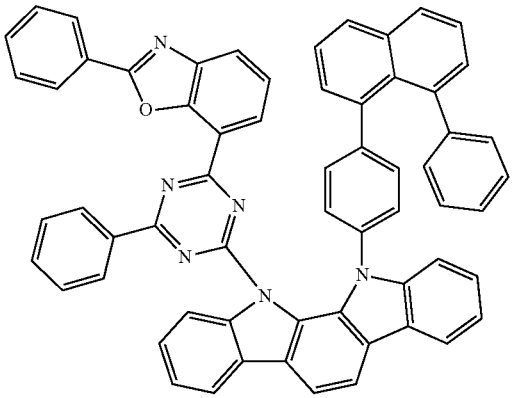

218
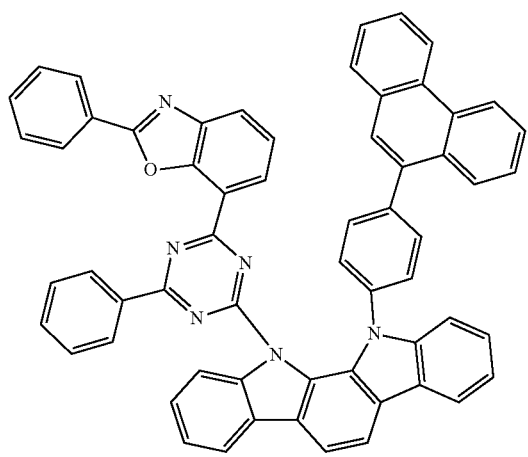
219
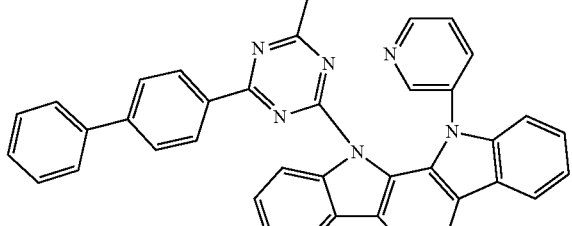
220
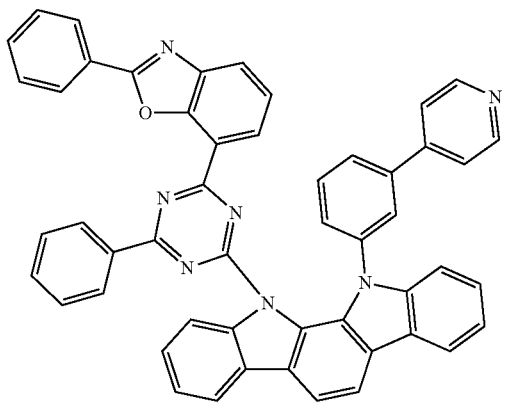
221
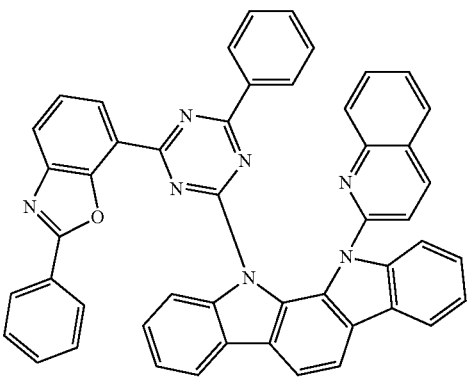
222
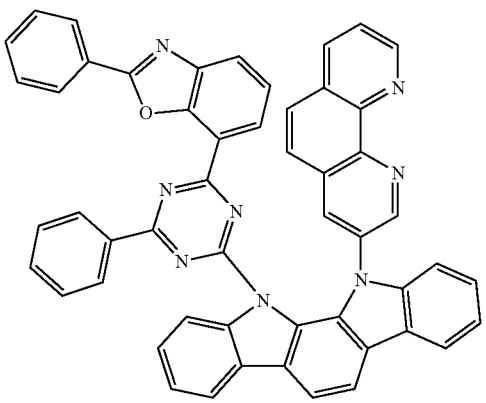
223
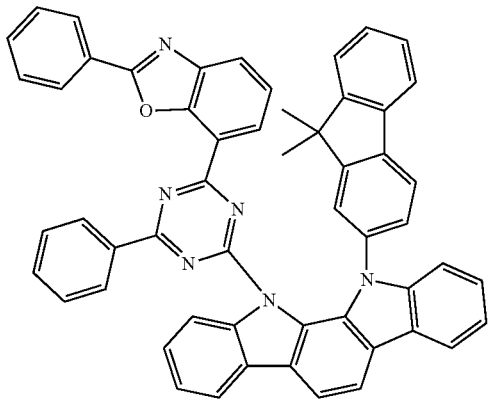
224
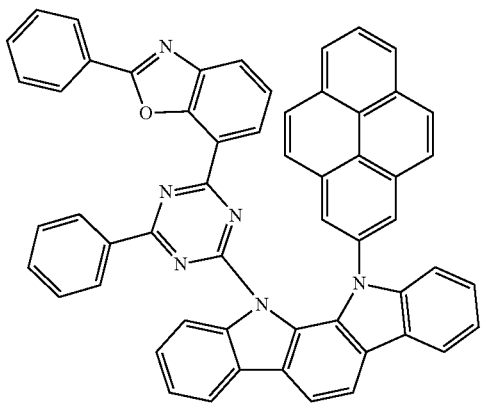

-continued
225
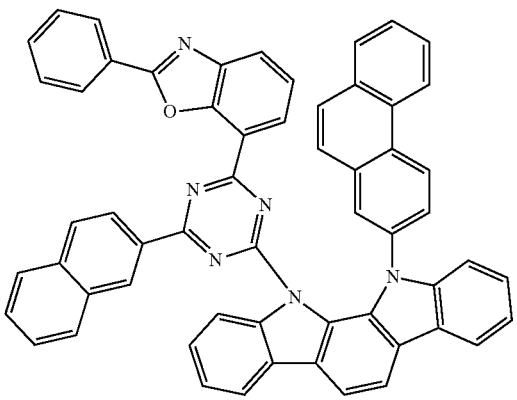
226
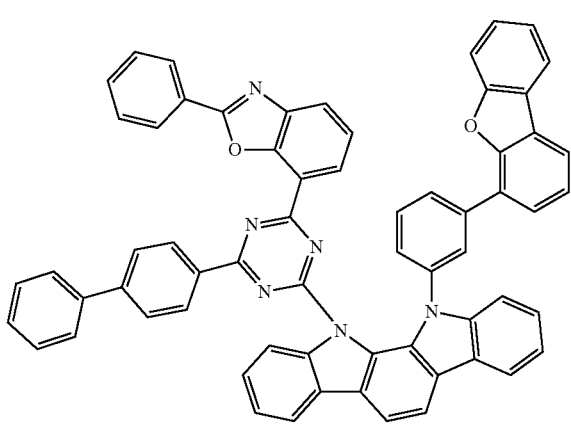
227
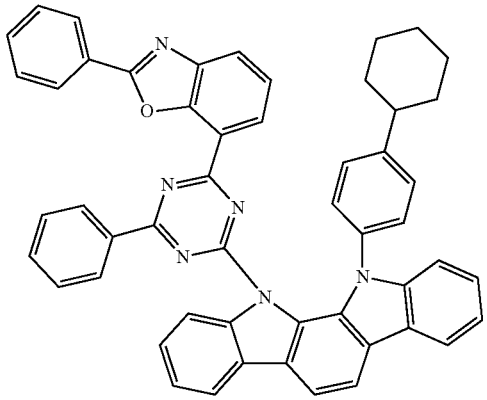
-continued
228
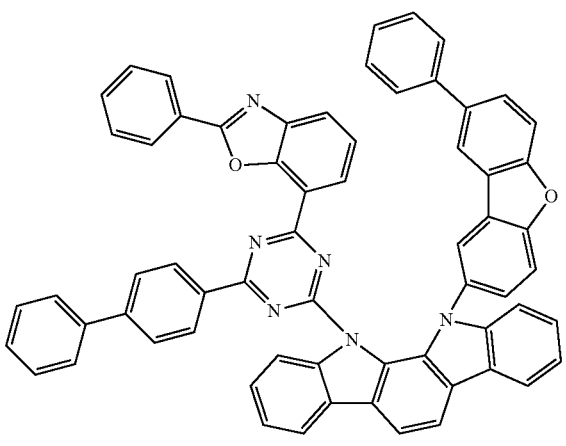
229
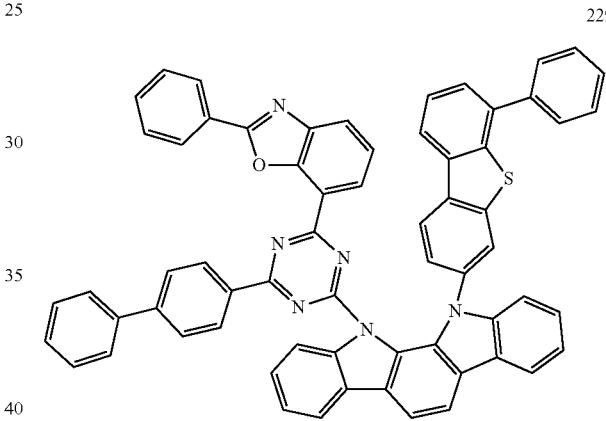
230
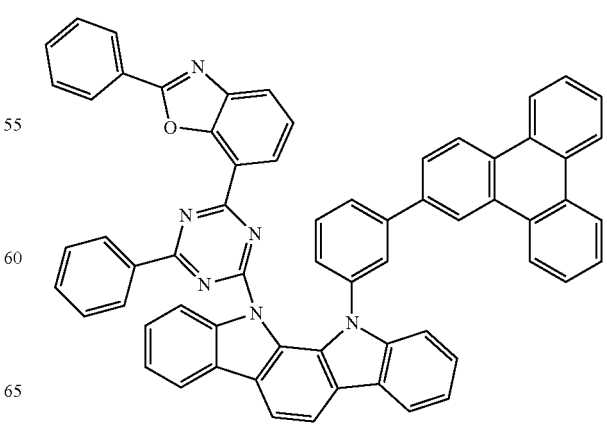

232
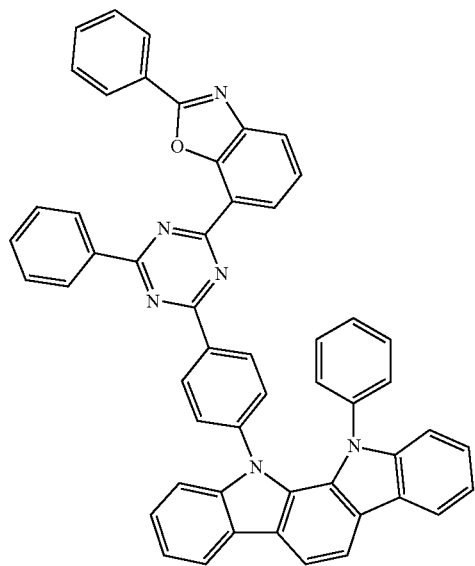
235
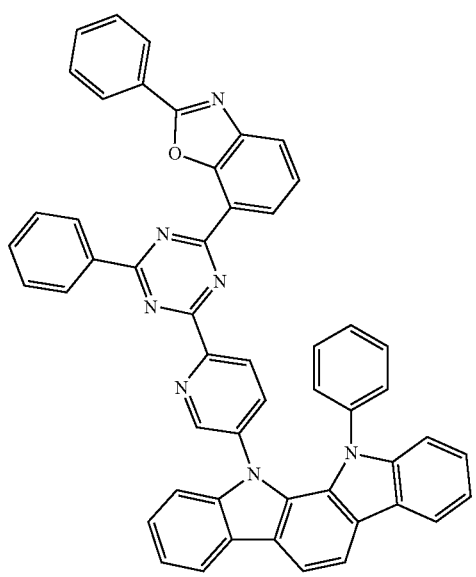
233
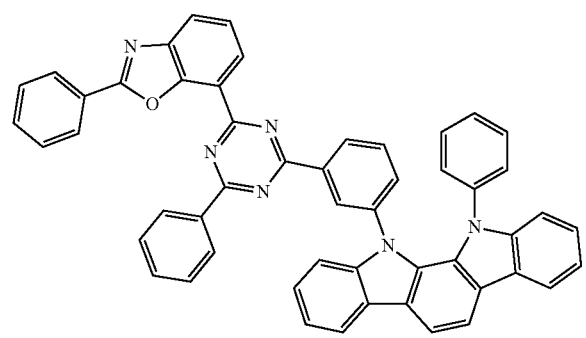
236
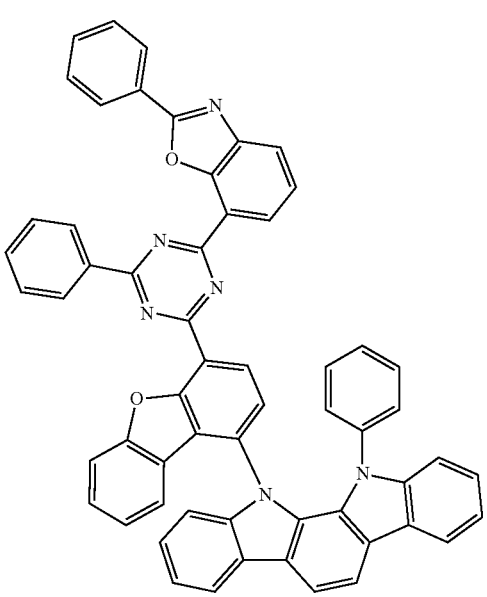
234
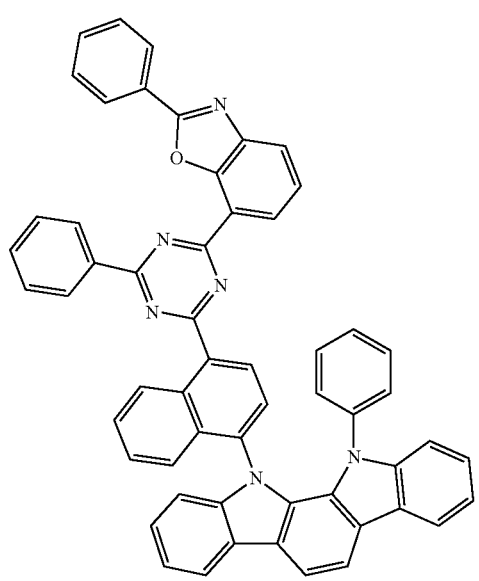
237
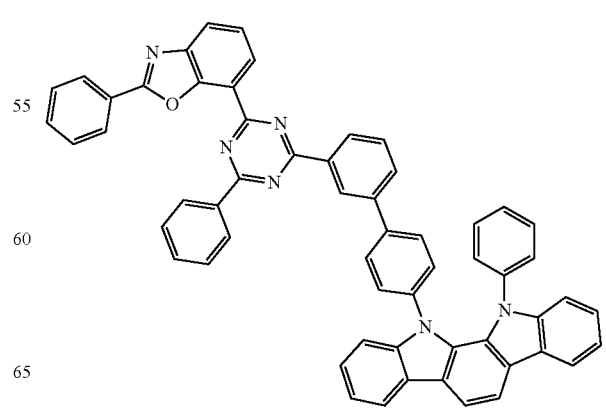

238
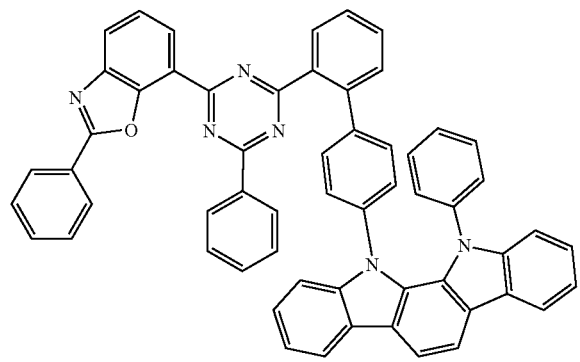
239
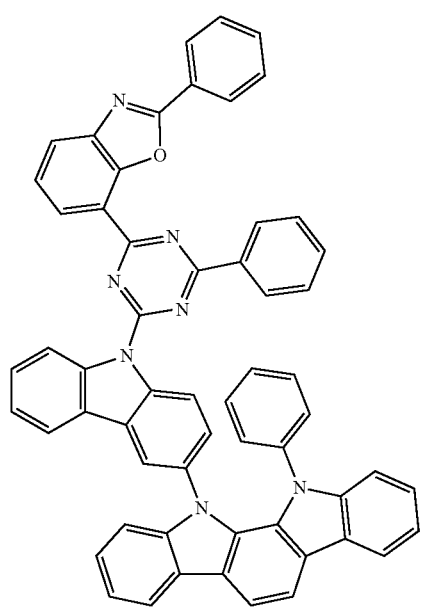
240
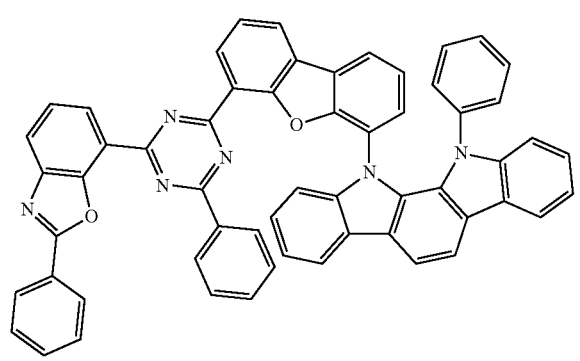
241
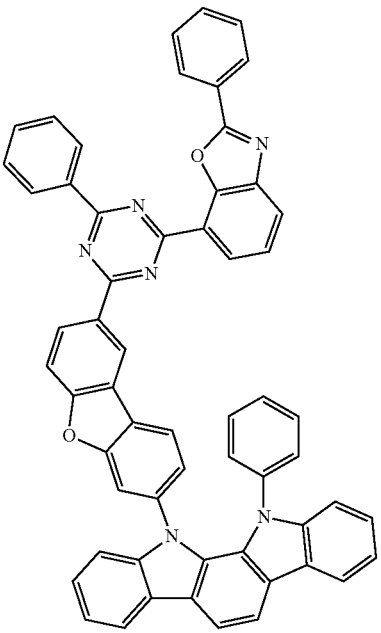
242
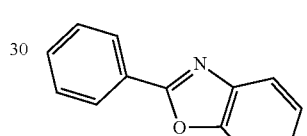
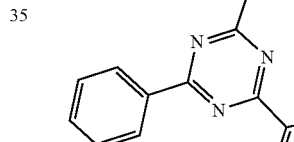
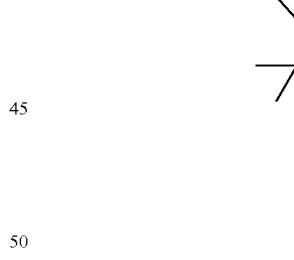
243
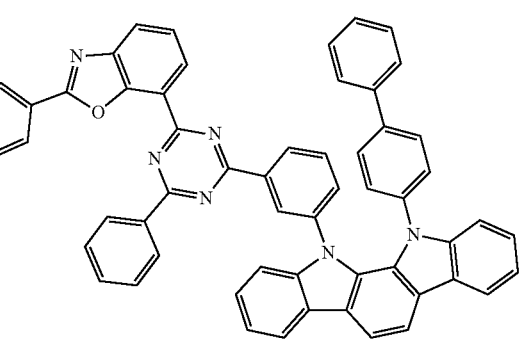

244
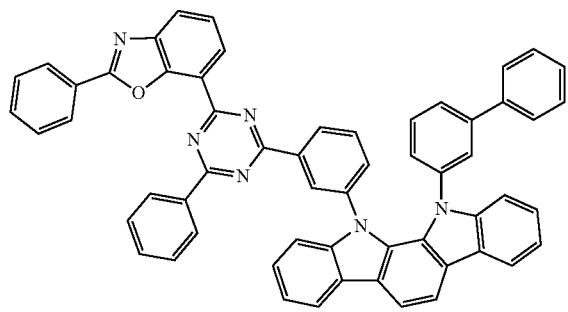
245
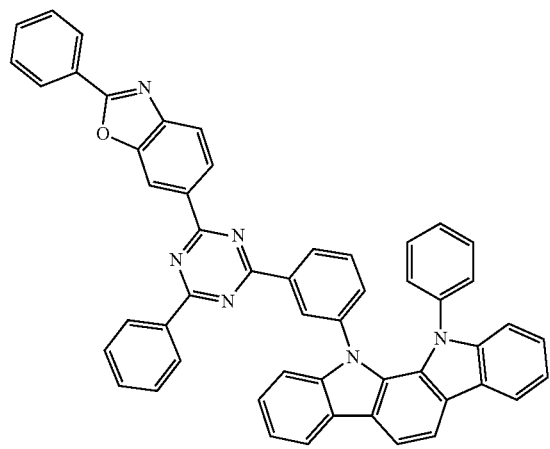
246
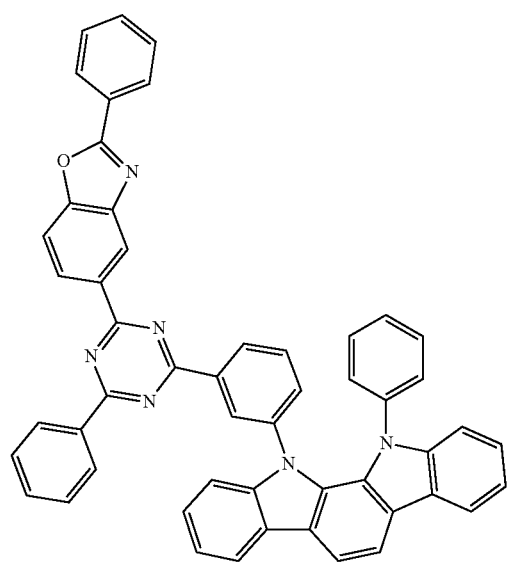
247
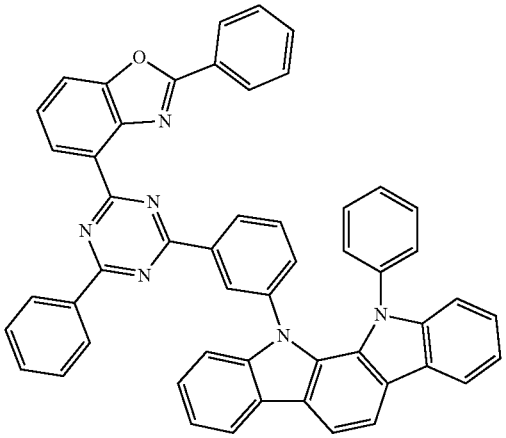
248
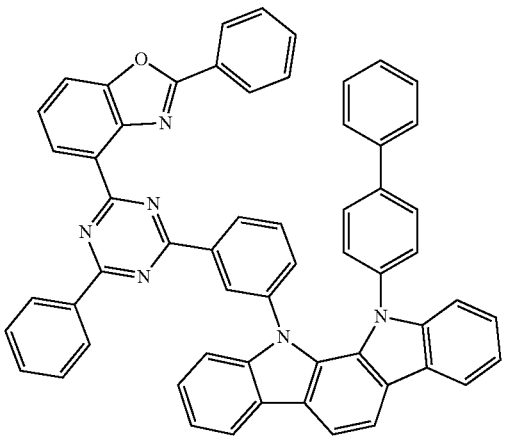
249
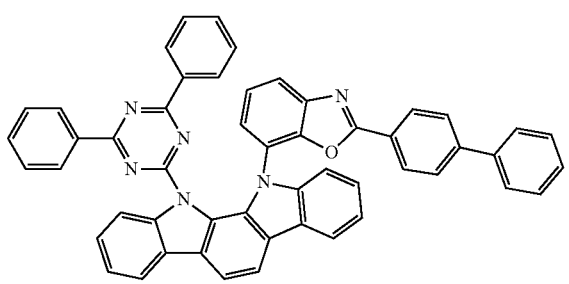
250
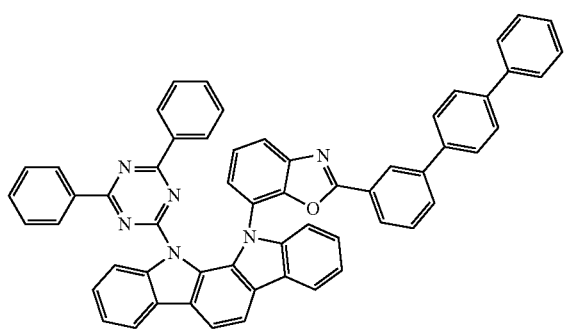

109
-continued
251
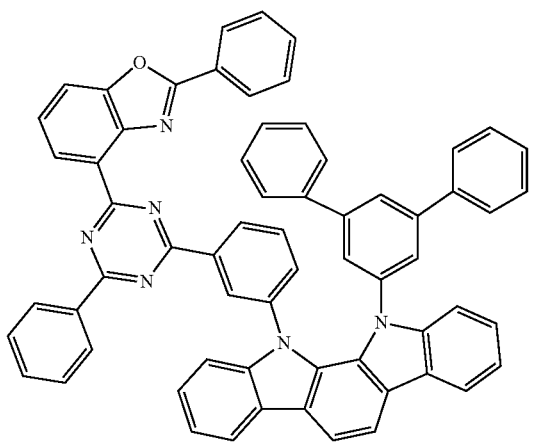
252
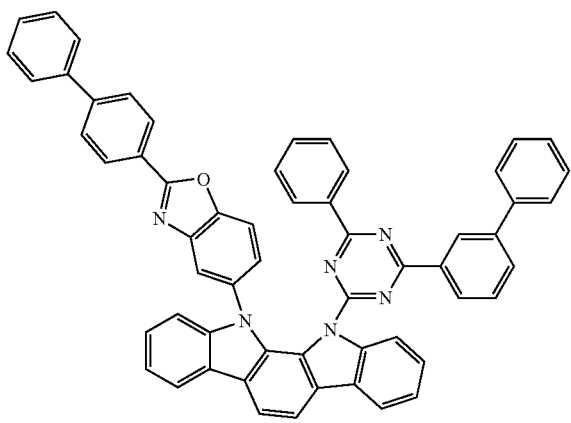
253
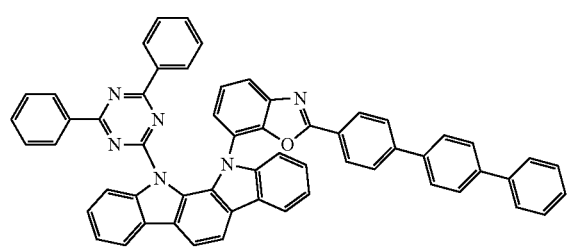
110
-continued
254
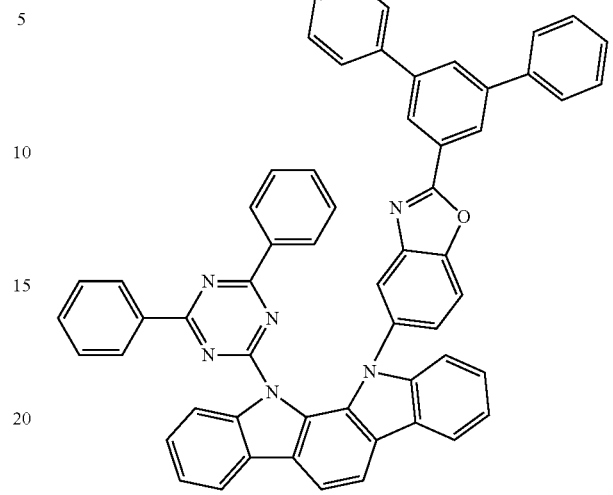
255
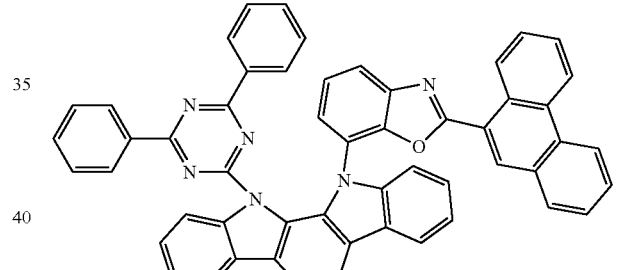
256
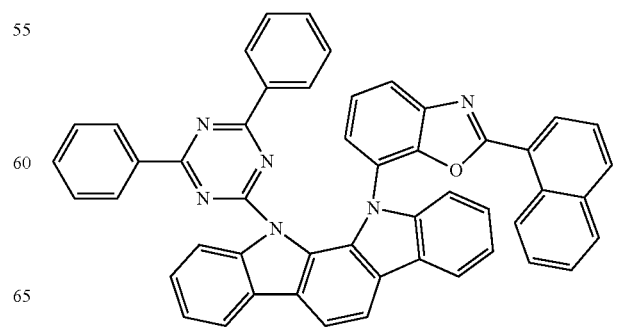

257
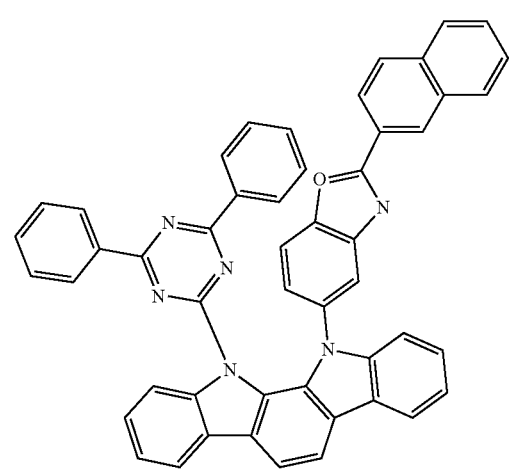
258
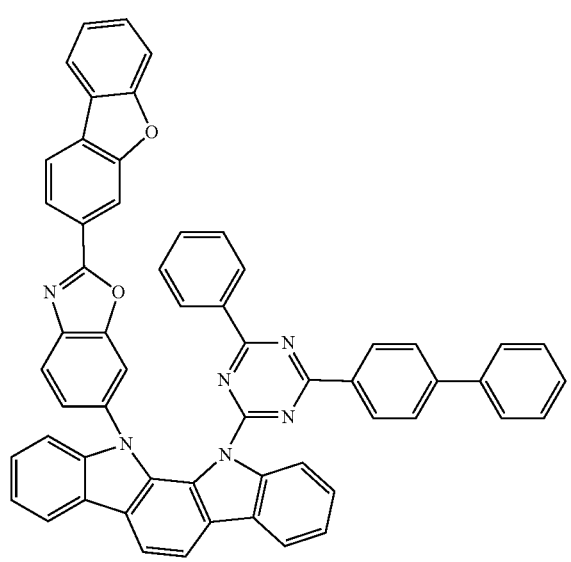
259
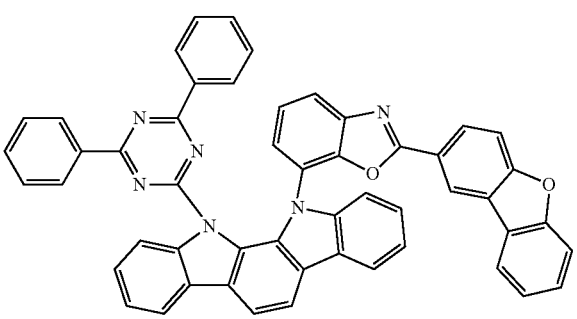
260
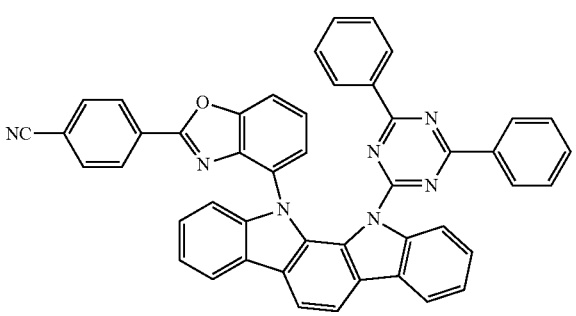
261
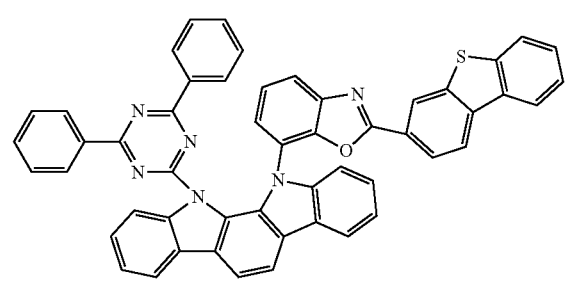
262
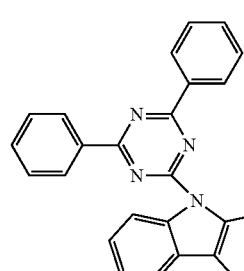
263
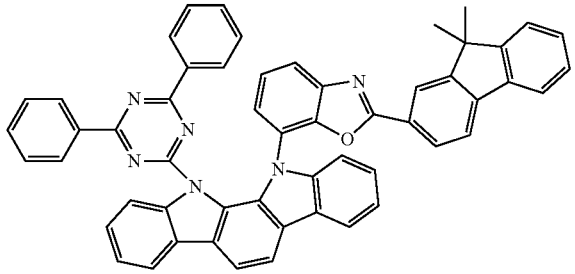
264

265
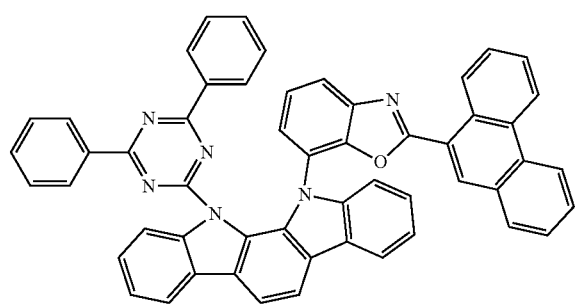
266
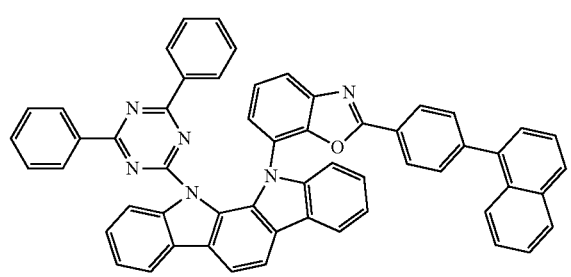
267
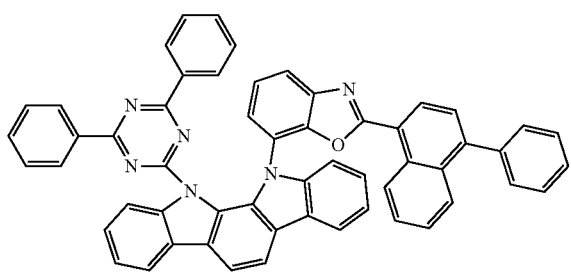
268
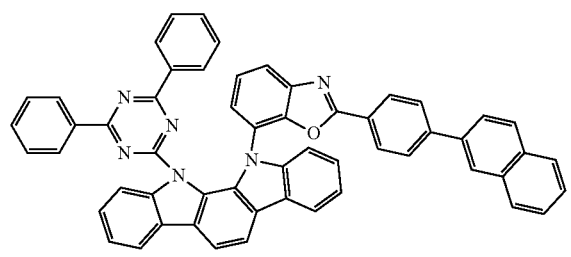
269
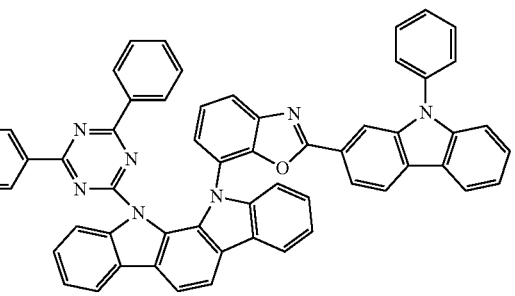
270
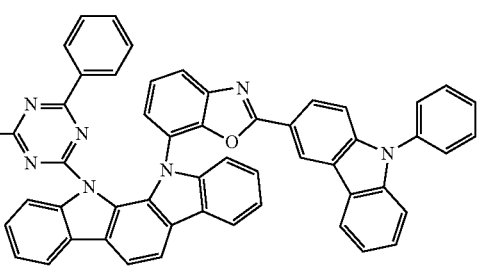
271
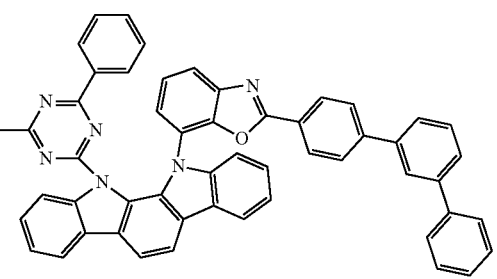
272
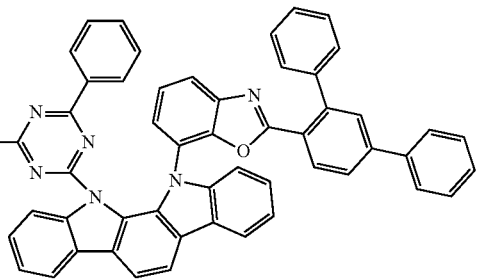

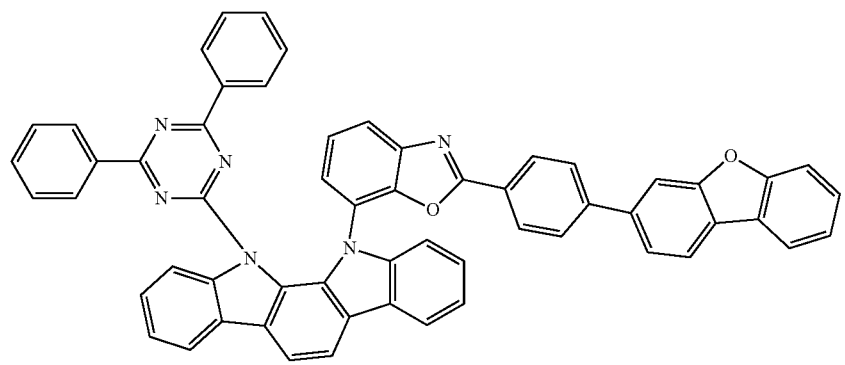 273
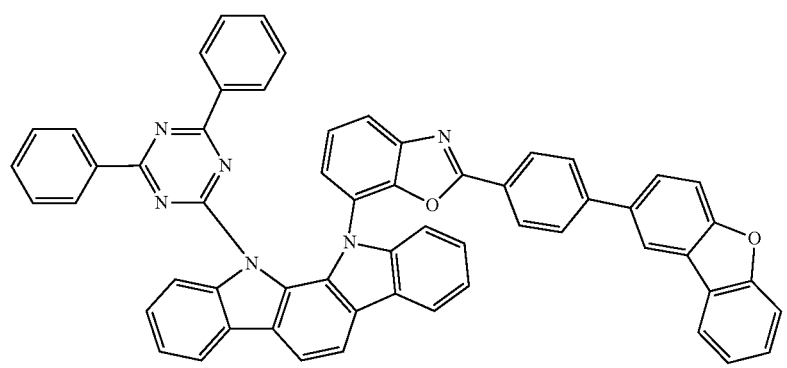 274
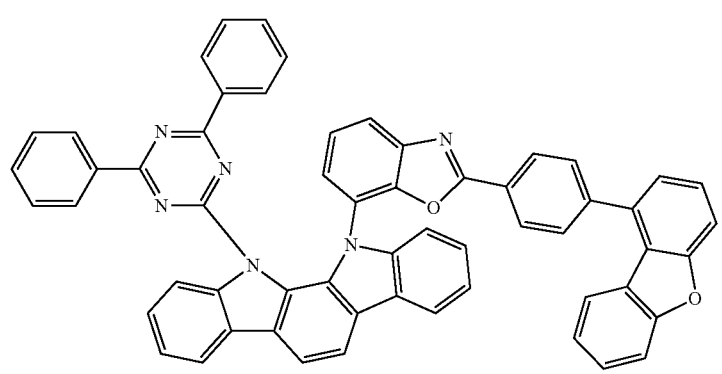 275
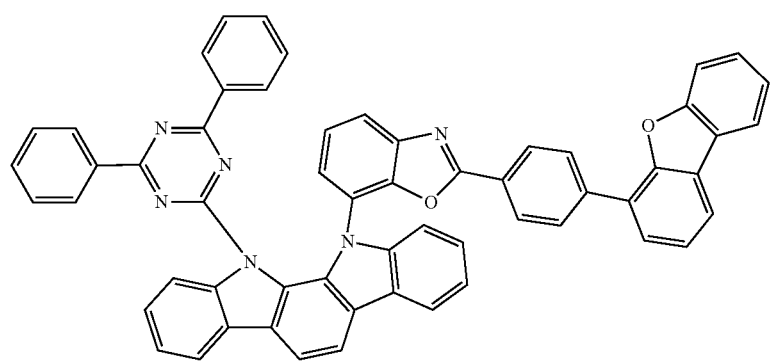 276

277
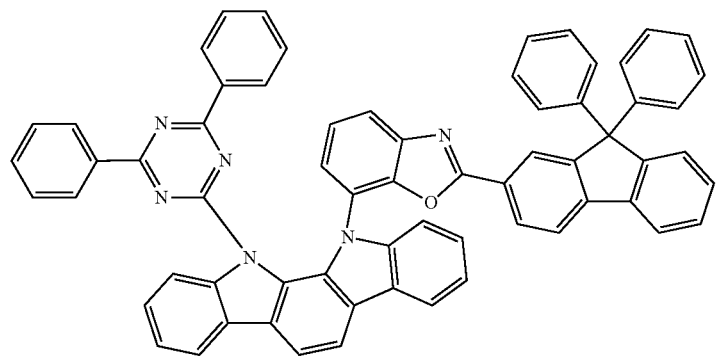
278
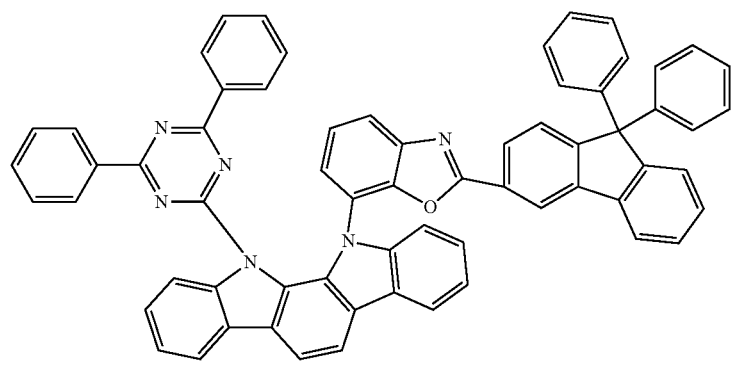
279
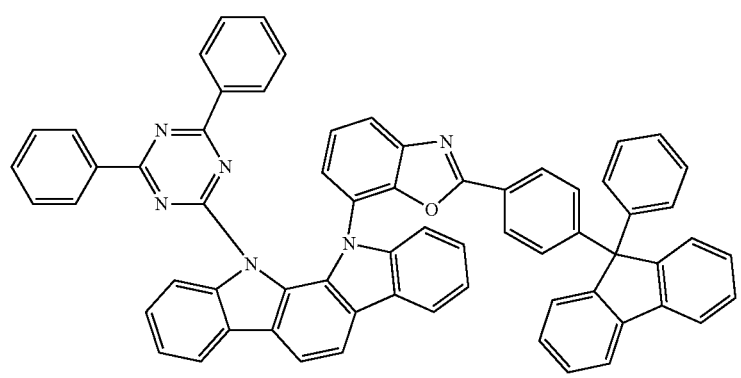
280
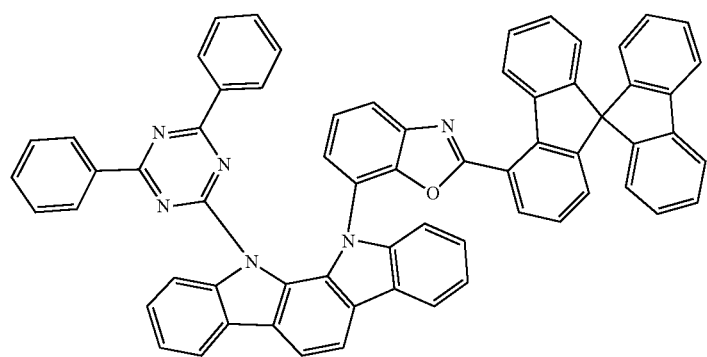

-continued
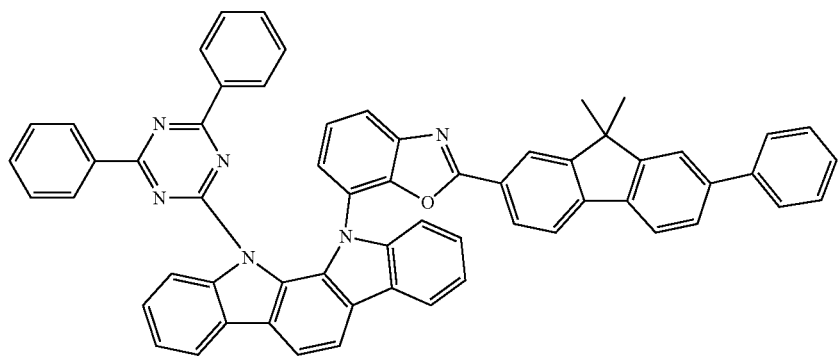
281
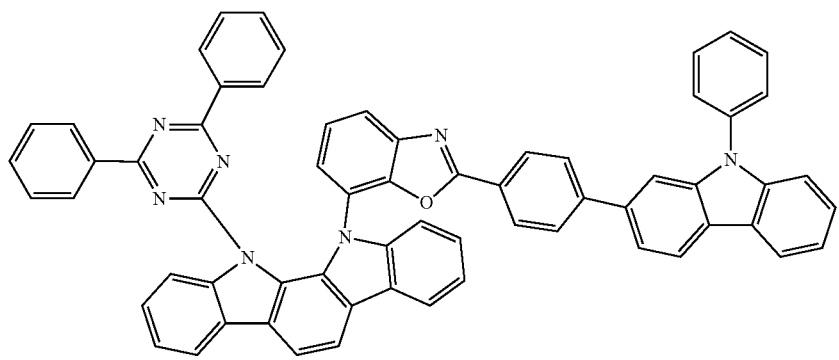
282
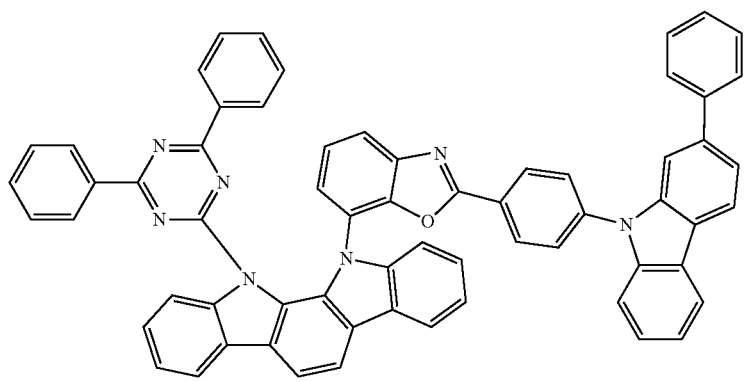
283
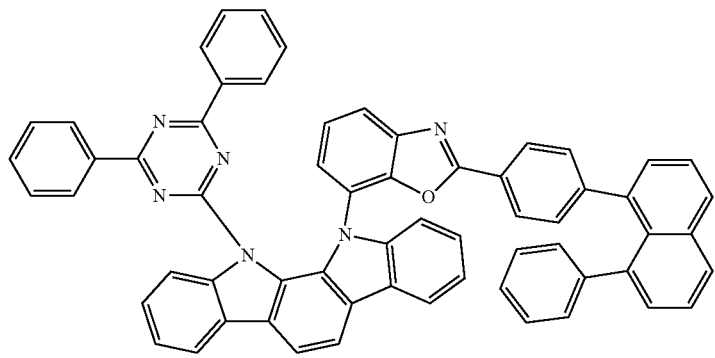
284

-continued
285
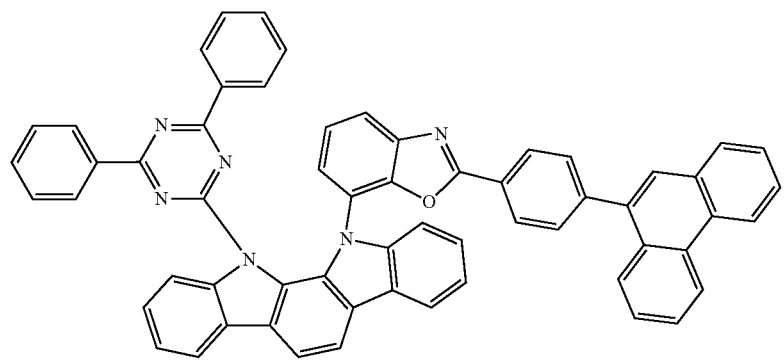
286
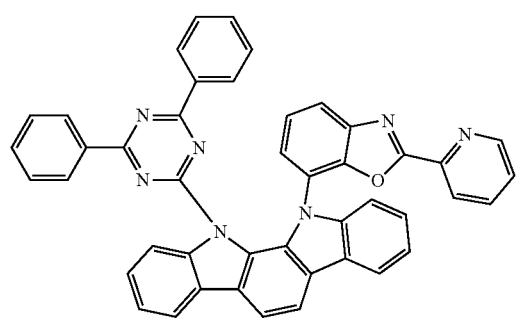
287
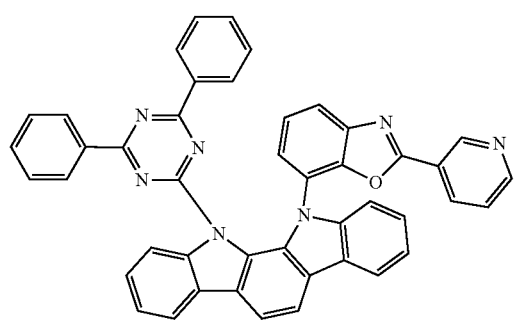
288
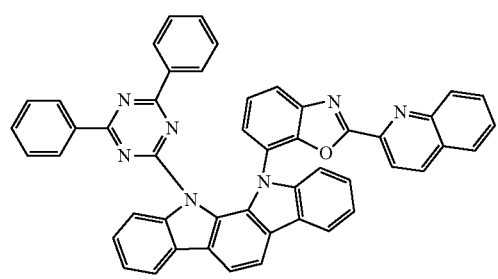
289
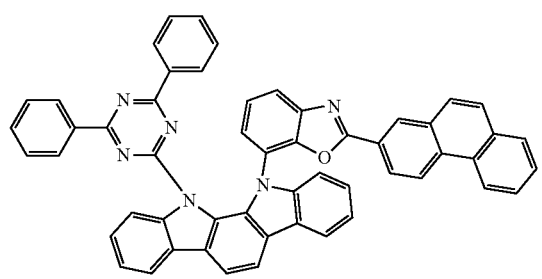
290
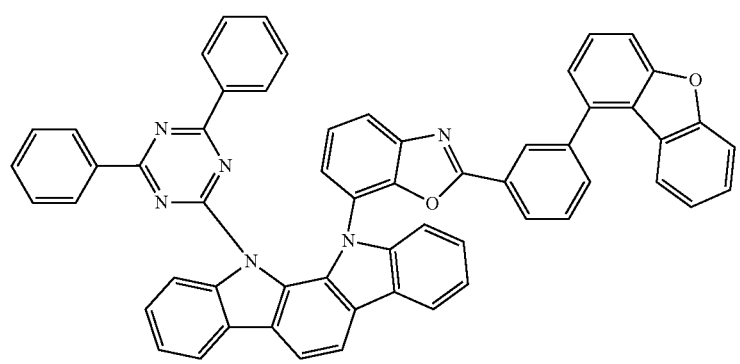

291
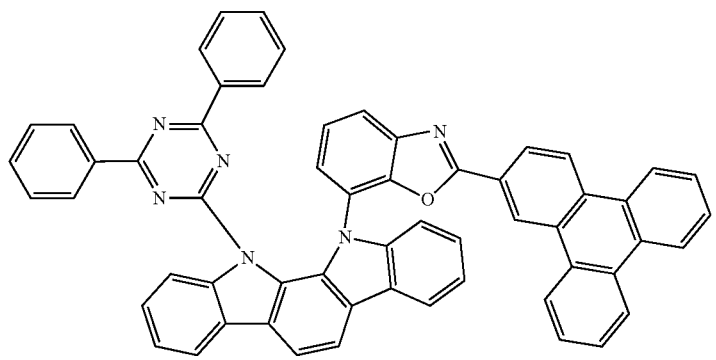
292
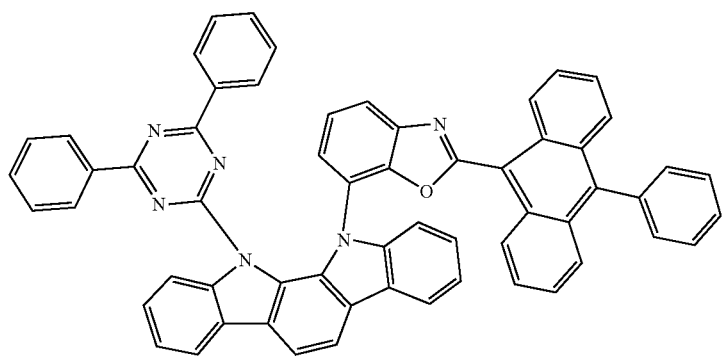
293
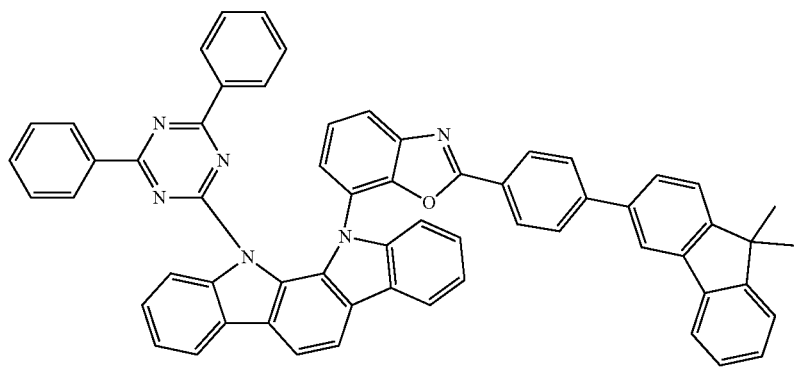
294
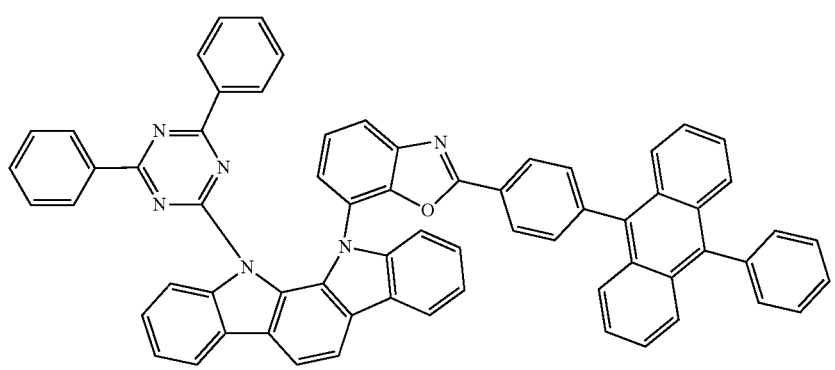

295
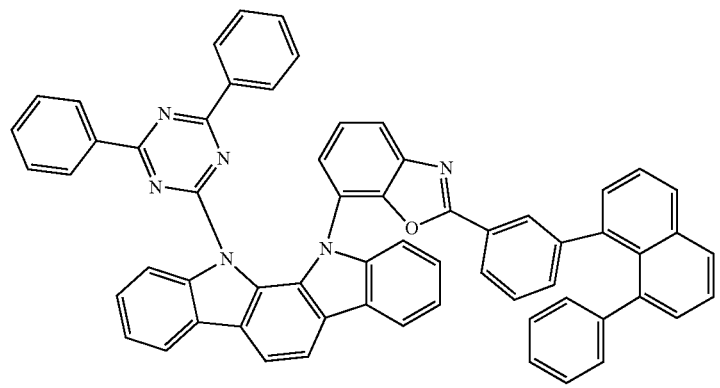
296
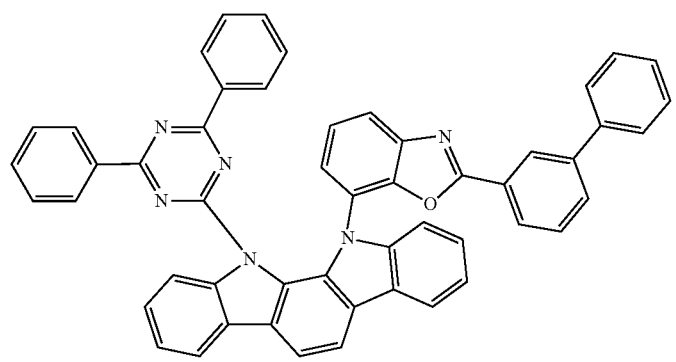
297
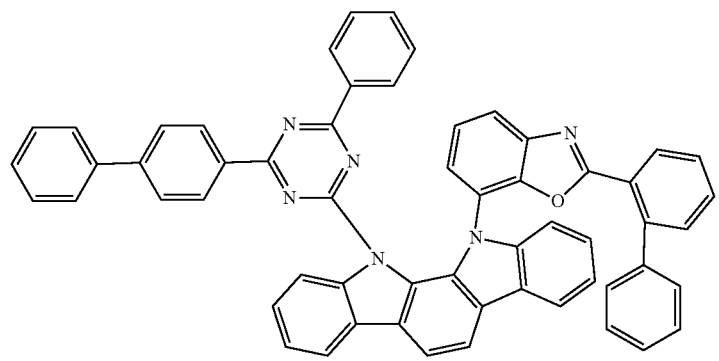
298
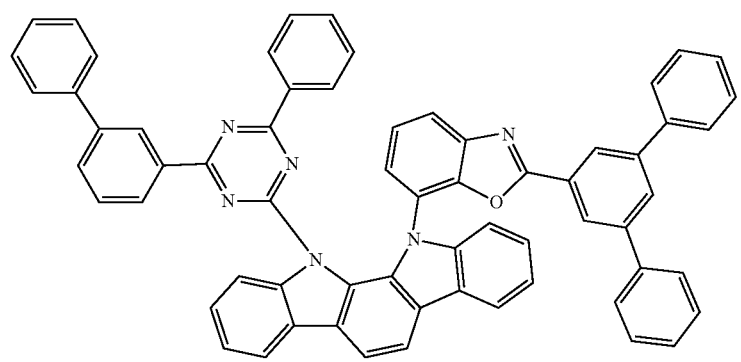

299
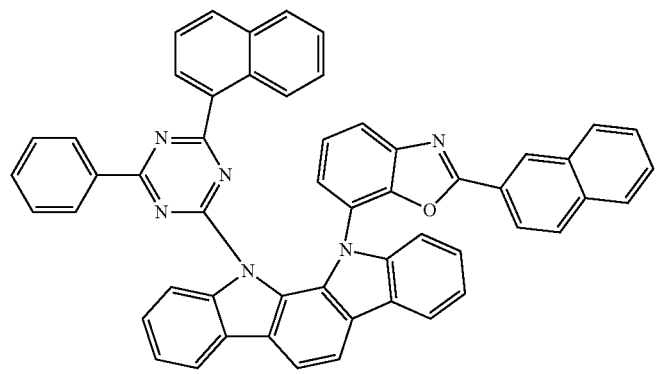
300
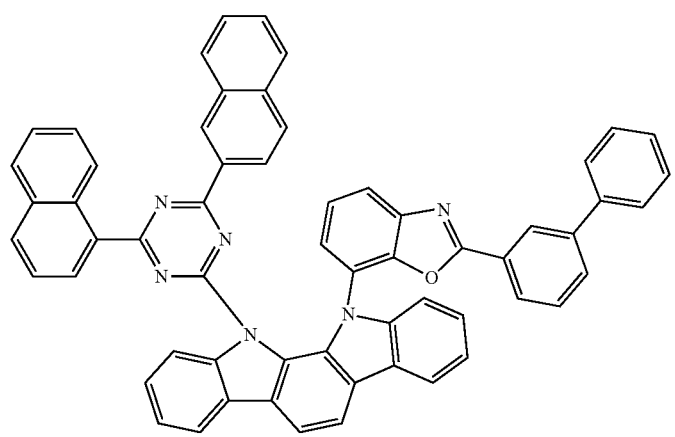
301
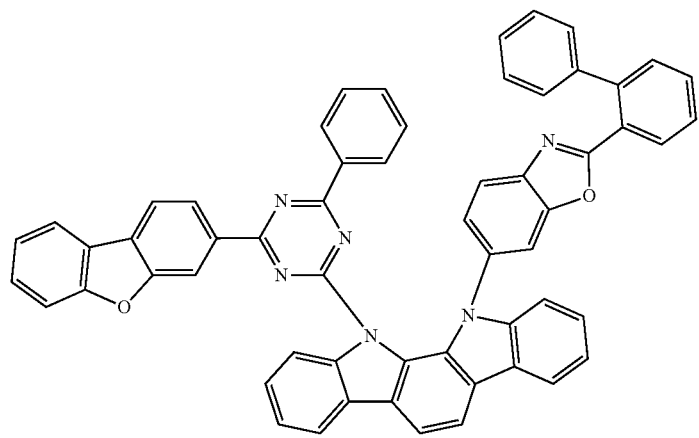
302
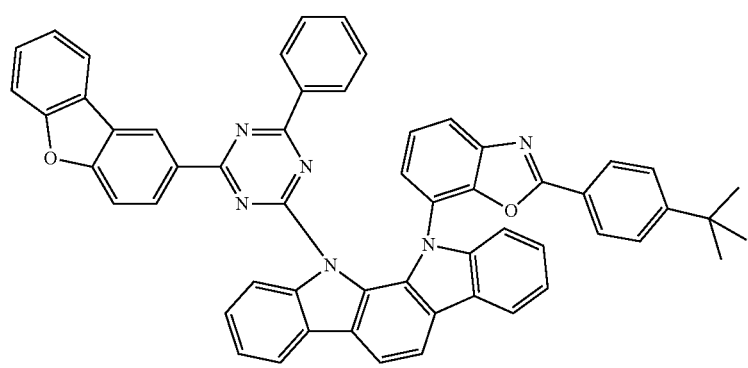

-continued
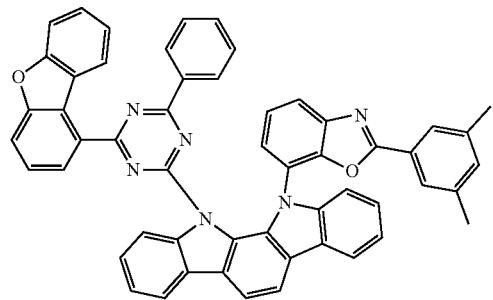
303
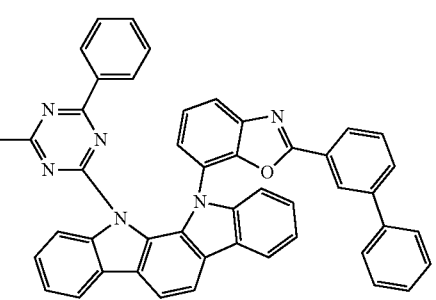
304
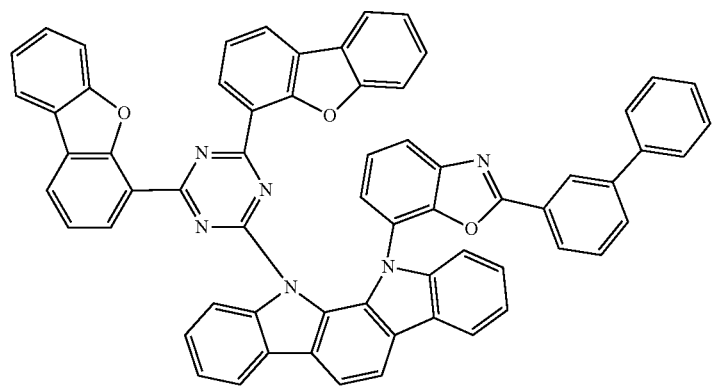
305
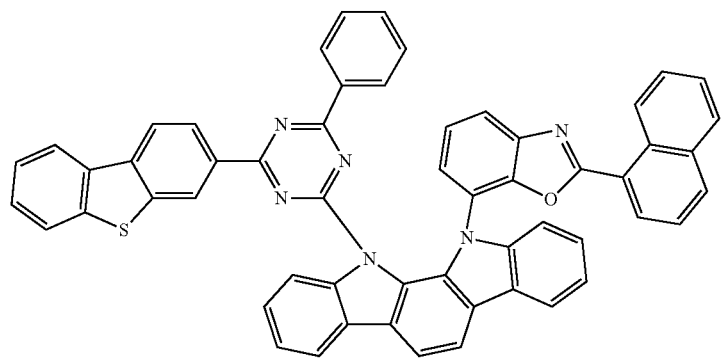
306
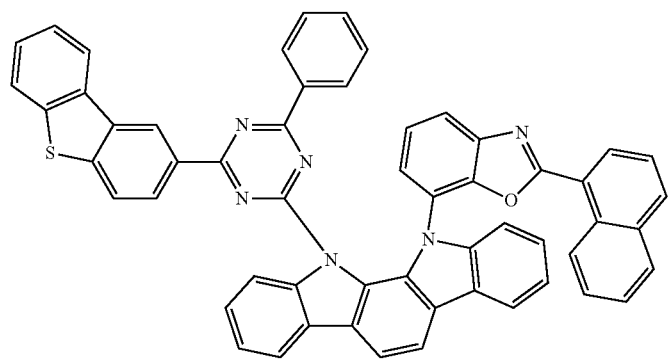
307

-continued
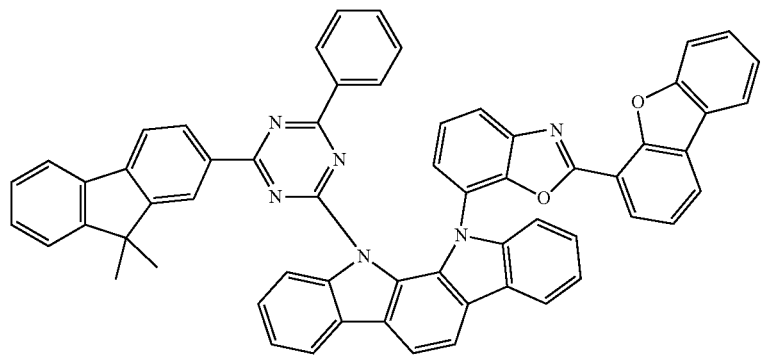
308
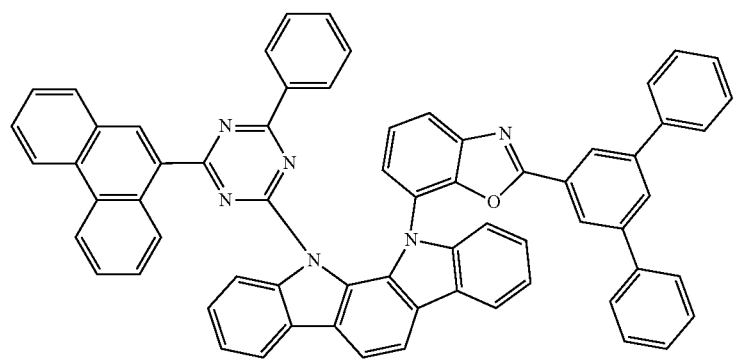
309
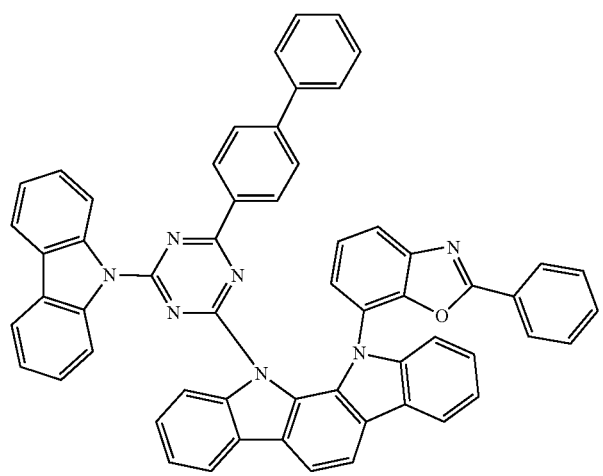
310
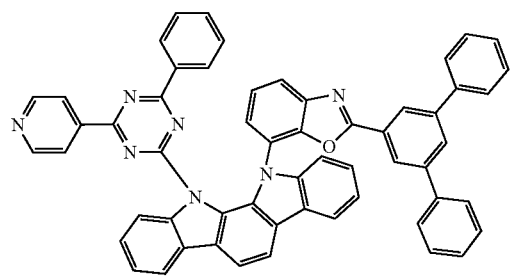
311
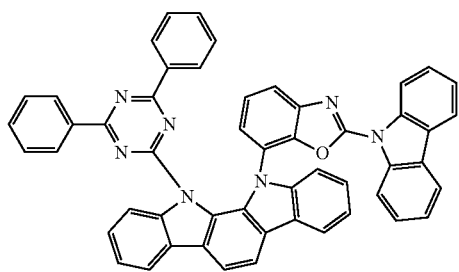
312

-continued
313
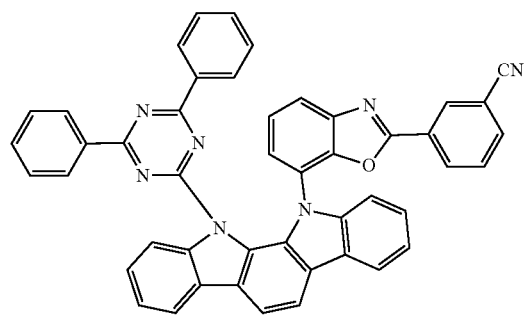
314
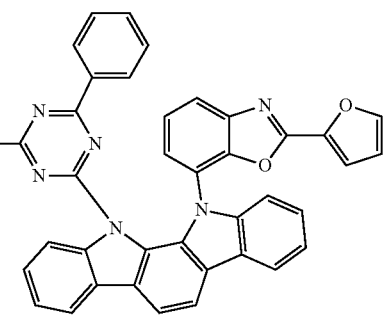
315
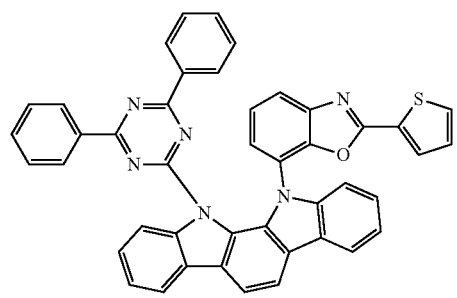
316
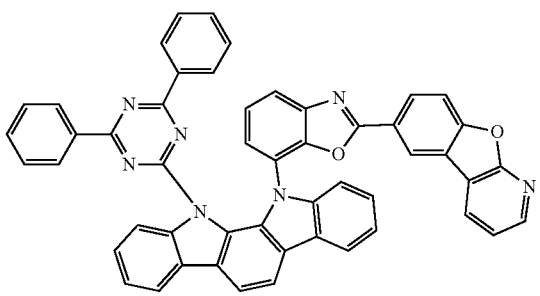
317
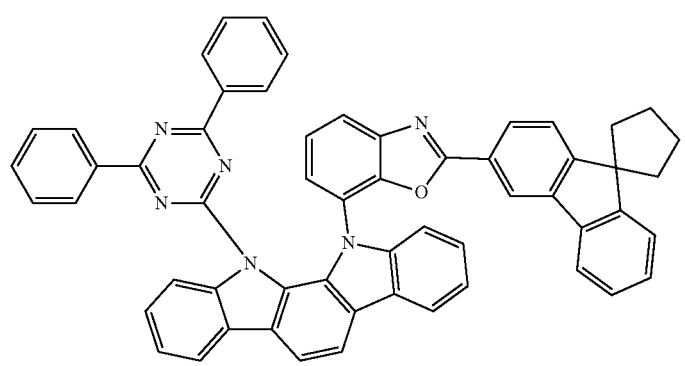

318
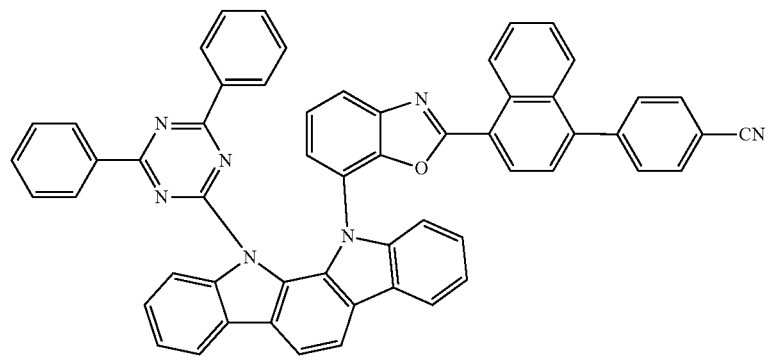
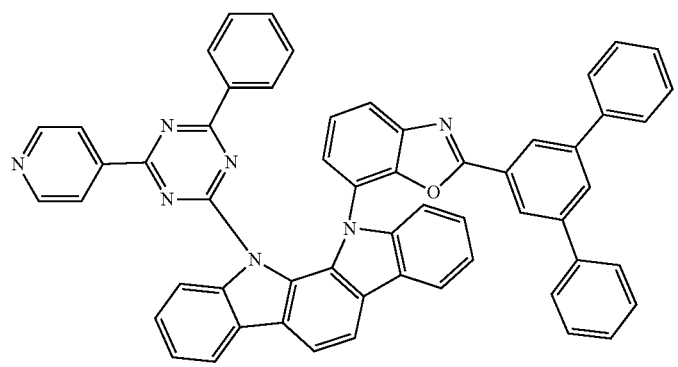
319
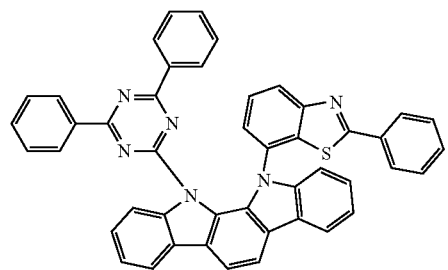
320
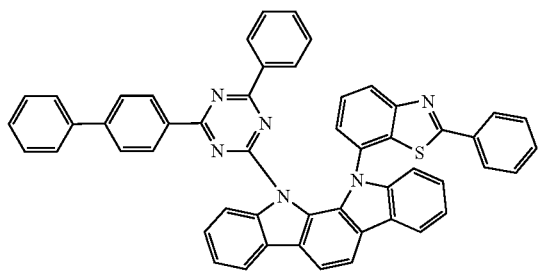

-continued
321
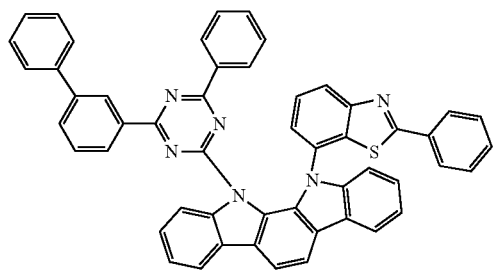
322
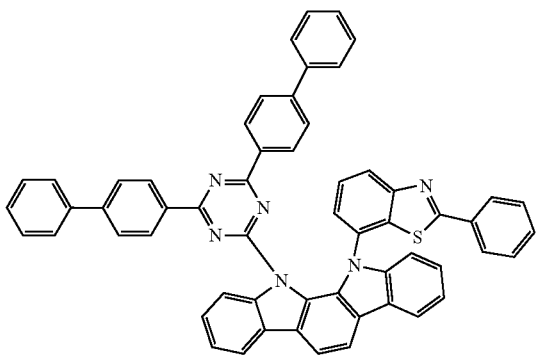
323
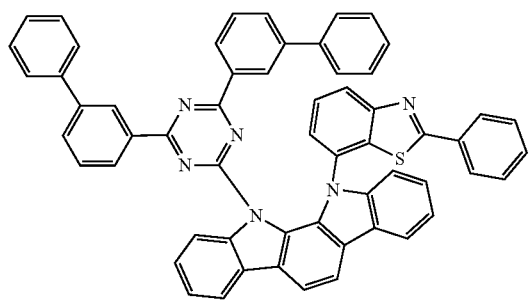
324
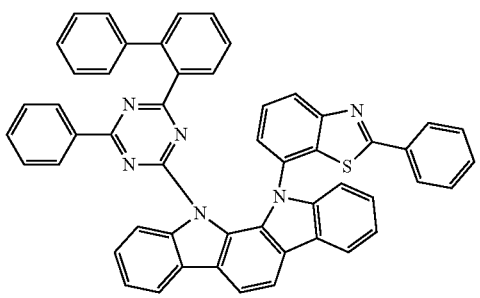
325
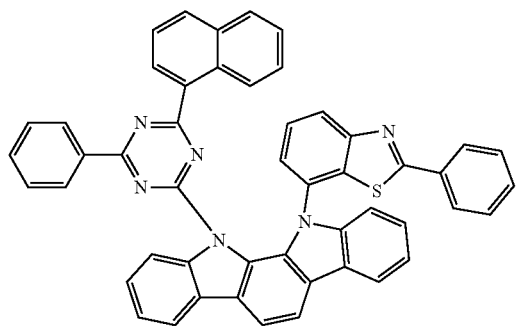
326
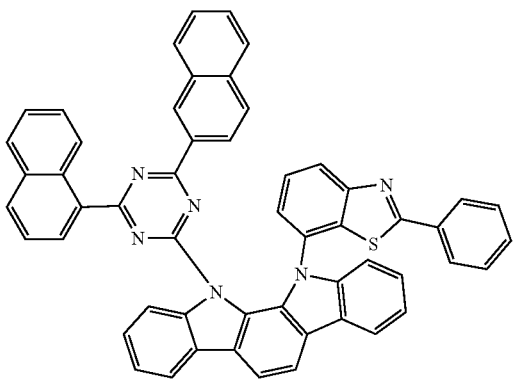
327
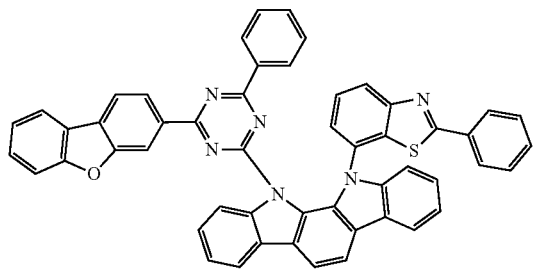
328
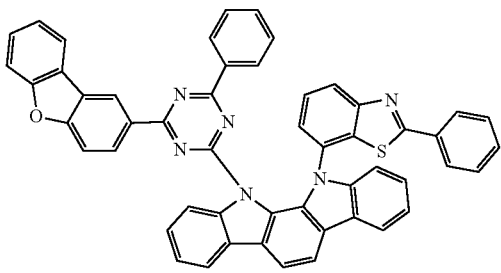
329
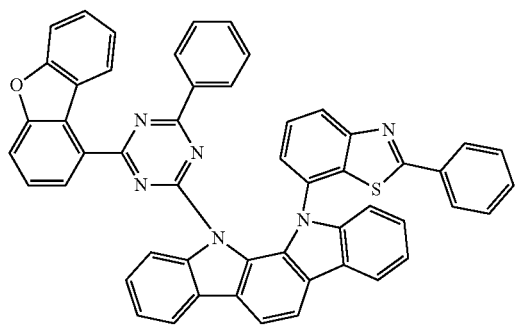
330
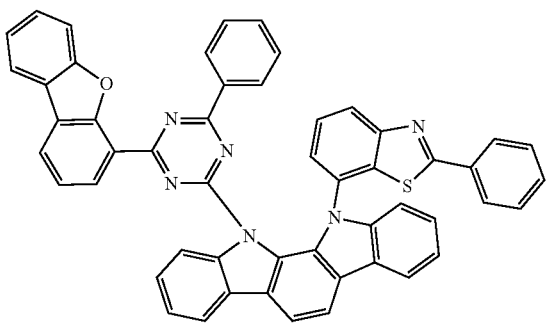

-continued
331
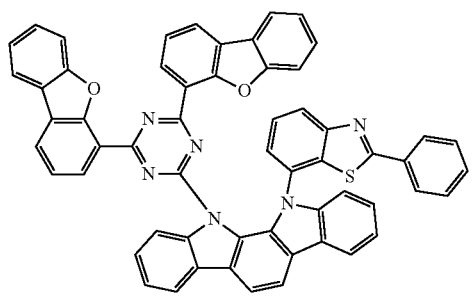
332
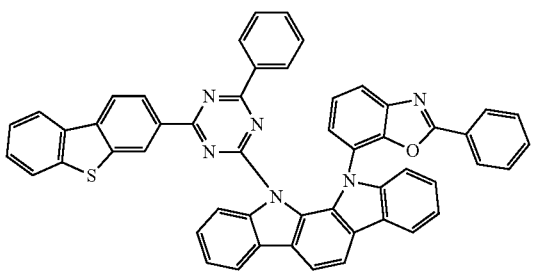
333
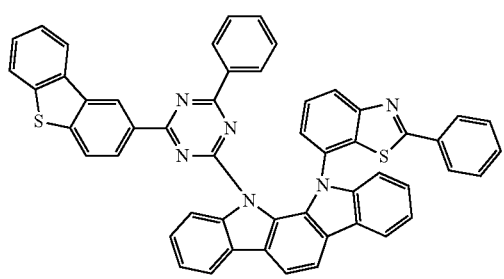
334
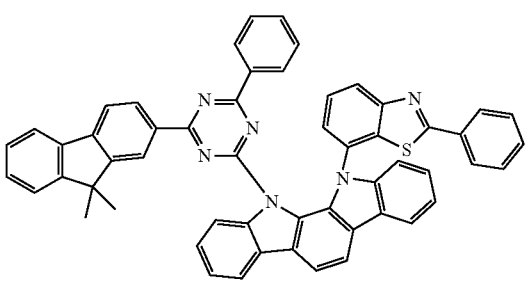
335
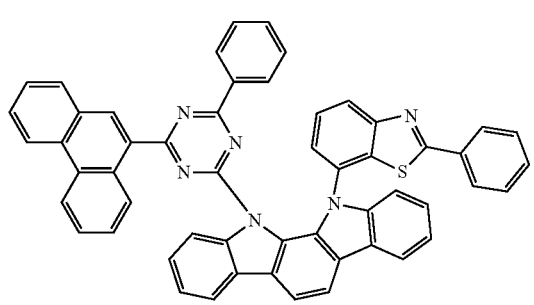
336
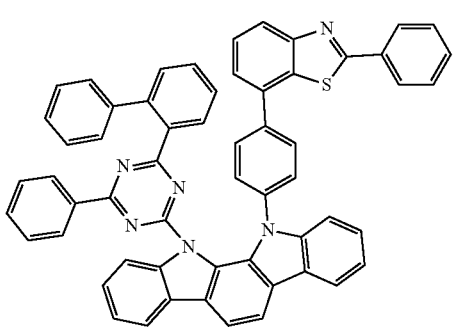
337
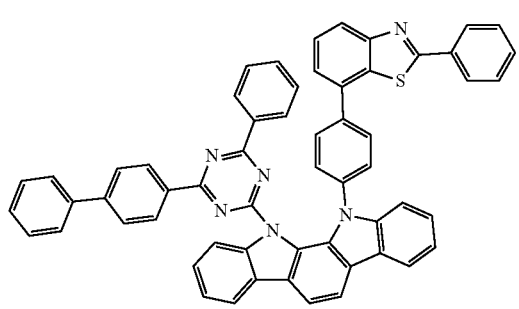
338
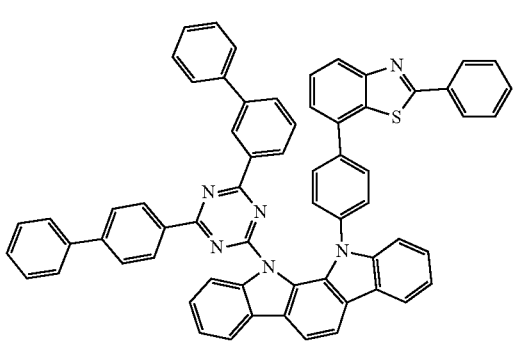
339
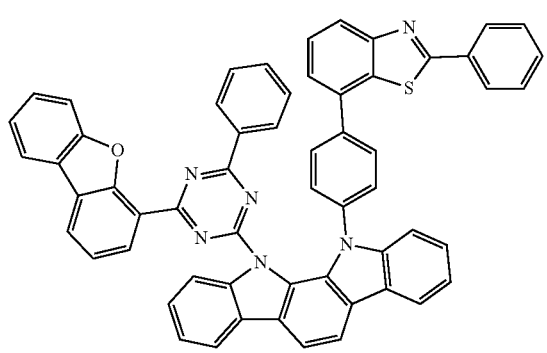
340
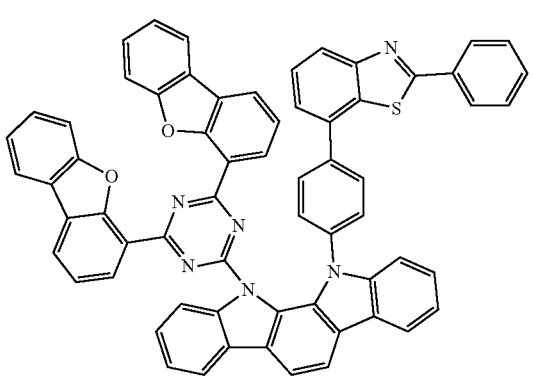

-continued
| 341 | 342 |
|---|---|
| 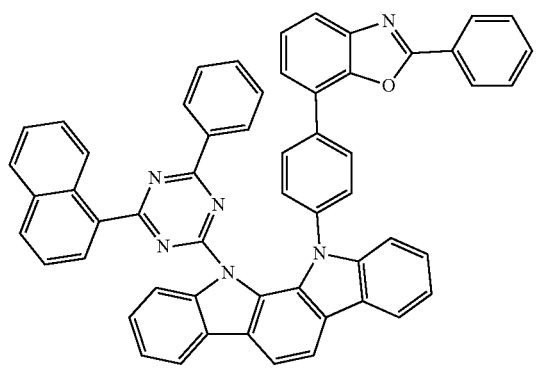 | 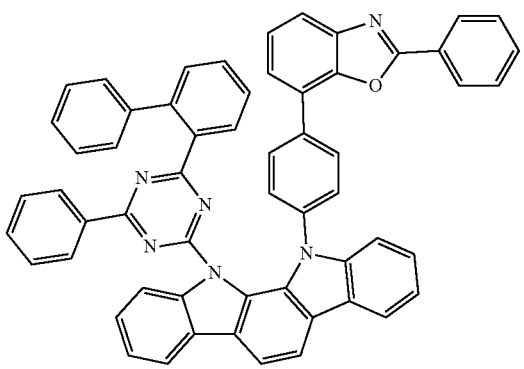 |
| 343 | 346 |
| 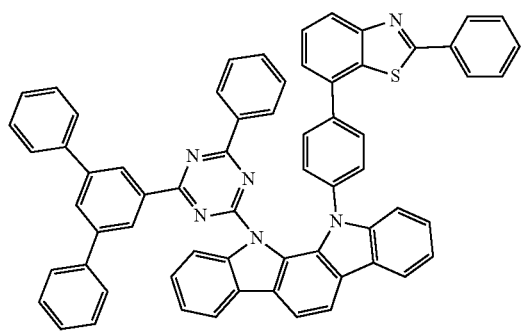 | 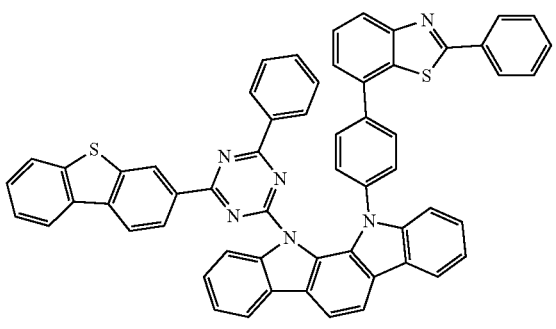 |
| 347 | 349 |
| 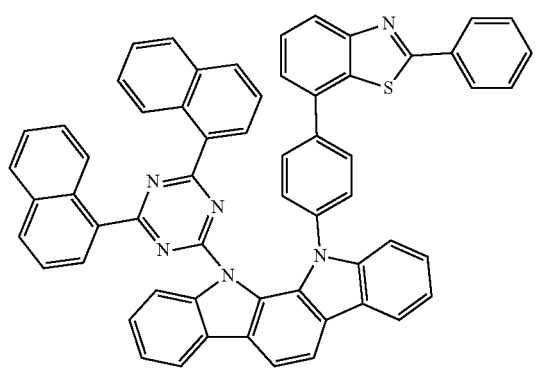 | 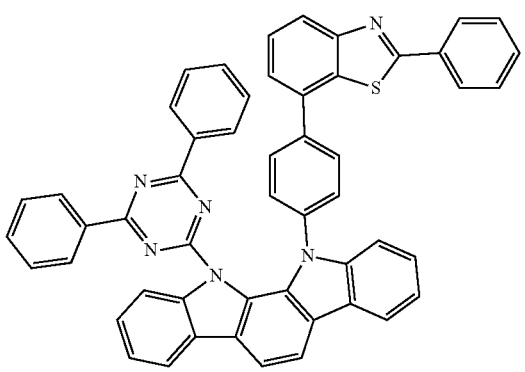 |
| 350 | 351 |
| 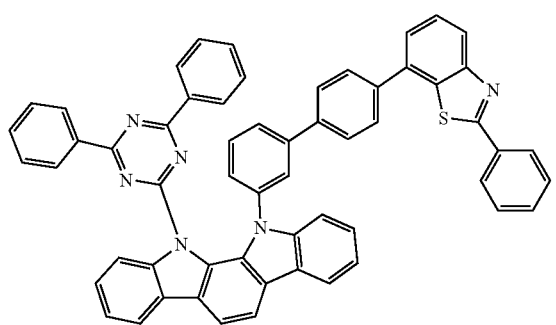 | 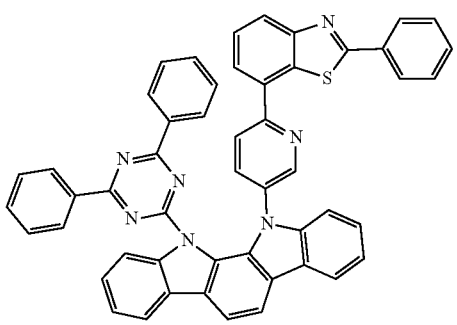 |

-continued
352
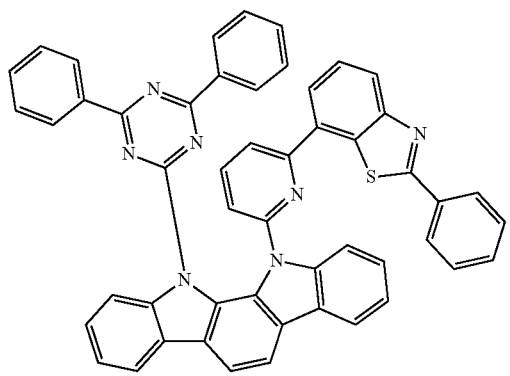
353
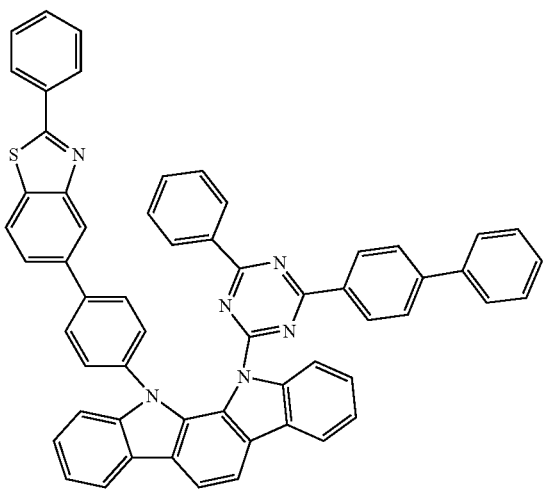
354
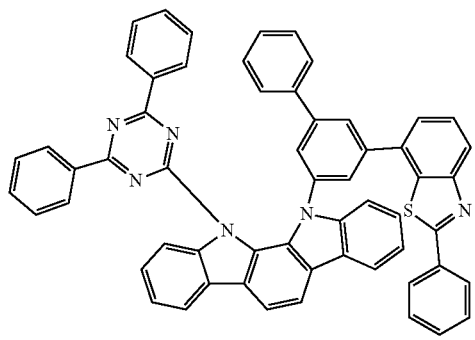
355
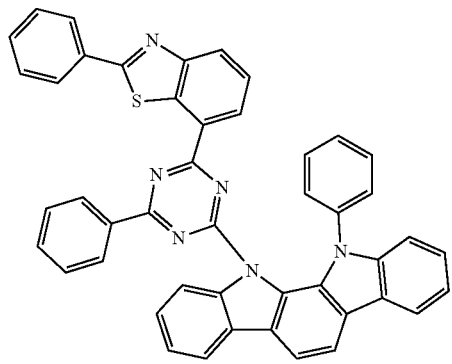
356
357
358
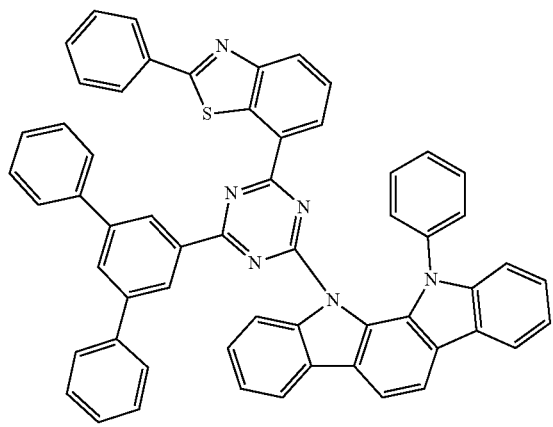
359
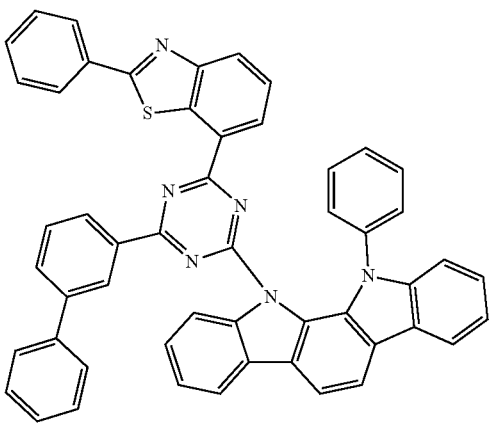

-continued
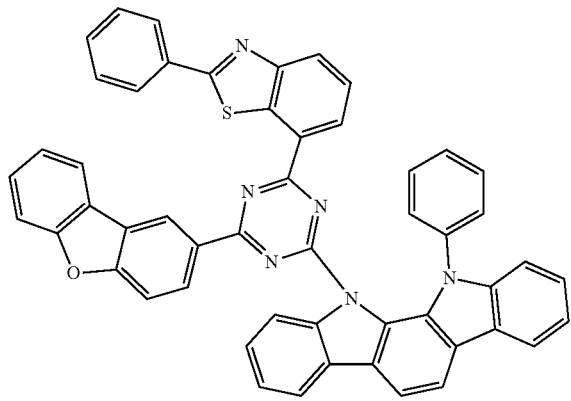
360
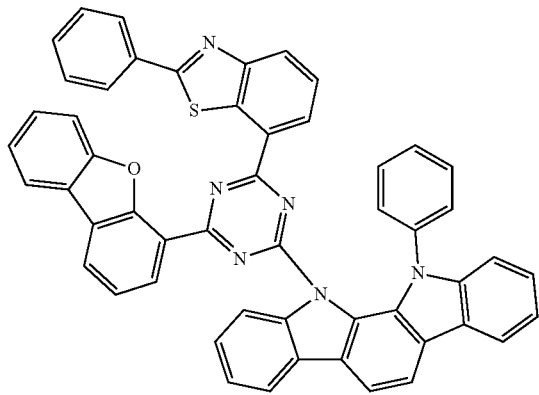
361
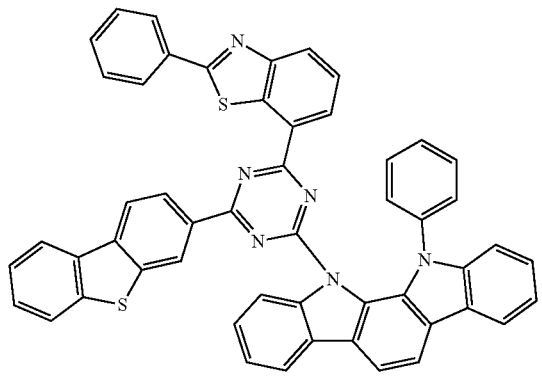
362
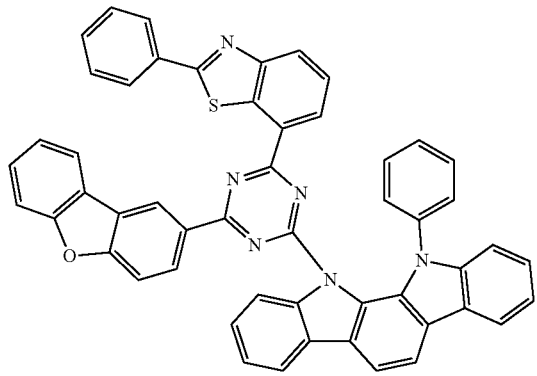
363
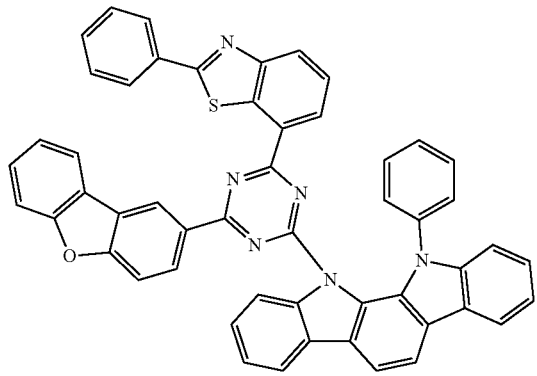
364
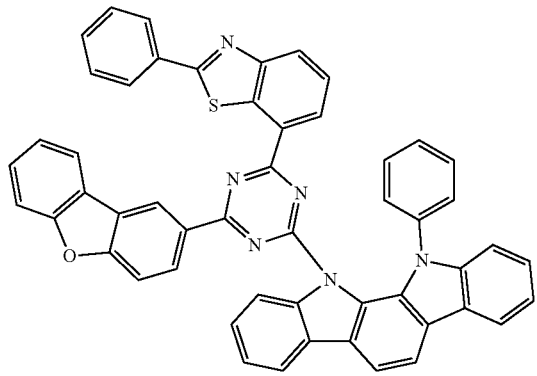
365
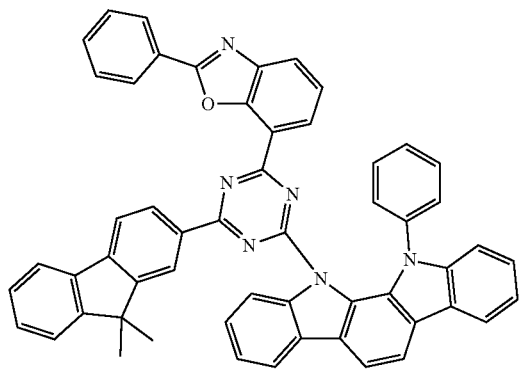
366
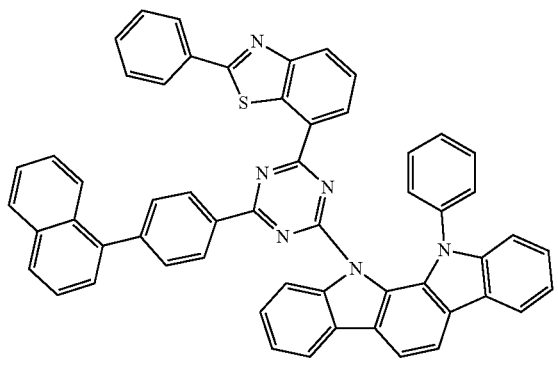
367

-continued
368
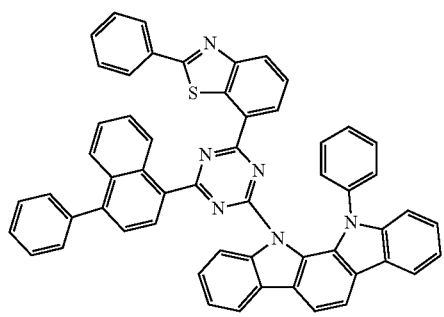
369
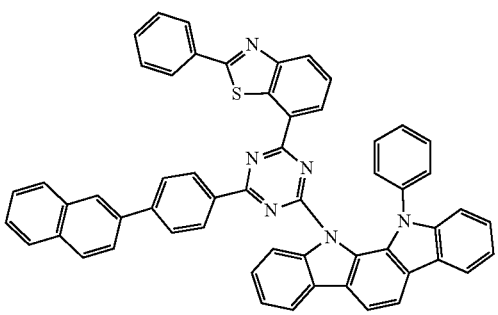
370
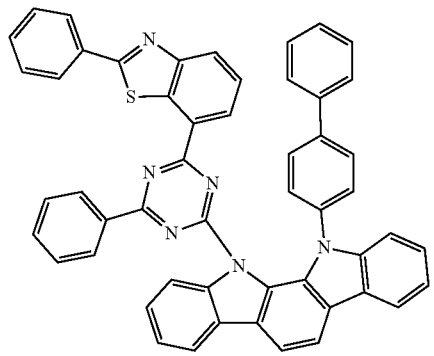
371
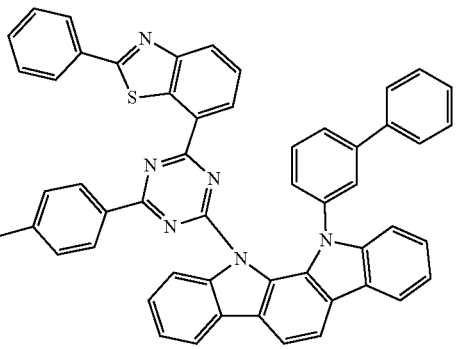
372
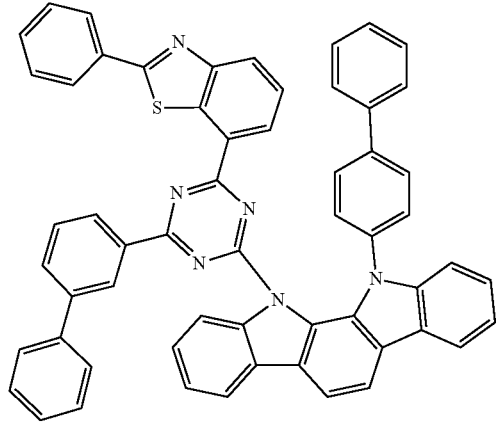
373
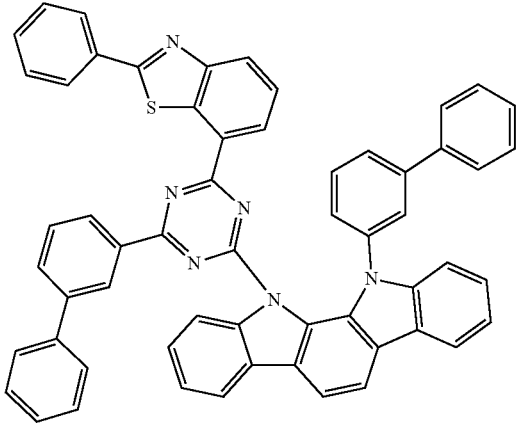
374
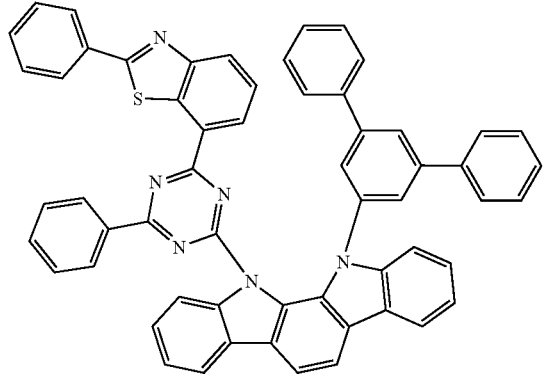
375
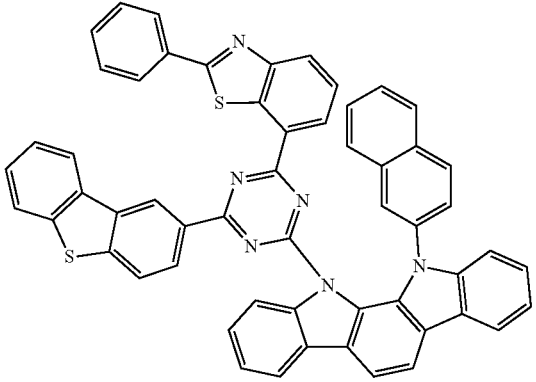

-continued
376
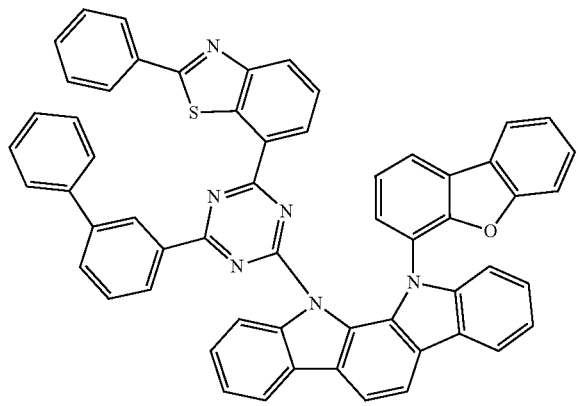
377
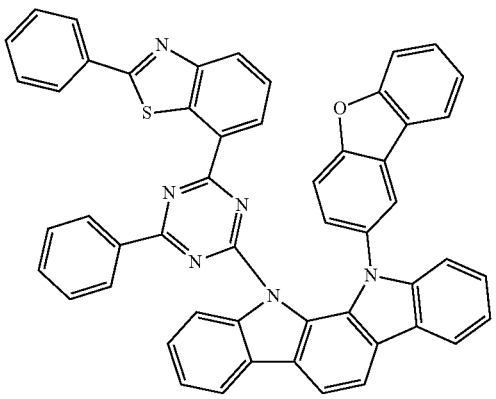
378
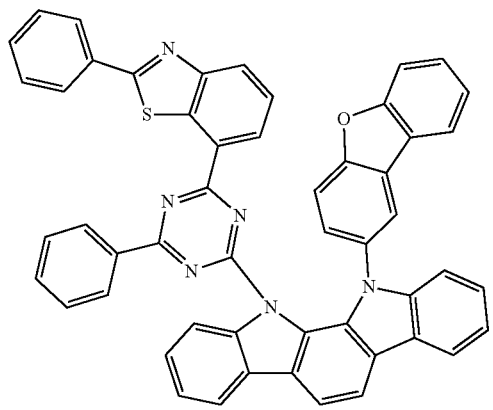
379
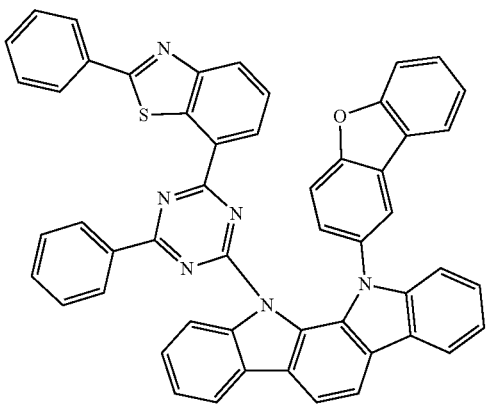
380
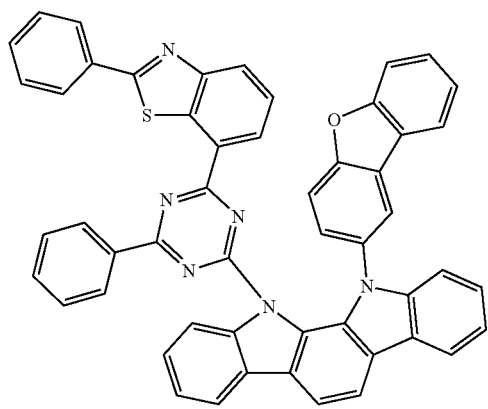
381
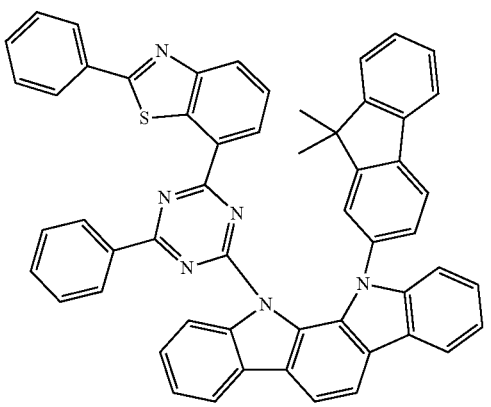
382
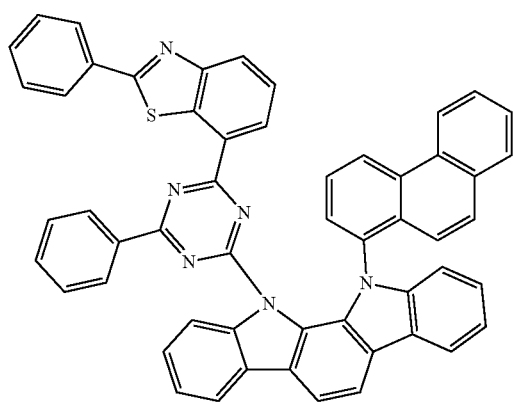
383
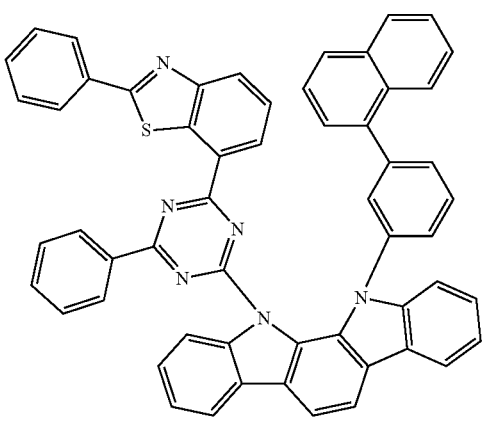

-continued
384
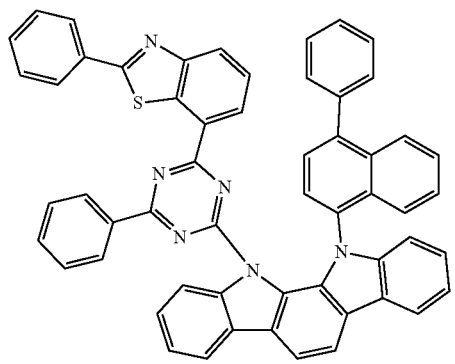
385
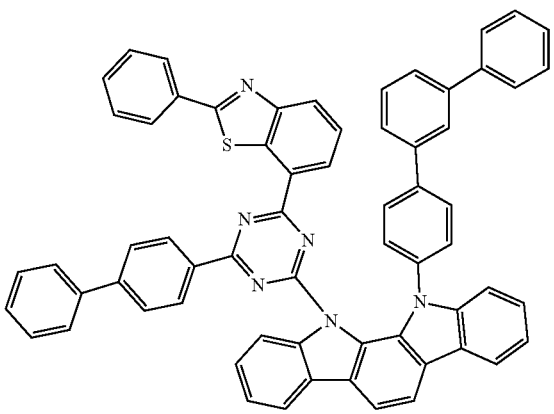
389
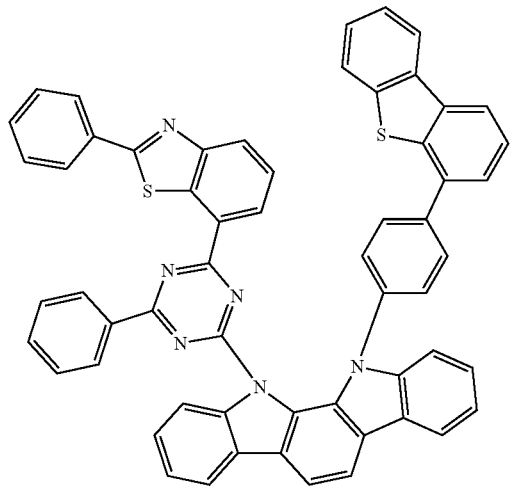
390
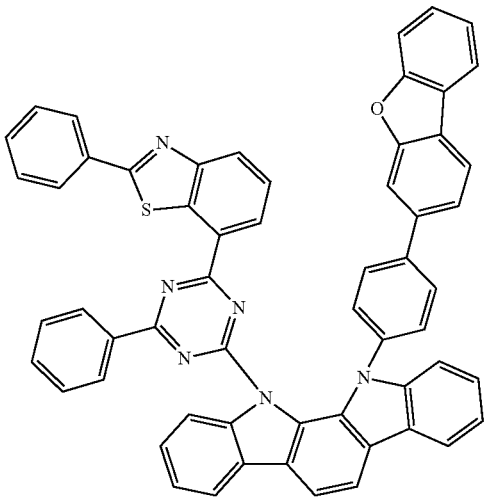
391
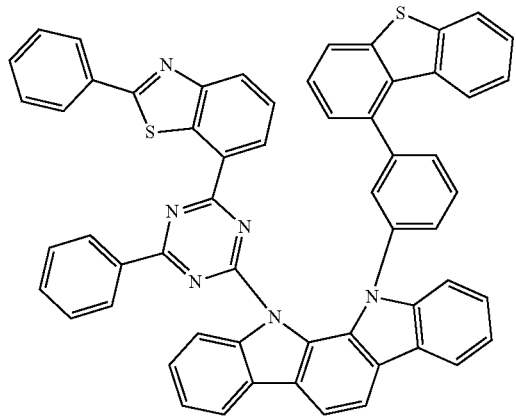
392
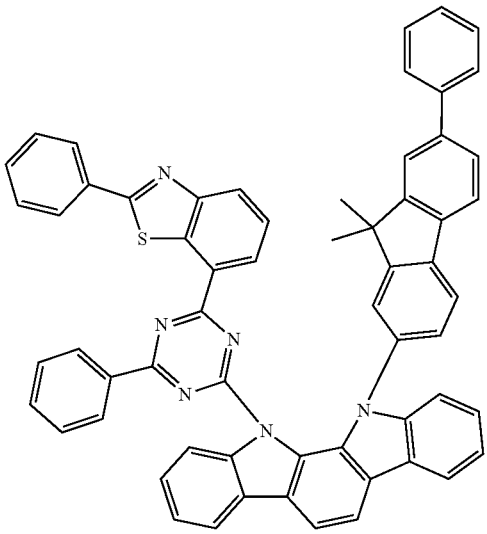

-continued
393
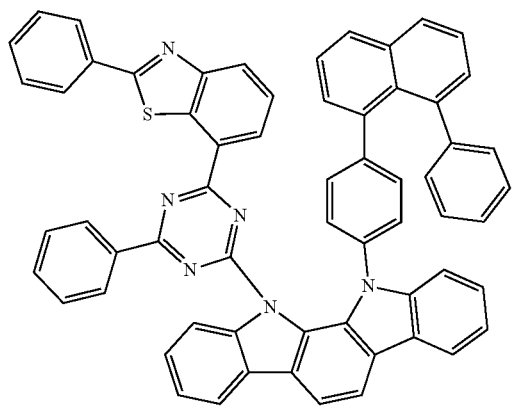
394
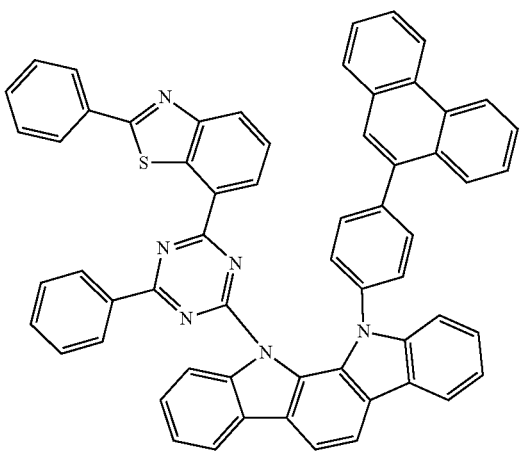
395
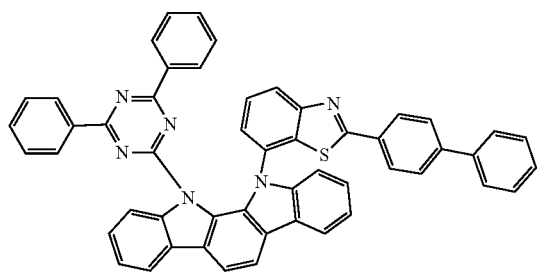
396
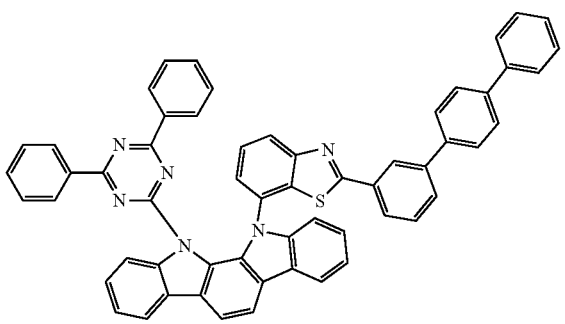
397
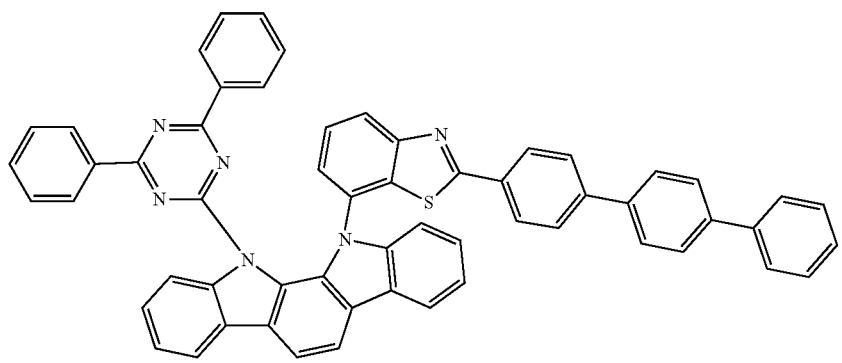
398
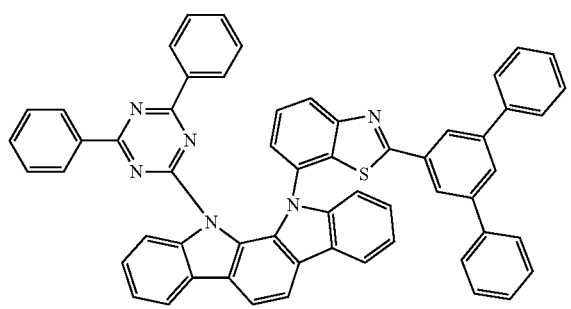
399
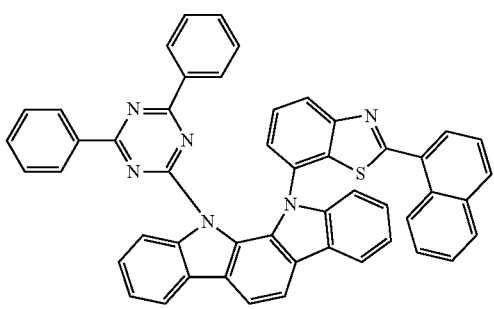

400 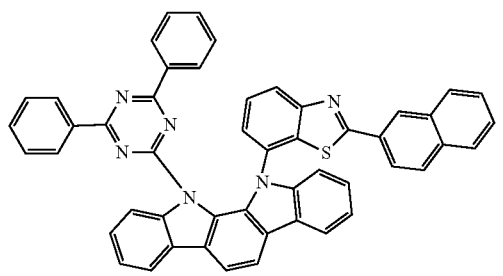
401 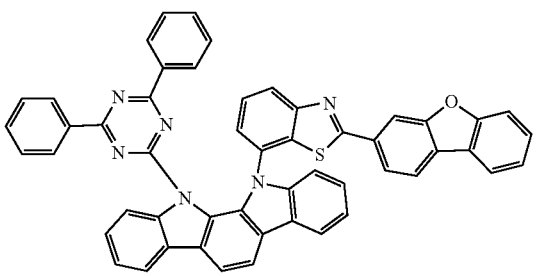
402 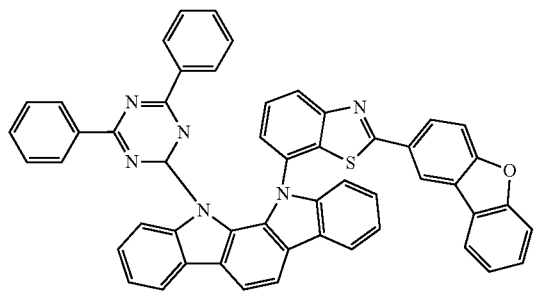
403 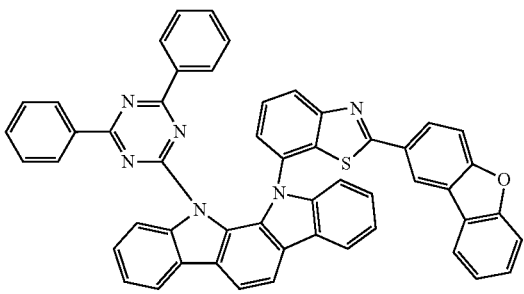
404 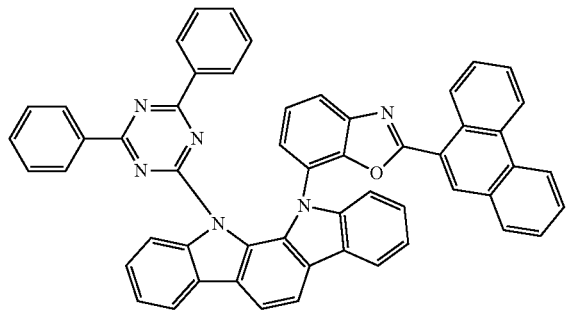
405 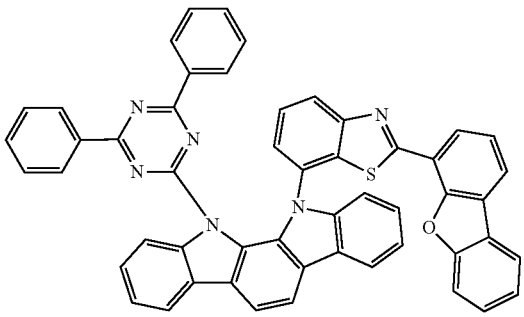
406 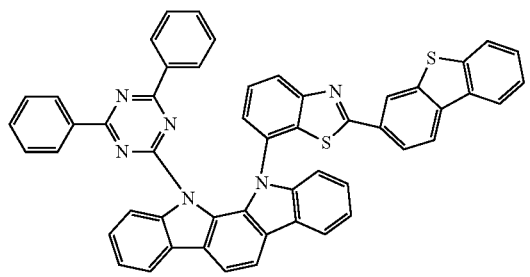
407 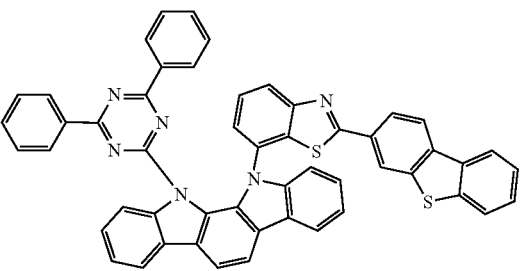
408 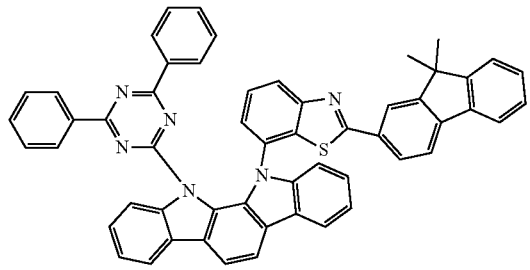
409 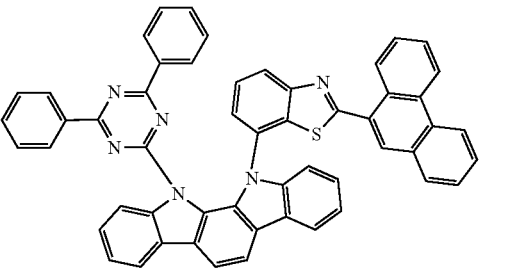

-continued
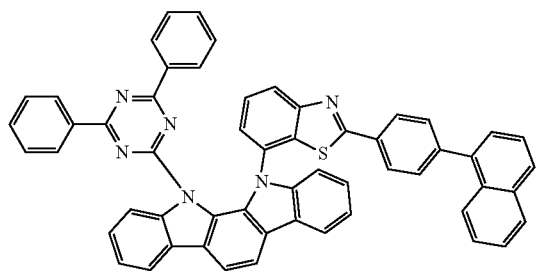
410
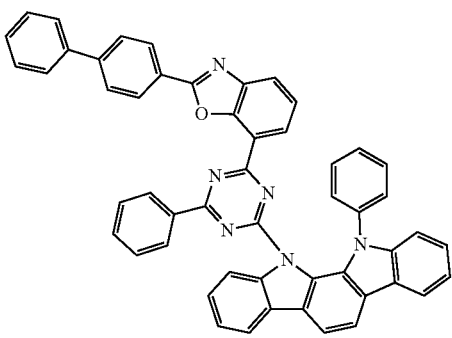
411
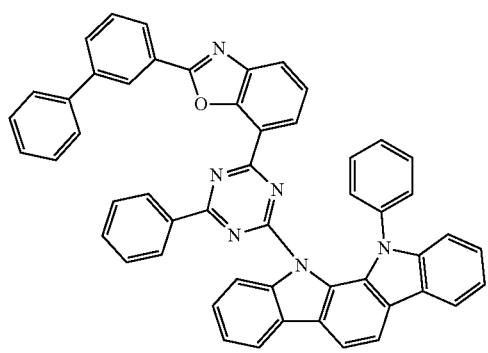
412
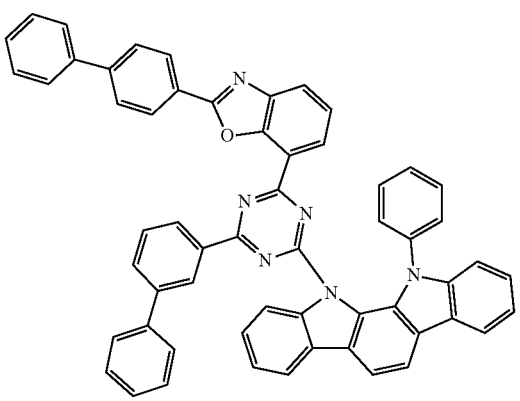
413
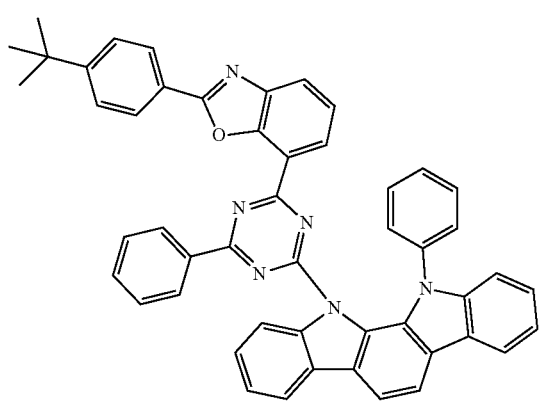
414
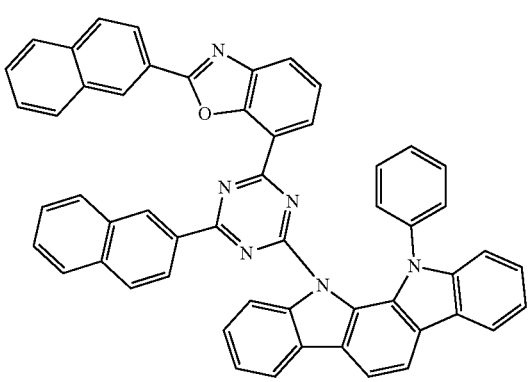
415
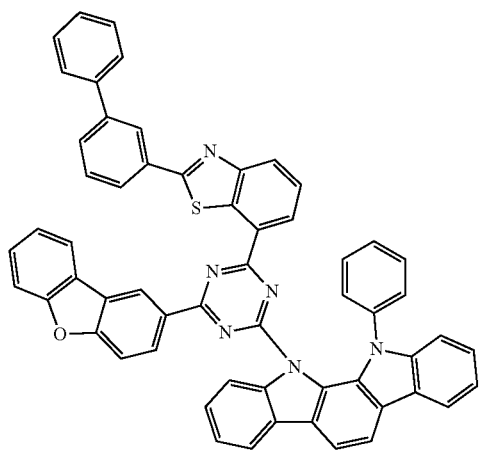
416
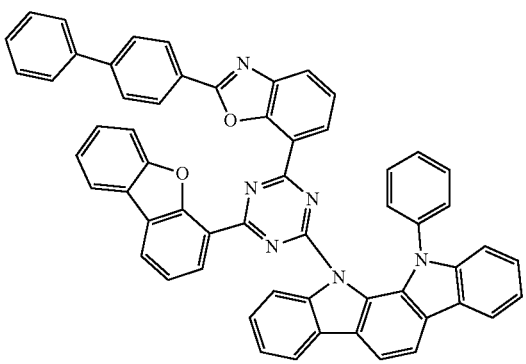
417

-continued
418
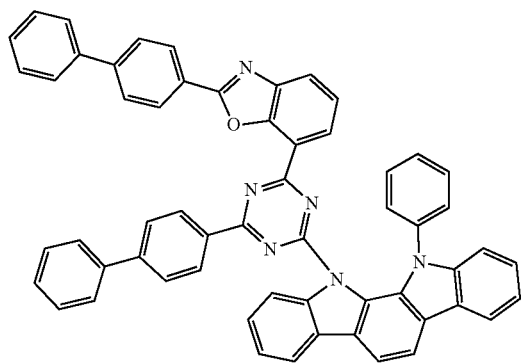
419
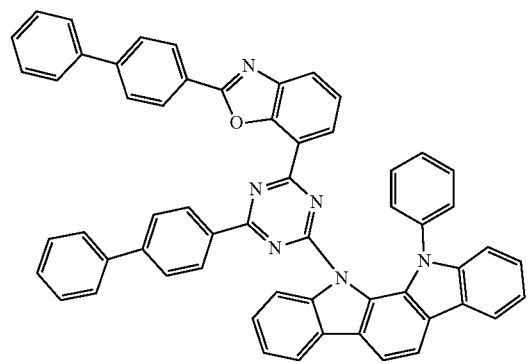
420
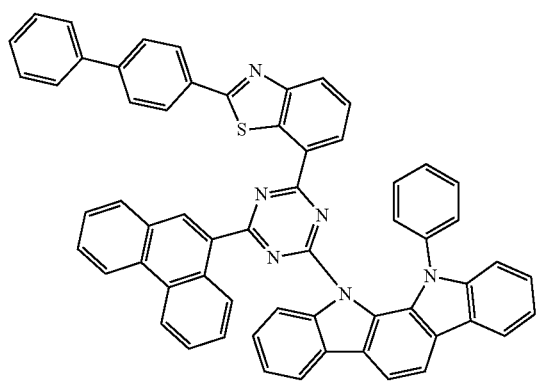
421
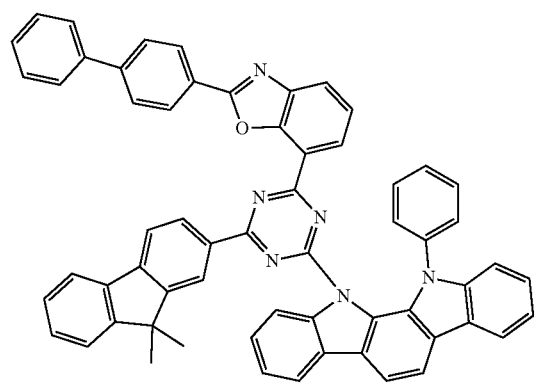
422
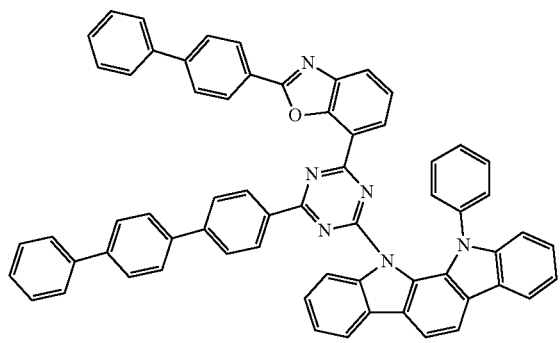
423
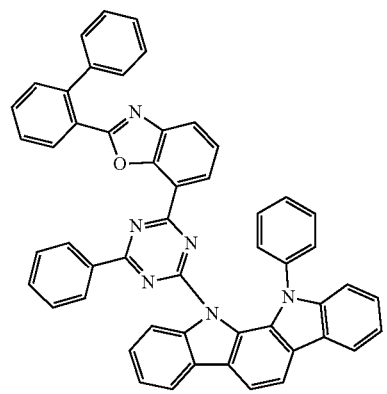
424
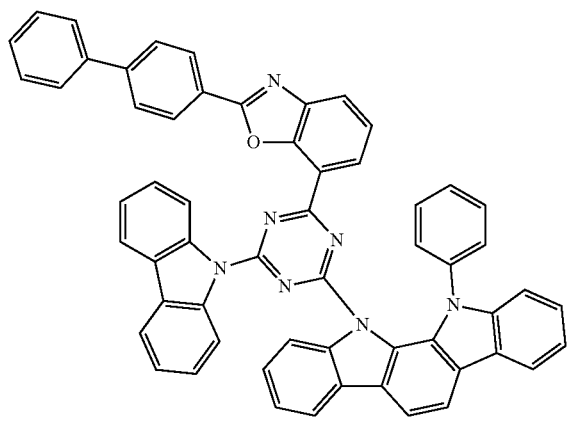
425
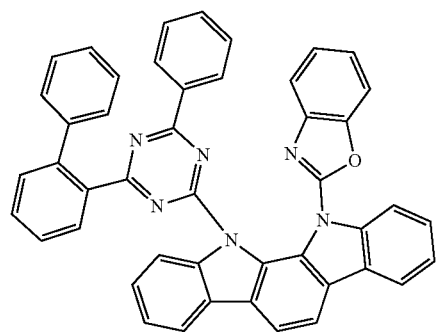

-continued
426
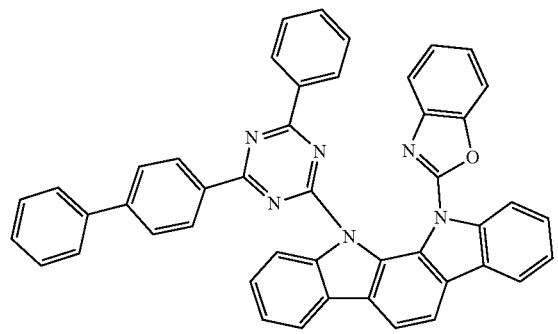
427
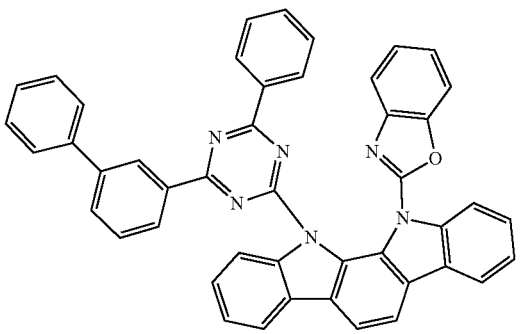
428
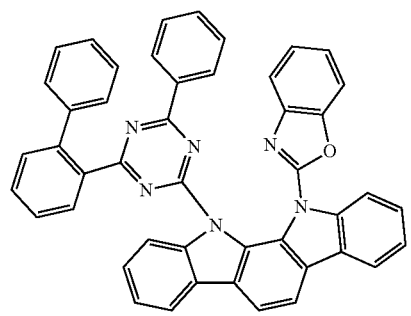
429
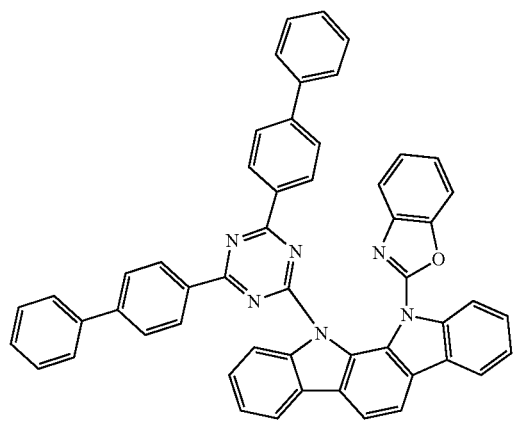
430
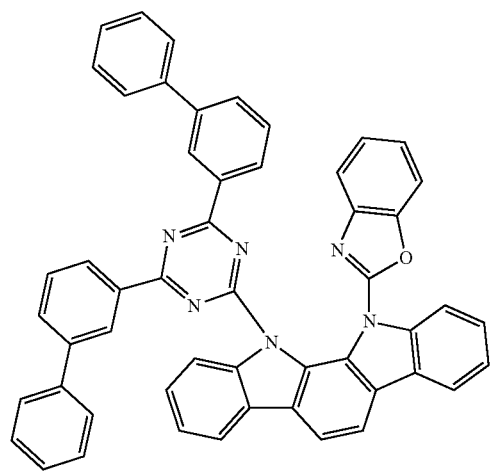
431
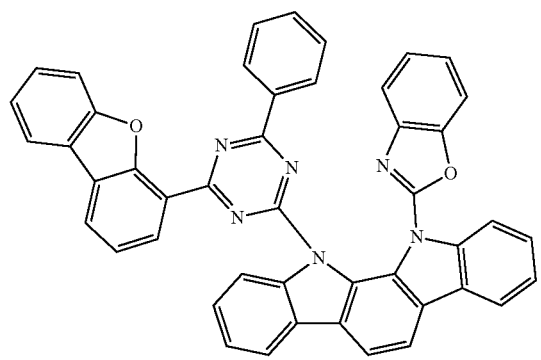
432
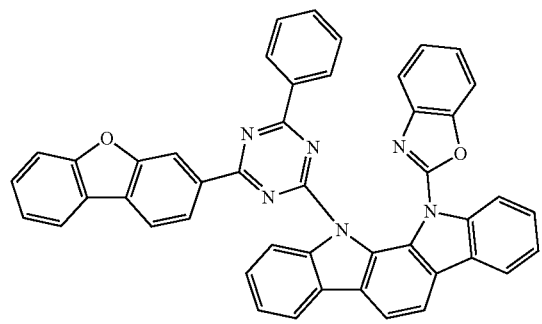
433
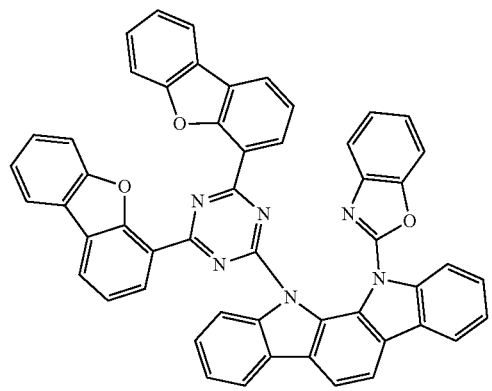

-continued
433
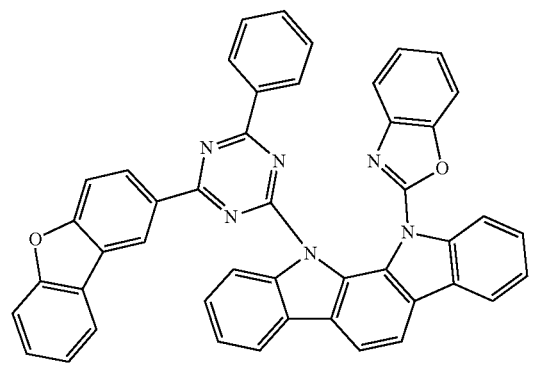
-continued
435
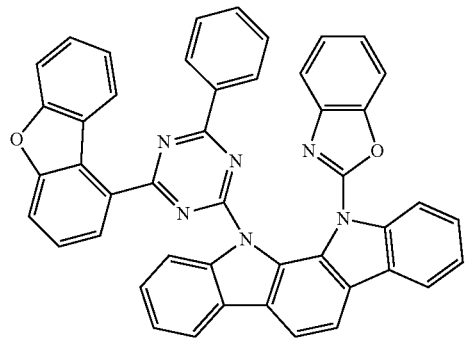
438
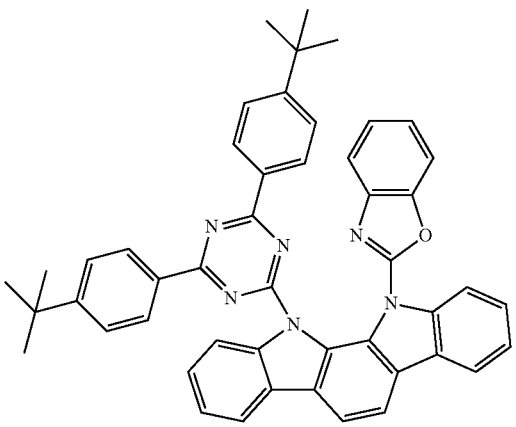
436
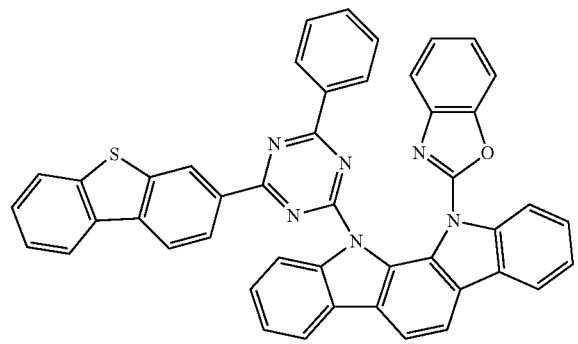
439
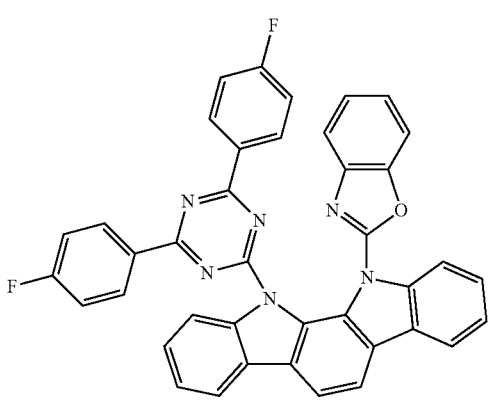
437
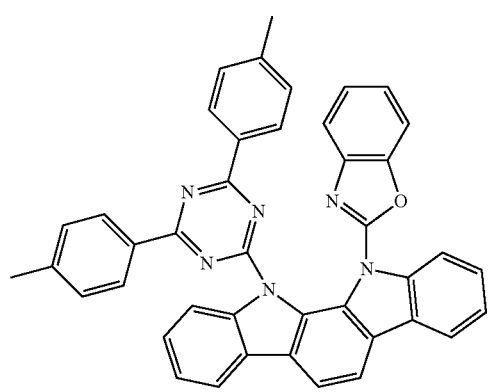
440
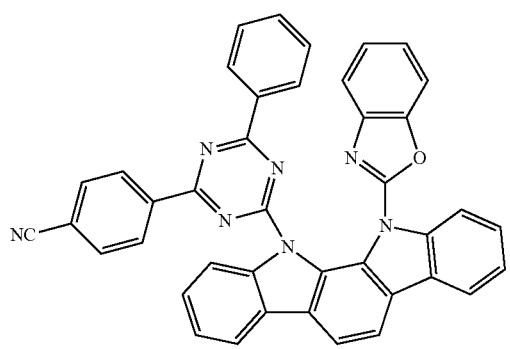

441
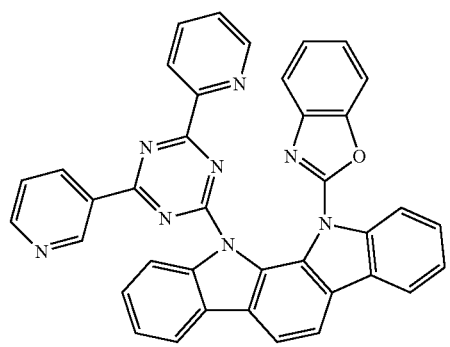
442
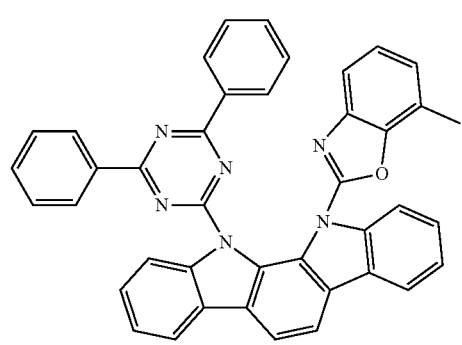
443
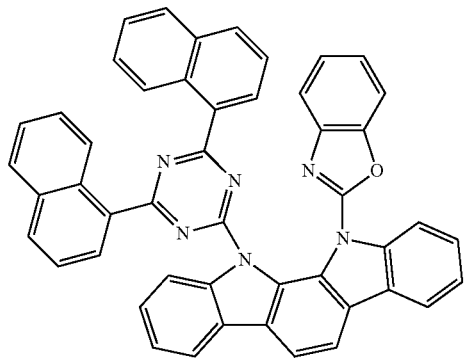
444
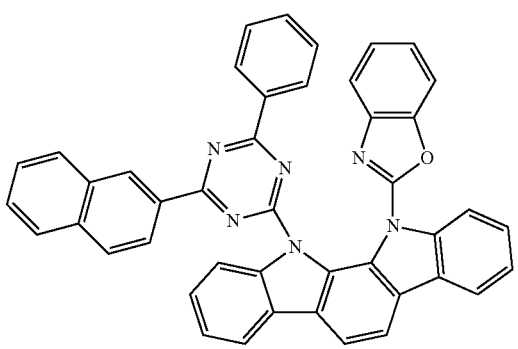
445
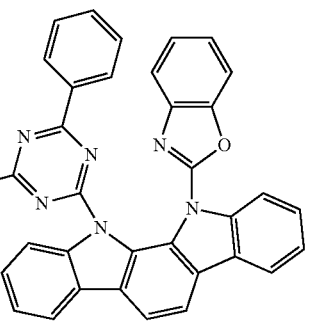
446
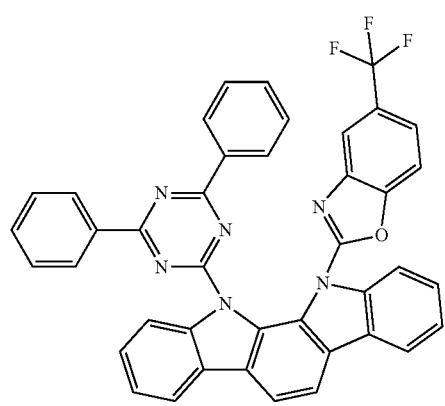
447
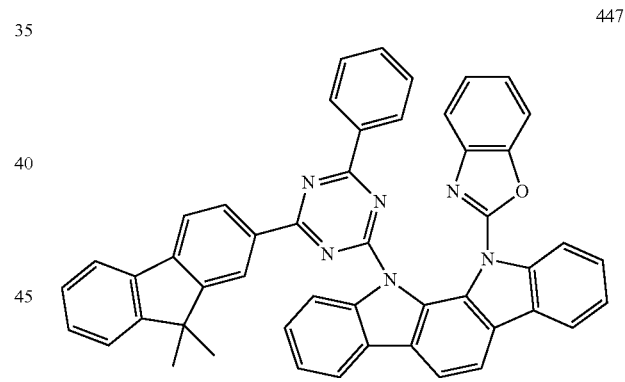
448
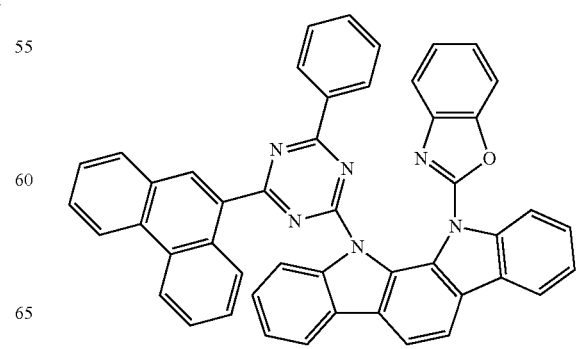

449
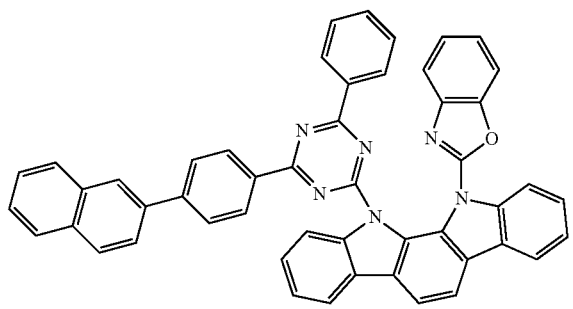
450
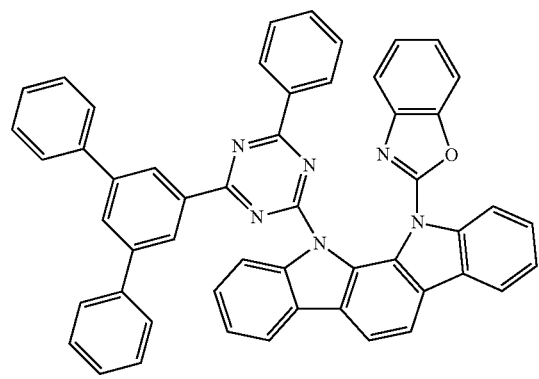
451
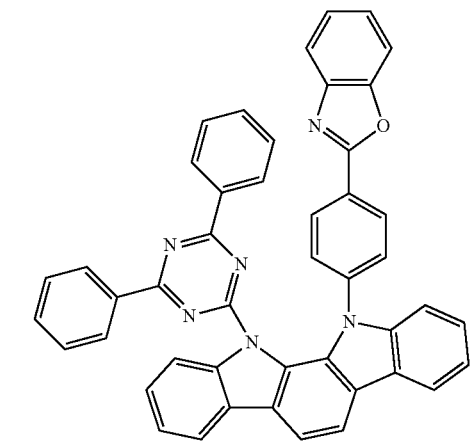
452
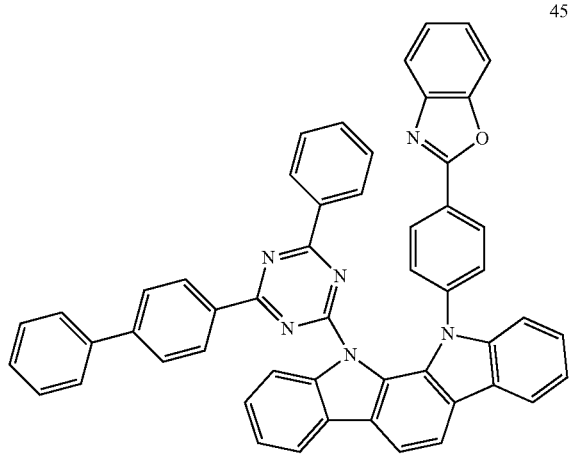
453
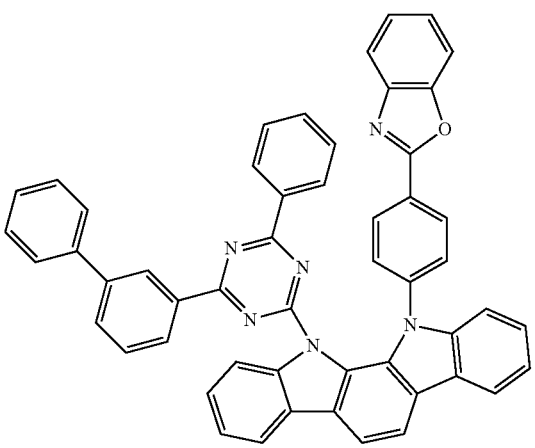
454
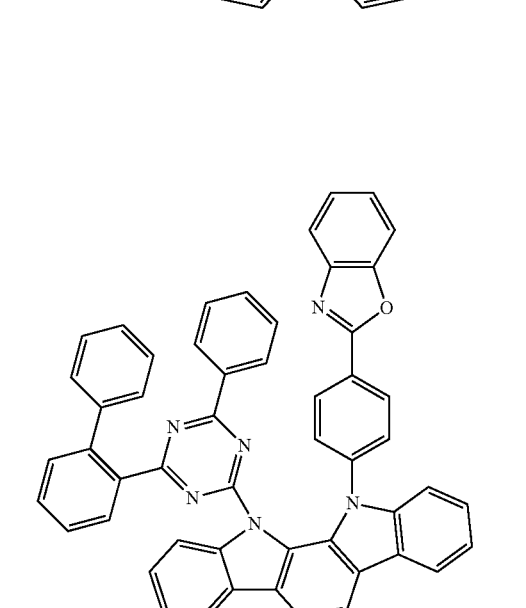
455
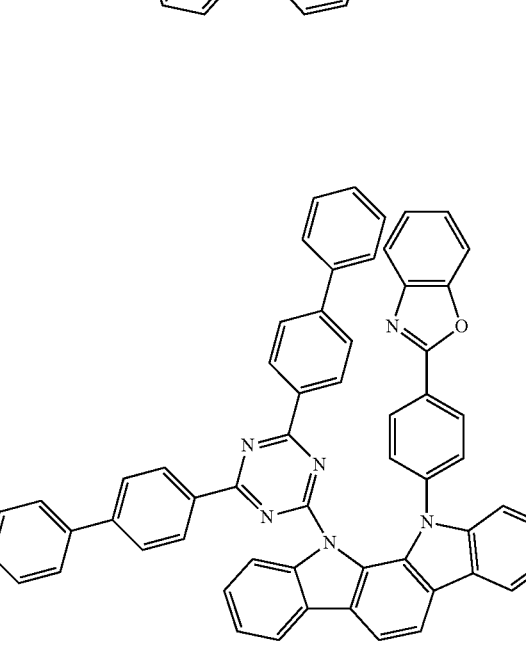

-continued
456
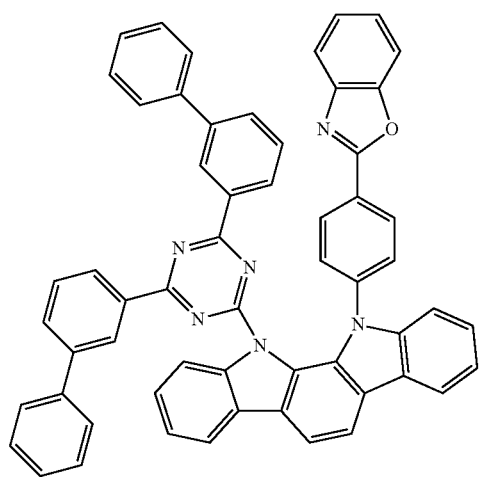
457
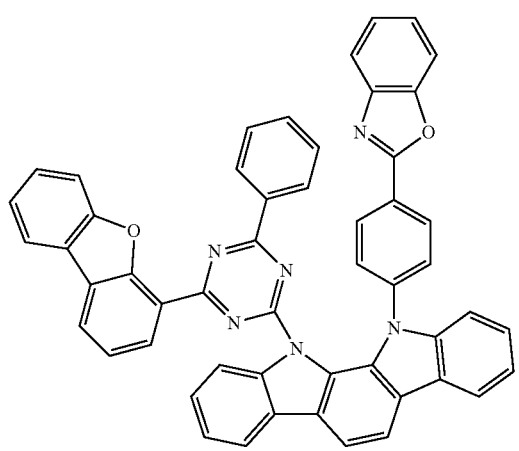
458
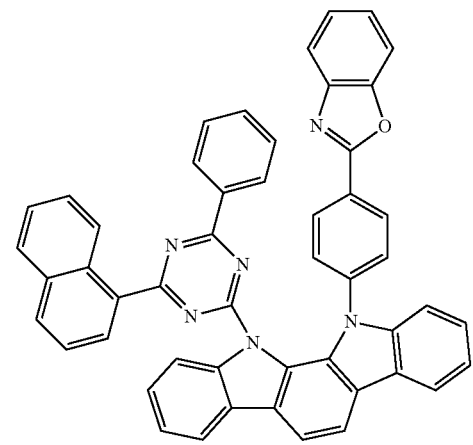
-continued
459
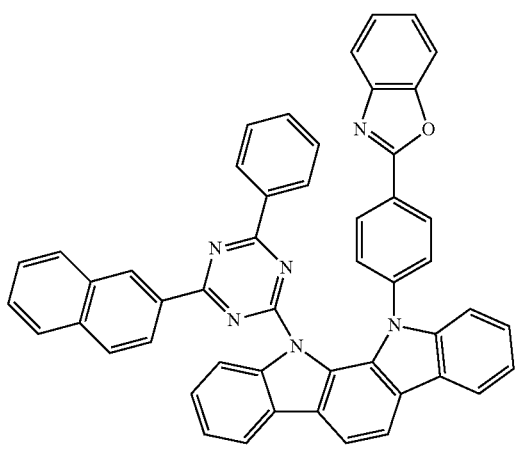
460
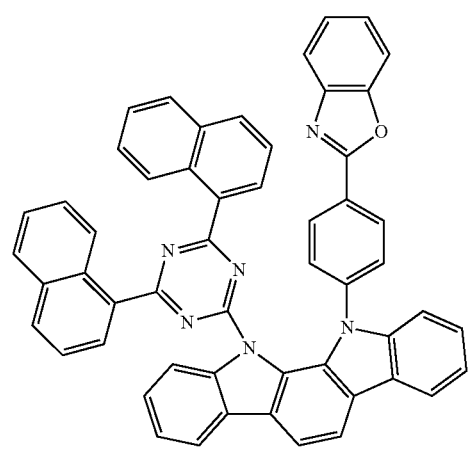
461
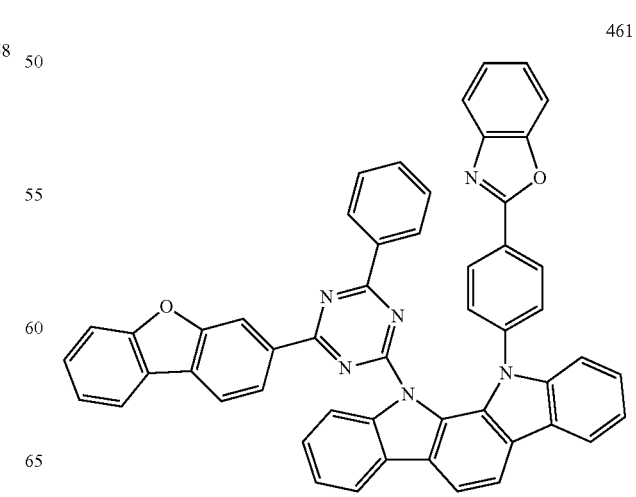

462
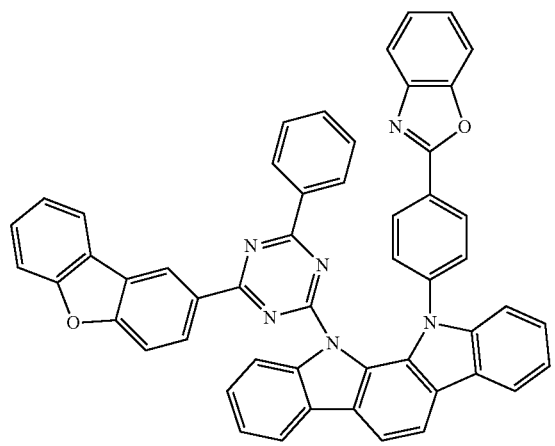
465
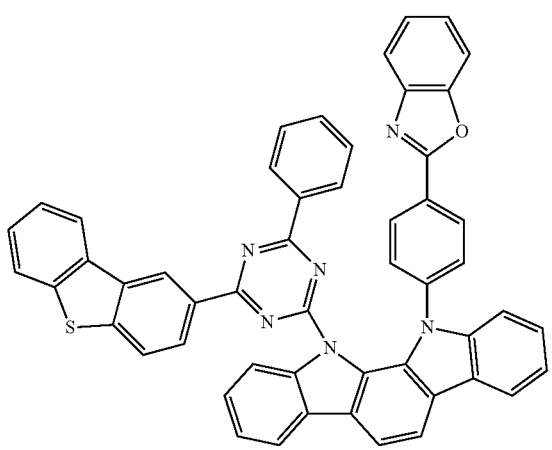
463
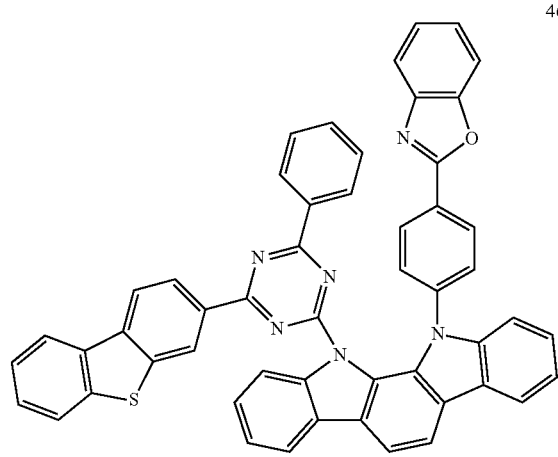
466
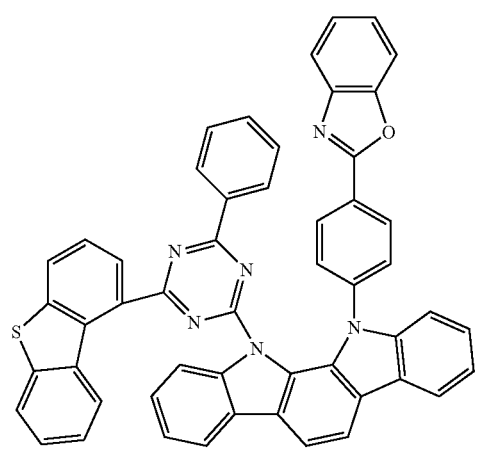
464
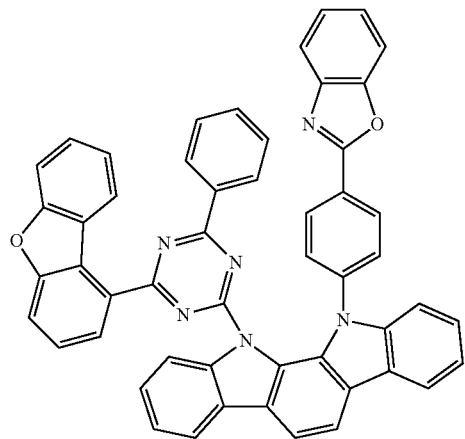
467
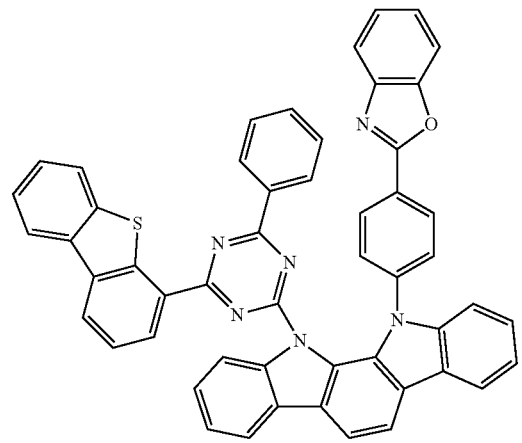

468
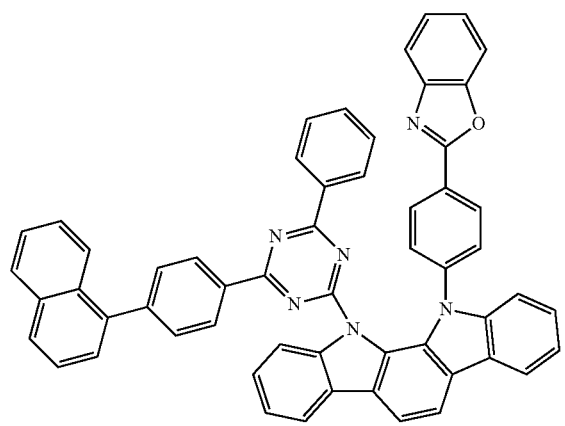
469
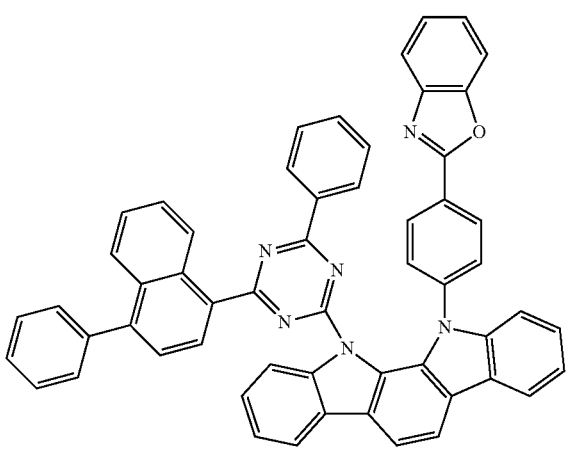
470
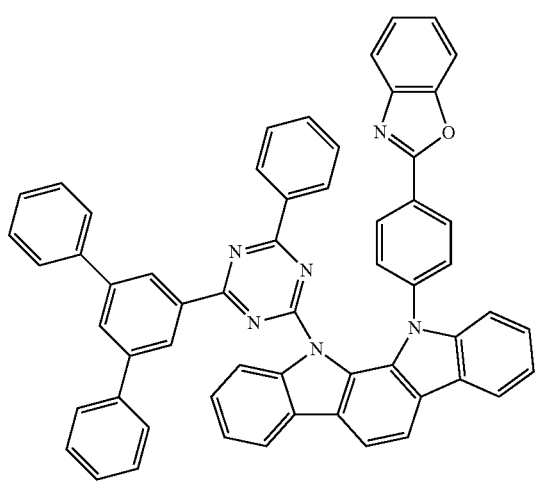
471
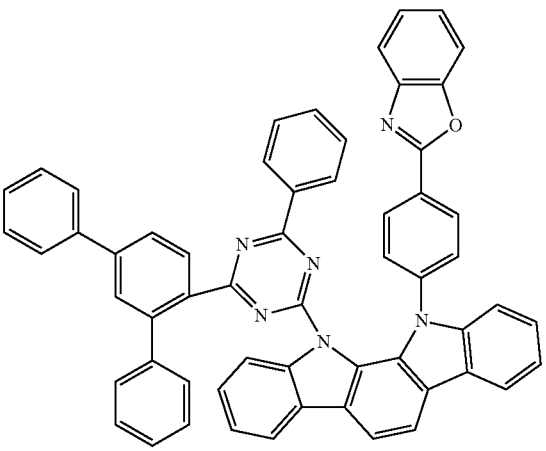
472
473
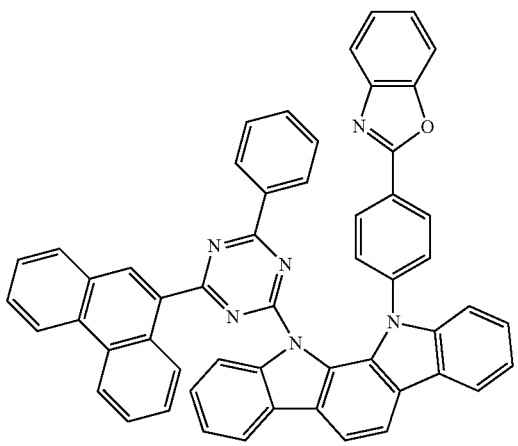

474
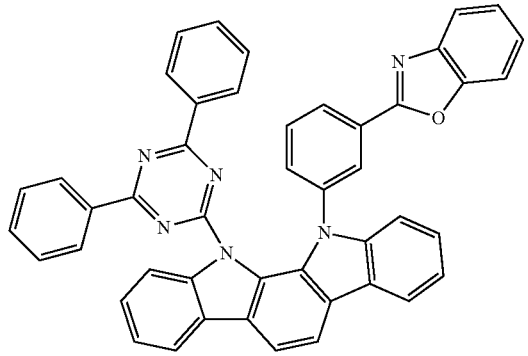
475
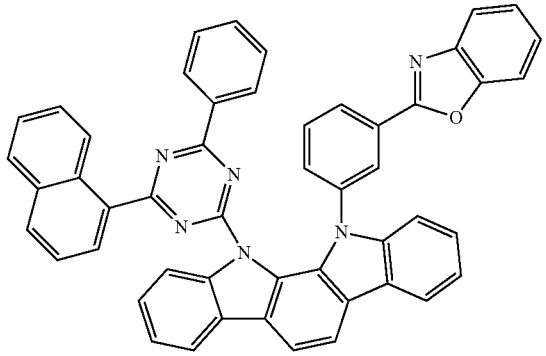
476
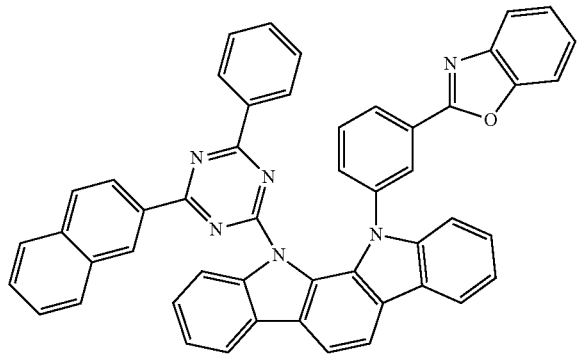
477
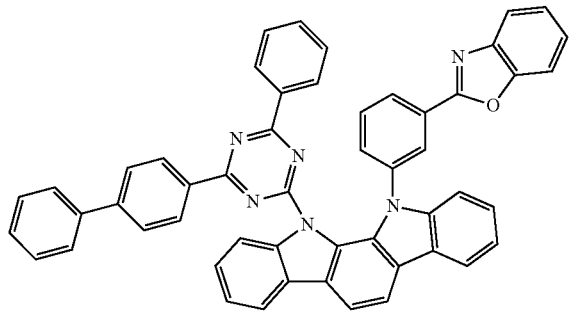
478
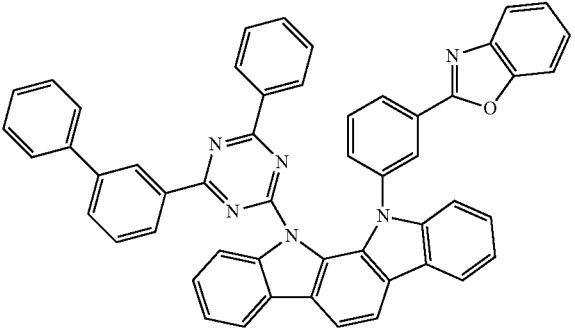
479
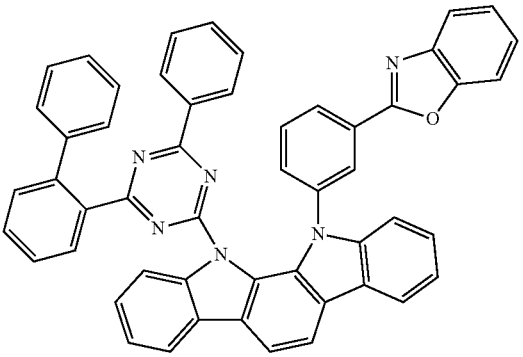
480
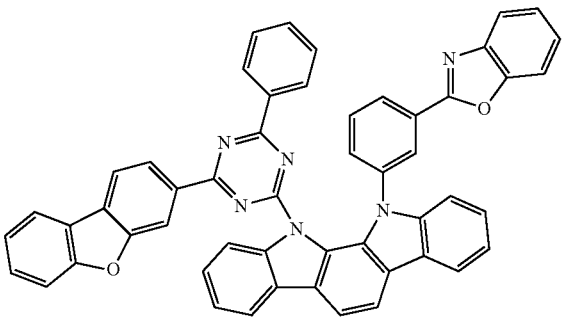
481
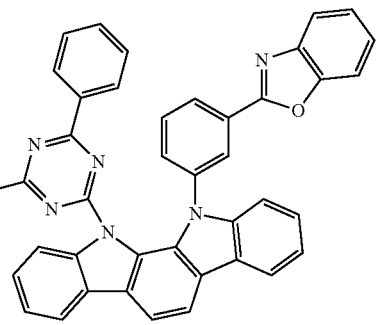

482
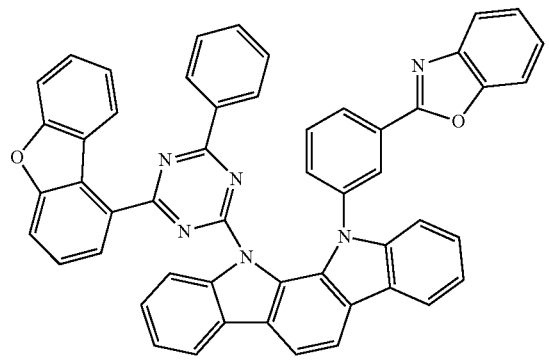
486
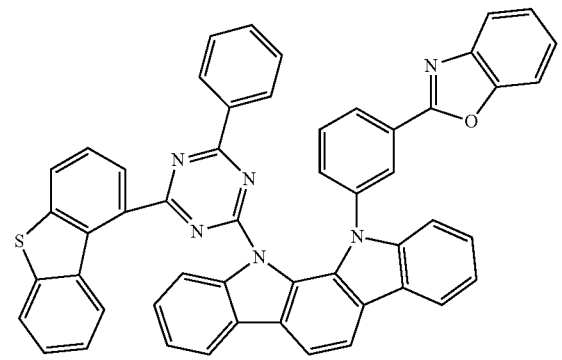
483
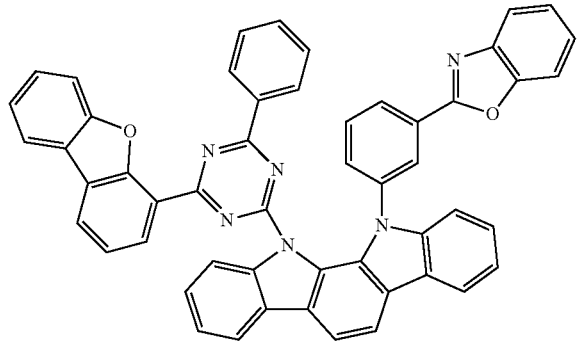
487
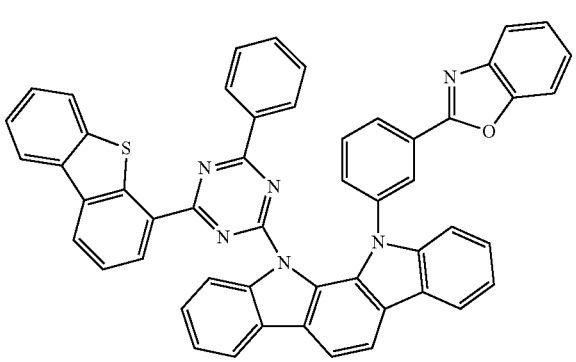
484
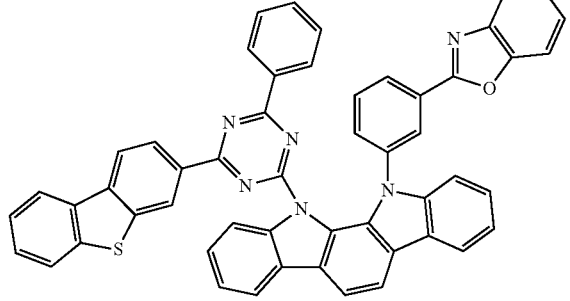
488
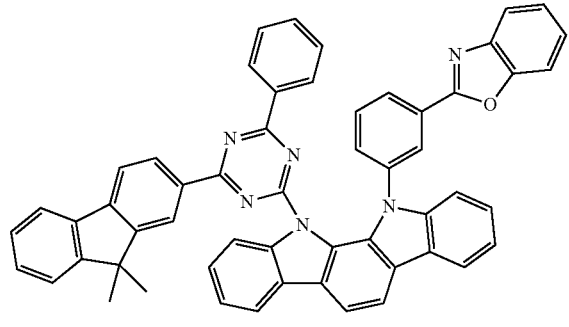
485
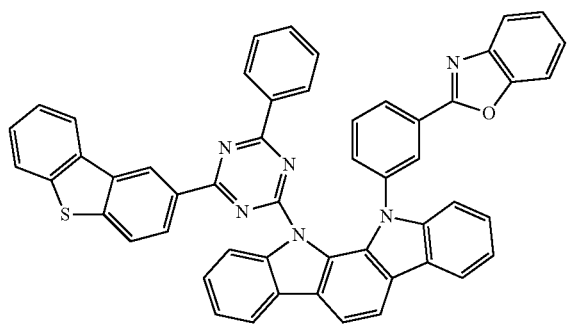
489
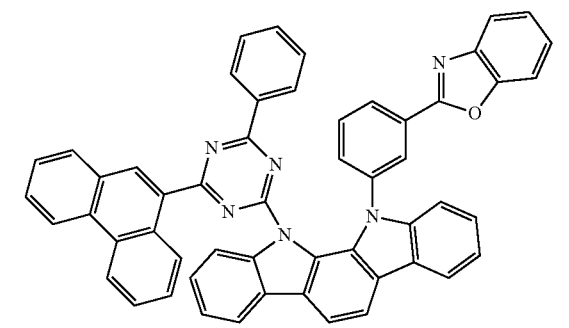

-continued
490
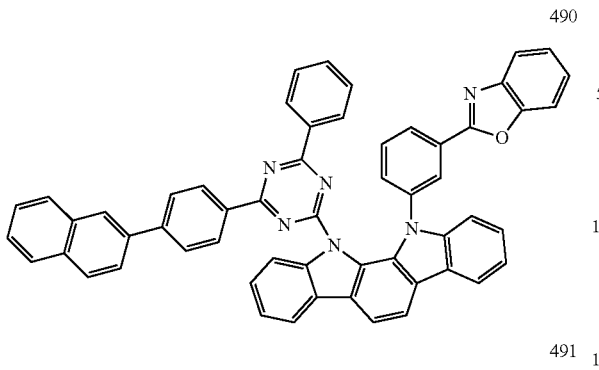
491
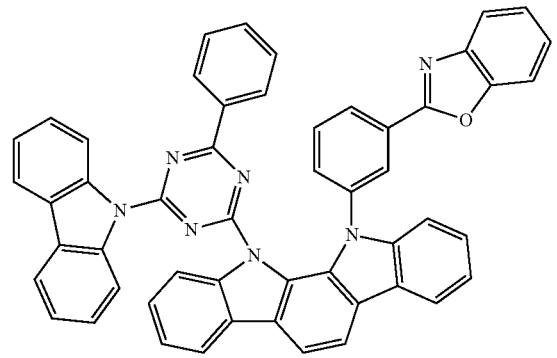
492
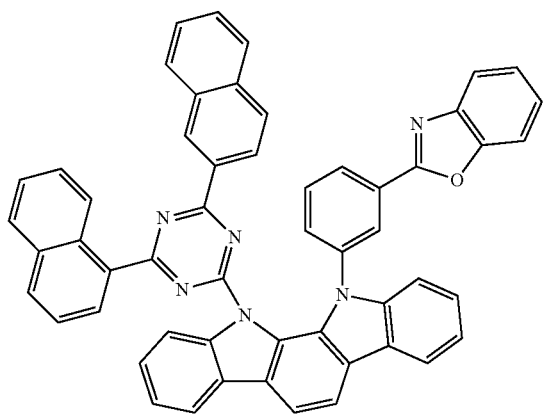
493
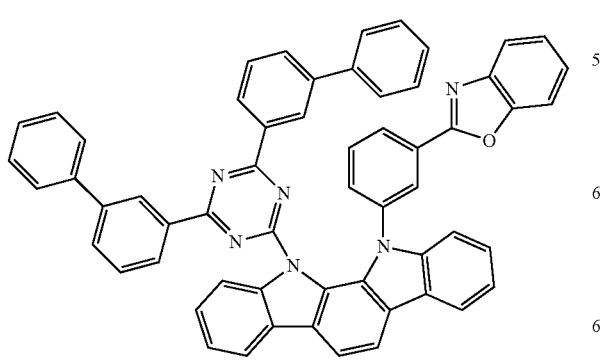
-continued
494
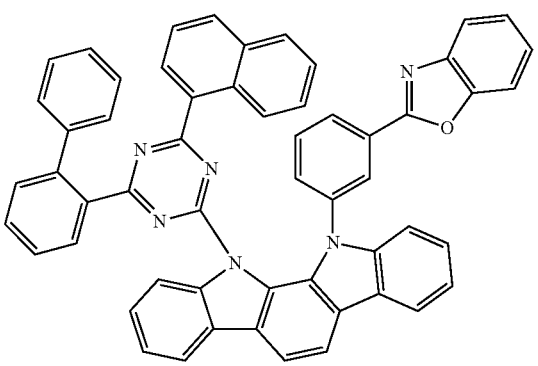
495
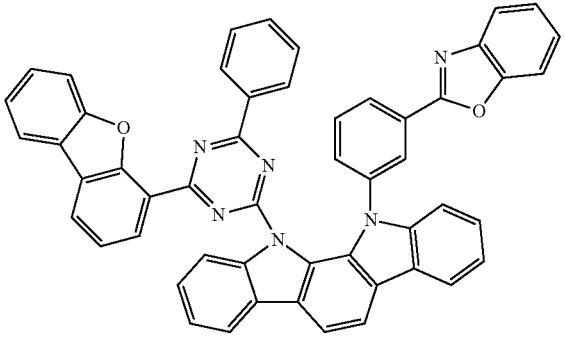
496
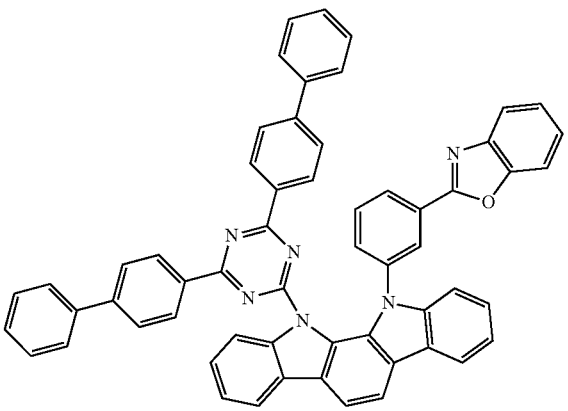
497
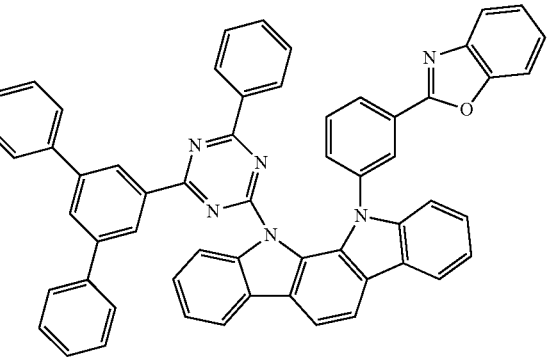

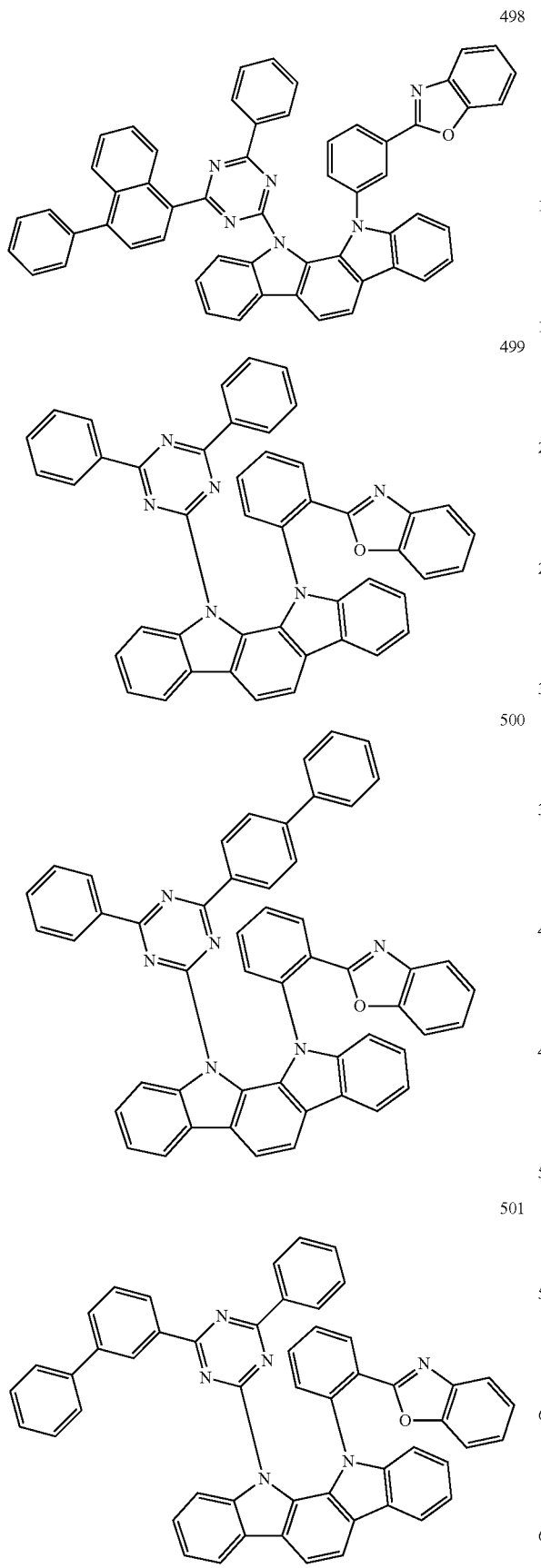
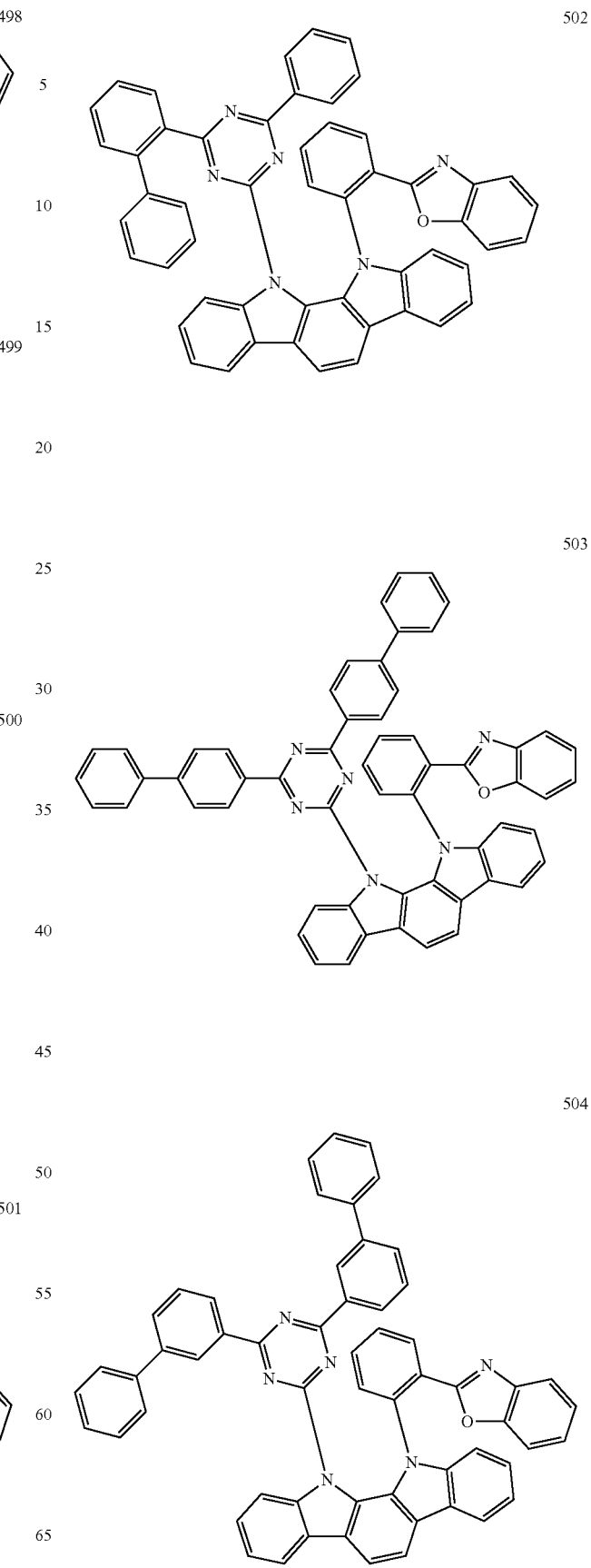

505
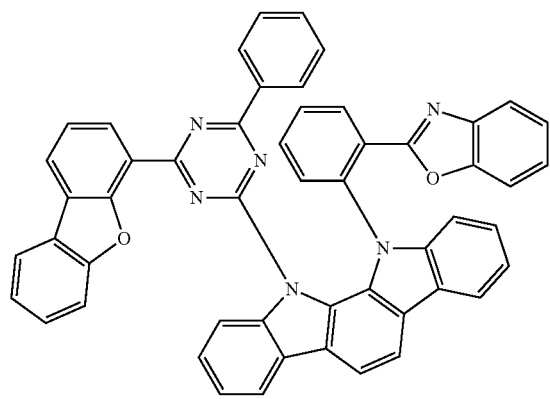
506
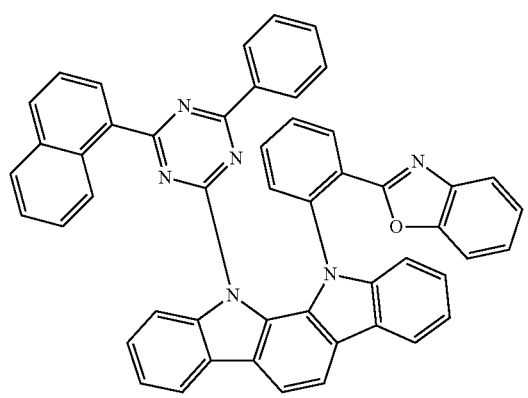
507
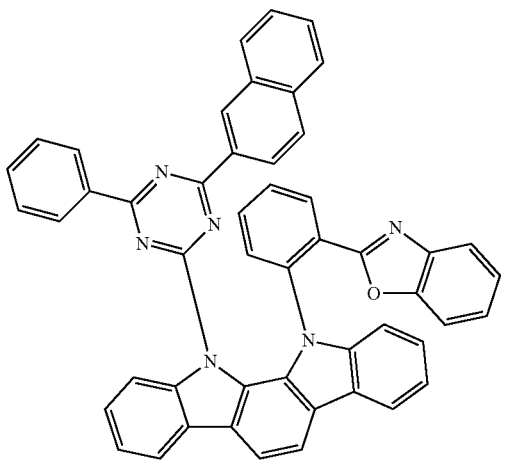
508
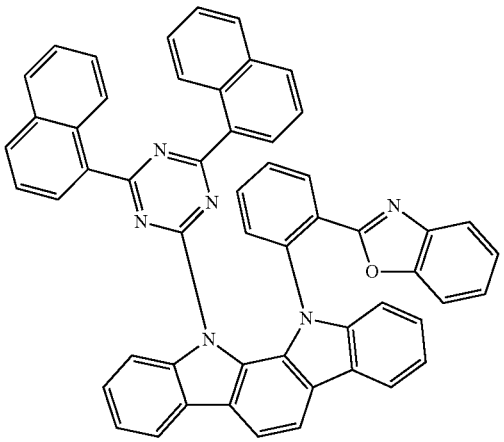
509
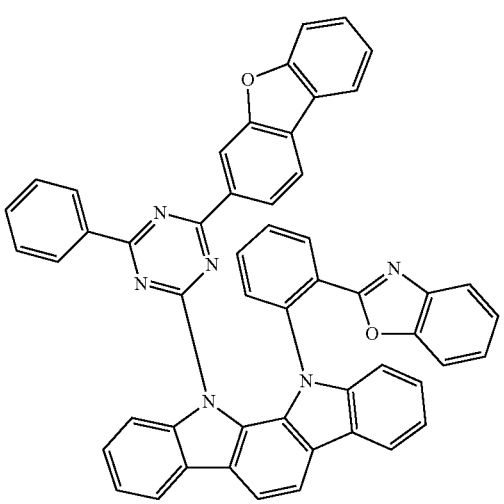
510
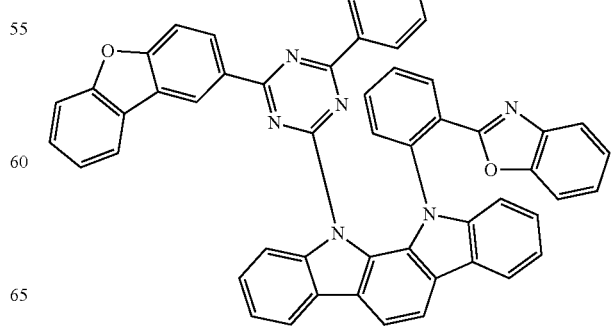

-continued
511
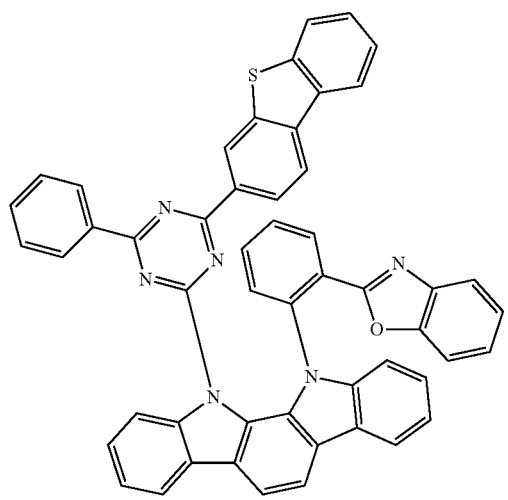
512
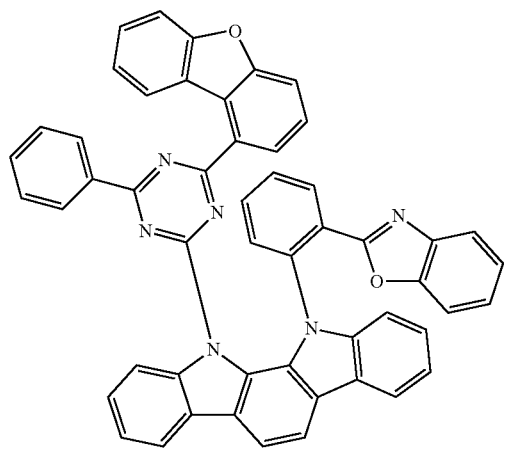
513
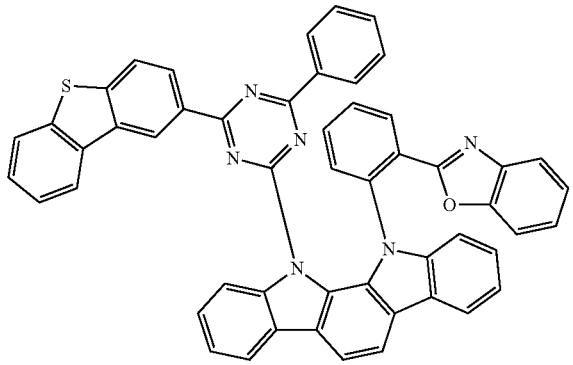
-continued
514
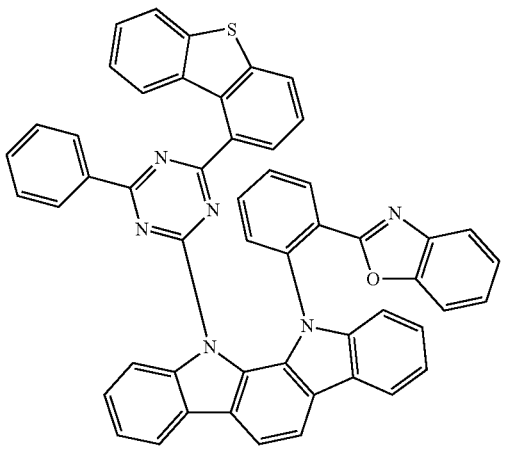
515
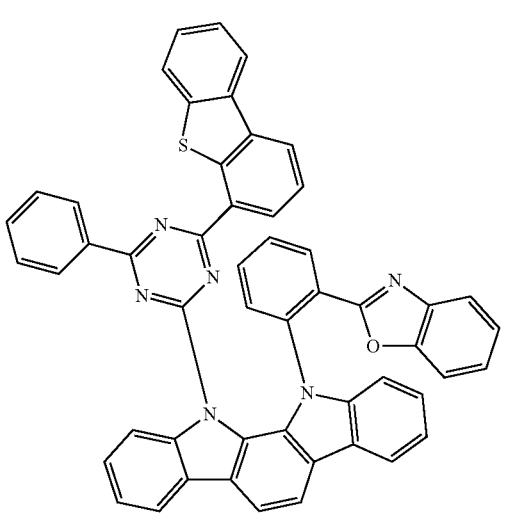
516
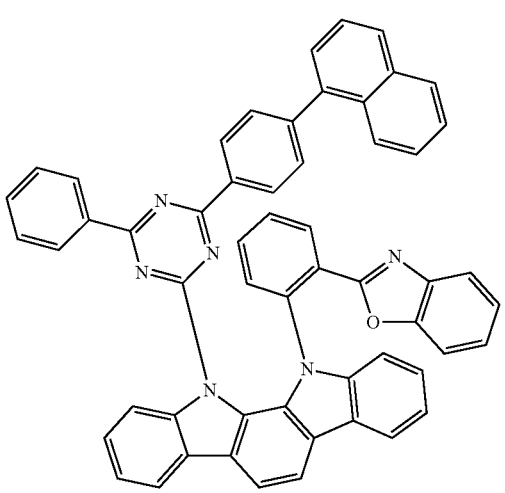

517
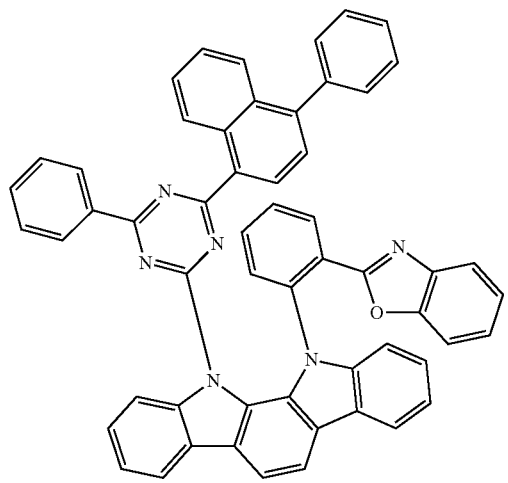
518
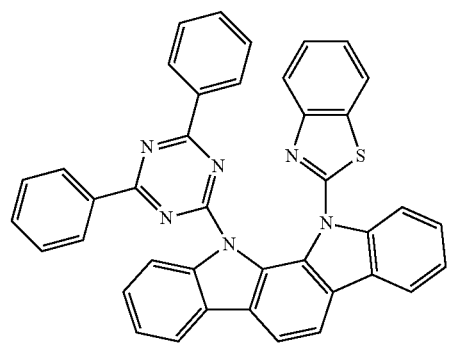
519
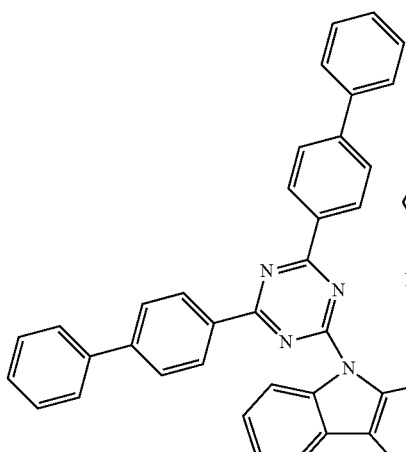
520
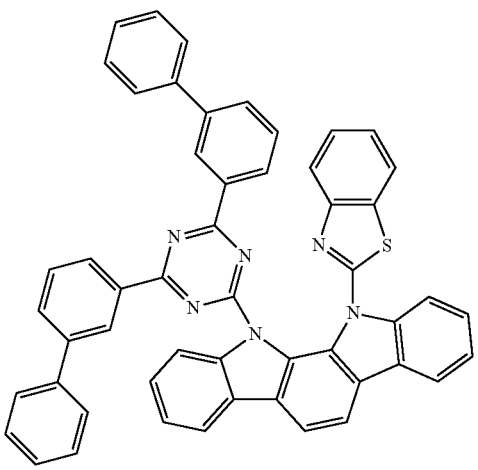
521
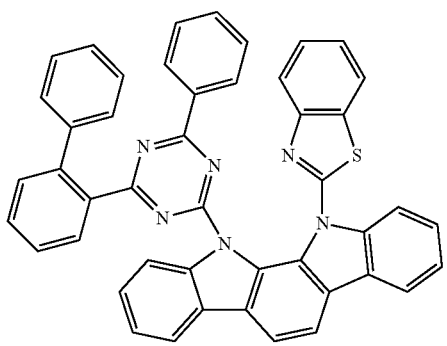
522
523
524
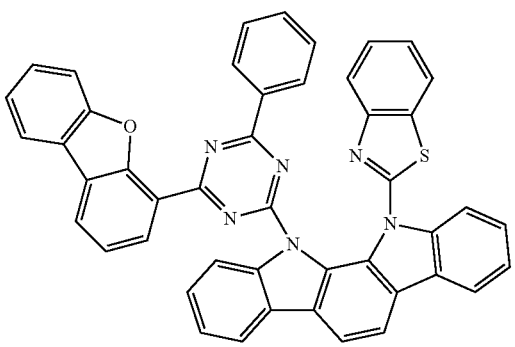

189
-continued
525
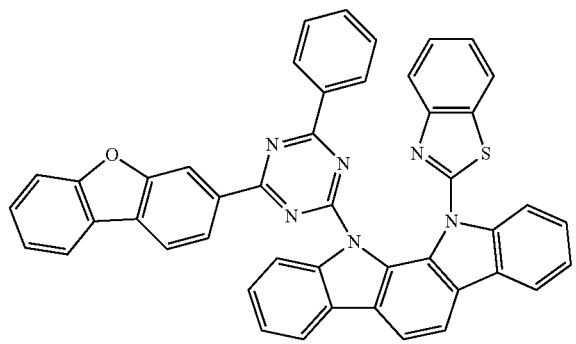
526
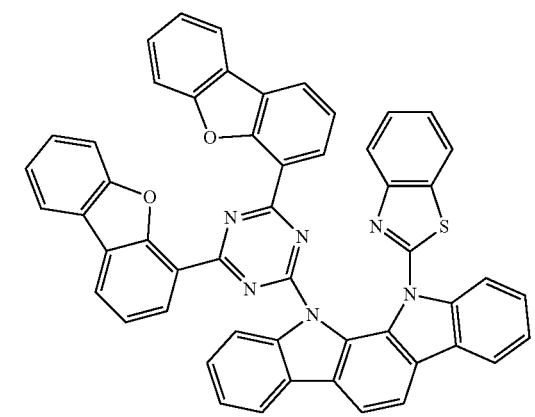
527
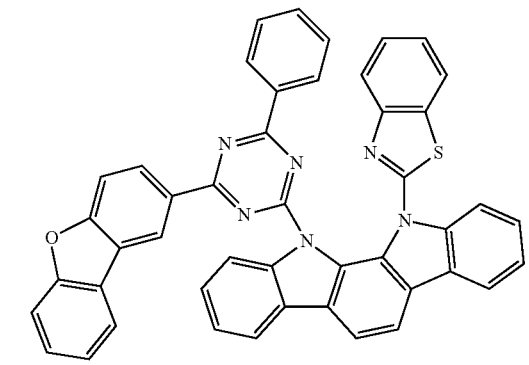
528
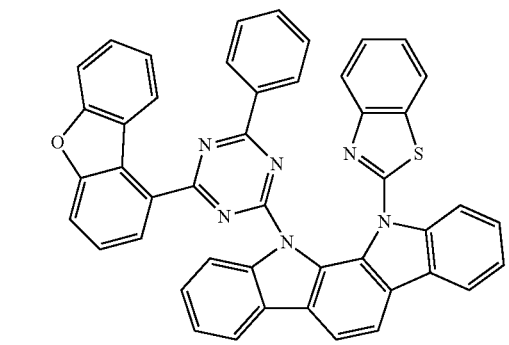
190
-continued
529
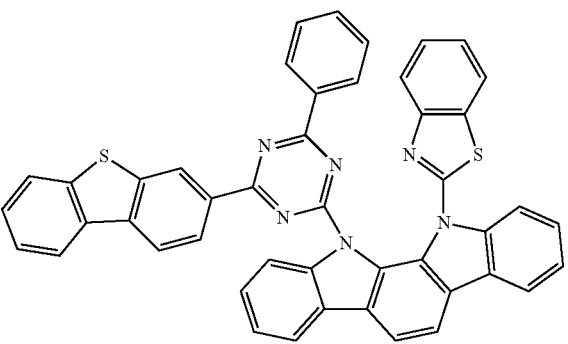
530
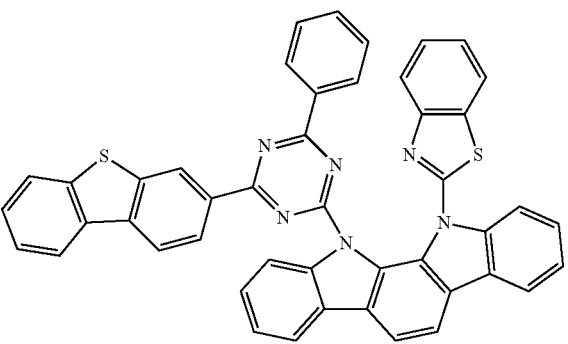
531
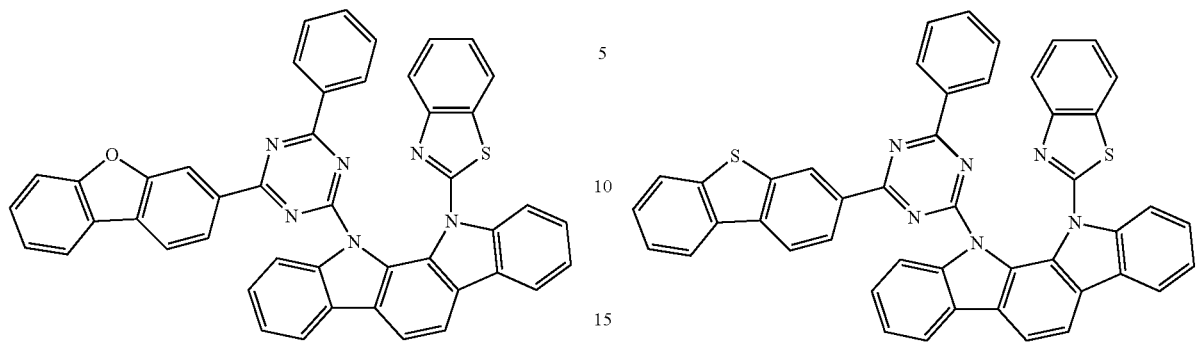
532

533
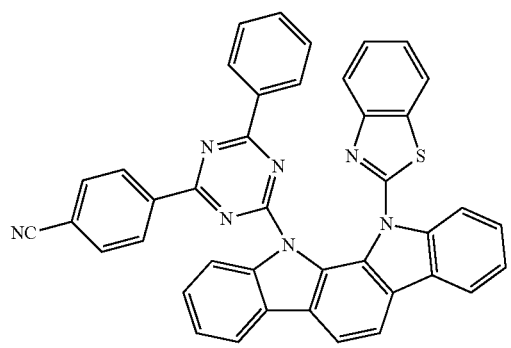
534
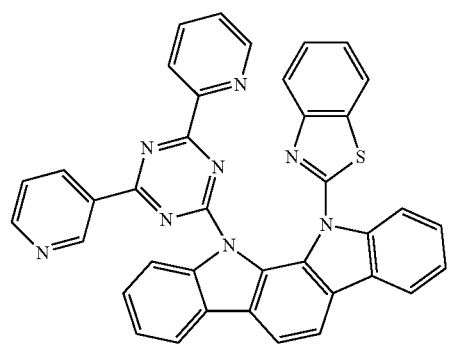
535
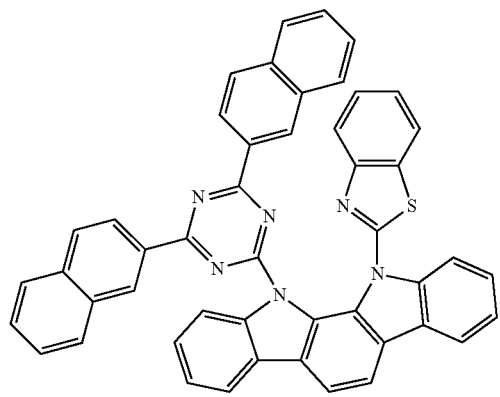
536
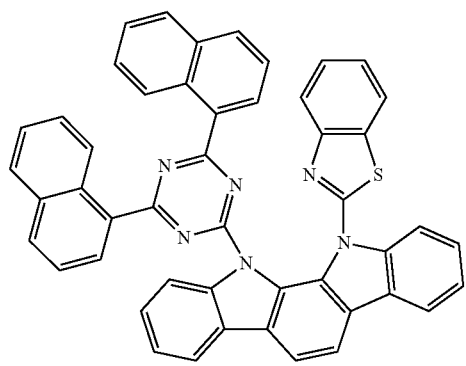
537
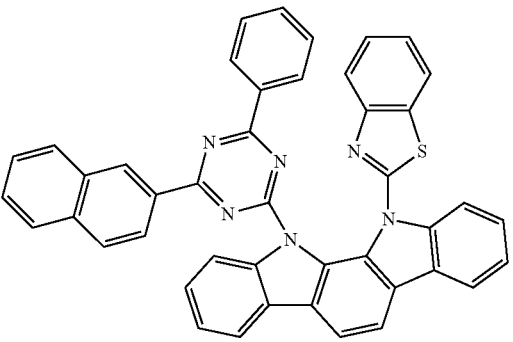
538
543
544
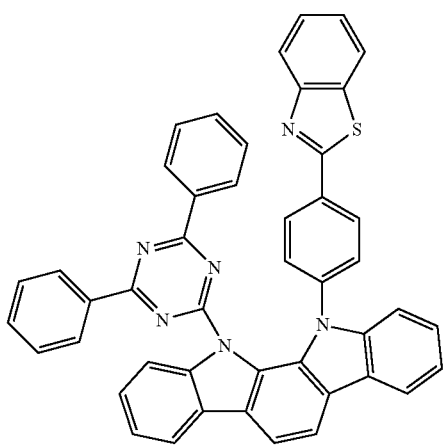

-continued
545
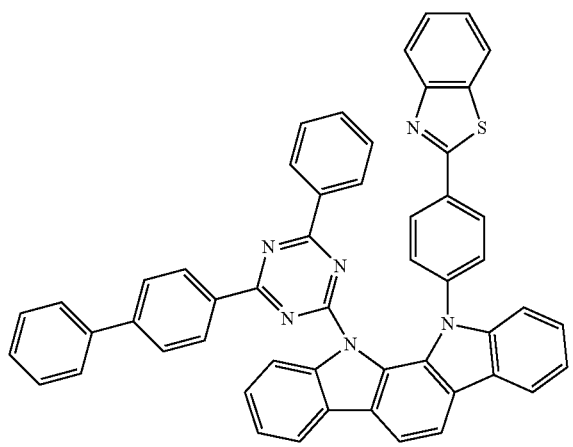
548
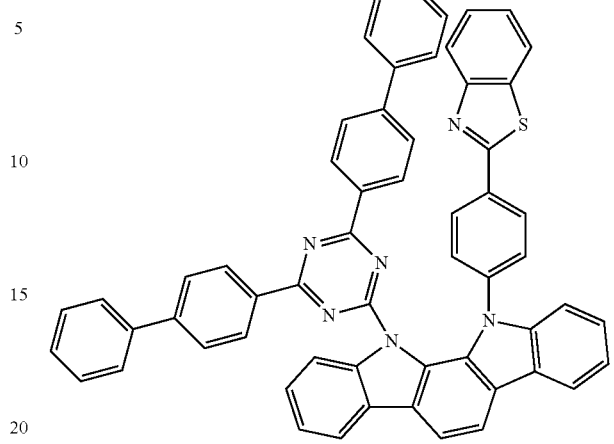
546
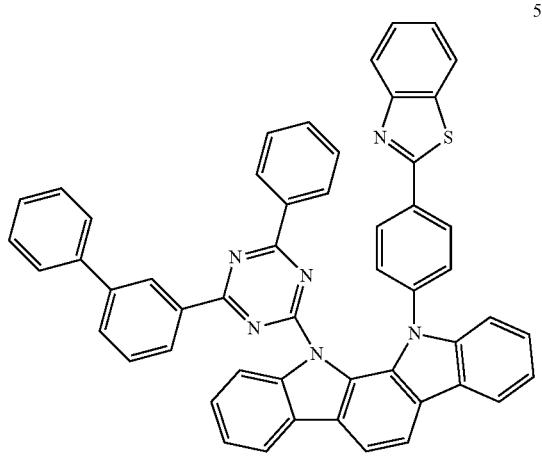
549
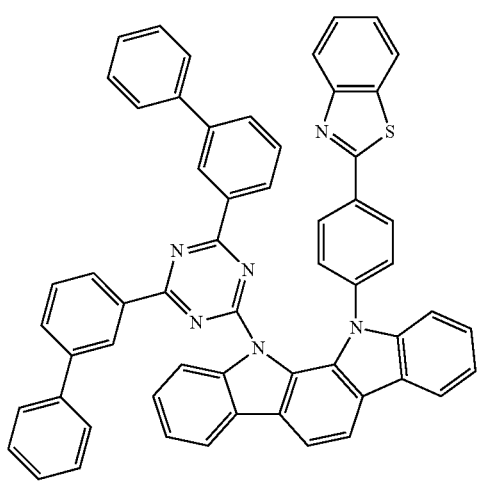
547
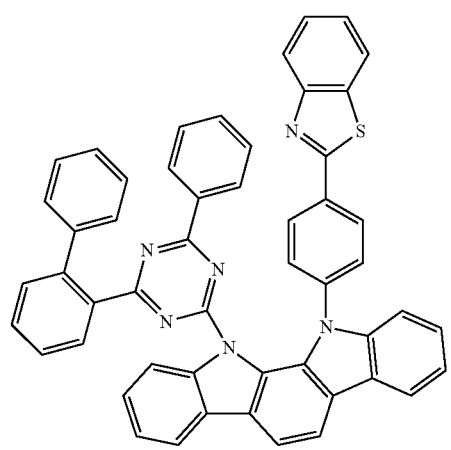
550
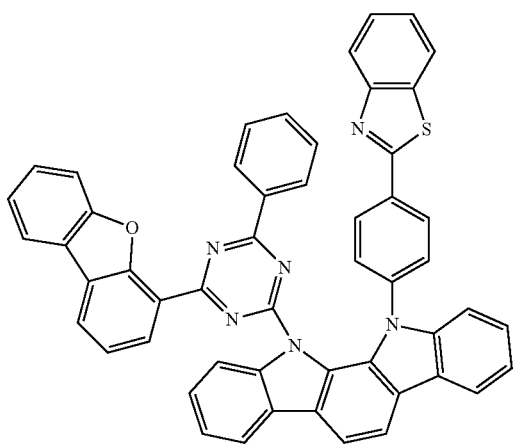

551 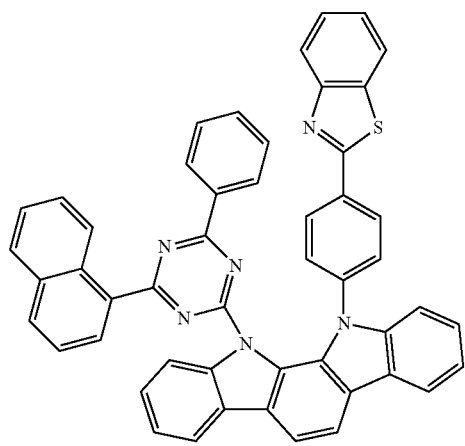
552 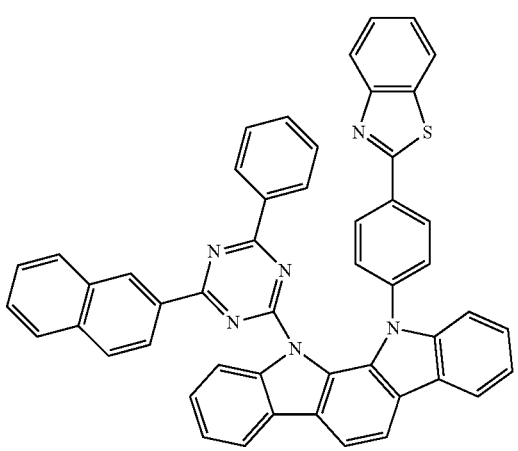
553 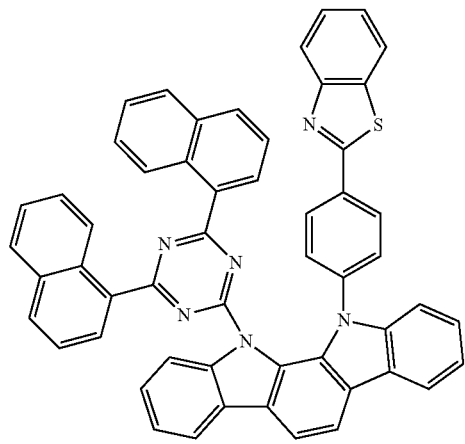
554 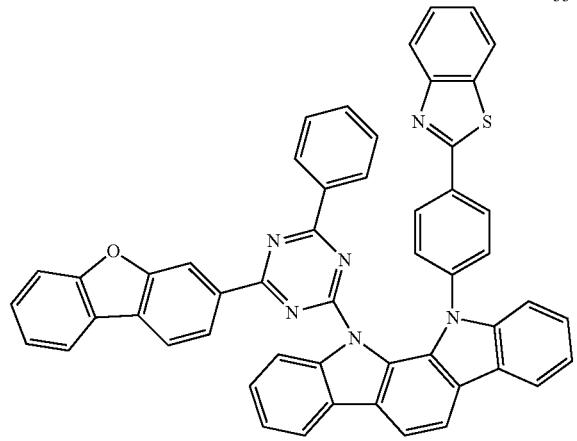
555 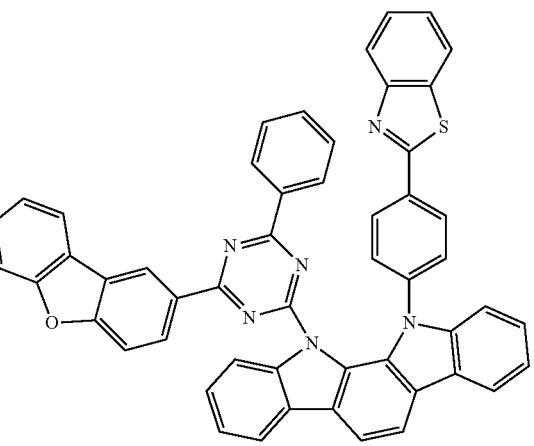
556 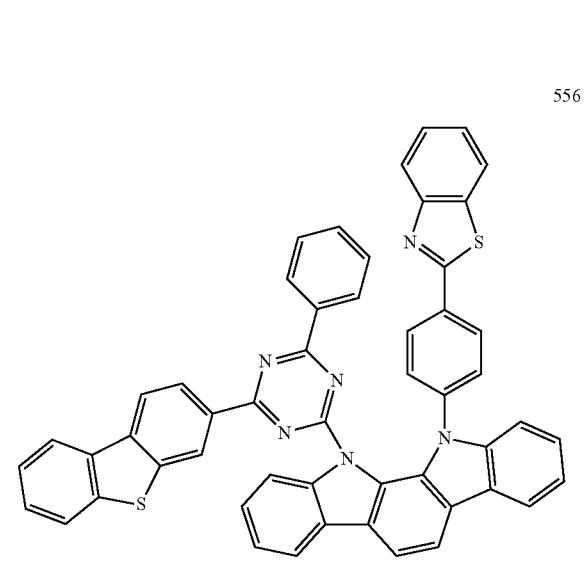

197
-continued
557
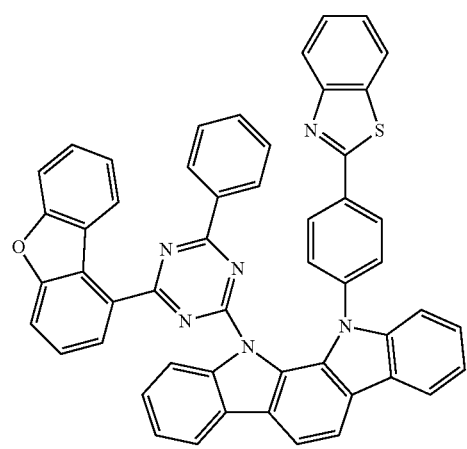
558
560
-continued
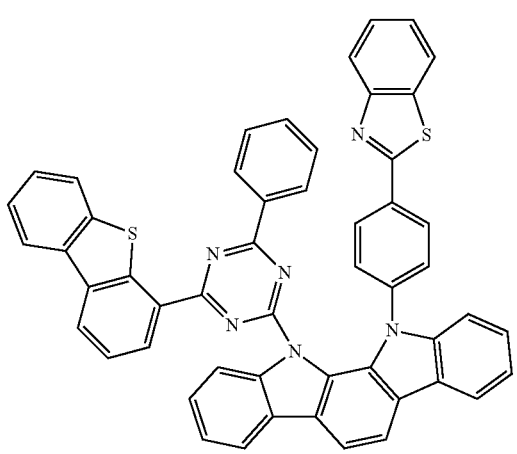
561
559
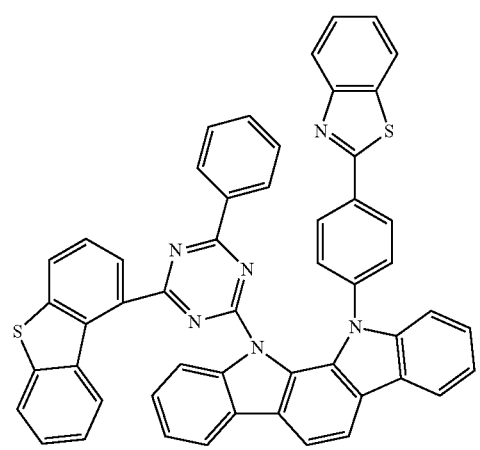
562

199
-continued
563
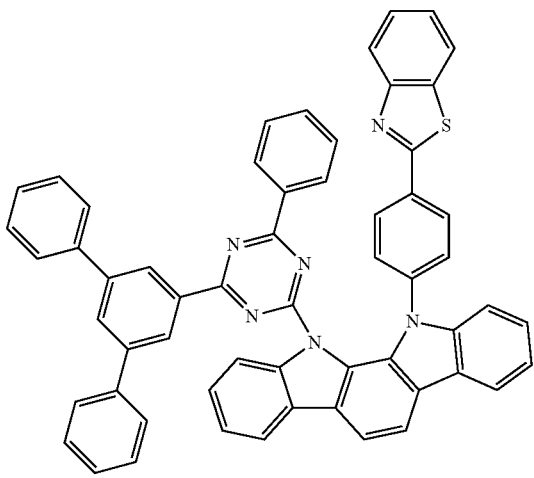
564
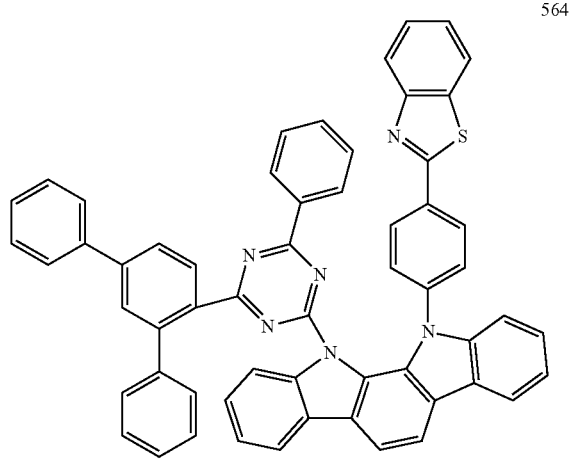
565
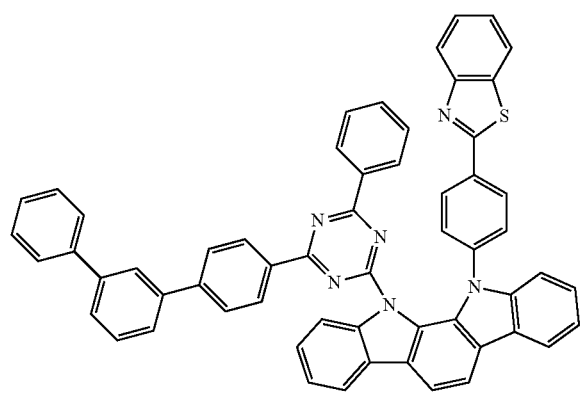
200
-continued
566
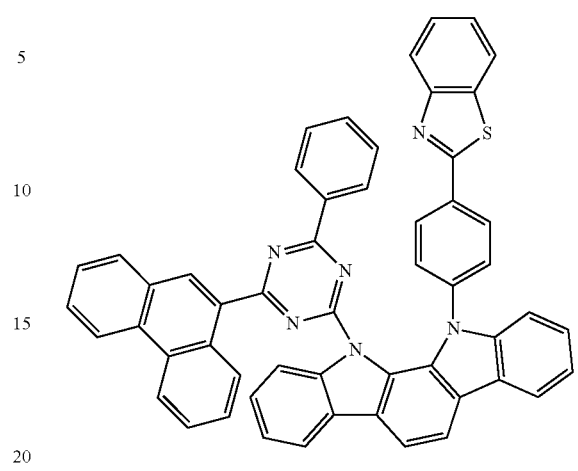
567
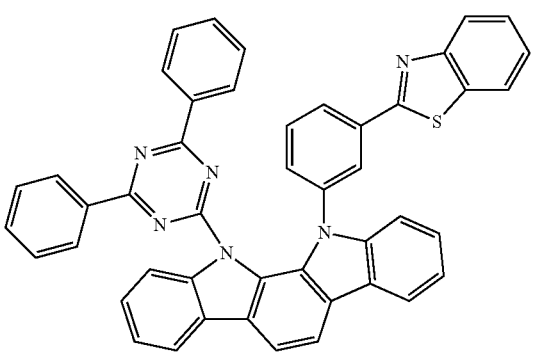
568
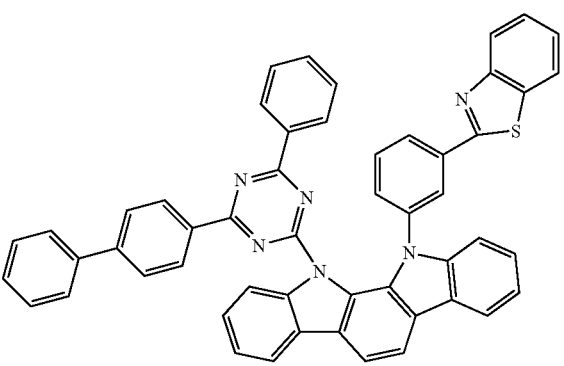

201
-continued
569
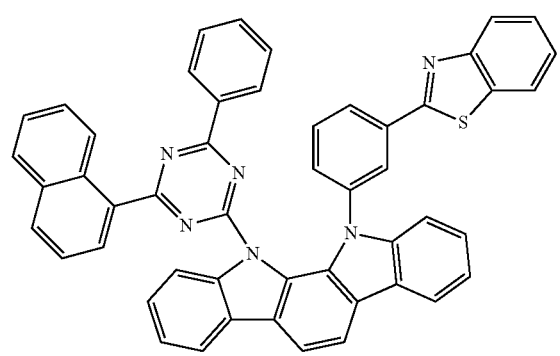
570
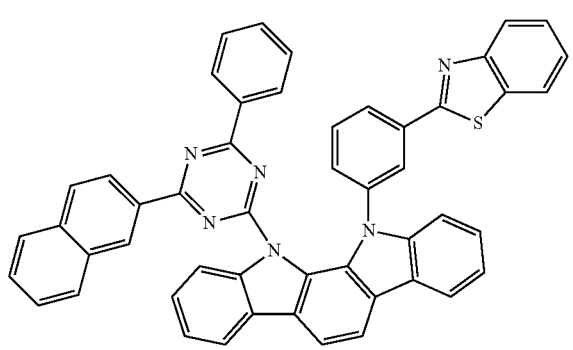
571
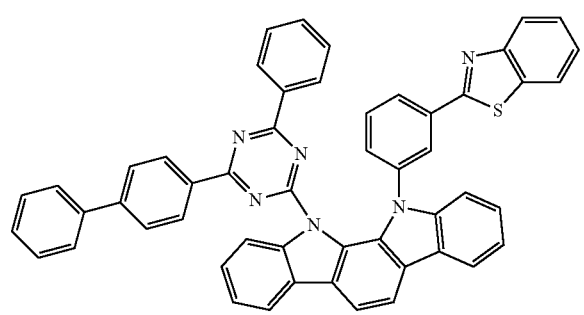
572
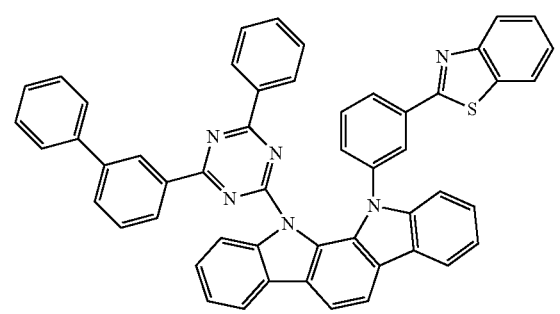
202
-continued
573
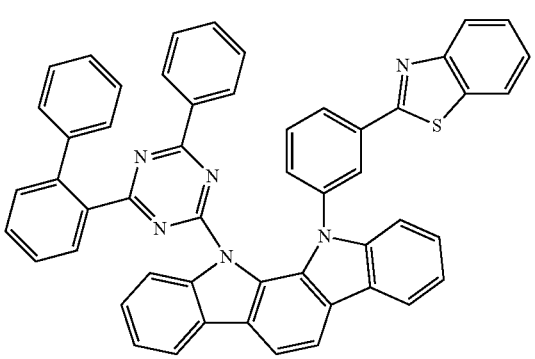
574
575
576
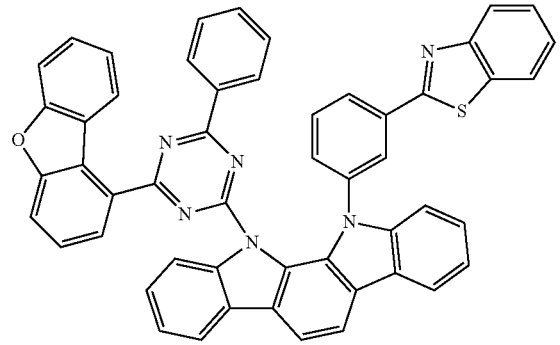

577
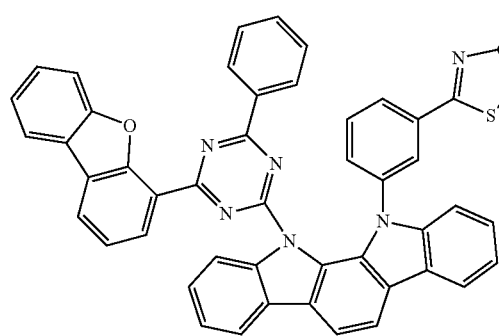
581
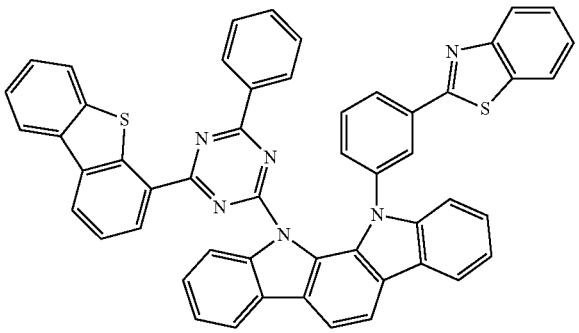
578
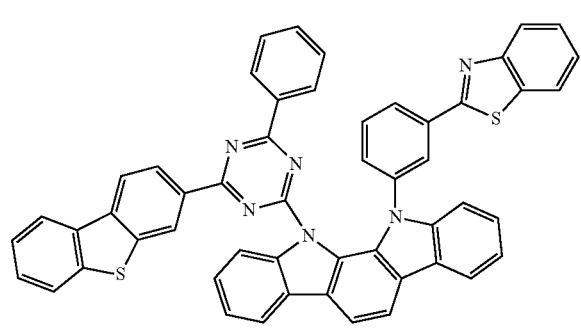
582
579
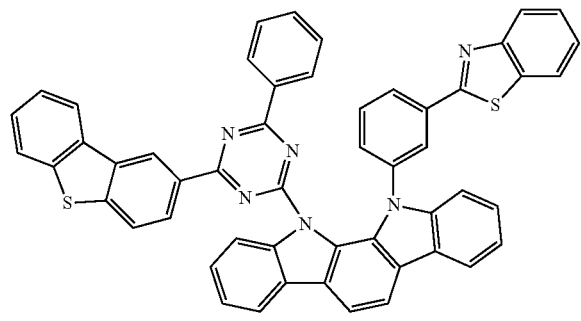
583
580
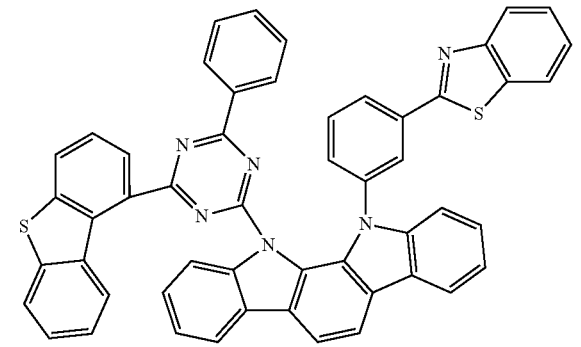
584
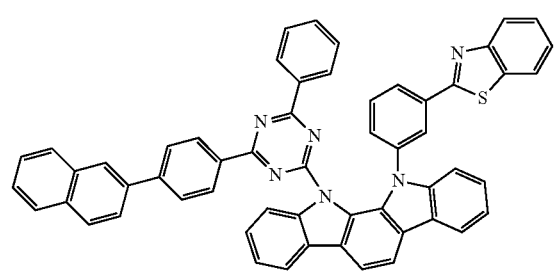

585
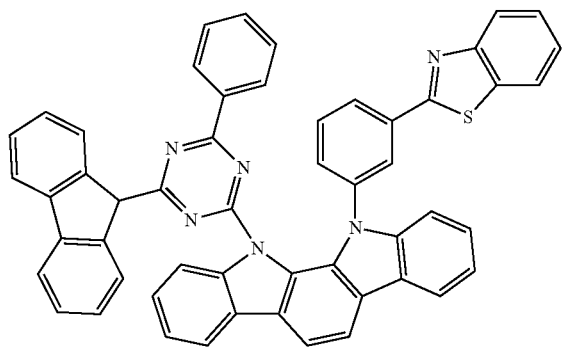
586
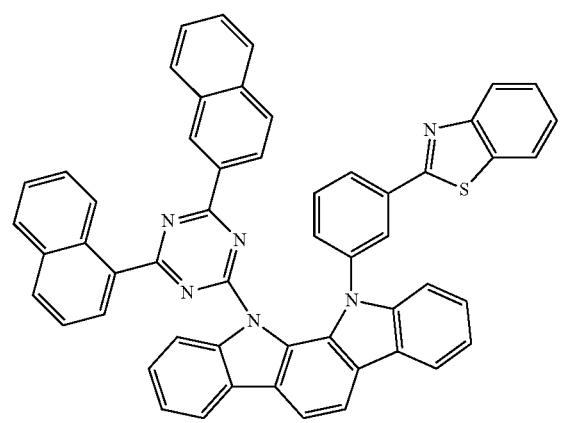
587
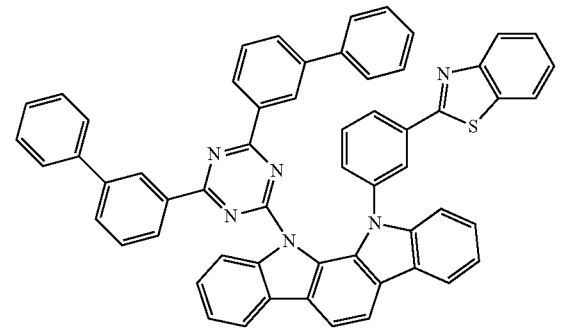
588
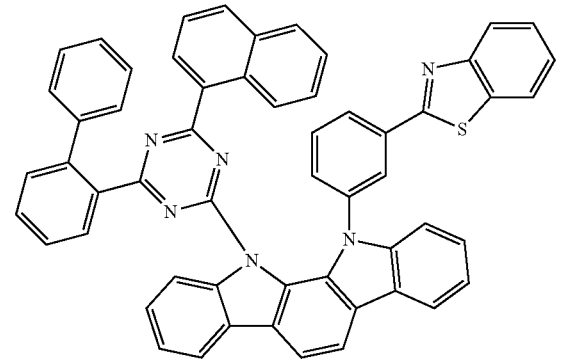
589
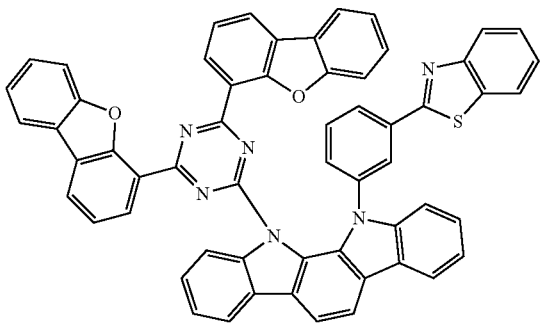
590
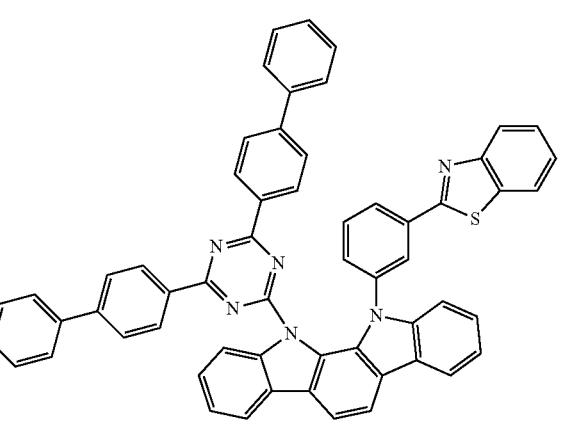
591
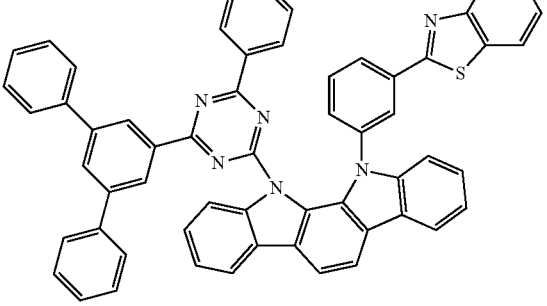
592
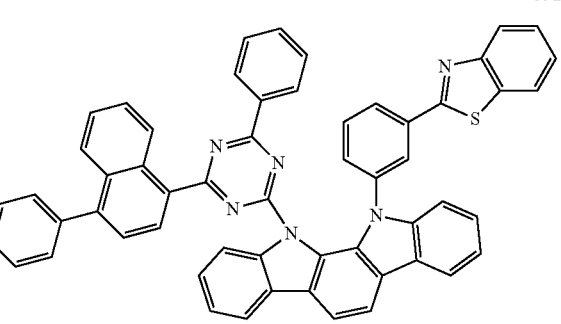

593
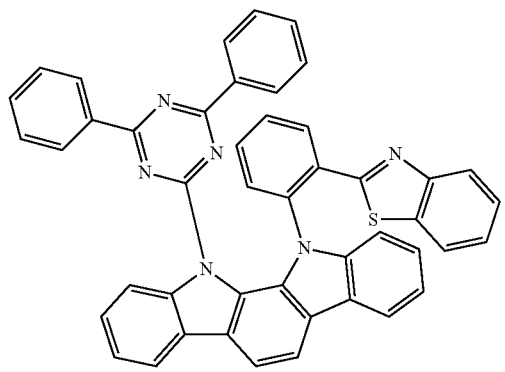
594
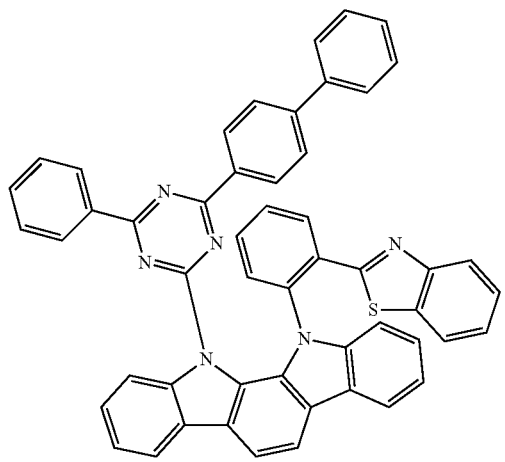
595
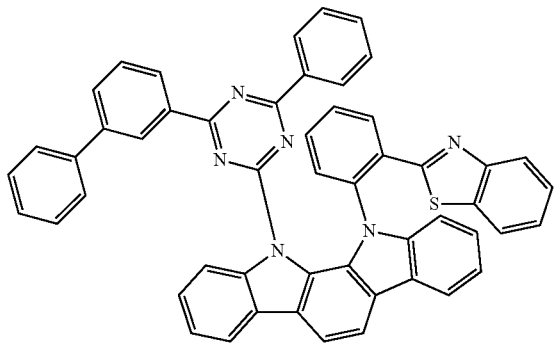
596
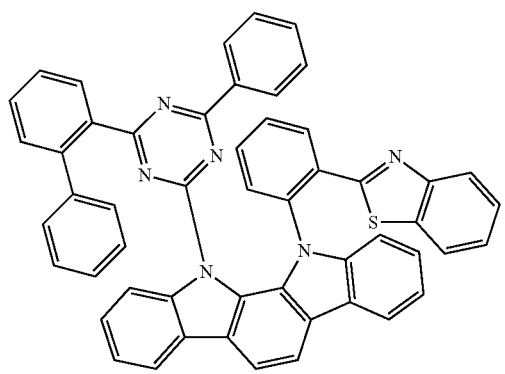
597
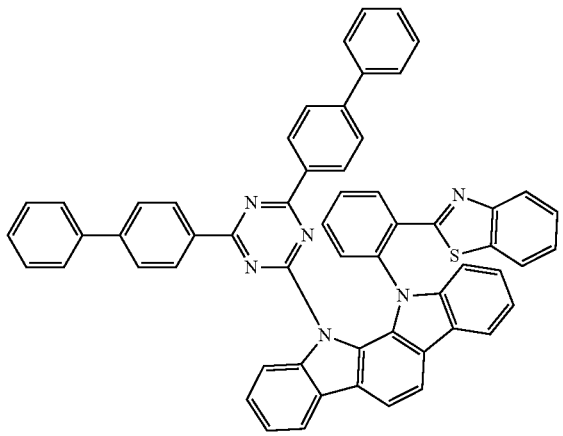
598
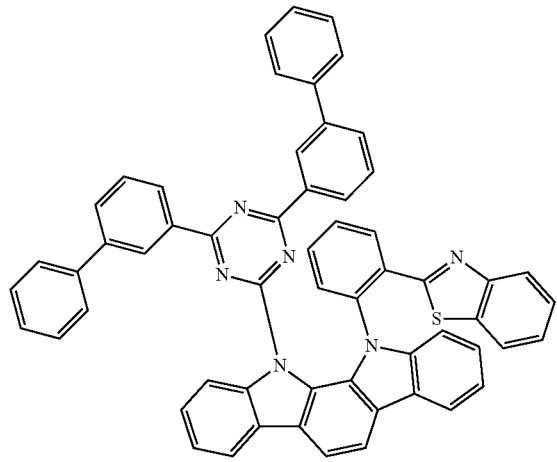
599
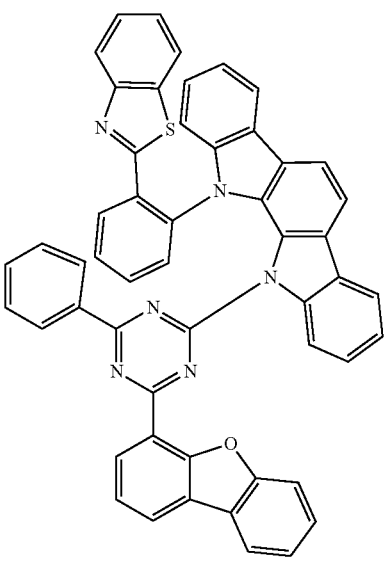

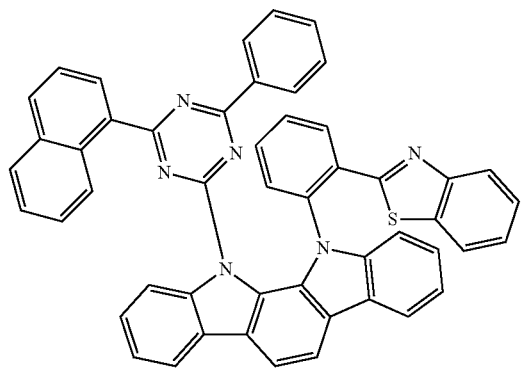
600
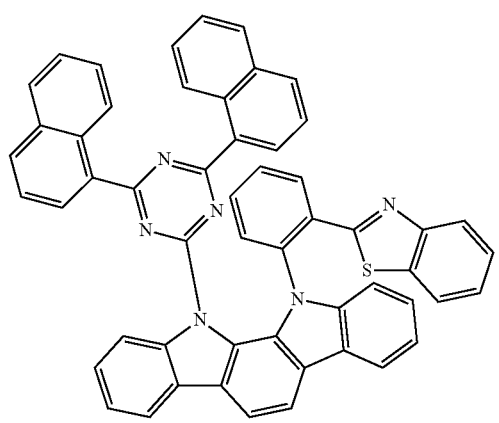
601
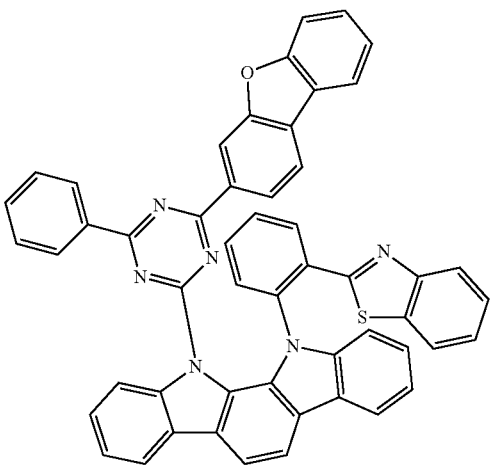
603
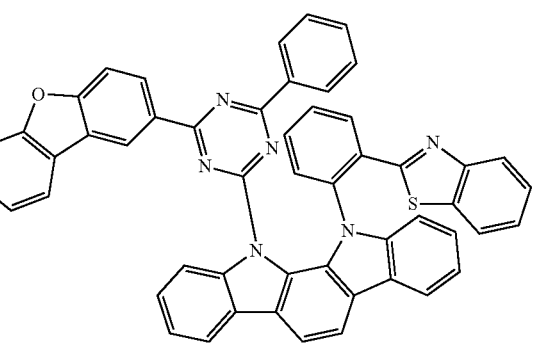
604
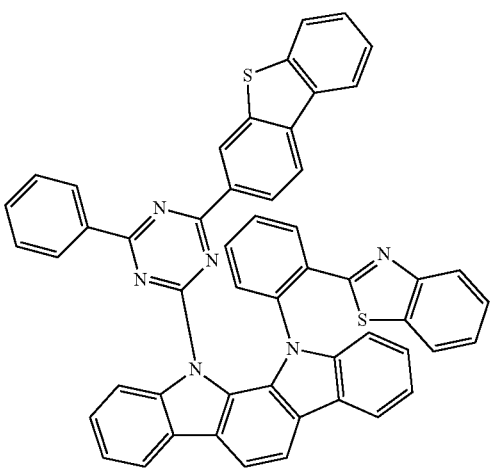
605
602

606
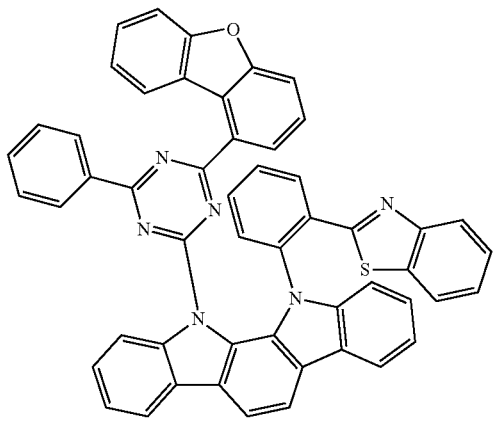
607
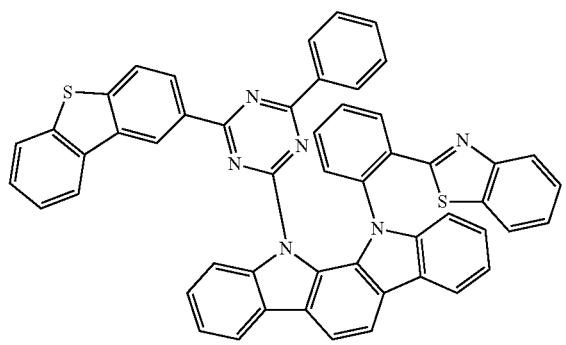
608
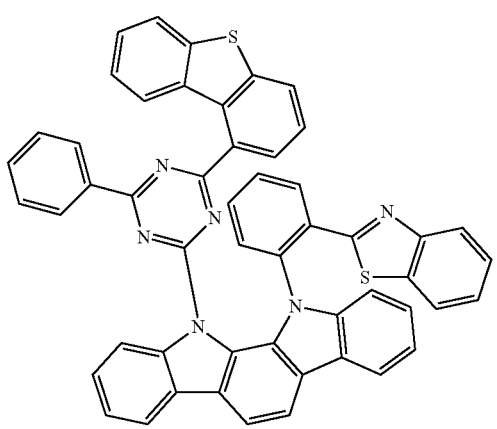
609
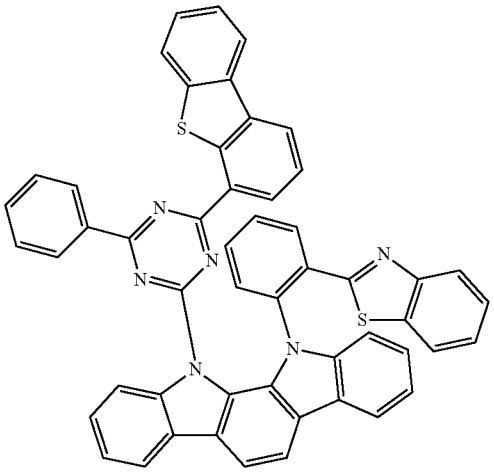
610
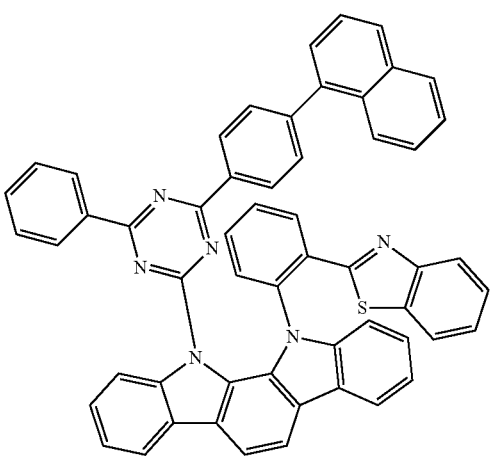
611
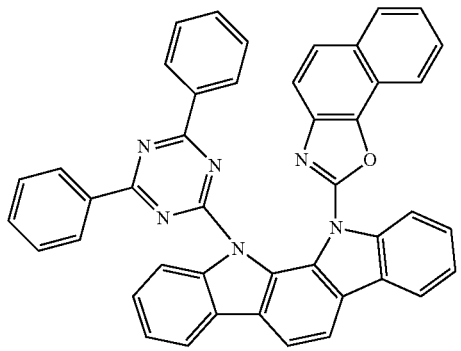

-continued
612
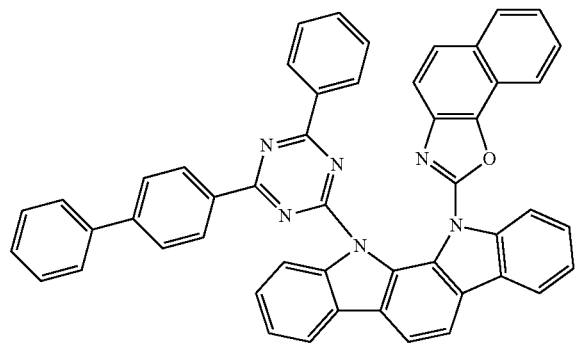
613
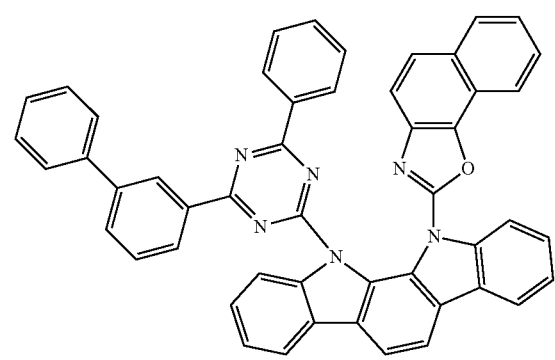
614
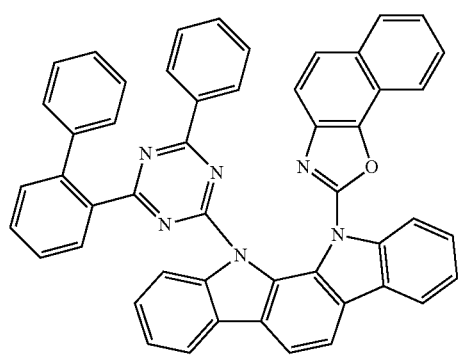
615
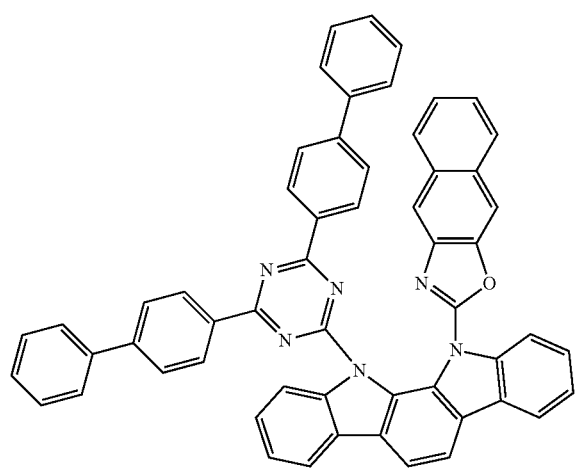
-continued
616
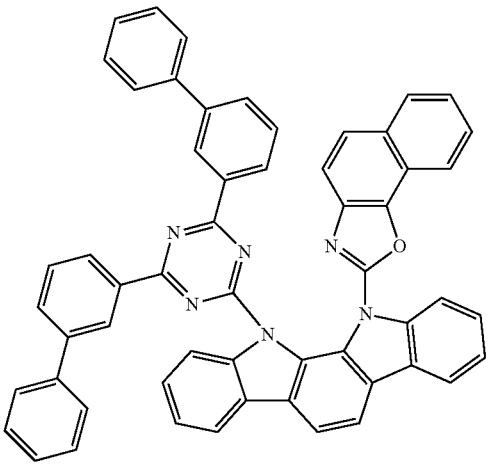
617
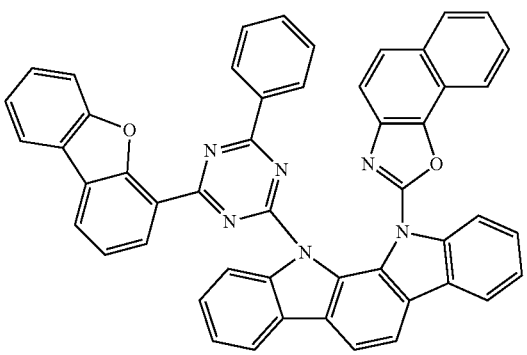
618
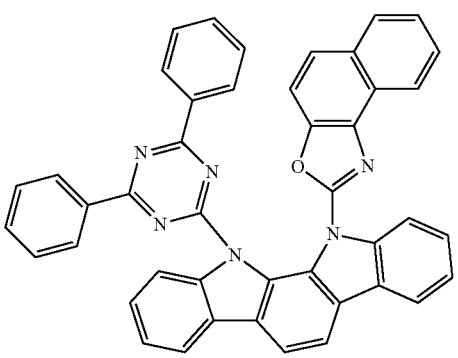
619
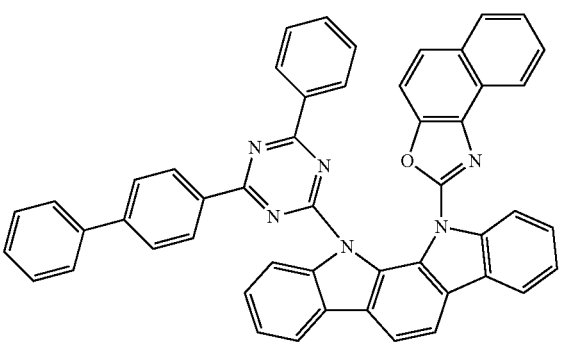

-continued
620
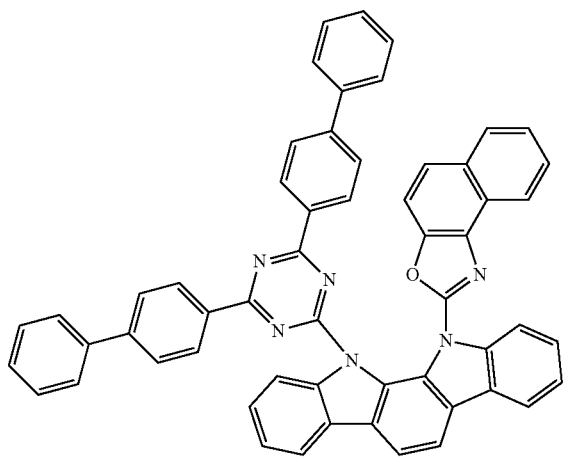
621
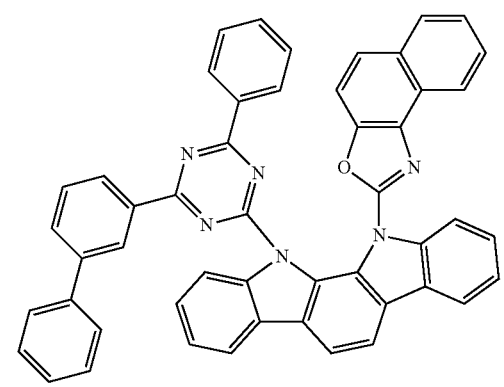
622
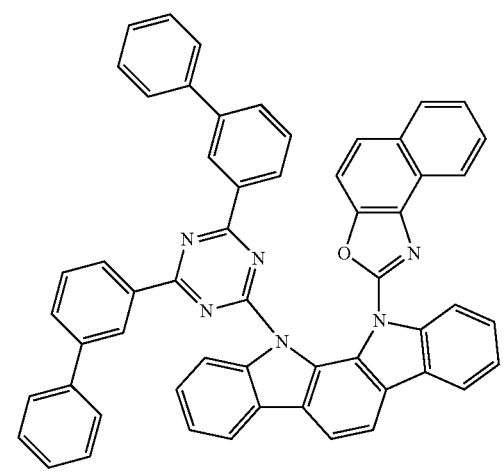
-continued
623
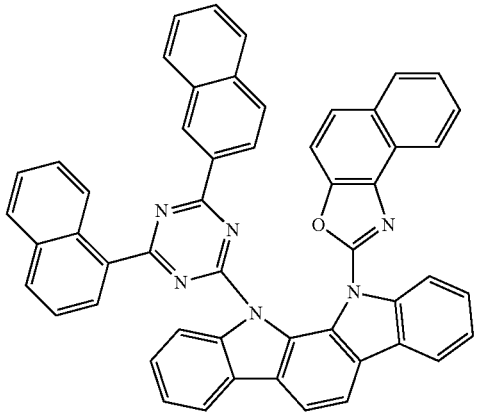
624
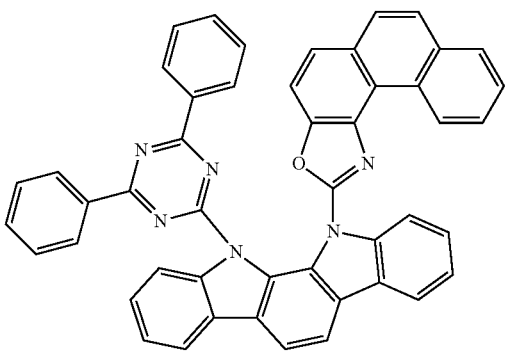
625
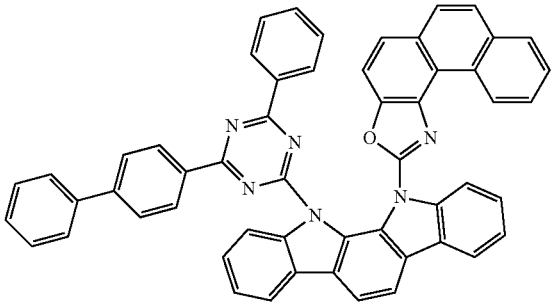
626
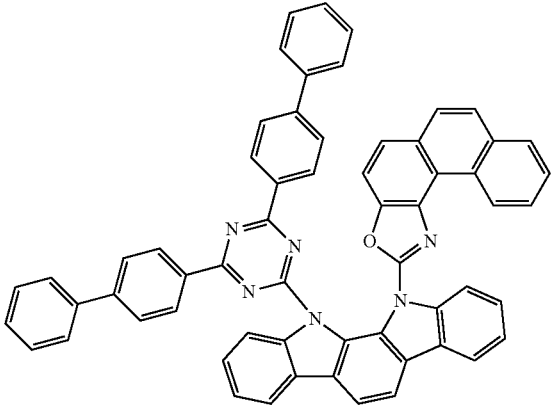

-continued
627
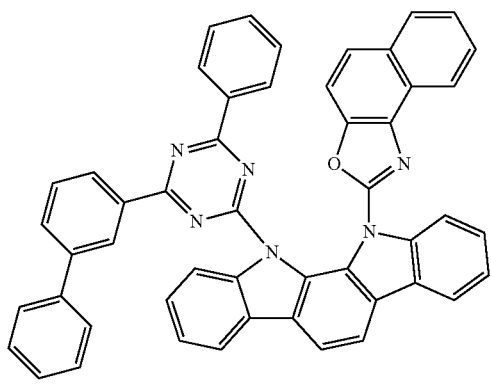
628
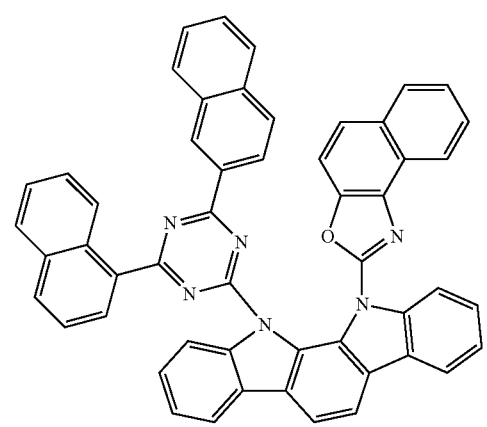
-continued
630
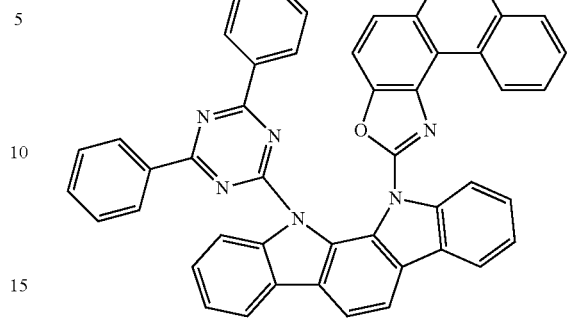
631
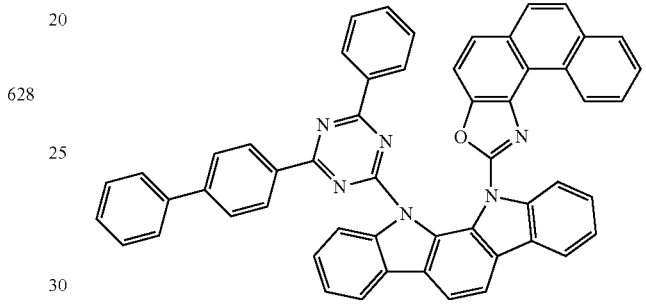
632
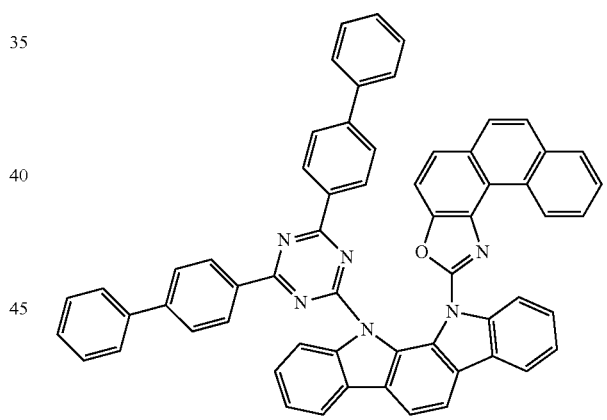
633
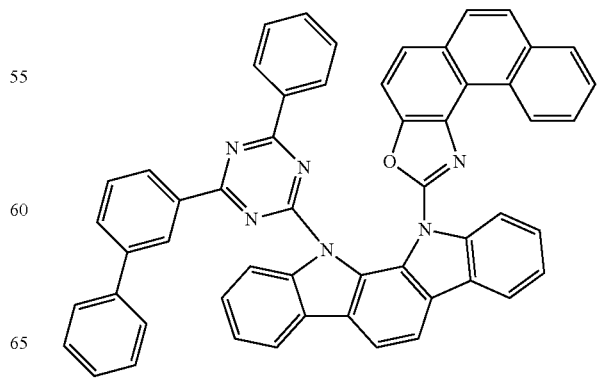

634
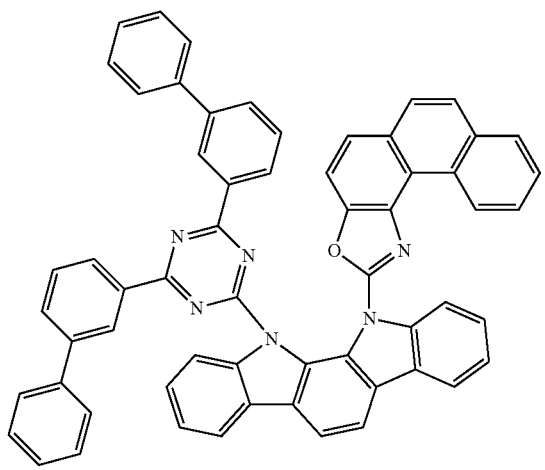
635
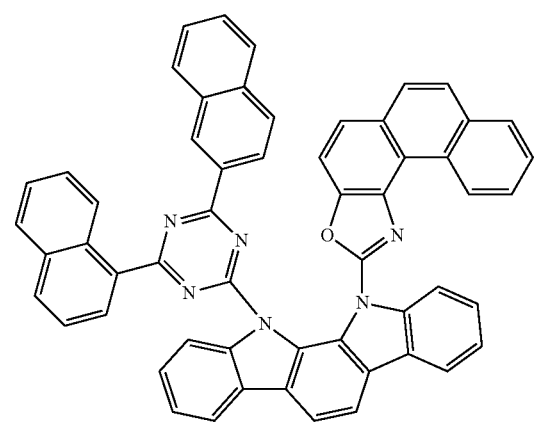
636
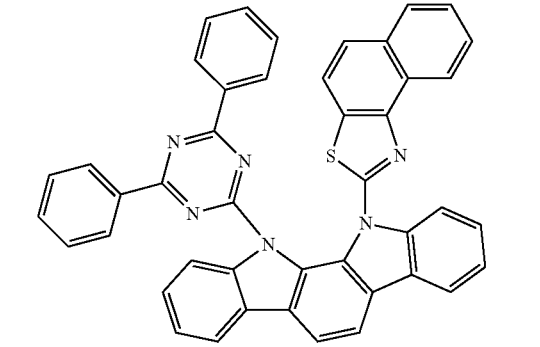
637
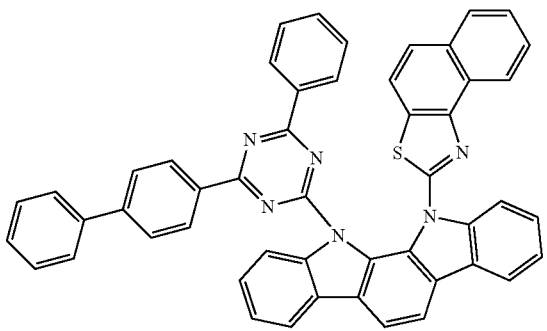
638
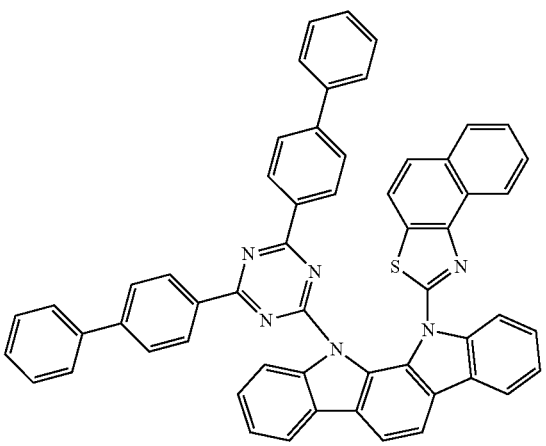
639
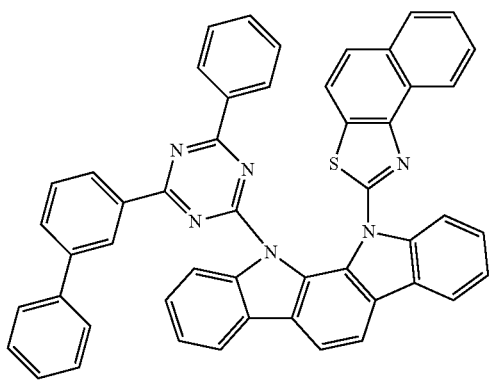
640
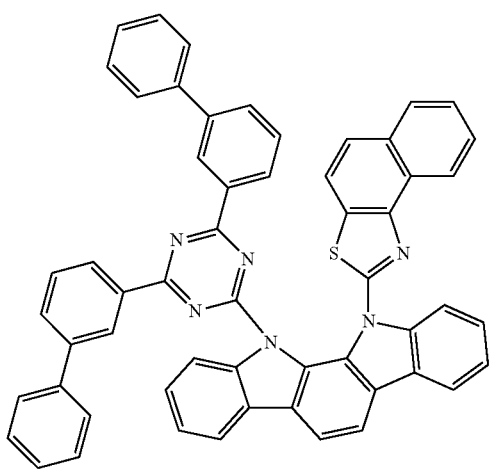

221
-continued
641
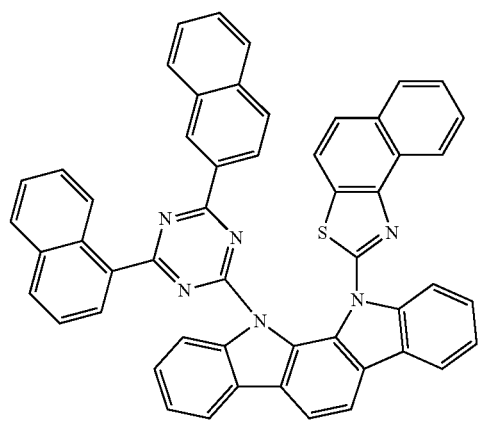
642
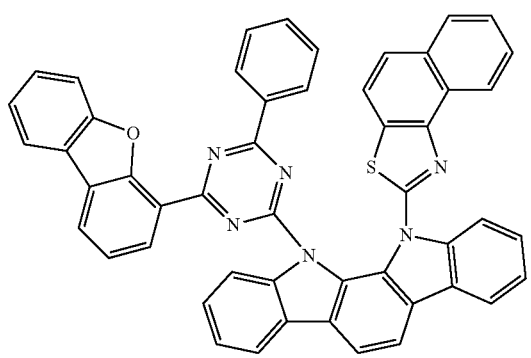
645
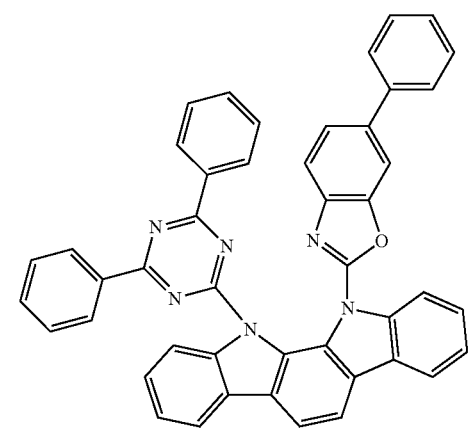
646
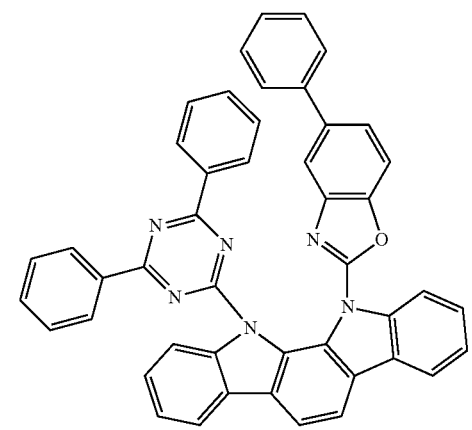
222
-continued
647
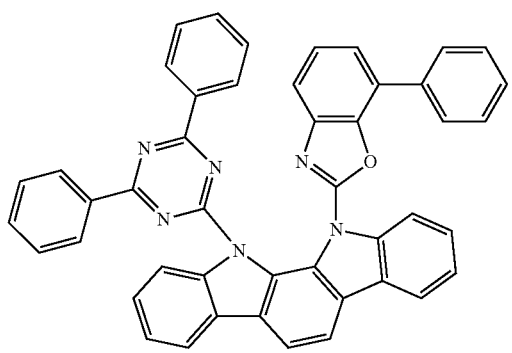
648
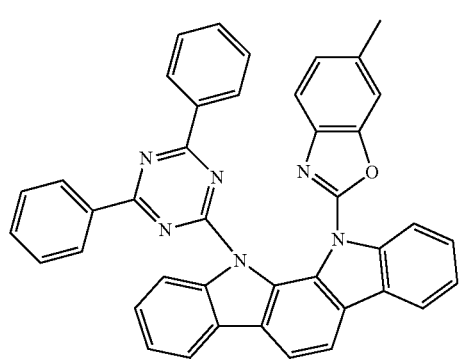
649
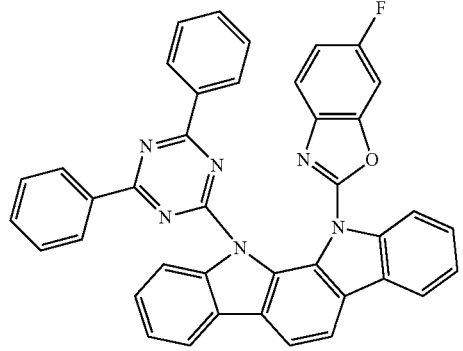
650
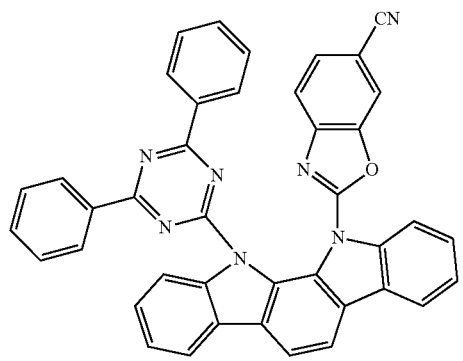

223
-continued
651
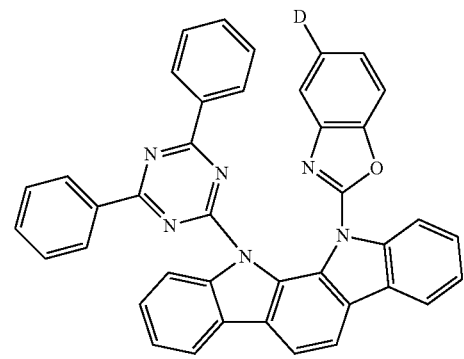
652
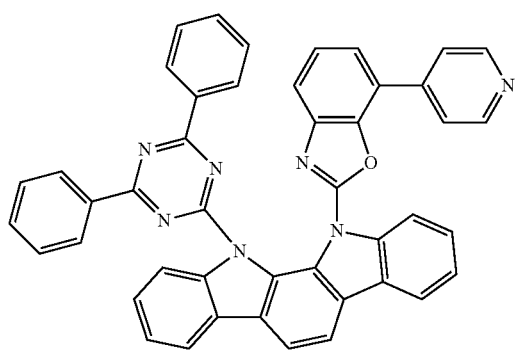
653
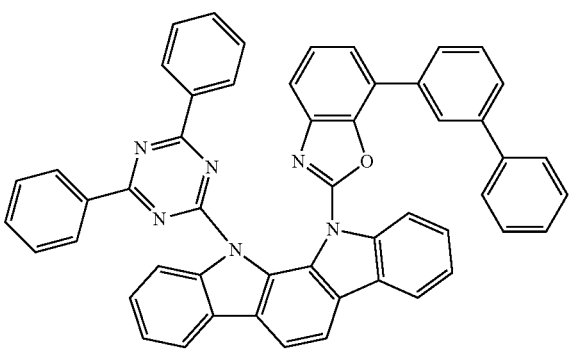
654
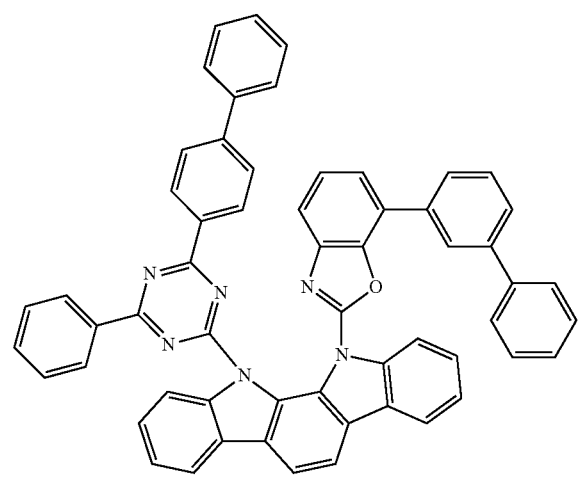
224
-continued
655
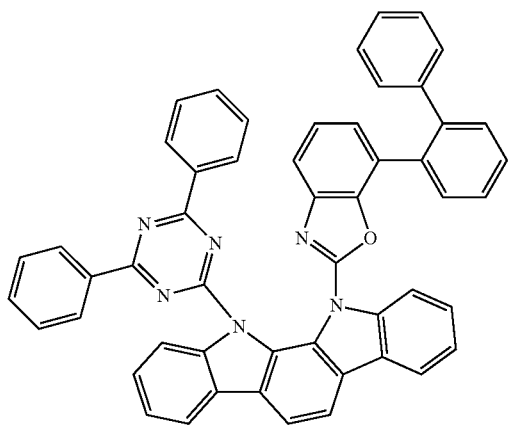
656
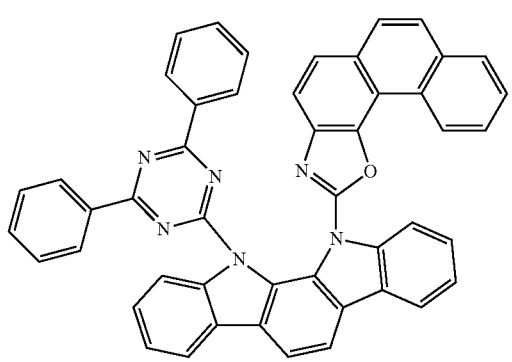
657
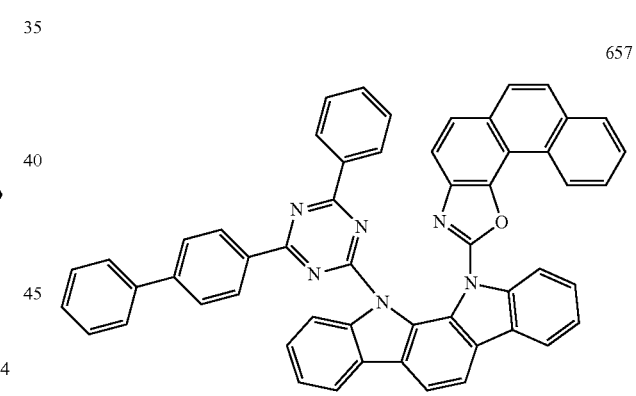
658
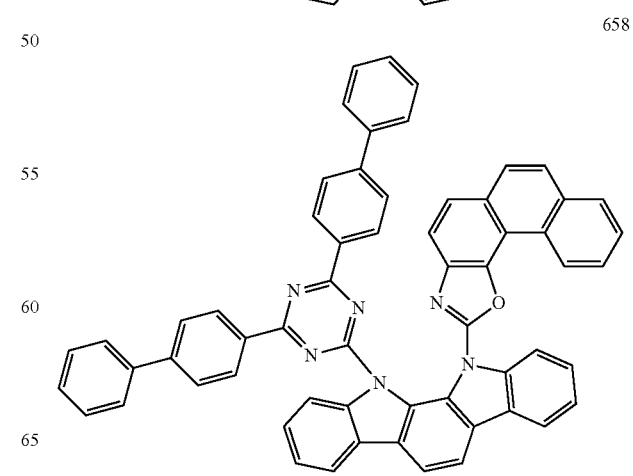

225 -continued
659
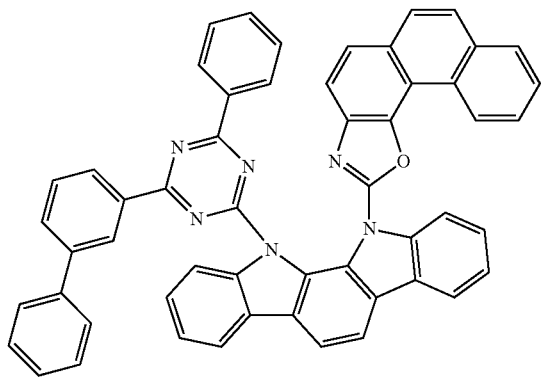
660
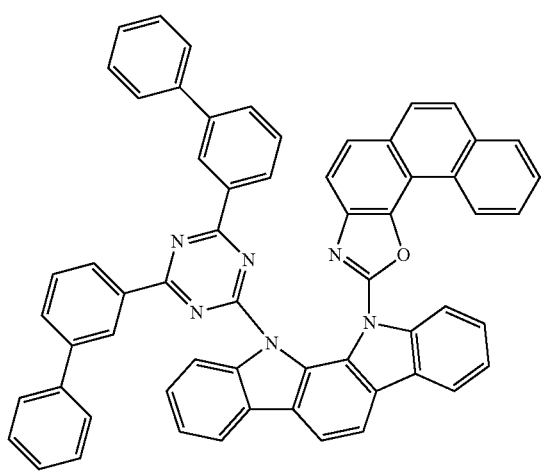
661
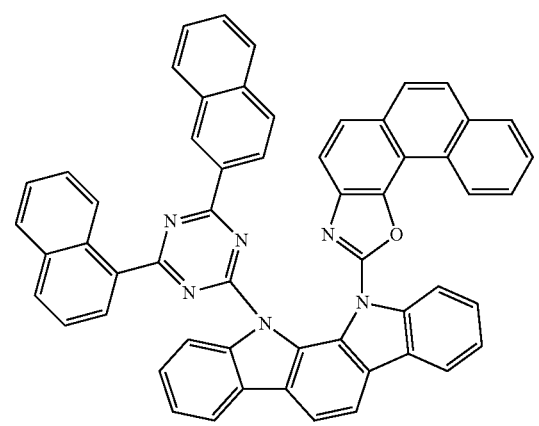
226 -continued
662
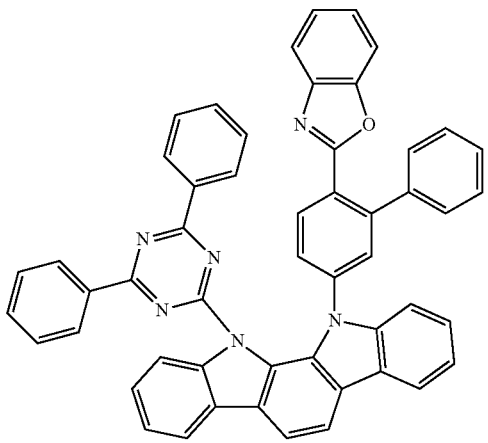
663
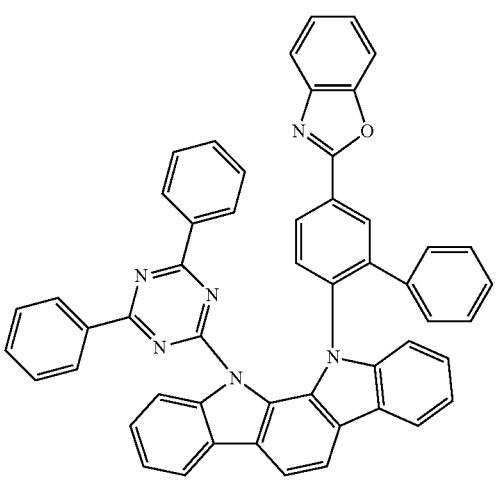
664
665
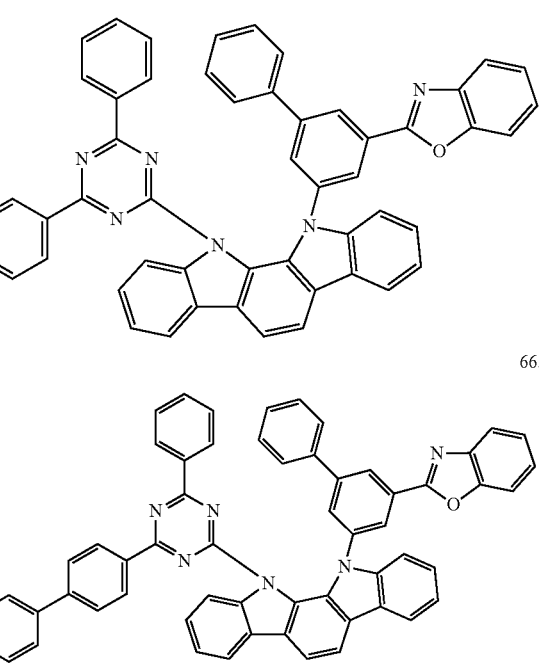

666
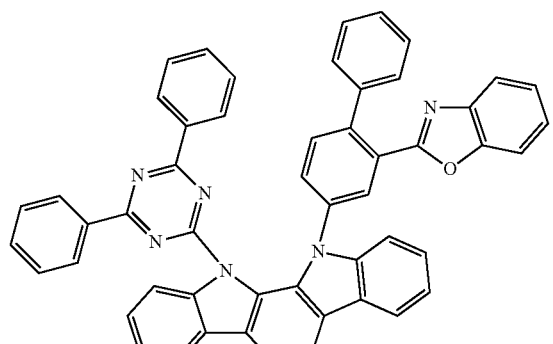
667
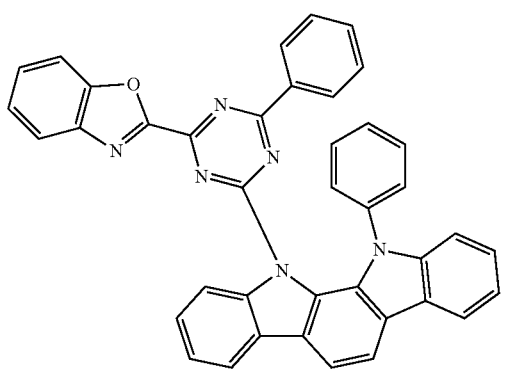
668
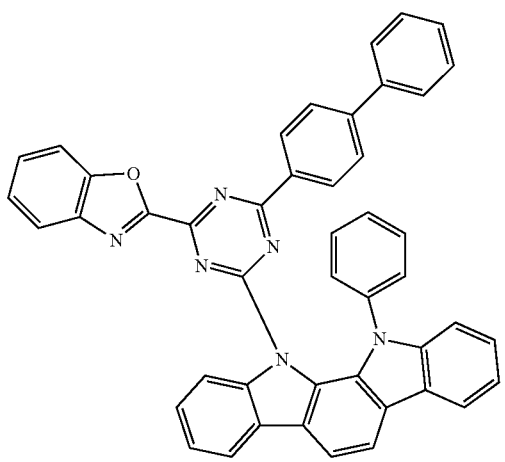
669
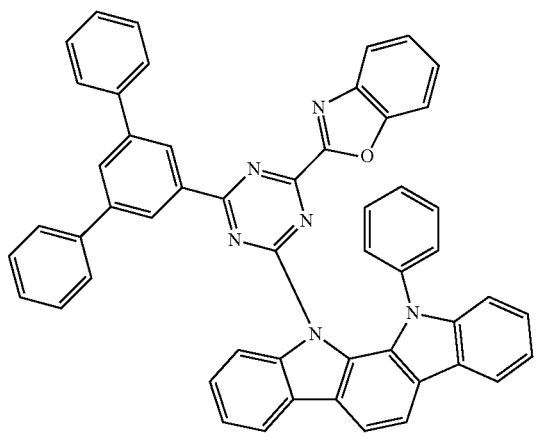
670
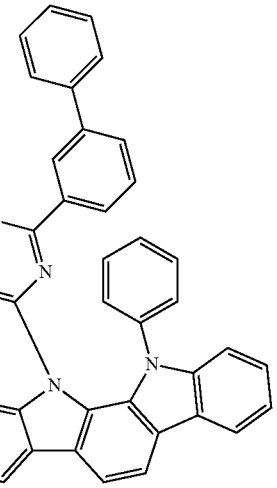
671
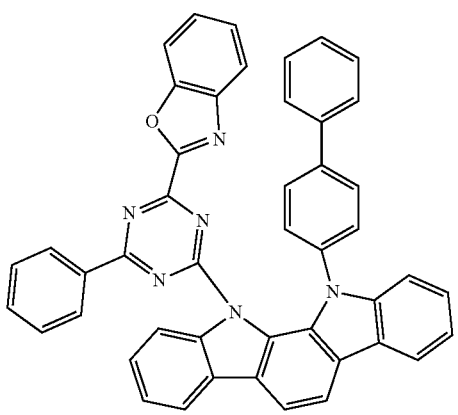

-continued
672
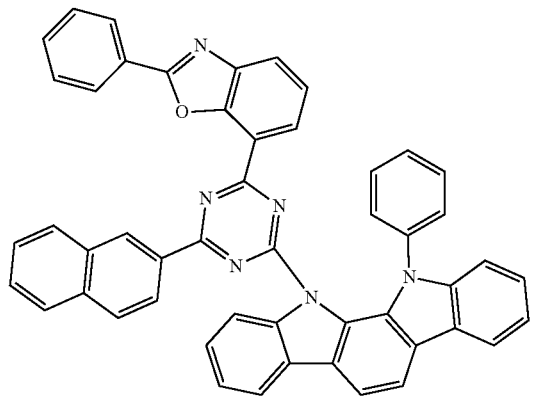
673
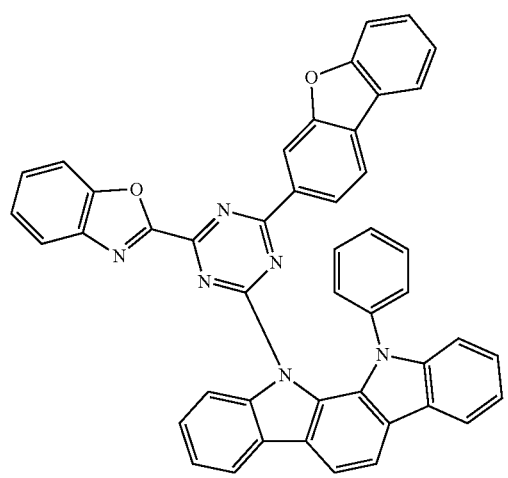
674
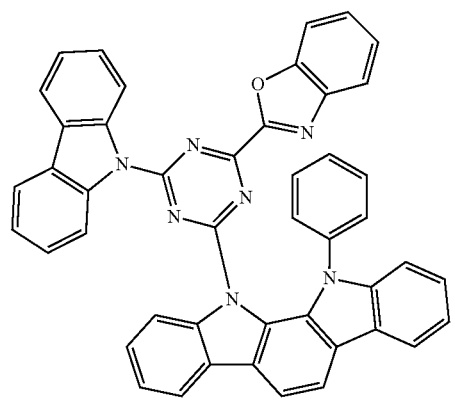
-continued
675
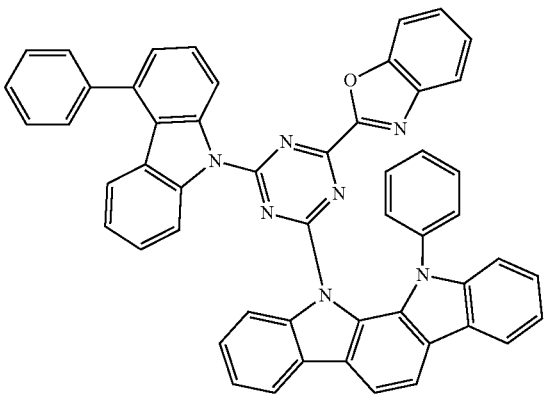
676
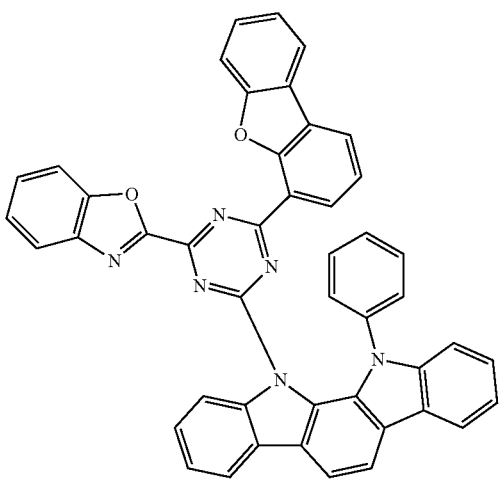
677
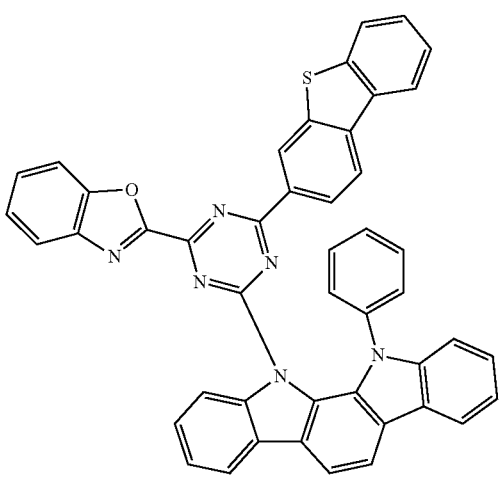

-continued
678
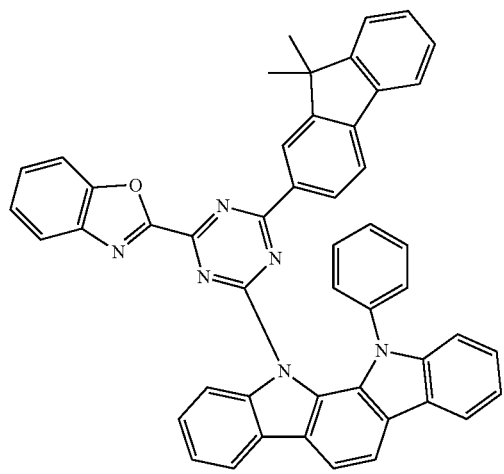
679
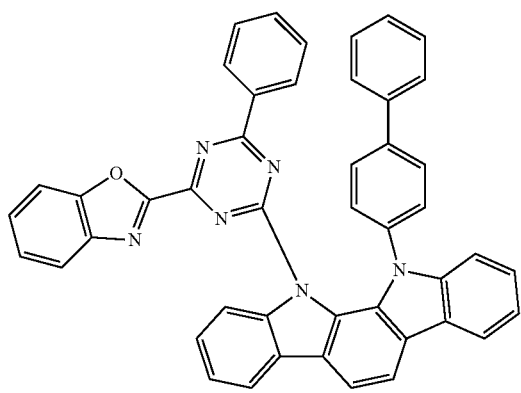
680
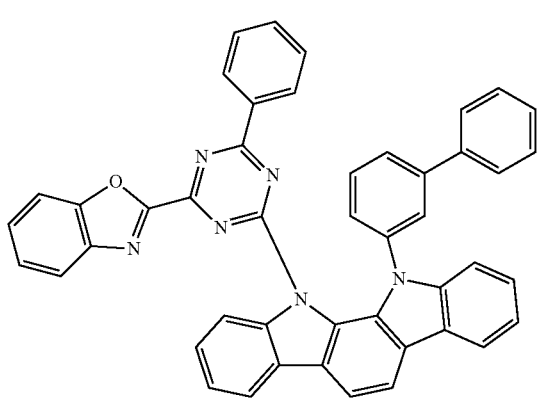
-continued
681
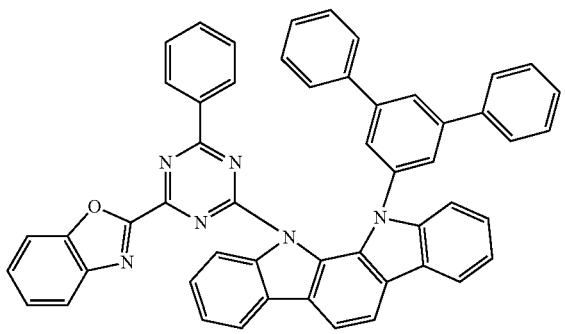
682
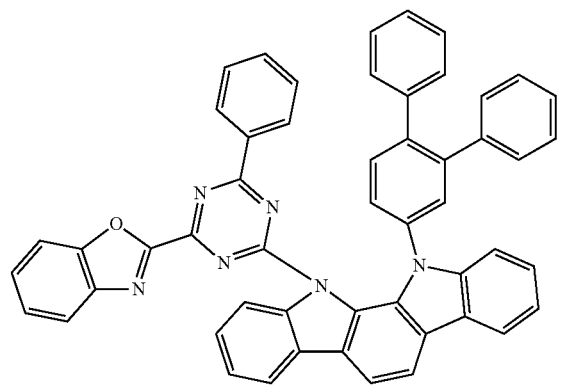
683
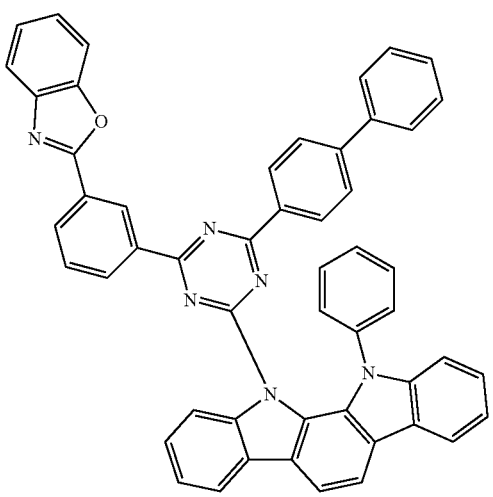

233
-continued
684
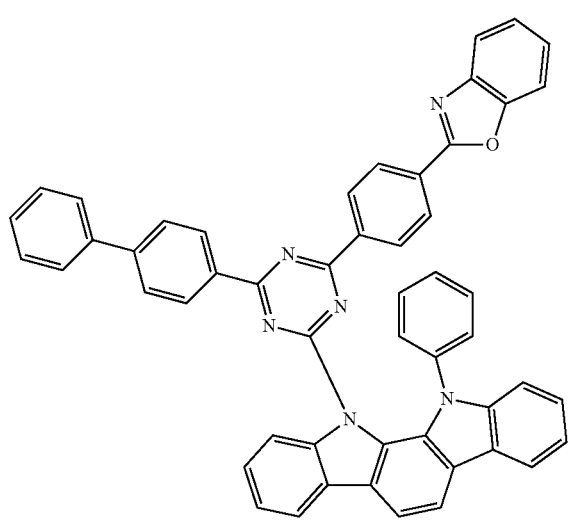
685
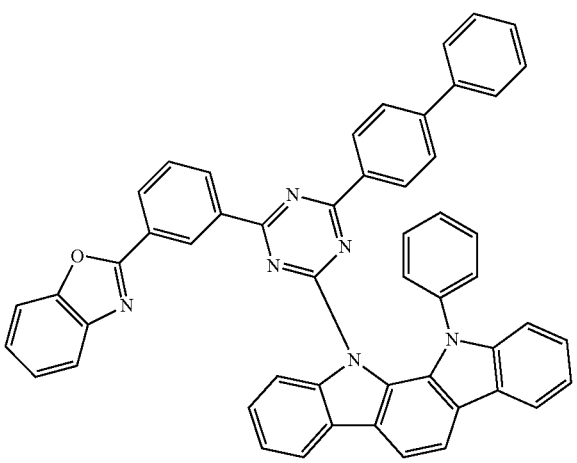
686
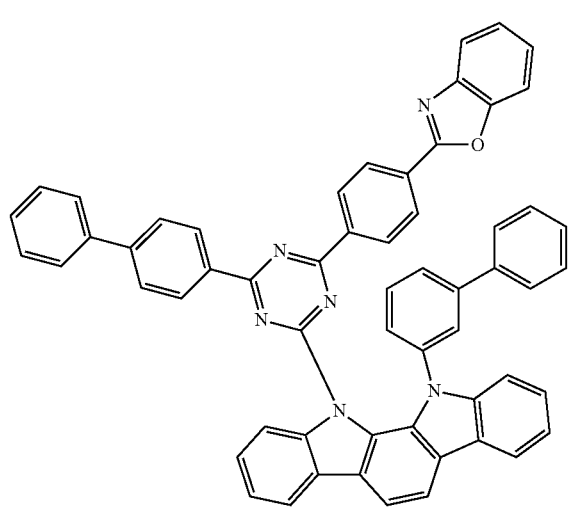
234
-continued
687
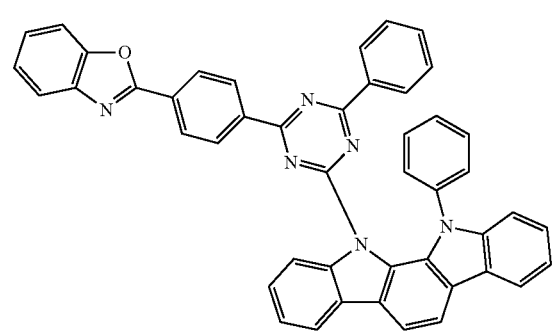
688
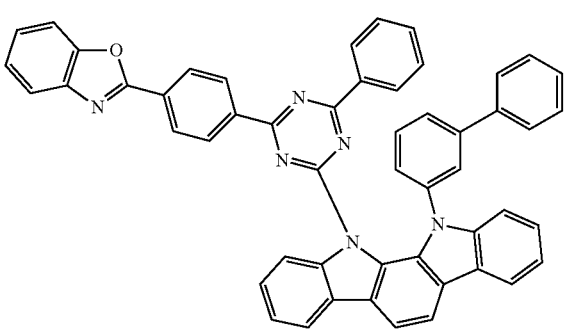
689
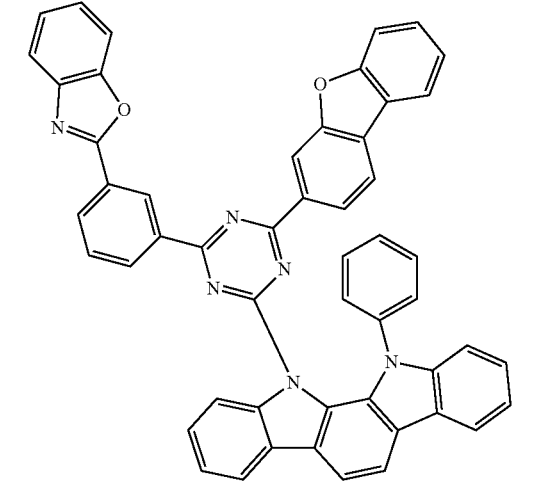
690
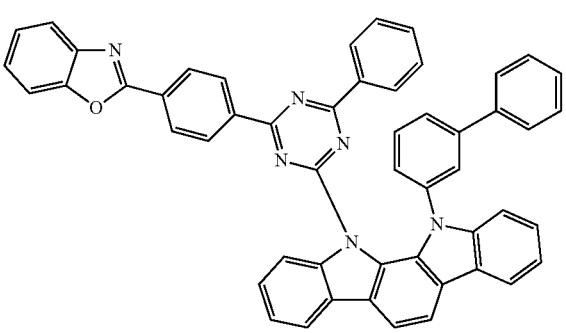

691 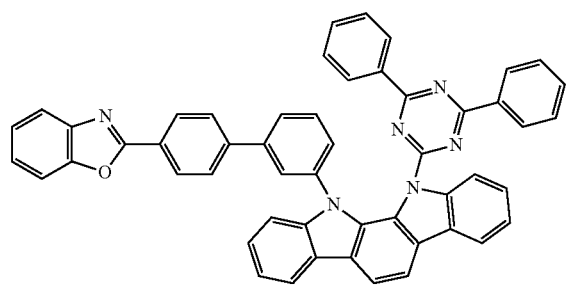
692 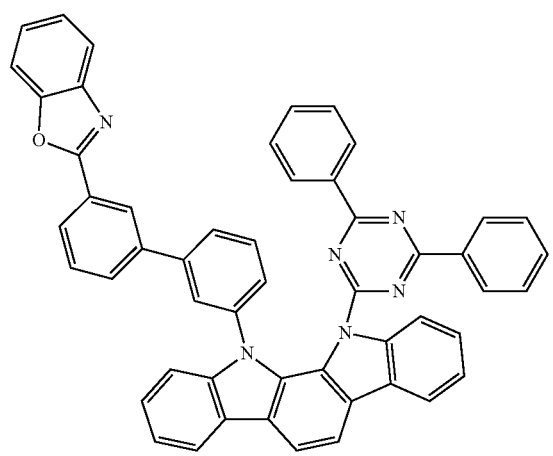
693 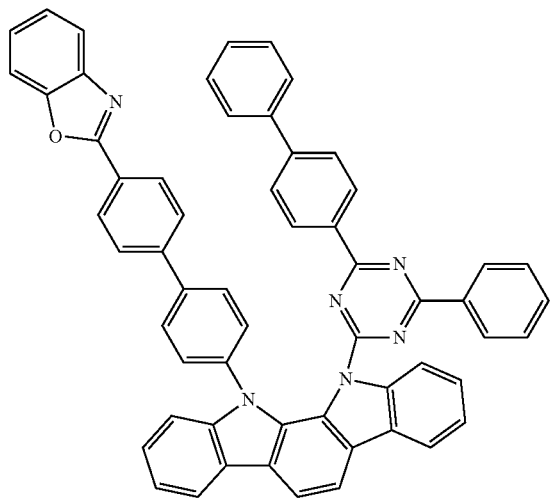
694 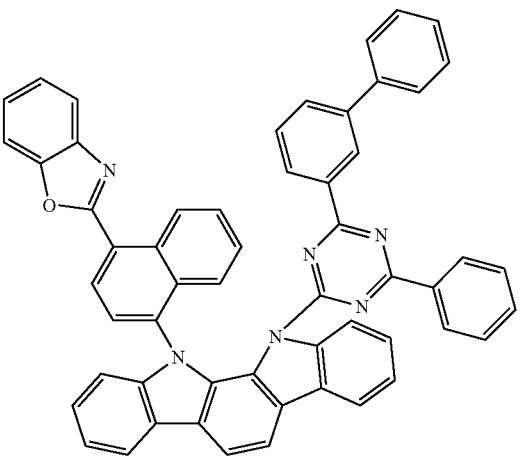
695 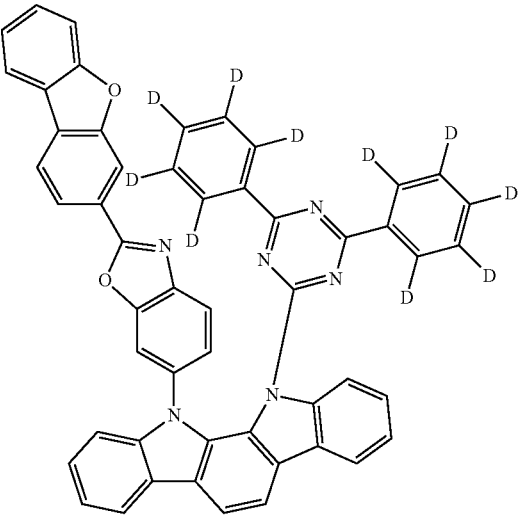
696 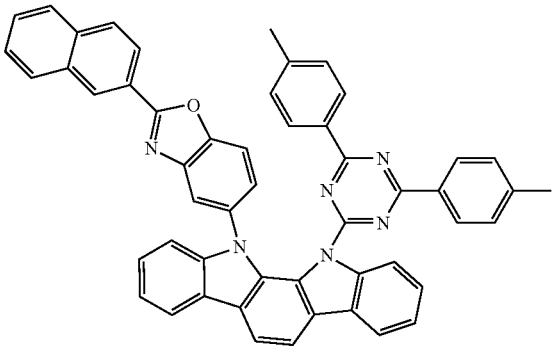

-continued

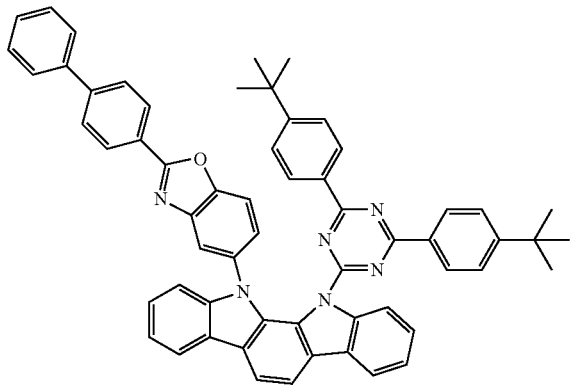

697

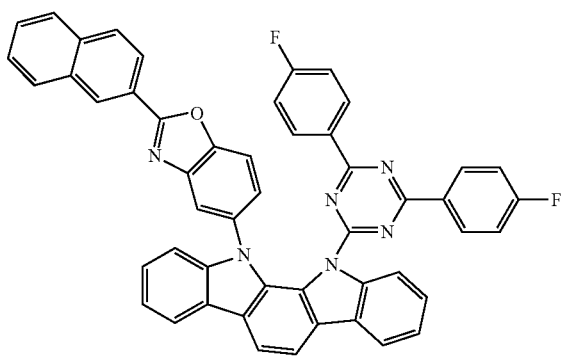

698

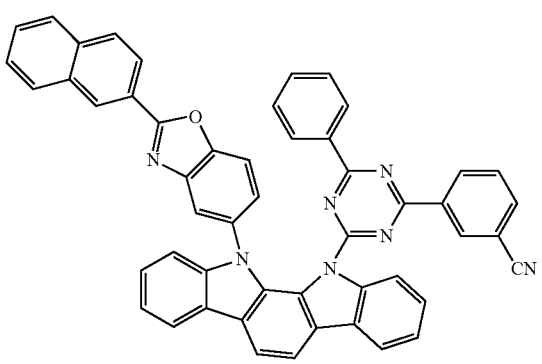

699

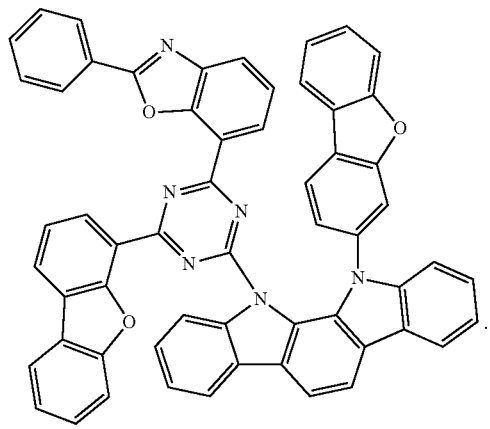

700

The present disclosure also provides an electronic component for realizing photoelectric conversion or electro- optical conversion. The electronic component comprises an anode, a cathode and at least one functional layer between the anode and the cathode, and the functional layer includes the nitrogen-containing compound of the present disclosure.

In one specific embodiment of the present disclosure, as shown in FIG. 1, the organic electroluminescence device according to the present disclosure includes an anode 100, a cathode 200, as well as at least one functional layer 300 between an anode layer and a cathode layer, the functional layer 300 includes a hole injection layer 310, a hole transport layer, an organic electroluminescence layer 330, a hole blocking layer 340, an electron transport layer 350 and an electron injection layer 360; the hole transport layer includes the first hole transport layer 321 and the second hole transport layer 322, where the first hole transport layer 321 is closer to the anode 100 relative to the second hole transport layer 322; the hole injection layer 310, the hole transport layer, the organic electroluminescence layer 330, the hole blocking layer 340, the electron transport layer 350 and the electron injection layer 360 may be successively formed on the anode 100, the organic electroluminescence layer 330 may contain the nitrogen-containing compound of the first aspect of the present disclosure, preferably at least one of the compounds 1 to 700.

Optionally, the anode 100 includes the following anode material, which is preferably a material having a large work function that facilitates hole injection into the functional layer. The specific example of the anode material includes: metals such as nickel, platinum, vanadium, chromium, copper, zinc and gold or alloy thereof; metallic oxides such as zinc oxide, indium oxide, indium tin oxide (ITO) and indium zinc oxide (IZO); a combination of metal and oxide such as ZnO:Al or $SnO_2$:Sb; or conductive polymers such as poly (3-methylthiophene), poly[3,4-(ethylene-1,2-dioxy)thio- phene] (PEDT), polypyrrole and polyaniline, but is not limited thereto. It is preferable to include a transparent electrode which includes Indium tin oxide (Indium tin oxide) (ITO) as the anode.

Optionally, the hole transport layer may include one or more hole transport materials, the hole transport material may be selected from a carbazole polymer, carbazole-linked triarylamines or other types of compounds, which is not specially limited in the present disclosure. For instance, in one embodiment of the present disclosure, the hole transport layer includes the first hole transport layer 321 and the second hole transport layer 322, the first hole transport layer 321 is composed of a compound NPB, and the second hole transport layer 322 is composed of a compound TCBPA.

Optionally, the organic electroluminescence layer 330 may be composed of a single light-emitting material, and may also include a host material and a guest material. Optionally, the organic electroluminescence layer 330 is composed of the host material and the guest material, the holes and electrons injected into the organic electroluminescence layer 330 may be recombined in the organic electroluminescence layer 330 to form excitons, the excitons transfer energy to the host material, and the host material transfers energy to the guest material, thereby further enabling the guest material to emit light.

The host material in the organic electroluminescence layer 330 is composed of the nitrogen-containing compound provided by the present disclosure and GH-P1. The nitrogen-containing compound provided by the present disclosure has polycyclic conjugation properties, and the core structure of fused indolocarbazole. The bond energy between the atoms is high, thus the compound has a good thermal stability, and facilitates solid state accumulation between the molecules. The organic electroluminescence device with the compound as a luminescent layer material has a long service life. A structure is formed by respectively connecting the indolocarbazole structure to a benzoxazole or benzothiazole group and a nitrogen-containing group (triazine, pyridine and pyrimidine). The structure has a high dipole moment, thereby improving the polarity of the material. The nitrogen-containing compounds provided by the present disclosure have a high T1 energy, being suitable for use as a host material, particularly a green host material, of the luminescent layer in the OLED device. Using the compound of the present disclosure as a luminescent layer material in the organic electroluminescence device, the electron transport performance of the device can be effectively improved, thereby the balance degree of the hole injection with the electron injection can be enhanced, and the luminous efficiency and service life of the device can be improved.

The guest material in the organic electroluminescence layer 330 may be a compound having a fused aryl ring or its derivative, a compound having a heteroaryl ring or its derivative, an aromatic amine derivative or other materials, which is not specially limited in the present disclosure. In one embodiment of the present disclosure, the guest material of the organic electroluminescence layer 330 can be Ir(ppy)$_2$acac.

The electron transport layer 350 may be of a single layer structure, may also be of a multilayered structure, and may include one or more electron transport materials, the electron transport material may be selected from a benzimidazole derivative, an oxadiazole derivative, a quinoxaline derivative or other electron transport materials, which is not specially limited in the present disclosure. For instance, in one embodiment of the present disclosure, the electron transport layer 350 can be composed of HNBphen and $L_1Q$.

Optionally, the cathode 200 includes the following cathode material, which is a material having a small work function that facilitates electron injection to the functional layer. The specific example of the cathode material includes: metals such as magnesium, calcium, sodium, potassium, titanium, indium, yttrium, lithium, gadolinium, aluminium, silver, tin and lead or alloy thereof; or multi-layer materials such as $L_1F/Al$, $L_1q/Al$, $L_1O_2/Al$, $L_1F/Ca$, $L_1F/Al$ and $BaF_2/Ca$, but is not limited thereto. It is preferable to include a metal electrode including silver and magnesium as the cathode.

Optionally, a hole injection layer 310 may be also disposed between the anode 100 and the hole transport layer, to enhance the ability of injecting the holes into the hole transport layer. The hole injection layer 310 may be selected from biphenylamine derivatives, starburst arylamine compounds, phthalocyanine derivatives or other materials, which is not specially limited in the present disclosure. In one embodiment of the present disclosure, the hole injection layer 310 may be composed of HAT-CN.

Optionally, an electron injection layer 360 may also be disposed between the cathode 200 and the electron transport layer 350, to enhance the ability of injecting electrons into the electron transport layer 350. The electron injection layer 360 may include inorganic materials such as alkali metal sulfide, and alkali metal halide, or may include a complex of an alkali metal with an organic matter. In one embodiment of the present disclosure, the electron injection layer 360 may include ytterbium (Yb).

The present disclosure also provides an electronic device, including the electronic component of the present disclosure.

Figure 2:
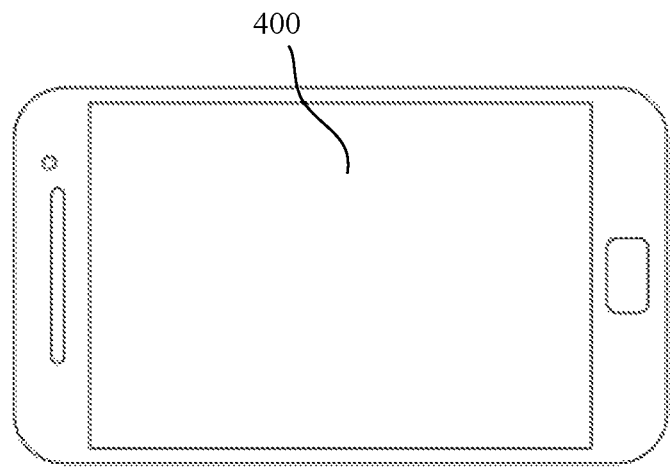
FIG. 2 is a structural schematic diagram of one embodiment of an electronic device according to the present disclosure.

For instance, as shown in FIG. 2, the electronic device provided by the present disclosure is the first electronic device 400, the first electronic device 400 includes any one organic electroluminescence device described in the above-mentioned embodiments of the organic electroluminescence device. The electronic device can be a display device, a lighting device, an optical communication device or other types of electronic devices, for example, the electronic device can include, but is not limited to, a computer screen, a mobile phone screen, a television, electronic paper, an emergency lighting lamp, an optical module, etc. Because the first electronic device 400 is provided with the above-mentioned organic electroluminescence device, the electronic device has the same beneficial effect, and no more detailed description is provided herein.

The present disclosure will be described in detail in conjunction with the embodiments, but the following description is used to explain the present disclosure, rather than limit the scope of the present disclosure in any way.

SYNTHESIS EXAMPLE

Those skilled in the art should recognize that, the chemical reaction described in the present disclosure can be used to properly prepare many other compounds of the present disclosure, and other methods for preparing the compounds of the present disclosure are all deemed within the scope of the present disclosure. For example, synthesis of those non-exemplary compounds according to the present disclosure can be successfully accomplished by those skilled in the art via a modification method, such as properly protecting an interfering group, by using other known reagents to replace the reagents described in the present disclosure, or making some routine modifications to the reaction condition. In addition, the compounds disclosed by the present disclosure were synthesized.

Synthesis Example 1: Synthesis of Compound 67

(1) Synthesis of Reactant B-1

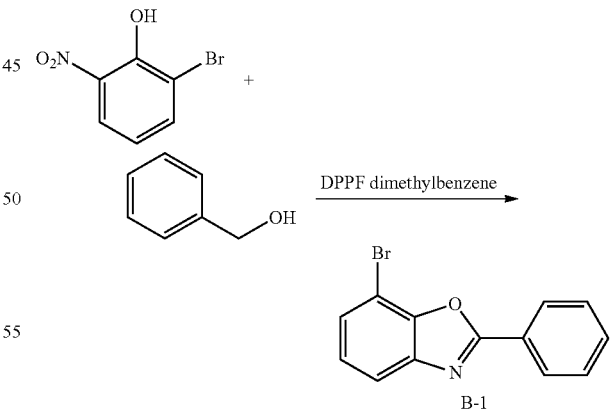

Nitrogen gas (0.100 L/min) was introduced into a three-necked flask equipped with a mechanical stirrer, a thermometer, and an Allihn condenser for replacement for 15 min, and 2-bromo-6-nitrophenol (50.0 g, 229.3 mmol), benzyl alcohol (29.76 g, 275.2 mmol), 1,1'-bis(diphenylphosphino)ferrocene (3.71 g, 6.8 mmol) and xylene (500 mL) were successively added, turned on the mechanical stirrer and heated, after the temperature was raised to 125 to 135° C., a reflux reaction was carried out for 36 h, after the reaction was finished, turned off the mechanical stirrer and stopped heating, and when the temperature was decreased to room temperature, the reaction solution was started to be treated; toluene and water were added to extract the reaction solution, the organic phases were combined, and the organic layer was dried over anhydrous magnesium sulfate, filtered, and concentrated; the crude product was purified by silica gel column chromatography using a dichloromethane/n-heptane system to obtain a solid compound B-1 (40.23 g, 64%).

(2) Synthesis of Intermediate Sub 1-I-A1

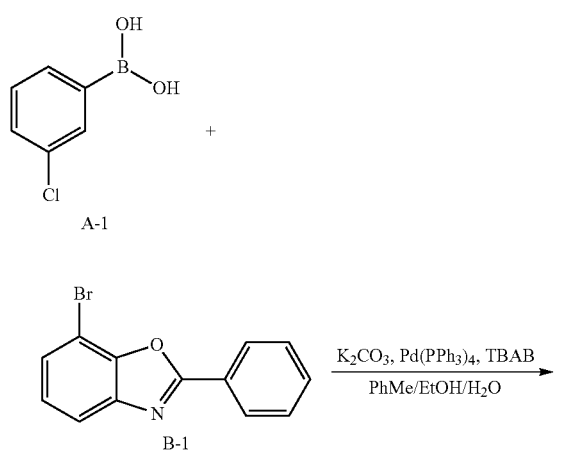

(3) Synthesis of Intermediate Sub A-1

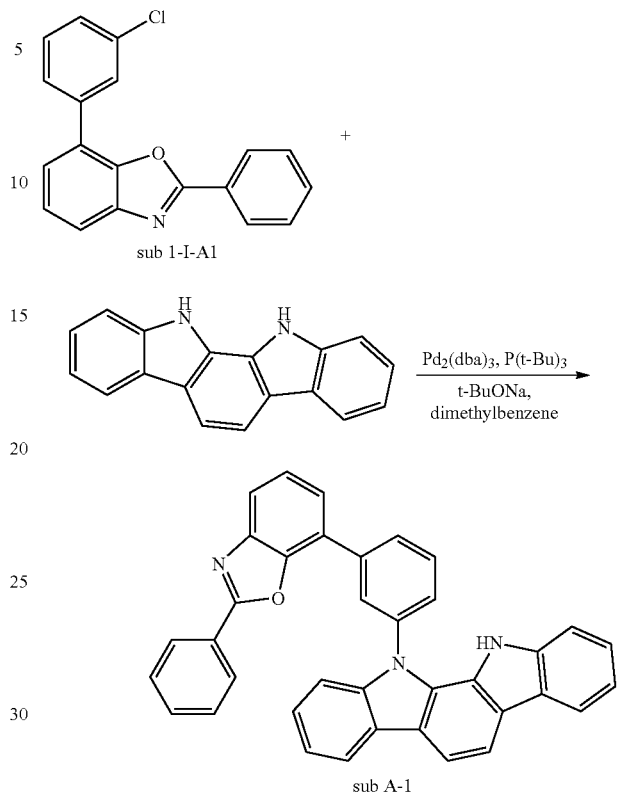

Nitrogen gas (0.100 L/min) was introduced into a three-necked flask equipped with a mechanical stirrer, a thermometer, and an Allihn condenser for replacement for 15 min, and the intermediate sub 1-I-A1 (35.0 g, 114.5 mmol), indolo[2,3-A]carbazole (35.3 g, 137.6 mmol), Pd$_2$(dba)$_3$ (2.1 g, 2.3 mmol), tri-tert-butylphosphine (0.92 g, 4.6 mmol), sodium tert-butoxide (27.5 g, 286.2 mmol), and xylene (500 mL) were added. Turned on the mechanical stirrer and heated, after the temperature was raised to 135 to 145° C., a reflux reaction was carried out for 10 h, and after the reaction was finished, the reaction solution was cooled to room temperature. After the reaction solution was washed with water, an organic phase was separated, dried over anhydrous magnesium sulfate, and filtered, the filtrate was distilled under reduced pressure to remove the solvent, and the crude product was recrystallized by using a dichloromethane/ethanol system to obtain a white solid intermediate sub A-1 (45.1 g, 75%).

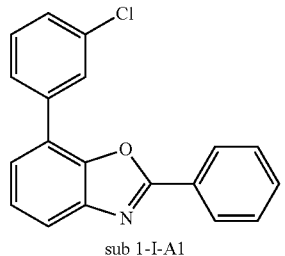

Nitrogen gas (0.100 L/min) was introduced into a three-necked flask equipped with a mechanical stirrer, a thermometer, and an Allihn condenser for replacement for 15 min, and B-1 (50.0 g, 182.40 mmol), m-chlorophenylboronic acid (31.37 g, 200.64 mmol) (A-1), potassium carbonate (55.5 g, 401.3 mmol), tetrakis(triphenylphosphine)palladium (4.2 g, 3.6 mmol), and tetrabutylammonium bromide (1.2 g, 3.6 mmol) were added, and a mixed solvent of toluene (400 mL), ethanol (200 mL) and water (100 mL) were added. Turned on the mechanical stirrer and heated, after the temperature was raised to 75 to 80° C., a reflux reaction was carried out for 8 h, and after the reaction was finished, the reaction solution was cooled to room temperature. An organic phase was extracted with toluene and water and separated, washed with water to be neutral, dried over anhydrous magnesium sulfate, and filtered, and the filtrate was concentrated by distillation under reduced pressure; the crude product was purified by silica gel column chromatography using a dichloromethane/n-heptane system to obtain a solid compound intermediate sub 1-I-A1 (39.6 g, 71%).

Referring to the synthesis method of the intermediate sub A-1, the intermediates shown in the following Table 1 were synthesized, and an intermediate sub A-X (X is 2 to 18) as shown in the following Table 1 was synthesized. Where, an intermediate sub A-2 to an intermediate sub A-10 shown in the following Table 1 were synthesized by referring to the second step (2) and the third step (3) of the intermediate sub A-1, the reactant A-1 was replaced with a reactant A-X (X is 1 to 7), and the reactant B-1 was replaced with a reactant B-X (X is 1 to 6). Intermediates sub A-11-sub A-18 shown in Table 1 were synthesized by referring to the third step (3) of the sub A-1, and the reactant B-1 was replaced with a reactant B-X (X is 7 to 14).

TABLE 1
| Reactant (A-X) | Reactant (B-X) | Intermediate (sub A-X) | Yield % |
|---|---|---|---|
| 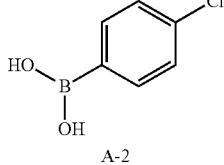<br>A-2 | 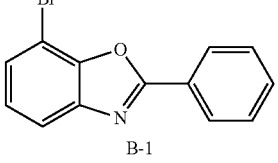<br>B-1 | 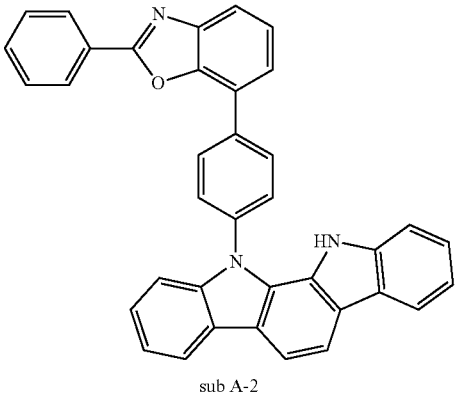 [SMILES: c1ccc(-c2nc3cccc(-c4ccc(-n5c6ccccc6c6ccc7c8ccccc8[nH]c7c65)cc4)c3o2)cc1]<br>sub A-2 | 69 |
| 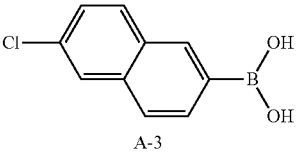<br>A-3 | 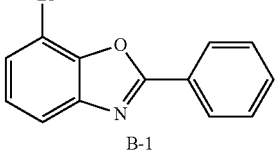<br>B-1 | 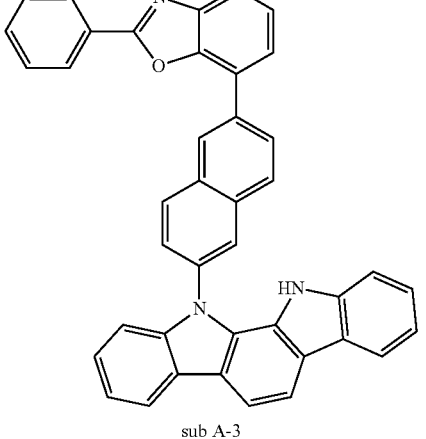<br>sub A-3 | 57 |
| 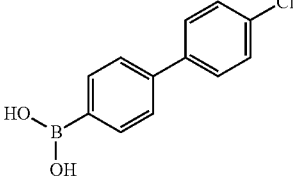<br>A-4 | 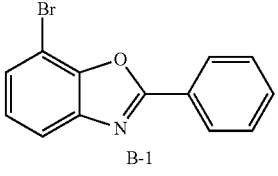<br>B-1 | 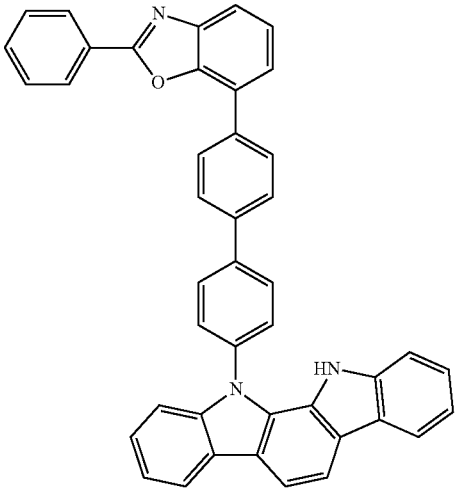<br>sub A-4 | 71 |

TABLE 1-continued
| Reactant (A-X) | Reactant (B-X) | Intermediate (sub A-X) | Yield % |
|---|---|---|---|
| 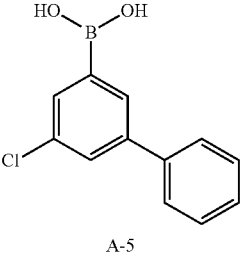 [SMILES: OB(O)c1cc(Cl)cc(-c2ccccc2)c1 ; "A-5"] A-5 | 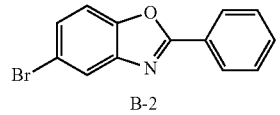 B-2 | 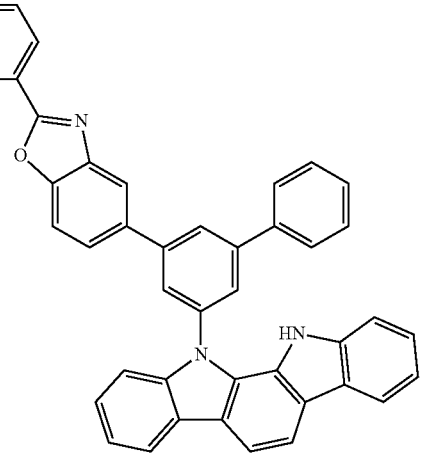 sub A-5 | 65 |
| 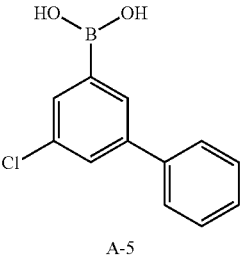 [SMILES: OB(O)c1cc(Cl)cc(-c2ccccc2)c1 ; "A-5"] A-5 | 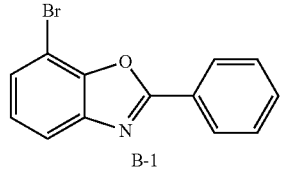 B-1 | 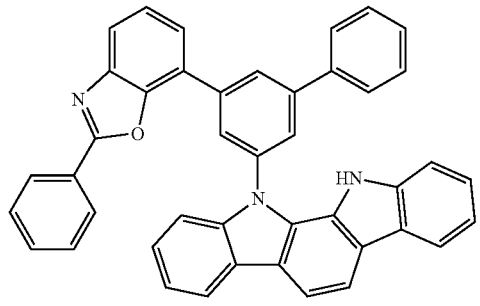 sub A-6 | 66 |
| 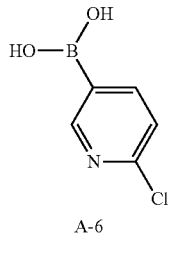 A-6 | 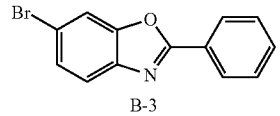 B-3 | 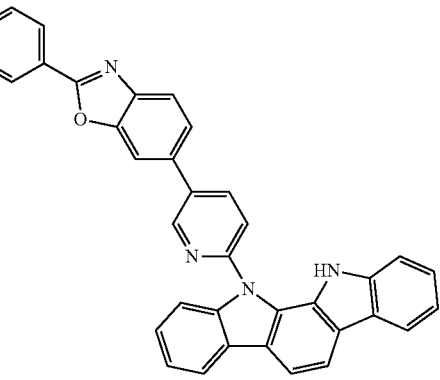 sub A-7 | 57 |
| 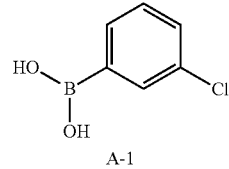 A-1 | 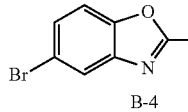 B-4 | 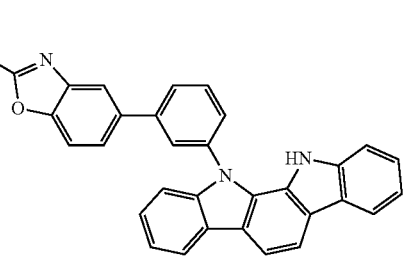 sub A-8 | 60 |

TABLE 1-continued
| Reactant (A-X) | Reactant (B-X) | Intermediate (sub A-X) | Yield % |
|---|---|---|---|
| 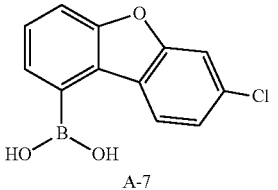 A-7 | 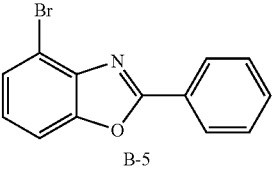 B-5 | 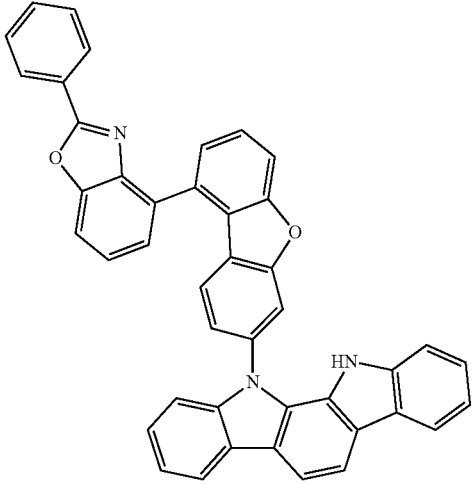 sub A-9 | 52 |
| 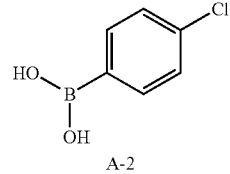 A-2 | 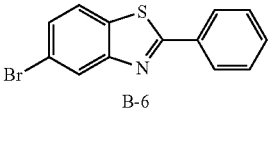 B-6 | 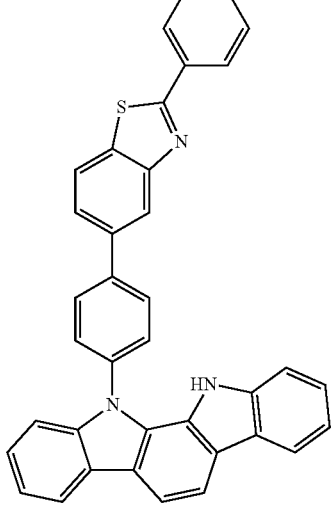 sub A-10 | 56 |
| — | 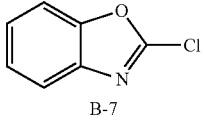 B-7 | 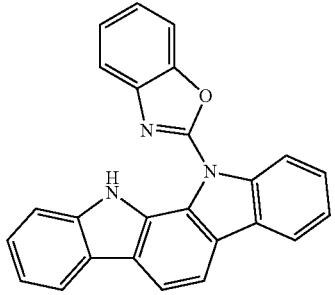 sub A-11 | 67 |

TABLE 1-continued
| Reactant (A-X) | Reactant (B-X) | Intermediate (sub A-X) | Yield % |
|---|---|---|---|
| — | 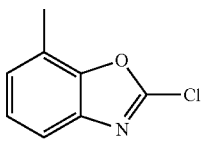<br>B-8 | 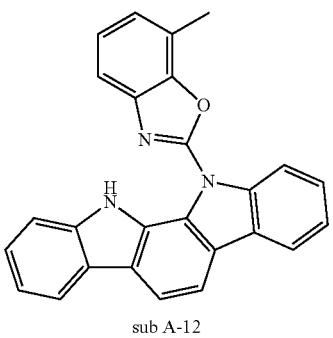 [SMILES: Cc1cccc2nc(-n3c4ccccc4c4ccc5c6ccccc6[nH]c5c43)oc12]<br>sub A-12 | 61 |
| — | 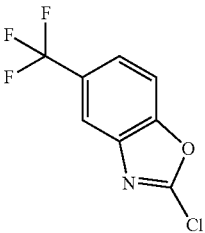<br>B-9 | 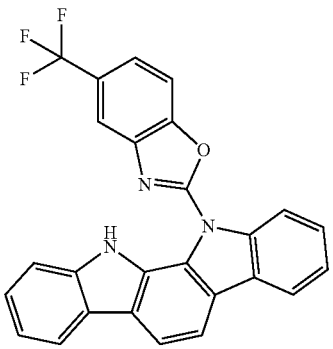<br>sub A-13 | 56 |
| — | 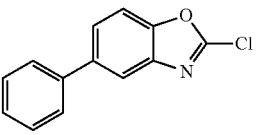<br>B-10 | 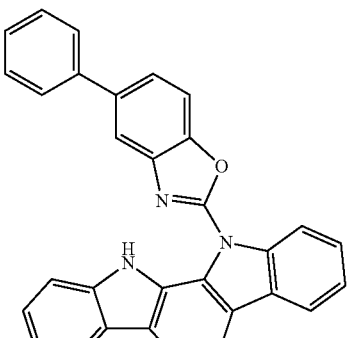<br>sub A-14 | 55 |
| — | 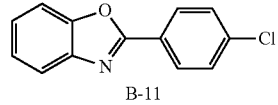<br>B-11 | 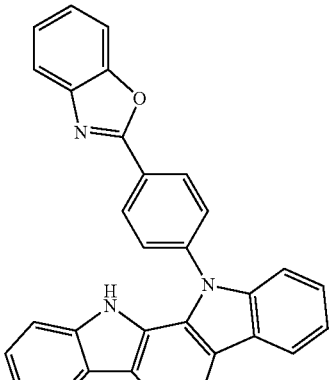<br>sub A-15 | 72 |

TABLE 1-continued
| Reactant (A-X) | Reactant (B-X) | Intermediate (sub A-X) | Yield % |
|---|---|---|---|
| — | 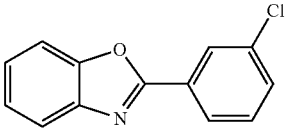<br>B-12 | 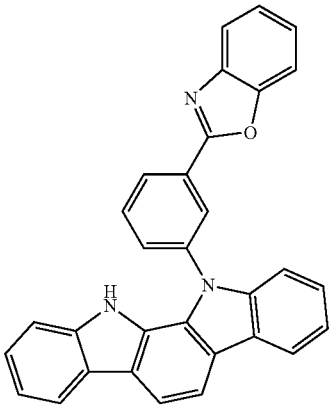<br>sub A-16 | 68 |
| — | 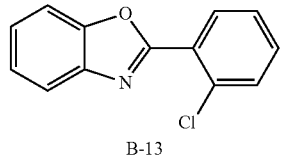<br>B-13 | 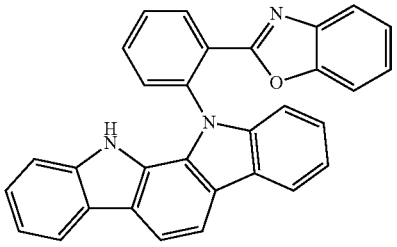<br>sub A-17 | 60 |
| — | 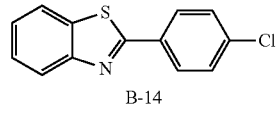<br>B-14 | 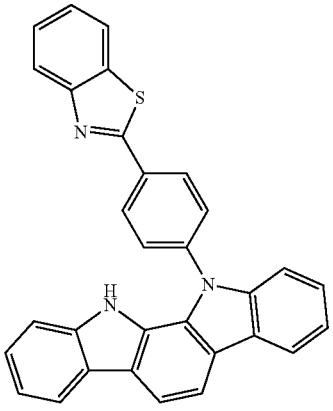<br>sub A-18 | 59 |

(4) Synthesis of Compound 67

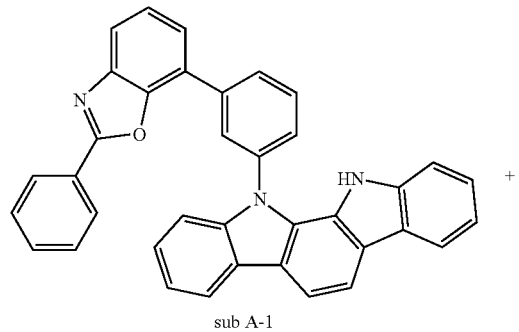

sub A-1

+

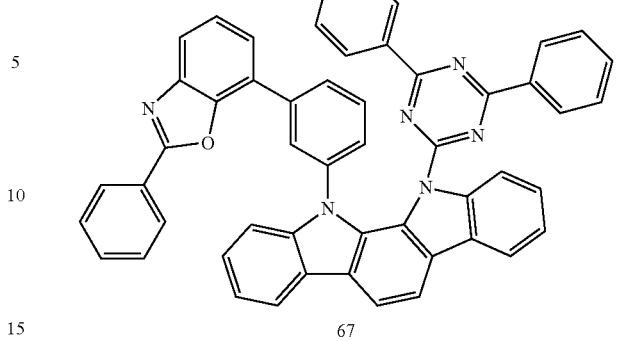

67

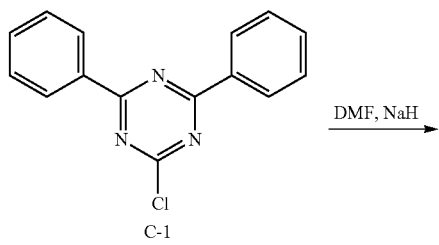

C-1

DMF, NaH →

Nitrogen gas (0.100 L/min) was introduced into a three-necked flask equipped with a mechanical stirrer, a thermometer and an Allihn condenser for replacement for 15 min, and the intermediate sub A-1 (20.0 g, 38.0 mmol), 2-chloro-4,6-diphenyl-1,3,5-triazine (35.3 g, 137.6 mmol) (a reactant C-1), and DMF (200 mL) were added, the mixture was cooled to 0° C., after NaH (1.0 g, 41.8 mmol) was added to the mixture, the system was changed to white from yellow in color, after the temperature of the system was naturally raised to room temperature, a solid was precipitated, and the reaction was finished. The reaction liquid was washed with water, and filtered to obtain a solid product, which was rinsed with a small amount of ethanol, and the crude product was recrystallized with toluene to obtain the compound 67 (13.2 g, 46%). Mass spectrometry: m/z=757.26[M+H]$^+$.

Referring to the synthesis method of the compound 67, compounds shown in the following Table 2 were synthesized, where the intermediate sub A-1 was replaced with the intermediate sub A-X (X is 1 to 18), and the reactant C-1 was replaced with a reactant C-X (X is 1 to 13) to synthesize the compounds as shown in the following Table 2.

TABLE 2

| Preparation examples | Intermediate (sub A-X) | Reactant (C-X) | Compounds | Yield | Mass spectrometry |
|---|---|---|---|---|---|
| 2 | sub A-2 | C-1 | 53 | 81 | 757.26 |
| 3 | sub A-2 | C-2 | 55 | 75 | 833.30 |

TABLE 2-continued

| Preparation examples | Intermediate (sub A-X) | Reactant (C-X) | Compounds | Yield | Mass spectrometry |
|---|---|---|---|---|---|
| 4 | sub A-2 | C-3 | 63 | 65 | 833.30 |
| 5 | sub A-2 | C-4 | 54 | 74 | 833.30 |
| 6 | sub A-1 | C-4 | 80 | 85 | 833.30 |

TABLE 2-continued

| Preparation examples | Intermediate (sub A-X) | Reactant (C-X) | Compounds | Yield | Mass spectrometry |
|---|---|---|---|---|---|
| 7 | sub A-3 | C-5 | 78 | 71 | 857.30 |
| 8 | sub A-4 | C-6 | 114 | 65 | 861.33 |

TABLE 2-continued

| Preparation examples | Intermediate (sub A-X) | Reactant (C-X) | Compounds | Yield | Mass spectrometry |
|---|---|---|---|---|---|
| 9 | sub A-5 | C-7 | 119 | 62 | 869.28 |
| 10 | sub A-6 | C-1 | 120 | 64 | 833.30 |

TABLE 2-continued

| Preparation examples | Intermediate (sub A-X) | Reactant (C-X) | Compounds | Yield | Mass spectrometry |
|---|---|---|---|---|---|
| 11 | sub A-7 | C-8 | 118 | 53 | 910.32 |
| 12 | sub A-8 | C-9 | 68 | 58 | 760.25 |

TABLE 2-continued
| Preparation examples | Intermediate (sub A-X) | Reactant (C-X) | Compounds | Yield | Mass spectrometry |
|---|---|---|---|---|---|
| 13 | 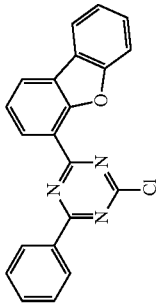 sub A-1 | 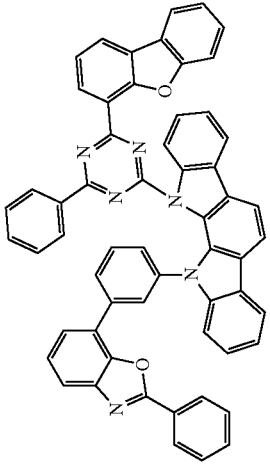 C-10 | 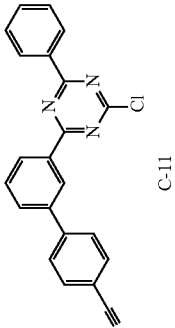 82 | 59 | 847.27 |
| 14 | 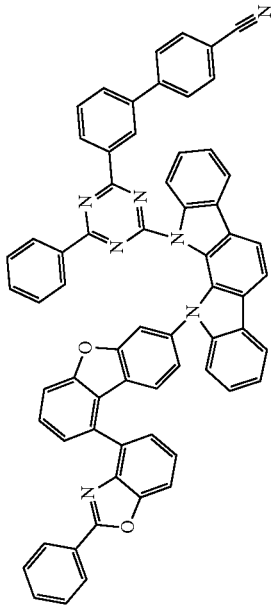 sub A-9 | C-11 | 73 | 62 | 948.30 |

TABLE 2-continued

| Preparation examples | Intermediate (sub A-X) | Reactant (C-X) | Compounds | Yield | Mass spectrometry |
|---|---|---|---|---|---|
| 15 | sub A-10 | C-4 | 353 | 58 | 849.27 |
| 16 | | C-1 | 425 | 71 | 605.20 |

TABLE 2-continued

| Preparation examples | Intermediate (sub A-X) | Reactant (C-X) | Compounds | Yield | Mass spectrometry |
|---|---|---|---|---|---|
| 17 | sub A-11 | C-4 | 426 | 68 | 681.23 |
| 18 | | C-12 | 429 | 85 | 757.26 |

TABLE 2-continued

| Preparation examples | Intermediate (sub A-X) | Reactant (C-X) | Compounds | Yield | Mass spectrometry |
|---|---|---|---|---|---|
| 19 | sub A-12 | C-1 | 442 | 61 | 619.22 |
| 20 | sub A-13 | C-1 | 446 | 64 | 673.19 |

TABLE 2-continued

| Preparation examples | Intermediate (sub A-X) | Reactant (C-X) | Compounds | Yield | Mass spectrometry |
|---|---|---|---|---|---|
| 21 | sub A-14 | C-1 | 646 | 58 | 681.23 |
| 22 | sub A-15 | C-1 | 451 | 77 | 681.23 |

TABLE 2-continued
| Preparation examples | Intermediate (sub A-X) | Reactant (C-X) | Compounds | Yield | Mass spectrometry |
|---|---|---|---|---|---|
| 23 | 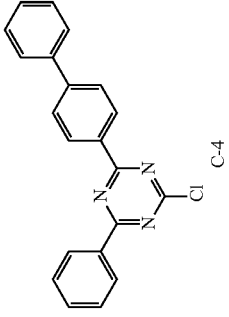 sub A-15 | 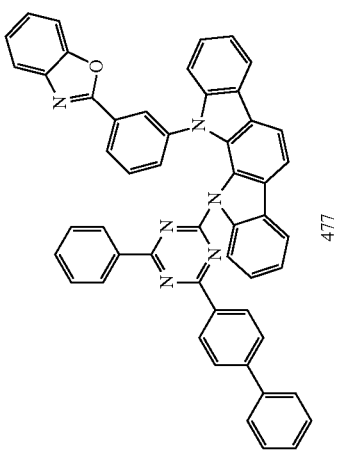 C-4 | 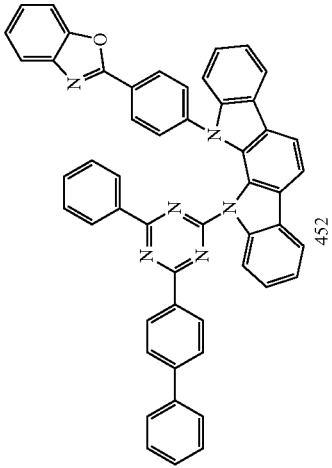 452 | 73 | 757.26 |
| 24 | 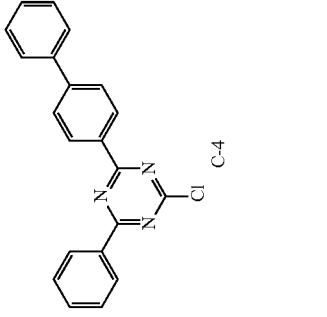 sub A-16 | 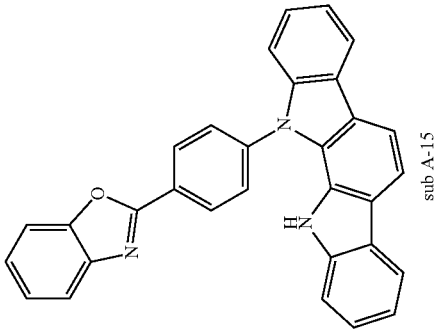 C-4 | 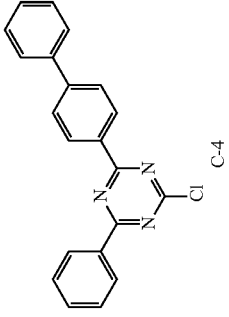 477 | 63 | 757.26 |

TABLE 2-continued

| Preparation examples | Intermediate (sub A-X) | Reactant (C-X) | Compounds | Yield | Mass spectrometry |
|---|---|---|---|---|---|
| 25 | sub A-16 | C-13 | 480 | 70 | 771.25 |
| 26 | sub A-17 | C-4 | 500 | 57 | 757.26 |

TABLE 2-continued
| Preparation examples | Intermediate (sub A-X) | Reactant (C-X) | Compounds | Yield | Mass spectrometry |
|---|---|---|---|---|---|
| 27 | 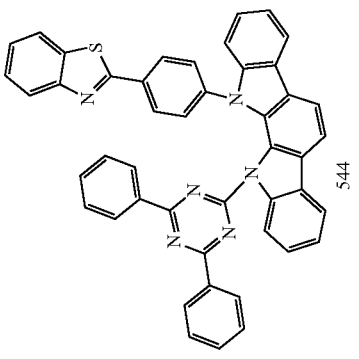 sub A-18 | 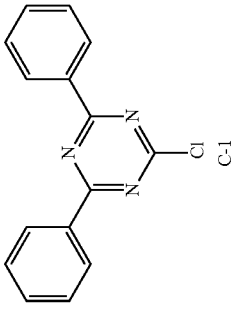 C-1 | 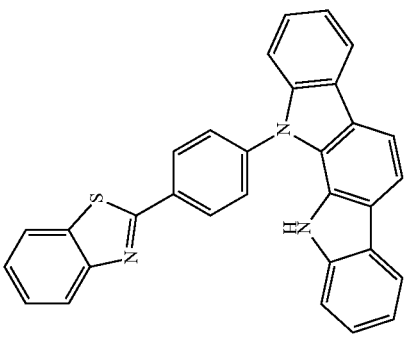 544 | 68 | 697.21 |

Synthesis Example 28: Synthesis of Compound 257

(1) Synthesis of Intermediate sub 1-I-A11

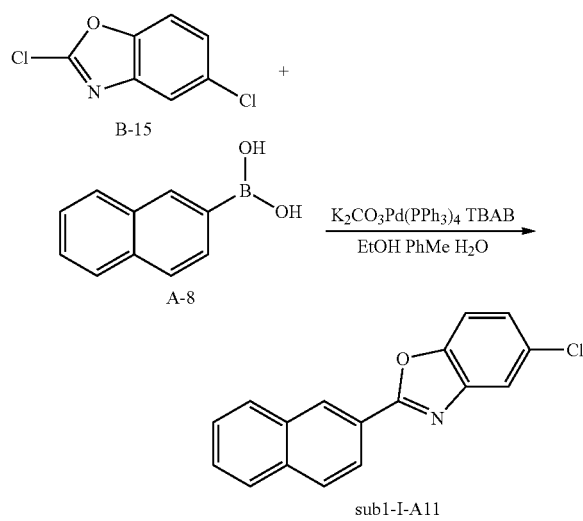

Nitrogen gas (0.100 L/min) was introduced into a three-necked flask equipped with a mechanical stirrer, a thermometer and an Allihn condenser for replacement for 15 min, 2,5-dichlorobenzoxazole (35.0 g, 186.1 mmol) (a reactant B-15), 2-naphthaleneboronic acid (32.0 g, 186.1 mmol) (a reactant A-8), potassium carbonate (64.3 g, 465.4 mmol), tetrakis(triphenylphosphine)palladium (4.3 g, 3.7 mmol), and tetrabutylammonium bromide (1.2 g, 3.72 mmol) were added, and a mixed solvent of toluene (280 mL), ethanol (70 mL) and water (70 mL) was added. Turned on the mechanical stirrer and heated, after the temperature was raised to 75 to 80° C., a reflux reaction was carried out for 15 h, and after the reaction was finished, the reaction solution was cooled to room temperature. An organic phase was extracted with toluene and water and separated, washed with water to be neutral, dried over anhydrous magnesium sulfate, and filtered, the filtrate was concentrated by distillation under reduced pressure; the crude product was purified by silica gel column chromatography using a dichloromethane/n-heptane system to obtain a solid compound intermediate sub 1-I-A11 (31.7 g, 61%).

Referring to the synthesis method of the intermediate sub 1-I-A11, intermediates shown in the following Table 3 were synthesized, where the reactant B-1 was replaced with a reactant B-X (X is 15, 16 or 17), and the reactant A-8 was replaced with a reactant A-X (X is 9, 10, 11, or 14) to synthesize intermediates sub 1-I-AX (X is 12, 13, 14, or 17) shown in the following Table 3.

TABLE 3

| Reactant (B-X) | Reactant (A-X) | Intermediate (sub 1-I-AX) | Yield % |
|---|---|---|---|
| B-15 | A-9 | sub1-I-A12 | 69 |
| B-15 | A-10 | sub1-I-A13 | 56 |
| B-16 | A-11 | sub1-I-A14 | 54 |

TABLE 3-continued

| Reactant (B-X) | Reactant (A-X) | Intermediate (sub 1-I-AX) | Yield % |
|---|---|---|---|
| 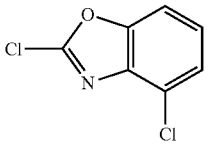 B-17 | 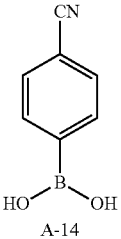 A-14 | 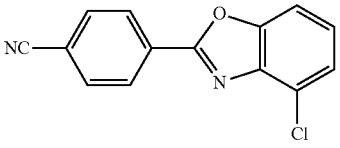 sub1-I-A17 | 54 |

(2) Synthesis of Compound 257

Referring to the synthesis method of the compound 67, compounds shown in the following Table 4 were synthesized, where the intermediate sub 1-I-A1 was replaced with an intermediate sub 1-I-AX (X is 11, 12, 13, 14 or 17), and the reactant C-1 was replaced with the reactant C-X (X is 1, 2, 4 or 14 to 18) to synthesize the compounds shown in the following Table 4.

TABLE 4
| Preparation examples | Intermediate (sub 1-1-AX) | Reactant (C-X) | Compounds | Yield % | Mass spectrometry |
|---|---|---|---|---|---|
| 28 | 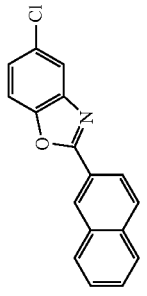 sub1-I-A11 | 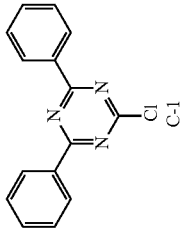 C-1 | 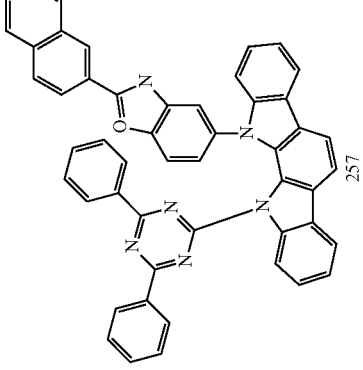 257 | 51 | 731.25 |
| 29 | 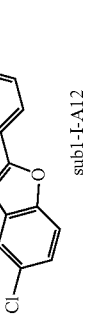 sub1-I-A12 | 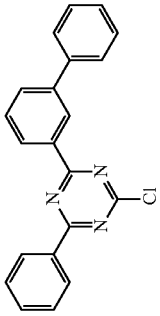 C-2 | 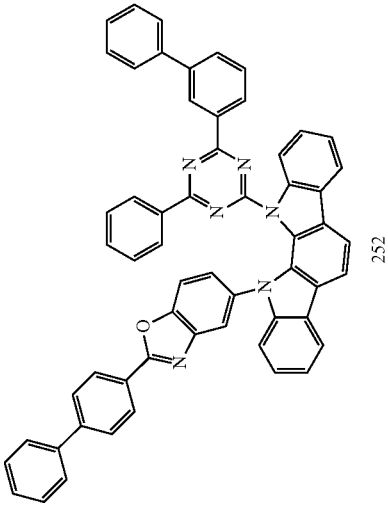 252 | 55 | 833.30 |

TABLE 4-continued

| Preparation examples | Intermediate (sub 1-1-AX) | Reactant (C-X) | Compounds | Yield % | Mass spectrometry |
|---|---|---|---|---|---|
| 30 | sub1-I-A13 | C-1 | 254 | 57 | 833.30 |
| 31 | sub1-I-A14 | C-4 | 258 | 46 | 847.27 |

TABLE 4-continued

| Preparation examples | Intermediate (sub 1-1-AX) | Reactant (C-X) | Compounds | Yield % | Mass spectrometry |
|---|---|---|---|---|---|
| 32 | sub1-I-A17 | C-1 | 260 | 64 | 706.23 |
| 33 | sub1-I-A14 | C-14 | 695 | 51 | 781.31 |

TABLE 4-continued

| Pre- paration ex- amples | Intermediate (sub 1-1-AX) | Reactant (C-X) | Compounds | Yield % | Mass spectro- metry |
|---|---|---|---|---|---|
| 34 | sub1-I-A11 | C-15 | 696 | 42 | 759.29 |
| 35 | sub1-I-A12 | C-16 | 697 | 60 | 869.40 |

TABLE 4-continued

| Preparation examples | Intermediate (sub 1-1-AX) | Reactant (C-X) | Compounds | Yield % | Mass spectrometry |
|---|---|---|---|---|---|
| 36 | sub1-I-A11 | C-17 | 698 | 46 | 767.24 |
| 37 | sub1-I-A11 | C-18 | 699 | 57 | 756.25 |

Preparation Example 38: Synthesis of Compound 121

(1) Synthesis of Intermediate sub A-19

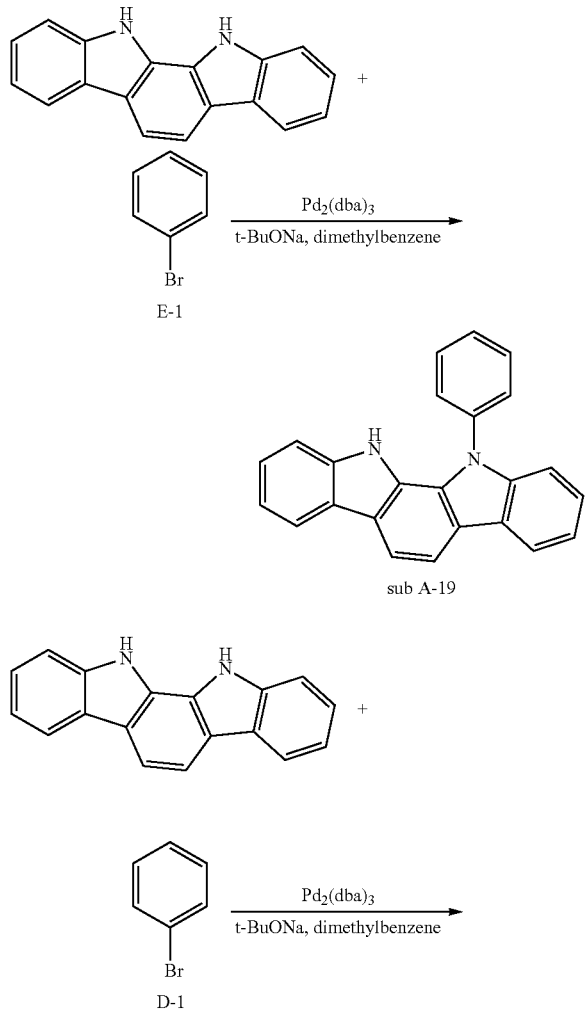

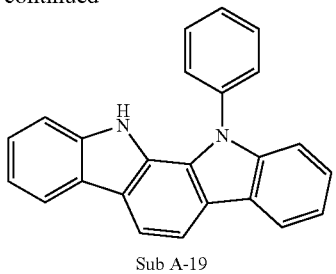

Sub A-19

Nitrogen gas (0.100 L/min) was introduced into a three-necked flask equipped with a mechanical stirrer, a thermometer, and an Allihn condenser for replacement for 15 min, and indolo[2,3-A]carbazole (50.0 g, 195.1 mmol), bromobenzene (27.5 g, 175.5 mmol) (a reactant D-1), $Pd_2(dba)_3$ (3.5 g, 3.9 mmol), tri-tert-butylphosphine (1.6 g, 7.8 mmol), sodium tert-butoxide (41.2 g, 429.2 mmol), and xylene (500 mL) were added. Turned on the mechanical stirrer and heated, after the temperature was raised to 135 to 145° C., a reflux reaction was carried out for 10 h, and after the reaction was finished, the reaction solution was cooled to room temperature. Toluene and water were added to extract the reaction solution, the organic phase was dried over anhydrous magnesium sulfate, after filtration, the filtrate was concentrated by distillation under reduced pressure, and the crude product was purified by silica gel column chromatography using a dichloromethane/n-heptane system to obtain a solid intermediate sub A-19 (47.3 g, 73%).

Referring to the synthesis method of the intermediate sub A-19, the intermediates shown in the following Table 5 were synthesized, where the reactant D-1 was replaced with a reactant D-X (X is 2 to 10) to synthesize the intermediates sub A-X (X is 20 to 24, 26 to 28) shown in the following Table 5.

TABLE 5

| Reactant (D-X) | Intermediate (sub A-X) | Yield % |
|---|---|---|
| D-2 | sub A-20 | 66 |

TABLE 5-continued
| Reactant (D-X) | Intermediate (sub A-X) | Yield % |
|---|---|---|
| 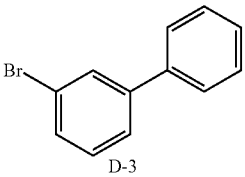<br>D-3 | 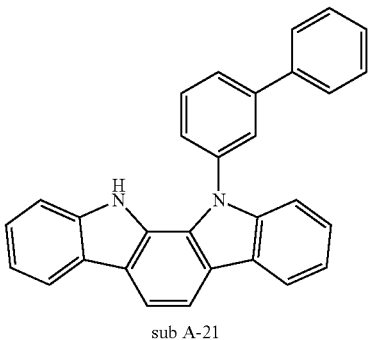 [SMILES: c1ccc(-c2cccc(-n3c4ccccc4c4ccc5c6ccccc6[nH]c5c43)c2)cc1]<br>sub A-21 | 64 |
| 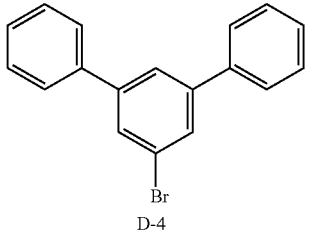<br>D-4 | 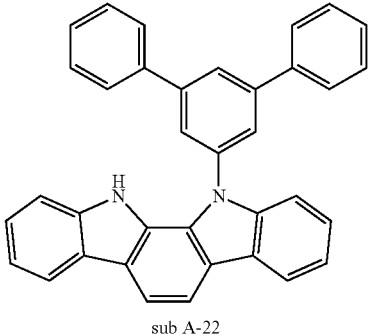 [SMILES: c1ccc(-c2cc(-c3ccccc3)cc(-n3c4ccccc4c4ccc5c6ccccc6[nH]c5c43)c2)cc1]<br>sub A-22 | 60 |
| 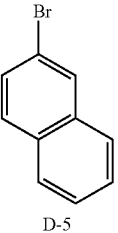<br>D-5 | 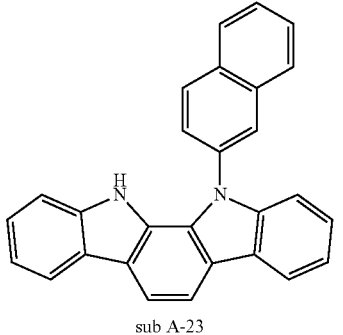 [SMILES: c1ccc2cc(-n3c4ccccc4c4ccc5c6ccccc6[nH]c5c43)ccc2c1]<br>sub A-23 | 62 |
| 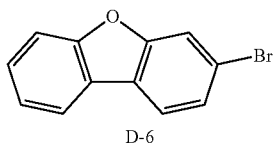<br>D-6 | 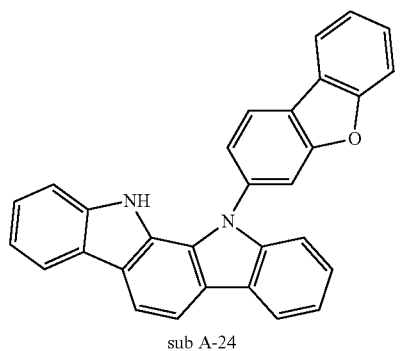<br>sub A-24 | 52 |

TABLE 5-continued
| Reactant (D-X) | Intermediate (sub A-X) | Yield % |
|---|---|---|
| 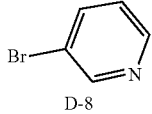<br>D-8 | 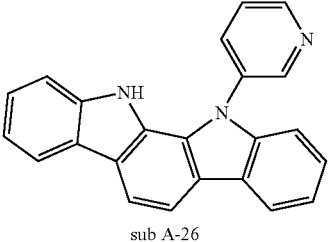<br>sub A-26 | 73 |
| 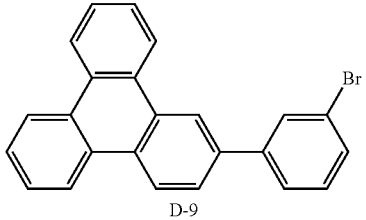<br>D-9 | 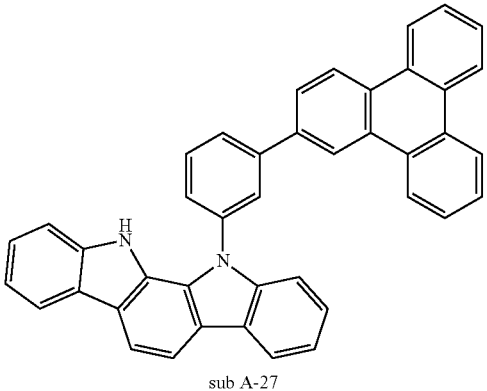 [SMILES: c1cc(-c2ccc3c4ccccc4c4ccccc4c3c2)cc(-n2c3ccccc3c3ccc4c5ccccc5[nH]c4c32)c1]<br>sub A-27 | 61 |
| 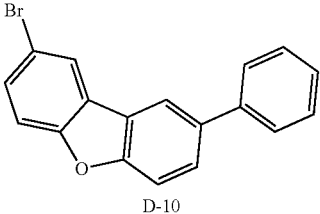<br>D-10 | 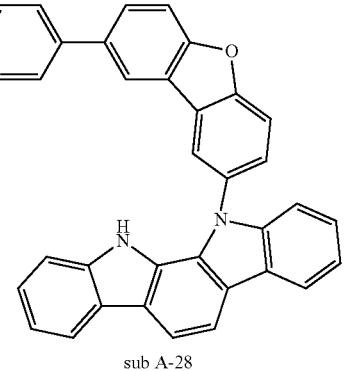<br>sub A-28 | 62 |

(2) Synthesis of Intermediate Sub B-1

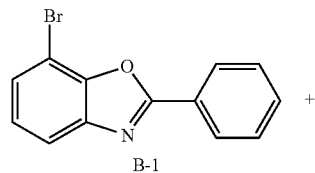
B-1

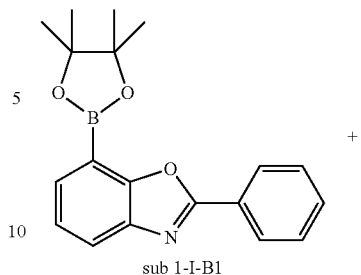
sub 1-I-B1

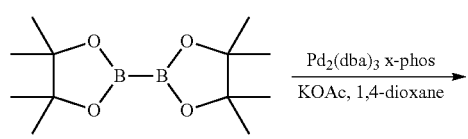
Pd₂(dba)₃ x-phos
KOAc, 1,4-dioxane

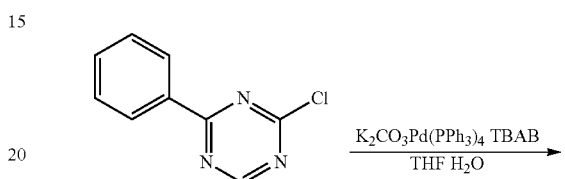
C-19
K₂CO₃Pd(PPh₃)₄ TBAB
THF H₂O

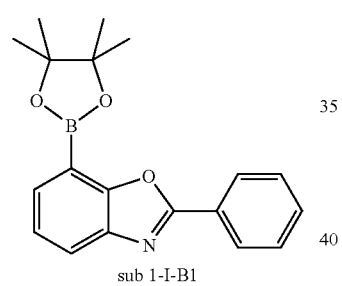
sub 1-I-B1

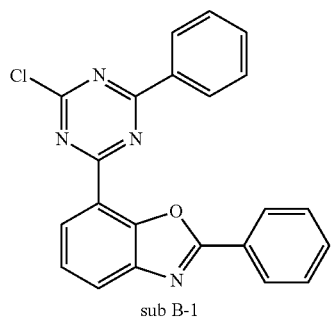
sub B-1

Nitrogen gas (0.100 L/min) was introduced into a three-necked flask equipped with a mechanical stirrer, a thermometer, and an Allihn condenser for replacement for 15 min, the reactant B-1 (55.0 g, 200.6 mmol), bis(pinacolato)diboron (76.4 g, 300.9 mmol), 1,4-dioxane (600 mL), potassium acetate (49.2 g, 501.6 mmol), x-phos (1.9 g, 4.0 mmol), and Pd₂(dba)₃ (1.8 g, 2.0 mmol) were successively added, the mixture was heated to 95-105° C., a reflux reaction was carried out for 14 h, and after the reaction is finished, the reaction solution was cooled to room temperature. Toluene and water were added to extract the reaction solution, the organic phase was dried over anhydrous magnesium sulfate, after filtration, the filtrate was concentrated by distillation under reduced pressure, and the product was pulped with ethanol, and filtered to obtain an intermediate sub 1-I-B1 (54.1 g, 84%).

Nitrogen gas (0.100 L/min) was introduced into a three-necked flask equipped with a mechanical stirrer, a thermometer, and an Allihn condenser for replacement for 15 min, and the intermediate sub 1-I-B1 (45.5 g, 141.5 mmol), 2,4-dichloro-6-phenyl-1,3,5-triazine (40.0 g, 176.9 mmol) (a reactant C-19), tetrakis(triphenylphosphine)palladium (2.0 g, 1.7 mmol), potassium carbonate (61.1 g, 442.3 mmol), tetrabutylammonium bromide (1.1 g, 3.5 mmol), tetrahydrofuran (320 mL) and deionized water (80 mL) were successively added; turned on the mechanical stirrer and heated, after the temperature was raised to 60 to 70° C., a reflux reaction was carried out for 10 h, and after the reaction was finished, the reaction solution was cooled to room temperature. The reaction solution was extracted with toluene and water, the organic phases were combined, dried over anhydrous magnesium sulfate, filtered and concentrated, and the crude product was purified by silica gel column chromatography using a dichloromethane/n-heptane system to obtain a solid intermediate sub B-1 (38.1 g, yield 56%).

Referring to the synthesis method of the intermediate sub B-1, intermediates shown in the following Table 6 were synthesized, where the reactant C-19 was replaced with a reactant C-X (X is 20 to 24) to synthesize the intermediates sub B-X (X is 2, 3, 4, 5 or 6) shown in the following Table 6.

TABLE 6
| Reactant (C-X) | Intermediate (sub B-X) | Yield % |
|---|---|---|
| 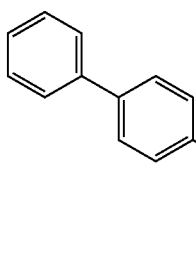 C-20 | 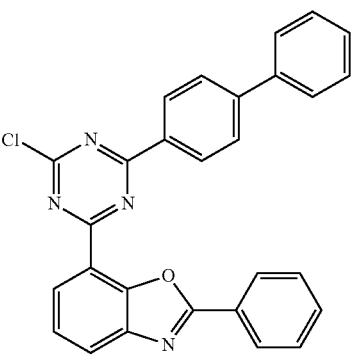 sub B-2 | 62 |
| 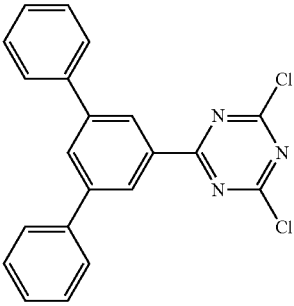 C-21 | 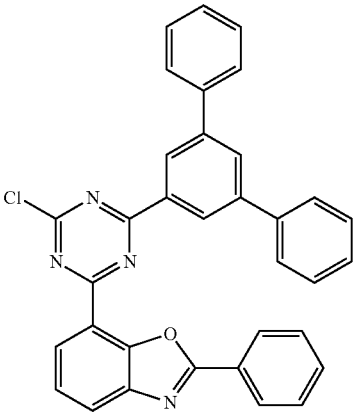 sub B-3 | 59 |
| 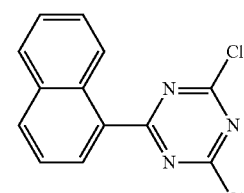 C-22 | 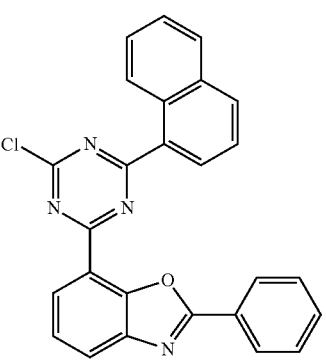 sub B-4 | 57 |
| 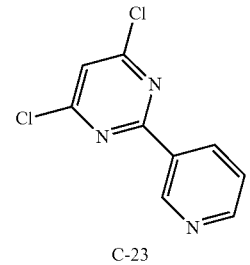 C-23 | 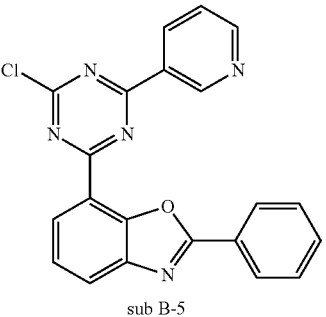 [SMILES: Clc1nc(-c2cccnc2)nc(-c2cccc3nc(-c4ccccc4)oc23)n1] sub B-5 | 60 |

TABLE 6-continued

| Reactant (C-X) | Intermediate (sub B-X) | Yield % |
|---|---|---|
| 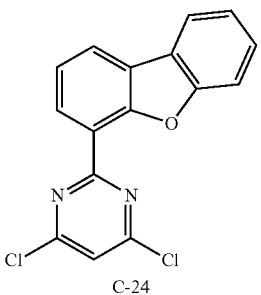<br>C-24 | 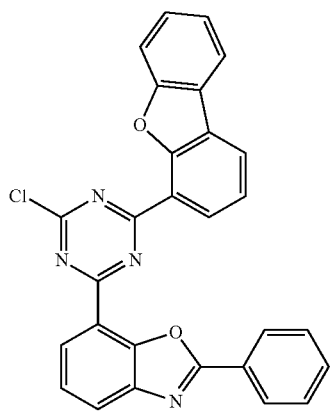<br>sub B-6 | 67 |

(3) Synthesis of Compound 121

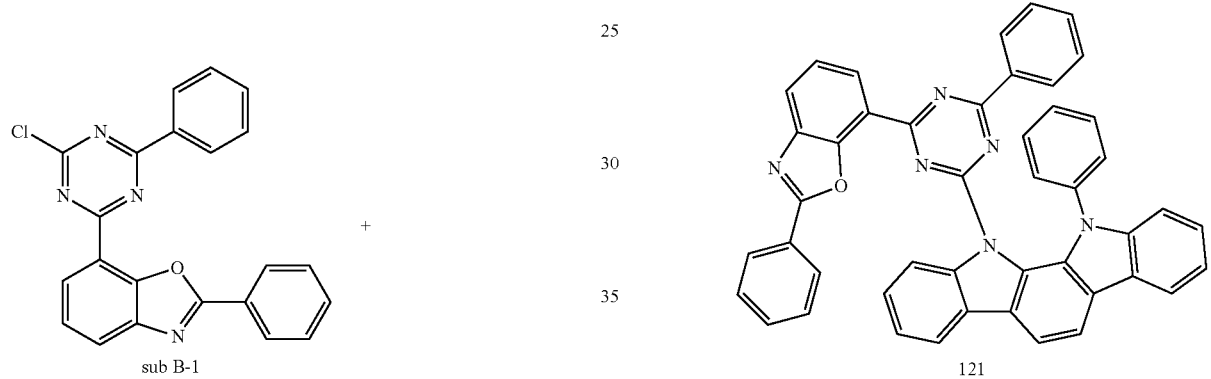

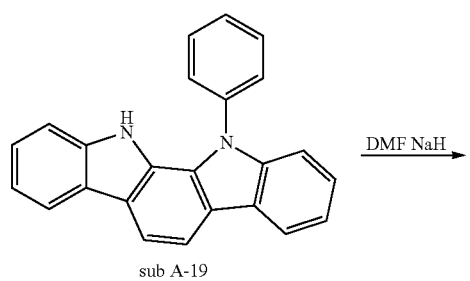

Nitrogen gas (0.100 L/min) was introduced into a three-necked flask equipped with a mechanical stirrer, a thermometer, and an Allihn condenser for replacement for 15 min, the intermediate sub A-19 (20.0 g, 60.2 mmol), the intermediate sub B-1 (27.7 g, 72.2 mmol), and DMF (200 mL) were added, the mixture was cooled to 0° C., after NaH (1.6 g, 66.2 mmol) was added to the mixture, the system was changed from white to yellow, after the temperature was naturally raised to room temperature, a solid was precipitated, and the reaction was finished. The reaction solution was washed with water, and filtered to obtain a solid product, rinsed with a small amount of ethanol, and the crude product was recrystallized with toluene to obtain the compound 121 (23.3 g, 57%). Mass spectrometry: m/z=681.23 [M+H]$^+$.

Referring to the synthesis method of the compound 121, the compounds shown in the following Table 7 were synthesized, where the intermediate sub A-19 was replaced with an intermediate sub A-X (X is 19 to 28), and the intermediate sub B-1 was replaced with an intermediate sub B-X (X is 2 to 6) to synthesize the compounds shown in the following Table 7.

TABLE 7

| Preparation examples | Intermediate (sub A-X) | Intermediate (sub B-X) | Compounds | Yield % | Mass spectrometry |
|---|---|---|---|---|---|
| 39 | sub A-20 | sub B-2 | 190 | 51 | 833.30 |
| 40 | sub A-21 | sub B-3 | 187 | 63 | 909.33 |

TABLE 7-continued

| Preparation examples | Intermediate (sub A-X) | Intermediate (sub B-X) | Compounds | Yield % | Mass spectrometry |
|---|---|---|---|---|---|
| 41 | sub A-19 | sub B-2 | 122 | 68 | 757.26 |
| 42 | sub A-22 | sub B-4 | 188 | 57 | 883.31 |

TABLE 7-continued
| Preparation examples | Intermediate (sub A-X) | Intermediate (sub B-X) | Compounds | Yield % | Mass spectrometry |
|---|---|---|---|---|---|
| 43 | 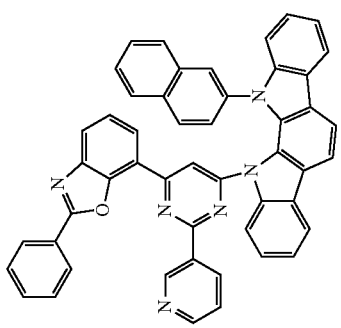 sub A-23 | 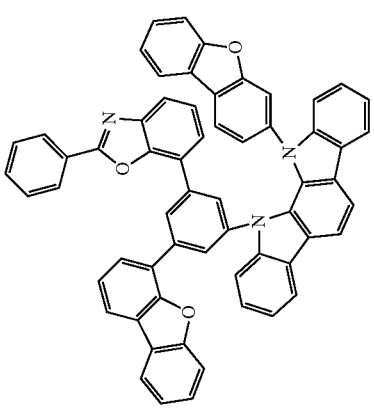 sub-B-5 | 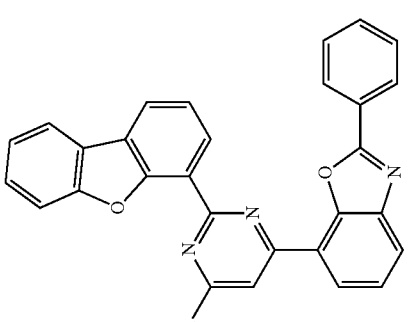 194 | 58 | 731.25 |
| 44 | 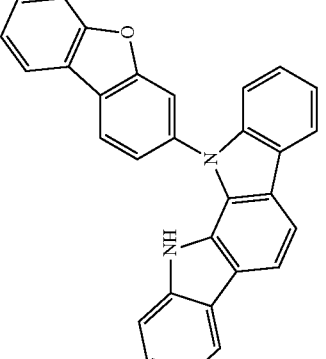 sub A-24 | 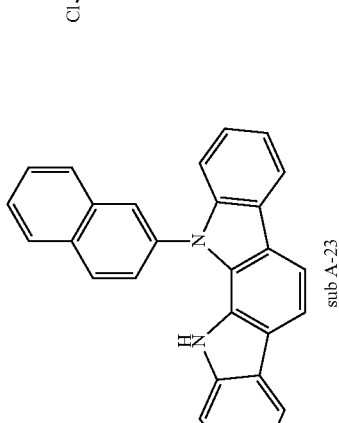 sub-B-6 | 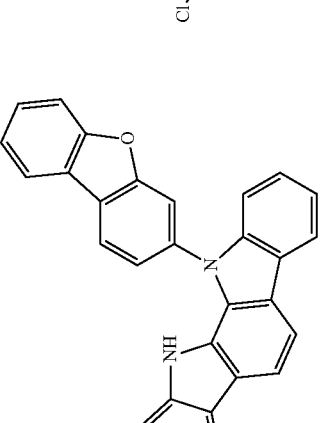 199 | 42 | 861.26 |

TABLE 7-continued
| Preparation examples | Intermediate (sub A-X) | Intermediate (sub B-X) | Compounds | Yield % | Mass spectrometry |
|---|---|---|---|---|---|
| 45 | 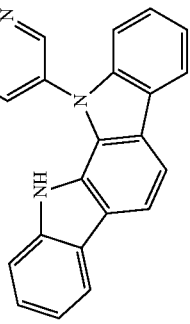 sub A-26 | 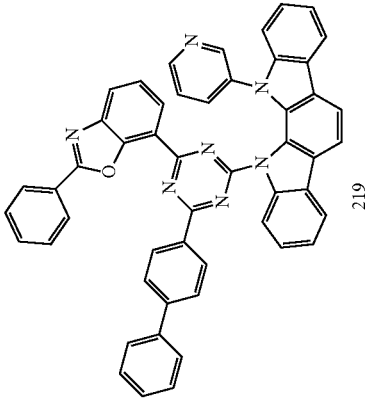 sub-B-2 | 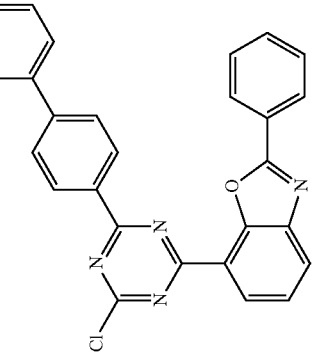 219 | 63 | 758.26 |
| 46 | 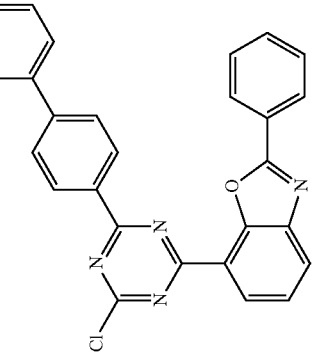 sub A-27 | 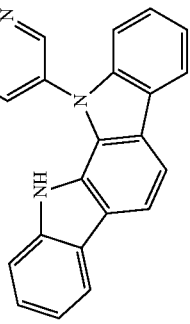 sub-B-1 | 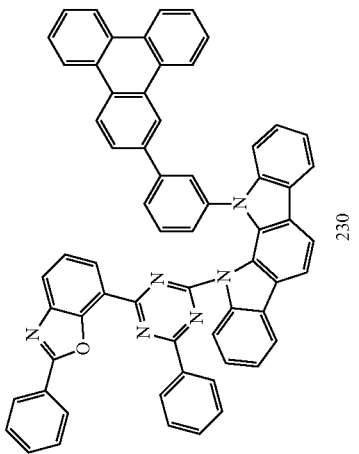 230 | 54 | 907.31 |

TABLE 7-continued
| Preparation examples | Intermediate (sub A-X) | Intermediate (sub B-X) | Compounds | Yield % | Mass spectrometry |
|---|---|---|---|---|---|
| 47 | 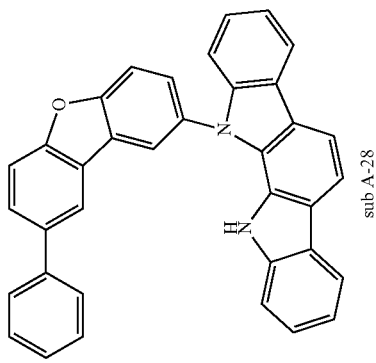 sub A-28 | 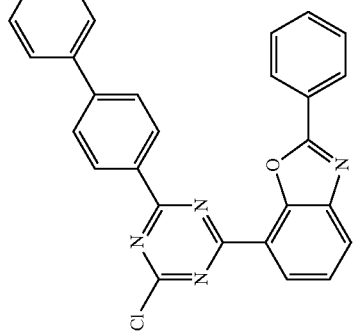 sub-B-2 | 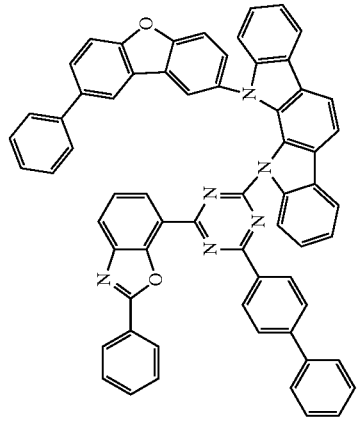 228 | 51 | 923.31 |

Synthesis Example 48: Synthesis of Compound 667

(1) Synthesis of Intermediate Sub B-7

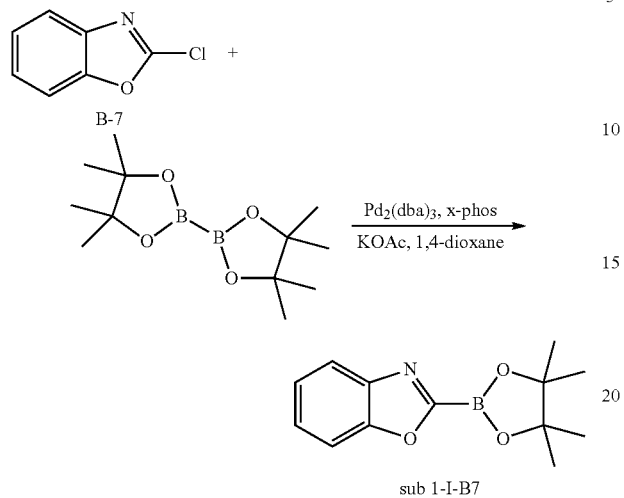

Nitrogen gas (0.100 L/min) was introduced into a three-necked flask equipped with a mechanical stirrer, a thermometer, and an Allihn condenser for replacement for 15 min, a reactant B-7 (30.0 g, 195.3 mmol), bis(pinacolato)diboron (74.4 g, 293.0 mmol), 1,4-dioxane (600 mL), potassium acetate (38.3 g, 390.70 mmol), x-phos (1.8 g, 3.9 mmol), and Pd$_2$(dba)$_3$ (1.7 g, 1.9 mmol) were successively added, the mixture was heated to 95 to 105° C., a reflux reaction was carried out for 14 h, and after the reaction was finished, the reaction solution was cooled to room temperature. Toluene and water were added to extract the reaction solution, the organic phase was dried over anhydrous magnesium sulfate, after filtration, the filtrate was concentrated by distillation under reduced pressure, and the product was pulped with ethanol, and filtered to obtain an intermediate sub 1-I-B7 (29.2 g, 61%).

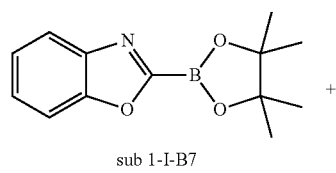

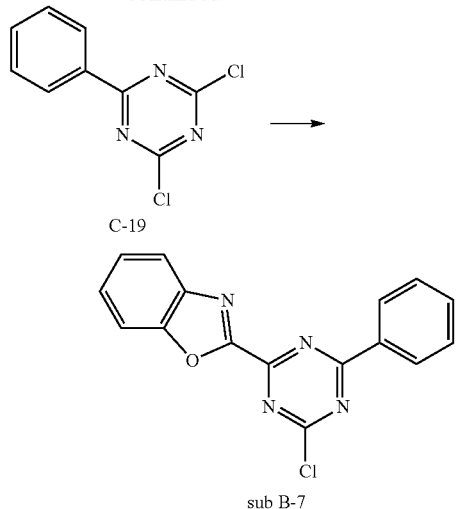

Nitrogen gas (0.100 L/min) was introduced into a three-necked flask equipped with a mechanical stirrer, a thermometer, and an Allihn condenser for replacement for 15 min, and the intermediate sub 1-I-B7 (25.0 g, 102.0 mmol), 2,4-dichloro-6-phenyl-1,3,5-triazine (23.0 g, 102.0 mmol) (a reactant C-19), tetrakis(triphenylphosphine)palladium (2.3 g, 2.0 mmol), potassium carbonate (28.2 g, 204.0 mmol), tetrabutylammonium bromide (0.6 g, 2.0 mmol), tetrahydrofuran (100 mL) and deionized water (25 mL) were successively added; turned on the mechanical stirrer and heated, after the temperature was raised to 60 to 70° C., a reflux reaction was carried out for 10 h, and after the reaction was finished, the reaction solution was cooled to room temperature. The reaction solution was extracted with toluene and water, the organic phases were combined, dried over anhydrous magnesium sulfate, filtered and concentrated, and the crude product was purified by silica gel column chromatography using a dichloromethane/n-heptane system to obtain a solid intermediate sub B-7 (17.3 g, yield 55%).

(2) Synthesis of Compound 667

Referring to the synthesis method of the intermediate sub B-7, intermediates shown in the following Table 8 were synthesized, where the reactant C-19 was replaced with a reactant C-X (X is 19 or 20), and the reactant B-7 was replaced with a reactant B-X (X is 7 or 11) to synthesize intermediates sub B-X (X is 8 or 9) shown in the following Table 8.

TABLE 8

| Reactant (C-X) | Reactant (B-X) | Intermediate (sub B-X) | Yield % |
|---|---|---|---|
| C-20 | B-7 | sub B-8 | 58 |

TABLE 8-continued

| Reactant (C-X) | Reactant (B-X) | Intermediate (sub B-X) | Yield % |
|---|---|---|---|
| 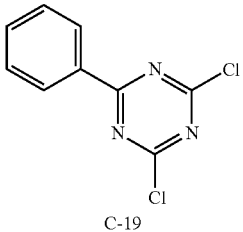<br>C-19 | 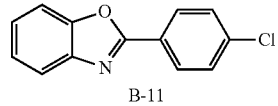<br>B-11 | 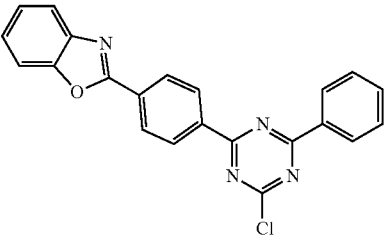<br>sub B-9 | 51 |

Referring to the synthesis method of the compound 121, compounds shown in the following Table 9 were synthesized, where the intermediate sub A-19 was replaced with an intermediate sub A-X (X is 19 to 21), and the intermediate sub B-1 was replaced with an intermediate sub B-X (X is 7 or 9) to synthesize the compounds shown in the following Table 9.

TABLE 9
| Preparation Examples | Intermediate (sub A-X) | Intermediate (sub B-X) | Compounds | Yield % | Mass spectrometry |
|---|---|---|---|---|---|
| 48 | 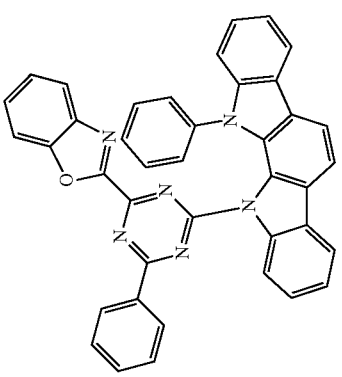 sub A-19 | 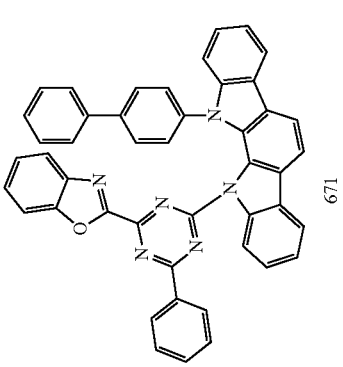 sub B-7 | 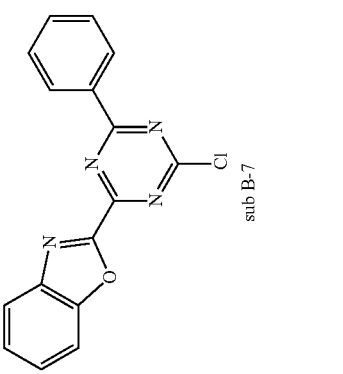 667 | 51 | 605.20 |
| 49 | 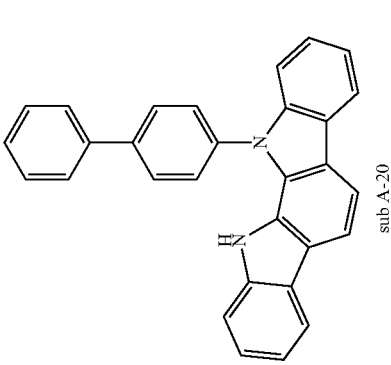 sub A-20 | 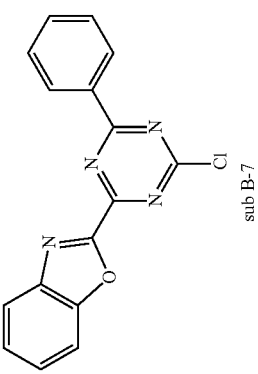 sub B-7 | 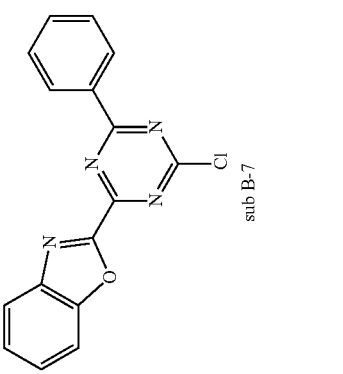 671 | 52 | 757.27 |

TABLE 9-continued
| Preparation Examples | Intermediate (sub A-X) | Intermediate (sub B-X) | Compounds | Yield % | Mass spectrometry |
|---|---|---|---|---|---|
| 50 | 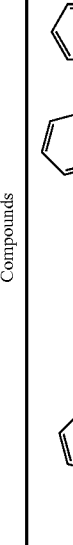 sub A-21 |  sub B-9 | 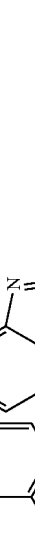 690 | 63 | 757.26 |

Preparation Example 51: Synthesis of Compound 664

(1) Synthesis of Intermediate sub A-29

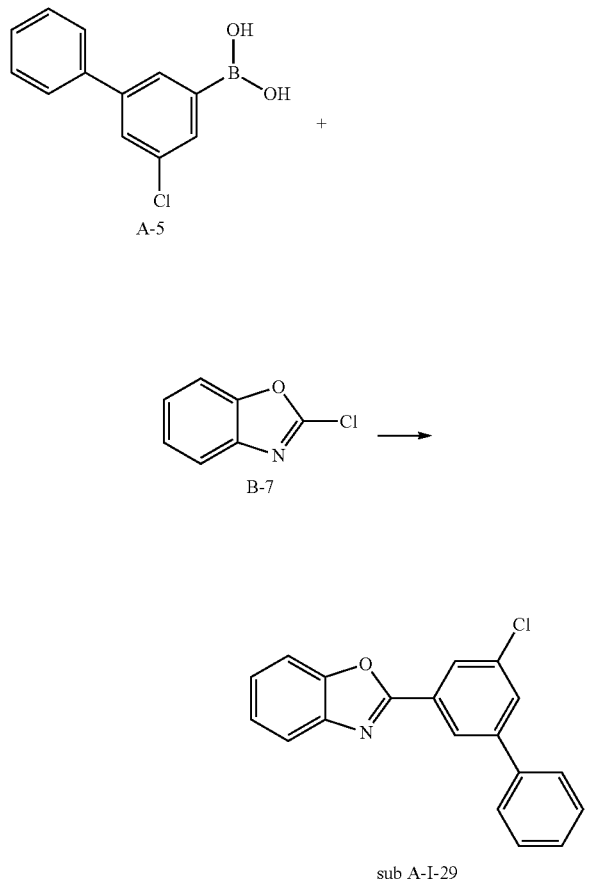

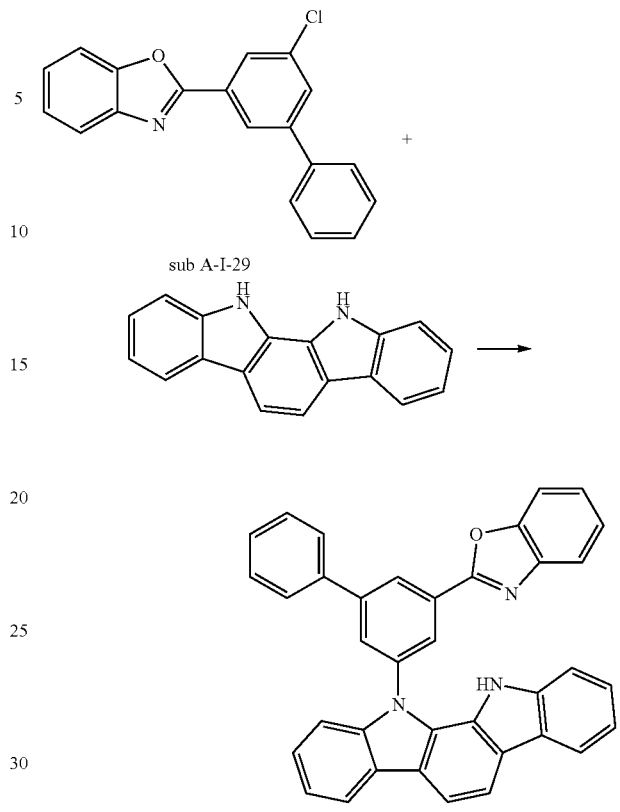

Nitrogen gas (0.100 L/min) was introduced into a three-necked flask equipped with a mechanical stirrer, a thermometer, and an Allihn condenser for replacement for 15 min, and (5-chloro-3-biphenyl)boronic acid (45.0 g, 193.5 mmol) (a reactant A-5), 2-chlorobenzoxazole (29.7 g, 193.5 mmol) (a reactant B-7), tetrakis(triphenylphosphine)palladium (4.4 g, 3.8 mmol), potassium carbonate (53.5 g, 387.1 mmol), tetrabutylammonium bromide (1.2 g, 3.8 mmol), tetrahydrofuran (180 mL) and deionized water (45 mL) were successively added; turned on the mechanical stirrer and heated, after the temperature was raised to 66° C., a reflux reaction was carried out for 15 h, and after the reaction was finished, the reaction solution was cooled to room temperature. The reaction solution was extracted with toluene and water, the organic phases were combined, dried over anhydrous magnesium sulfate, filtered and concentrated, and the crude product was purified by silica gel column chromatography using a dichloromethane/n-heptane system to obtain a solid intermediate sub A-I-29 (32.5 g, yield 55%).

Nitrogen gas (0.100 L/min) was introduced into a three-necked flask equipped with a mechanical stirrer, a thermometer, and an Allihn condenser for replacement for 15 min, and the intermediate sub A-I-29 (20.0 g, 65.4 mmol), indolo[2,3-A]carbazole (20.1 g, 78.5 mmol), Pd$_2$(dba)$_3$ (0.6 g, 0.6 mmol), tri-tert-butylphosphine (0.3 g, 1.3 mmol), sodium tert-butoxide (12.5 g, 130.8 mmol), and xylene (200 mL) were added. Turned on the mechanical stirrer and heated, after the temperature was raised to 140° C., a reflux reaction was carried out for 5 h, and after the reaction was finished, the reaction solution was cooled to room temperature. After the reaction solution was washed with water, the organic phase was separated, the organic phase was dried over anhydrous magnesium sulfate, after filtration, the filtrate was distilled under reduced pressure to remove the solvent, and the crude product was recrystallized by using a dichloromethane/ethanol system to obtain a white solid intermediate sub A-29 (20.9 g, 61%).

Referring to the synthesis method of the intermediate sub A-I-29, intermediates shown in the following Table 10 were synthesized, where the reactant A-5 was replaced with a reactant A-X (4, 12, 13 or 15), intermediates sub A-I-X (X is 30 to 33) shown in the following Table 10 were synthesized. Referring to the synthesis method of the intermediate sub A-29, intermediates sub A-X (X is 30 to 33) shown in the following Table 10 were synthesized.

TABLE 10
| Reactant (A-X) | Reactant (B-X) | Intermediate (subA-I-X) | sub A-X | Yield % |
|---|---|---|---|---|
| A-12 | B-7 | sub A-I-30 | sub A-30 | 48 |
| A-13 | B-7 | sub A-I-31 | sub A-31 | 46 |
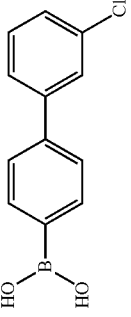

TABLE 10-continued

| Reactant (A-X) | Reactant (B-X) | Intermediate (subA-I-X) | sub A-X | Yield % |
|---|---|---|---|---|
| A-4 | B-7 | sub A-I-32 | sub A-32 | 52 |
| A-15 | B-7 | sub A-I-33 | sub A-33 | 40 |

(2) Synthesis of Compound 664

Referring to the synthesis method of the compound 67, the compounds shown in the following Table 11 were synthesized, where, the intermediate sub A-1 was replaced with an intermediate sub A-X (X is 29 to 33), and the reactant C-1 was replaced with a reactant C-X (X is 1, 2 or 4) to synthesize the compounds as shown in the following Table 11.

TABLE 11

| Preparation examples | Intermediate (sub A-X) | Reactant (C-X) | Compound | Yield | Mass spectrometry |
|---|---|---|---|---|---|
| 51 | sub A-29 | C-1 | 664 | 81 | 757.26 |
| 52 | sub A-29 | C-4 | 665 | 75 | 833.30 |

TABLE 11-continued

| Preparation examples | Intermediate (sub A-X) | Reactant (C-X) | Compound | Yield | Mass spectrometry |
|---|---|---|---|---|---|
| 53 | sub A-30 | C-1 | 691 | 65 | 757.26 |
| 54 | sub A-31 | C-1 | 692 | 74 | 757.26 |

TABLE 11-continued

| Preparation examples | Intermediate (sub A-X) | Reactant (C-X) | Compound | Yield | Mass spectrometry |
|---|---|---|---|---|---|
| 55 | sub A-32 | C-4 | 693 | 85 | 833.30 |
| 56 | sub A-33 | C-2 | 694 | 71 | 807.28 |

NMR data of a part of the compounds are as shown in the following Table 12.

TABLE 12

| Compounds | NMR data |
|---|---|
| compound 53 | $^1$HNMR (400 MHz, dichloromethane-D$_2$): δ8.56-8.62 (d, 2H), δ8.32-8.37 (m, 4H), δ8.13-8.18 (m, 4H), δ8.02-8.08 (d, 4H), δ7.85-7.89 (t, 2H), δ7.72-7.78 (m, 3H), δ7.51-7.57 (t, 1H), δ7.44-7.50 (m, 7H), 7.36-7.43 (m, 2H), δ7.21-7.26 (t, 2H), δ7.00-7.04 (d, 1H). |
| compound 67 | $^1$HNMR (400 MHz, dichloromethane-D$_2$): δ8.56-8.62 (d, 2H), δ8.32-8.37 (m, 4H), δ8.13-8.18 (m, 4H), δ8.02-8.08 (d, 4H), δ7.85-7.89 (t, 2H), δ7.72-7.78 (m, 3H), δ7.51-7.57 (t, 1H), δ7.44-7.50 (m, 7H), 7.36-7.43 (m, 2H), δ7.21-7.26 (t, 2H), δ7.00-7.04 (d, 1H). |
| compound 80 | $^1$HNMR (400 MHz, dichloromethane-D$_2$): δ8.55 (d, 3H), δ8.32-8.29 (m, 2H), δ8.15-8.08 (m, 2H), δ7.97-7.70 (m, 8H), δ7.60-6.35 (m, 11H), δ7.28-6.75 (m, 10H). |
| Compound 54 | $^1$HNMR (400 MHz, dichloromethane-D$_2$): δ8.50-8.45 (m, 1H), δ8.33-8.25 (m, 8H), δ8.17-8.09 (m, 2H), δ7.68 (d, 2H), δ7.62-7.50 (m, 6H), δ7.46-7.33 (m, 11H), δ7.23-7.16 (m, 5H), δ7.08 (t, 1H) |
| Compound 429 | $^1$HNMR (400 MHz, dichloromethane-D$_2$): δ8.96 (d, 1H), δ8.45-8.21 (m, 9H), δ7.72-7.37 (m, 18H), δ7.25-7.23 (m, 1H), δ7.13-7.10 (m, 1H), δ6.93-6.87 (m, 2H). |
| Compound 480 | $^1$HNMR (400 MHz, dichloromethane-D$_2$): δ8.52-8.60 (d, 1H), δ8.26-8.49 (m, 4H), δ8.09-8.23 (m, 4H), δ.7.99-8.07 (d, 1H), δ7.89-7.95 (s, 1H), δ7.51-7.82 (m, 6H), δ7.31-7.50 (m, 10H), δ7.71-7.24 (m, 3H). |
| Compound 452 | $^1$HNMR (400 MHz, dichloromethane-D$_2$): δ8.52 (d, 1H), δ8.36-8.40 (d, 2H), δ8.36-8.40 (d, 2H), δ8.27-8.34 (m, 4H), δ7.96 (d, 2H), δ7.33-7.56 (m, 15H), δ7.17-7.30 (m, 6H). |

Preparation and Performance Evaluation of the Organic Electroluminescence Device Example 1

Green Organic Electroluminescence Device

An anode 100 ITO substrate with a thickness of 110 nm was cut into a size of 40 mm (length)×40 mm (width)×0.7 mm (thickness), then making into an experimental substrate having a cathode 200, an anode 100 and an insulating layer pattern by the photolithography process, surface treatment was conducted by using ultraviolet ozone and O$_2$:N$_2$ plasma to increase the work function of the anode 100 (the experimental substrate), and the ITO substrate surface was cleaned with an organic solvent, to remove scum and oil stain on the ITO substrate surface.

HAT-CN (its structural formula was seen hereinafter) was vacuum evaporated onto the experimental substrate to form the hole injection layer (HIL) 310 with a thickness of 10 nm; and NPB was vacuum evaporated onto the hole injection layer 310 to form a first hole transport layer 321 (HTL1) with a thickness of 115 nm.

TCBPA was vacuum evaporated onto the first hole transport layer 321 (HTL1) to form a second hole transport layer 322 (HTL2) with a thickness of 35 nm.

Compound 67: GH-P1: Ir(ppy)$_2$acac were evaporated onto the second hole transport layer 322 (HTL2) at a film thickness ratio of 45%:50%:5% to form a green light emitting layer 330 (G-EML) with a thickness of 38 nm.

HNBphen and L$_1$Q were mixed in a weight ratio of 1:1 and evaporated to form an electron transport layer 350 (ETL) with a thickness of 30 nm, and then Yb was evaporated onto the electron transport layer to form an electron injection layer 360 (EIL) with a thickness of 1 nm.

Magnesium (Mg) and silver (Ag) were vacuum evaporated onto the electron injection layer at a film thickness ratio of 1:9 to form a cathode 200 with a thickness of 13 nm.

Furthermore, CP-1 was vapor-deposited on the cathode 200 with a thickness of 65 nm to form a capping layer (CPL), thereby completing the manufacture of the organic light-emitting device.

Among them, the structural formulas of HAT-CN, NPB, TCBPA, GH-P1, Ir(ppy)$_2$acac, HNBphen, L$_1$Q, and CP-1 are as shown in the following Table 13:

TABLE 13

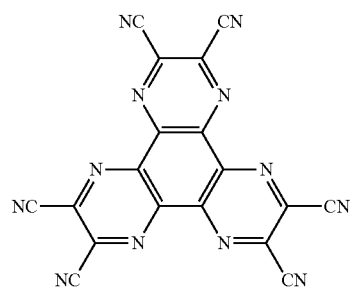

HAT-CN

TABLE 13-continued
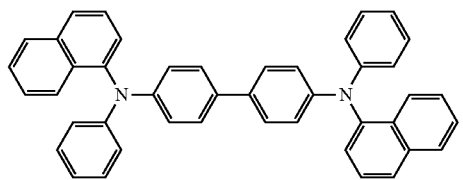
NPB
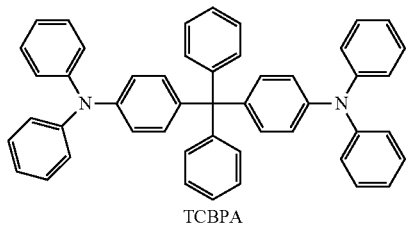
TCBPA
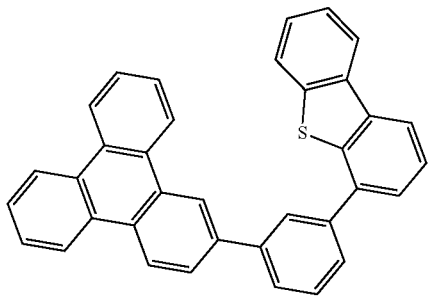
GH-P1
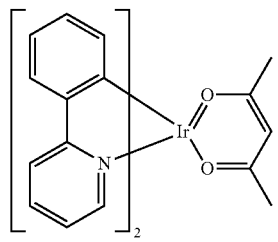
Ir(ppy)$_2$acac
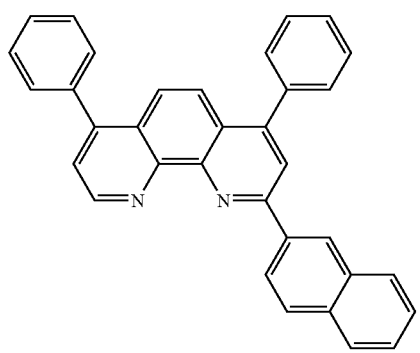
HNBphen TABLE 13-continued
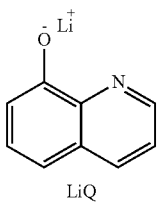
LiQ
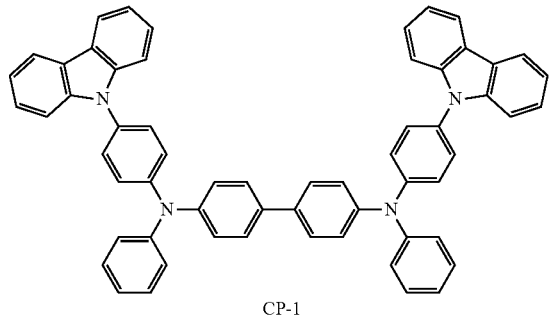 [SMILES: c1ccc(N(c2ccc(-c3ccc(N(c4ccccc4)c4ccc(-n5c6ccccc6c6ccccc65)cc4)cc3)cc2)c2ccc(-n3c4ccccc4c4ccccc43)cc2)cc1 ; "CP-1"]
CP-1
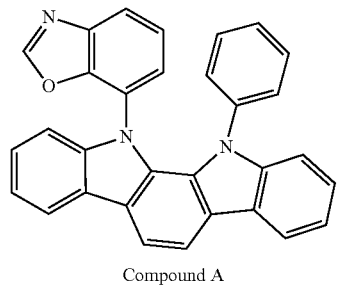 [SMILES: c1ccc(-n2c3ccccc3c3ccc4c5ccccc5n(-c5cccc6ncoc56)c4c32)cc1]
Compound A
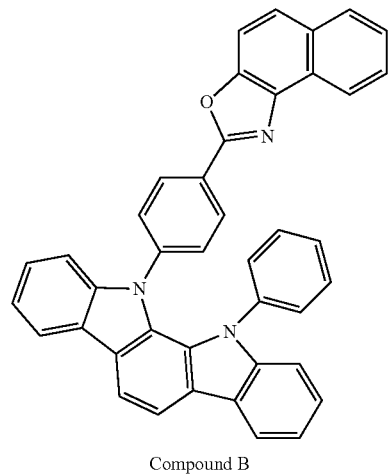 [SMILES: c1ccc(-n2c3ccccc3c3ccc4c5ccccc5n(-c5ccc(-c6nc7c(ccc8ccccc87)o6)cc5)c4c32)cc1]
Compound B

TABLE 13-continued

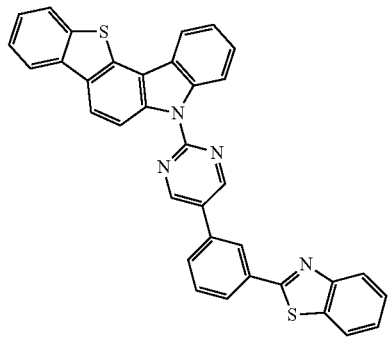

Compound C

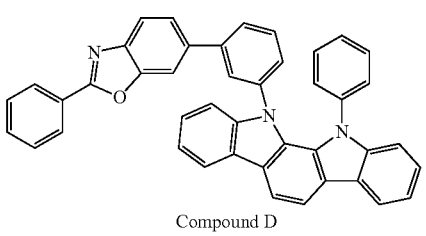 [SMILES: c1ccc(-c2nc3ccc(-c4cccc(-n5c6ccccc6c6ccc7c8ccccc8n(-c8ccccc8)c7c65)c4)cc3o2)cc1]

Compound D

Examples 2-56

Except using the compounds shown in Table 14 instead of the compound 67 during forming the luminescent layer (EML), a green organic electroluminescence device was manufactured by the same method as in Example 1.

Comparative Example 1

Using a compound A instead of the compound 67, the green organic electroluminescence device was manufactured by the same method as in Example 1.

Comparative Example 2

Using a compound B instead of the compound 67, the green organic electroluminescence device was manufactured by the same method as in Example 1.

Comparative Example 3

Using a compound C instead of the compound 67, the green organic electroluminescence device was manufactured by the same method as in Example 1.

Comparative Example 4

Using a compound D instead of the compound 67, the green organic electroluminescence device was manufactured by the same method as in Example 1.

For the organic electroluminescence device manufactured as above, the IVL performance of the device was tested under a condition of 10 mA/cm², the service life of a T95 device was tested under a condition of 20 mA/cm², and the results are shown in Table 14.

TABLE 14

Performance test results of the green organic electroluminescence device

| Examples | Compound X | Working voltage Volt (V) | Current efficiency (Cd/A) | External quantum efficiency EQE (%) | Color coordinate CIEx | Color coordinate CIEy | Service life of T95 device (h) |
|---|---|---|---|---|---|---|---|
| Example 1 | Compound 67 | 4.21 | 96.14 | 24.04 | 0.25 | 0.68 | 330 |
| Example 2 | Compound 53 | 4.08 | 96.44 | 24.11 | 0.25 | 0.68 | 328 |
| Example 3 | Compound 55 | 4.09 | 96.75 | 24.19 | 0.25 | 0.68 | 315 |
| Example 4 | Compound 63 | 4.11 | 97.08 | 24.27 | 0.25 | 0.68 | 316 |
| Example 5 | Compound 54 | 4.01 | 97.16 | 24.29 | 0.25 | 0.68 | 334 |
| Example 6 | Compound 80 | 4.13 | 95.71 | 23.93 | 0.25 | 0.68 | 322 |
| Example 7 | Compound 78 | 4.12 | 97.12 | 24.28 | 0.25 | 0.68 | 315 |
| Example 8 | Compound114 | 4.14 | 96.20 | 24.05 | 0.25 | 0.68 | 323 |
| Example 9 | Compound119 | 4.12 | 95.86 | 23.97 | 0.25 | 0.68 | 276 |
| Example 10 | Compound120 | 4.09 | 95.56 | 23.89 | 0.25 | 0.68 | 318 |
| Example 11 | Compound 118 | 4.17 | 96.75 | 24.19 | 0.25 | 0.68 | 278 |
| Example 12 | Compound 68 | 4.08 | 96.56 | 24.14 | 0.25 | 0.68 | 278 |
| Example 13 | Compound 82 | 4.15 | 95.93 | 23.98 | 0.25 | 0.68 | 326 |
| Example 14 | Compound 73 | 4.21 | 95.84 | 23.96 | 0.25 | 0.68 | 283 |
| Example 15 | Compound 353 | 4.15 | 97.28 | 24.32 | 0.25 | 0.68 | 282 |

TABLE 14-continued

Performance test results of the green organic electroluminescence device

| Examples | Compound X | Working voltage Volt (V) | Current efficiency (Cd/A) | External quantum efficiency EQE (%) | Color coordinate CIEx | Color coordinate CIEy | Service life of T95 device (h) |
|---|---|---|---|---|---|---|---|
| Example 16 | Compound 425 | 4.12 | 96.40 | 24.10 | 0.25 | 0.68 | 271 |
| Example 17 | Compound 426 | 4.09 | 96.46 | 24.12 | 0.25 | 0.68 | 281 |
| Example 18 | Compound 429 | 4.12 | 96.52 | 24.13 | 0.25 | 0.68 | 280 |
| Example 19 | Compound257 | 4.16 | 95.93 | 23.98 | 0.25 | 0.68 | 274 |
| Example 20 | Compound 252 | 4.09 | 96.52 | 24.13 | 0.25 | 0.68 | 274 |
| Example 21 | Compound 254 | 4.09 | 97.01 | 24.25 | 0.25 | 0.68 | 273 |
| Example 22 | Compound 258 | 4.06 | 95.66 | 23.92 | 0.25 | 0.68 | 272 |
| Example 23 | Compound 260 | 4.10 | 96.14 | 24.04 | 0.25 | 0.68 | 322 |
| Example 24 | Compound 695 | 4.08 | 96.24 | 24.10 | 0.25 | 0.68 | 270 |
| Example 25 | Compound 696 | 4.13 | 96.31 | 24.08 | 0.25 | 0.68 | 271 |
| Example 26 | Compound 697 | 4.14 | 95.72 | 23.94 | 0.25 | 0.68 | 278 |
| Example 27 | Compound 698 | 4.07 | 95.67 | 23.98 | 0.25 | 0.68 | 281 |
| Example 28 | Compound 699 | 4.09 | 96.10 | 24.05 | 0.25 | 0.68 | 279 |
| Example 29 | Compound 442 | 4.08 | 96.98 | 24.25 | 0.25 | 0.68 | 273 |
| Example 30 | Compound 446 | 4.14 | 95.96 | 23.99 | 0.25 | 0.68 | 271 |
| Example 31 | Compound 646 | 4.14 | 96.44 | 24.11 | 0.25 | 0.68 | 283 |
| Example 32 | Compound 451 | 4.16 | 96.23 | 24.06 | 0.25 | 0.68 | 282 |
| Example 33 | Compound 452 | 4.13 | 96.56 | 24.14 | 0.25 | 0.68 | 272 |
| Example 34 | Compound 477 | 4.20 | 95.62 | 23.91 | 0.25 | 0.68 | 273 |
| Example 35 | Compound 480 | 4.16 | 95.85 | 23.96 | 0.25 | 0.68 | 281 |
| Example 36 | Compound 500 | 4.18 | 96.62 | 24.16 | 0.25 | 0.68 | 281 |
| Example 37 | Compound 544 | 4.20 | 96.15 | 24.04 | 0.25 | 0.68 | 276 |
| Example 38 | Compound 664 | 4.01 | 95.75 | 23.93 | 0.25 | 0.68 | 273 |
| Example 39 | Compound 665 | 4.00 | 96.12 | 24.03 | 0.25 | 0.68 | 278 |
| Example 40 | Compound 691 | 4.12 | 96.31 | 24.07 | 0.25 | 0.68 | 281 |
| Example 41 | Compound 692 | 4.15 | 95.56 | 23.89 | 0.25 | 0.68 | 283 |
| Example 42 | Compound 693 | 4.07 | 96.33 | 24.08 | 0.25 | 0.68 | 280 |
| Example 43 | Compound 694 | 4.03 | 95.65 | 23.91 | 0.25 | 0.68 | 277 |
| Example 44 | Compound 121 | 4.07 | 84.26 | 19.99 | 0.25 | 0.68 | 238 |
| Example 45 | Compound 190 | 4.03 | 83.87 | 20.23 | 0.25 | 0.68 | 237 |
| Example 46 | Compound 187 | 4.04 | 86.48 | 20.56 | 0.25 | 0.68 | 231 |
| Example 47 | Compound 122 | 4.05 | 83.02 | 20.58 | 0.25 | 0.68 | 242 |
| Example 48 | Compound 188 | 4.18 | 84.67 | 20.30 | 0.25 | 0.68 | 234 |
| Example 49 | Compound 194 | 4.03 | 84.35 | 20.62 | 0.25 | 0.68 | 244 |
| Example 50 | Compound 199 | 4.01 | 85.41 | 20.03 | 0.25 | 0.68 | 238 |
| Example 51 | Compound 219 | 4.06 | 83.92 | 20.31 | 0.25 | 0.68 | 241 |
| Example 52 | Compound 230 | 4.17 | 85.32 | 20.19 | 0.25 | 0.68 | 230 |
| Example 53 | Compound 228 | 4.03 | 85.63 | 20.74 | 0.25 | 0.68 | 237 |
| Example 54 | Compound 667 | 4.01 | 85.21 | 20.45 | 0.25 | 0.68 | 233 |
| Example 55 | Compound 671 | 4.02 | 85.17 | 20.44 | 0.25 | 0.68 | 234 |
| Example 56 | Compound 690 | 4.12 | 85.16 | 20.43 | 0.25 | 0.68 | 239 |
| Comparative Example 1 | Compound A | 4.42 | 67.80 | 16.27 | 0.25 | 0.68 | 138 |
| Comparative Example 2 | Compound B | 4.31 | 59.71 | 14.32 | 0.25 | 0.68 | 180 |
| Comparative Example 3 | Compound C | 4.35 | 62.32 | 14.88 | 0.25 | 0.68 | 150 |
| Comparative Example 4 | Compound D | 4.54 | 65.31 | 15.67 | 0.25 | 0.68 | 144 |

According to the results in Table 14, in the OLED device in which these compounds are used as the organic electroluminescence layer, compared with those in the Comparative Examples, the performance of the organic electroluminescence devices prepared in Examples 1 to 56 are all improved. Wherein, in Examples 1 to 56 of compounds as the luminescent layer, compared with the device Comparative Examples 1 to 4 corresponding to the compounds in the prior art, the luminous efficiency (Cd/A) of the above-mentioned organic electroluminescence device prepared by using the compounds as the organic electroluminescence layer in the present disclosure is improved by at least 22.4%, the external quantum efficiency EQE (%) is improved by at least 22.9%, the service life is increased by at least 27.8%. It can be known from the above-mentioned data that when the nitrogen-containing compounds of the present disclosure are used as an organic electroluminescence layer of the electronic component, the luminous efficiency (Cd/A), external quantum efficiency (EQE) and service life (T95) of the electronic component are all significantly improved. Therefore, by using the nitrogen-containing compounds of the present disclosure in the organic electroluminescence layer, an organic electroluminescence device having high luminous efficiency and long service life can be prepared.

What is claimed is:

1. A nitrogen-containing compound, wherein the structural general formula of the nitrogen-containing compound is as shown in a Formula 1:

349

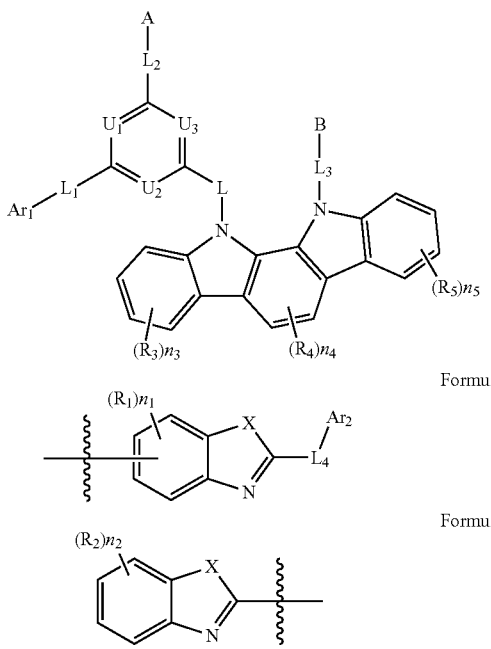

Formula 1

Formula 2-1

Formula 2-2 wherein,

represents a chemical bond, A and B are the same or different, and are each independently selected from substituted or unsubstituted aryl with 6 to 30 carbon atoms, substituted or unsubstituted heteroaryl with 3 to 30 carbon atoms, a structure shown in a Formula 2-1 or a structure shown in a Formula 2-2, and at least one of A and B is selected from the structure shown in the Formula 2-1 or the structure shown in the Formula 2-2;

$U_1$, $U_2$ and $U_3$ are the same, and are each independently selected from N;

each of $R_1$, $R_2$, $R_3$, $R_4$ and $R_5$ is respectively and independently selected from hydrogen, deuterium, a halogen group, cyano, aryl with 6 to 12 carbon atoms, heteroaryl with 5 to 12 carbon atoms, alkyl with 1 to 5 carbon atoms, haloalkyl with 1 to 5 carbon atoms, and cycloalkyl with 3 to 10 carbon atoms;

$n_1$ represents the number of a substituent $R_1$, $n_1$ is selected from 1, 2 or 3, and when $n_1$ is greater than 1, any two $R_1$ are the same or different;

$n_2$ represents the number of a substituent $R_2$, $n_2$ is selected from 1, 2, 3 or 4, when $n_2$ is greater than 1, any two $R_2$ are the same or different, and alternatively, any two adjacent $R_2$ form a ring;

$n_3$ represents the number of a substituent $R_3$, $n_3$ is selected from 1, 2, 3 or 4, and when $n_3$ is greater than 1, any two $R_3$ are the same or different;

$n_4$ represents the number of a substituent $R_4$, $n_4$ is selected from 1 or 2, and when $n_4$ is greater than 1, any two $R_4$ are the same or different;

$n_5$ represents the number of a substituent $R_5$, $n_5$ is selected from 1, 2, 3 or 4, and when $n_5$ is greater than 1, any two $R_5$ are the same or different;

350

X is selected from S or O;

L, $L_1$, $L_2$, $L_3$ and $L_4$ are the same or different, and are each independently selected from a single bond, substituted or unsubstituted arylene with 6 to 30 carbon atoms, and substituted or unsubstituted heteroarylene with 3 to 30 carbon atoms;

$Ar_1$ and $Ar_2$ are the same or different, and are each independently selected from substituted or unsubstituted aryl with 6 to 30 carbon atoms, and substituted or unsubstituted heteroaryl with 3 to 30 carbon atoms;

substituents in the A, B, L, $L_1$, $L_2$, $L_3$, $L_4$, $Ar_1$ and $Ar_2$ are the same or different, and are each independently selected from deuterium, a halogen group, cyano, heteroaryl with 3 to 20 carbon atoms, aryl with 6-20 carbon atoms, trialkylsilyl with 3-12 carbon atoms, alkyl with 1 to 10 carbon atoms, haloalkyl with 1 to 10, cycloalkyl with 3 to 10 carbon atoms, heterocycloalkyl with 2 to 10 carbon atoms, and alkoxy with 1 to 10 carbon atoms;

alternatively, in $Ar_1$ and $Ar_2$, any two adjacent substituents form a ring.

2. The nitrogen-containing compound according to claim 1, wherein each of $R_1$, $R_2$, $R_3$, $R_4$ and $R_5$ is independently selected from hydrogen, deuterium, fluorine, cyano, methyl, ethyl, n-propyl, isopropyl, tert-butyl, phenyl, pyridyl, trifluoromethyl, and biphenyl; or any two adjacent $R_2$ form a benzene ring, a naphthalene ring or a phenanthrene ring.

3. The nitrogen-containing compound according to claim 1, wherein the L, $L_1$, $L_2$, $L_3$ and $L_4$ are the same or different, and are each independently selected from a single bond, substituted or unsubstituted arylene with 6 to 20 carbon atoms, or substituted or unsubstituted heteroarylene with 5 to 20 carbon atoms.

4. The nitrogen-containing compound according to claim 1, wherein the L, $L_1$, $L_2$, $L_3$ and $L_4$ are the same or different, and are each independently selected from a single bond, substituted or unsubstituted phenylene, substituted or unsubstituted naphthylene, substituted or unsubstituted biphenylene, substituted or unsubstituted pyridylidene, substituted or unsubstituted dib enzofurylidene, substituted or unsubstituted dibenzothienylene, substituted or unsubstituted fluorenylidene, substituted or unsubstituted carbazolylene, and substituted or unsubstituted anthrylene;

preferably, substituents in the L, $L_1$, $L_2$, $L_3$ and $L_4$ are each independently selected from deuterium, a halogen group, cyano, aryl with 6 to 12 carbon atoms, and alkyl with 1 to 5 carbon atoms.

5. The nitrogen-containing compound according to claim 1, wherein the L, $L_1$, $L_2$, $L_3$ and $L_4$ are the same or different, and are each independently selected from a single bond or a substituted or unsubstituted group V, and the unsubstituted group V is selected from a group consisting of the following groups:

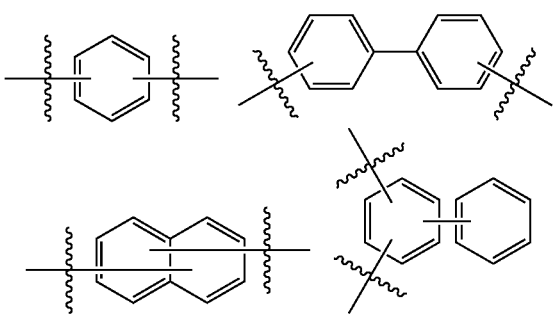

-continued

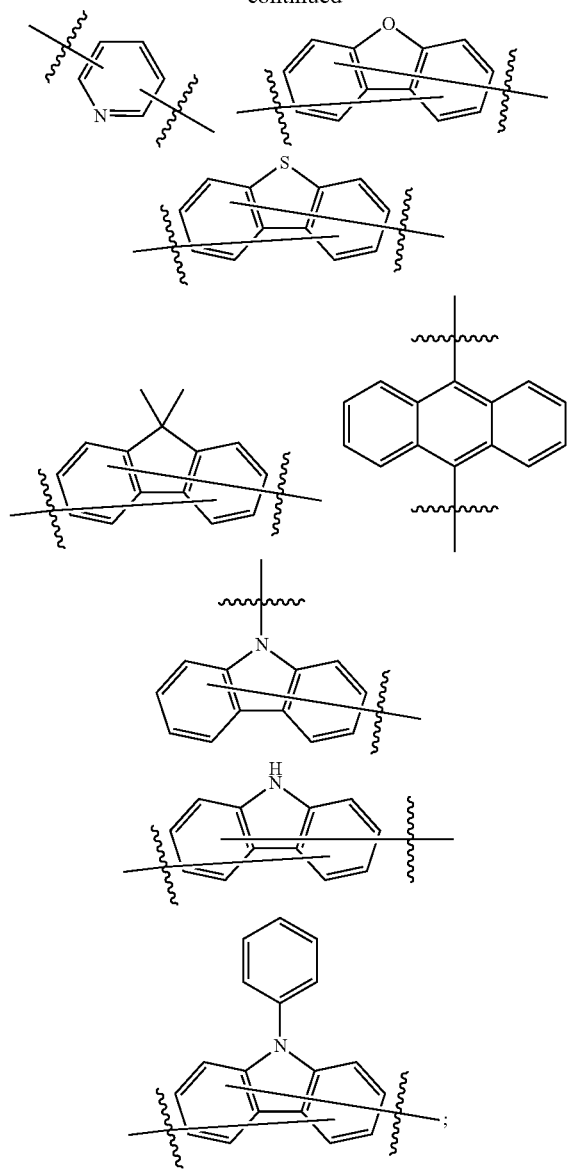

wherein,

represents a chemical bond; the substituted group V has one or more substituent(s), and the substituents are each independently selected from deuterium, cyano, fluorine, methyl, ethyl, n-propyl, isopropyl, tert-butyl or phenyl; when the number of the substituents of V is greater than 1, the substituents are the same or different.

6. The nitrogen-containing compound according to claim 1, wherein the Ar$_1$ and Ar$_2$ are each independently selected from substituted or unsubstituted aryl with 6 to 25 carbon atoms, or substituted or unsubstituted heteroaryl with 4 to 20 carbon atoms;

substituents in the Ar$_1$ are each independently selected from deuterium, a halogen group, cyano, aryl with 6 to 12 carbon atoms, heteroaryl with 5 to 12 carbon atoms, alkyl with 1 to 5 carbon atoms or cycloalkyl with 3 to 10 carbon atoms;

substituents in the Ar$_2$ are each independently selected from deuterium, a halogen group, cyano, aryl with 6 to 12 carbon atoms, heteroaryl with 5 to 12 carbon atoms, alkyl with 1 to 5 carbon atoms, haloalkyl having a carbon number of 1 to 5 carbon atoms, and cycloalkyl with 3 to 10 carbon atoms, and alternatively, adjacent substituents in the Ar$_2$ form a saturated or unsaturated ring with 5 to 13 carbon atoms.

7. The nitrogen-containing compound according to claim 1, wherein the Ar$_1$ and Ar$_2$ are each independently selected from substituted or unsubstituted group W$_1$, and the unsubstituted W$_1$ is selected from a group consisting of the following groups:

wherein,

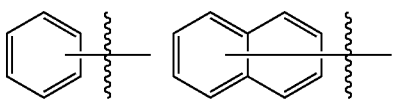

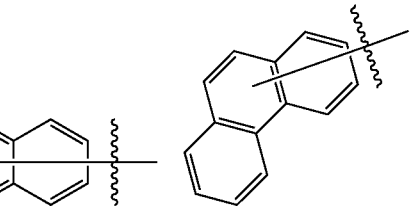

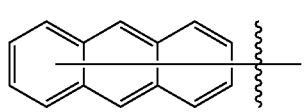

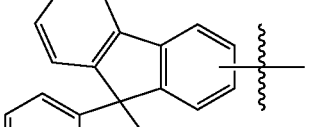

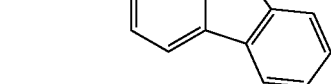

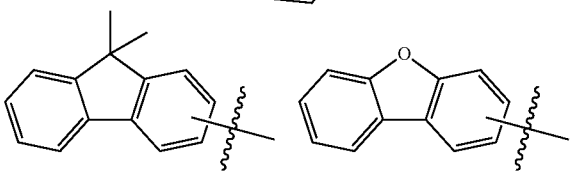

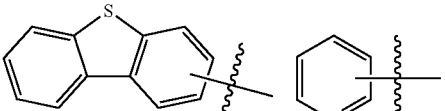

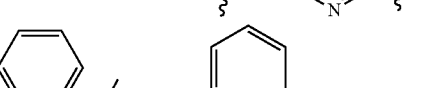

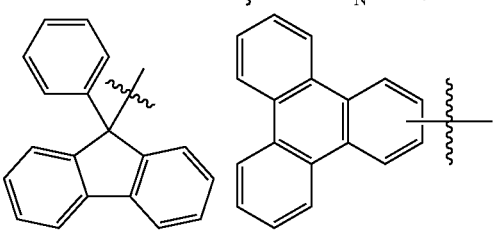

-continued

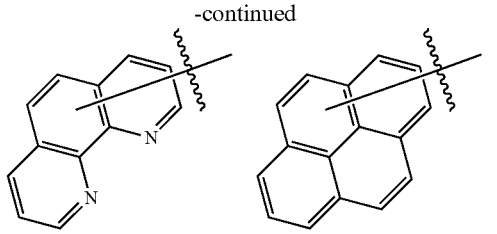

represents a chemical bond; me substituted group W₁ has one or more substituent(s), and the substituents are each independently selected from deuterium, cyano, fluorine, methyl, ethyl, n-propyl, isopropyl, tert-butyl, phenyl, naphthyl, biphenyl or carbazolyl; when the number of the substituents in W₁ is greater than 1, the substituents are the same or different.

8. The nitrogen-containing compound according to claim 1, wherein the $Ar_1$ and $Ar_2$ are each independently selected from substituted or unsubstituted phenyl, substituted or unsubstituted biphenyl, substituted or unsubstituted naphthyl, substituted or unsubstituted dibenzofuranyl, substituted or unsubstituted dibenzothienyl, substituted or unsubstituted fluorenyl, substituted or unsubstituted N-phenylcarbazolyl, substituted or unsubstituted carbazolyl, substituted or unsubstituted phenanthryl, substituted or unsubstituted anthryl, substituted or unsubstituted terphenyl, substituted or unsubstituted pyridyl, substituted or unsubstituted pyrenyl, substituted or unsubstituted quinolyl, substituted or unsubstituted isoquinolyl, substituted or unsubstituted phenanthrolinyl, substituted or unsubstituted benzophenanthryl, substituted or unsubstituted furyl, substituted or unsubstituted thienyl or the following substituted or unsubstituted group:

9. The nitrogen-containing compound according to claim 1, wherein the A and B are each independently selected from substituted or unsubstituted aryl with 6 to 25 carbon atoms, substituted or unsubstituted heteroaryl with 5 to 20 carbon atoms, the structure shown in the Formula 2-1 or the structure shown in the Formula 2-2, and only one of A and B is selected from the structure shown in the Formula 2-1 or the structure shown in the Formula 2-2;
substituents in the A and B are each independently selected from deuterium, a halogen group, cyano, aryl with 6 to 12 carbon atoms, heteroaryl with 5 to 12 carbon atoms, alkyl with 1 to 5 carbon atoms, and cycloalkyl with 3 to 10 carbon atoms.

10. The nitrogen-containing compound according to claim 1, wherein the A and B are each independently selected from substituted or unsubstituted phenyl, substituted or unsubstituted naphthyl, substituted or unsubstituted biphenyl, substituted or unsubstituted phenanthryl, substituted or unsubstituted anthryl, substituted or unsubstituted pyridyl, substituted or unsubstituted benzophenanthryl, substituted or unsubstituted spirobifluorenyl, substituted or unsubstituted quinolyl, substituted or unsubstituted isoquinolyl, substituted or unsubstituted dibenzofuranyl, substituted or unsubstituted carbazolyl, substituted or unsubstituted dibenzothienyl, substituted or unsubstituted fluorenyl, substituted or unsubstituted pyrenyl, substituted or unsubstituted phenanthrolinyl, the structure shown in the Formula 2-1 or the structure shown in the Formula 2-2, and only one of A and B is selected from the structure shown in the Formula 2-1 or the structure shown in the Formula 2-2.

11. The nitrogen-containing compound according to claim 1, wherein the nitrogen-containing compound is selected from a group consisting of the following compounds:

355  356
1
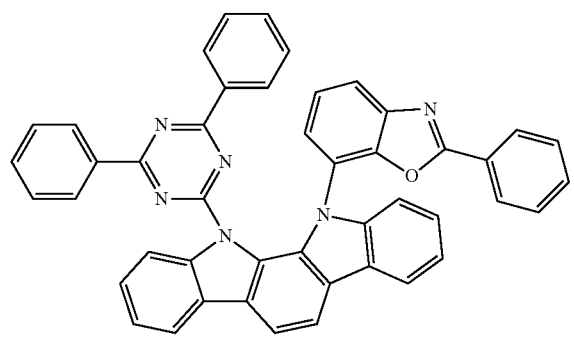
2
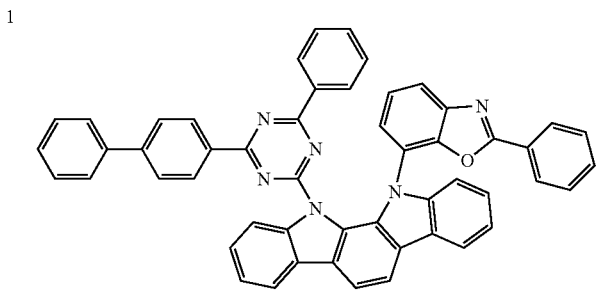
3
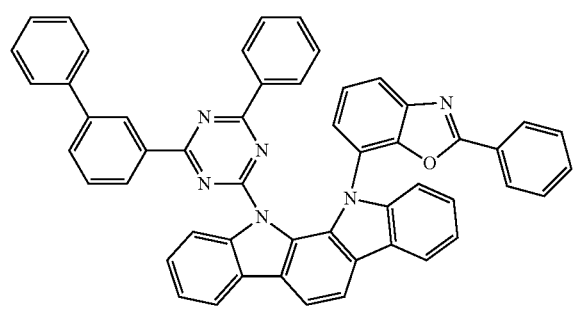
4
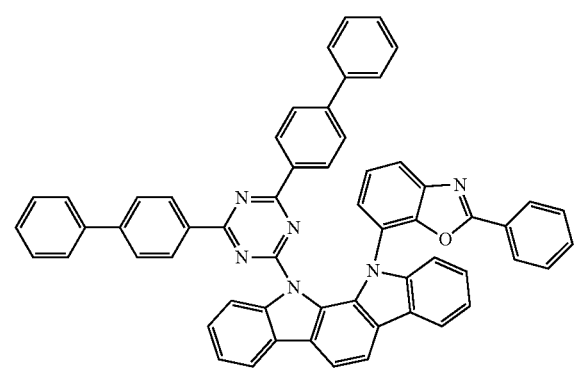
5
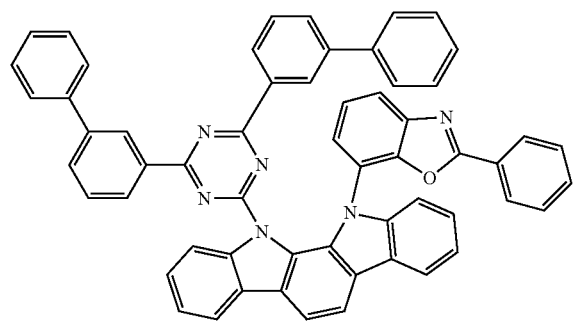
6
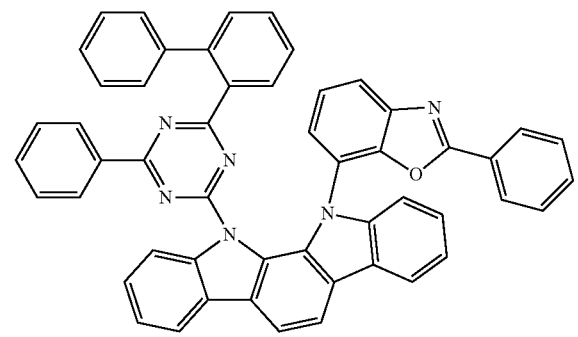
7
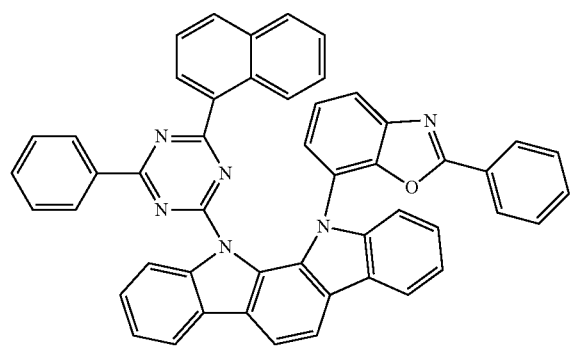
8
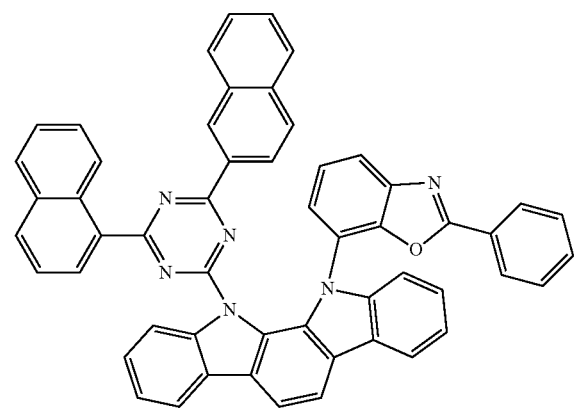

-continued
9
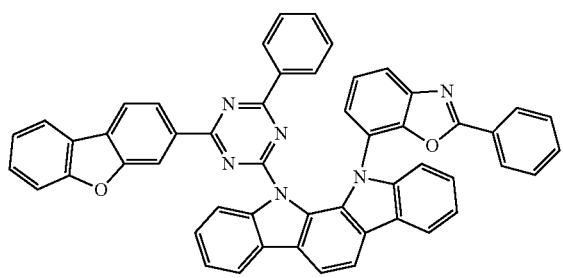
10
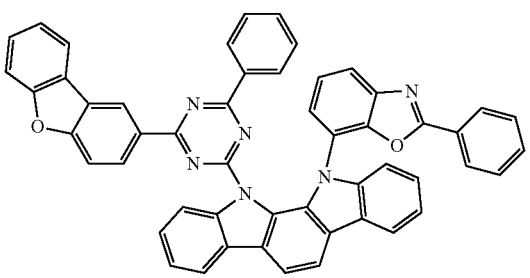
11
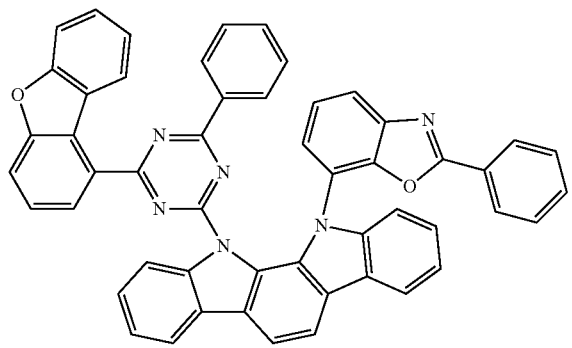
12
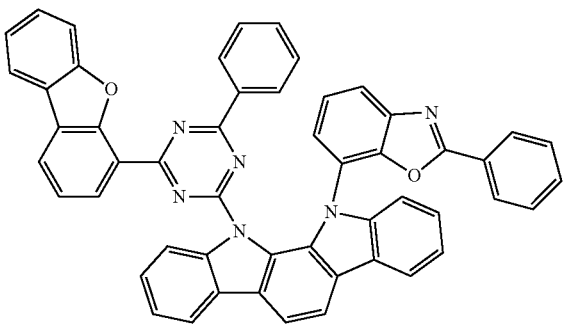
13
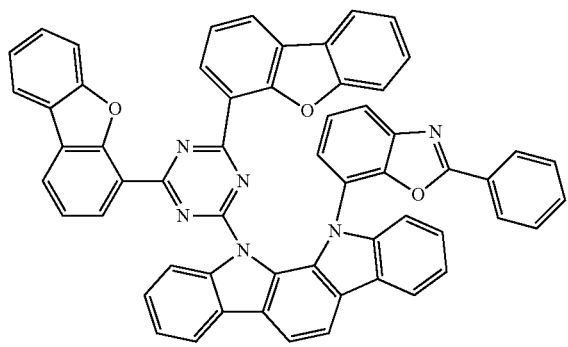
14
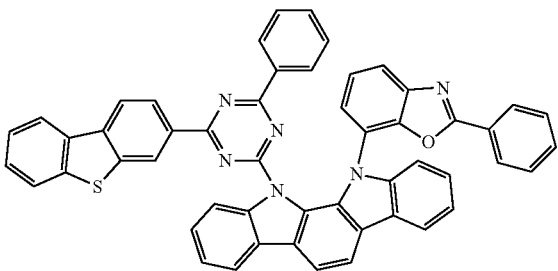
15
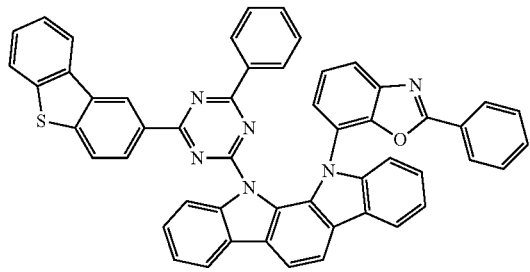
16
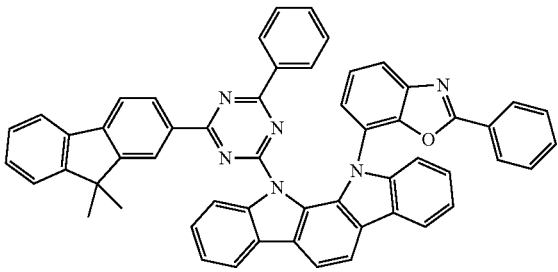
17
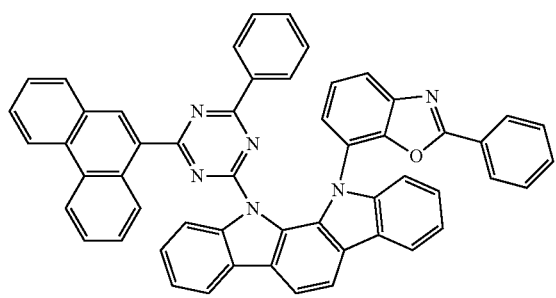
18
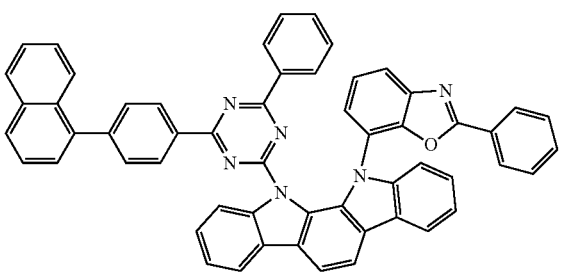

-continued
19
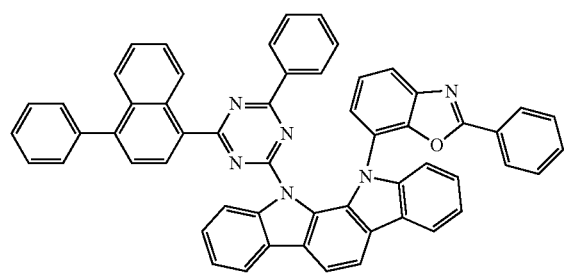
20
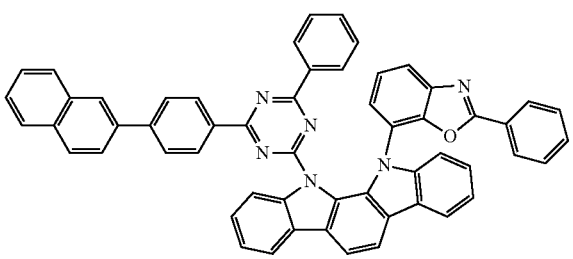
21
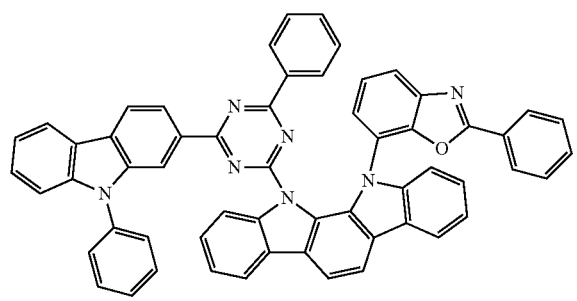
22
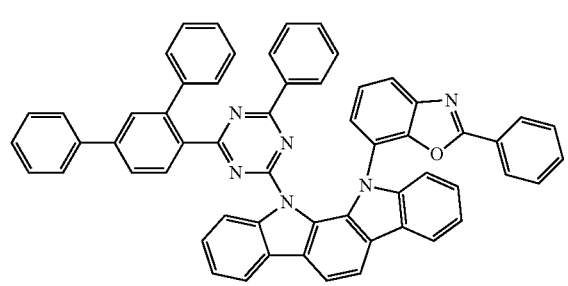
23
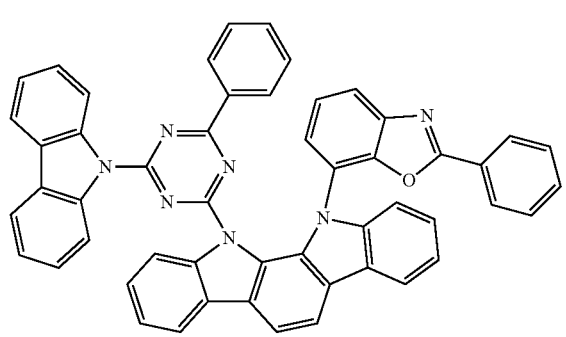
24
25
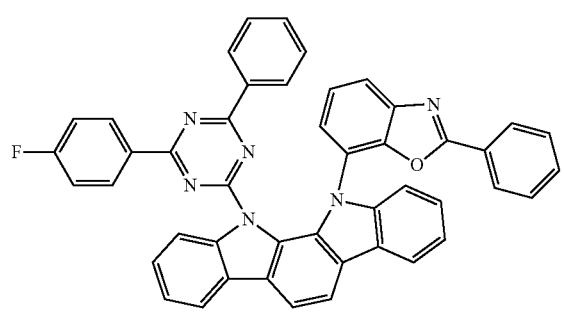
26
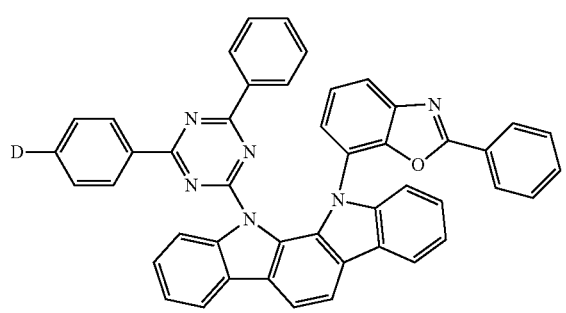

-continued
27
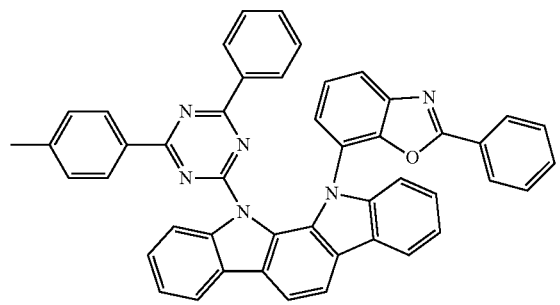
28
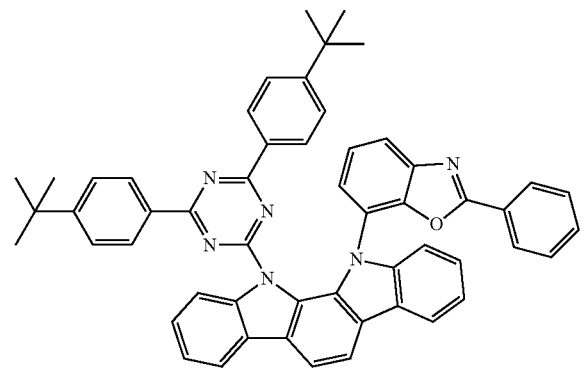
29
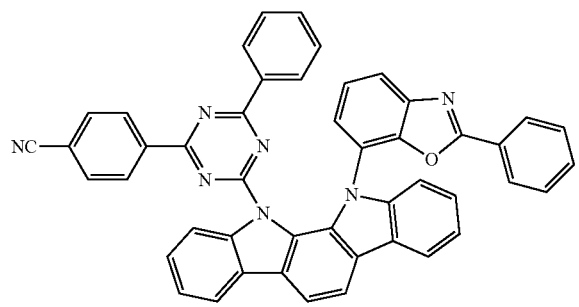
30
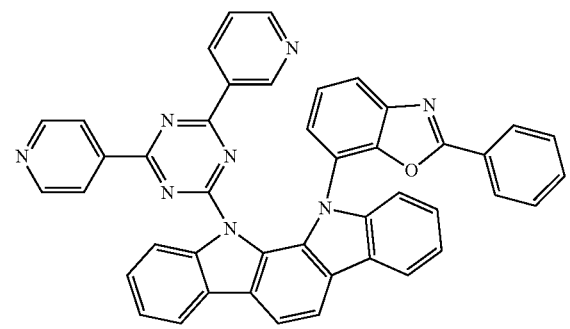
31
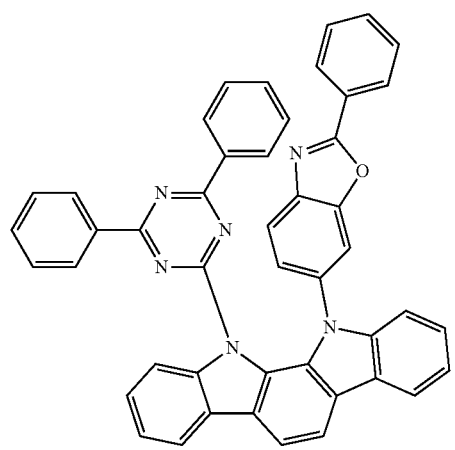
32
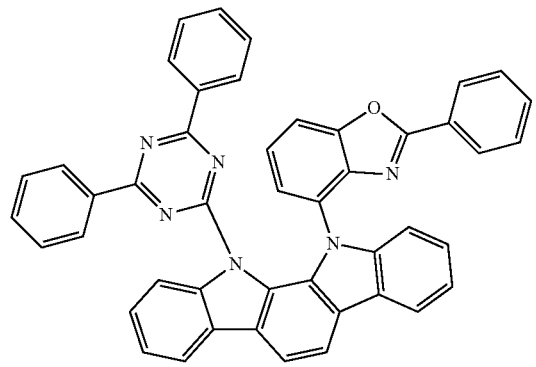
33
35
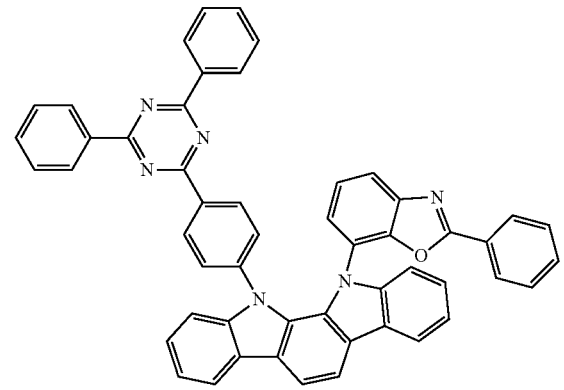

36
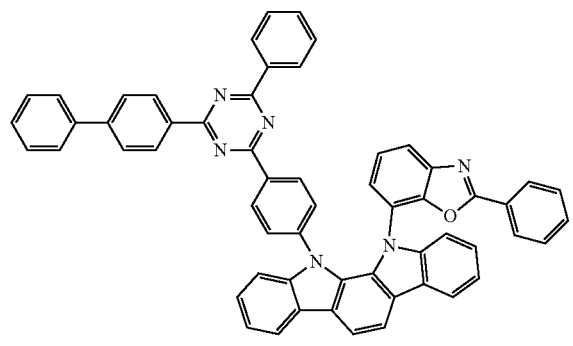
37
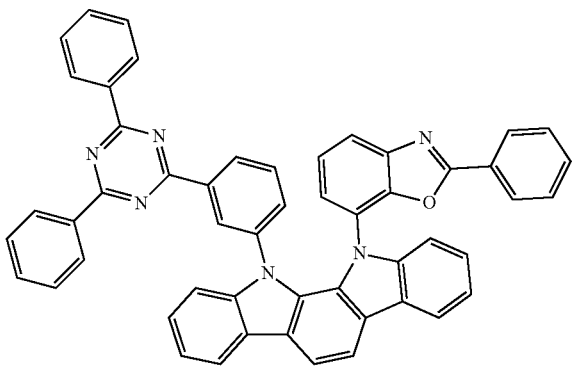
38
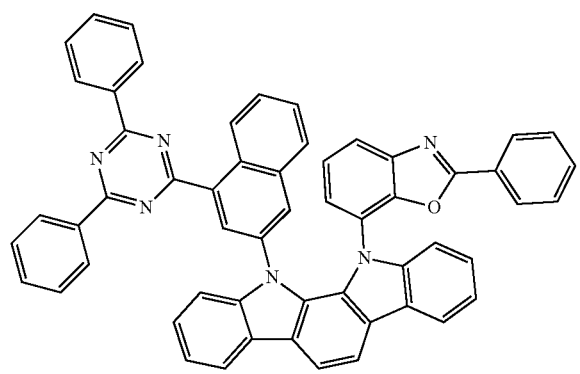
39
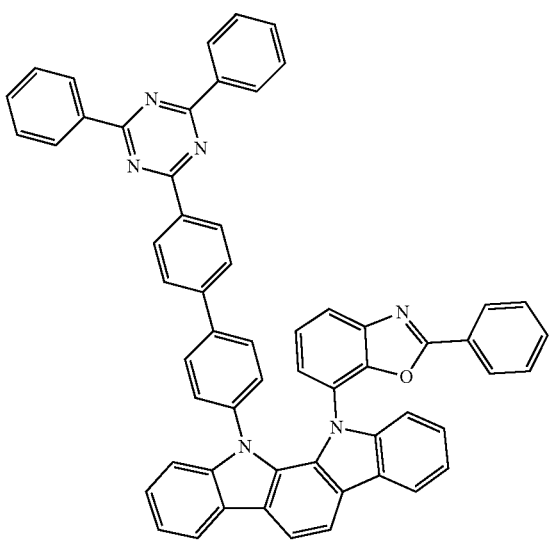
40
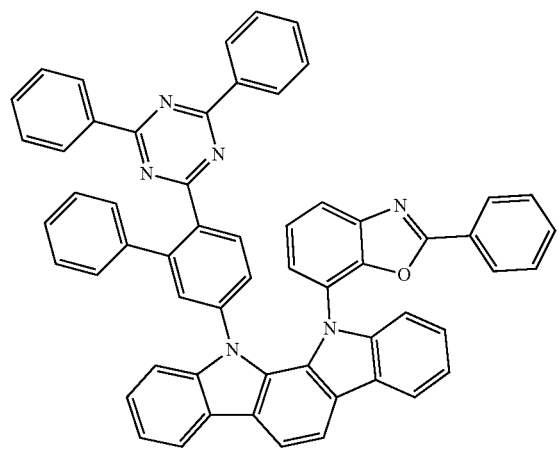
41
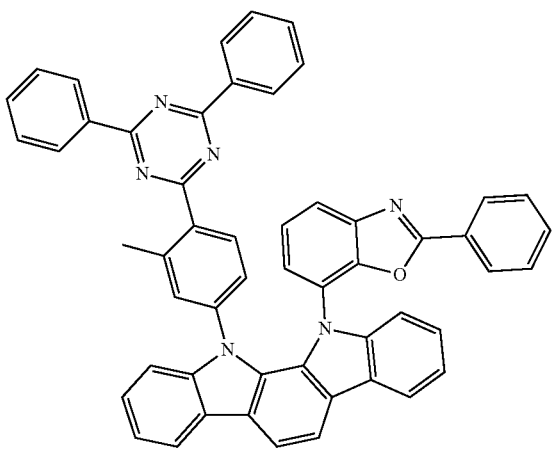

43
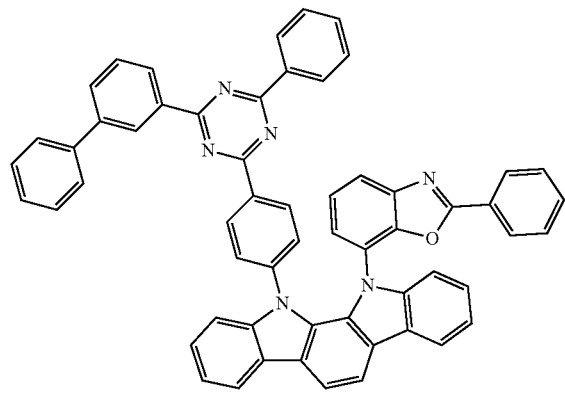
44
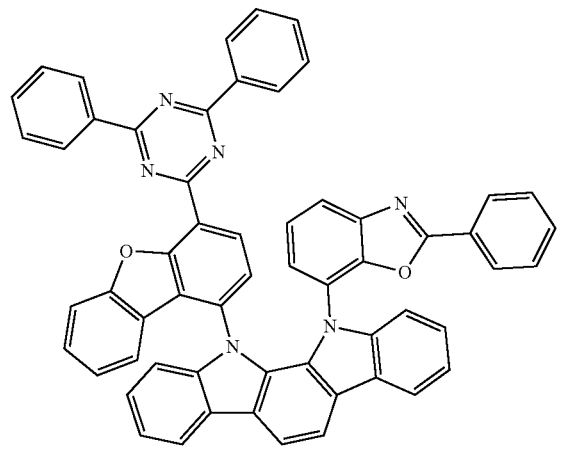
45
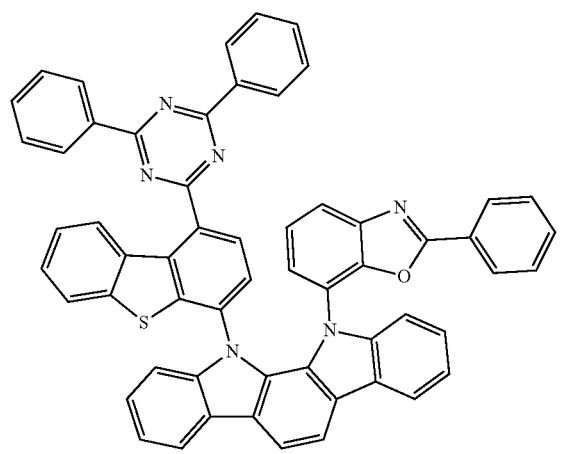
46
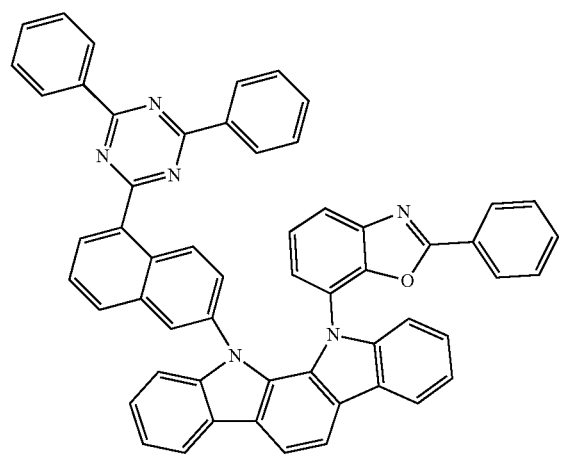
47
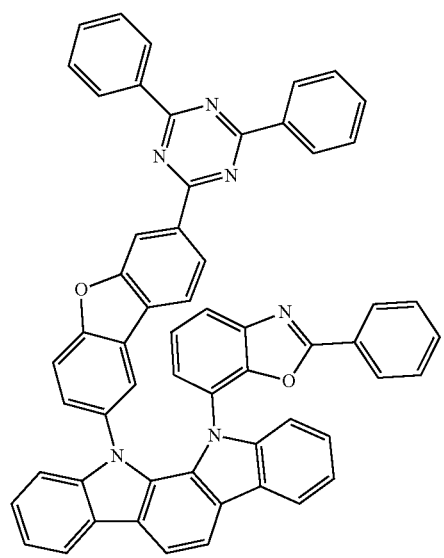
49
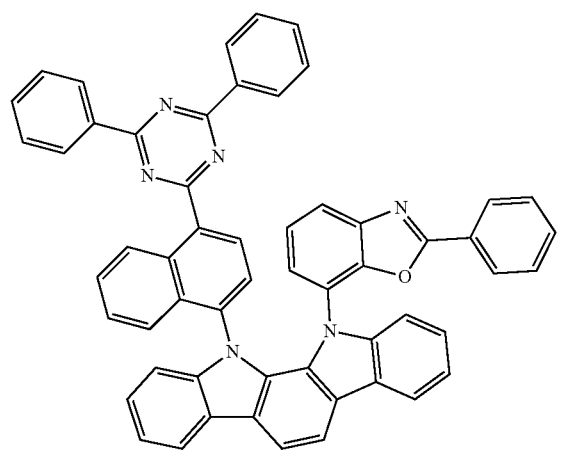

-continued
50
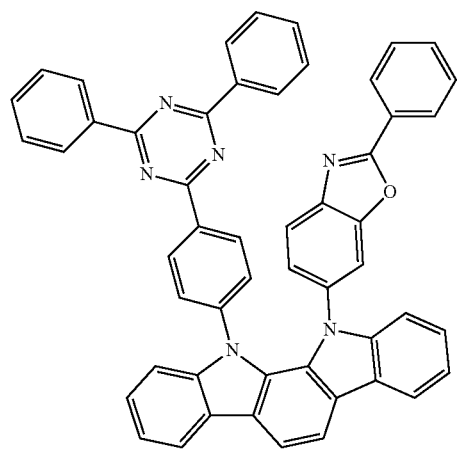
51
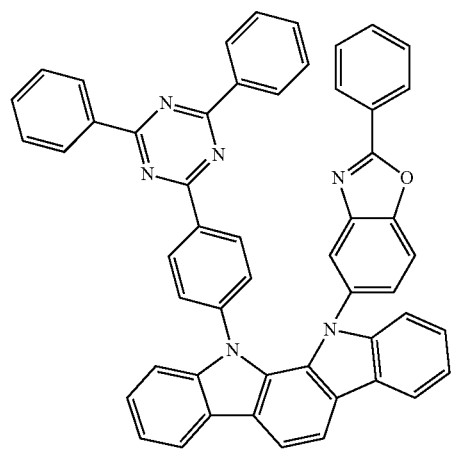
52
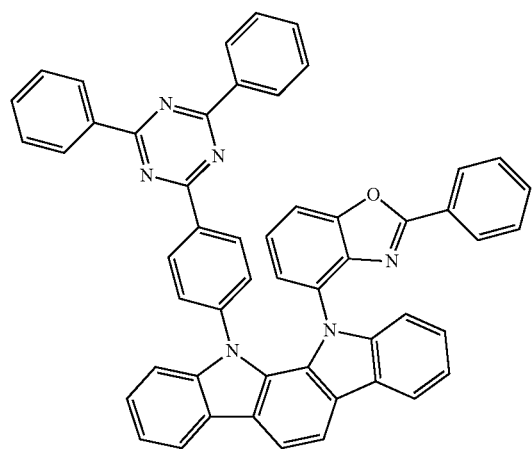
53
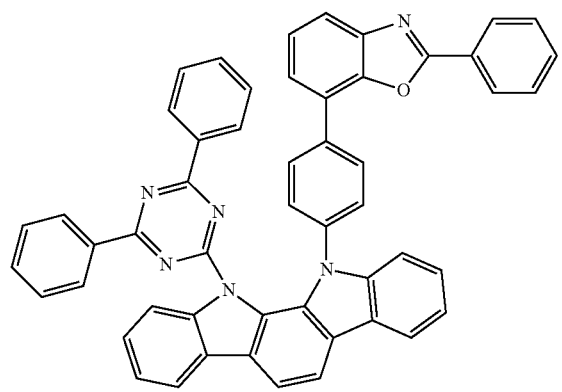
54
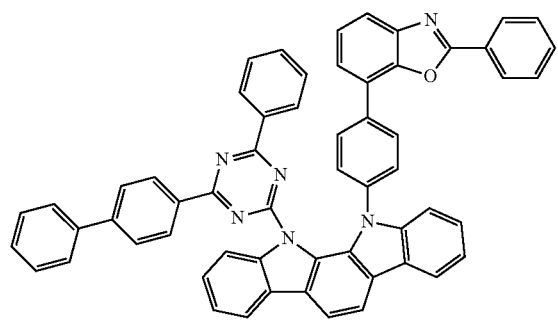
55
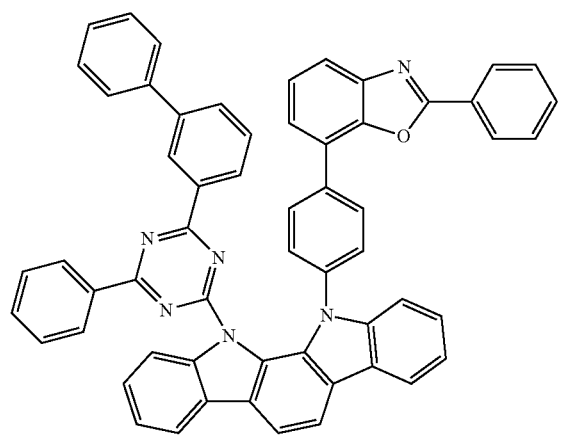

-continued
56
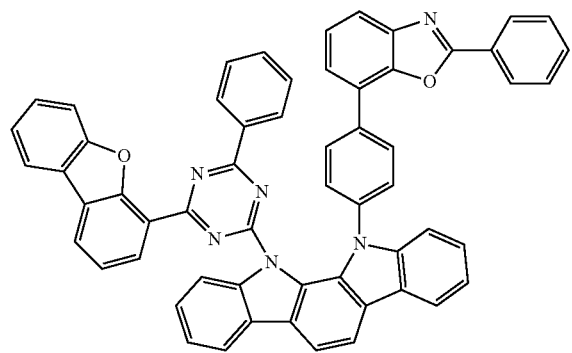
57
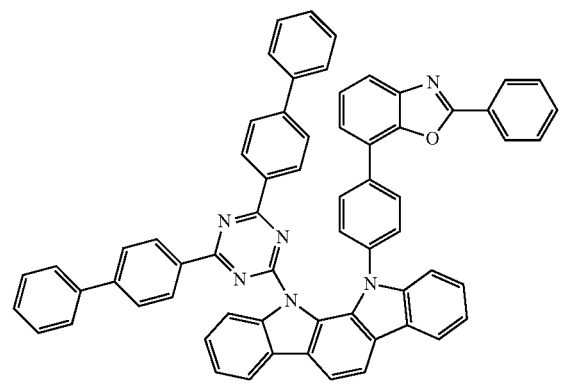
58
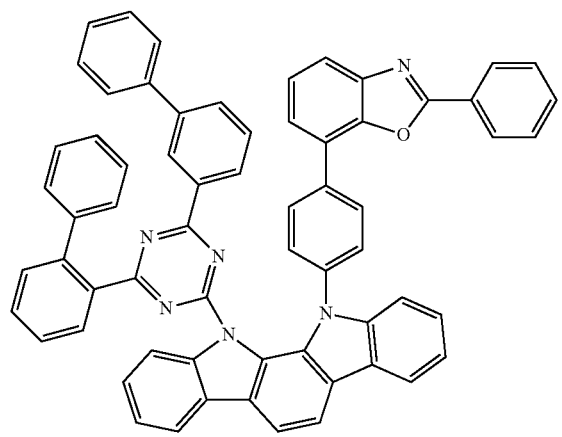
59
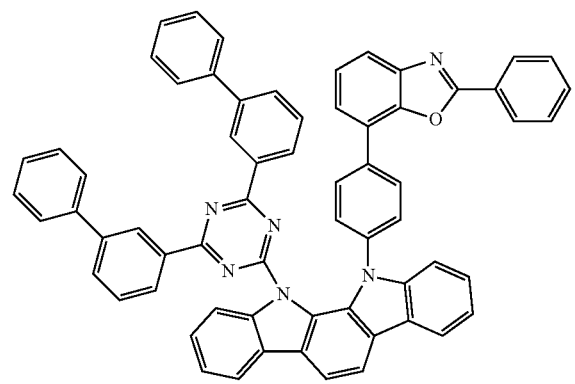
60
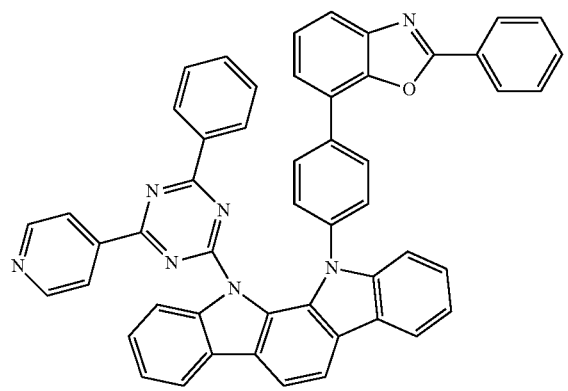
61
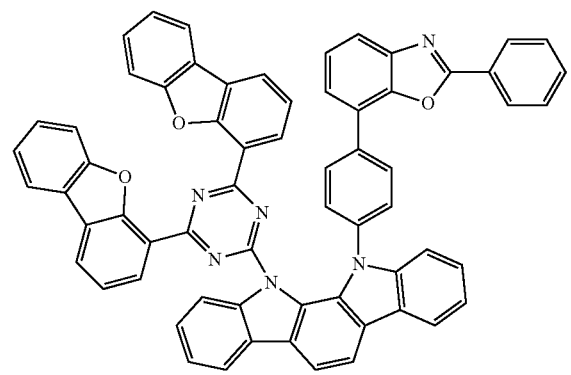

-continued
62
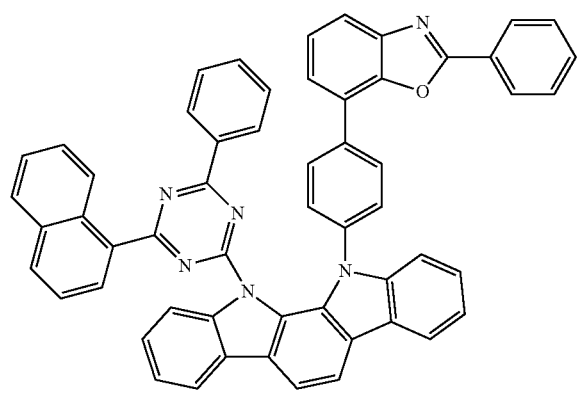
63
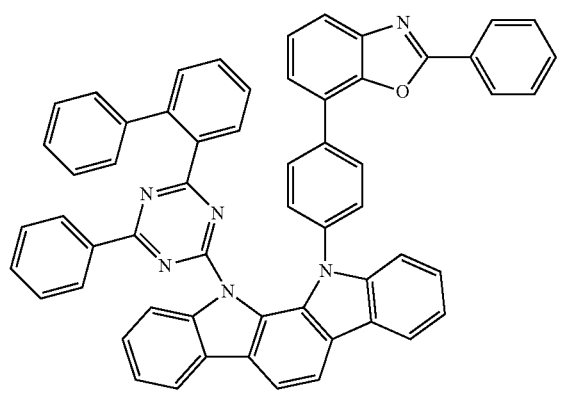
64
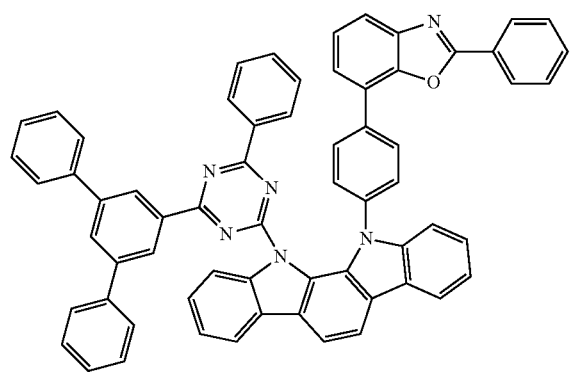
65
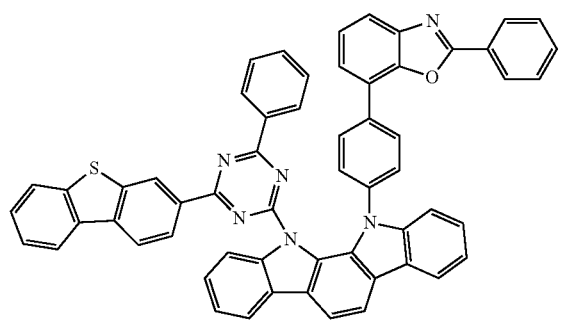
66
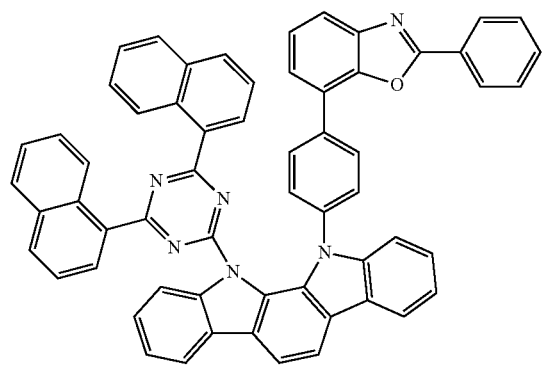
67
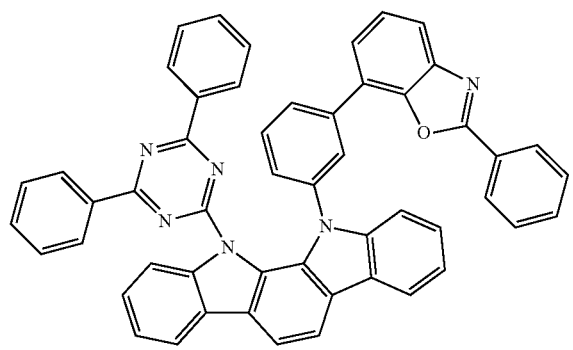

-continued
373
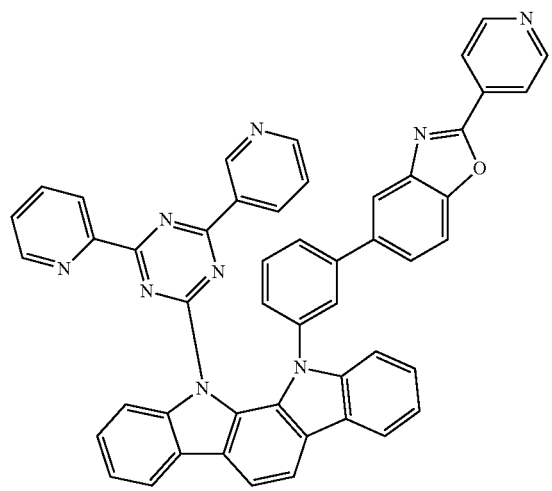
374
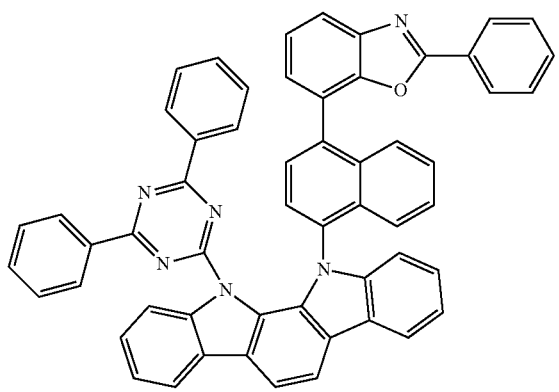
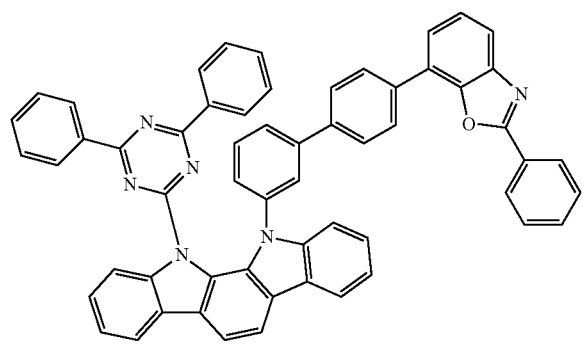
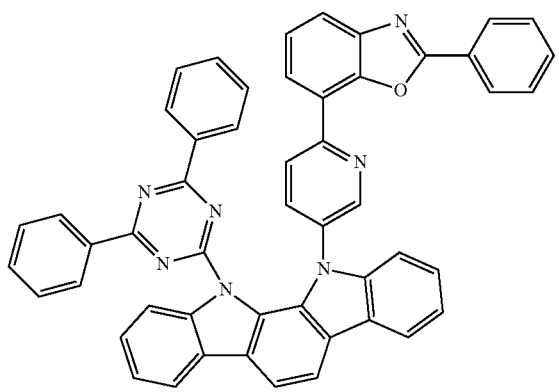
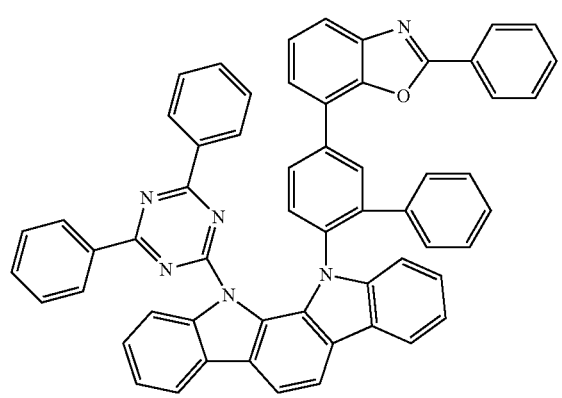

-continued
73
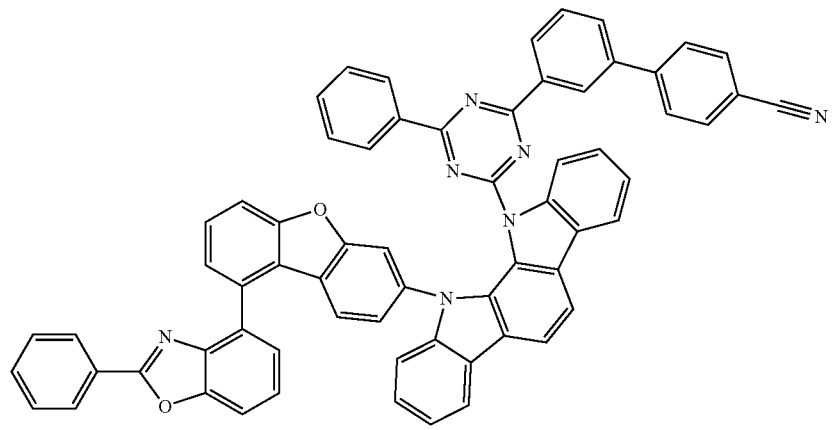
74
75
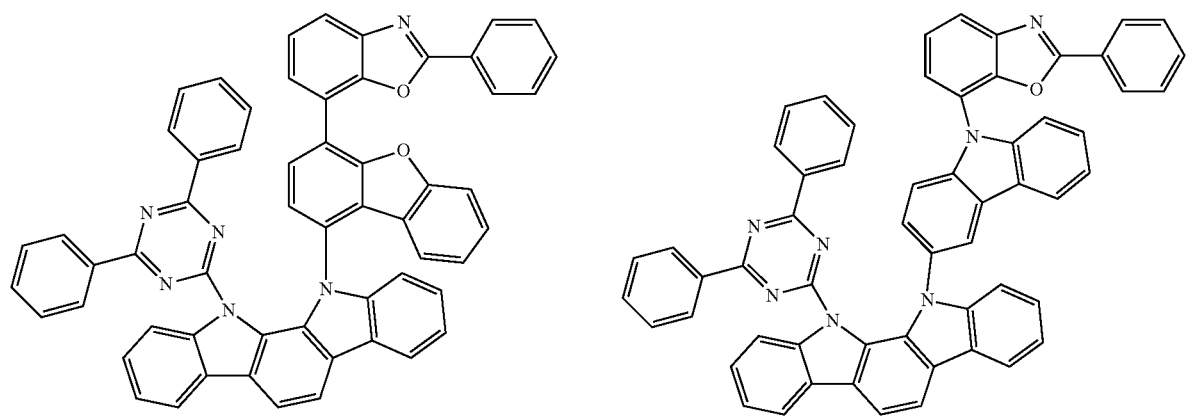
76
77
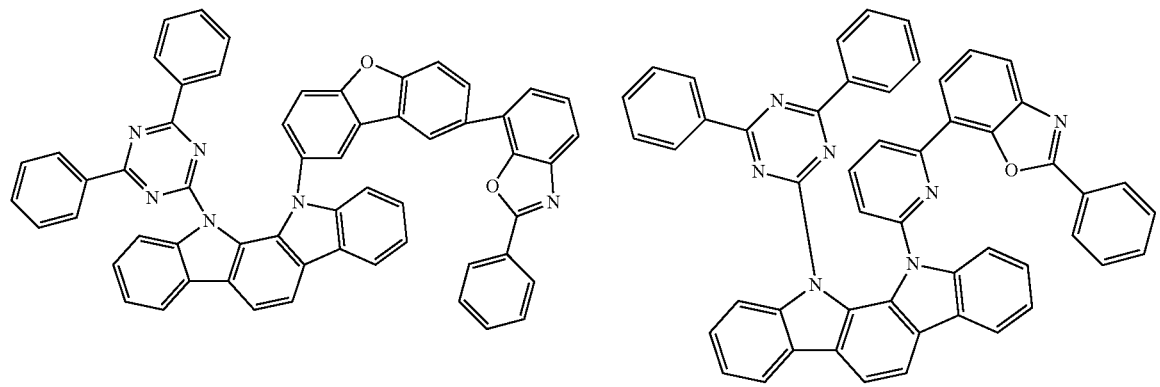

-continued
78
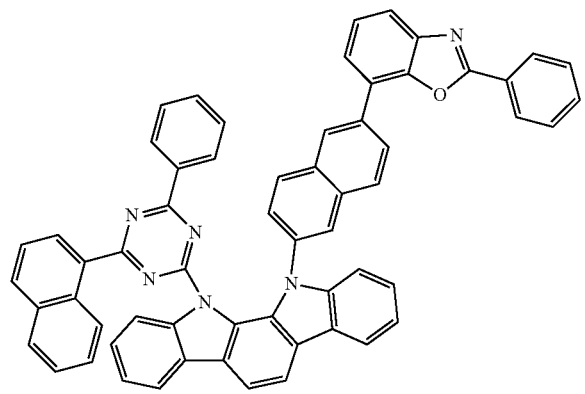
79
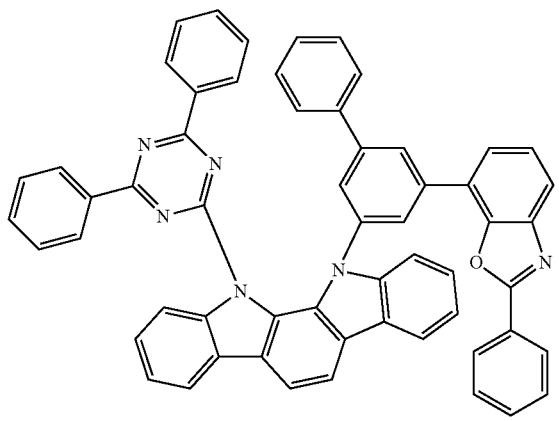
80
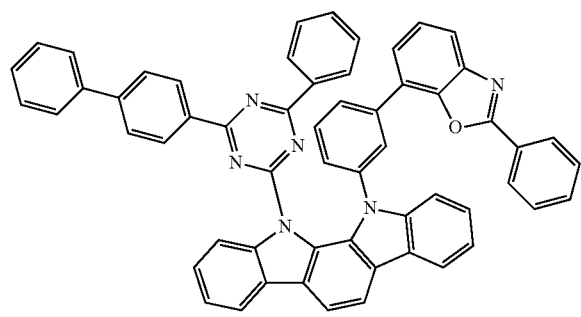
81
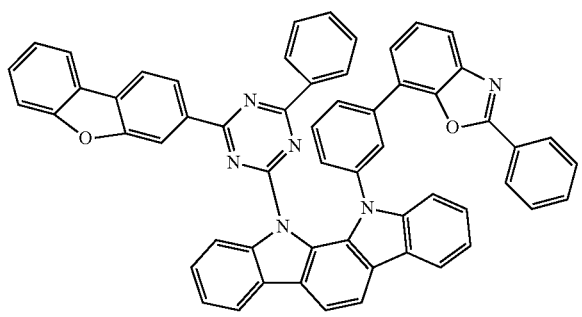
82
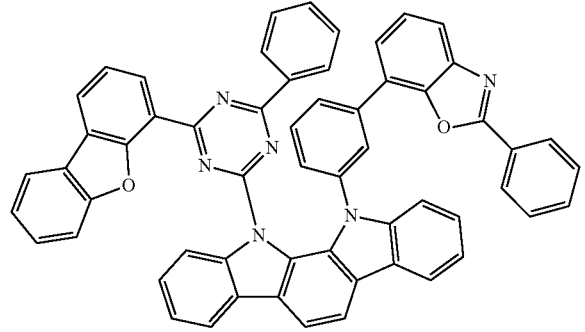
83
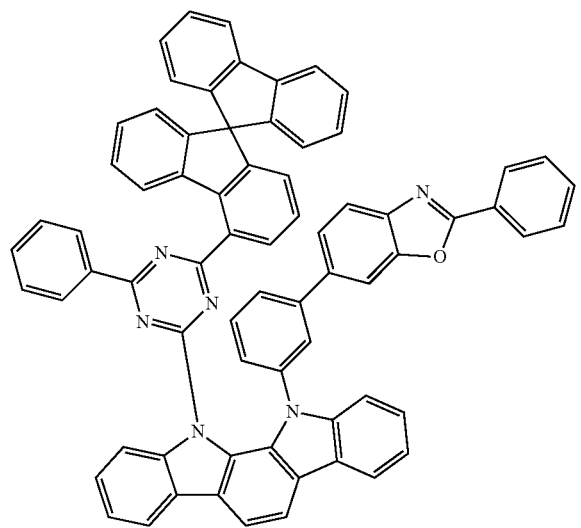
84
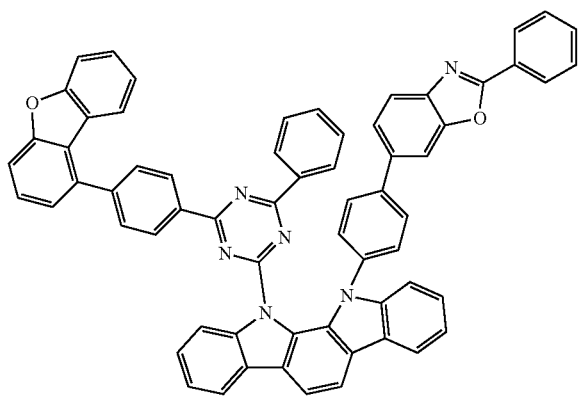

-continued
85
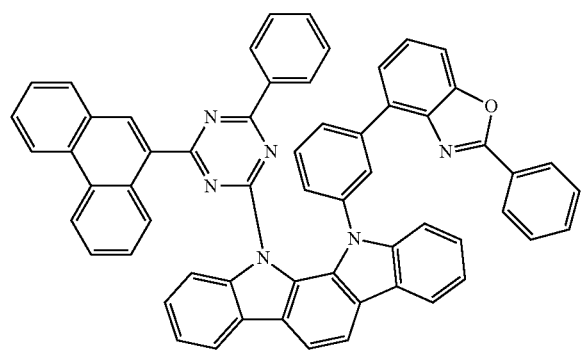
86
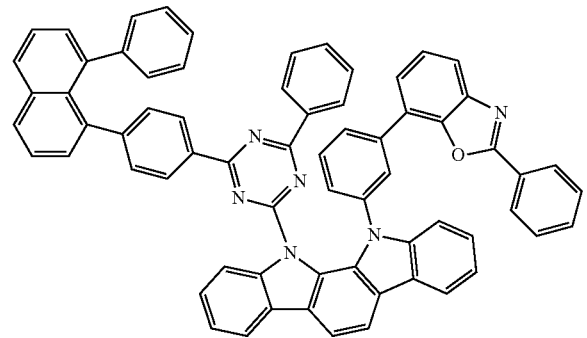
87
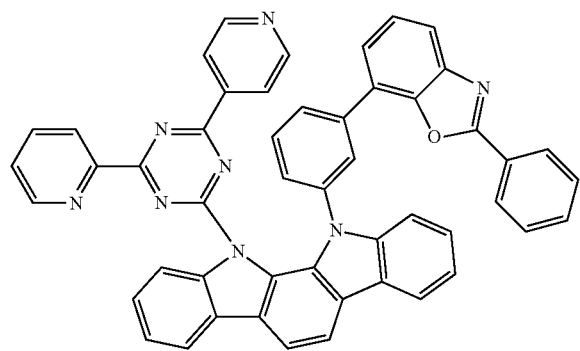
88
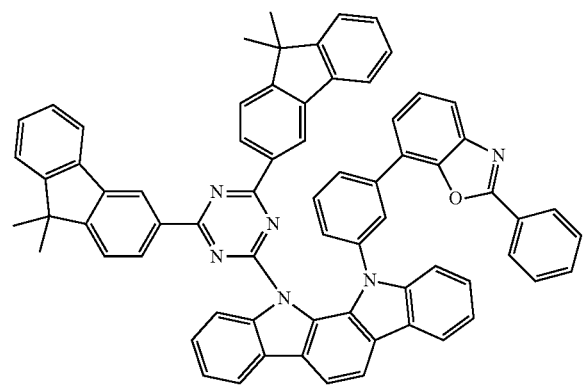
89
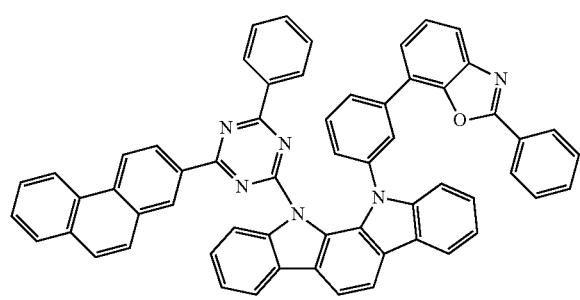
90
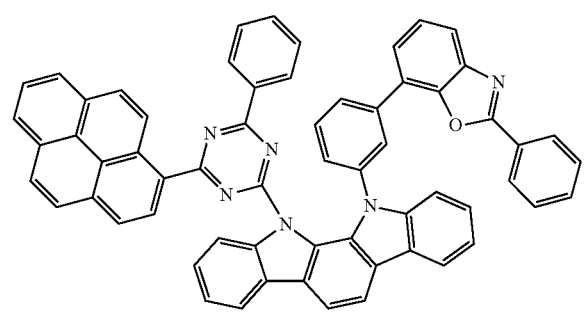

91
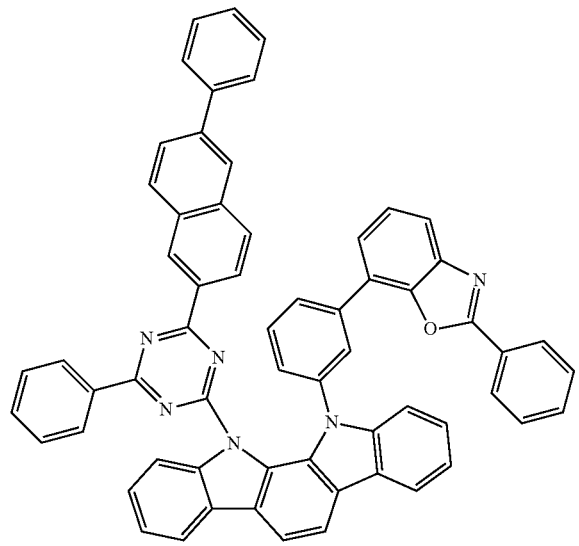
92
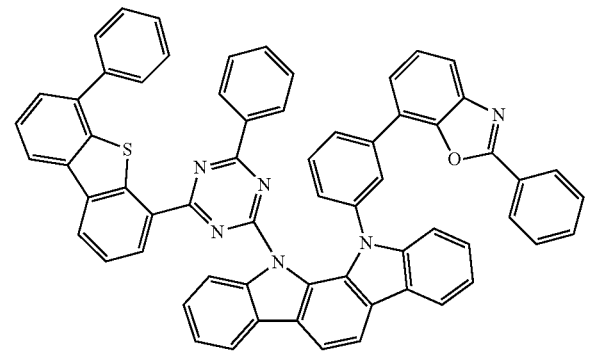
93
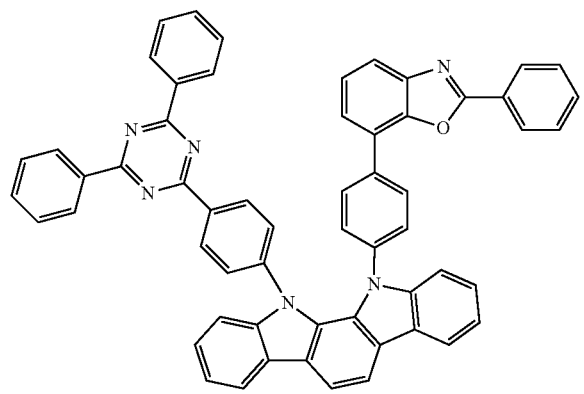
94
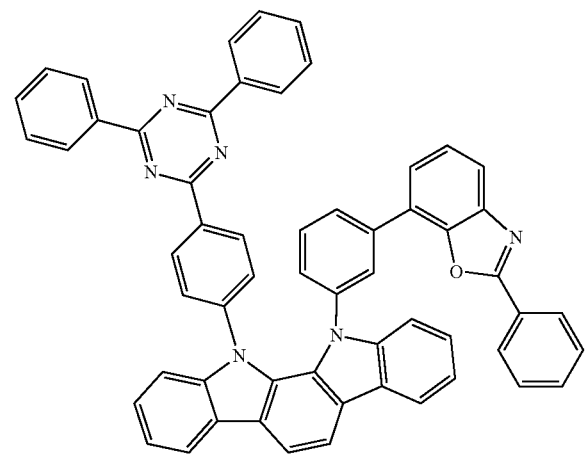
95
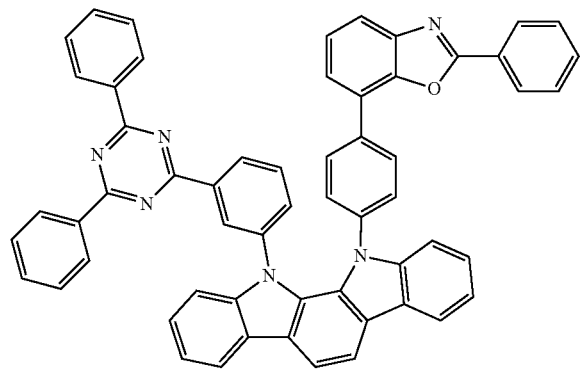
96
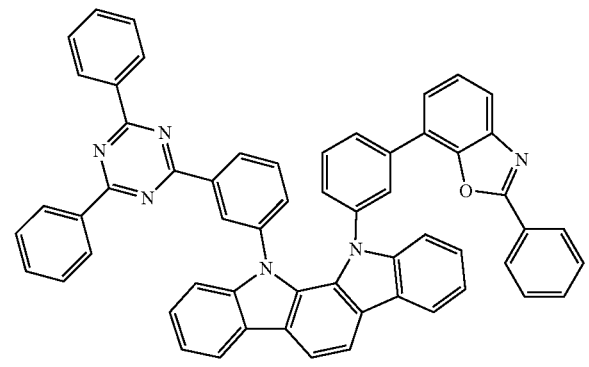

-continued
97
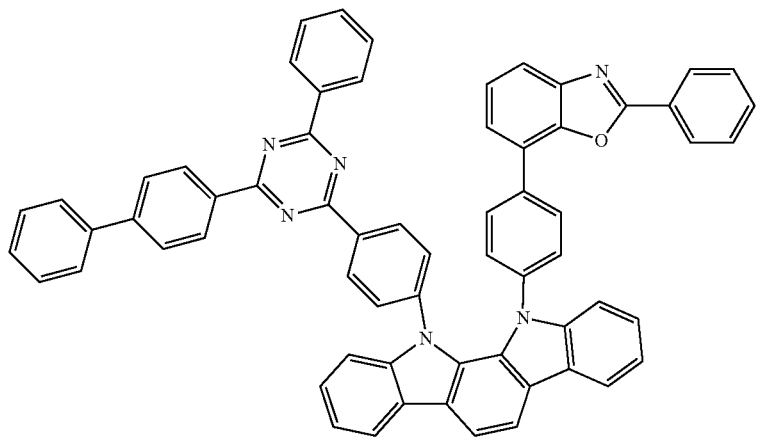
98
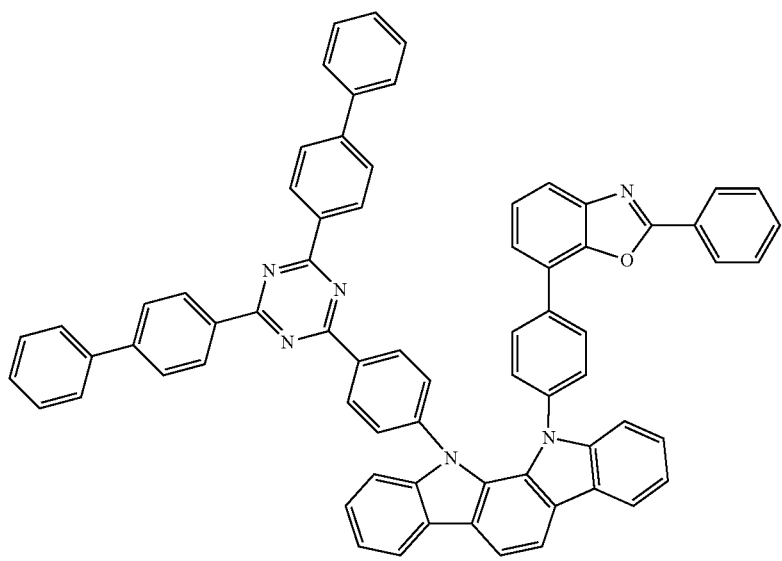
99
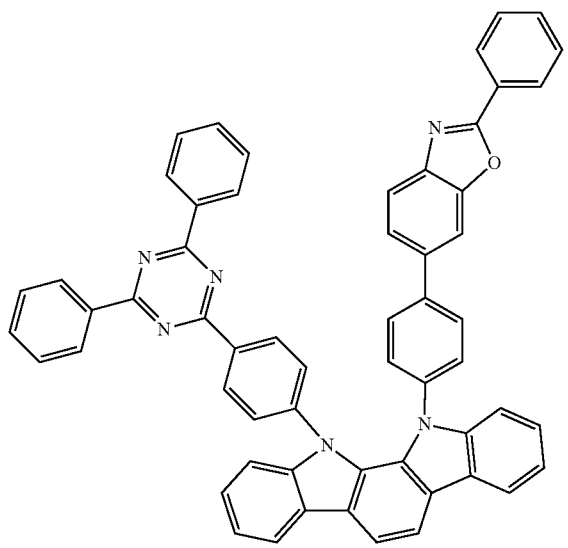
100
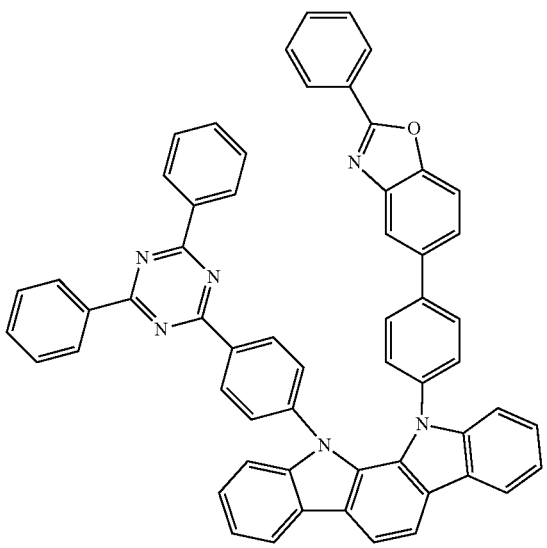

-continued
101
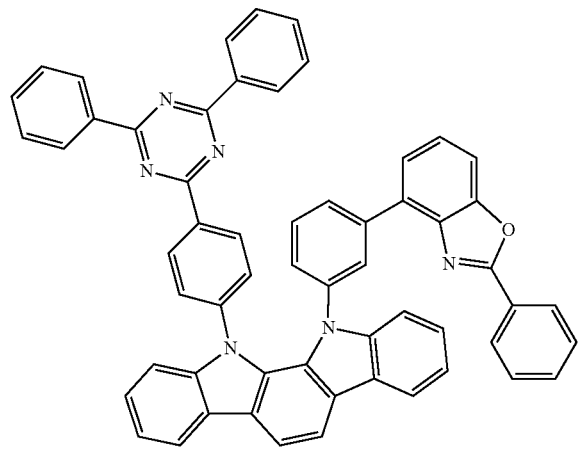
102
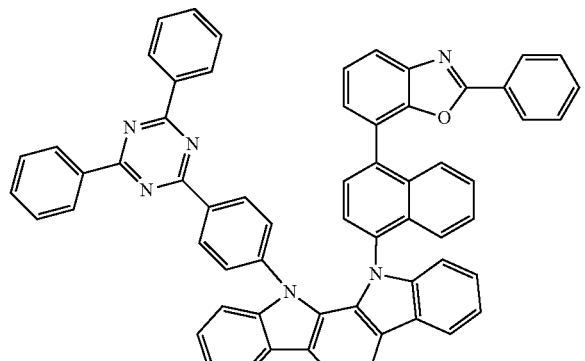
103
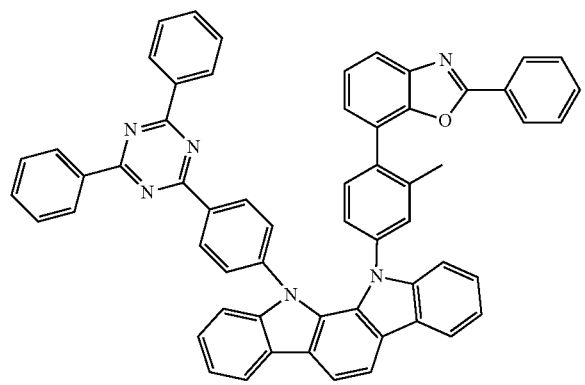
104
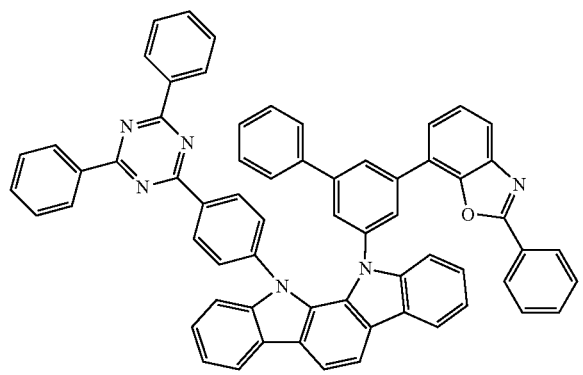
105
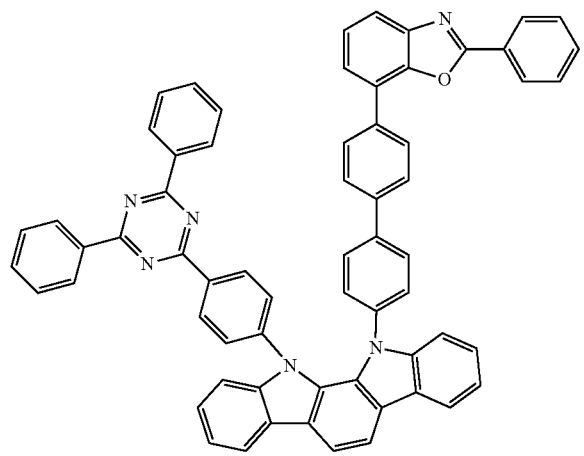
106
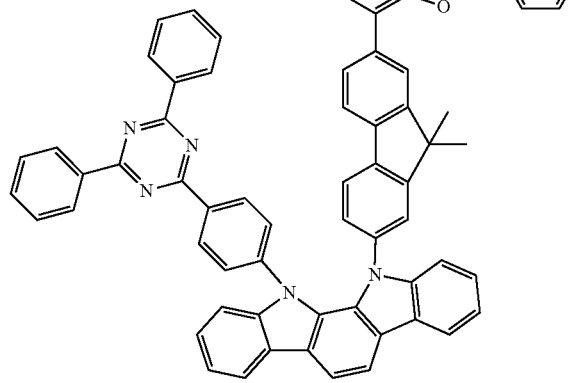

-continued
107
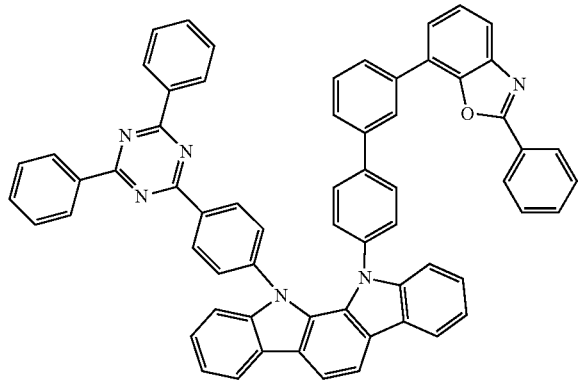
108
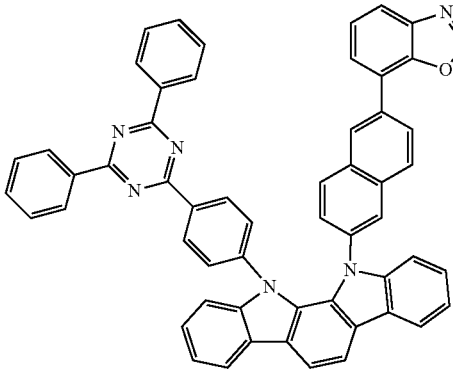
109
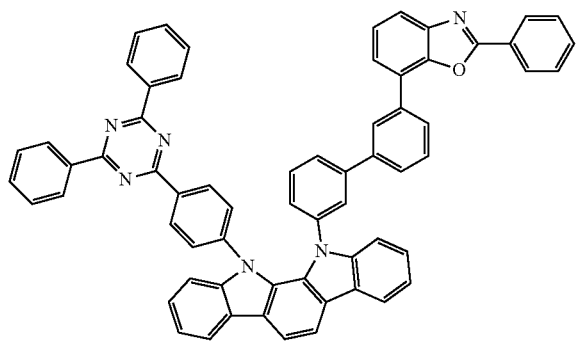
110
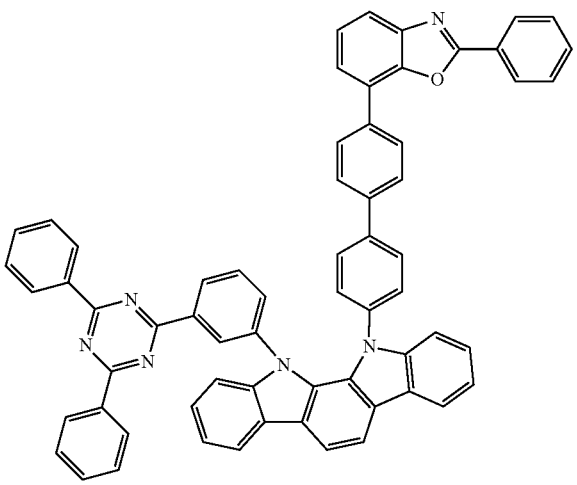
111
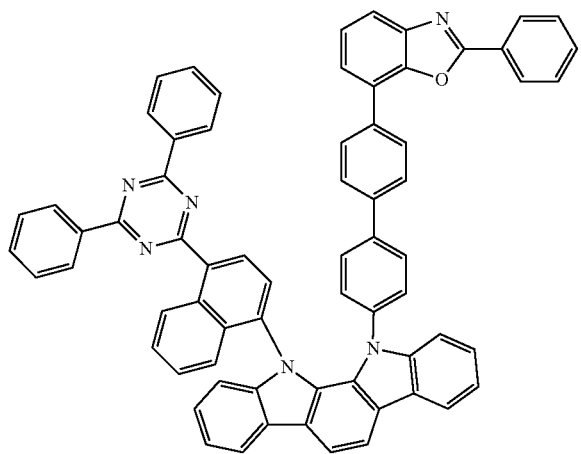
112
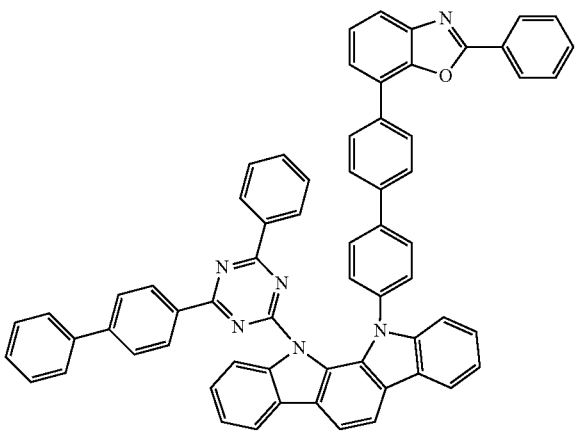

-continued
113
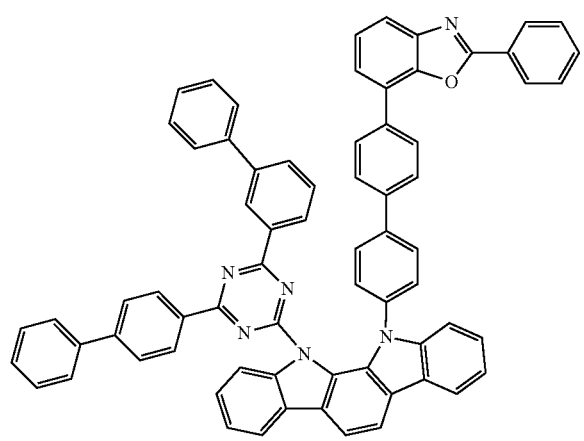
114
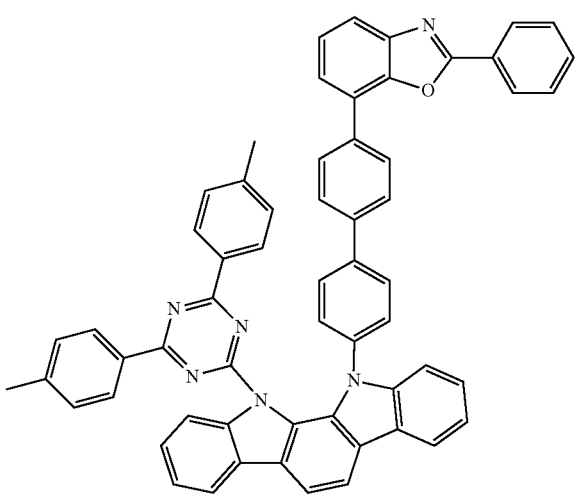
115
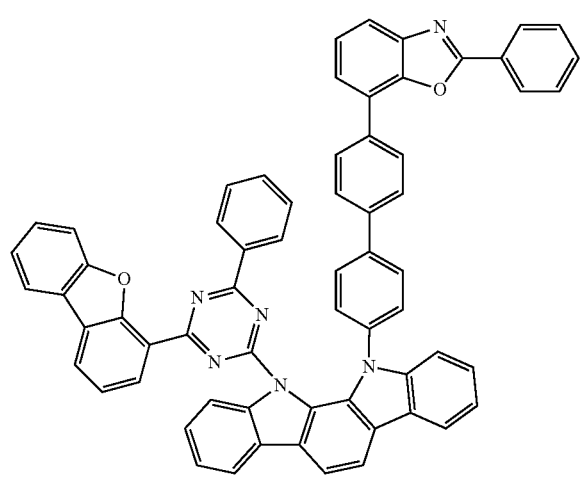
116
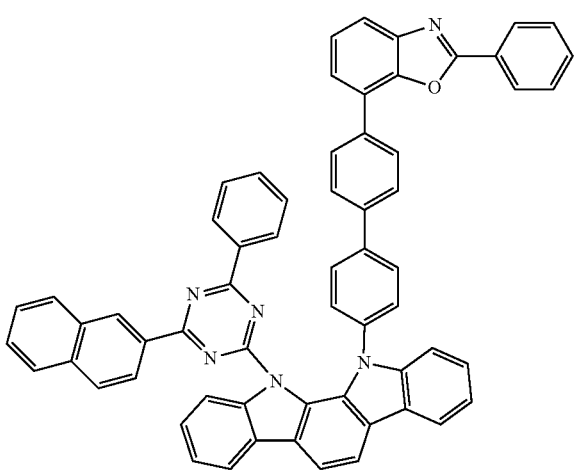
117
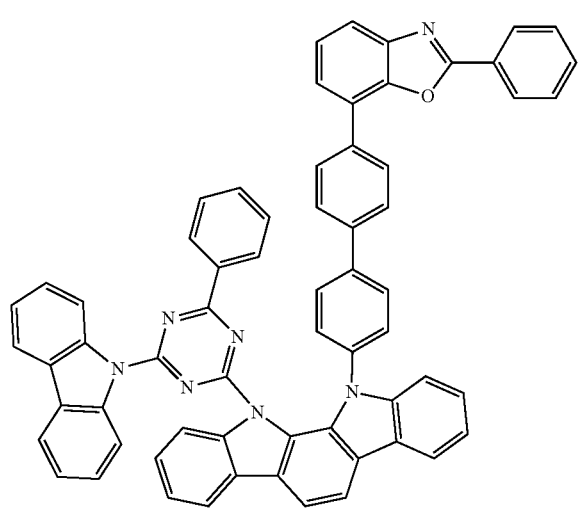
118
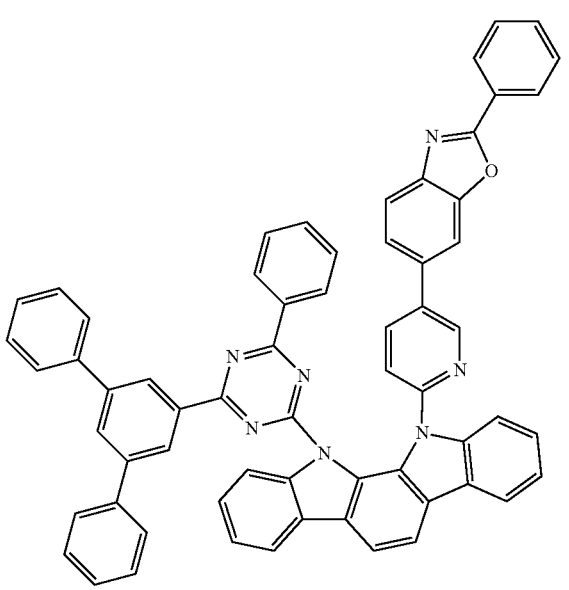

119
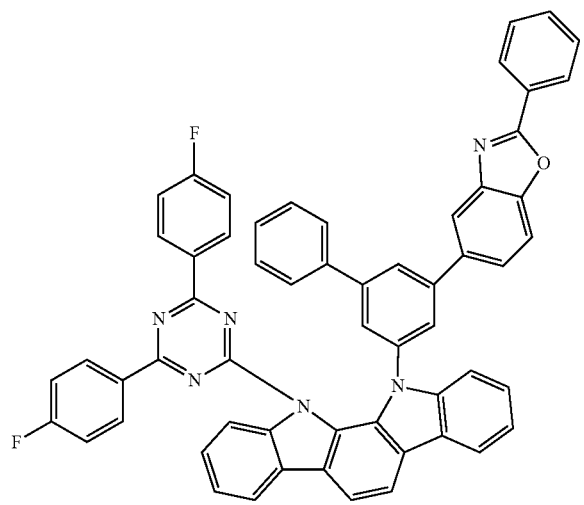
120
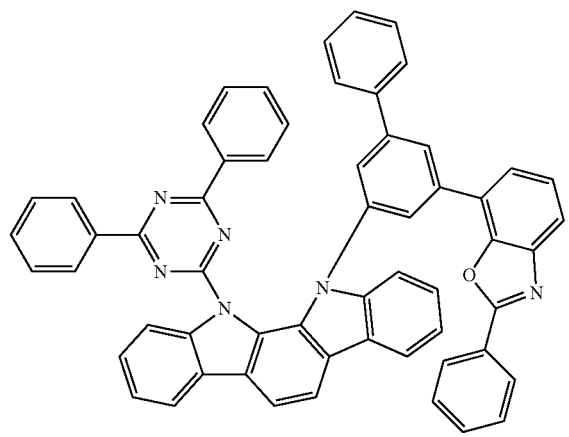
121
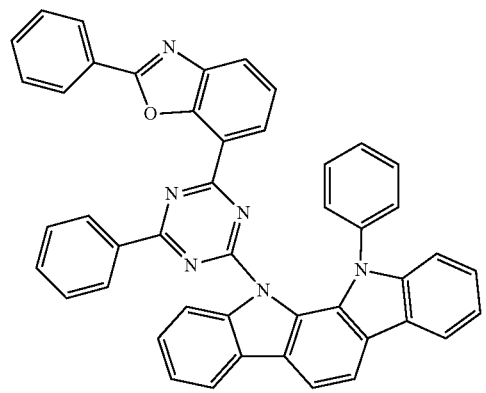
122
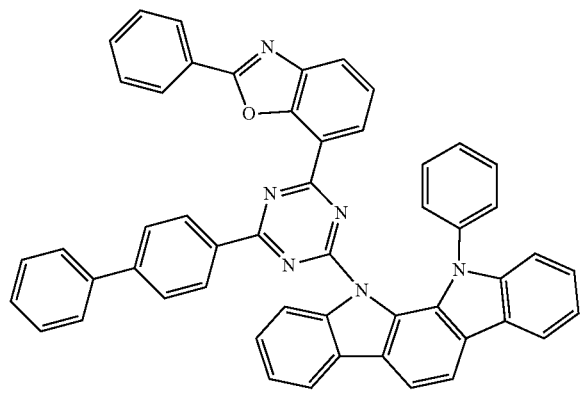
123
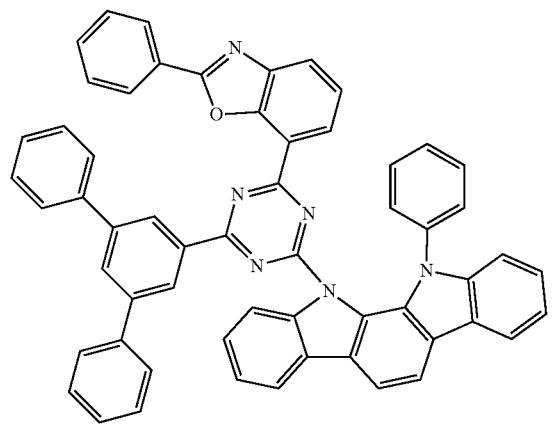
124
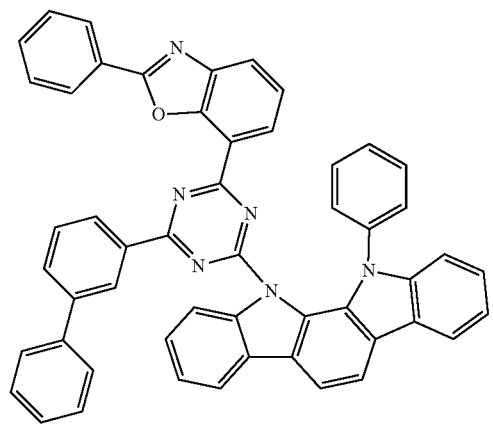

-continued
125
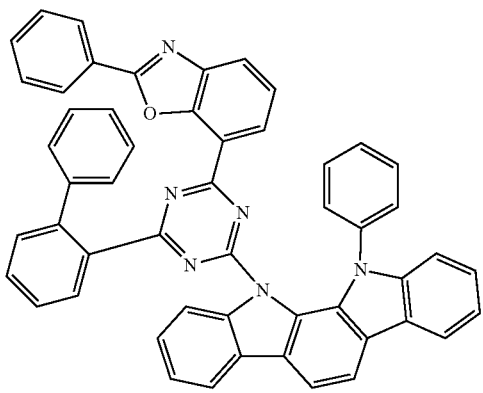
126
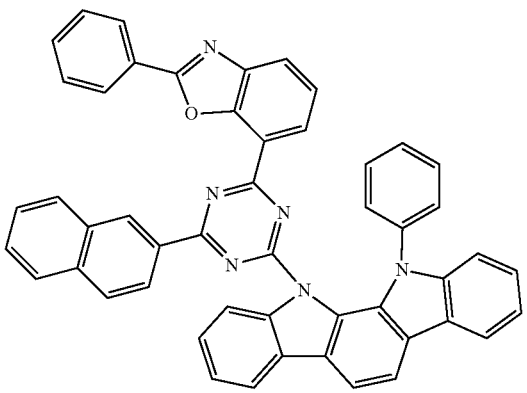
127
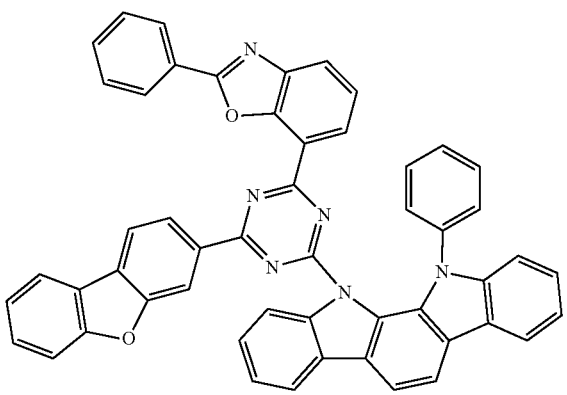
128
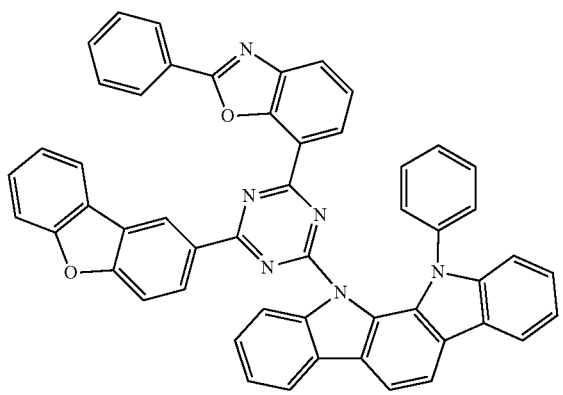
129
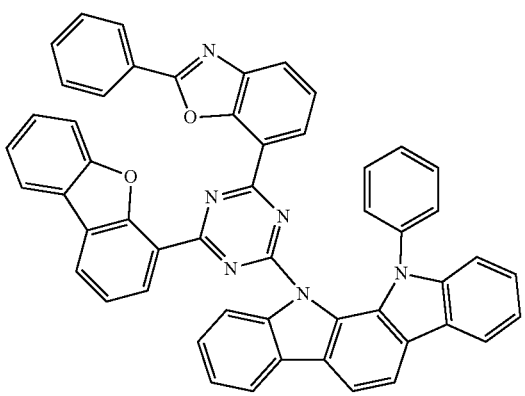
130
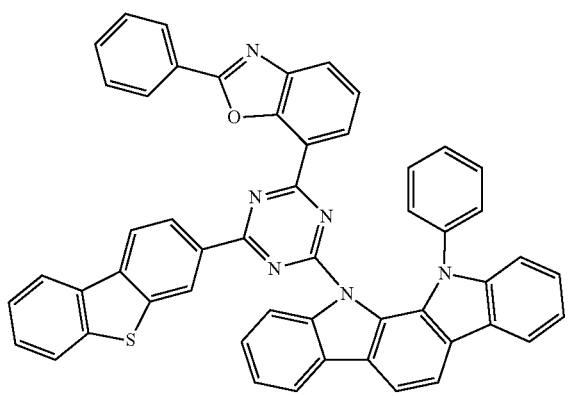
131
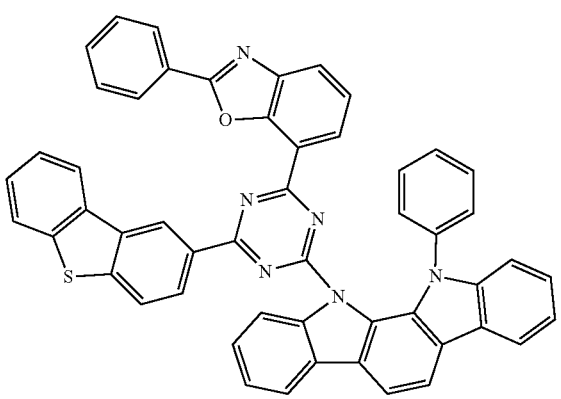
132
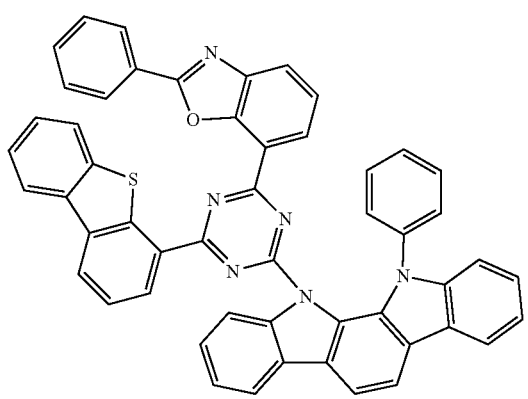

-continued
133
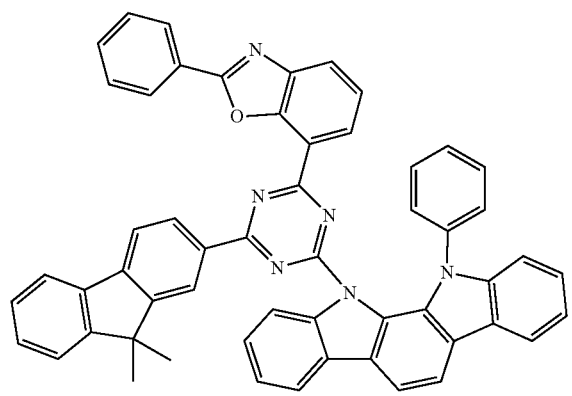
134
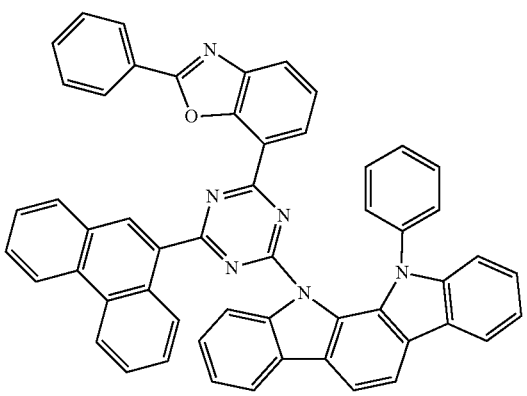
135
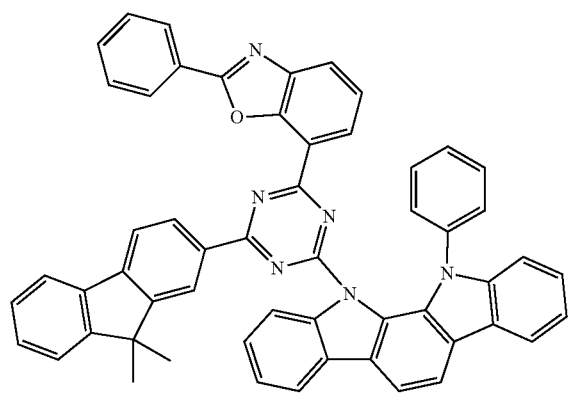
136
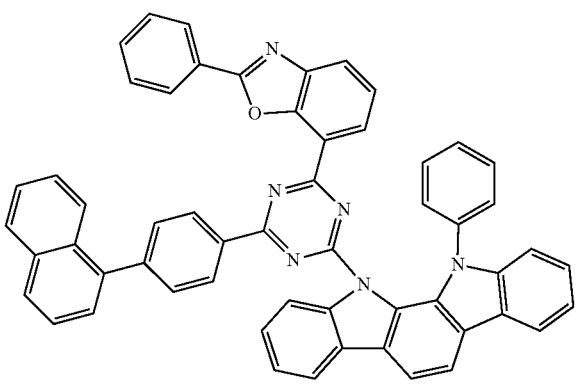
137
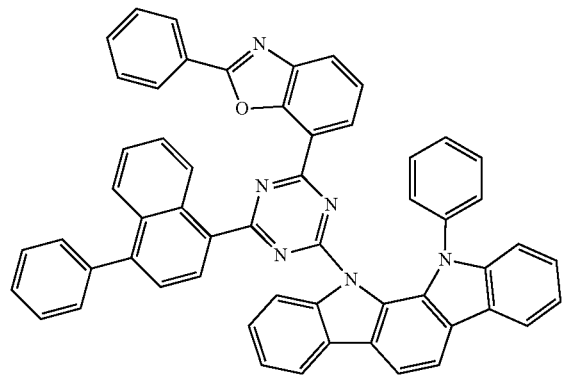
138
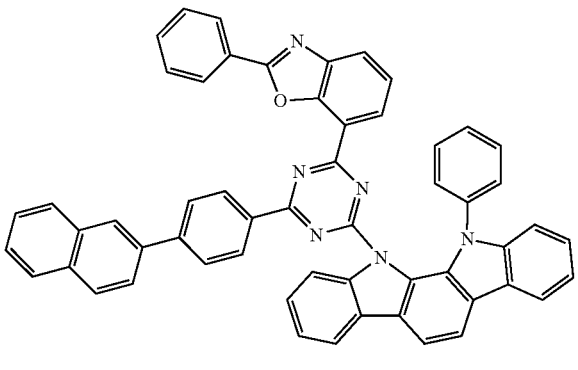

139 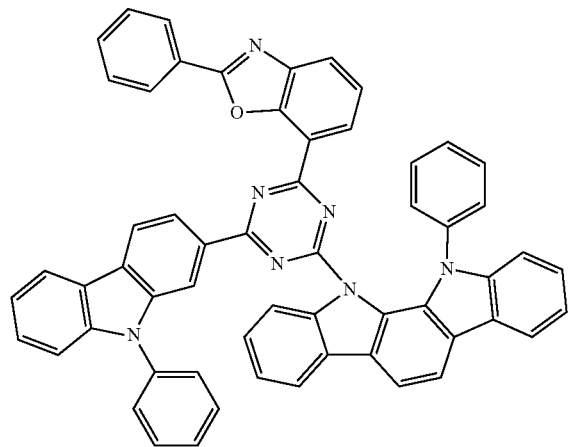
140 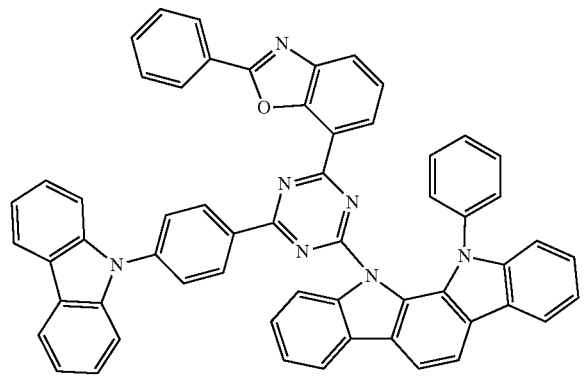
145 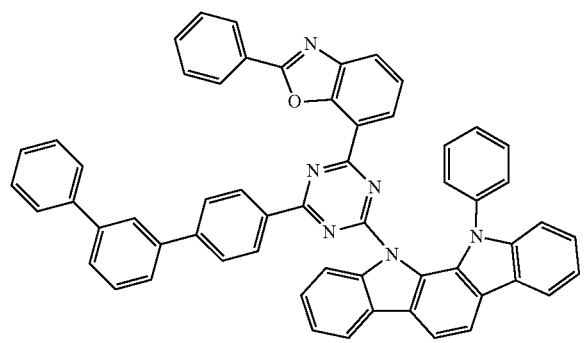
146 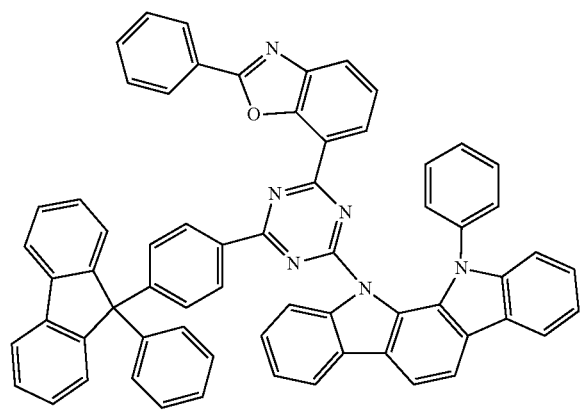
147 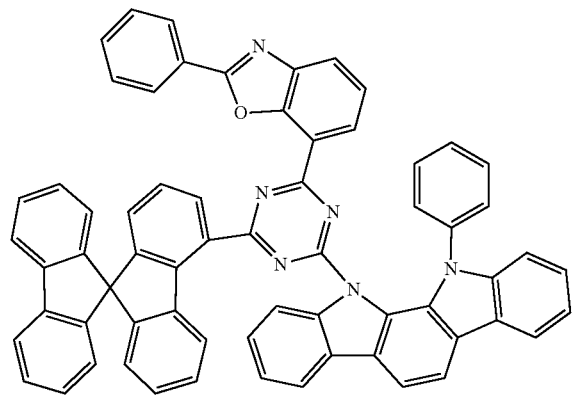
148 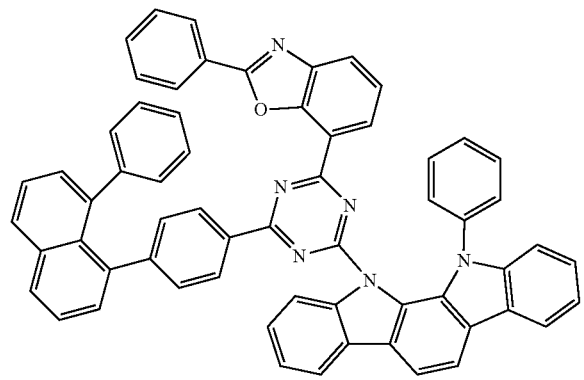

-continued
149
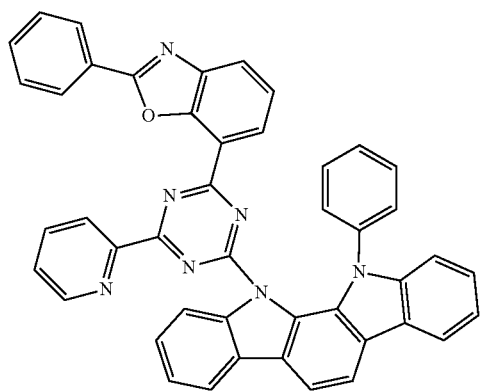
150
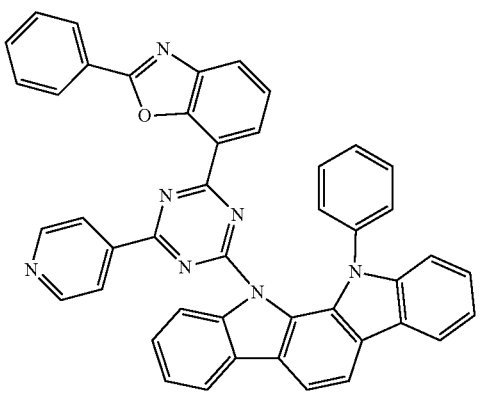
151
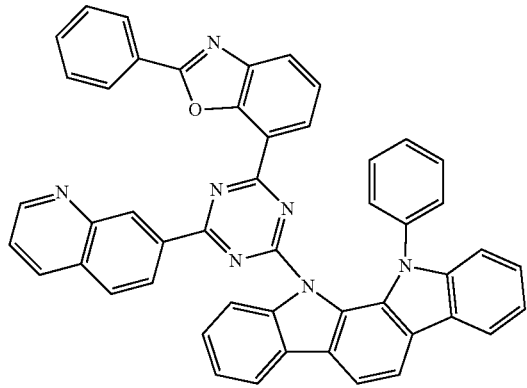
152
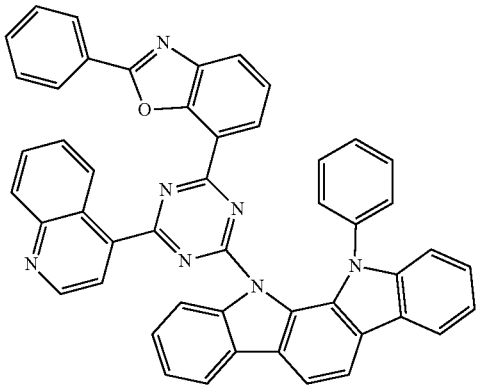
-continued
153
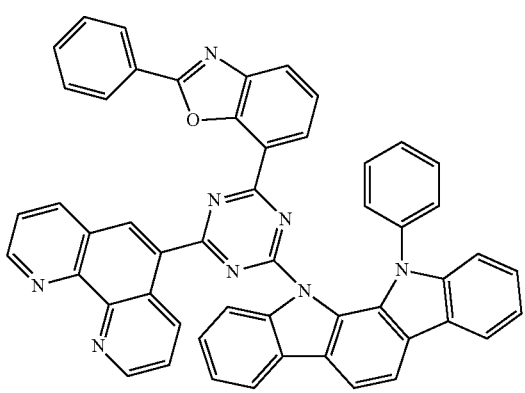
154
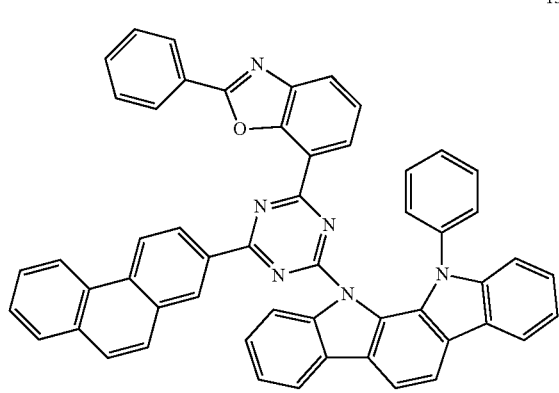

401
-continued
155
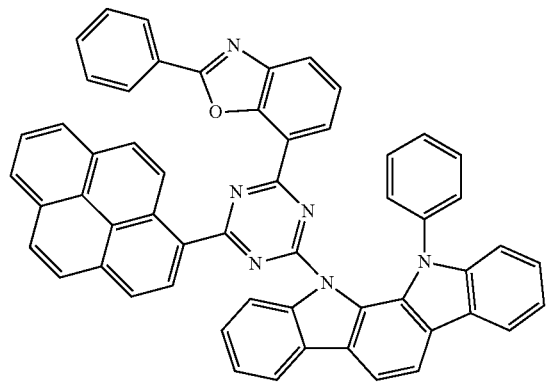
156
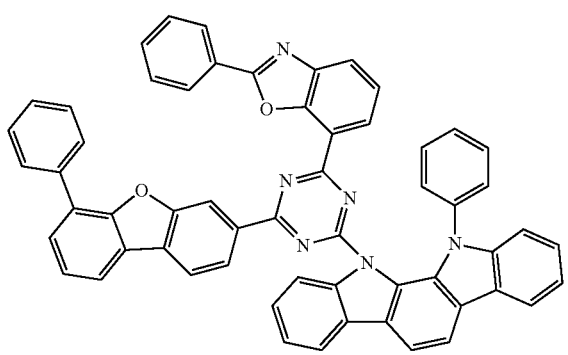
157
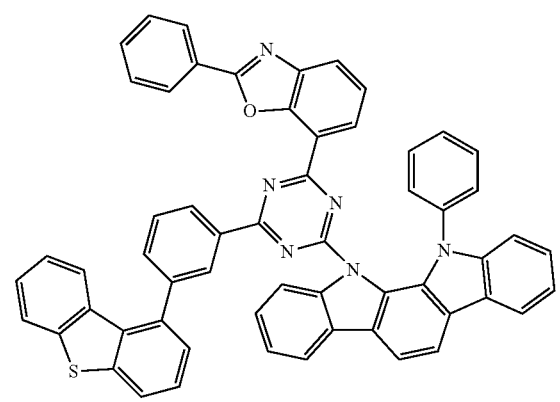
158
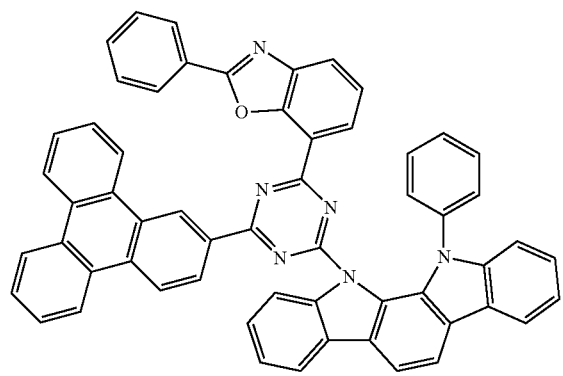
402
-continued
159
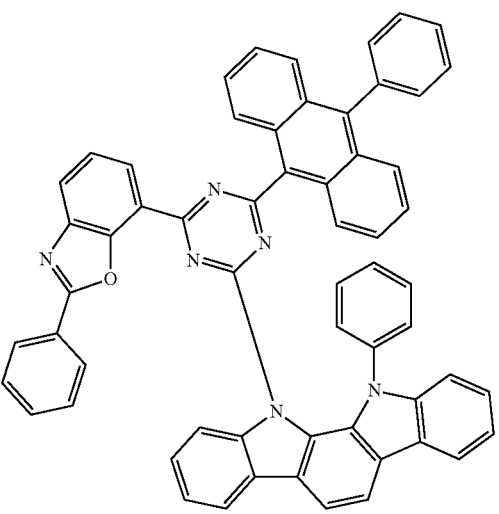
160
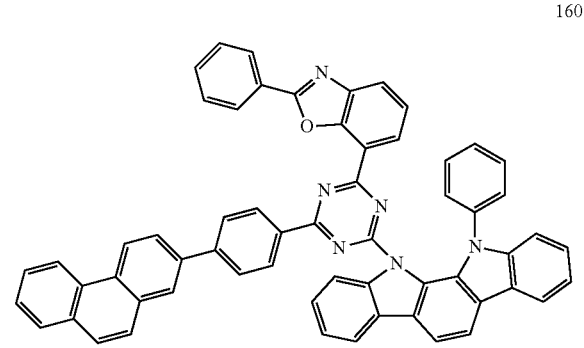
161
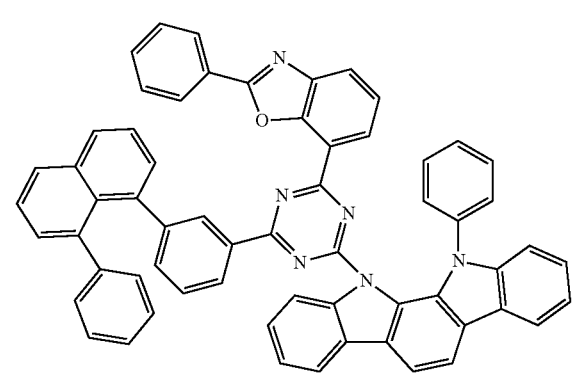
162
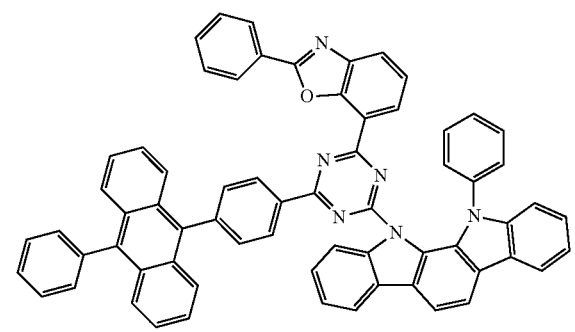

-continued
163
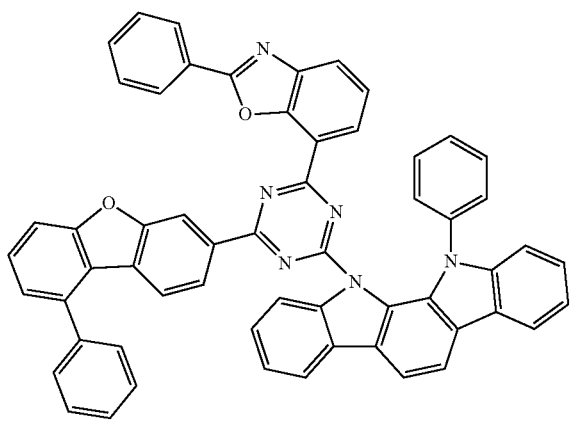
165
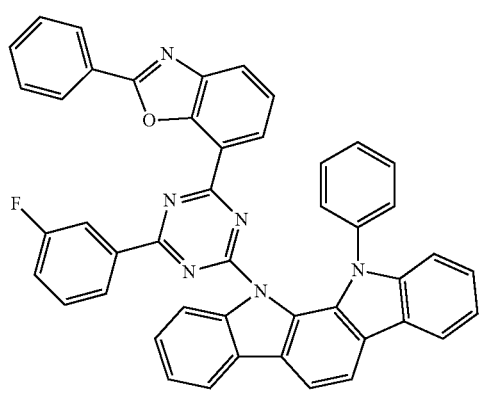
166
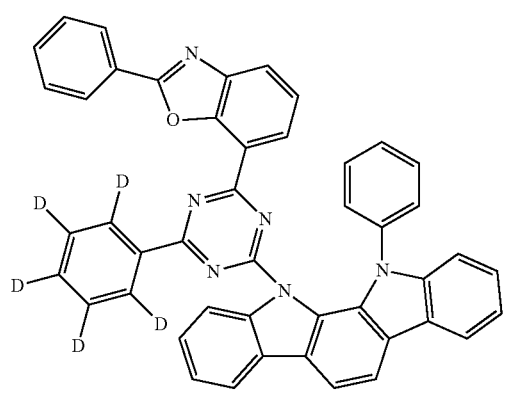
167
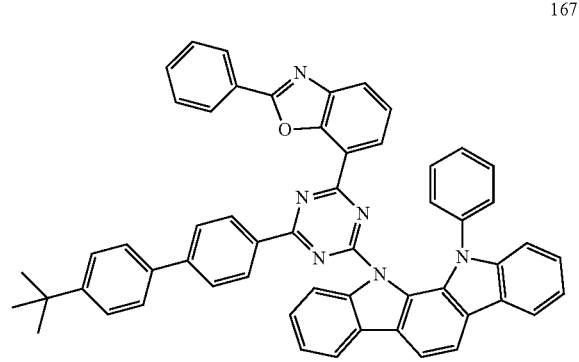
-continued
168
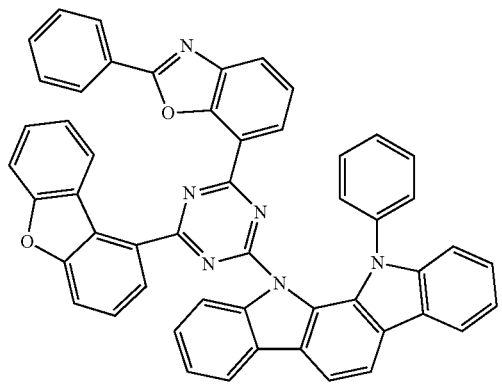
169
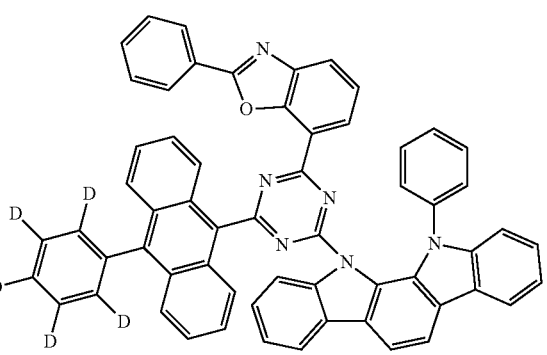
170
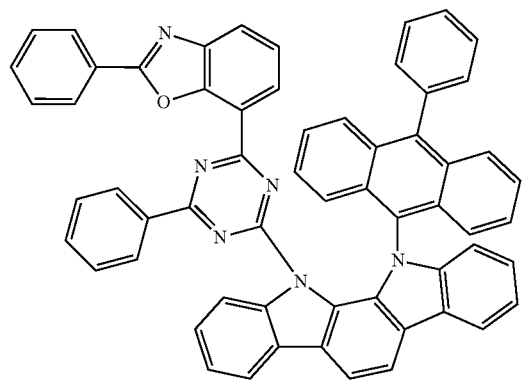
171
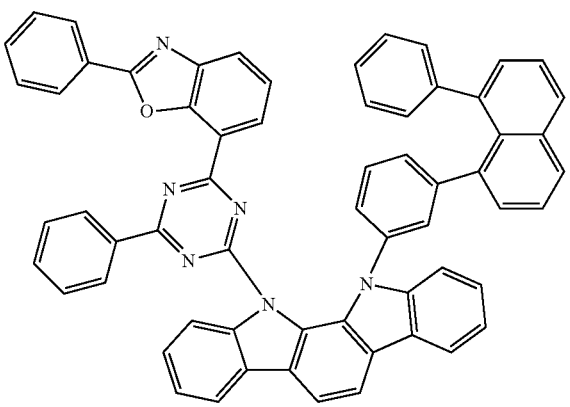

405
-continued
172
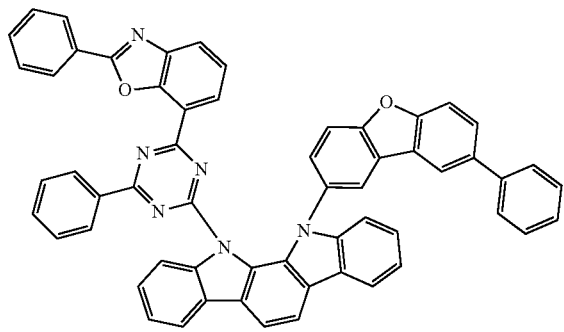
173
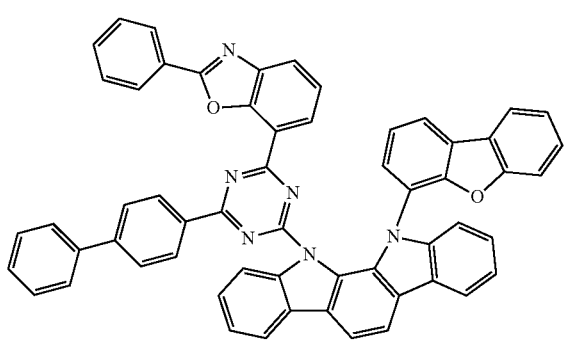
174
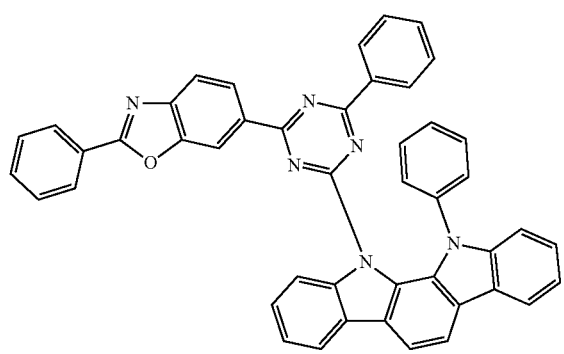
175
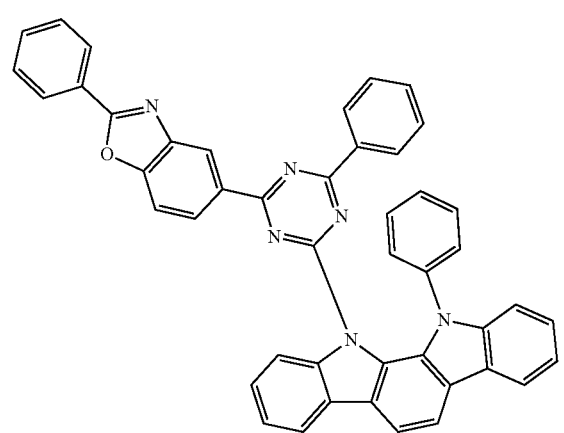
406
-continued
176
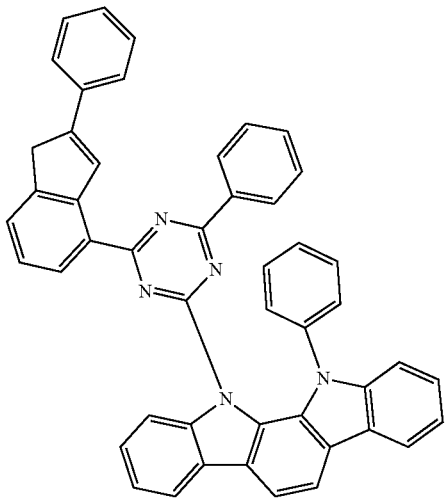
177
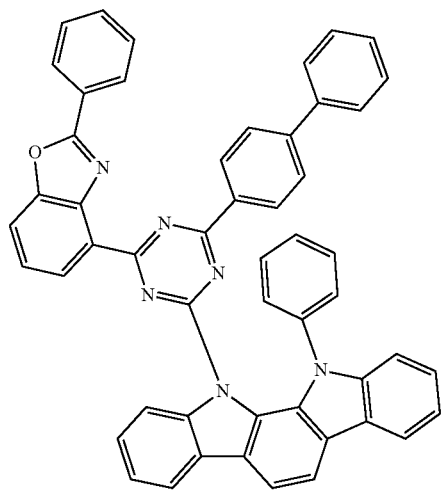
178
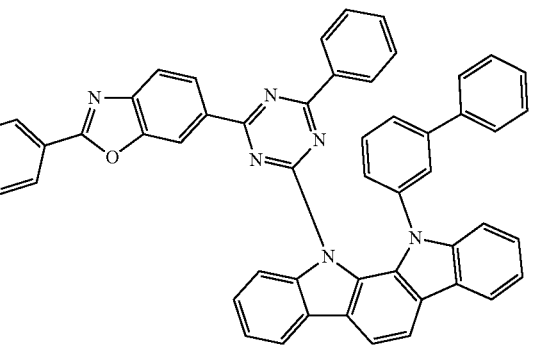

407
-continued
179
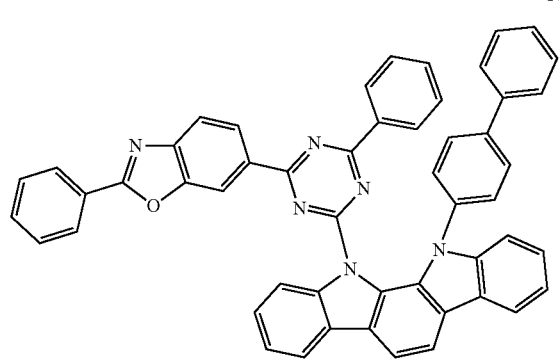
180
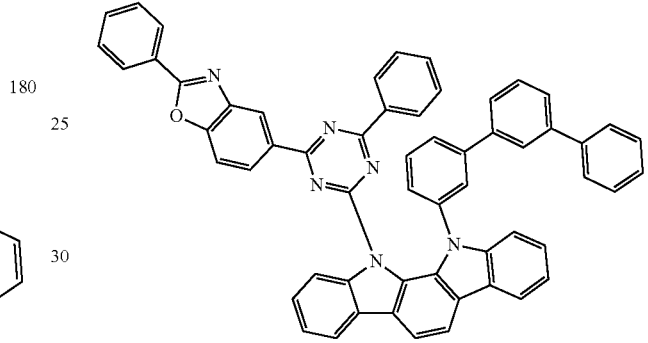
181
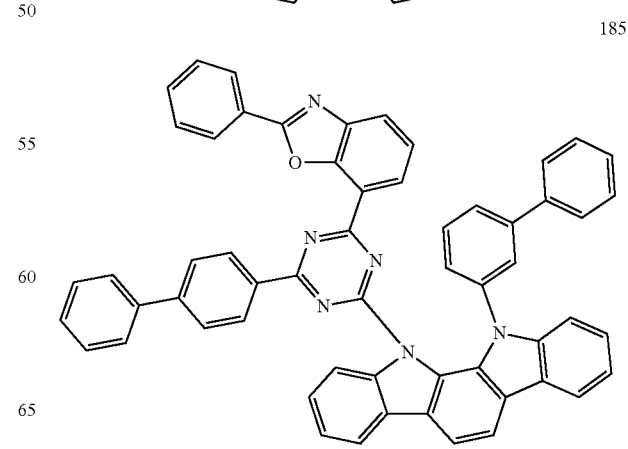
408
-continued
182
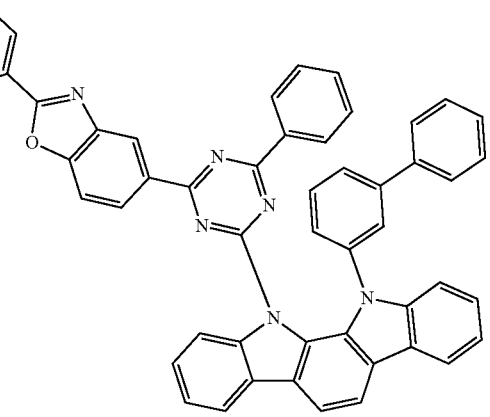
183
184
185

409
-continued
186
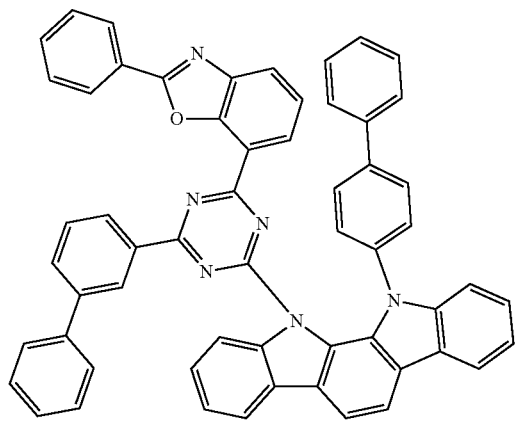
187
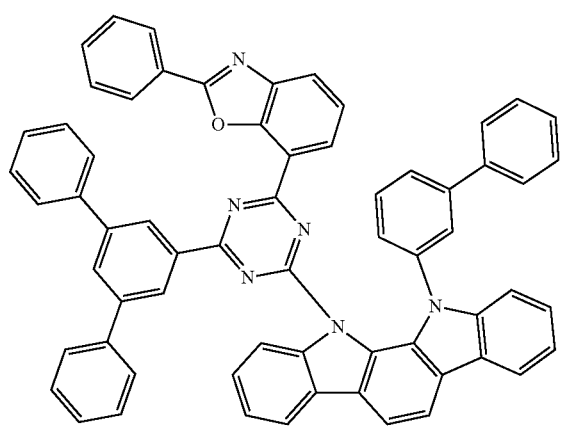
188
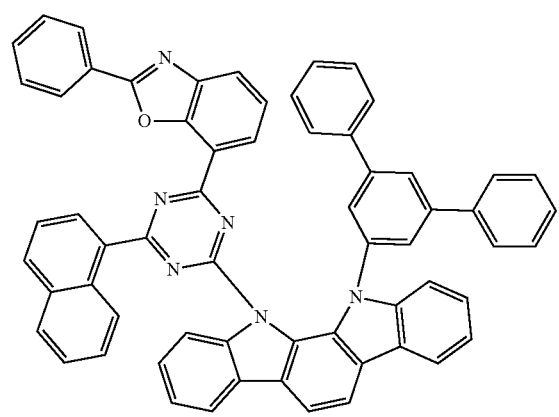
410
-continued
189
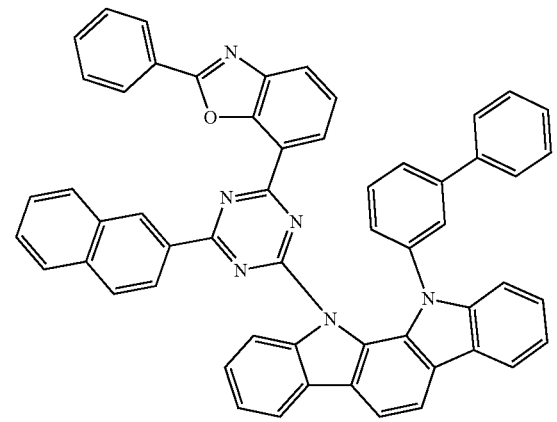
190
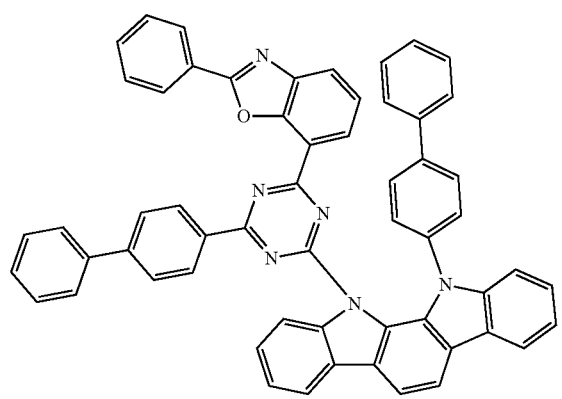
191
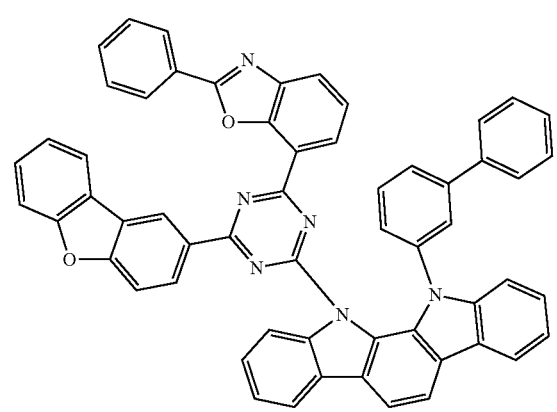

192
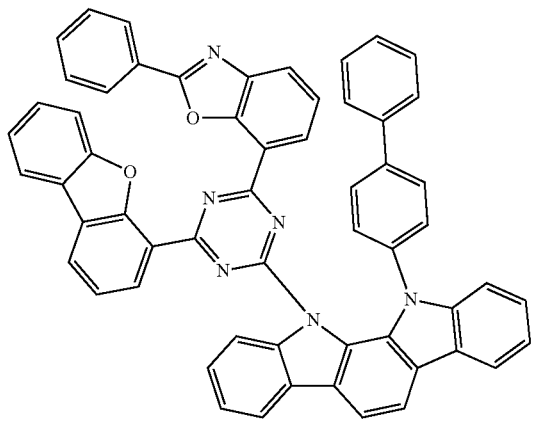
193
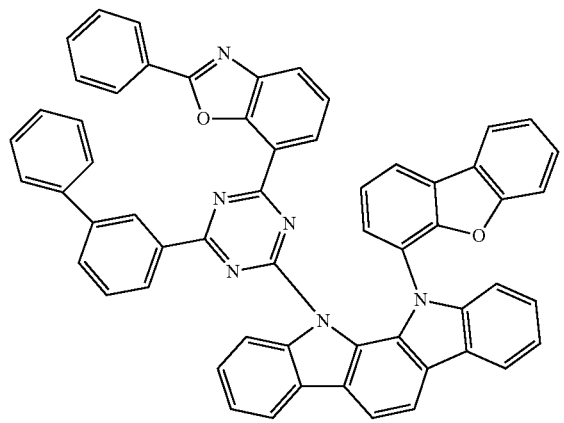
195
196
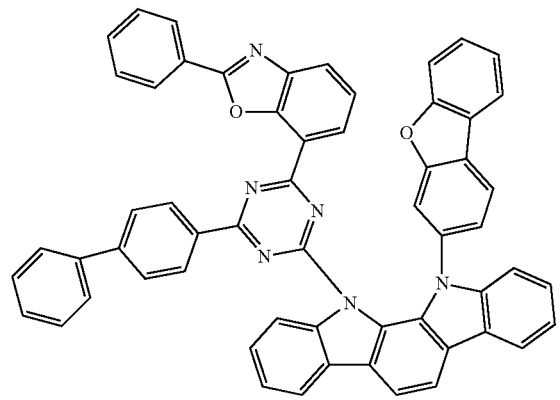
197
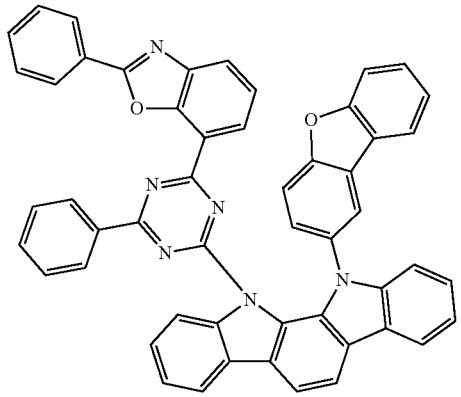
199
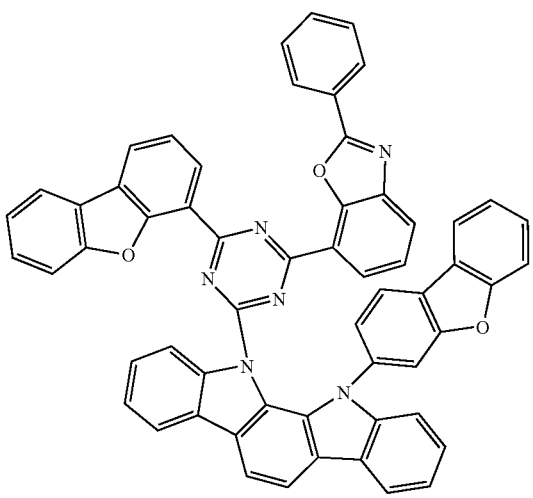

-continued
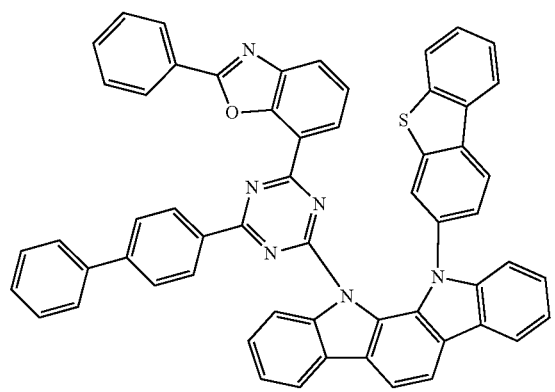
200
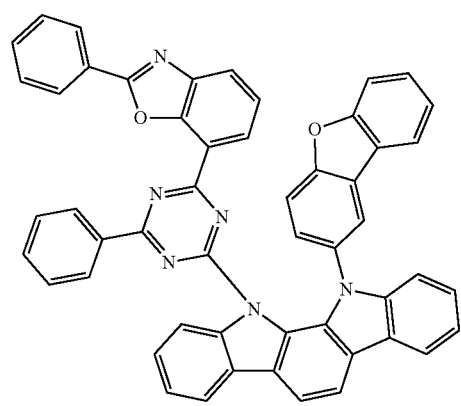
197
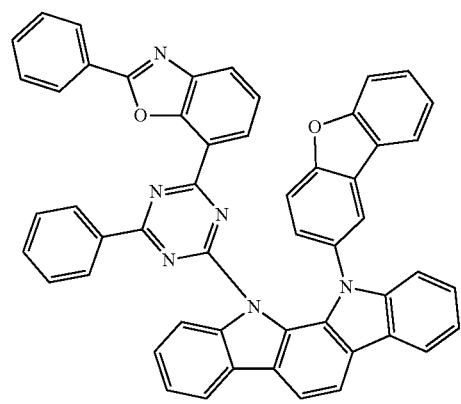
198
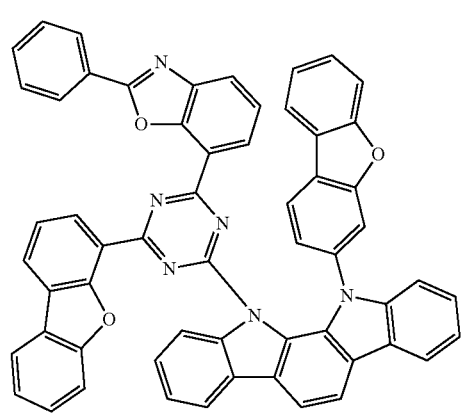
199
-continued
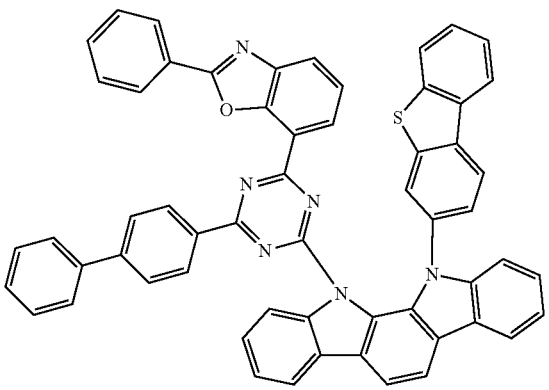
200
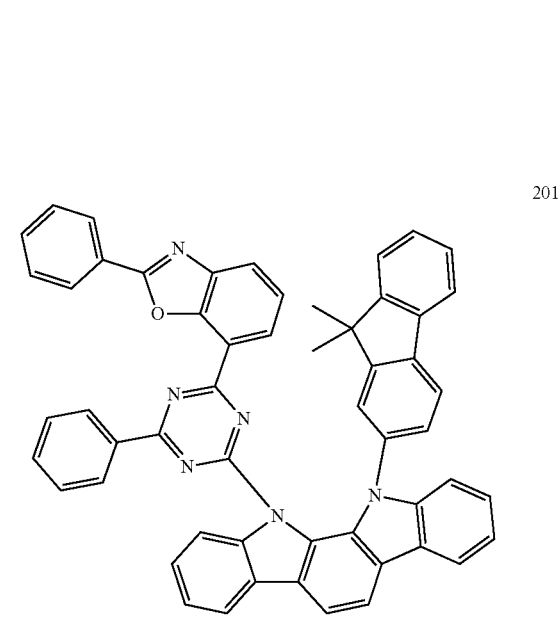
201
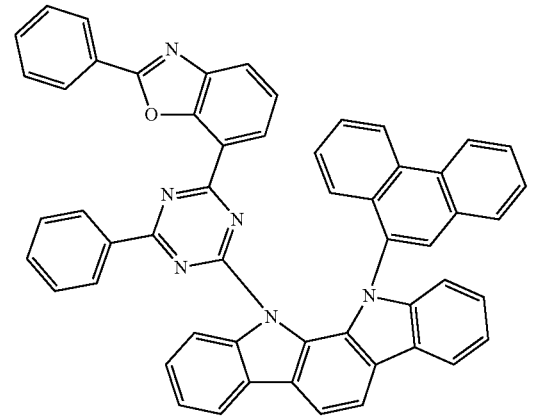
202

-continued
203
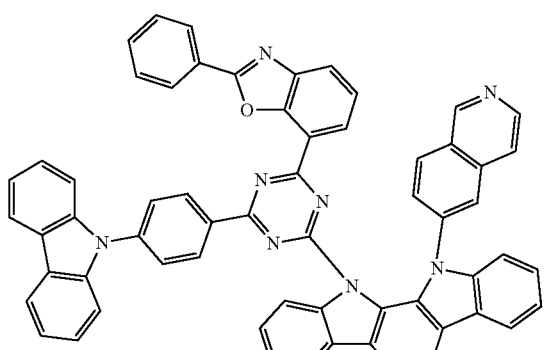
204
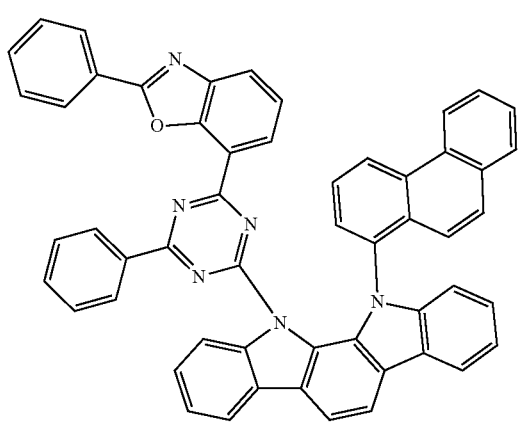
205
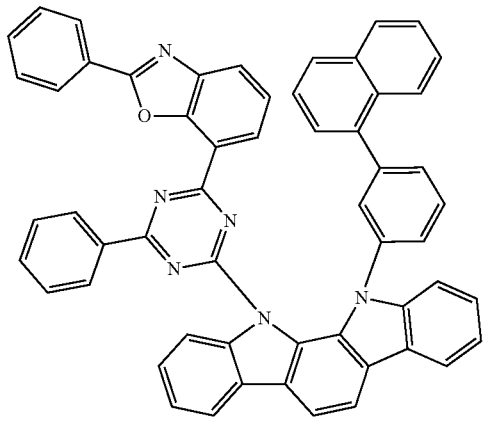
-continued
206
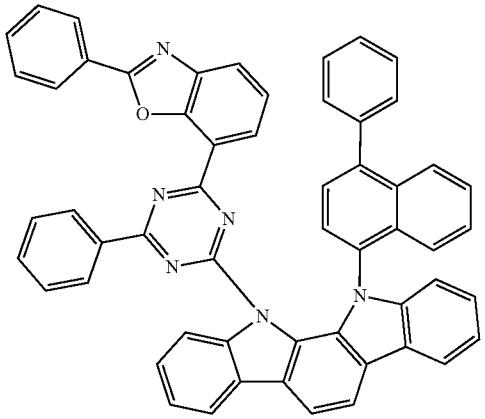
207
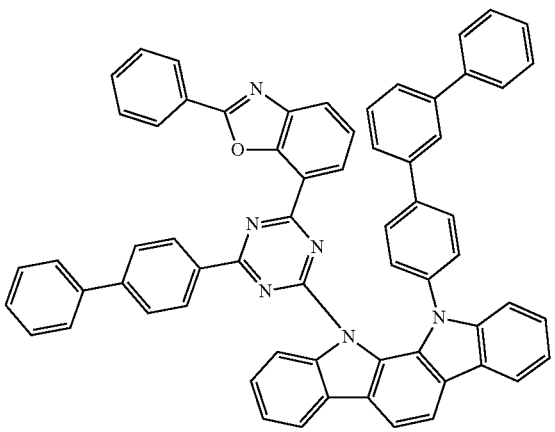
211
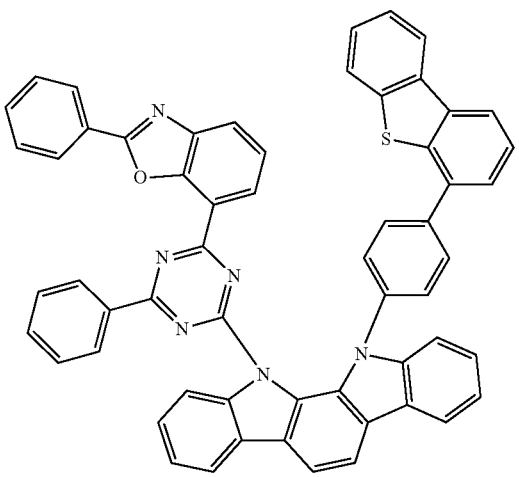

212
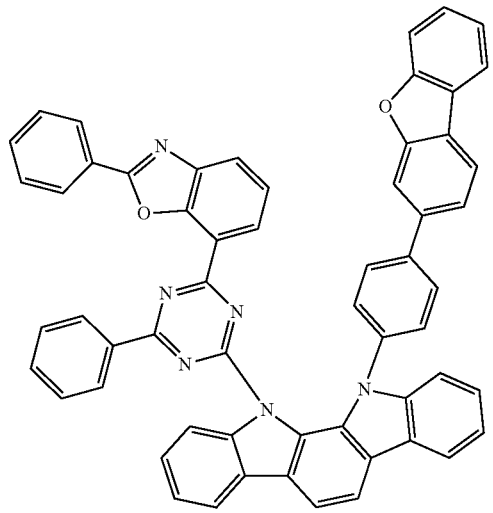
215
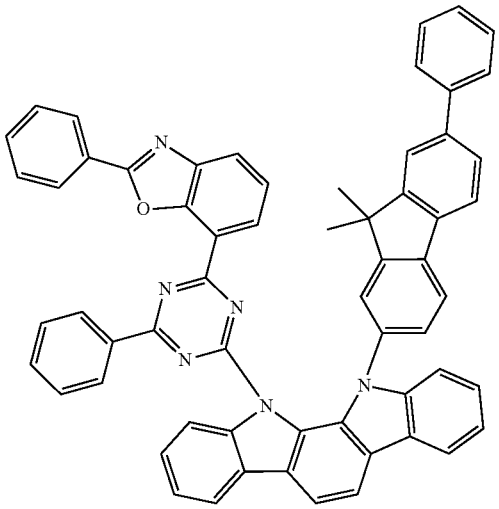
213
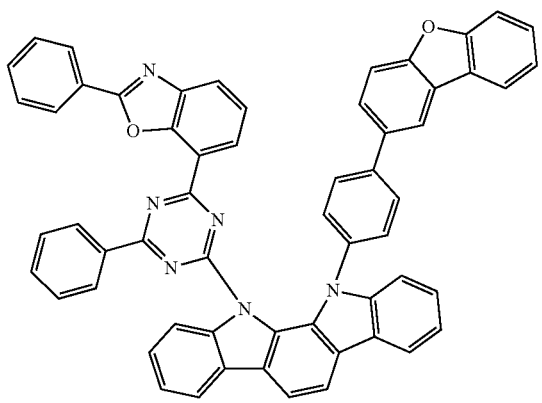
216
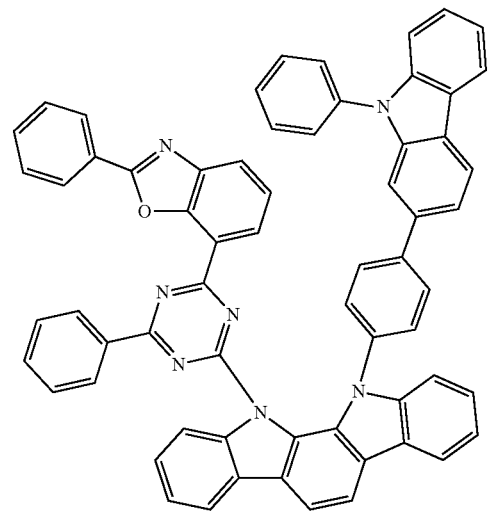
214
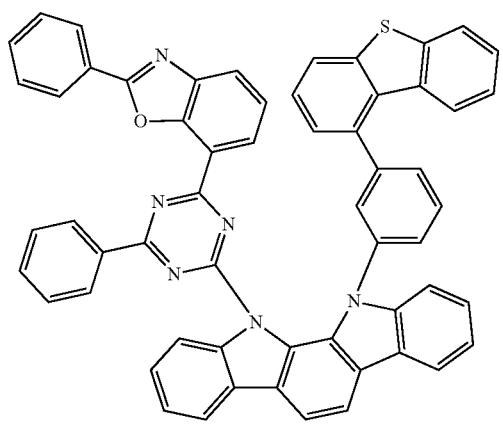
217
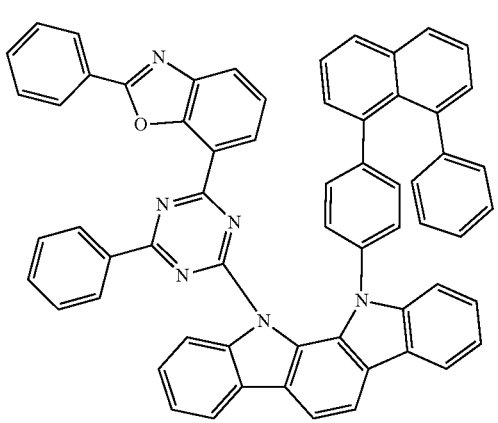

-continued
218
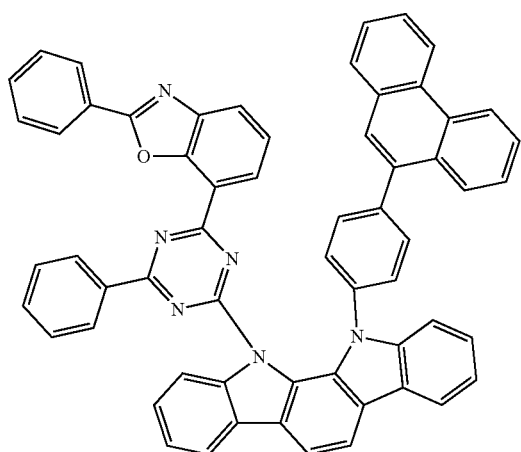
219
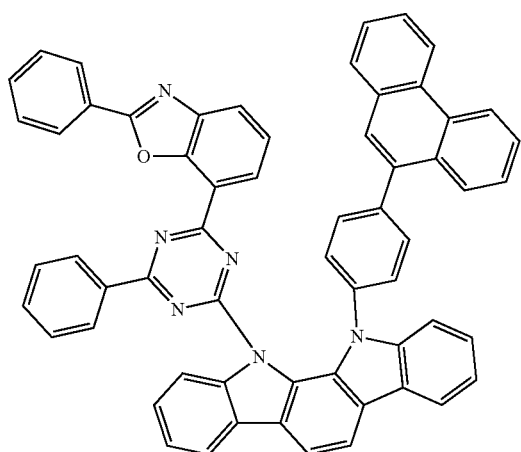
220
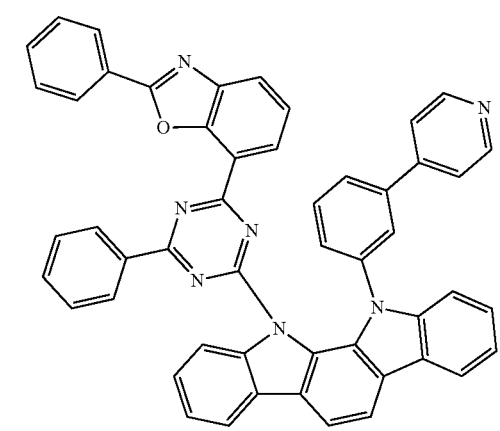
-continued
221
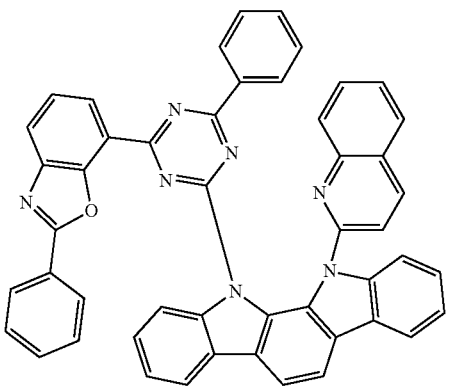
222
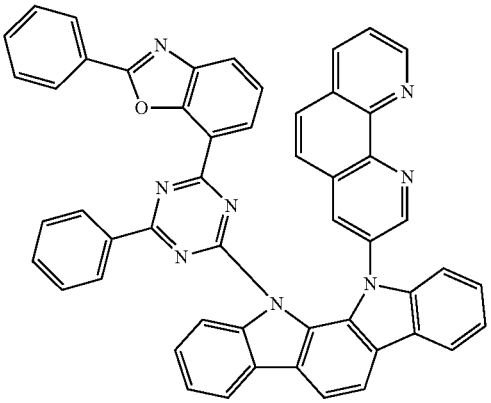
223
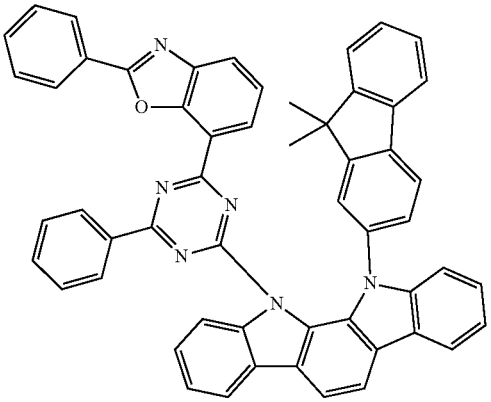
224
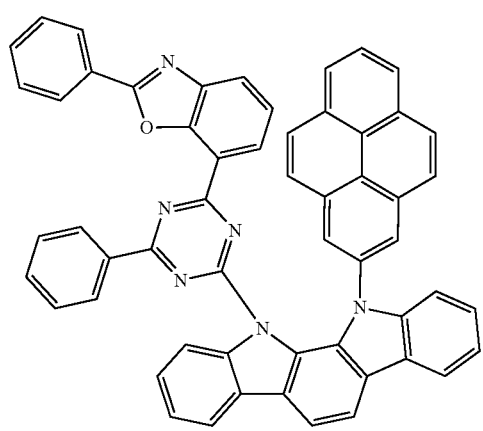

225
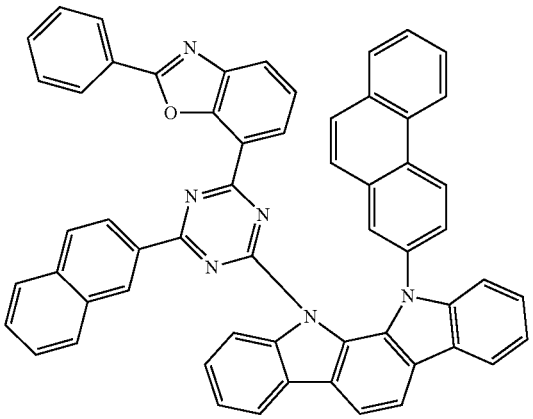
228
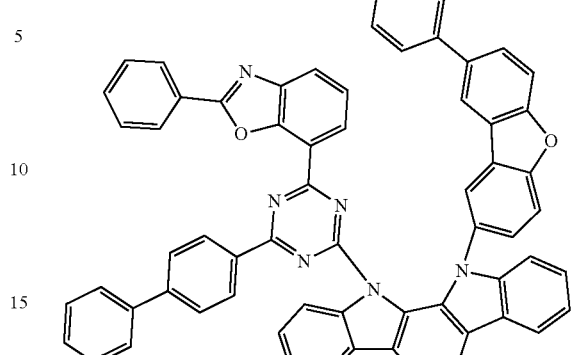
226
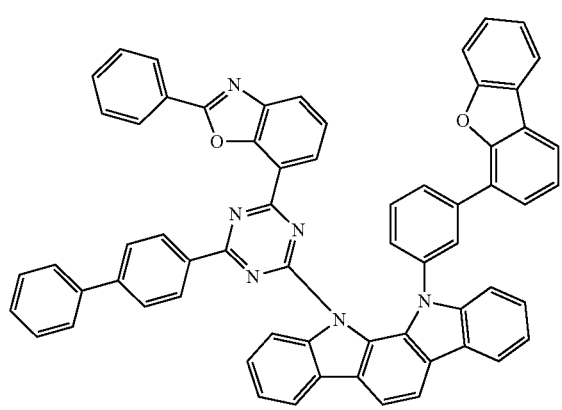
229
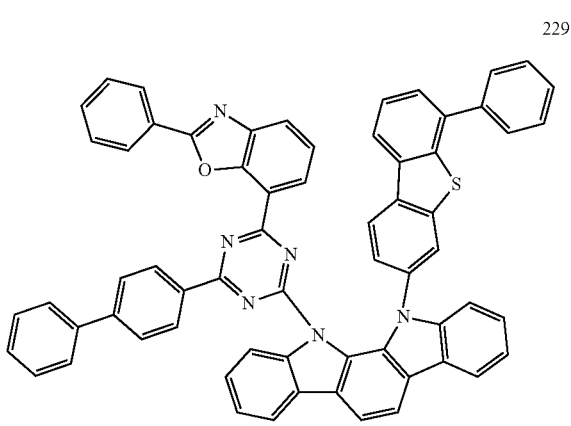
227
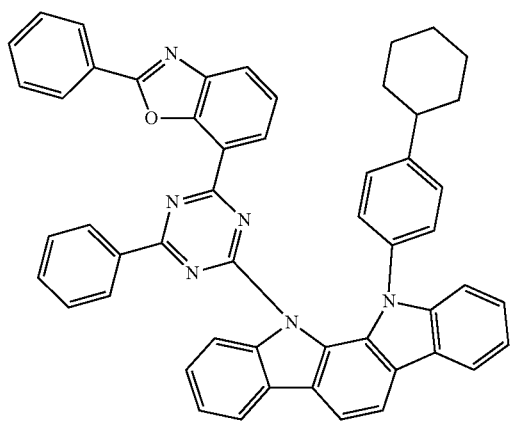
230
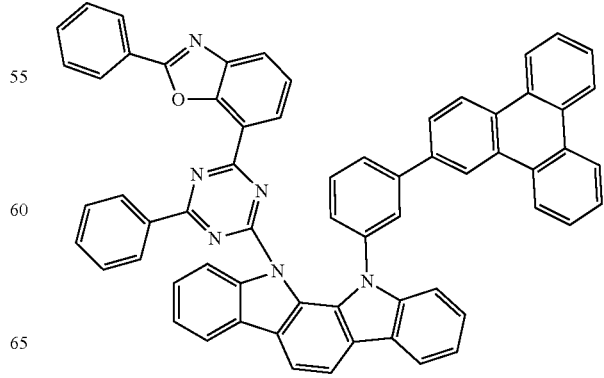

423
-continued
232
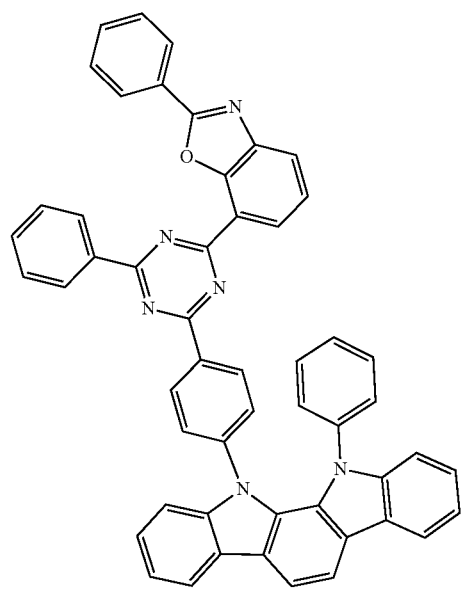
233
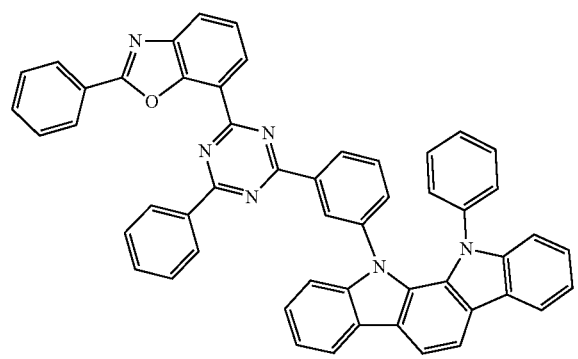
234
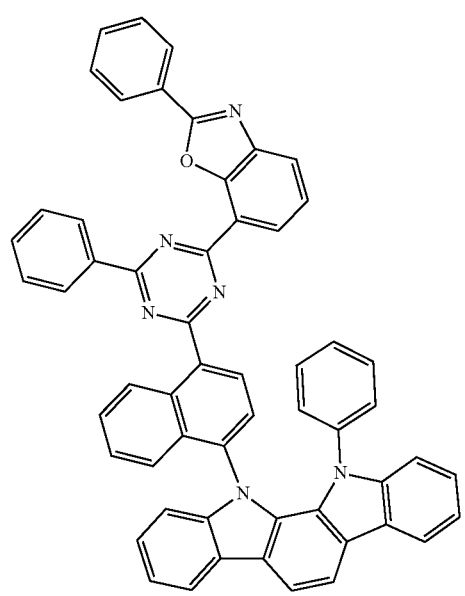
424
-continued
235
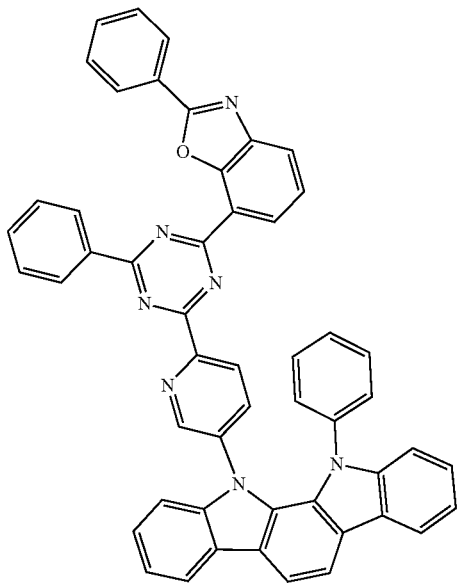
236
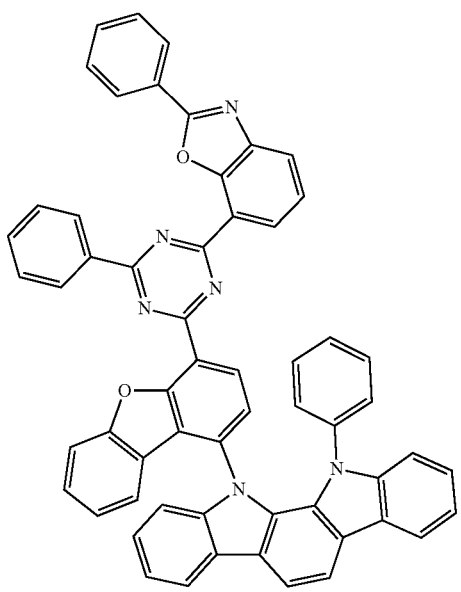
237
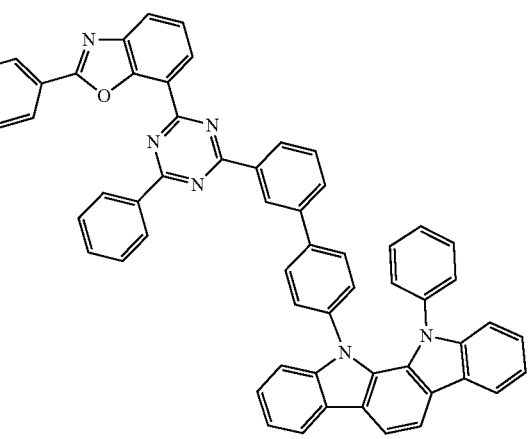

238
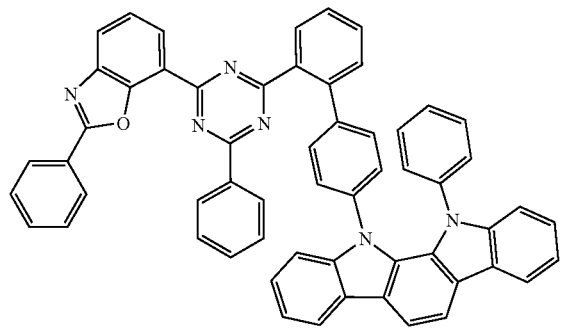
239
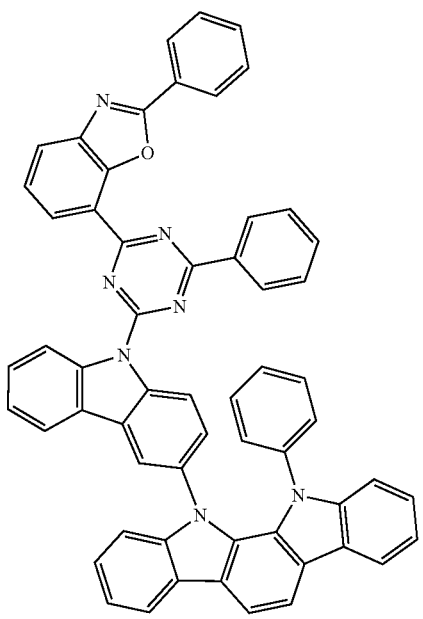
240
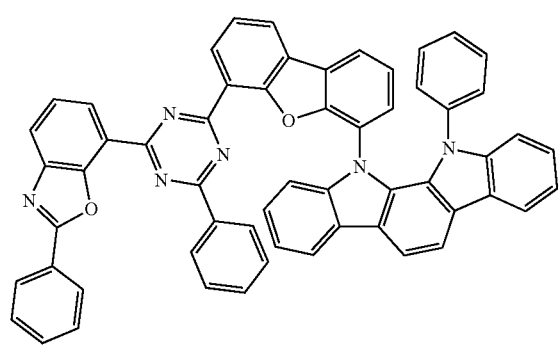
241
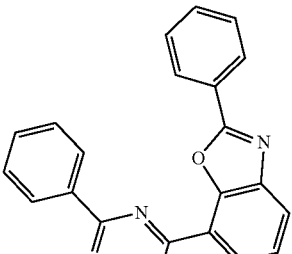
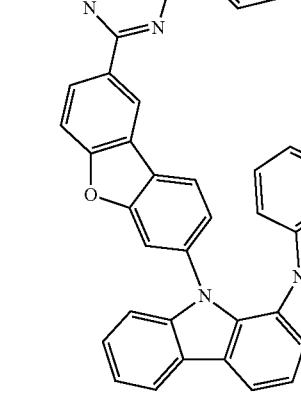
242
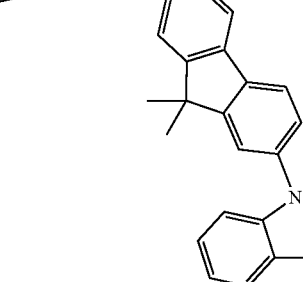
243
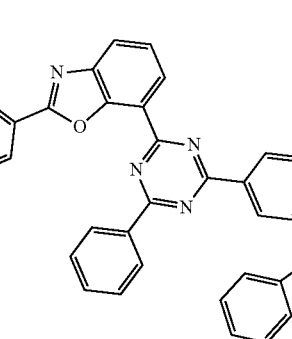

244
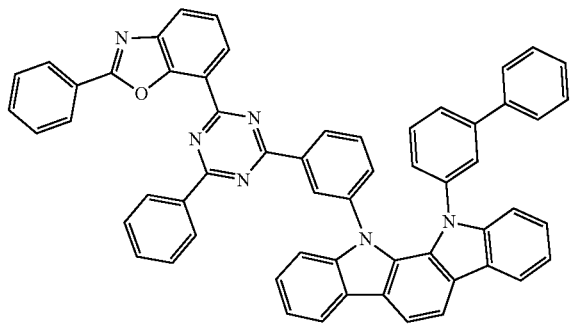
245
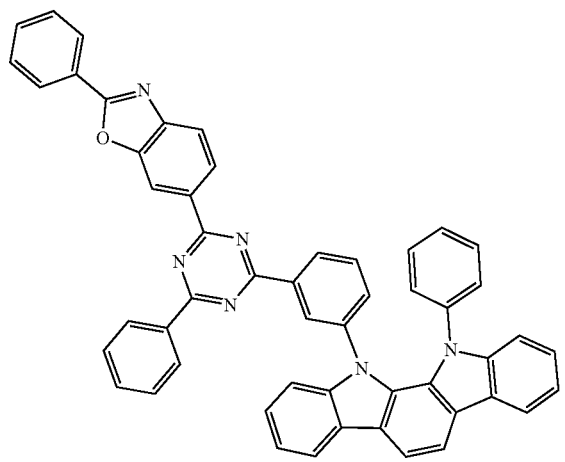
246
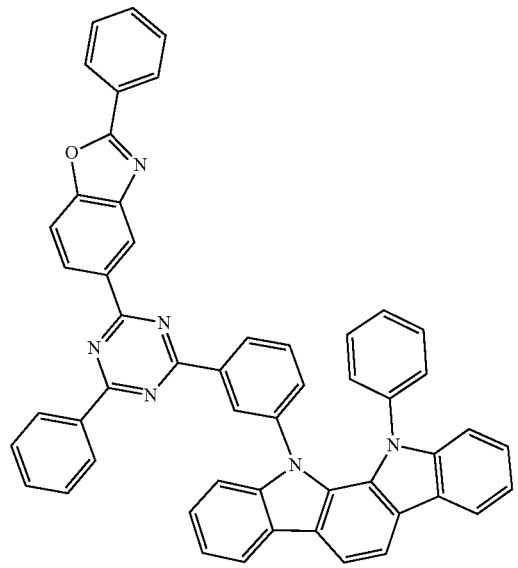
247
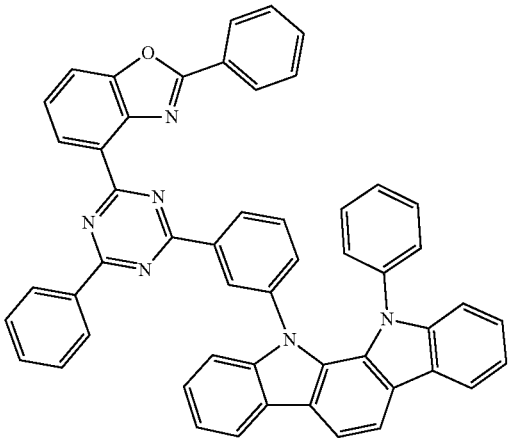
248
249
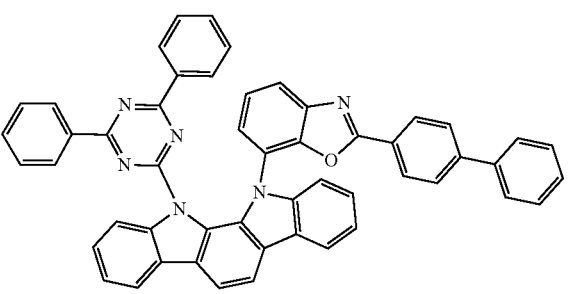
250
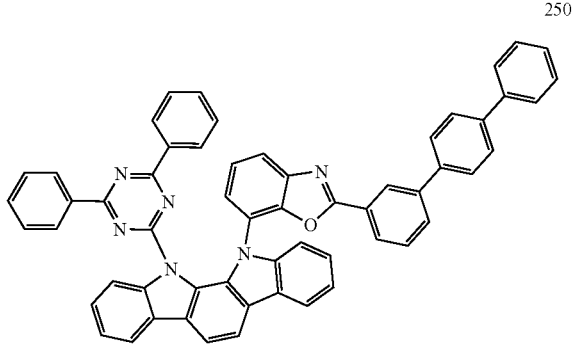

251
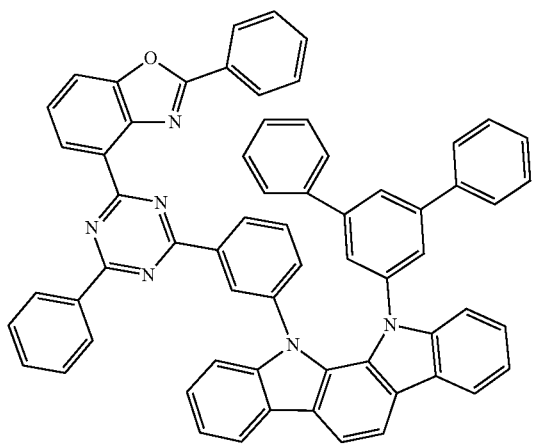
254
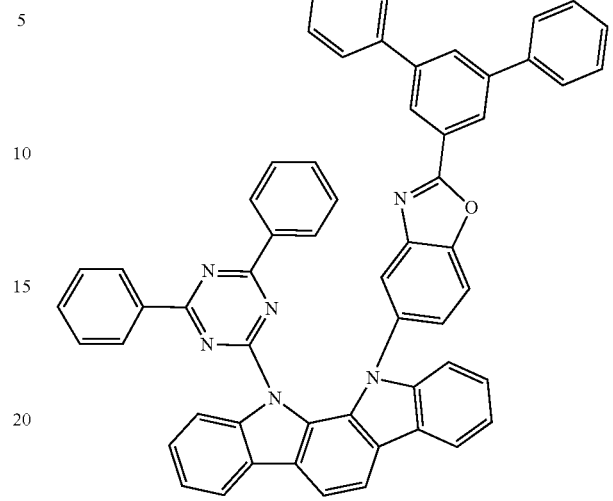
252
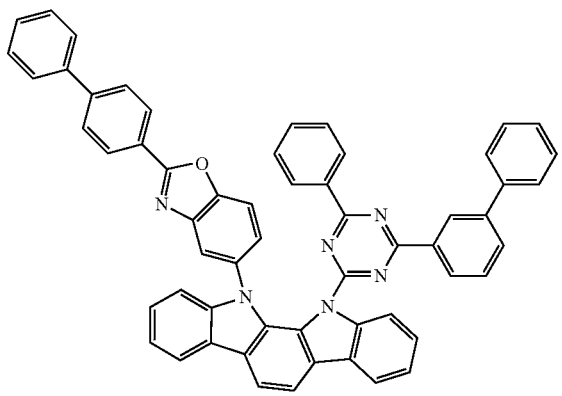
255
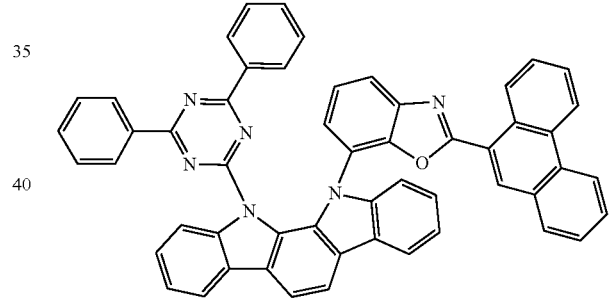
253
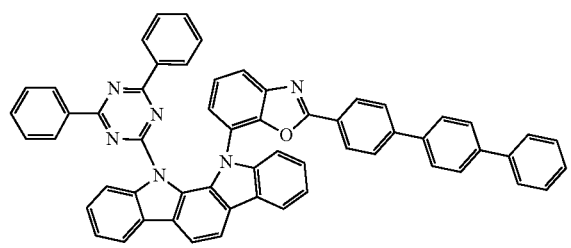
256
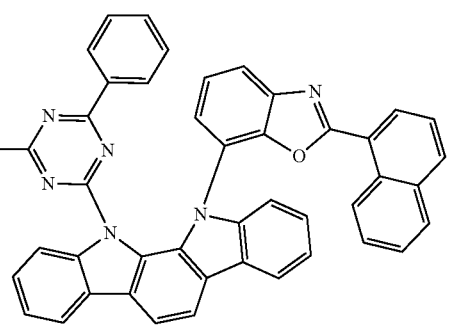

257
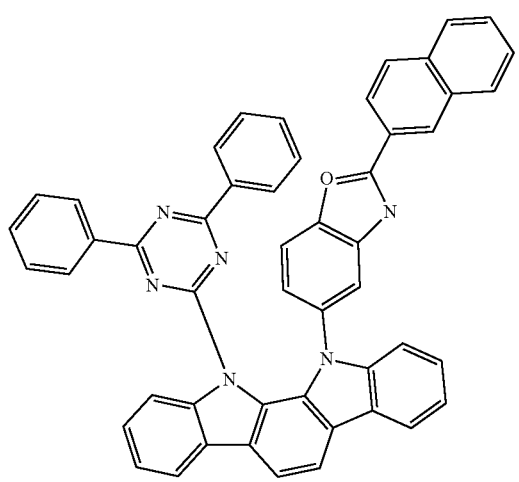
258
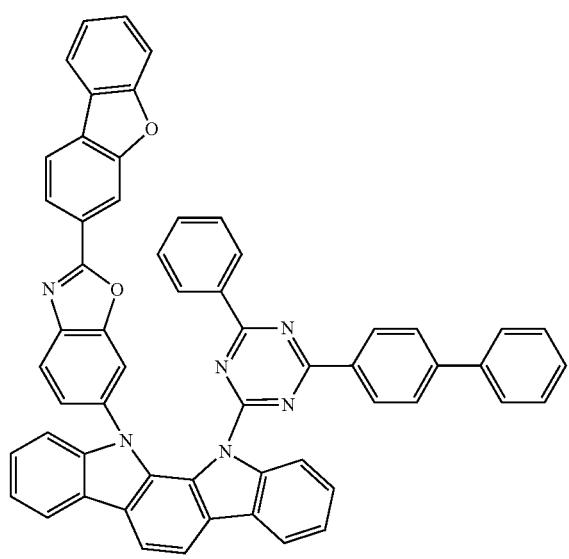
259
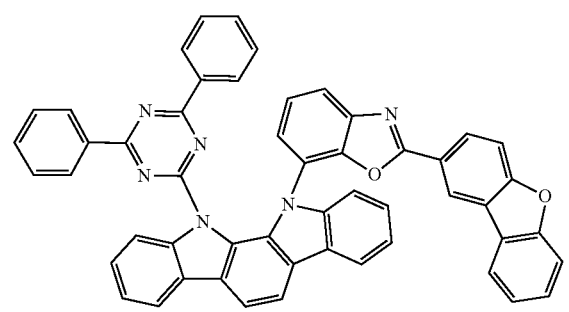
260
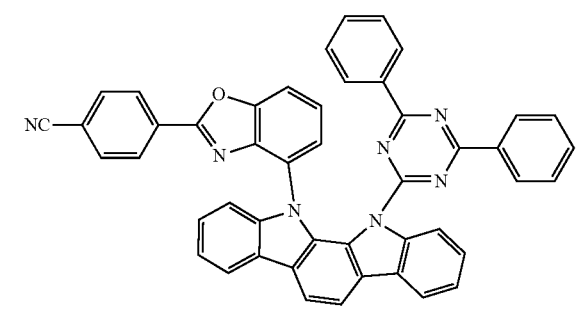
261
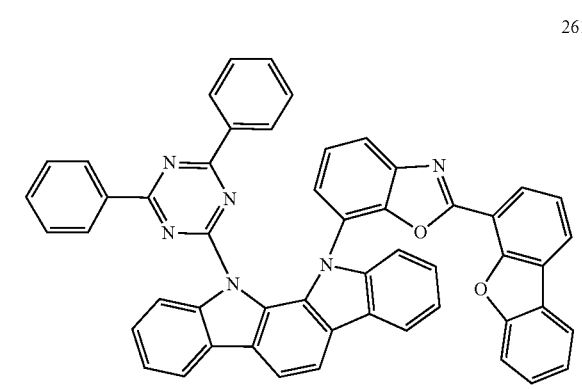
262
263
264
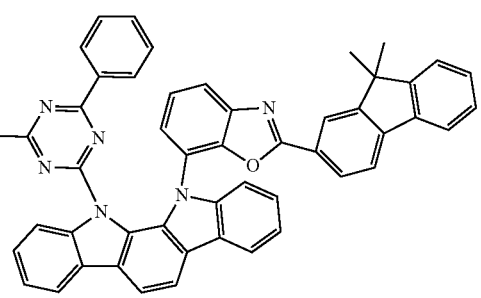

265
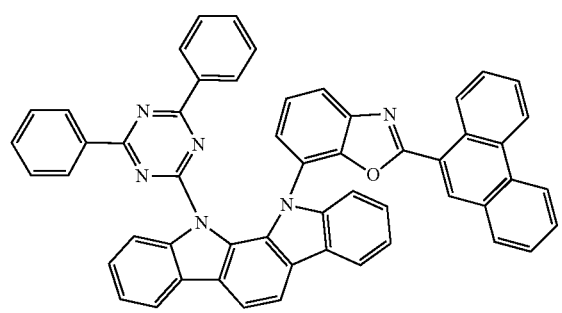
266
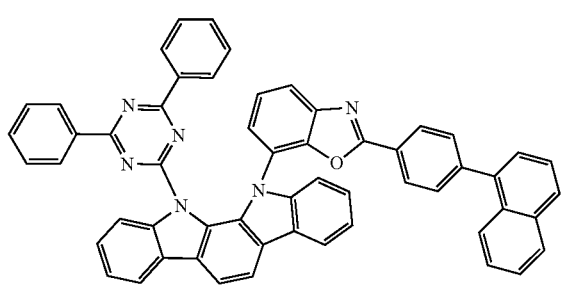
267
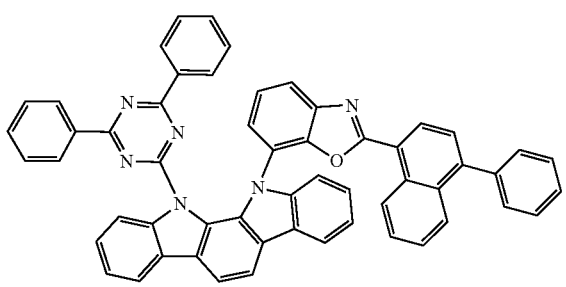
268
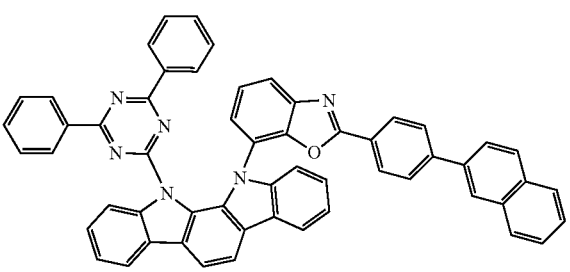
269
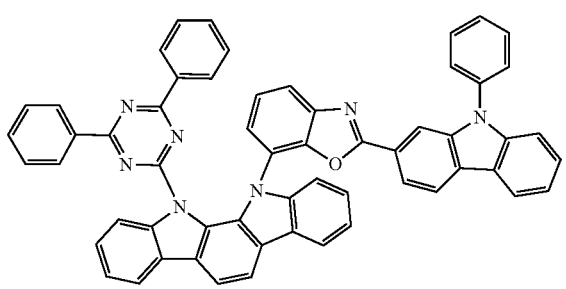
270
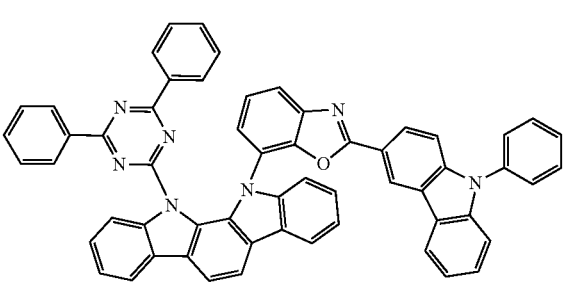
271
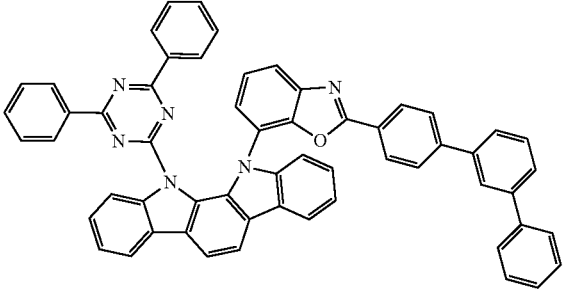
272
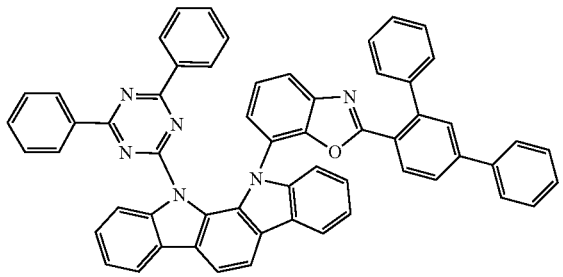
273
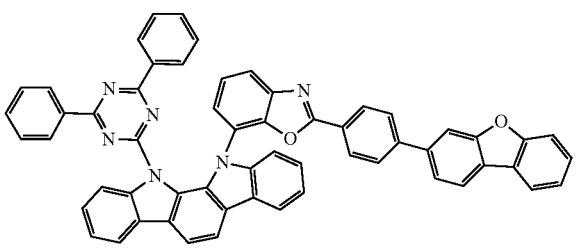
274
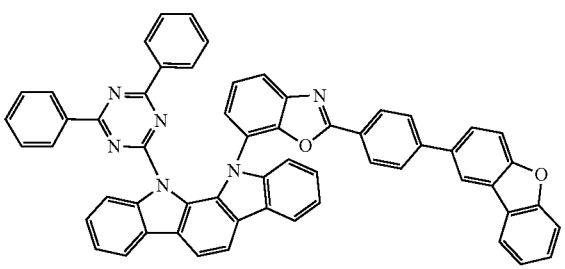

275
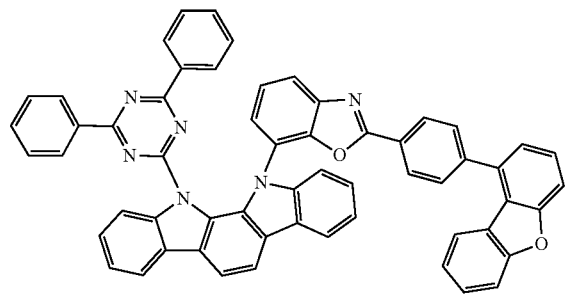
276
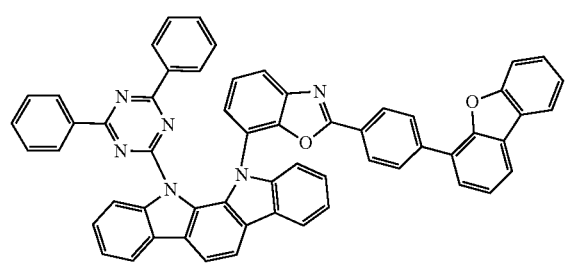
277
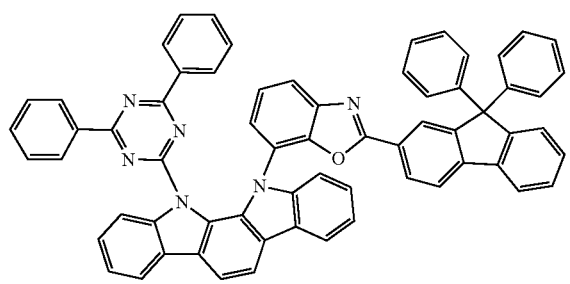
278
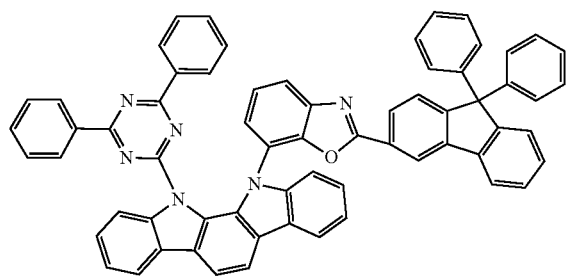
279
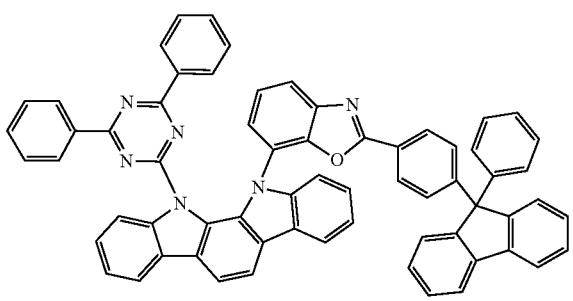
280
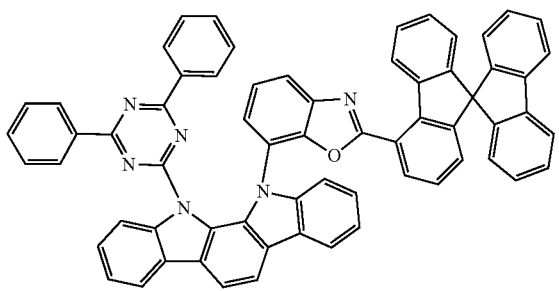
281
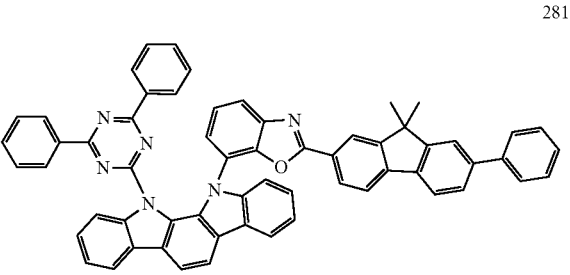
282
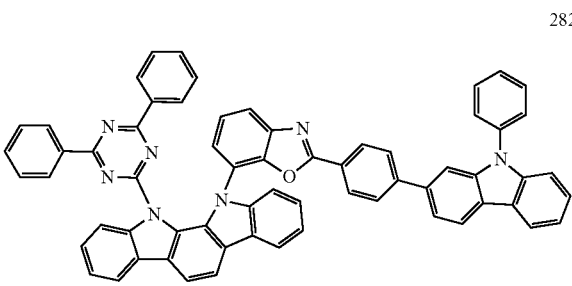
283
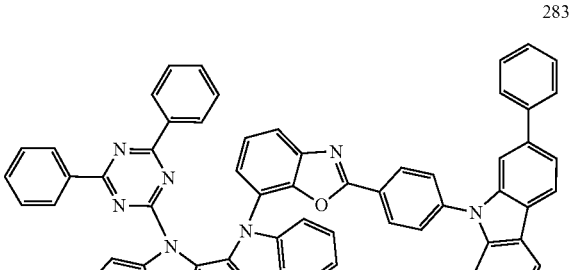
284
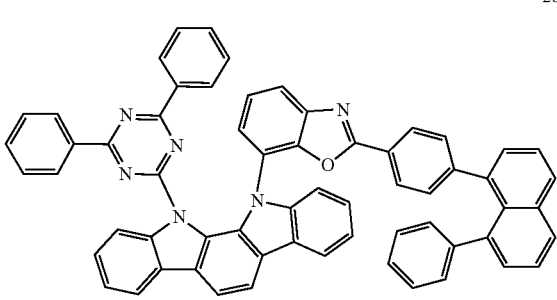

285
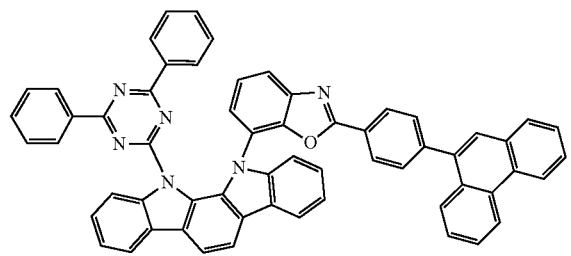
286
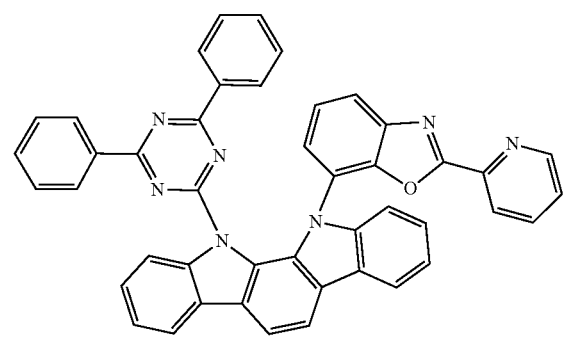
287
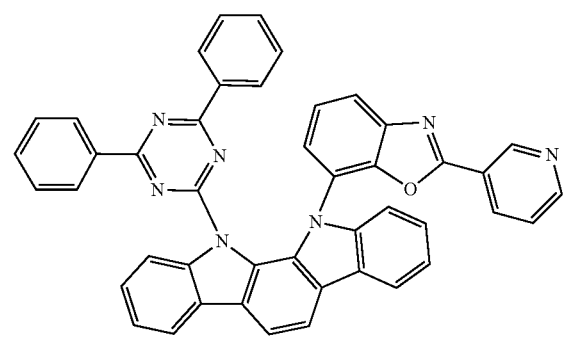
288
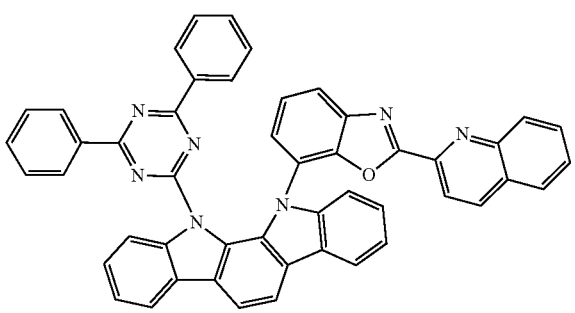
289
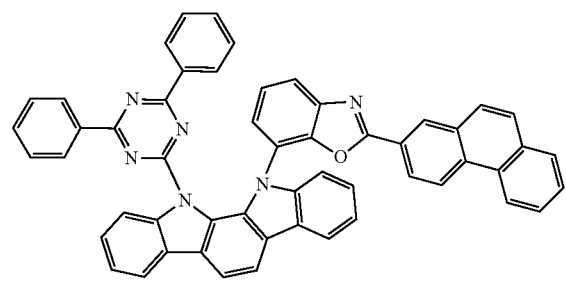
290
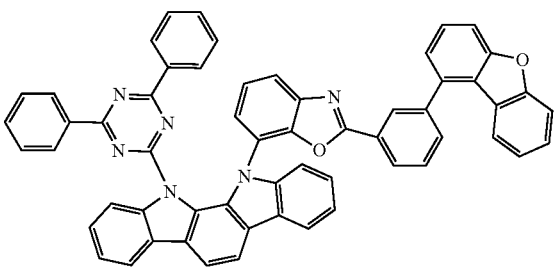
291
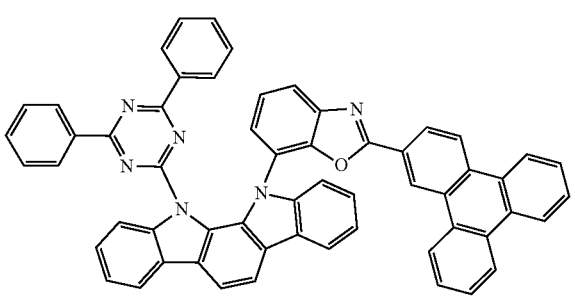
292
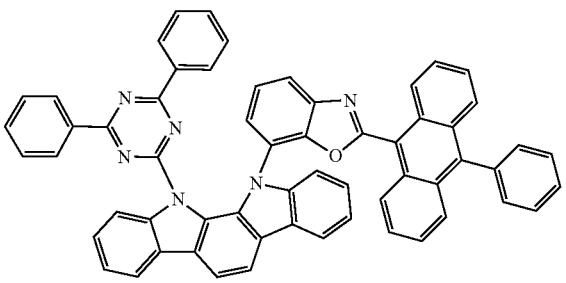
293
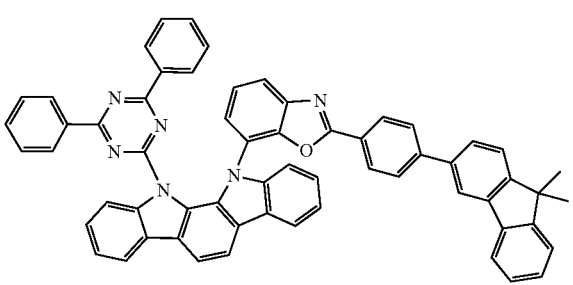
294
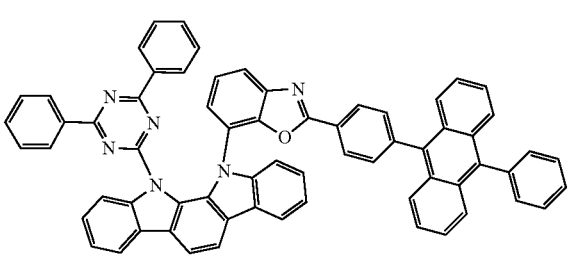

295
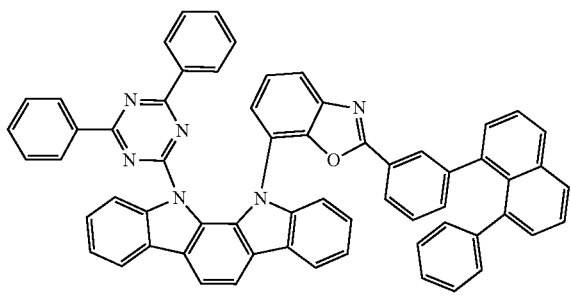
296
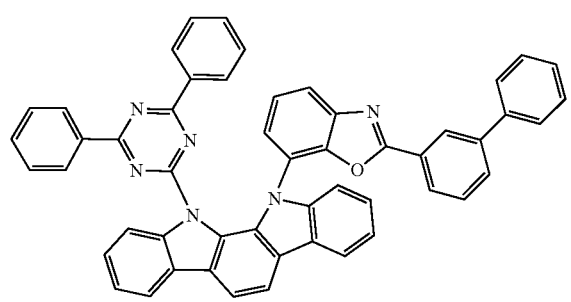
297
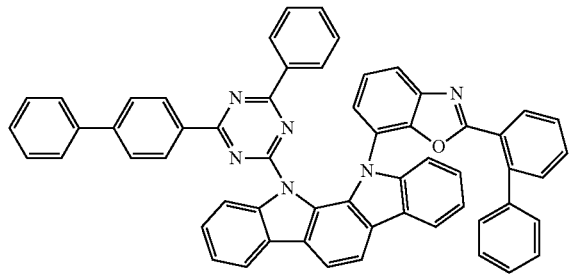
298
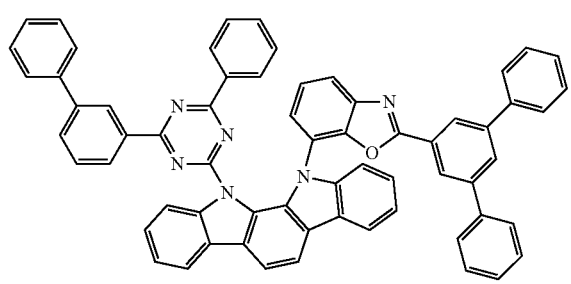
299
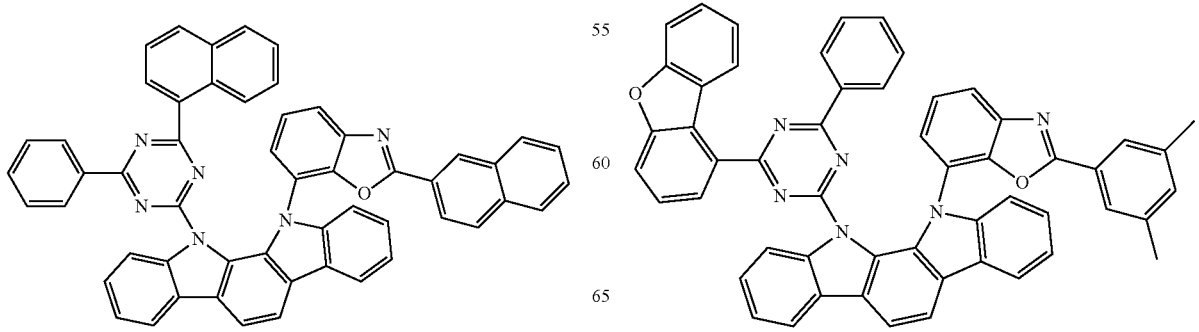
300
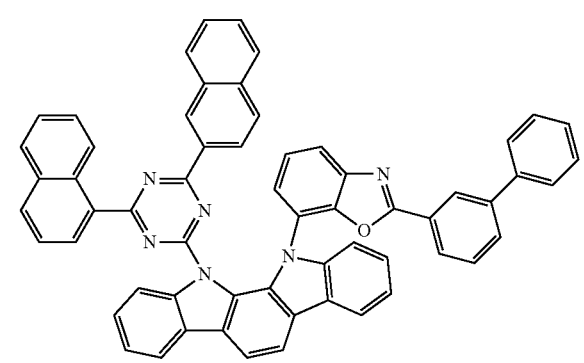
301
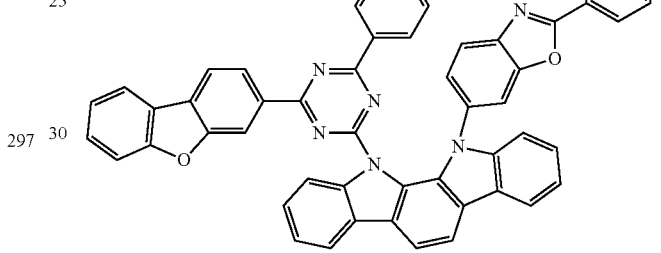
302
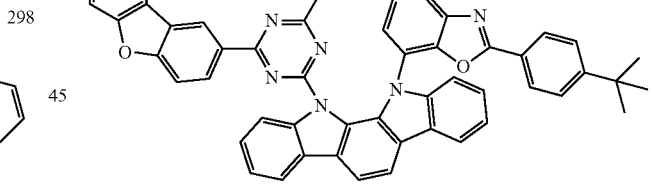
303

304
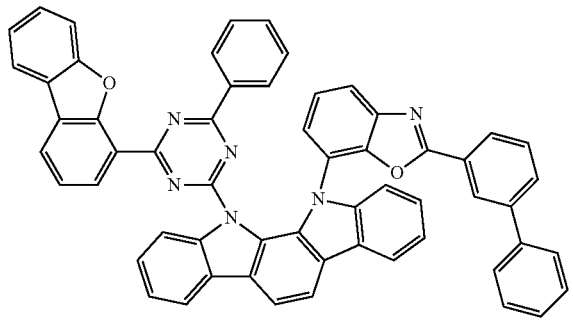
305
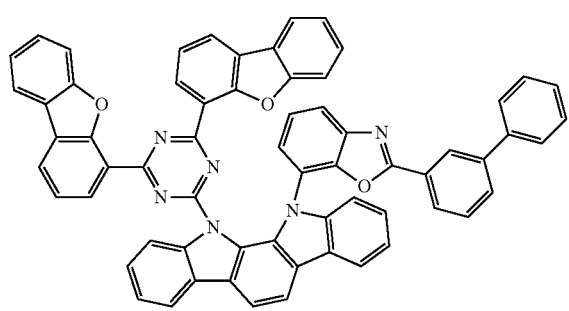
306
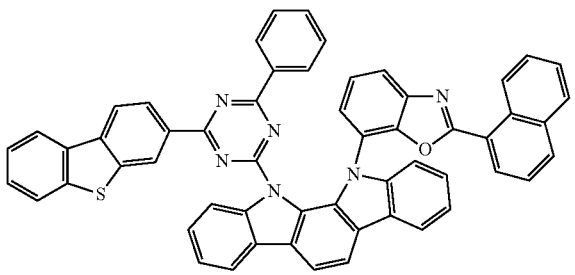
307
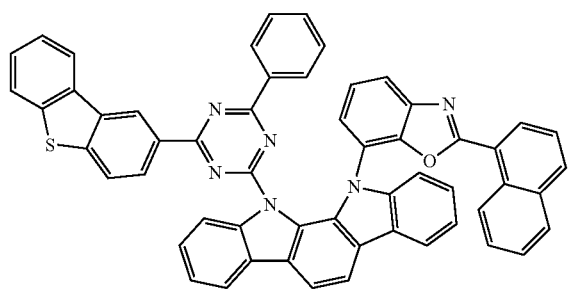
308
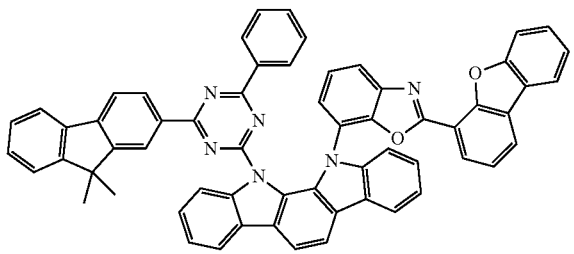
309
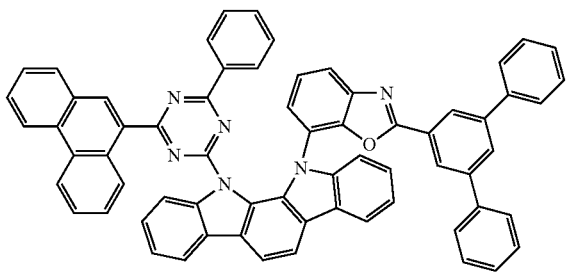
310
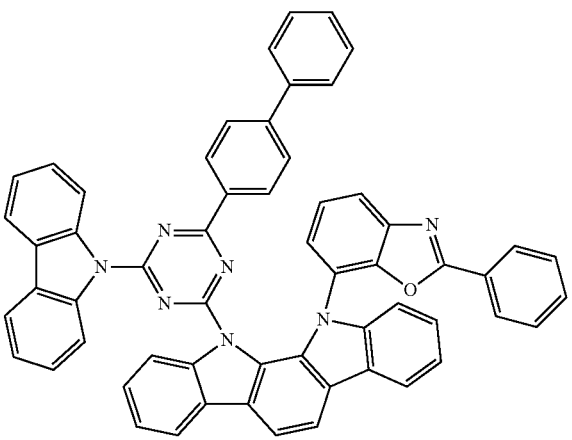
311
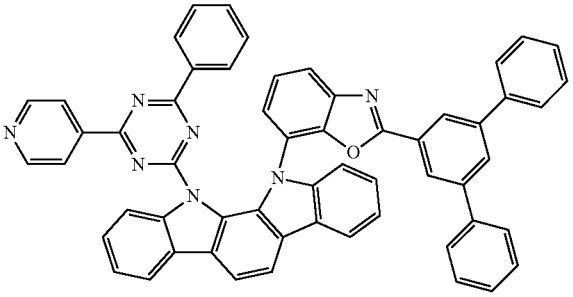
312
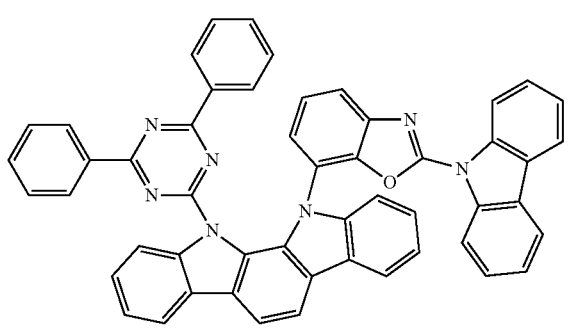

-continued
313
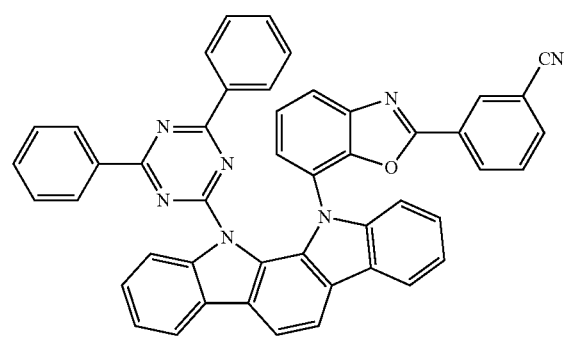
314
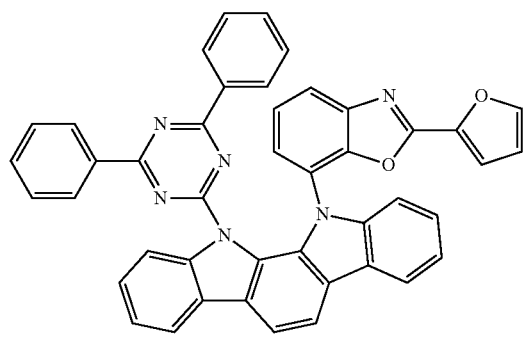
315
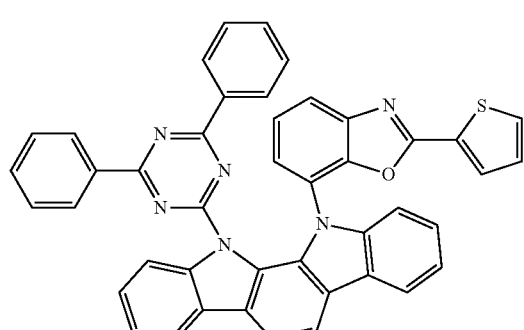
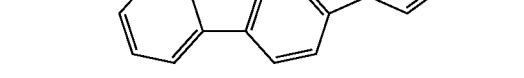
316
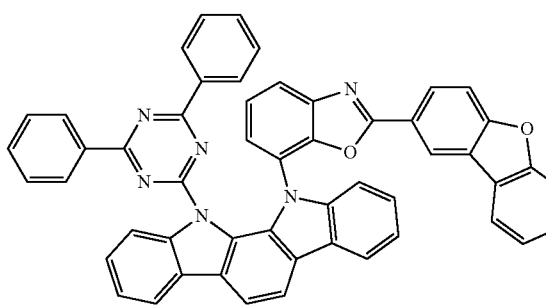
-continued
317
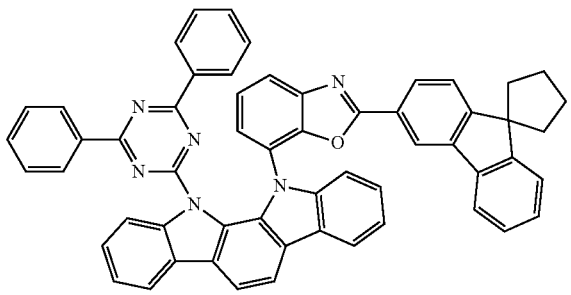
318
319
320
321
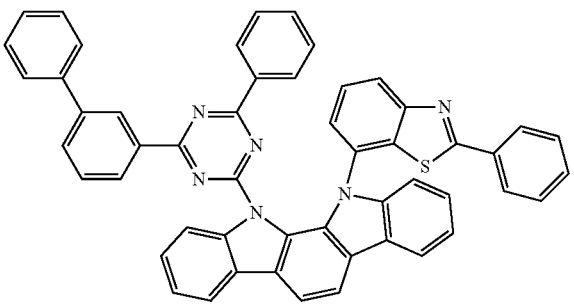

322
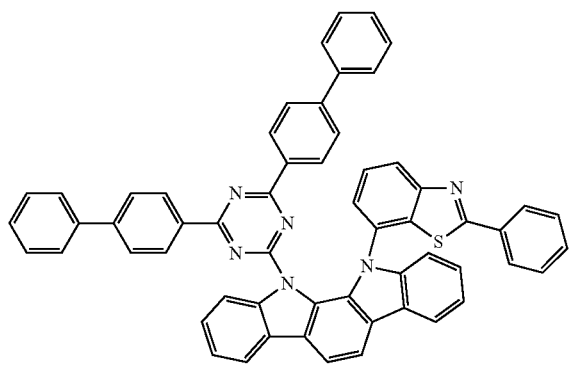
323
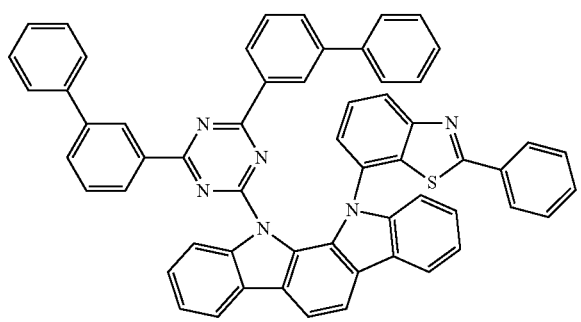
324
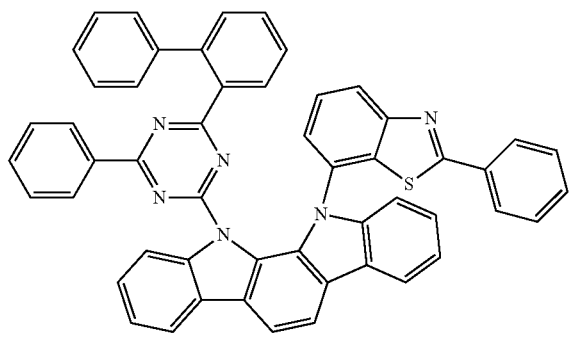
325
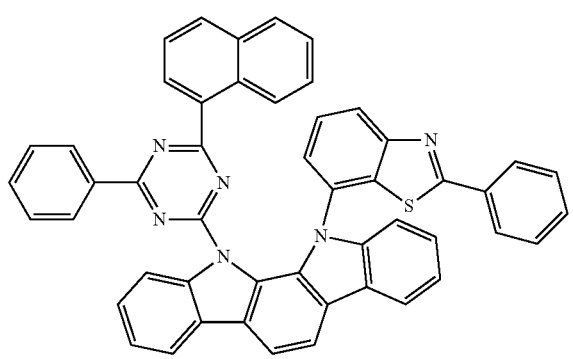
326
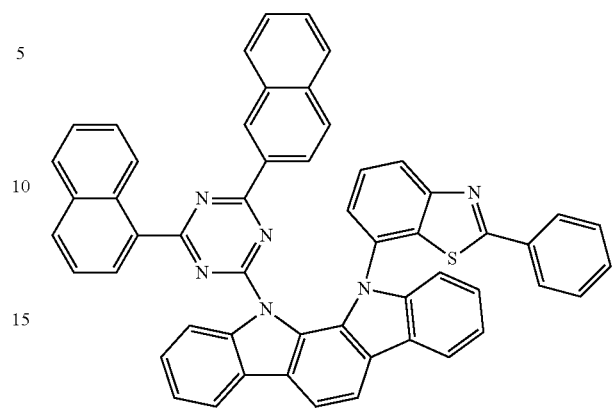
327
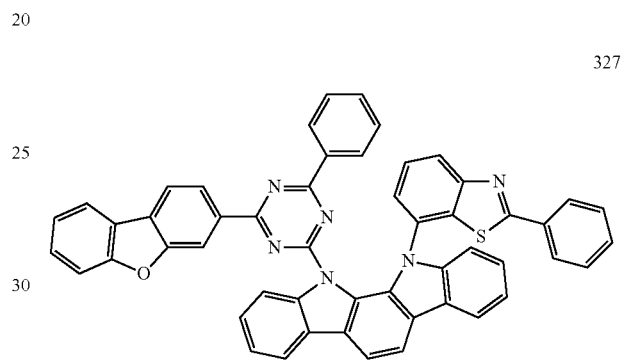
328
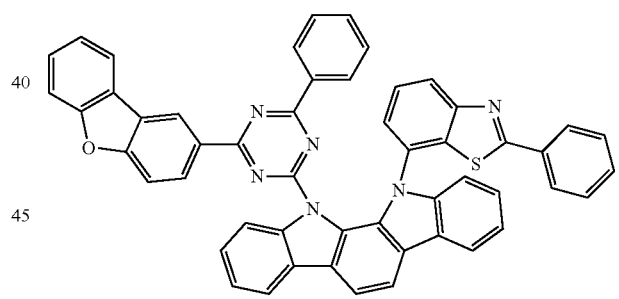
329
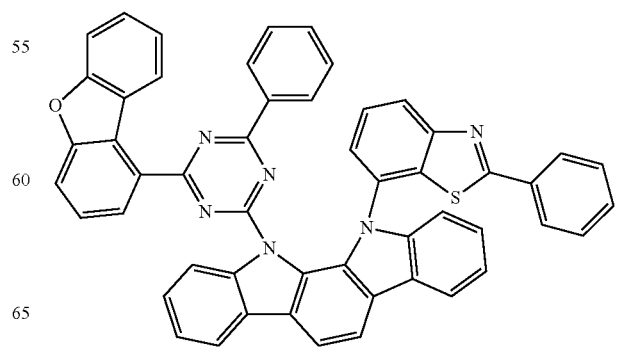

447
-continued
330
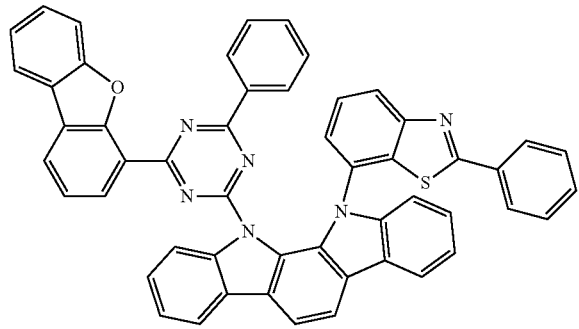
331
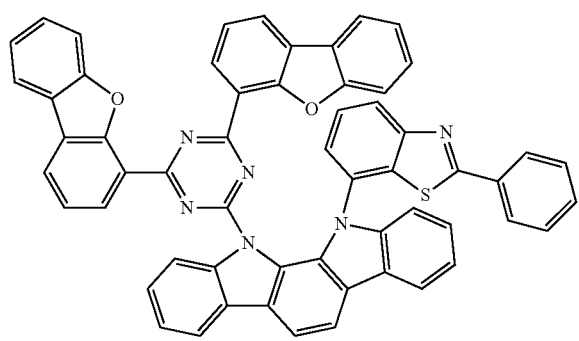
332
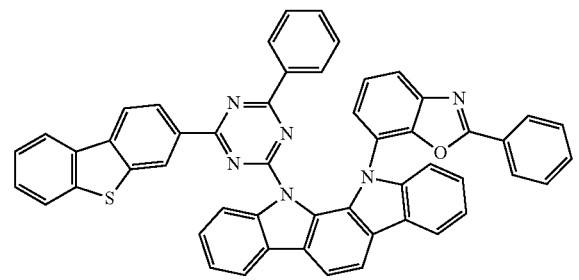
333
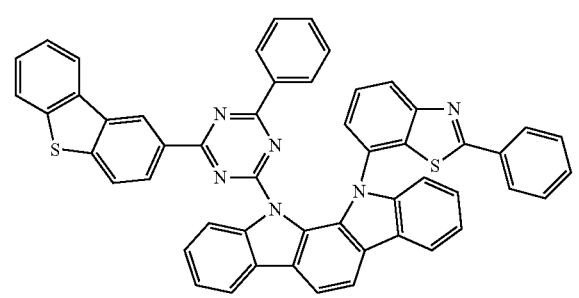
334
448
-continued
335
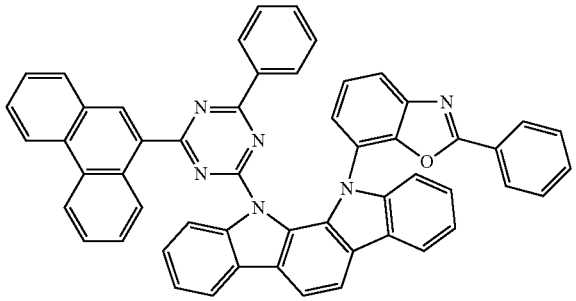
336
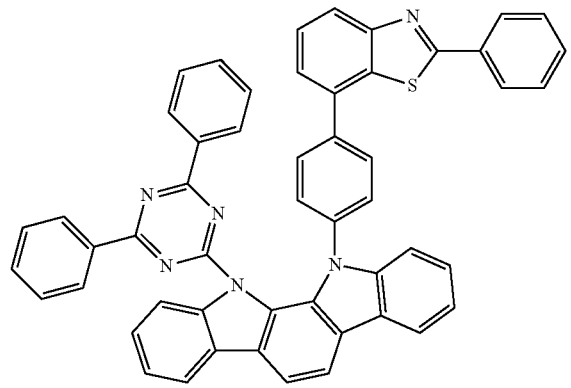
337
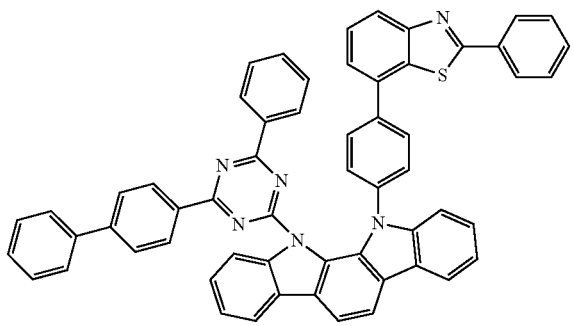
338
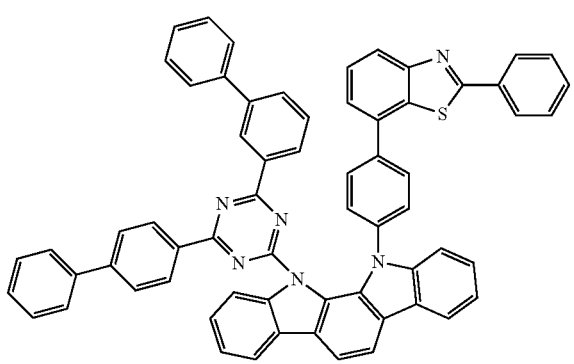

449
-continued
339
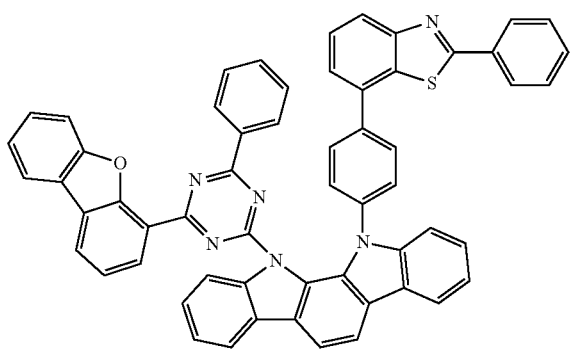
340
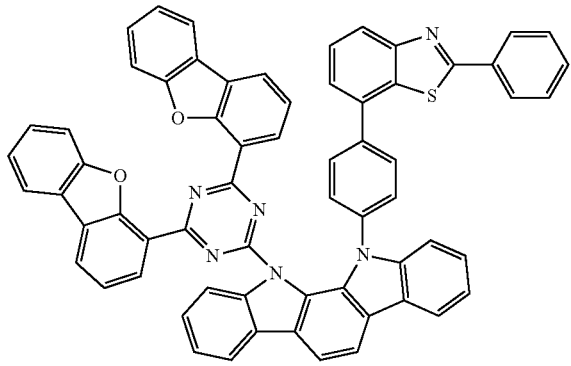
341
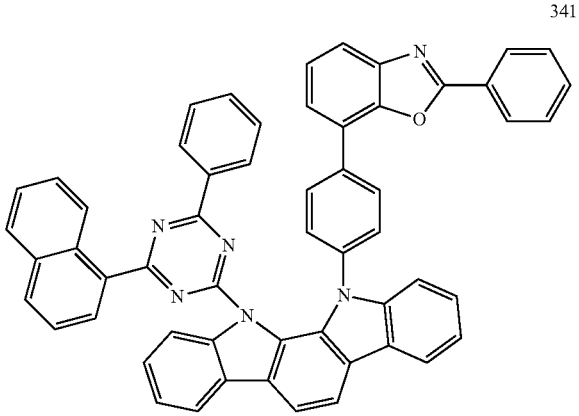
342
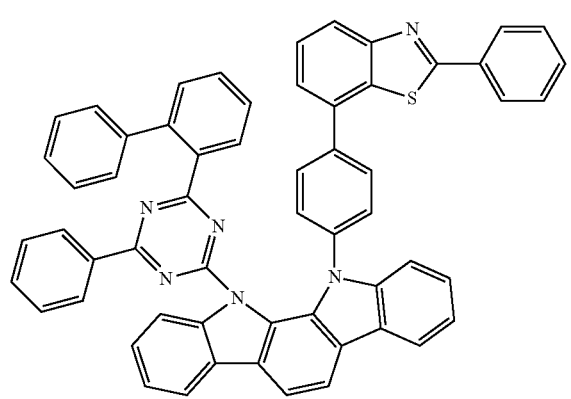
450
-continued
343
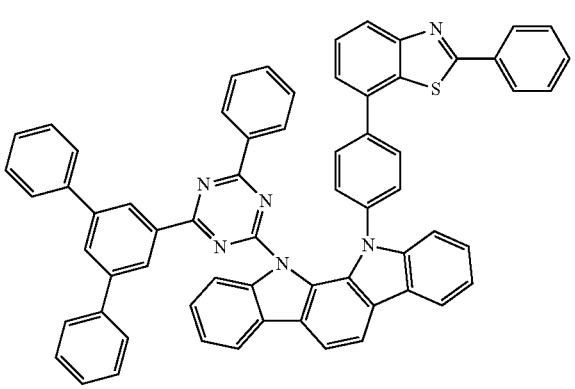
346
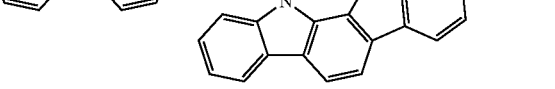
347
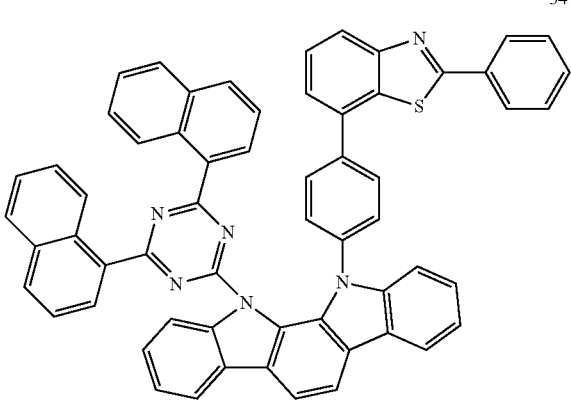
349
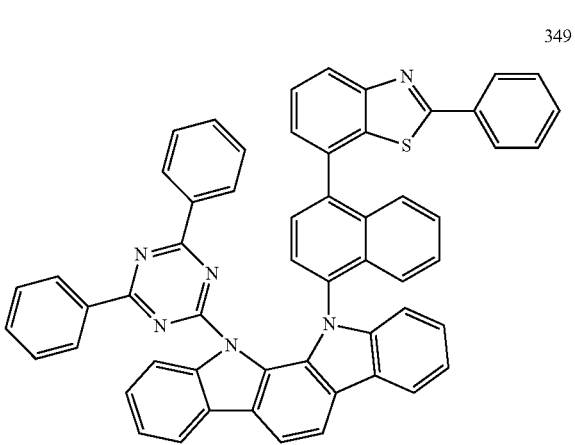

-continued
350
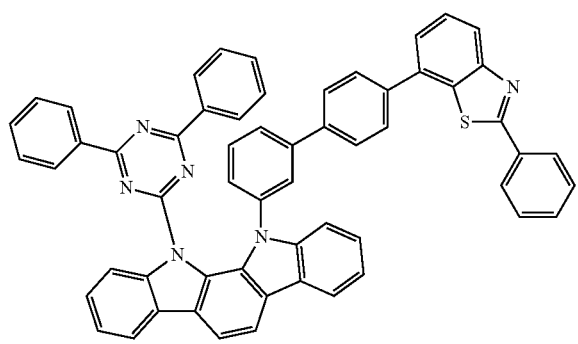
351
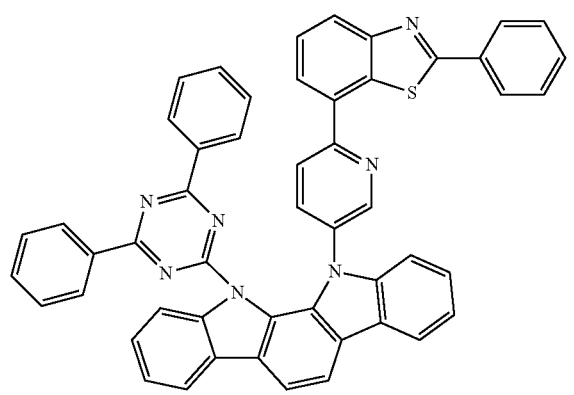
352
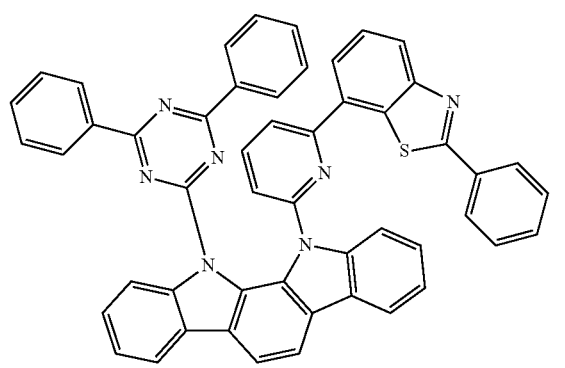
-continued
353
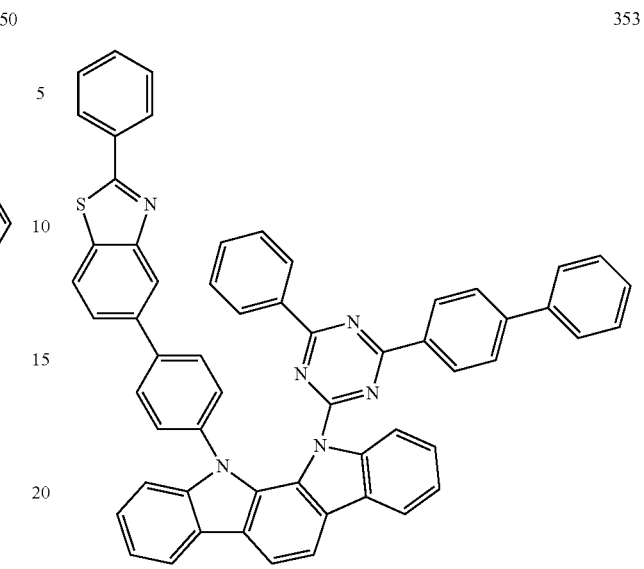
354
355
356
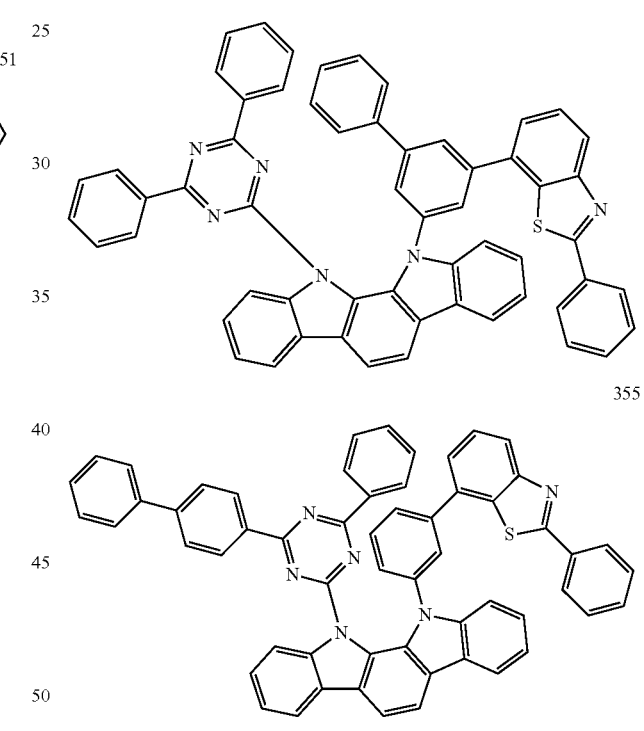
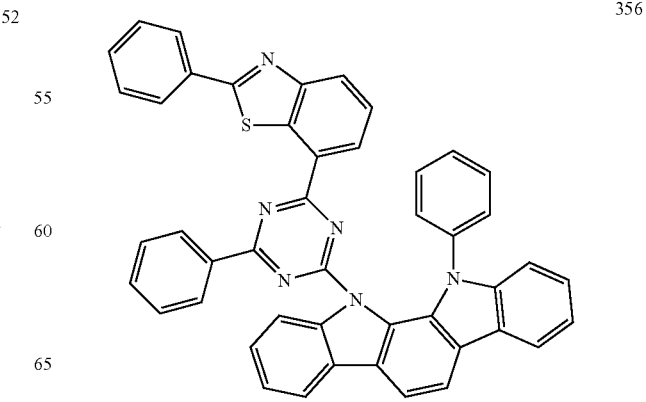

357
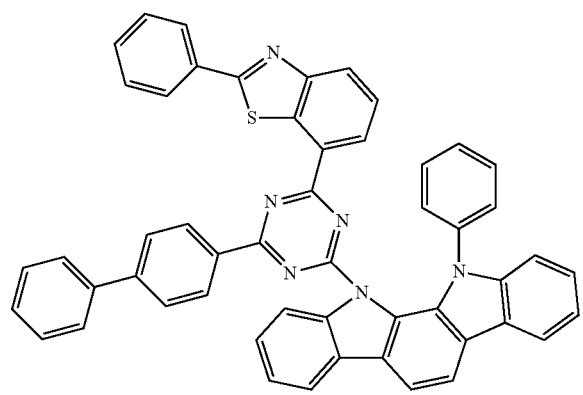
358
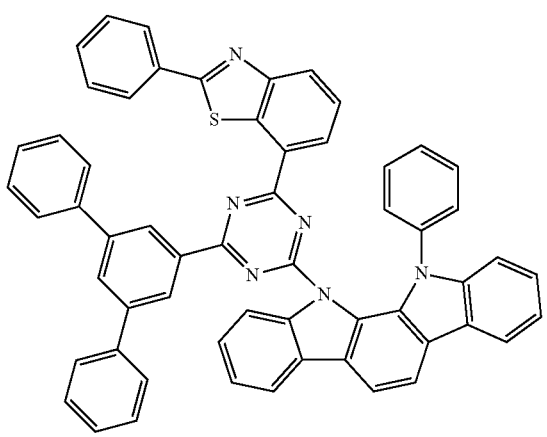
359
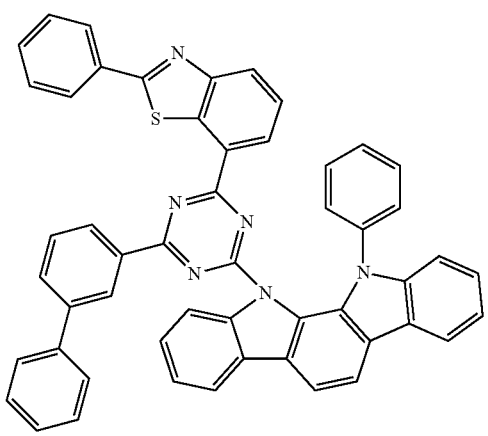
360
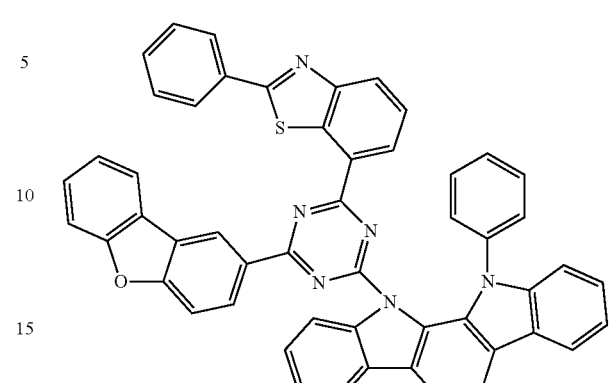
361
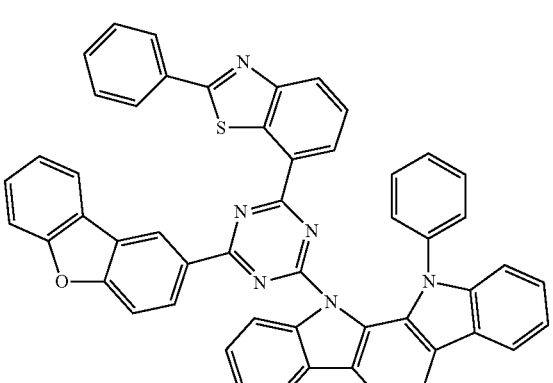
362
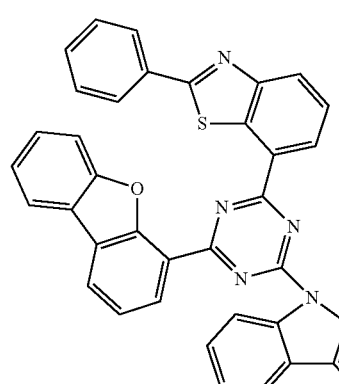
363
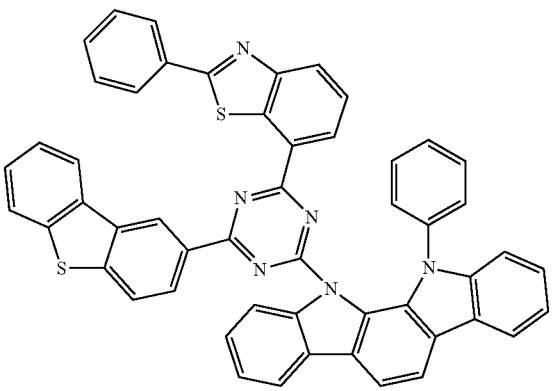

455
-continued
364
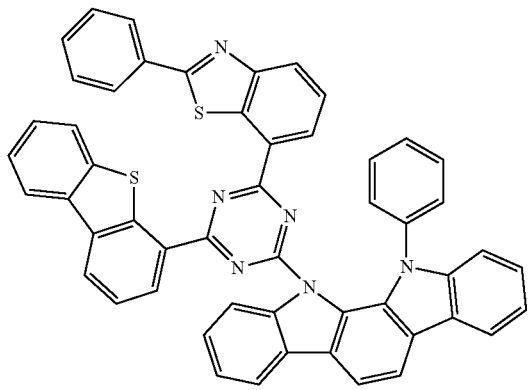
365
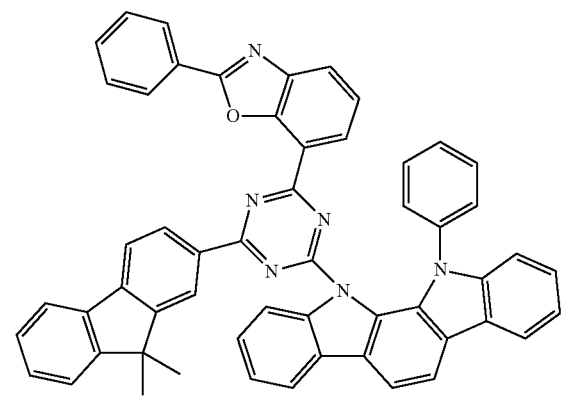
366
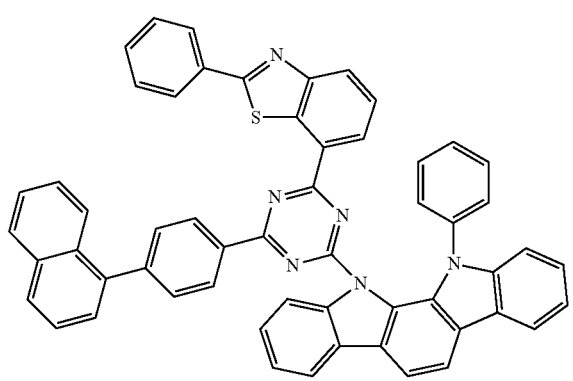
456
-continued
368
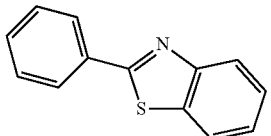
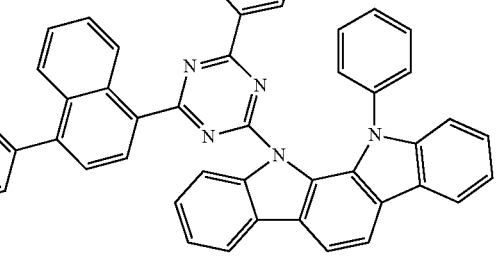
369
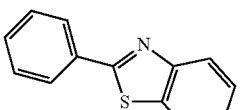
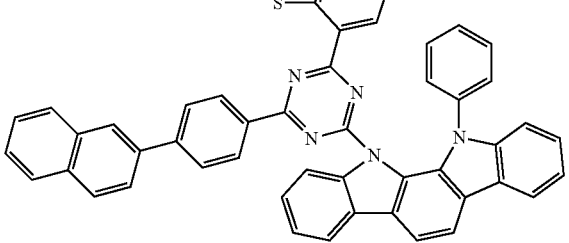
370
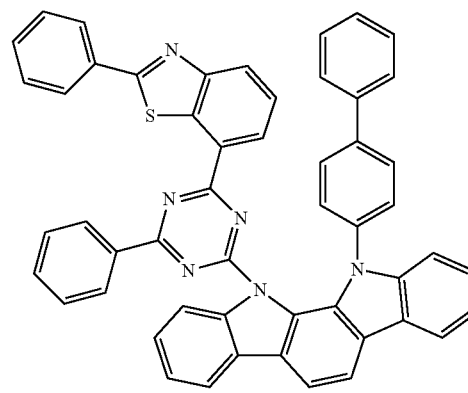
371
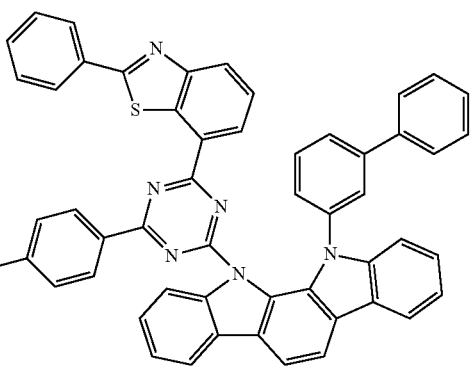

457
-continued
372
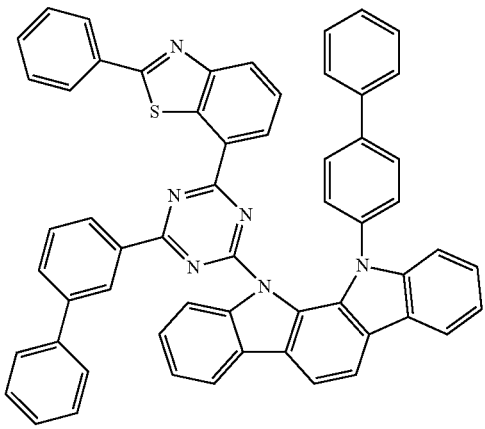
373
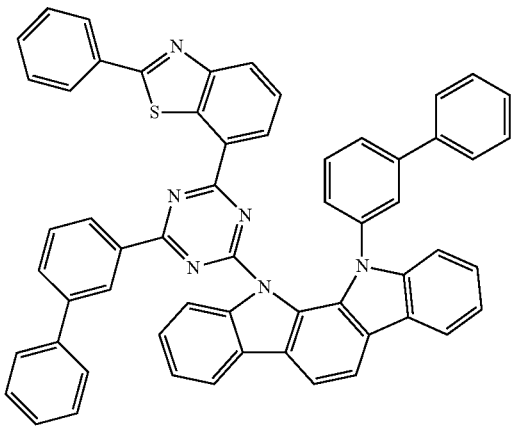
374
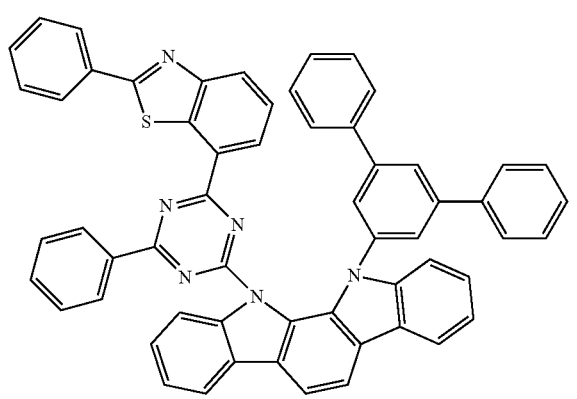
458
-continued
375
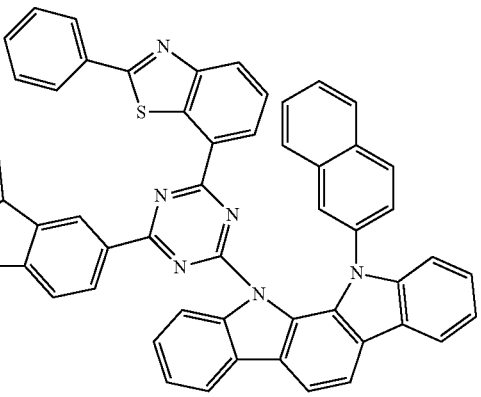
376
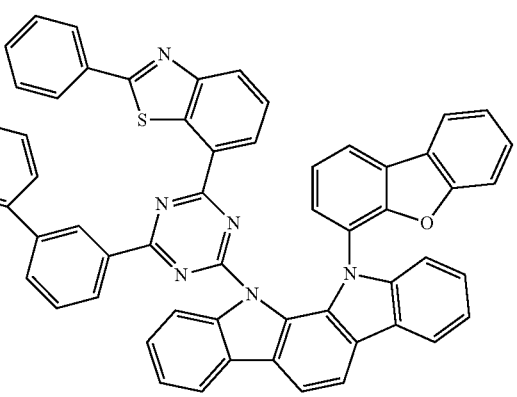
377
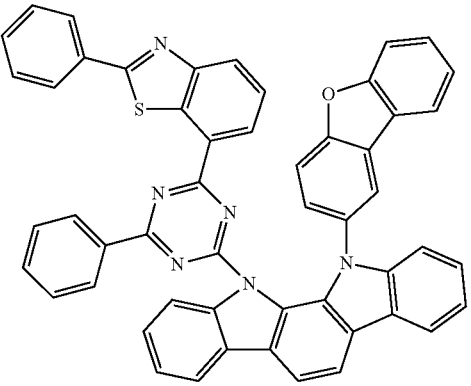
378
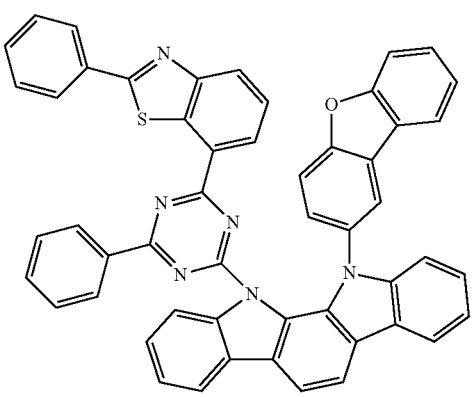

459
-continued
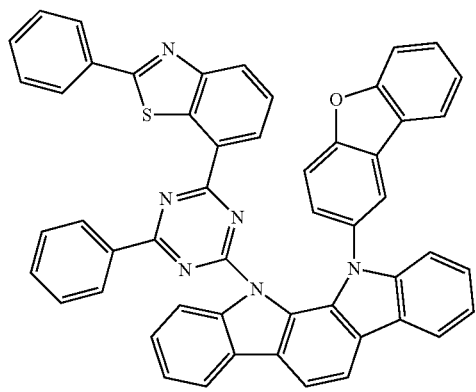
379
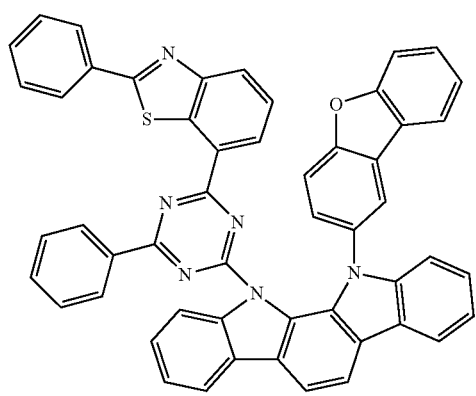
380
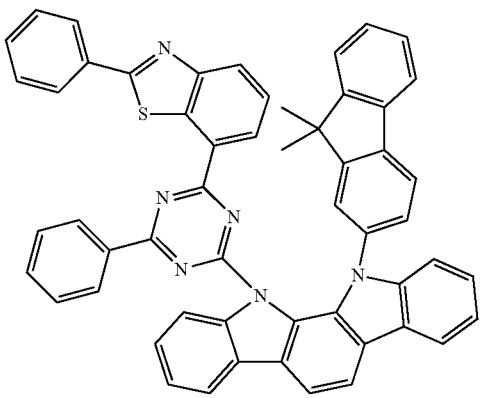
381
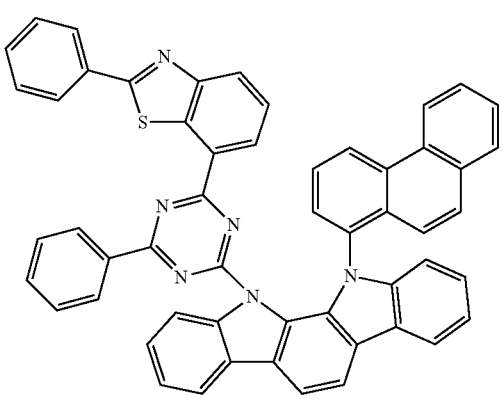
382
460
-continued
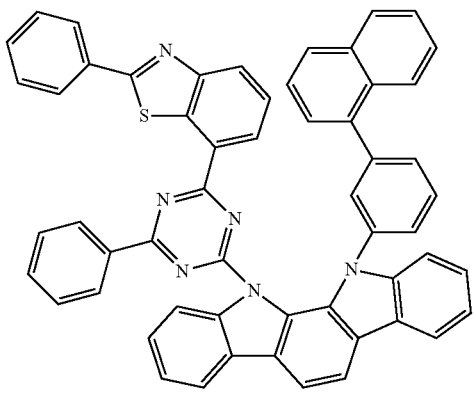
383
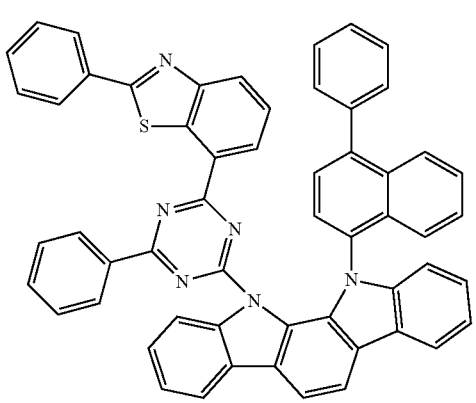
384
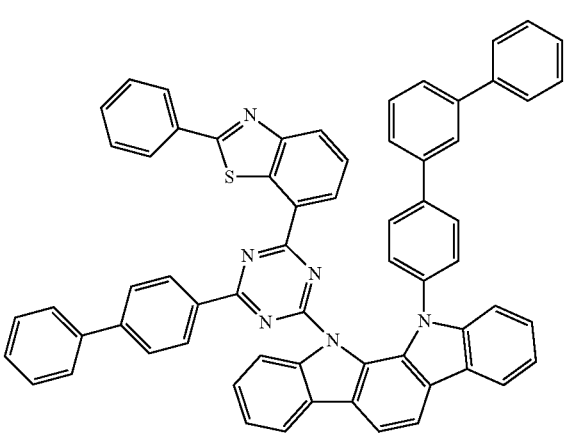
385

461
-continued
389
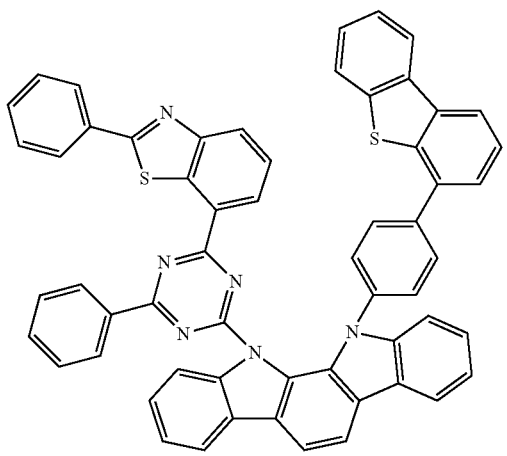
390
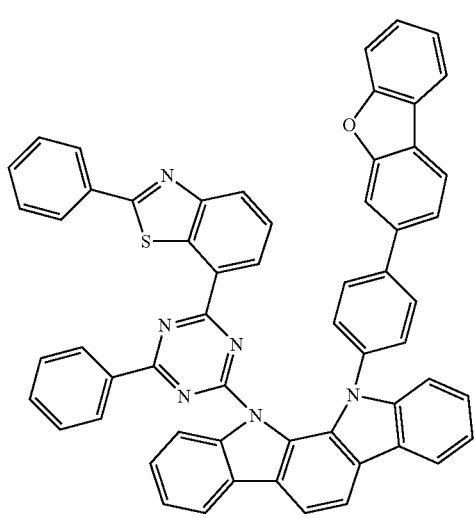
391
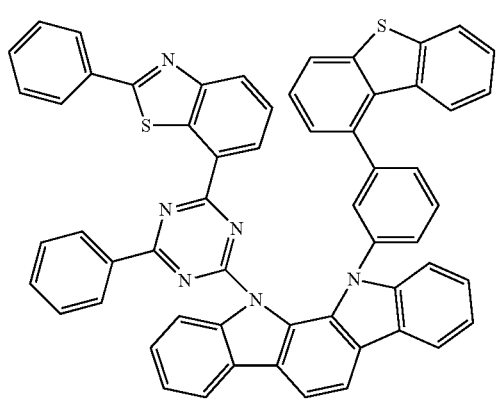
462
-continued
392
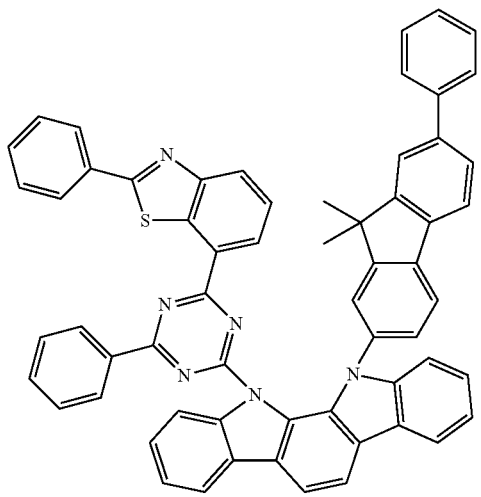
393
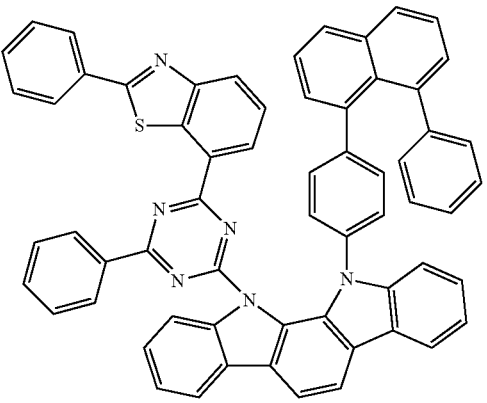
394
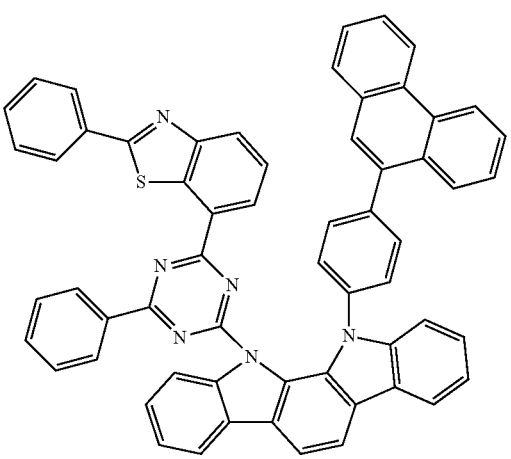
395
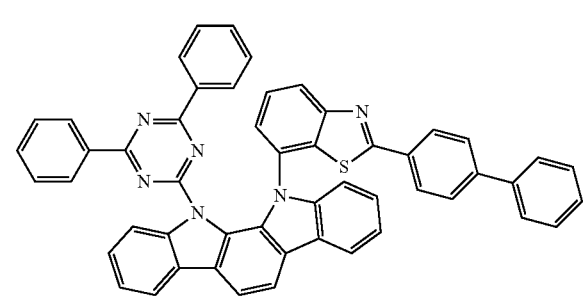

396
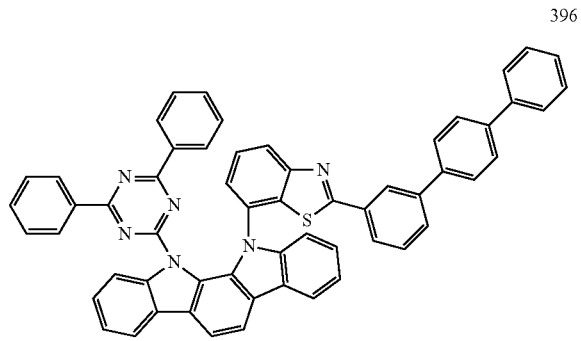
397
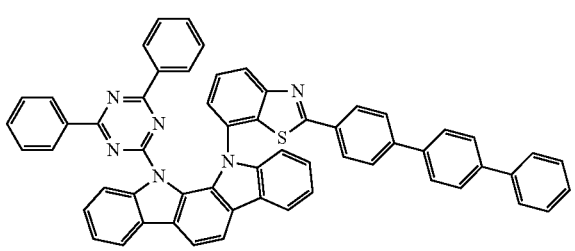
398
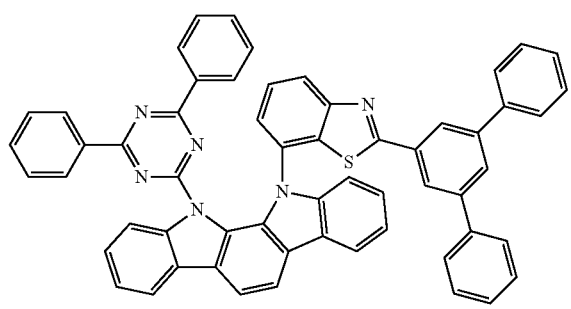
399
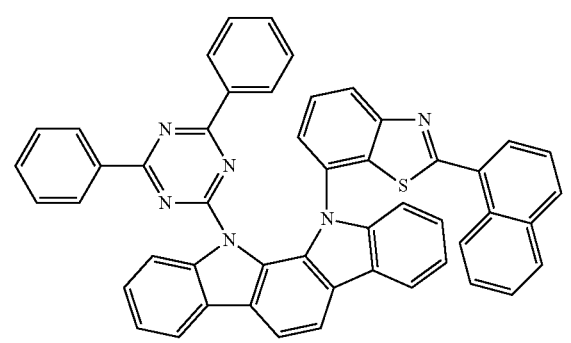
400
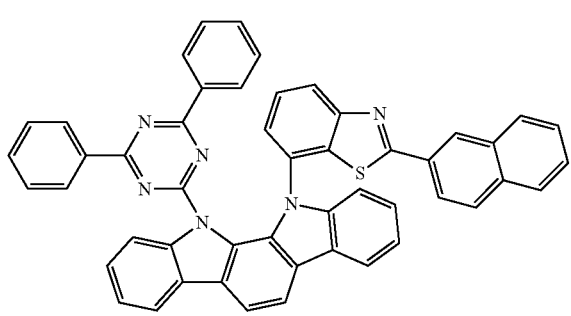
401
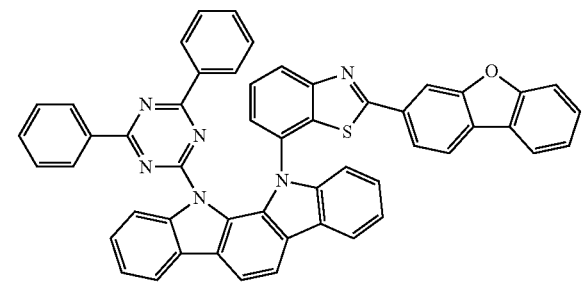
402
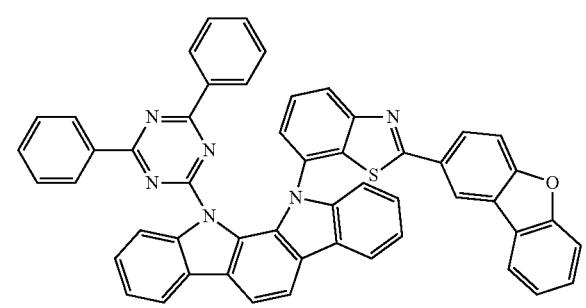
403
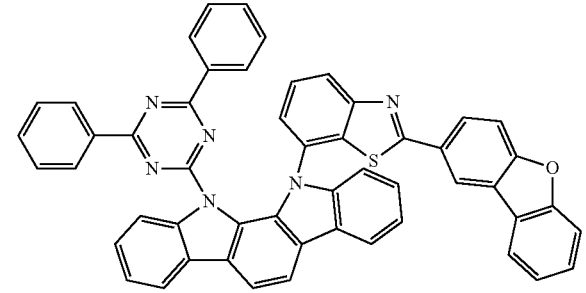
404
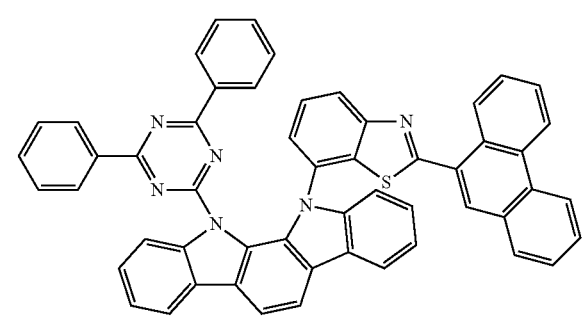
405
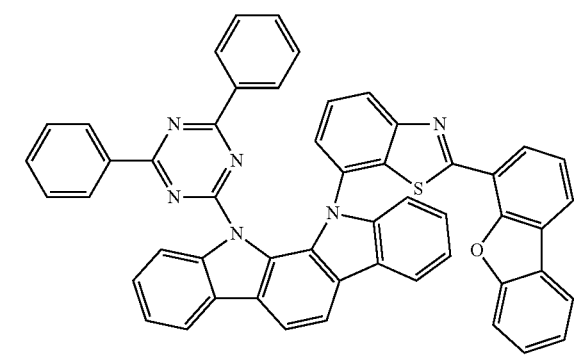

406
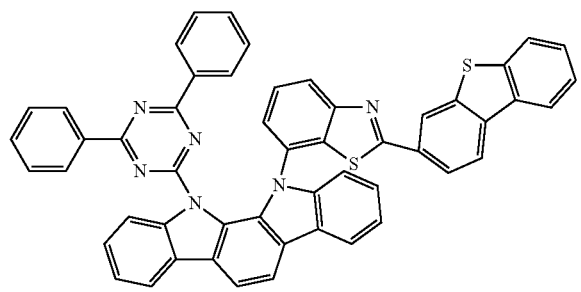
407
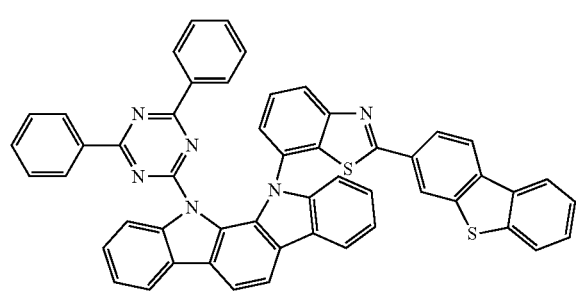
408
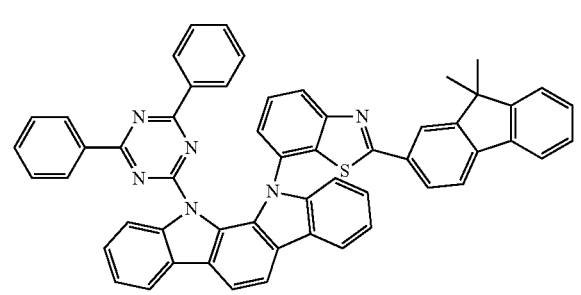
409
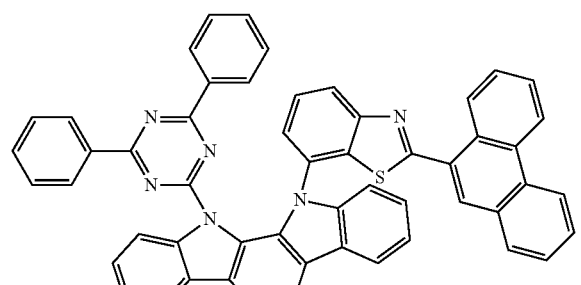
410
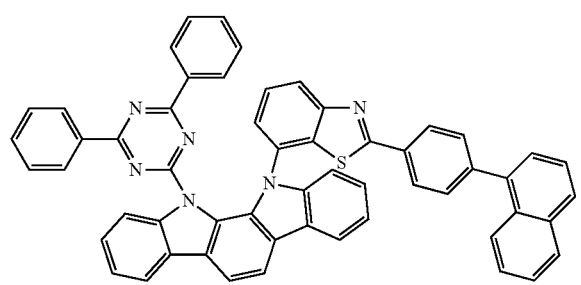
411
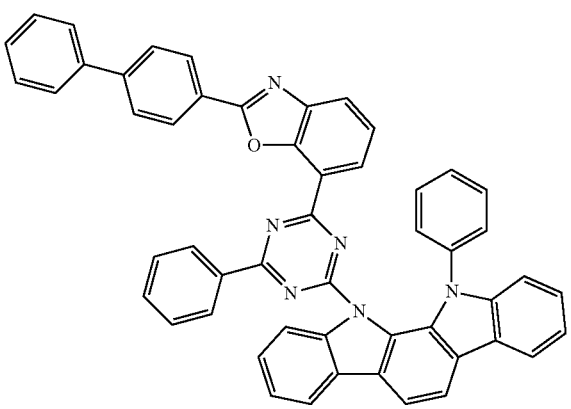
412
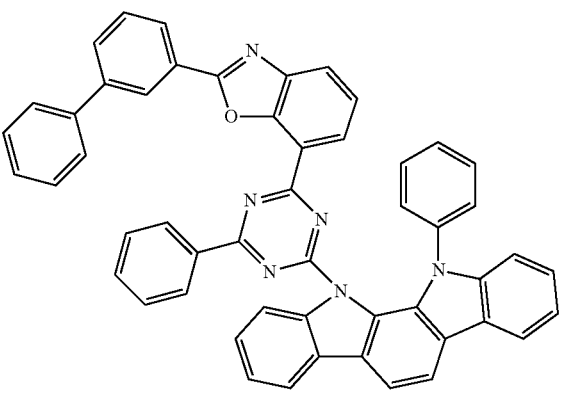
413
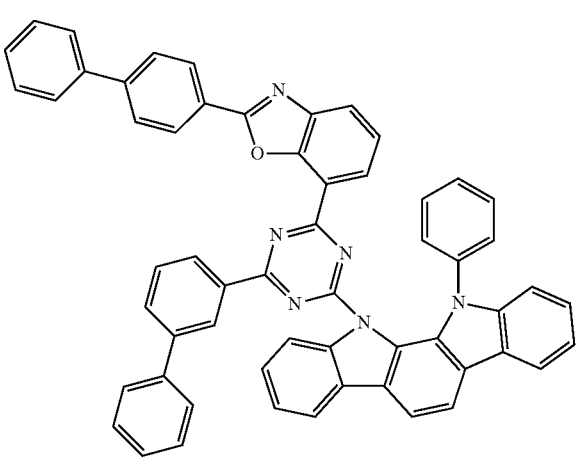

414
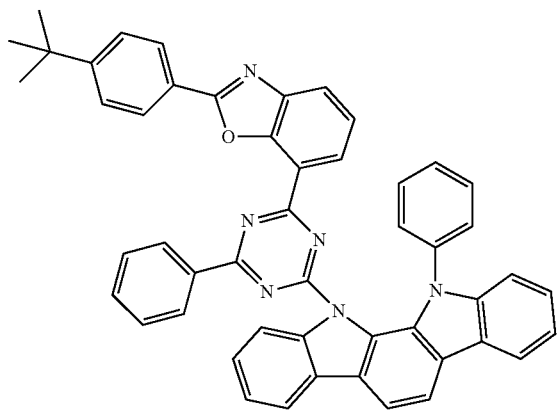
417
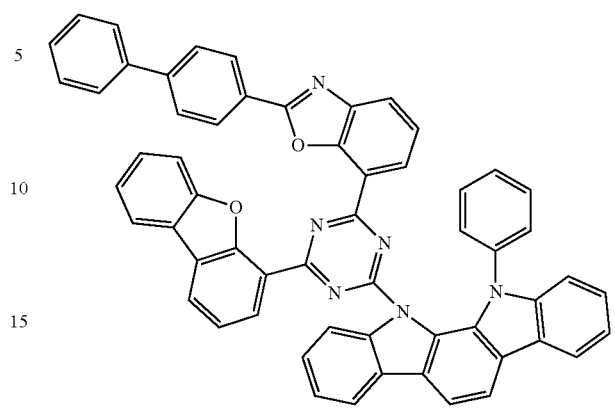
415
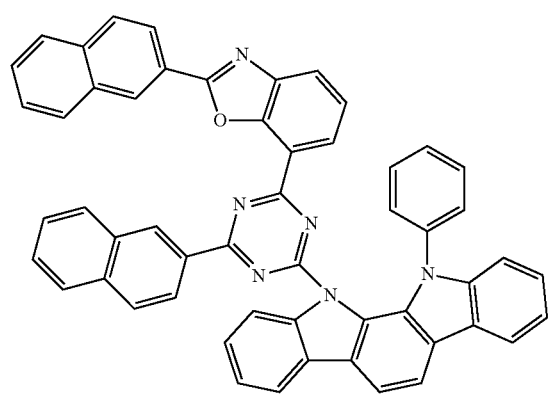
418
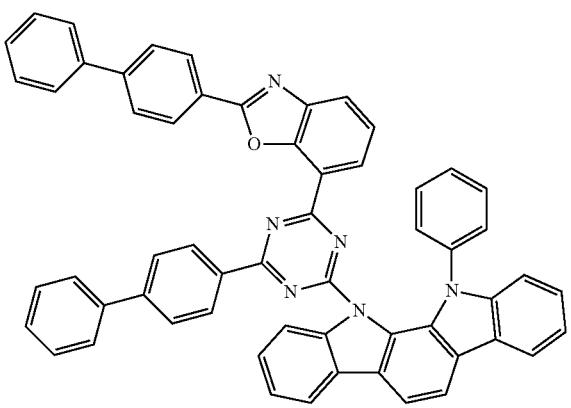
416
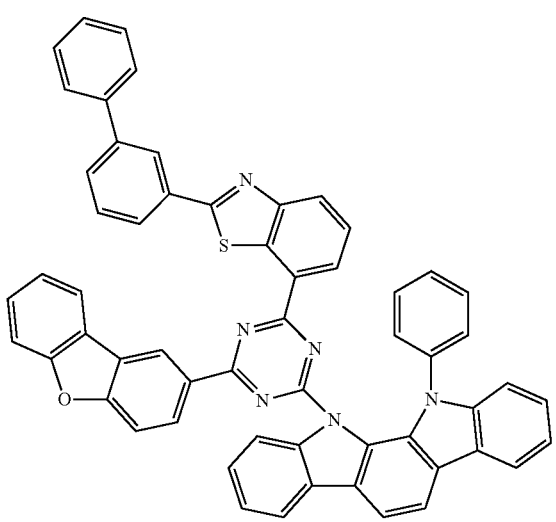
419
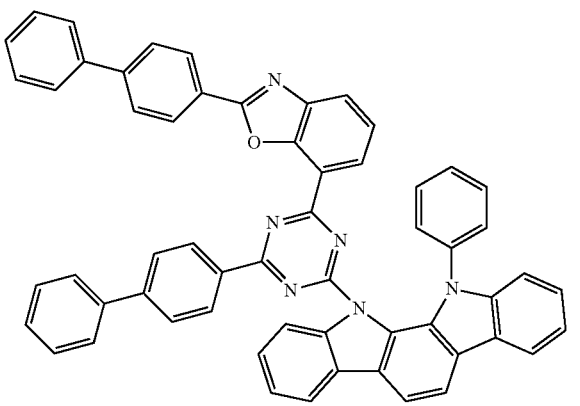

420
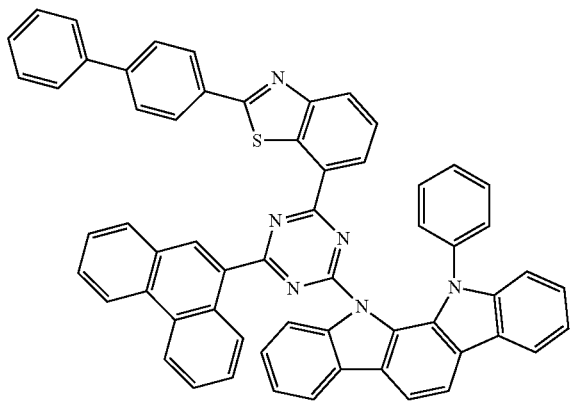
421
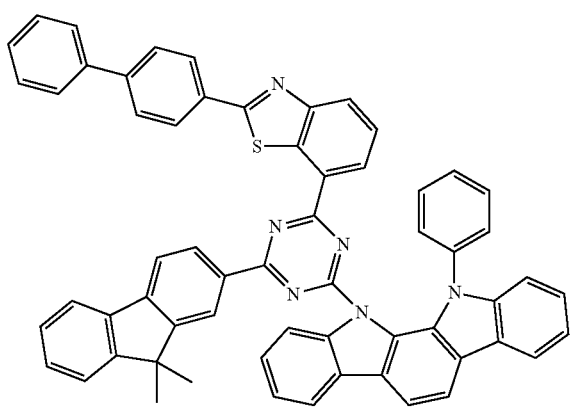
422
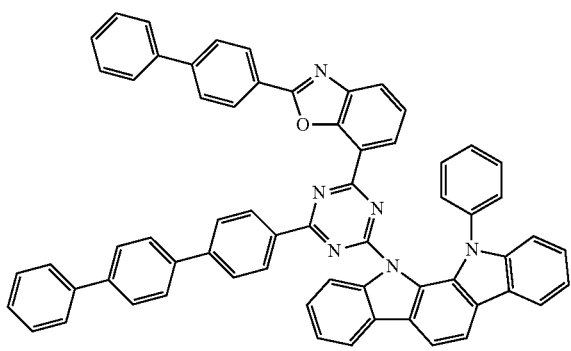
423
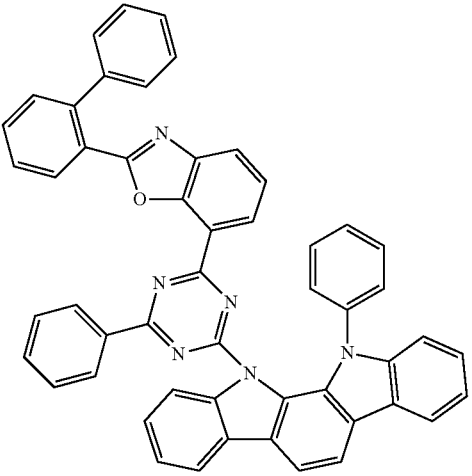
424
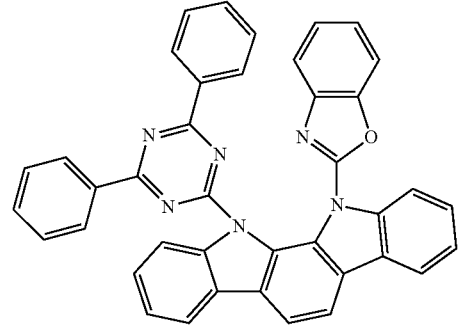
425
426
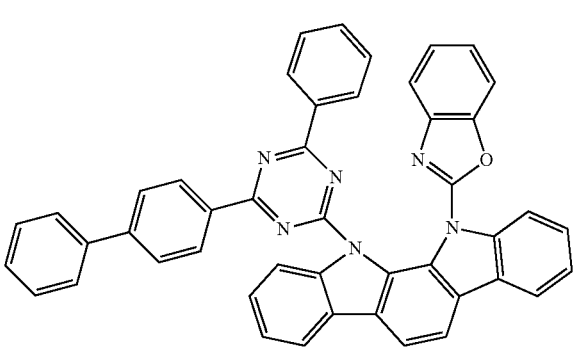

471
-continued
427
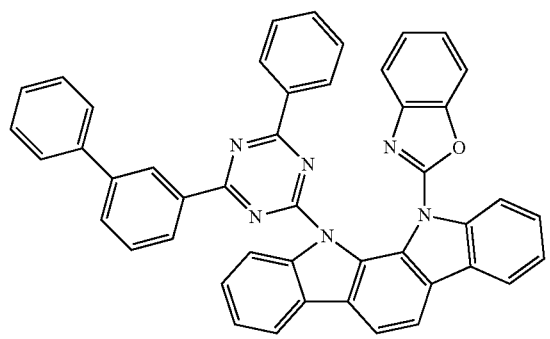
428
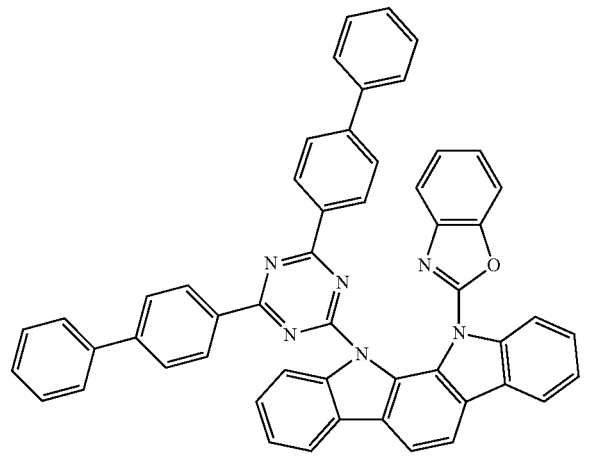
429
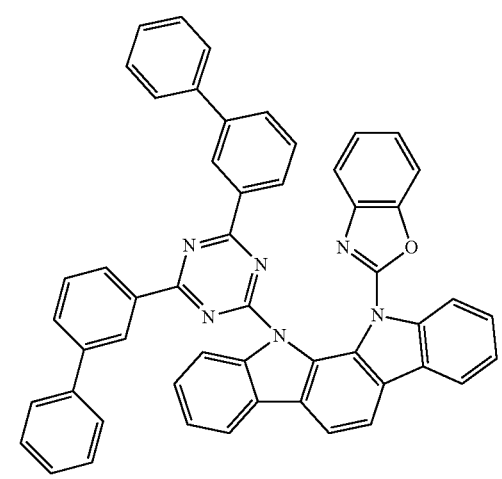
430
472
-continued
431
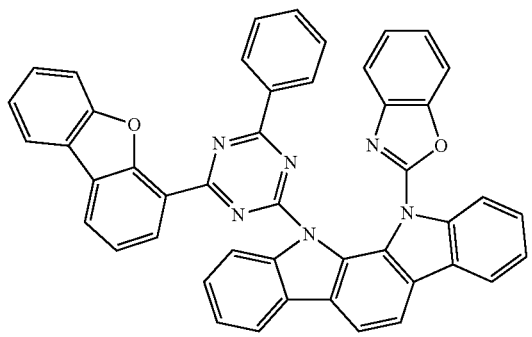
432
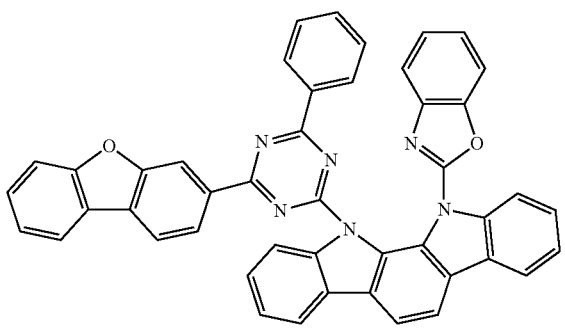
433
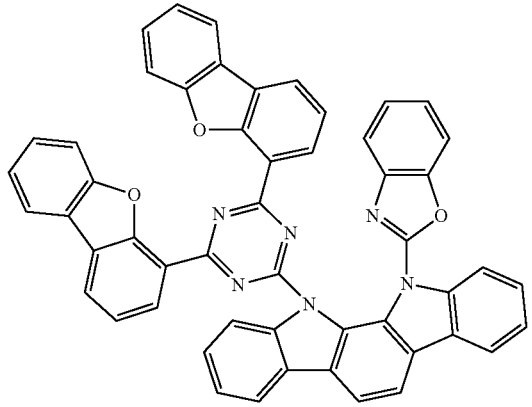
434
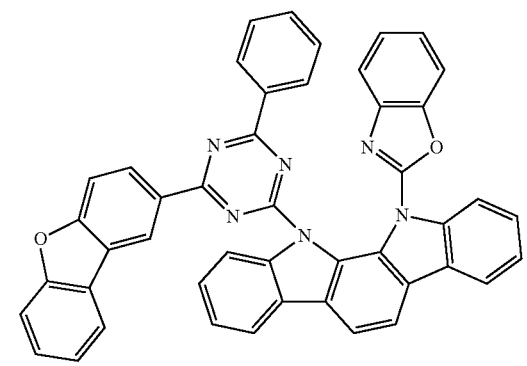

435
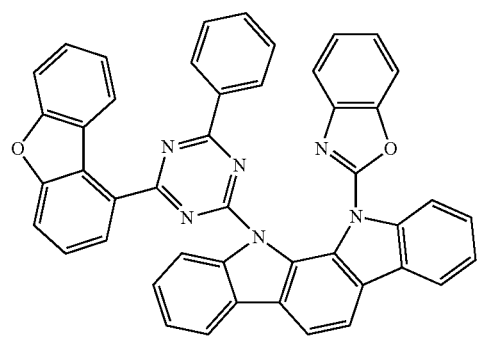
436
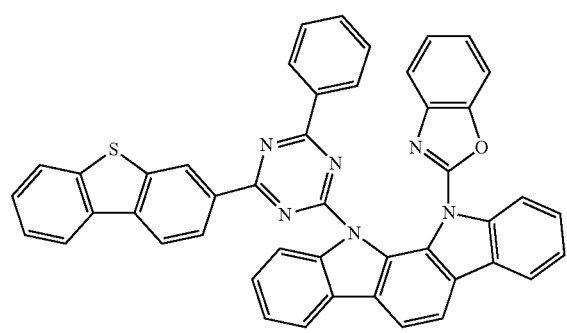
437
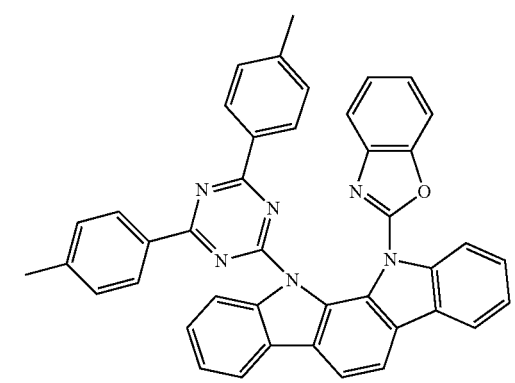
438
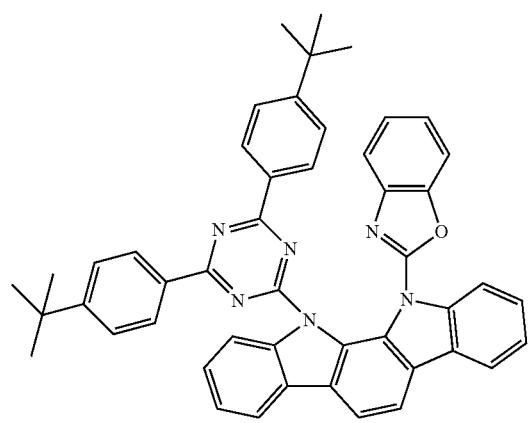
439
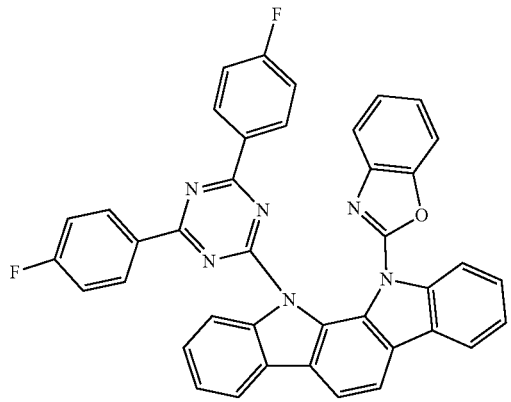
440
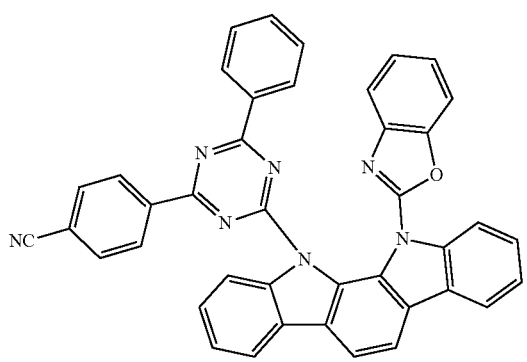
441
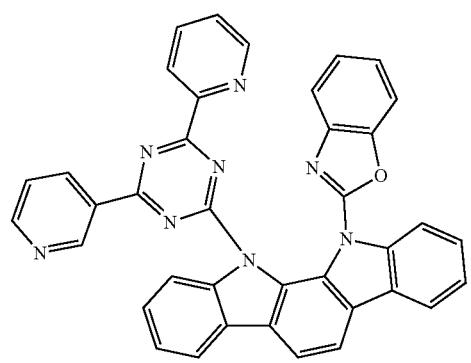
442
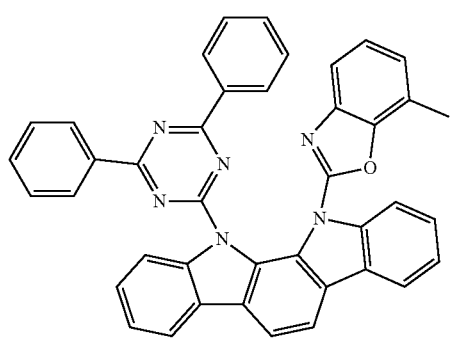

475
-continued
443
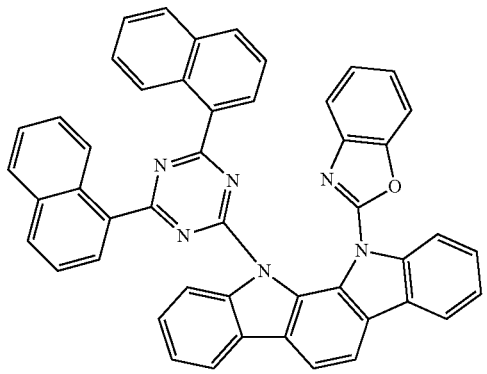
444
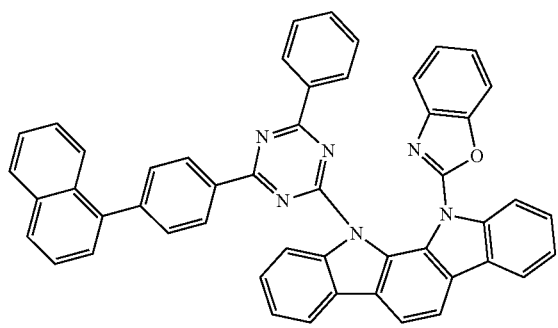
445
446
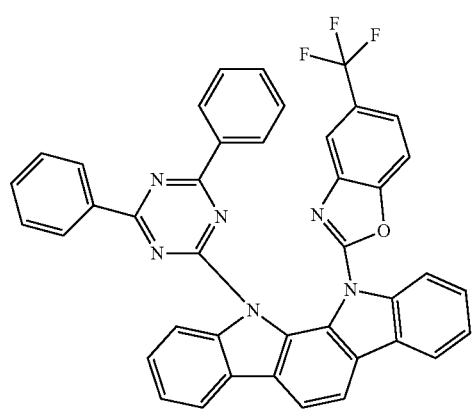
476
-continued
447
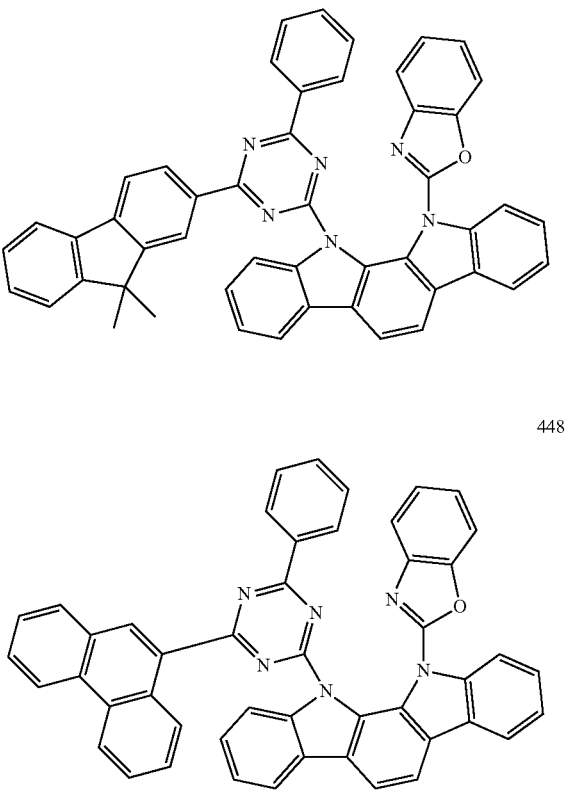
448
449
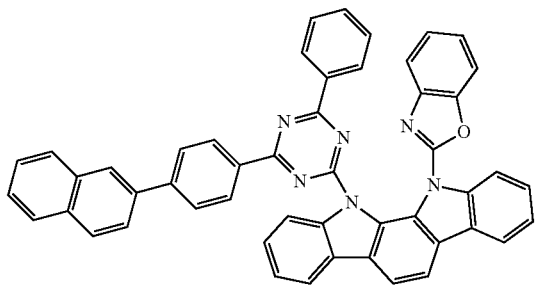
450
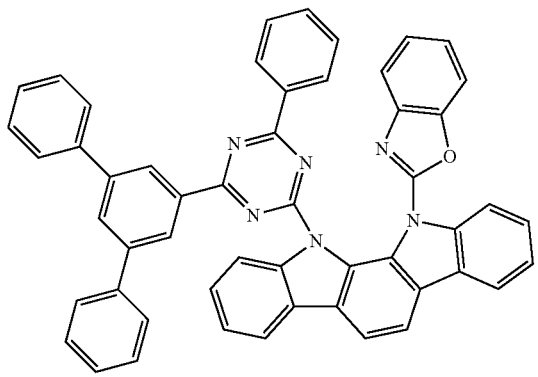

| 451 | 454 |
|---|---|
| 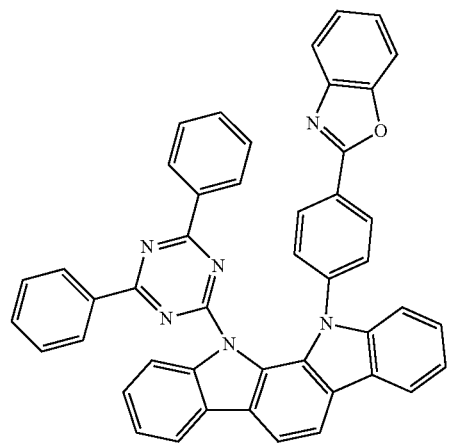 | 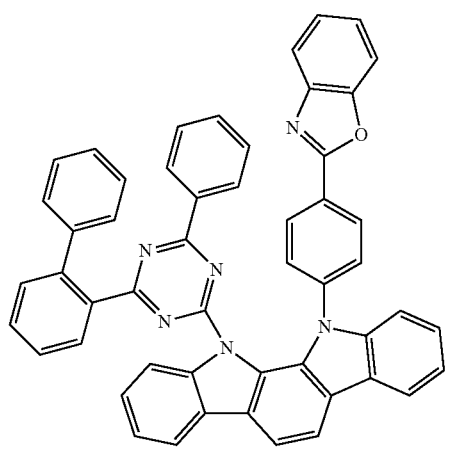 |
| 452 | 455 |
| 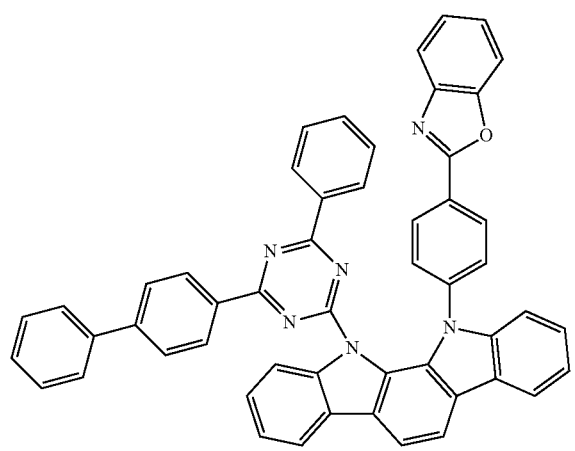 | 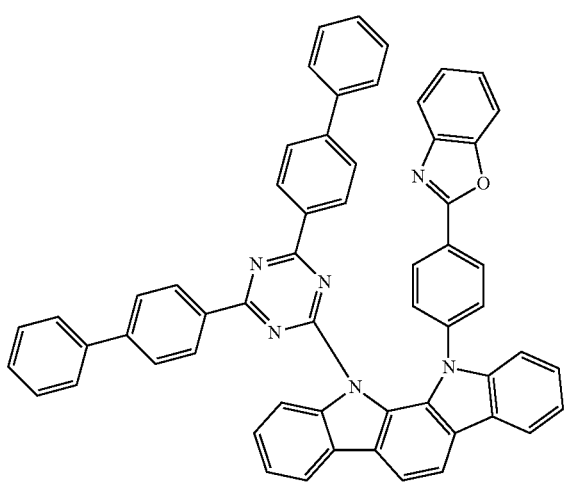 |
| 453 | 456 |
| 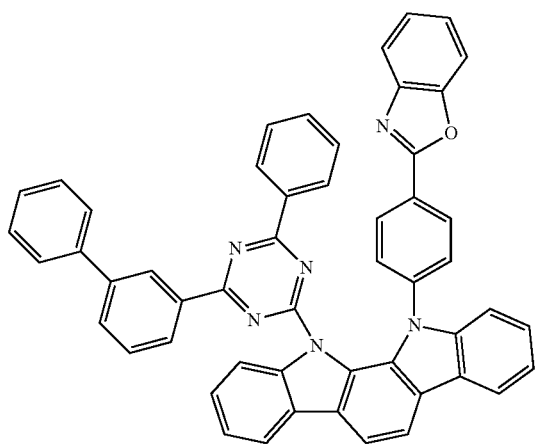 | 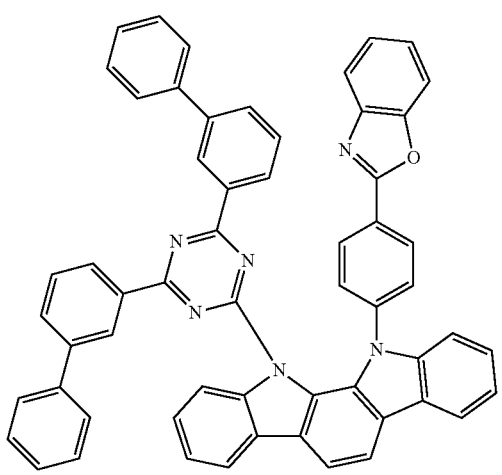 |

479
-continued
457
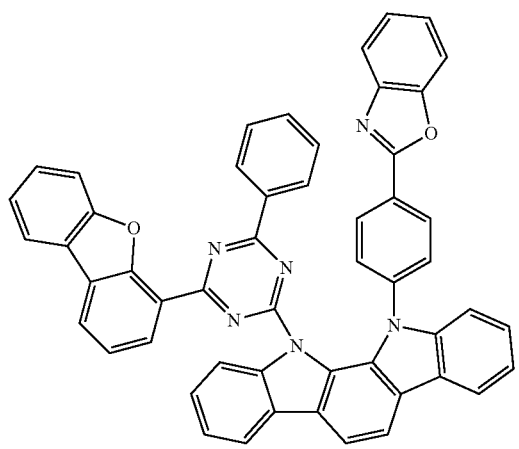
458
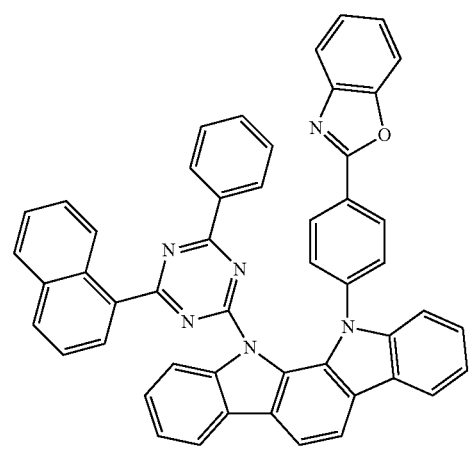
459
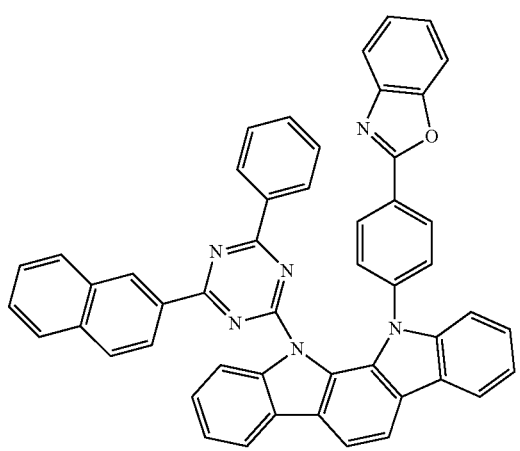
480
-continued
460
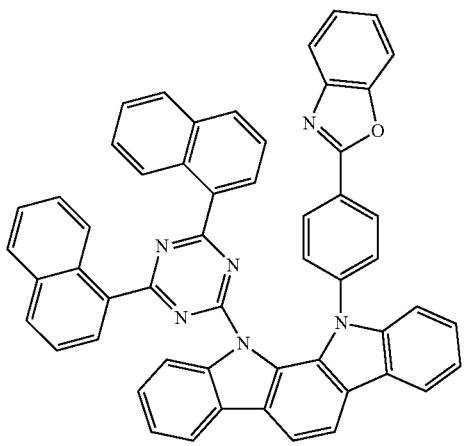
461
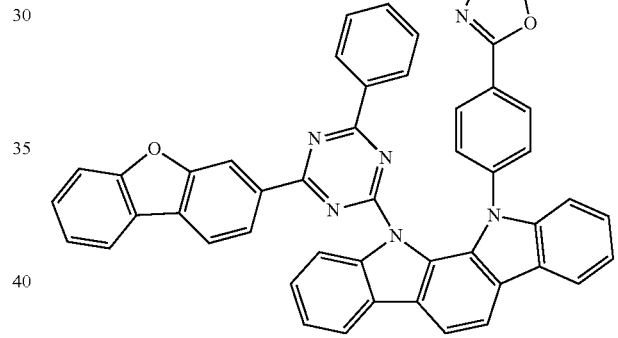
462
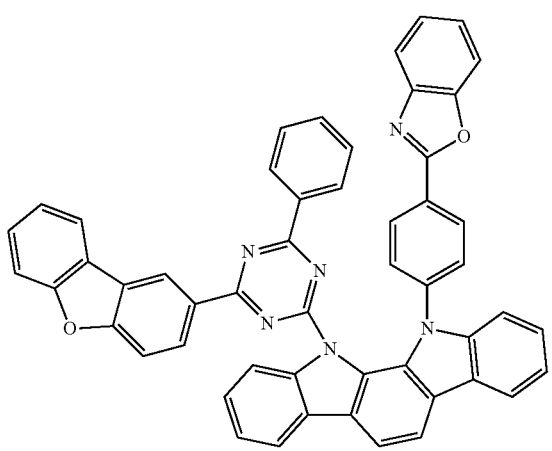

481
-continued
463
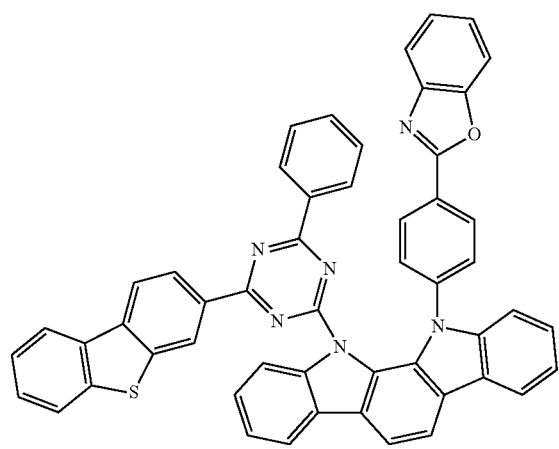
464
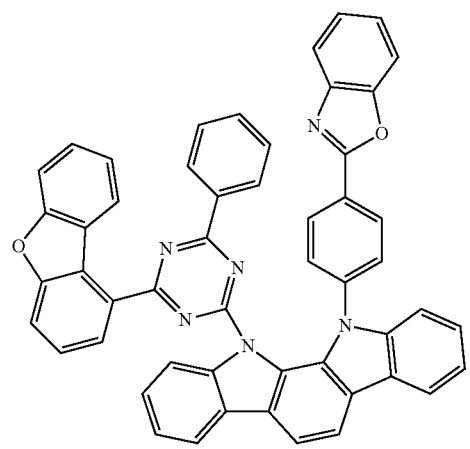
465
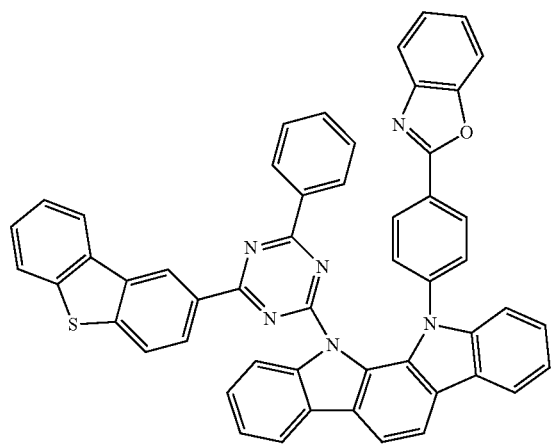
482
-continued
466
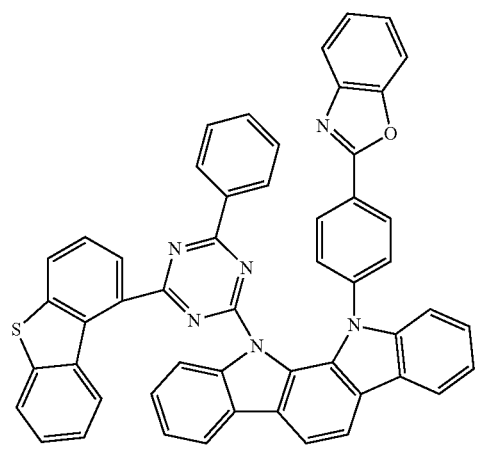
467
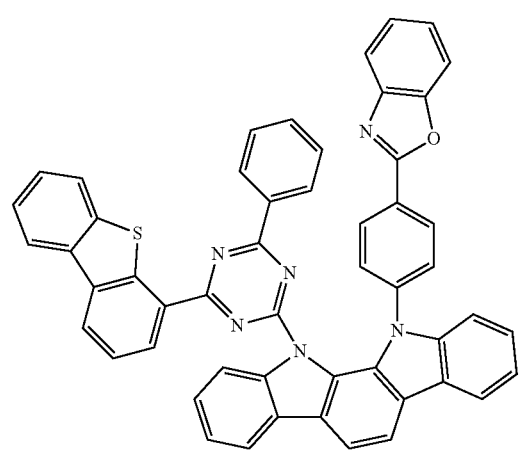
468
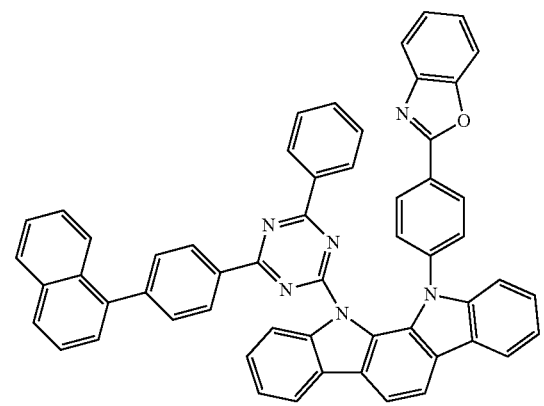

483
-continued
469
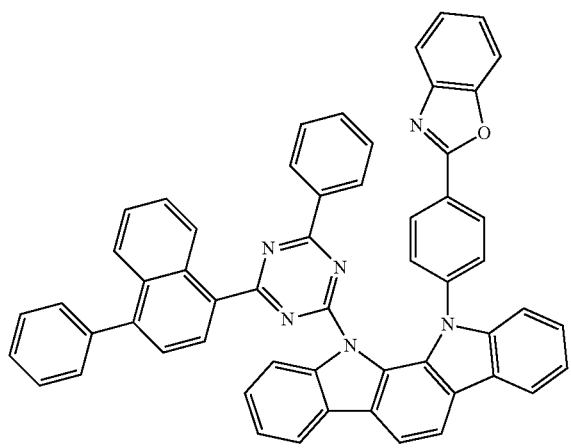
470
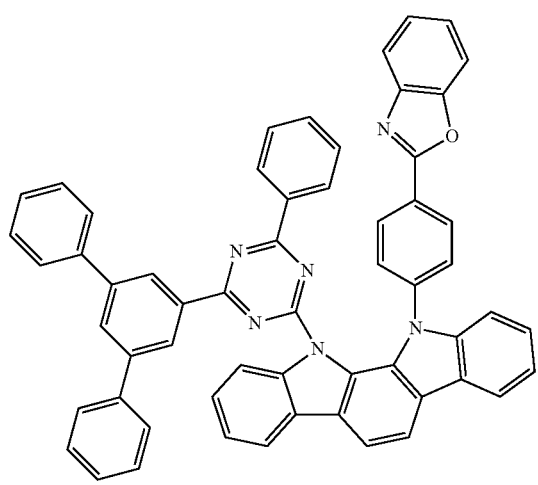
471
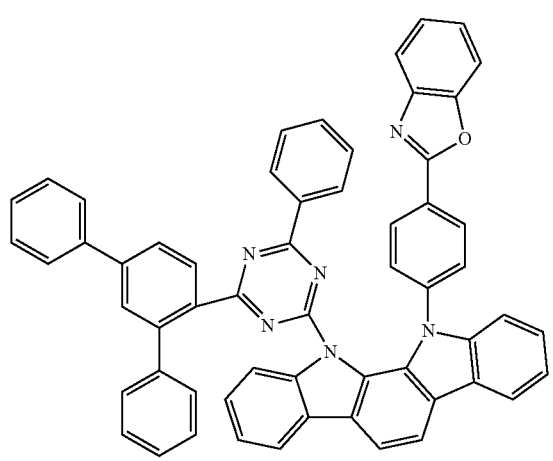
484
-continued
472
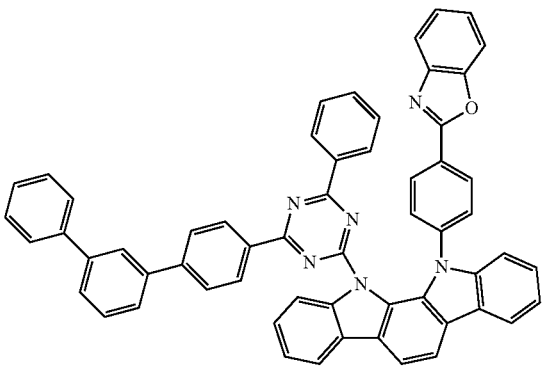
473
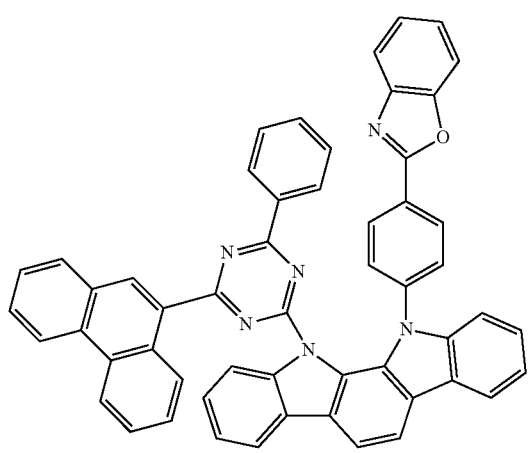
474
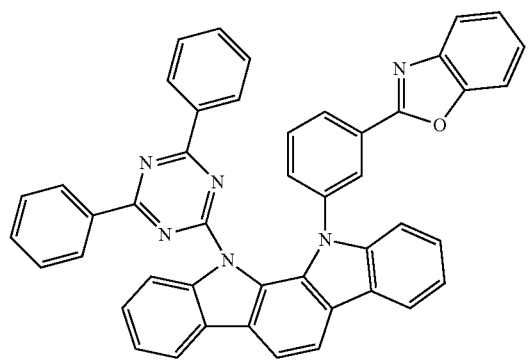
475
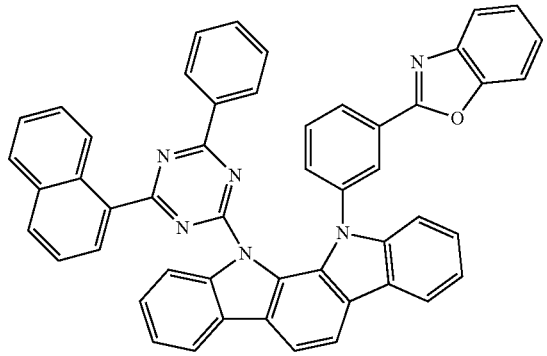

-continued
476
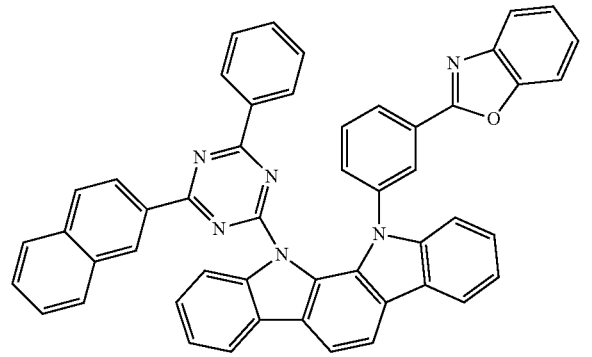
480
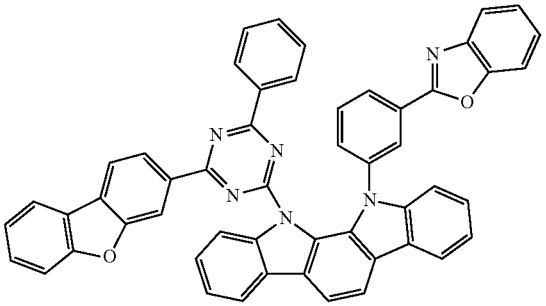
477
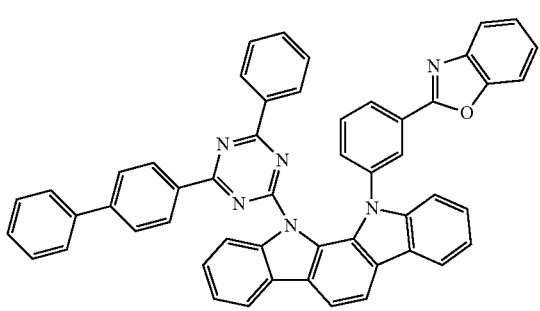
481
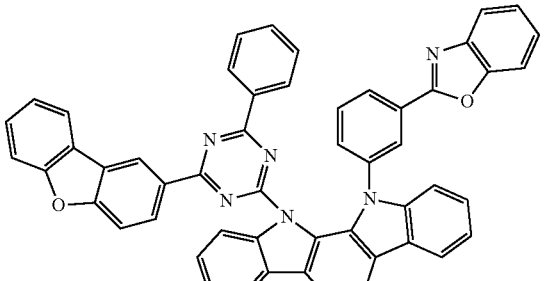
478
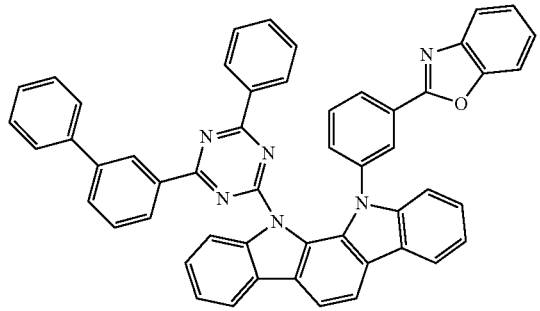
482
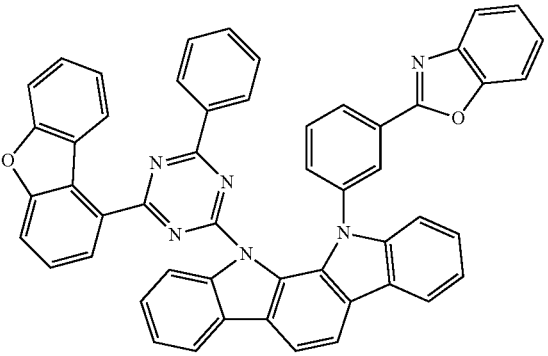
479
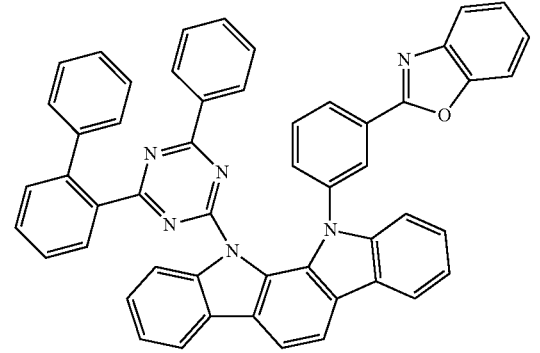
483
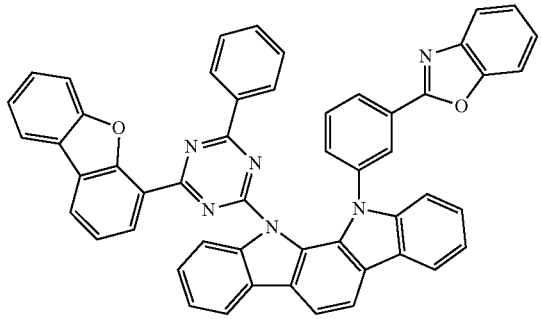

484
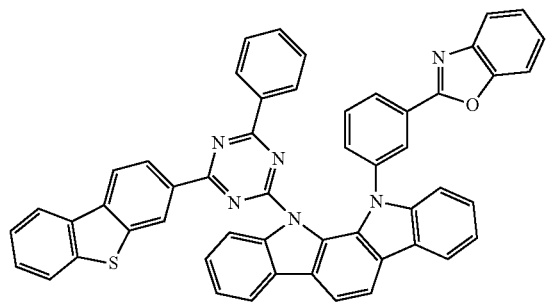
485
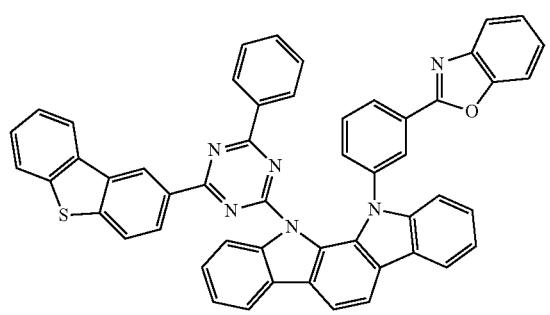
486
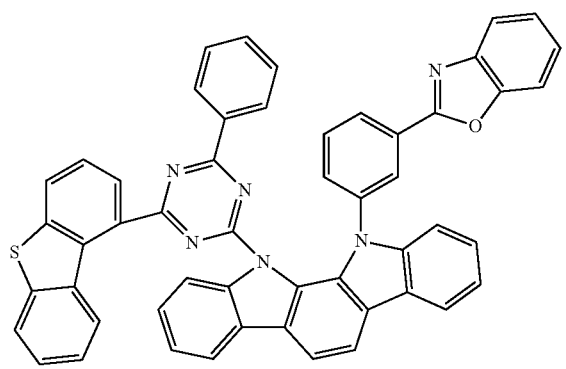
487
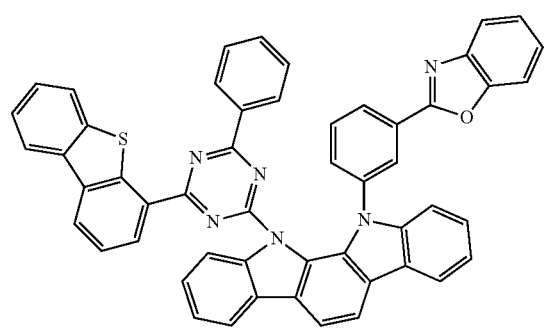
488
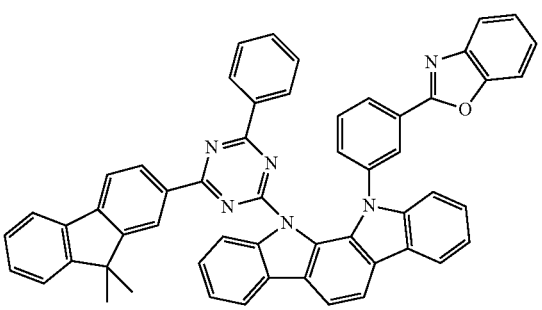
489
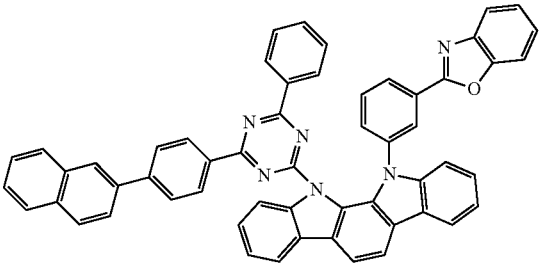
490
491
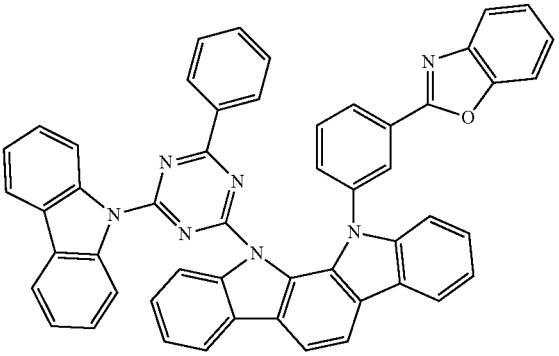

489
-continued
492
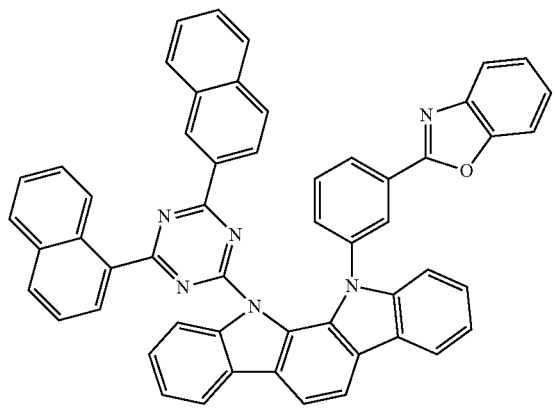
493
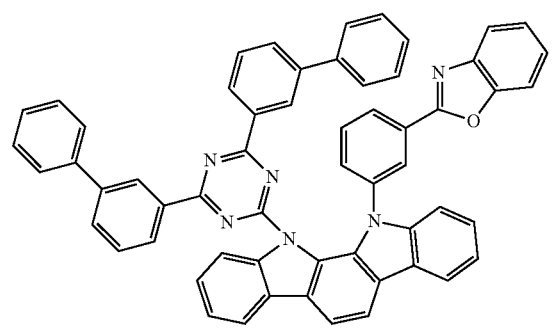
494
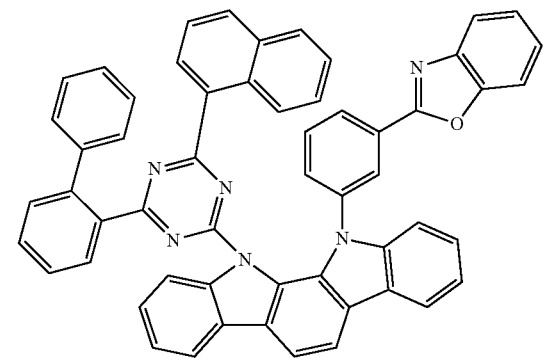
495
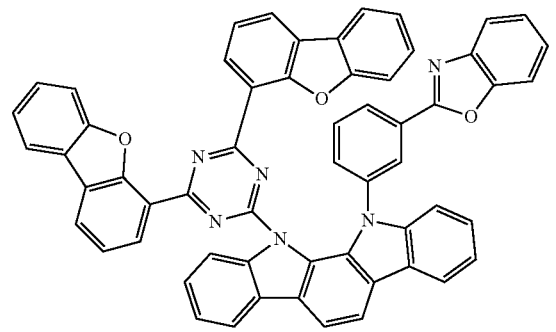
490
-continued
496
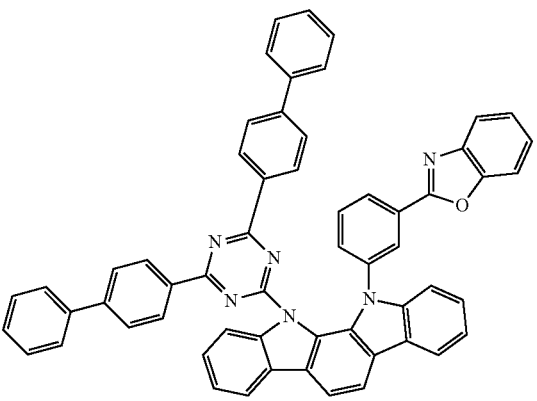
497
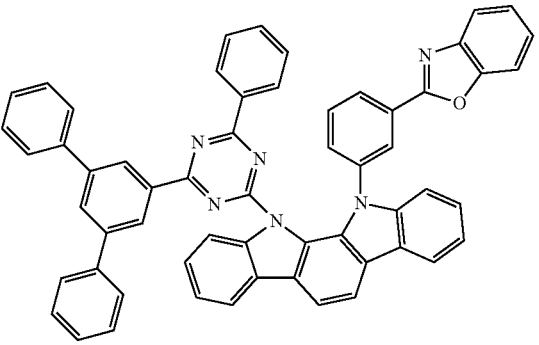
498
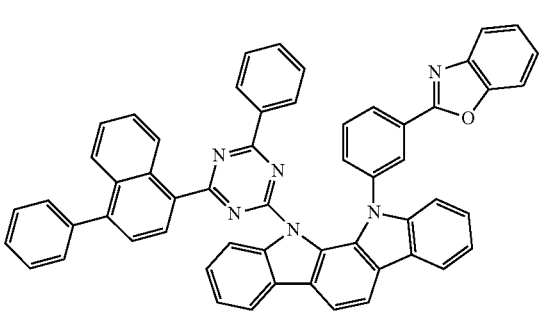
499
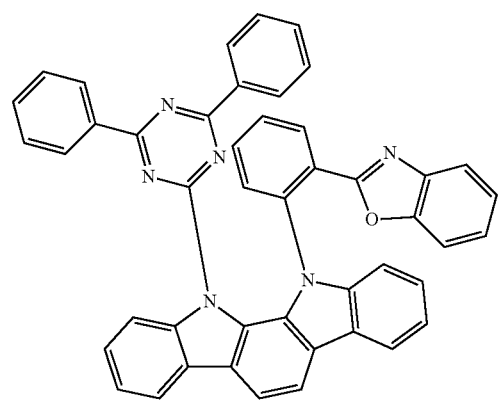

491
-continued
500
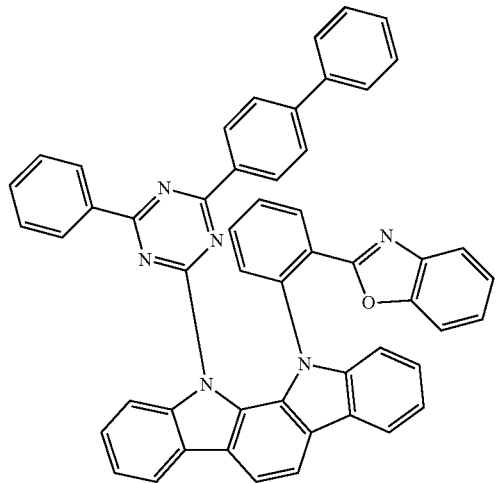
501
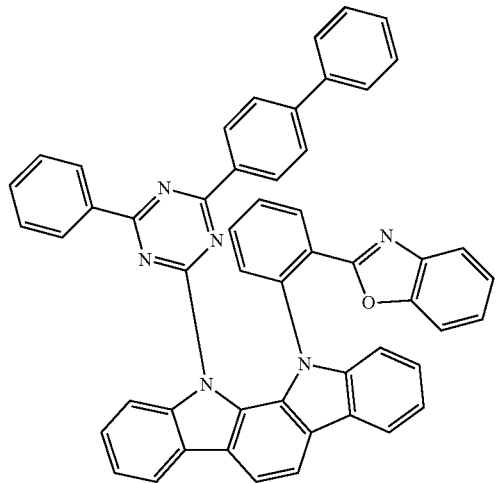
502
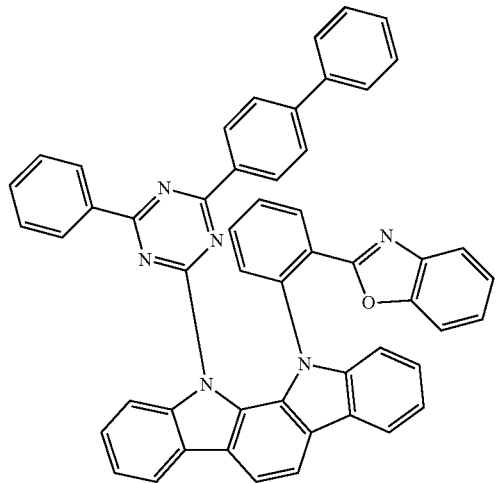
503
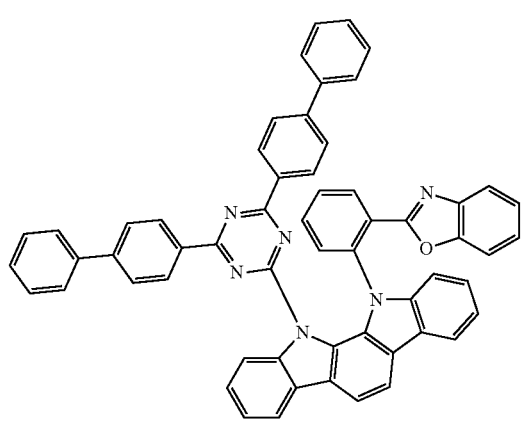
492
-continued
504
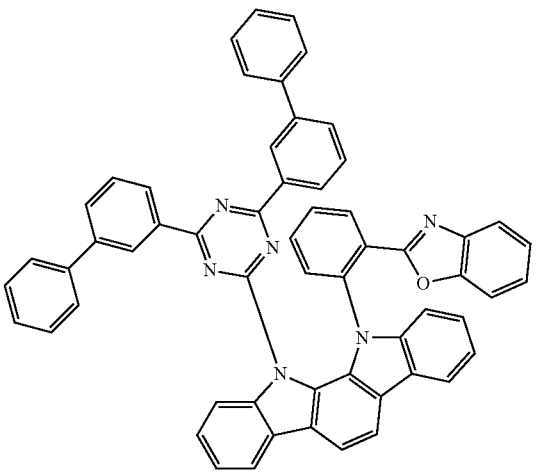
505
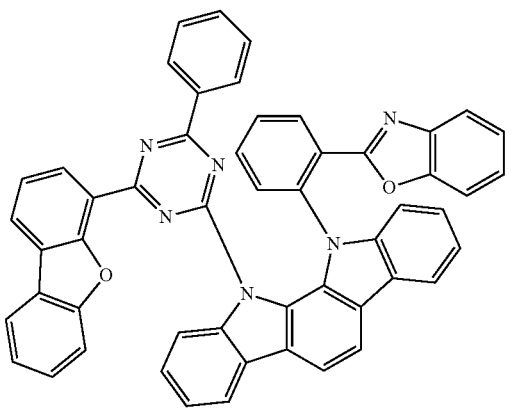
506
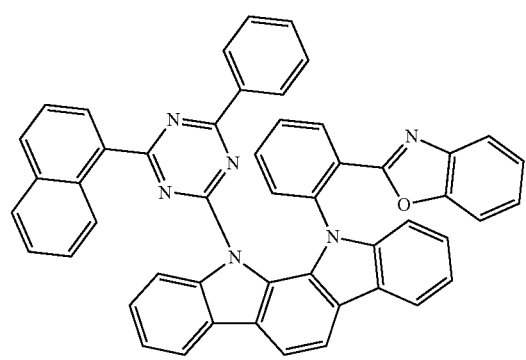

507 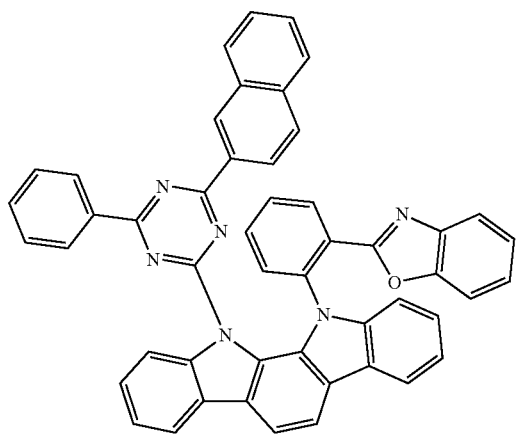
508 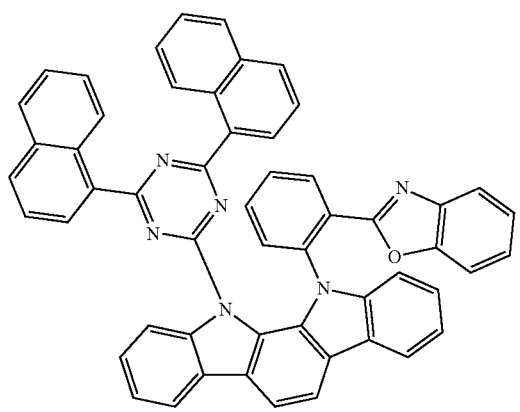
509 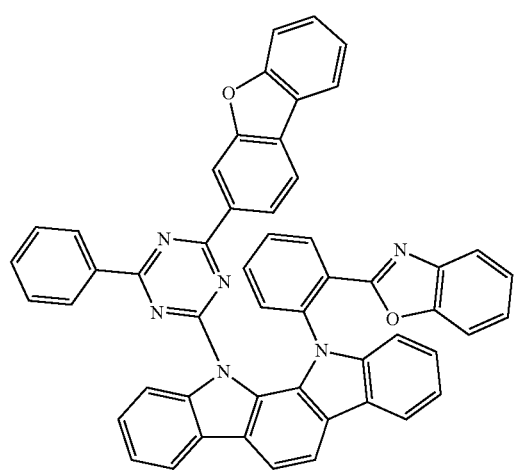
510 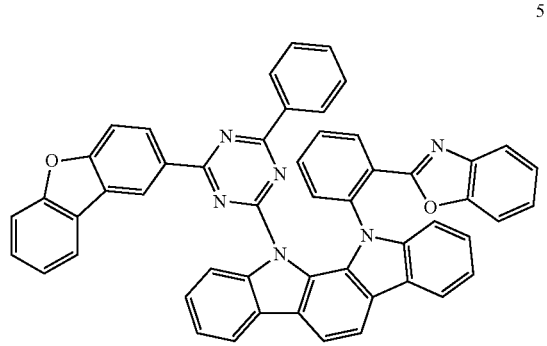
511 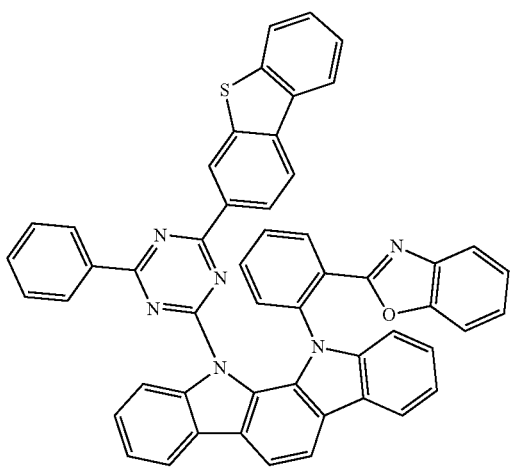
512 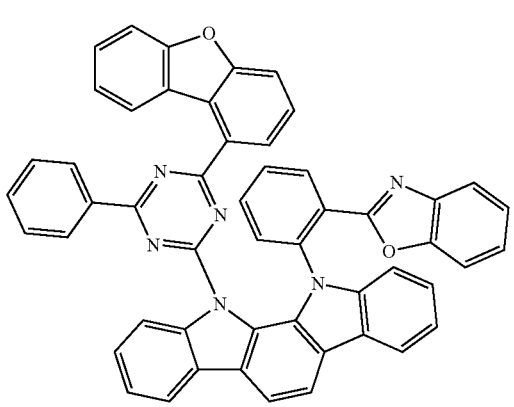
513 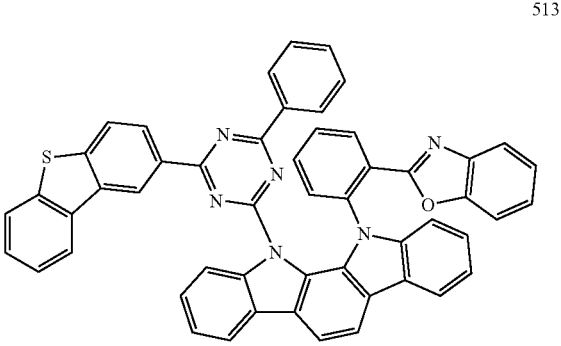
514 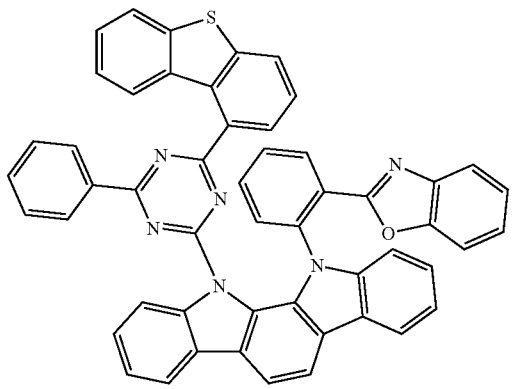

495
-continued
515
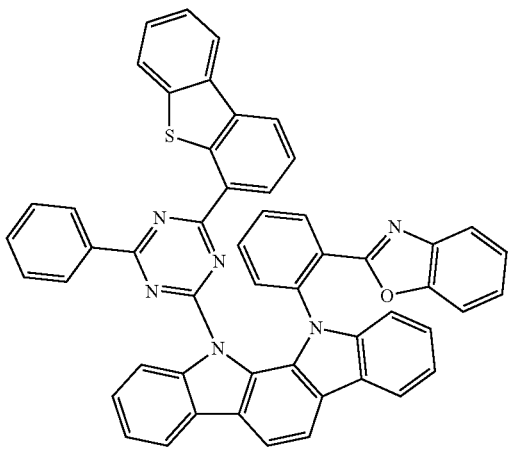
516
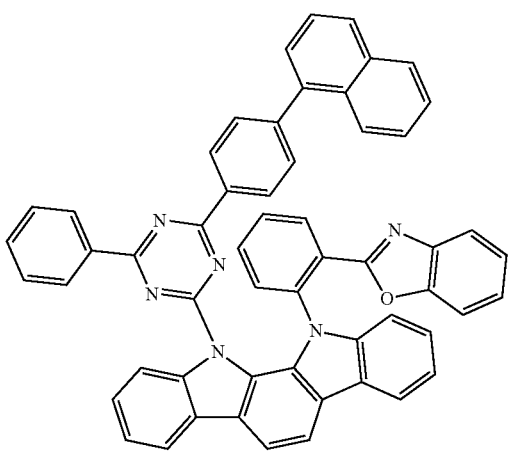
517
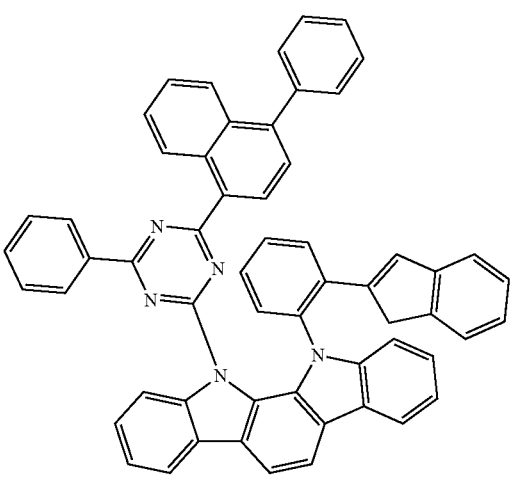
496
-continued
518
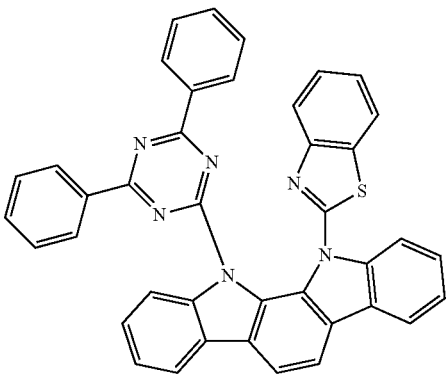
519
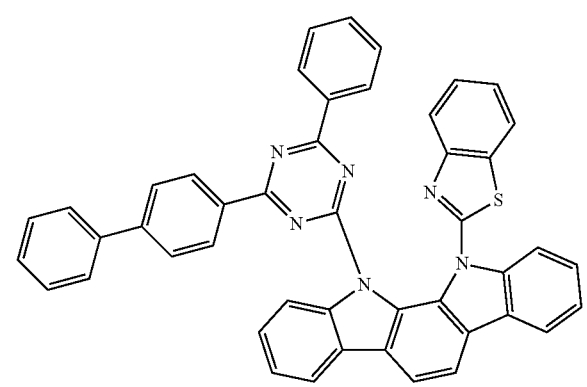
520
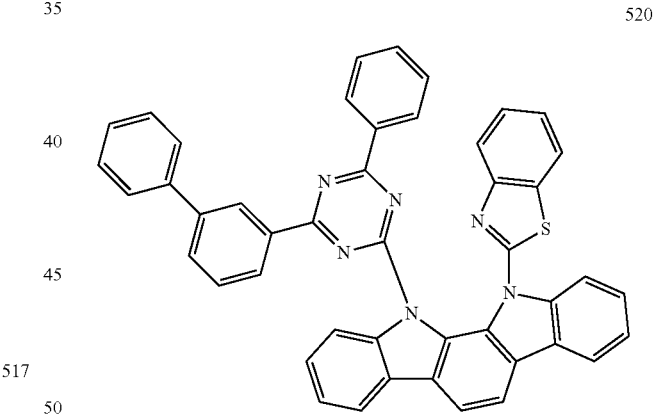
521
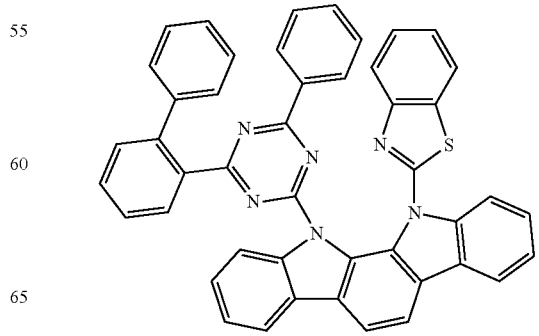

497
-continued

498
-continued

530 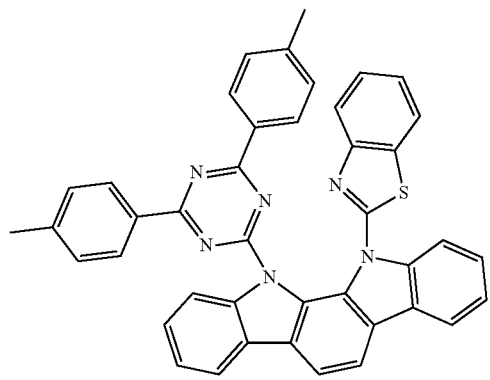
531 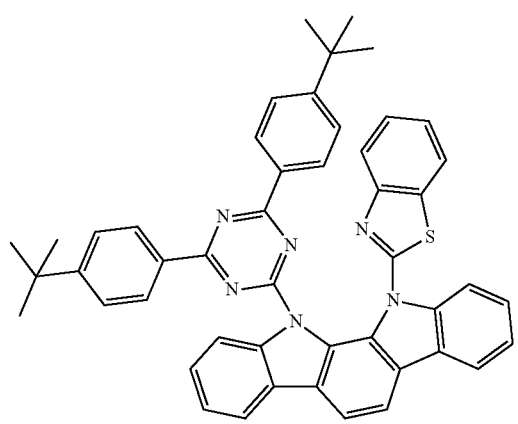
532 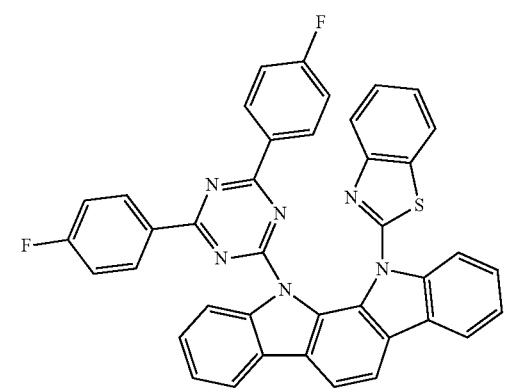
533 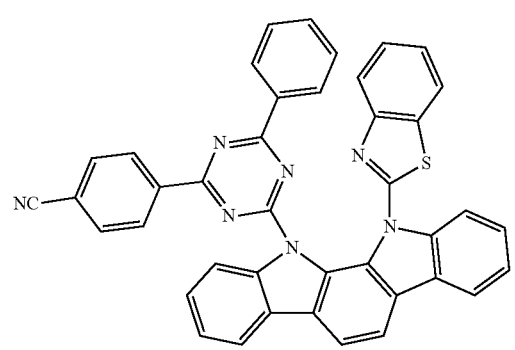
534 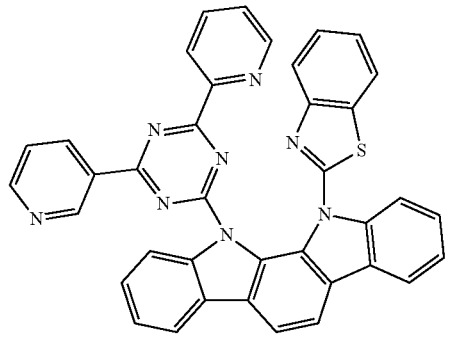
535 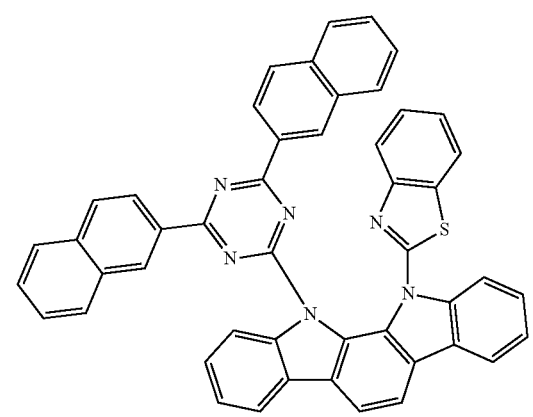
536 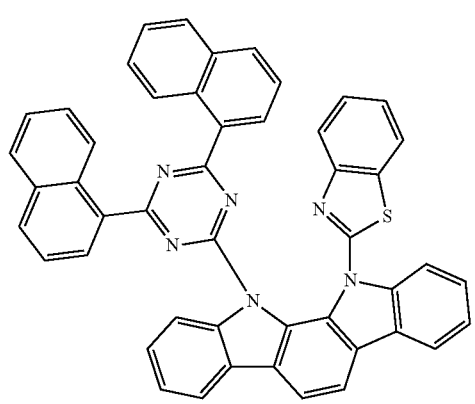
537 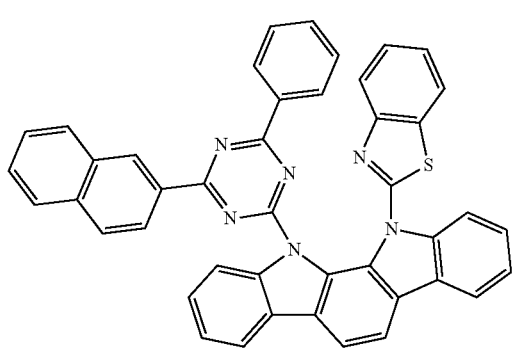

501
-continued
538
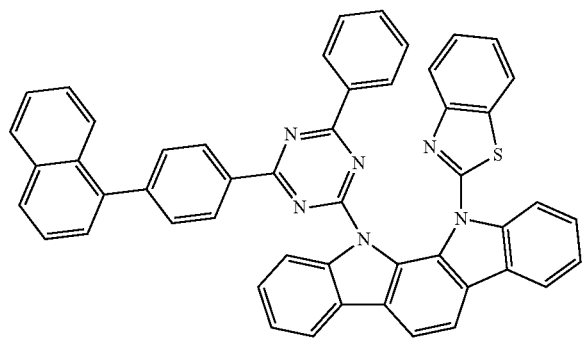
543
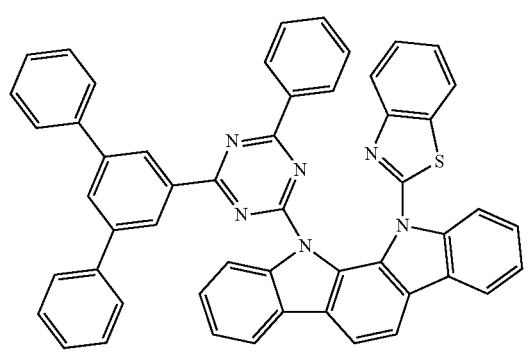
544
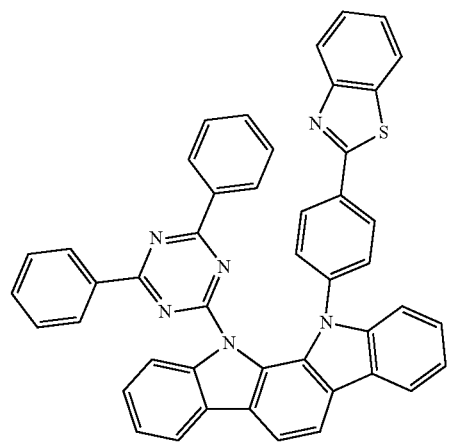
545
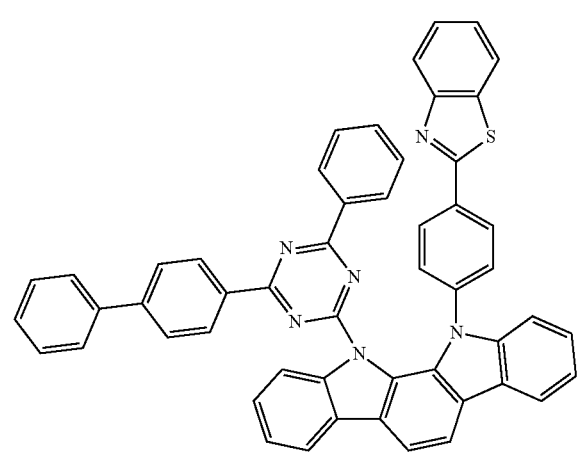
502
-continued
546
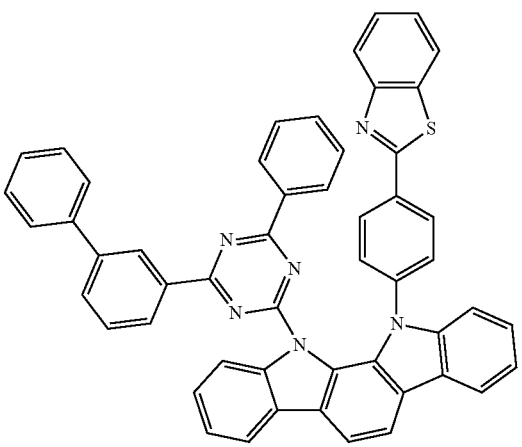
547
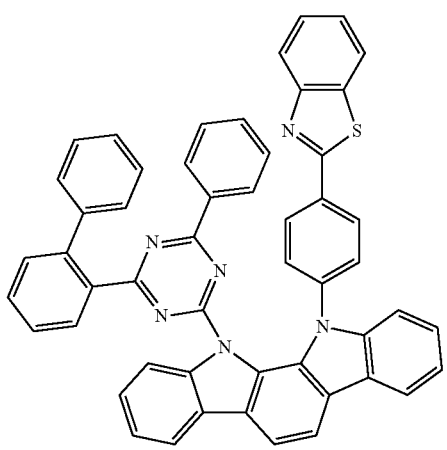
548
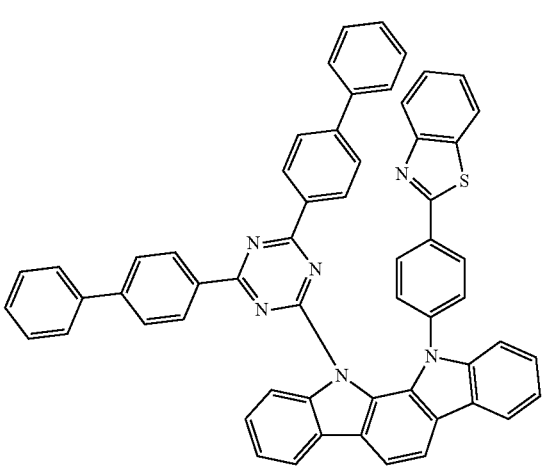

549
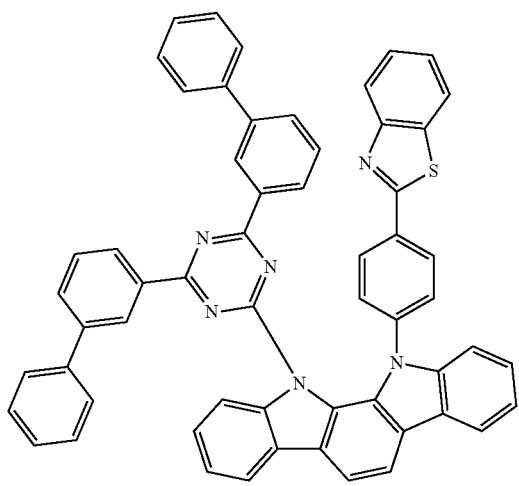
550
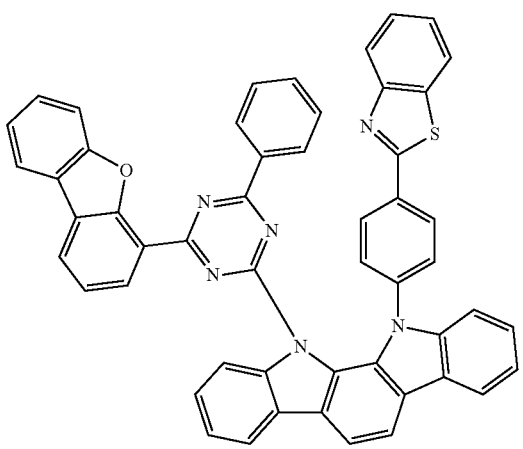
551
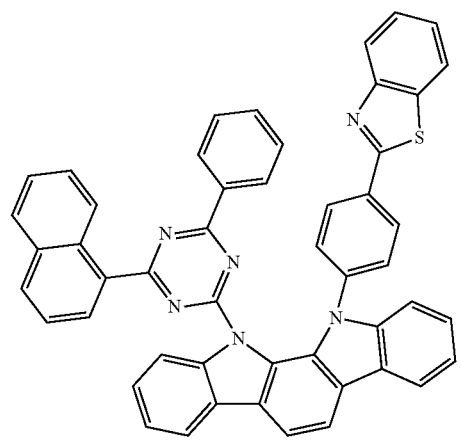
552
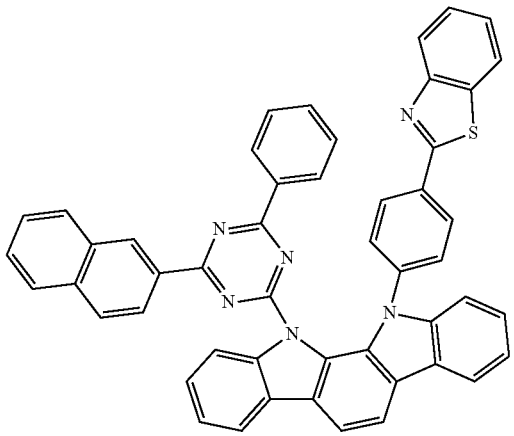
553
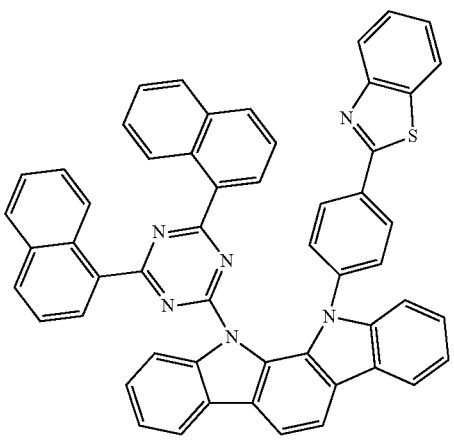
554
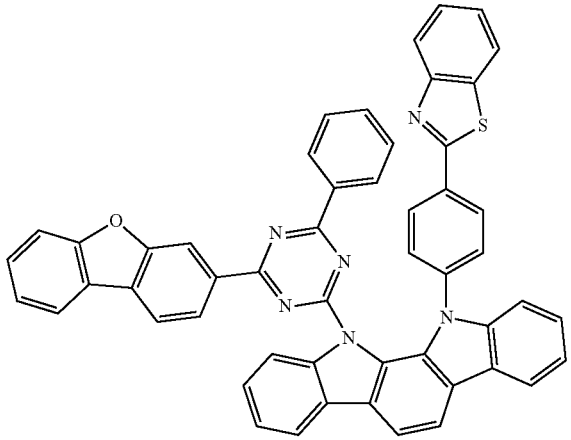

555
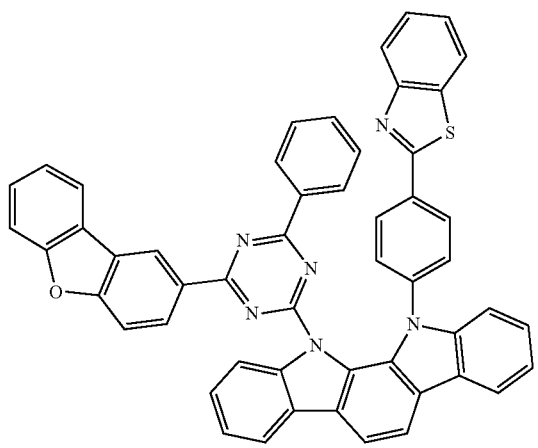
556
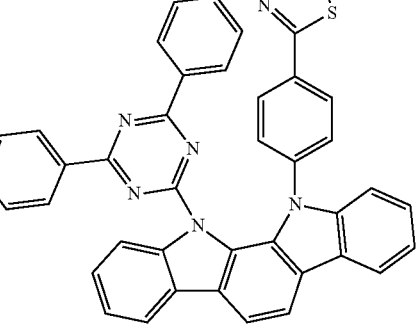
557
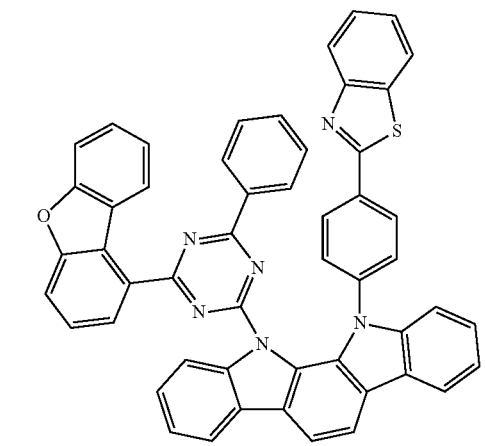
558
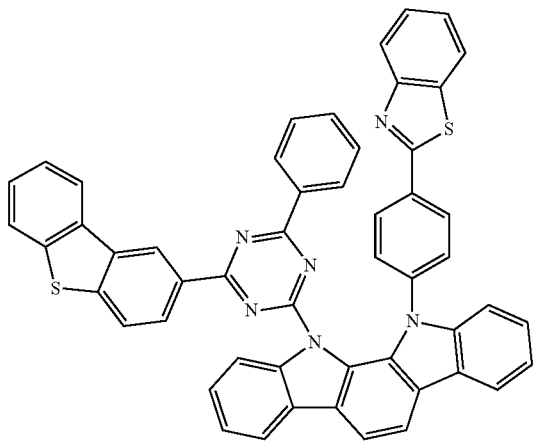
559
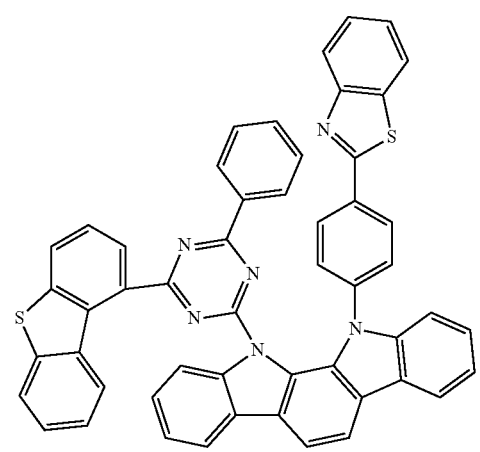
560
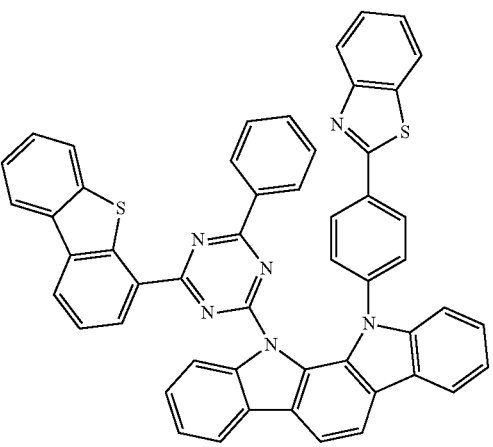

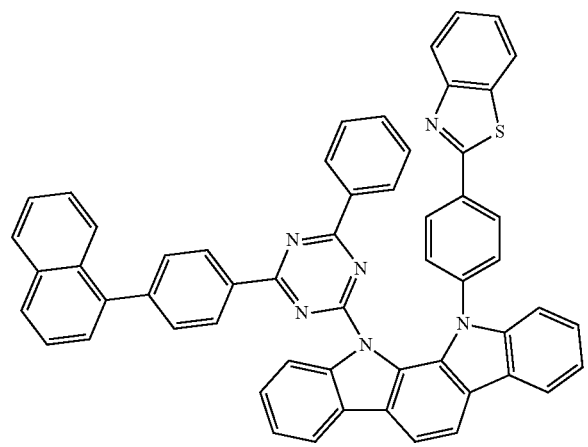
561
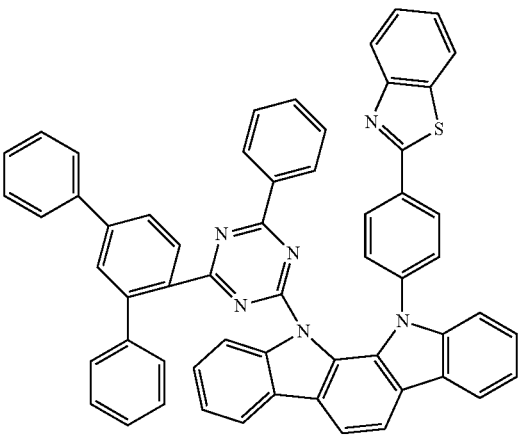
564
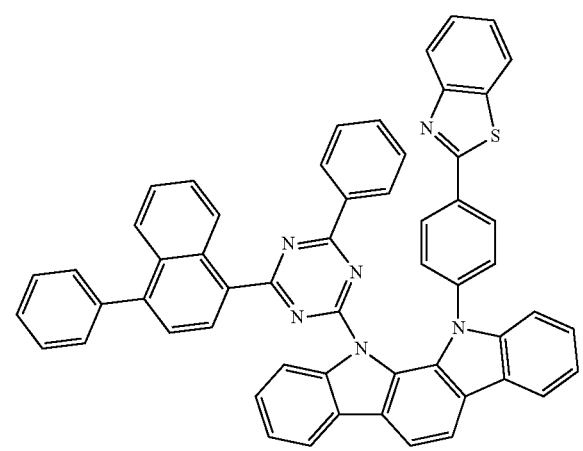
562
565
563
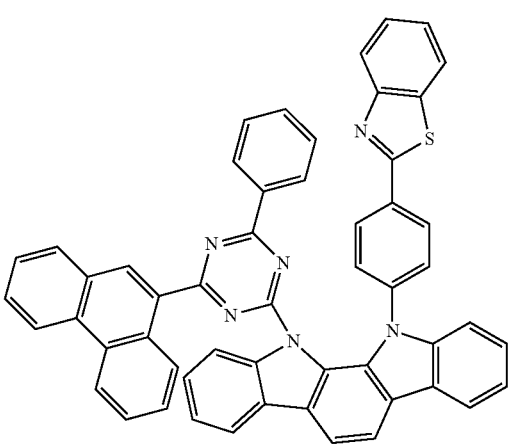
566

567
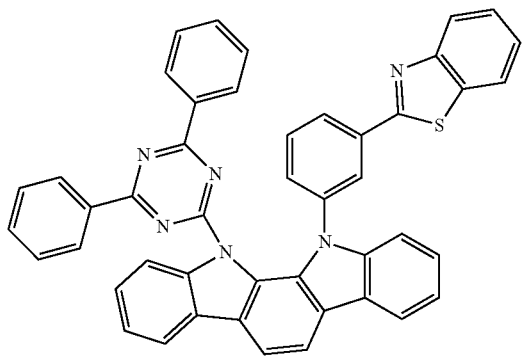
568
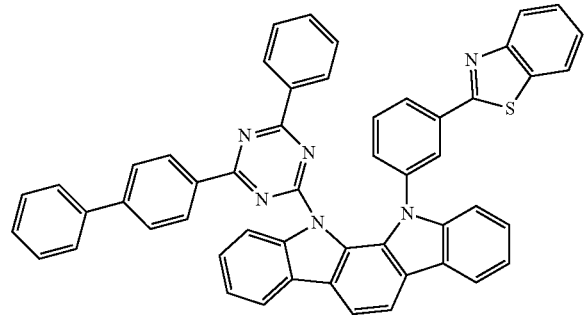
569
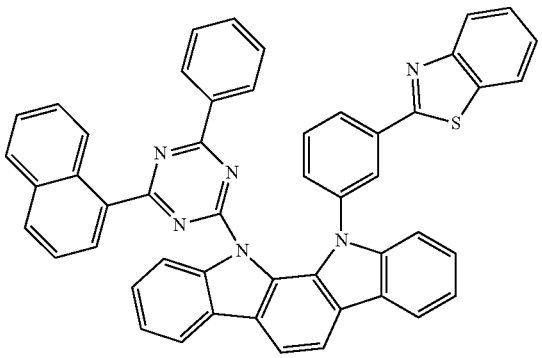
570
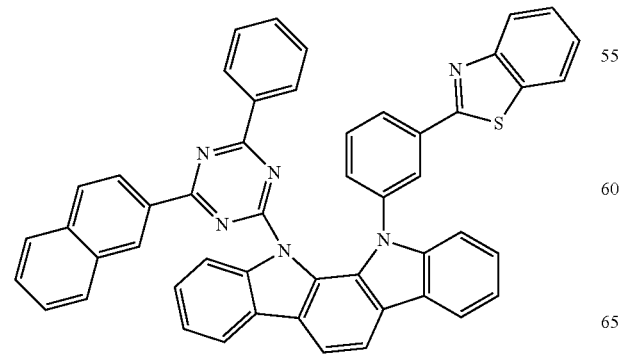
571
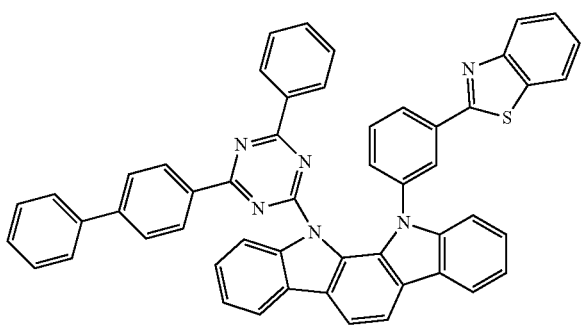
572
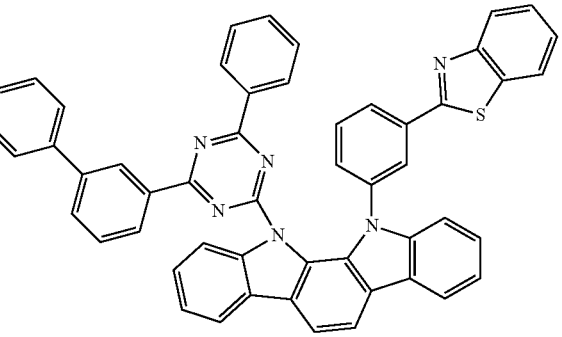
573
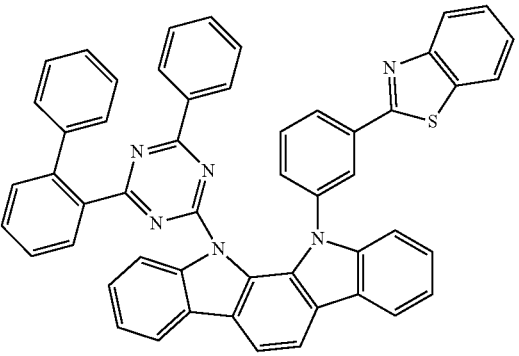
574
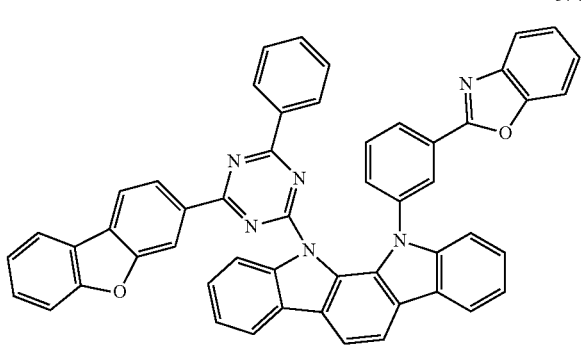

511
-continued
575
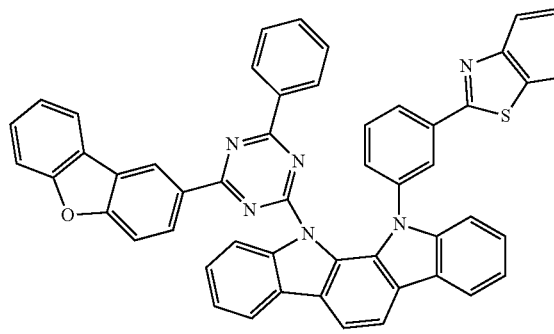
576
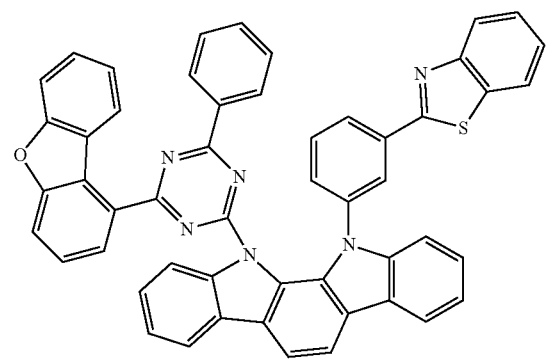
577
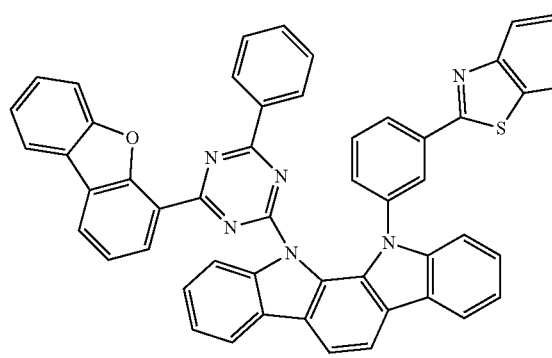
578
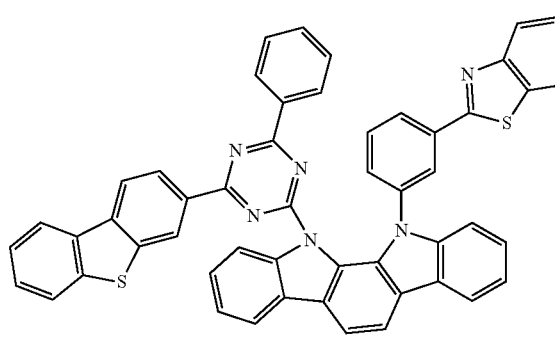
512
-continued
579
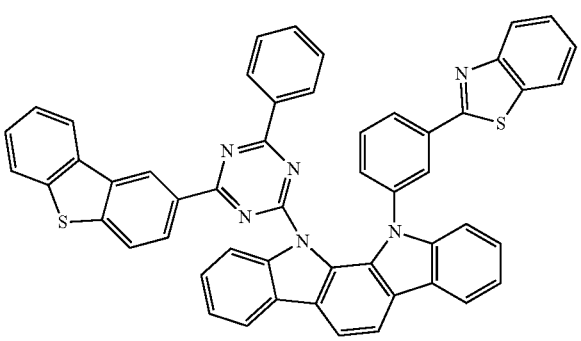
580
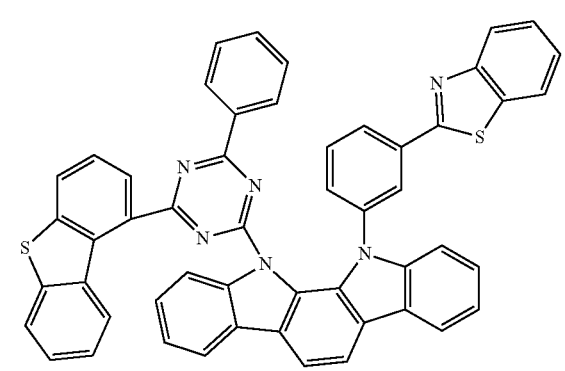
581
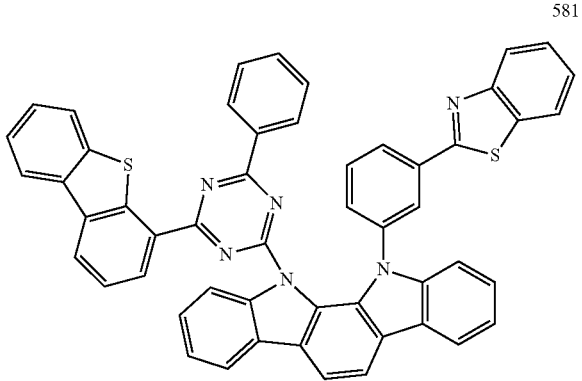
582
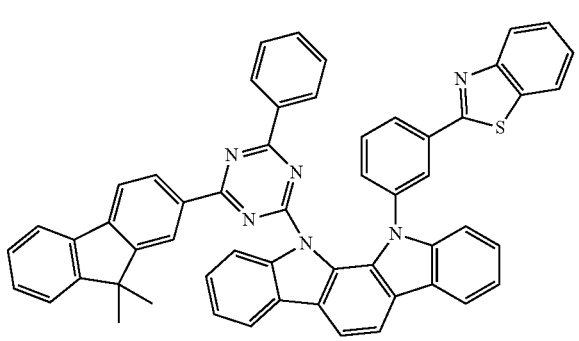

513
-continued
583
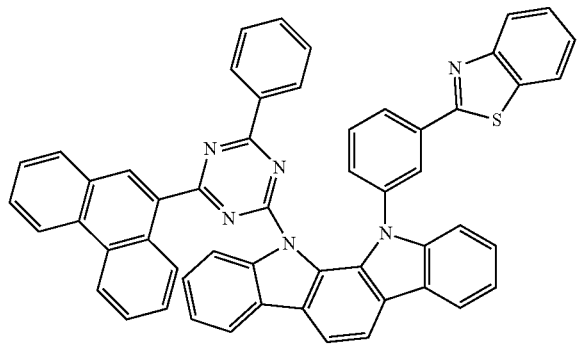
584
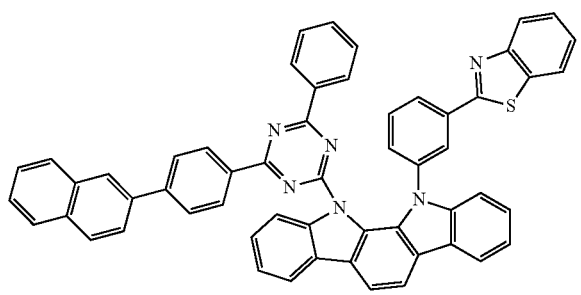
585
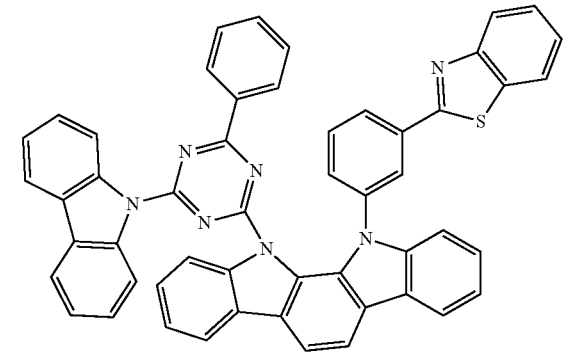
586
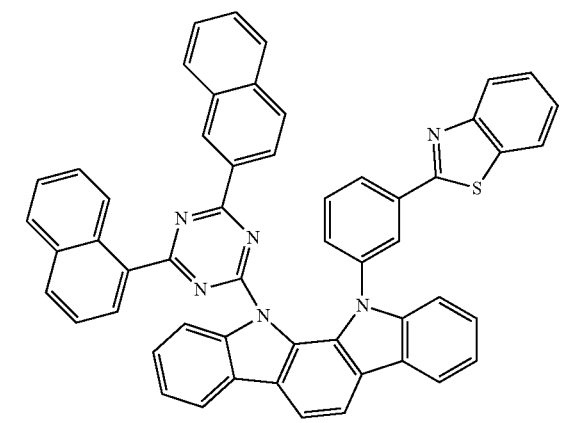
514
-continued
587
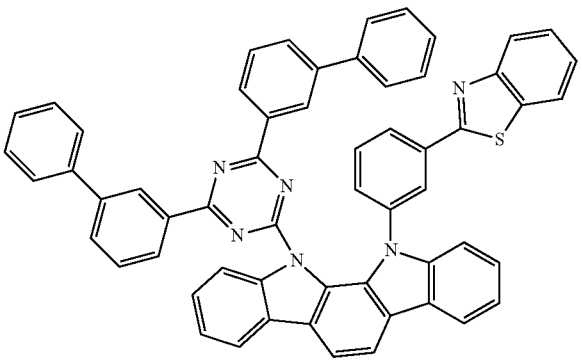
588
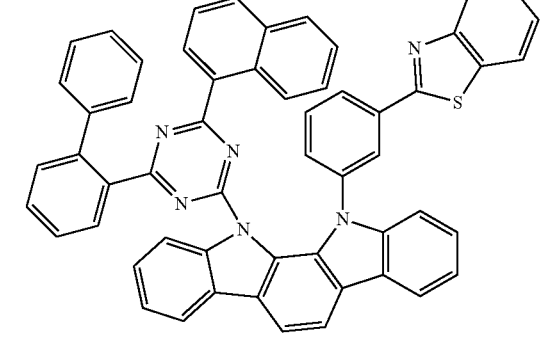
589
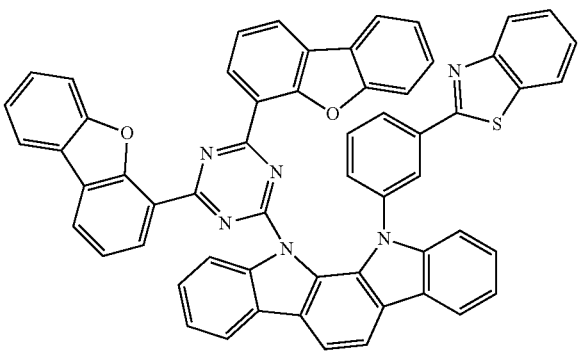
590
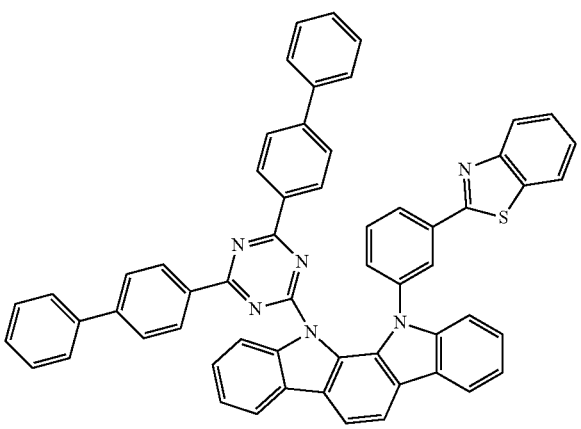

515
-continued
591
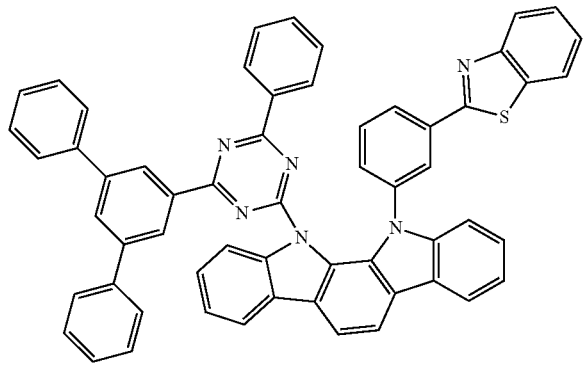
592
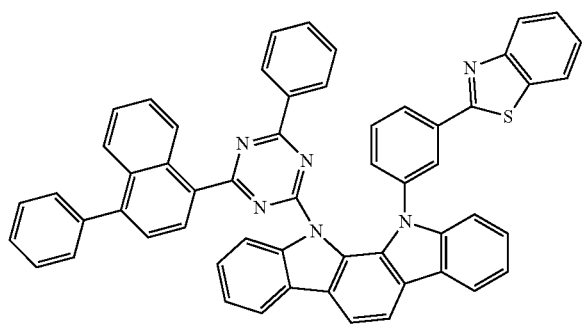
593
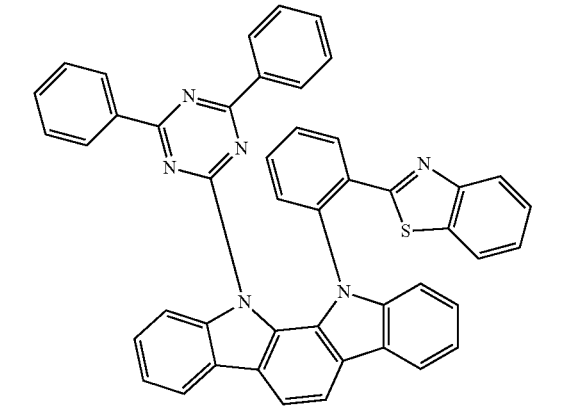
594
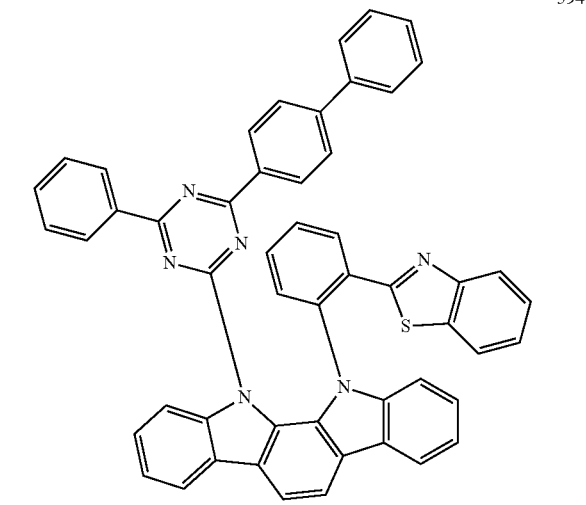
516
-continued
595
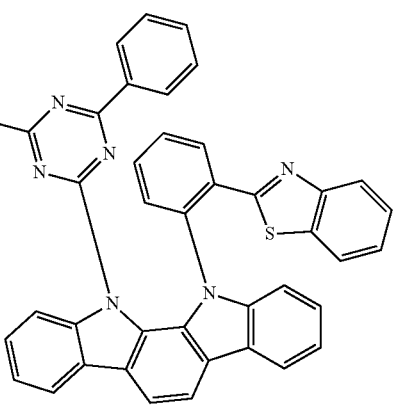
596
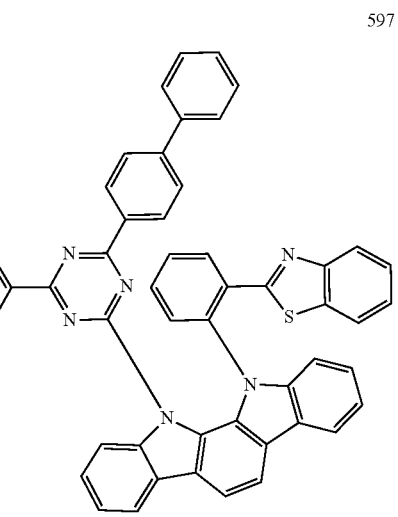
597

598
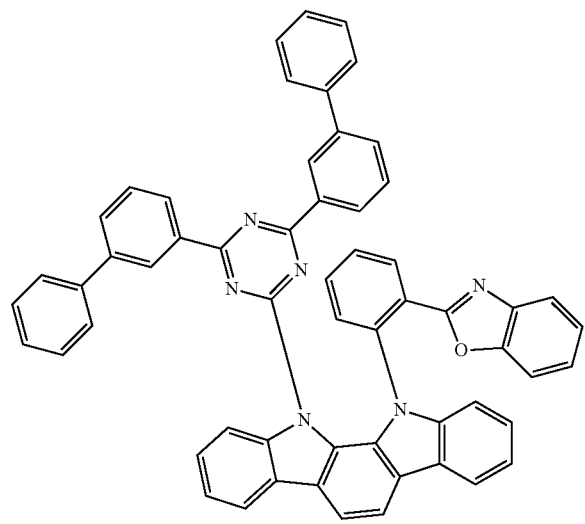
599
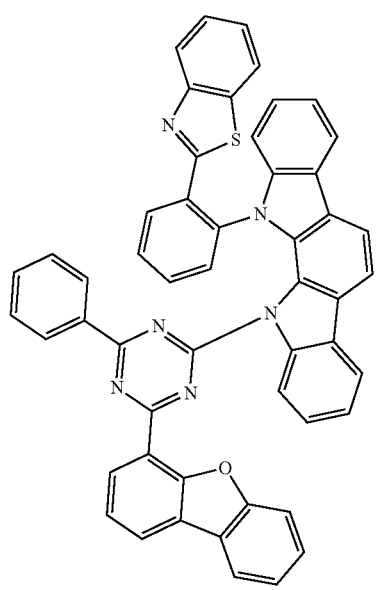
600
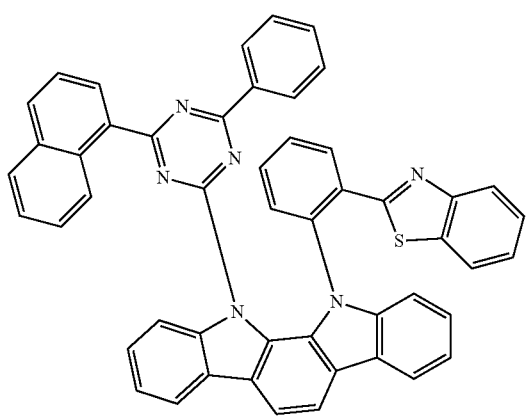
601
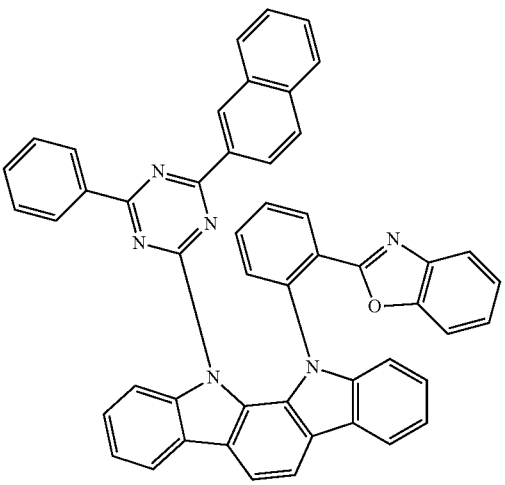
602
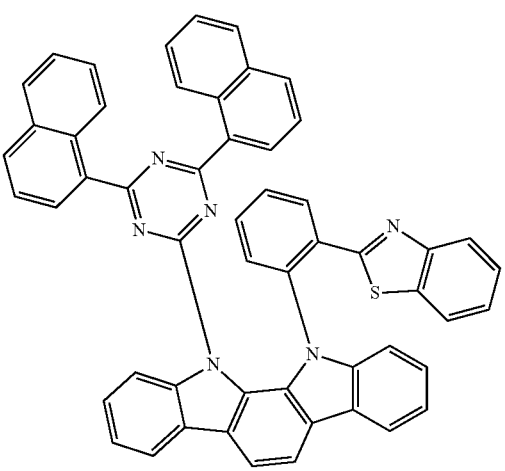
603
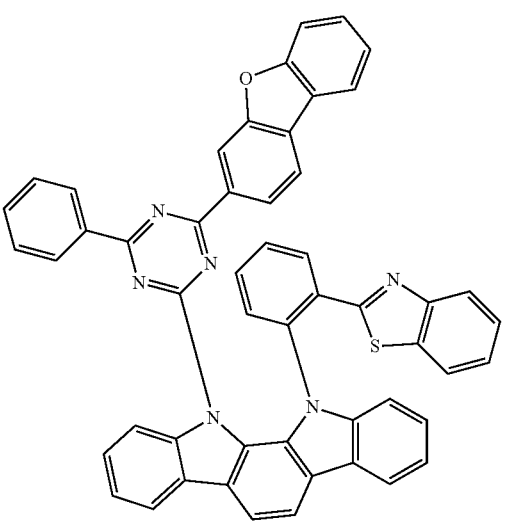

-continued
604
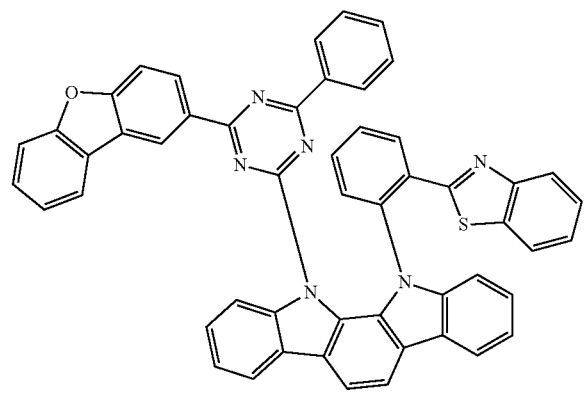
605
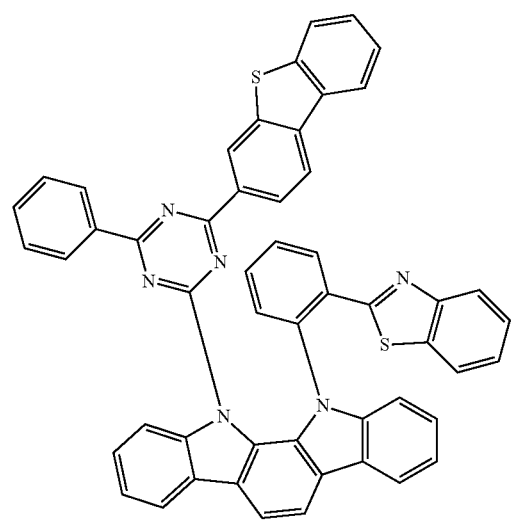
606
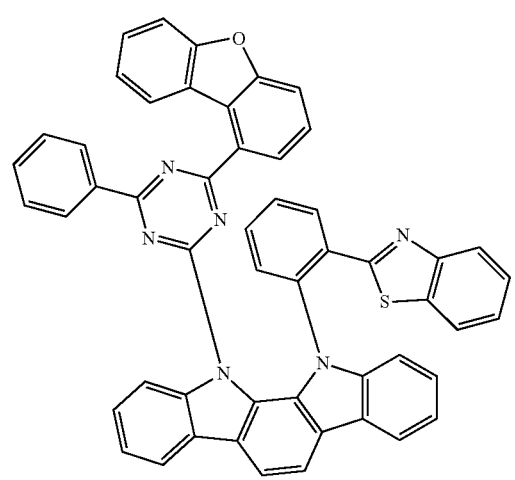
-continued
607
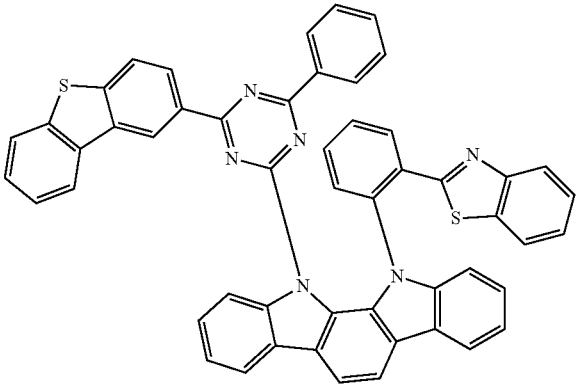
608
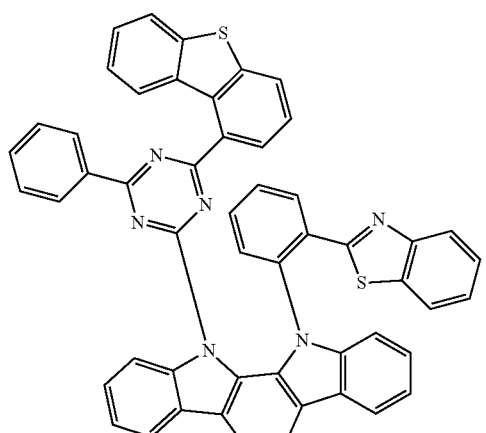
609
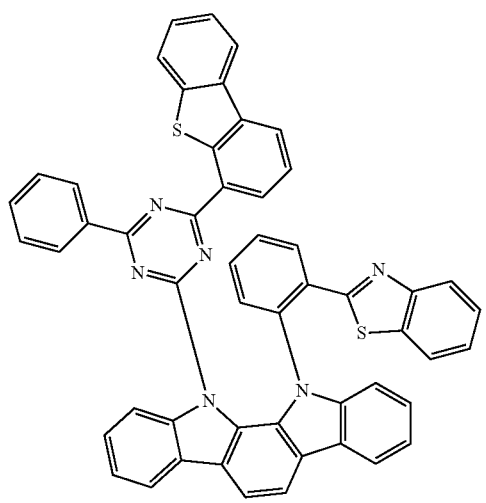

-continued
610
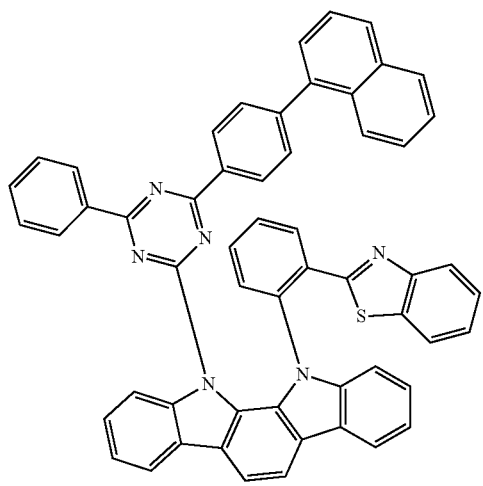
611
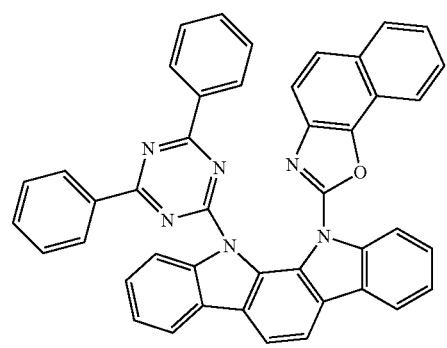
612
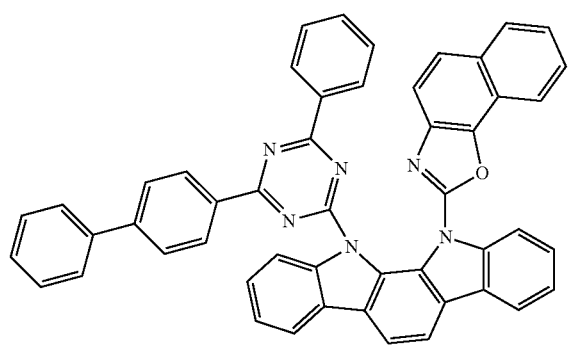
613
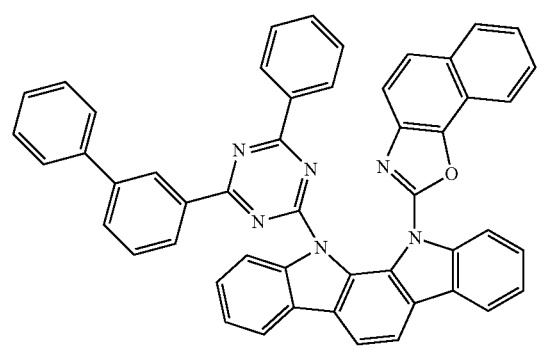
-continued
614
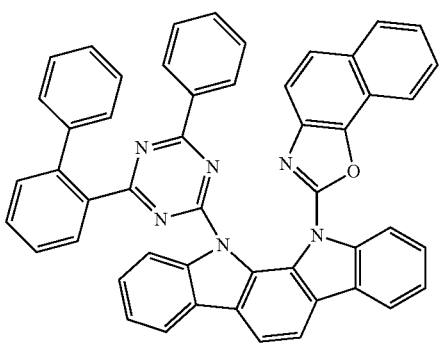
615
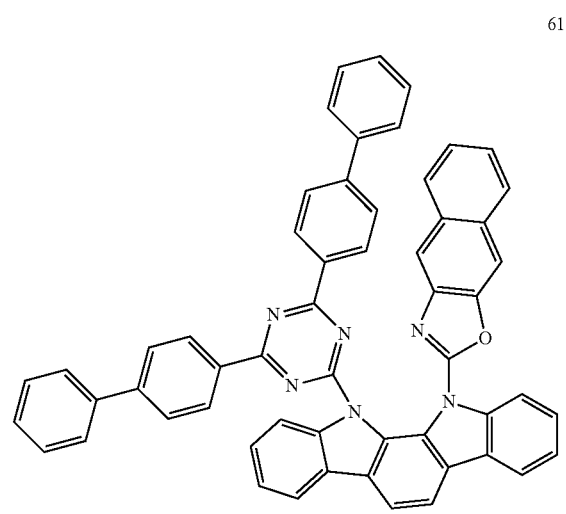
616
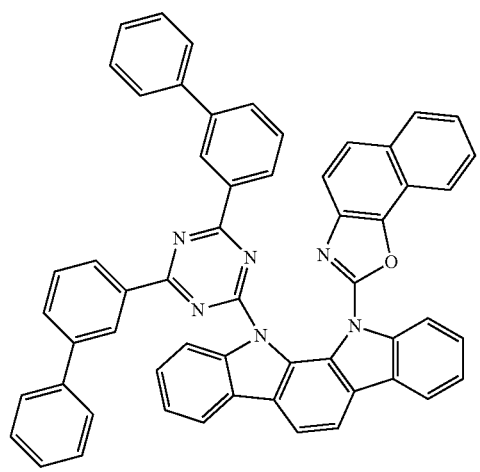
617
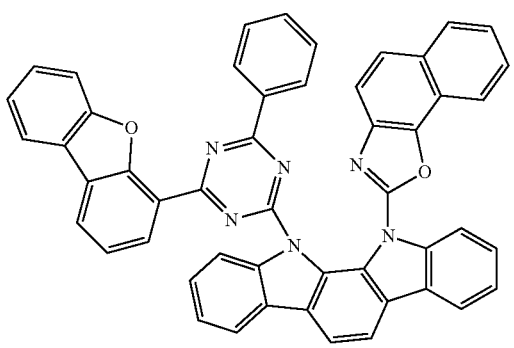

523
-continued
618
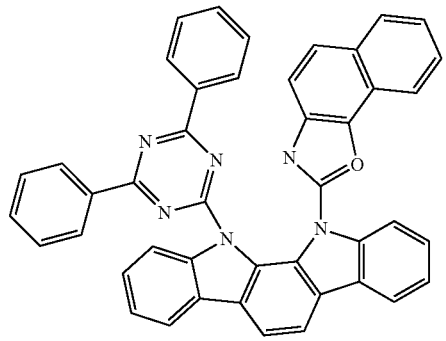
619
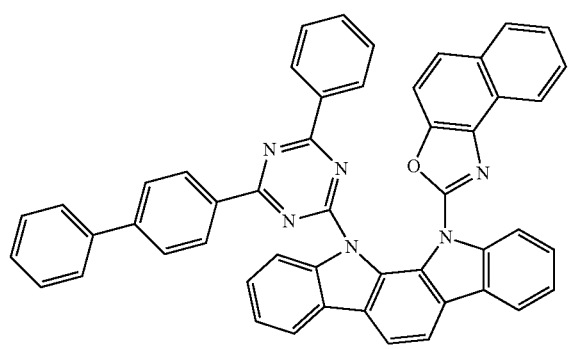
620
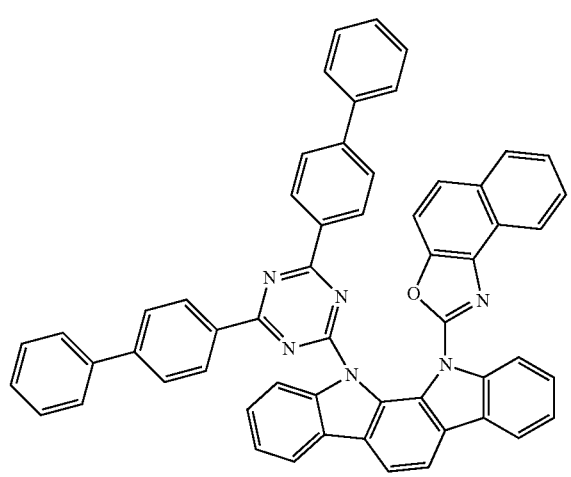
621
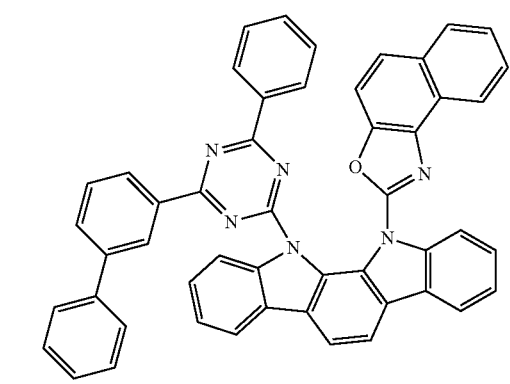
524
-continued
622
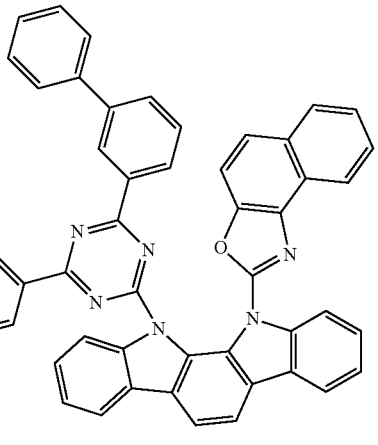
623
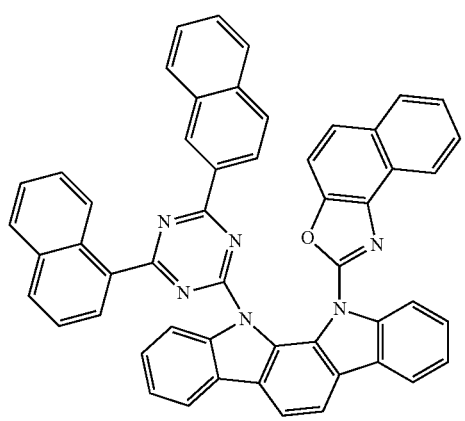
624
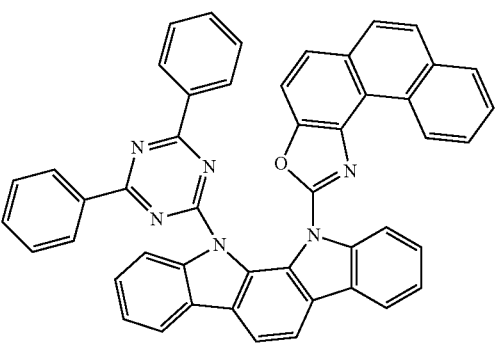
625
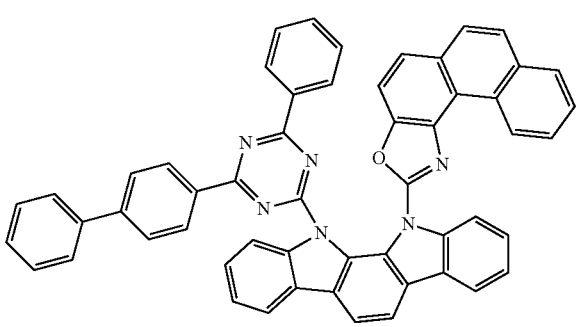

-continued
626
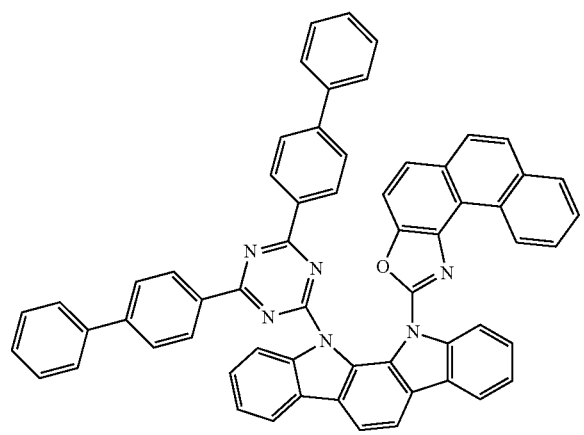
627
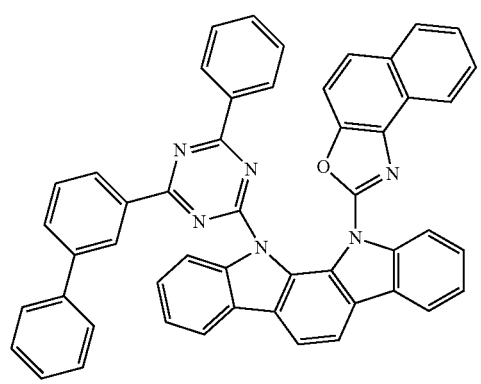
628
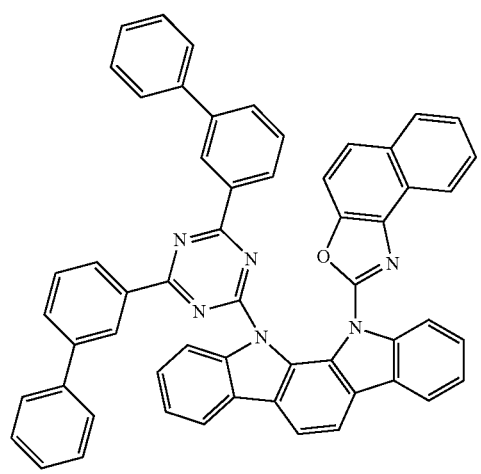
-continued
629
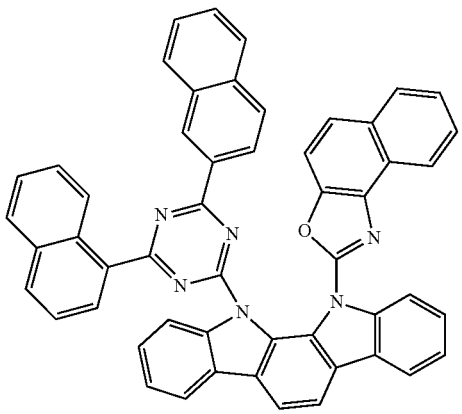
630
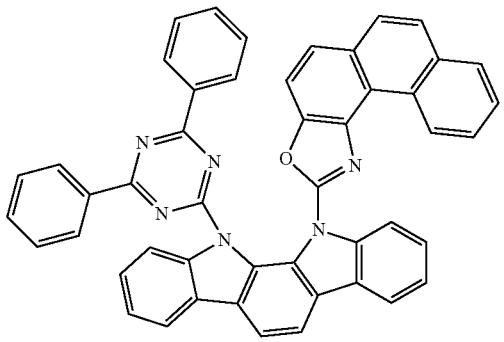
631
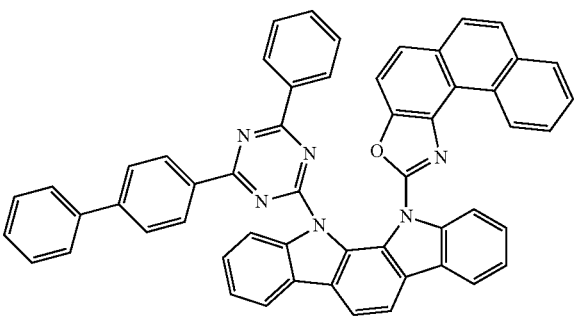
632
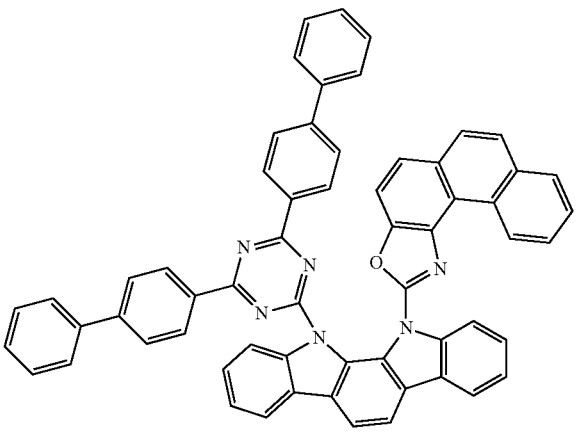

527
-continued
633
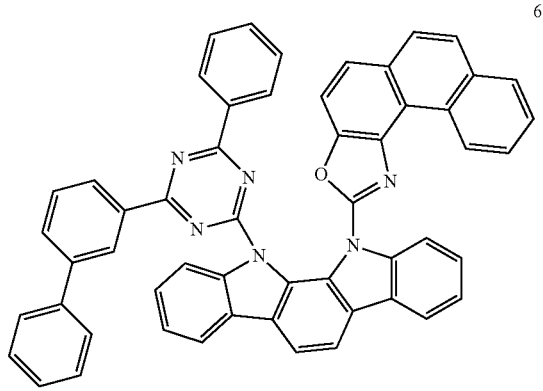
634
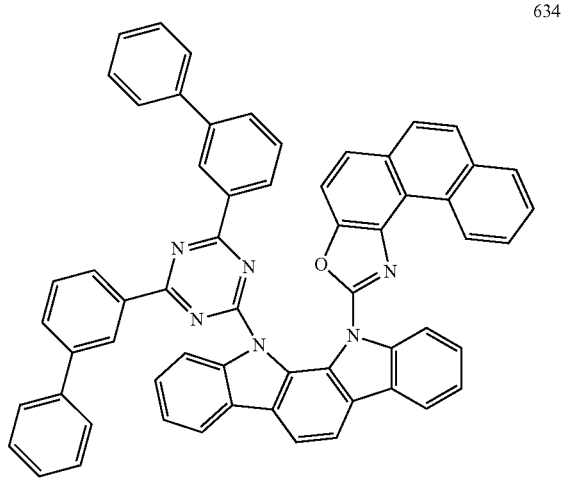
635
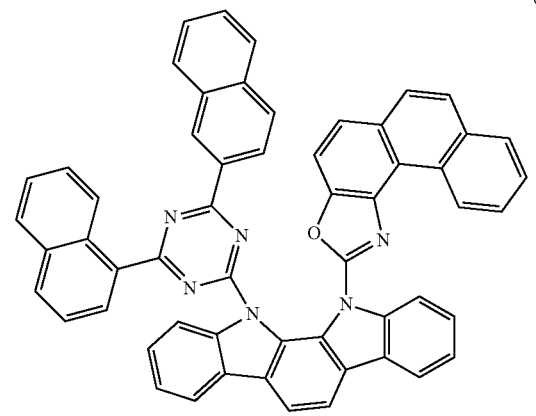
636
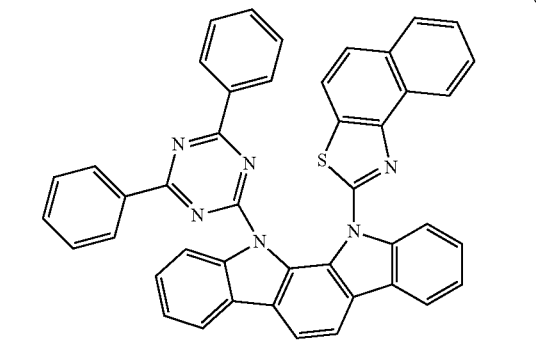
528
-continued
637
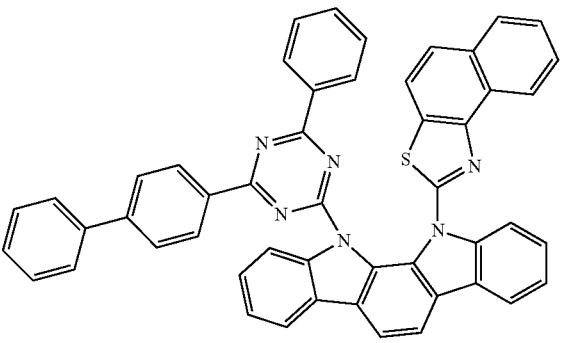
638
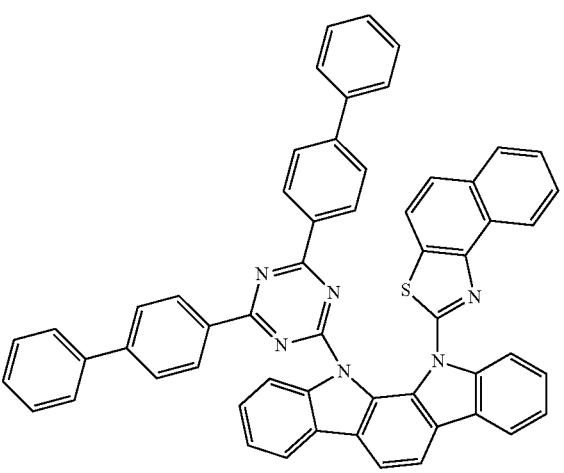
639
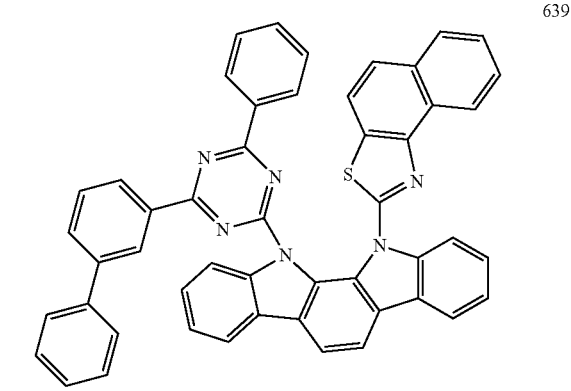

529
-continued
640
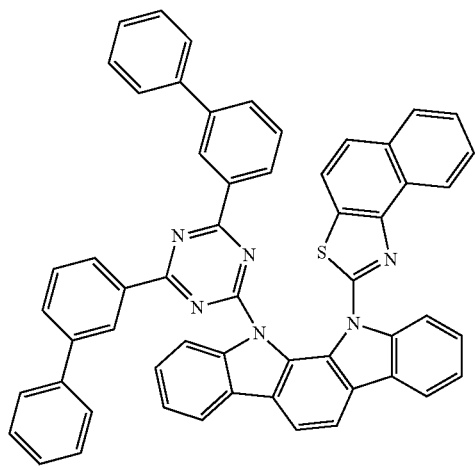
641
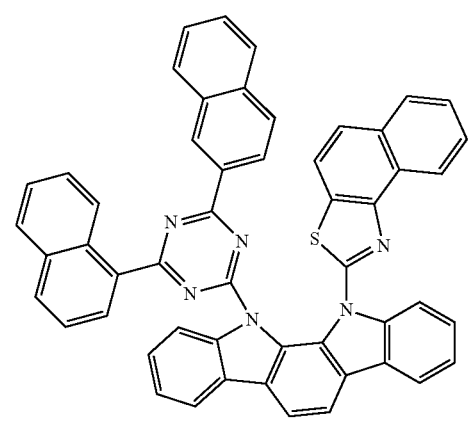
642
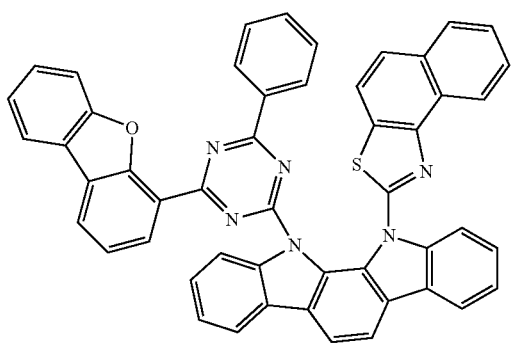
645
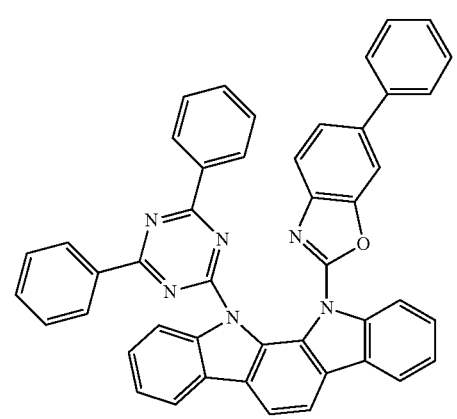
530
-continued
646
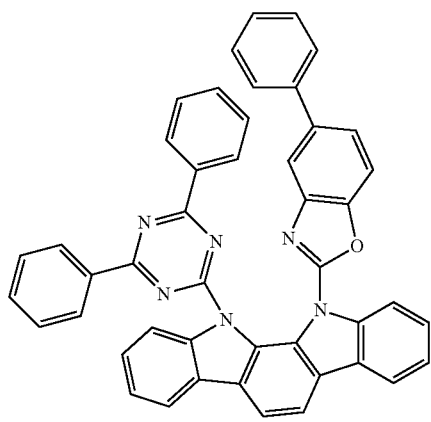
647
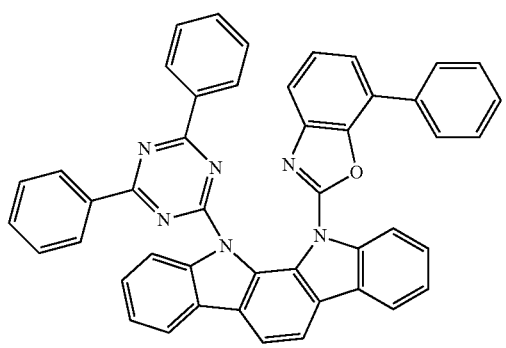
648
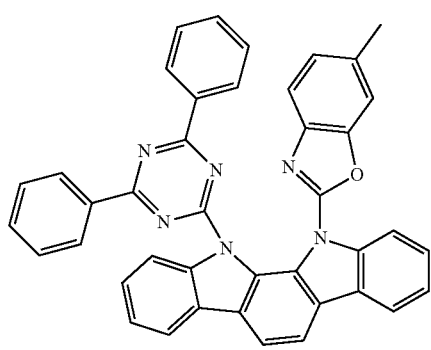
649
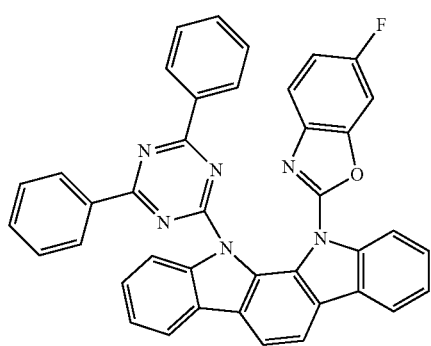

| 531 -continued | 532 -continued |
|---|---|
| 650 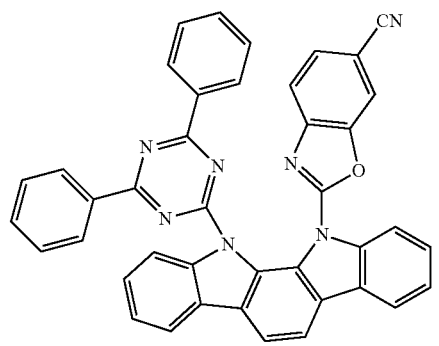 | 654 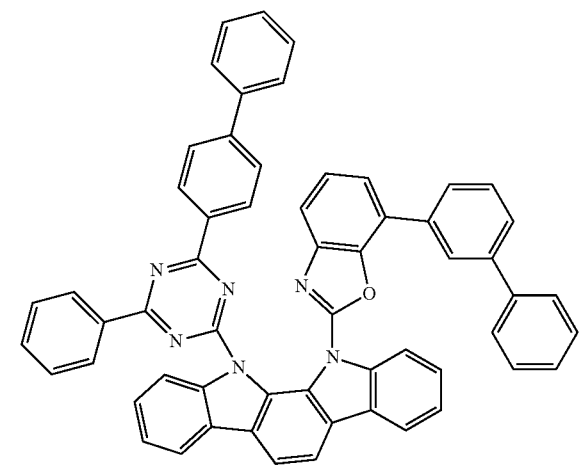 |
| 651 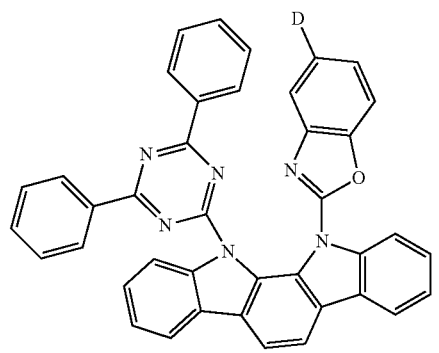 | 655 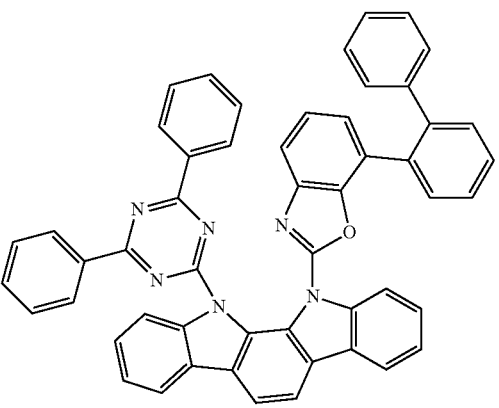 |
| 652 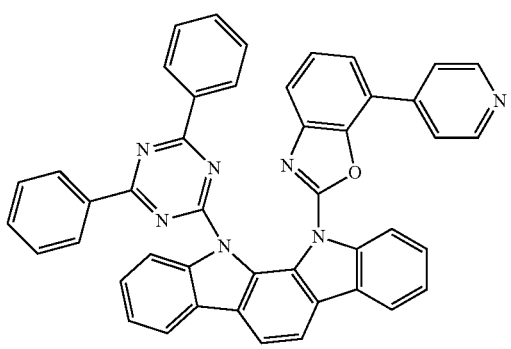 | 656 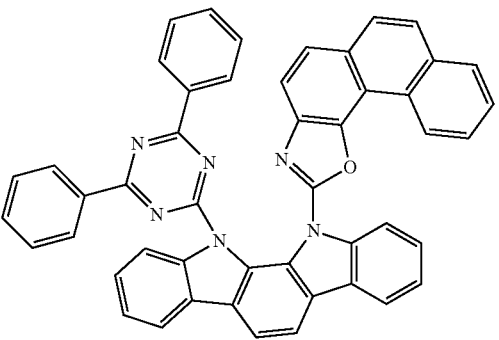 |
| 653 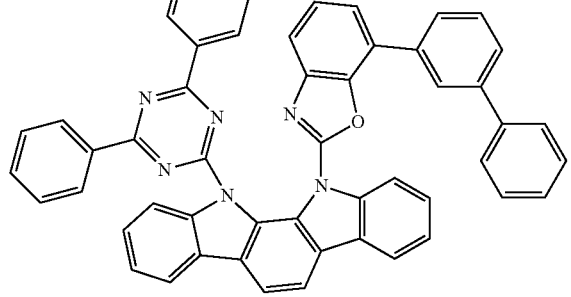 | 657 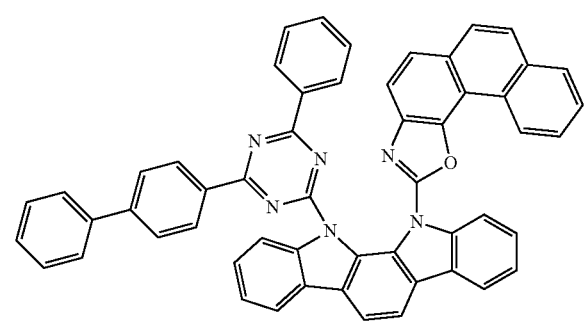 |

658
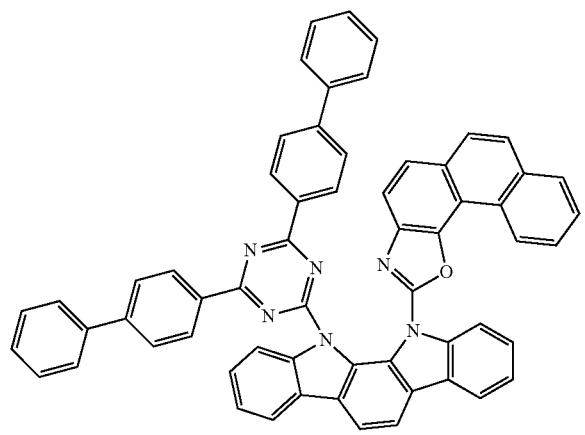
659
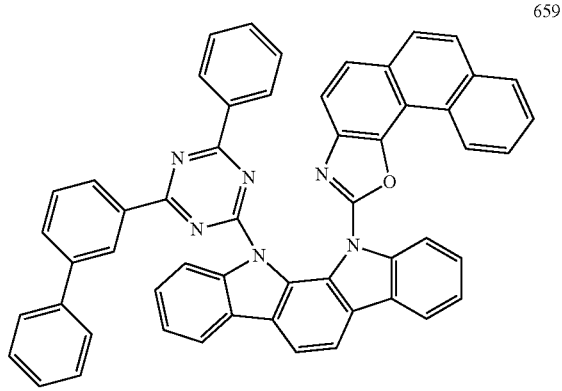
660
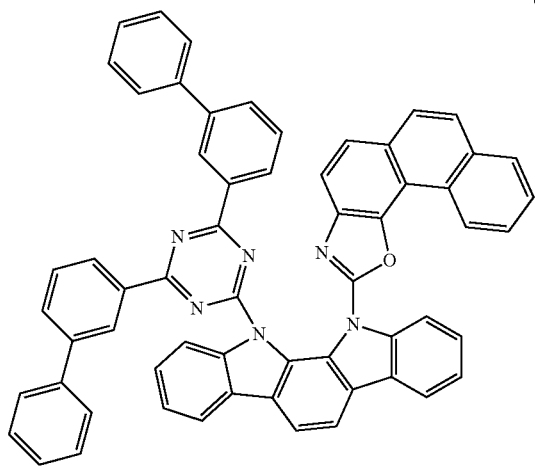
661
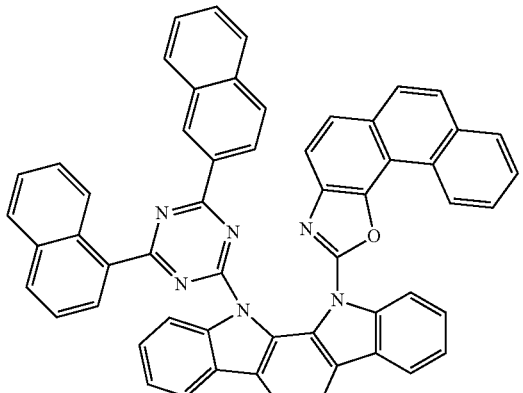
662
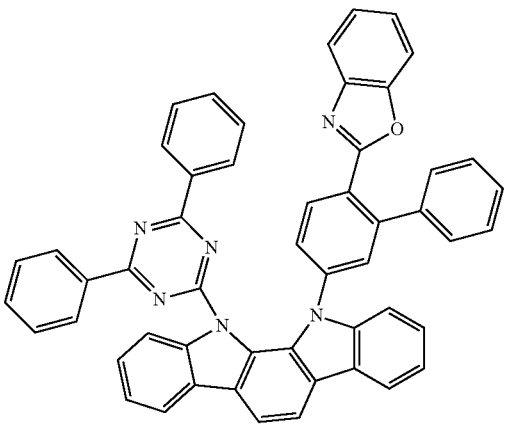
663
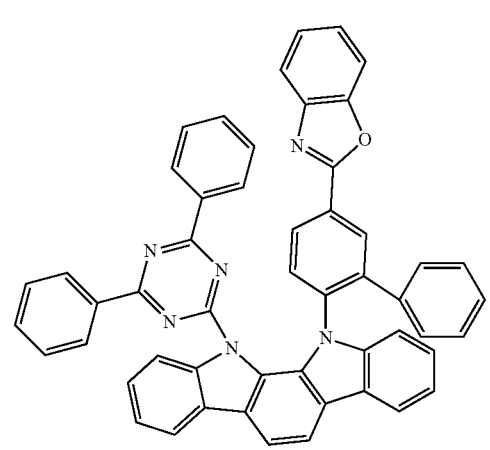

535
-continued
664
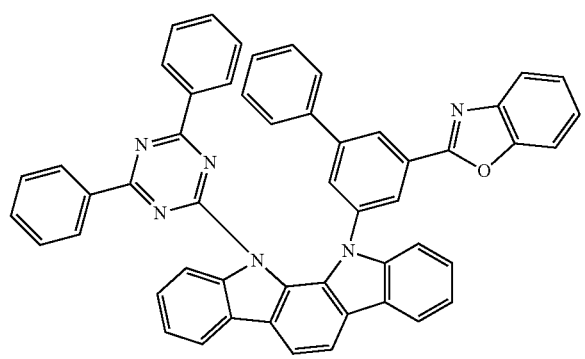
665
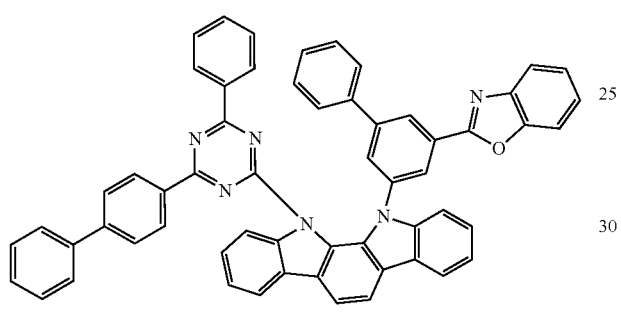
666
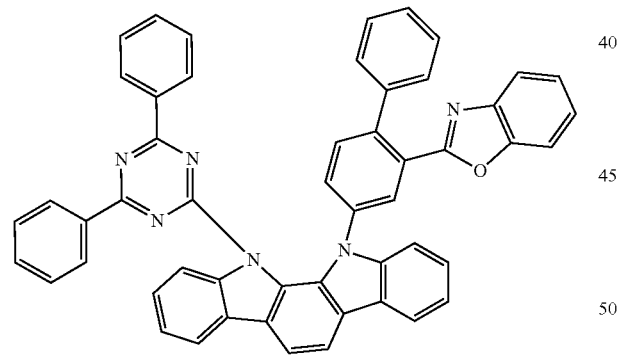
667
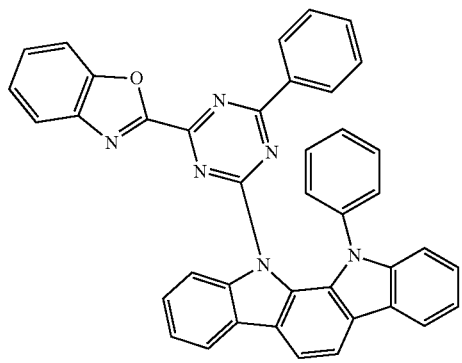
536
-continued
668
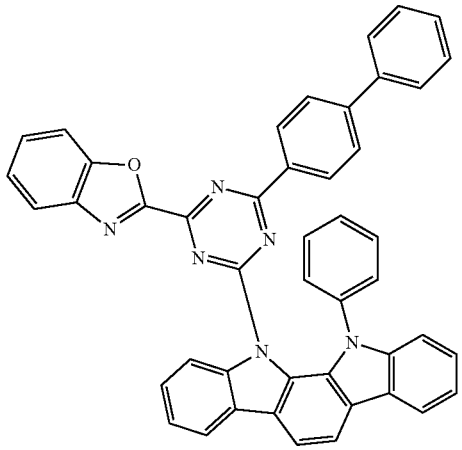
669
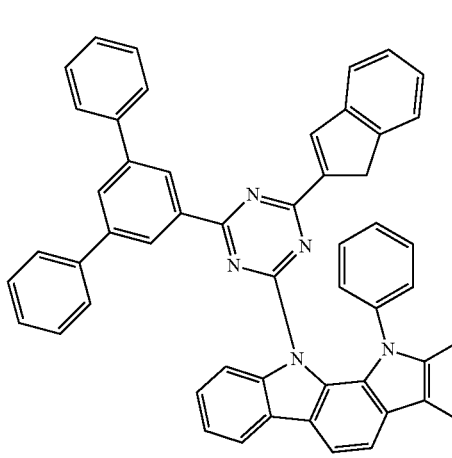
670
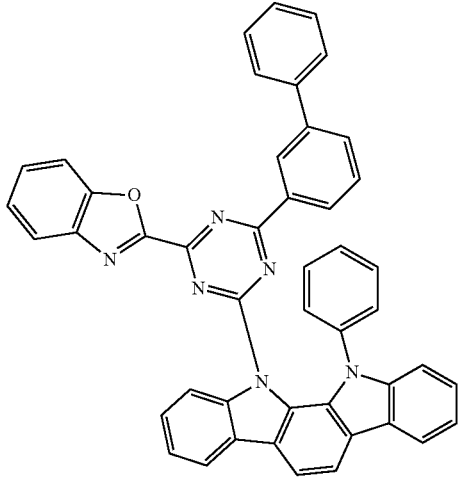

537
-continued
671
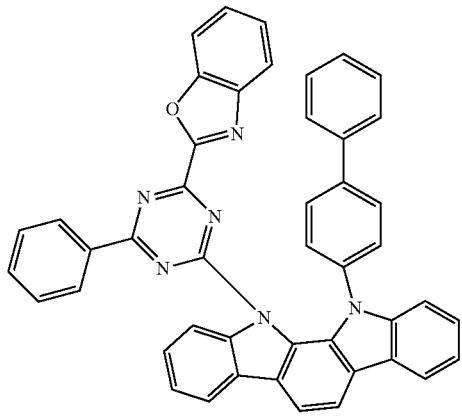
672
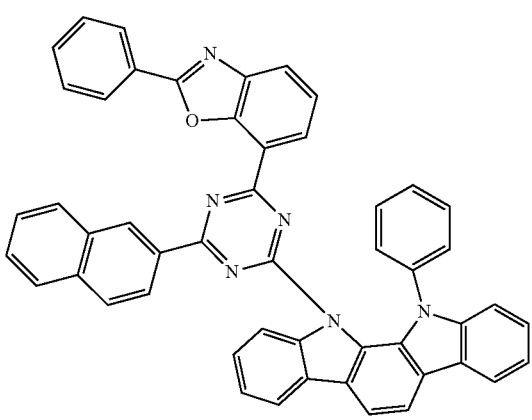
673
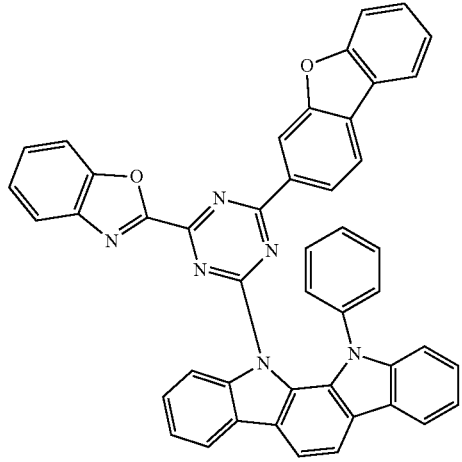
538
-continued
674
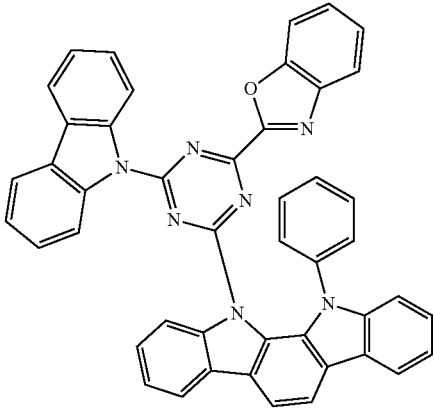
675
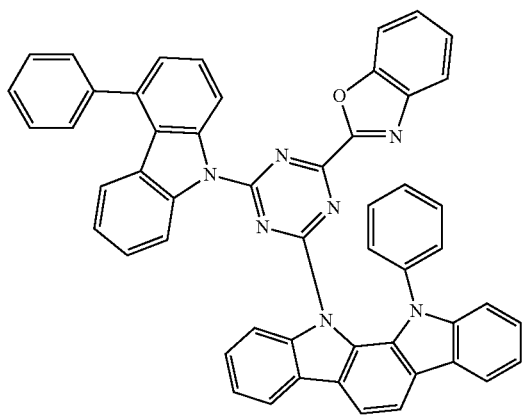
676
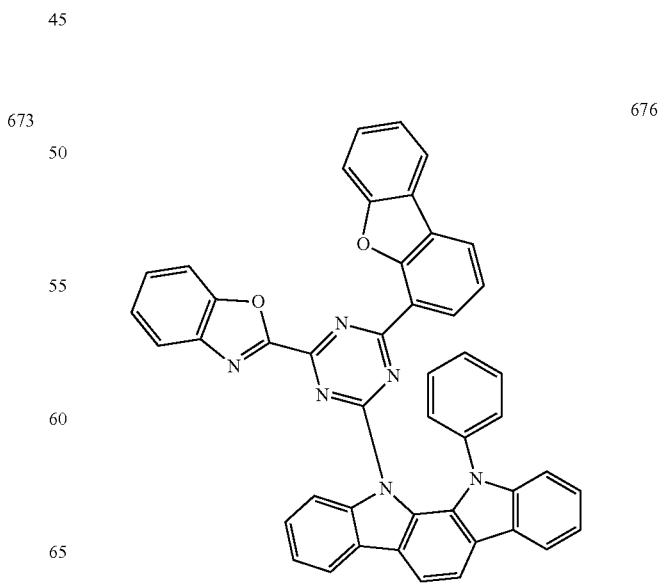

539
-continued
677
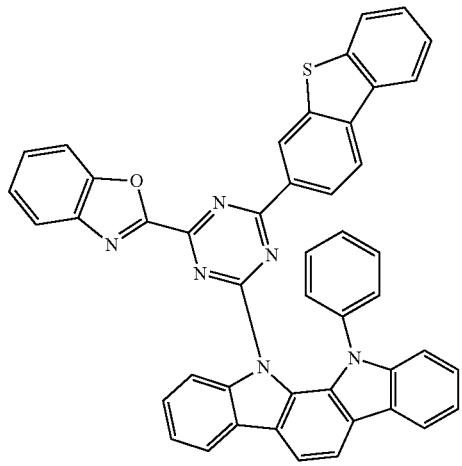
678
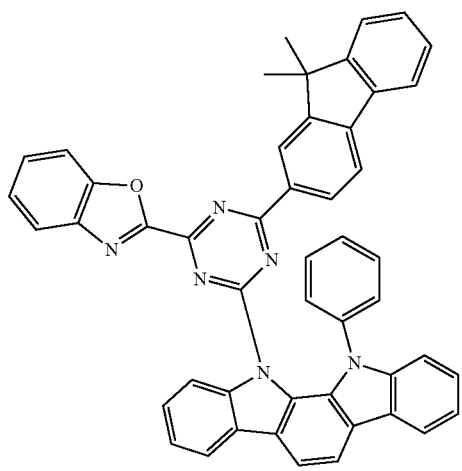
679
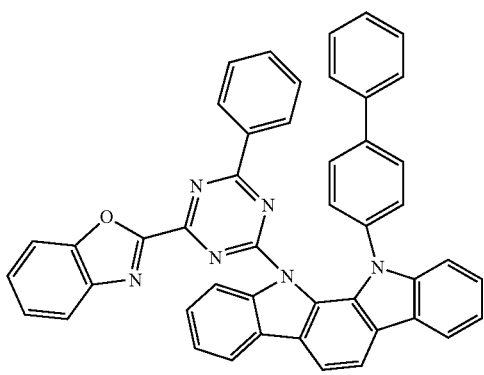
680
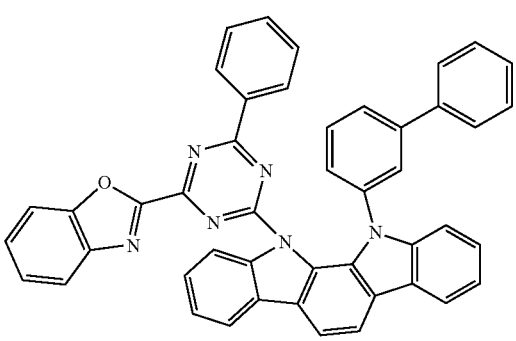
540
-continued
681
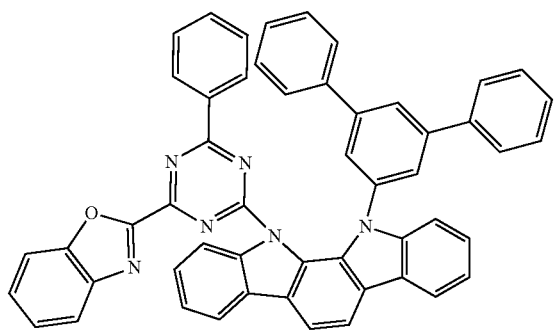
682
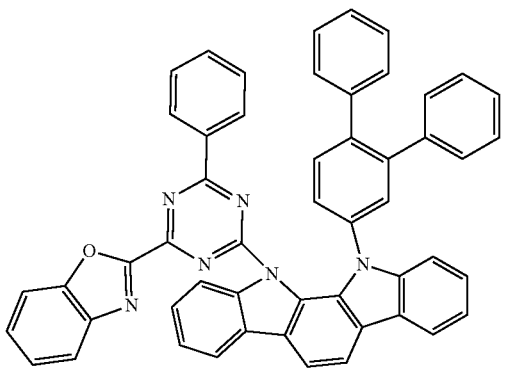
683
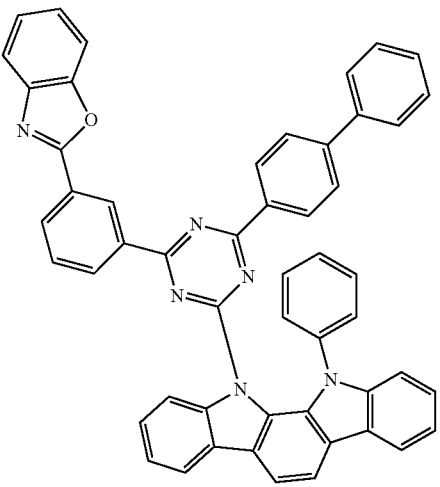

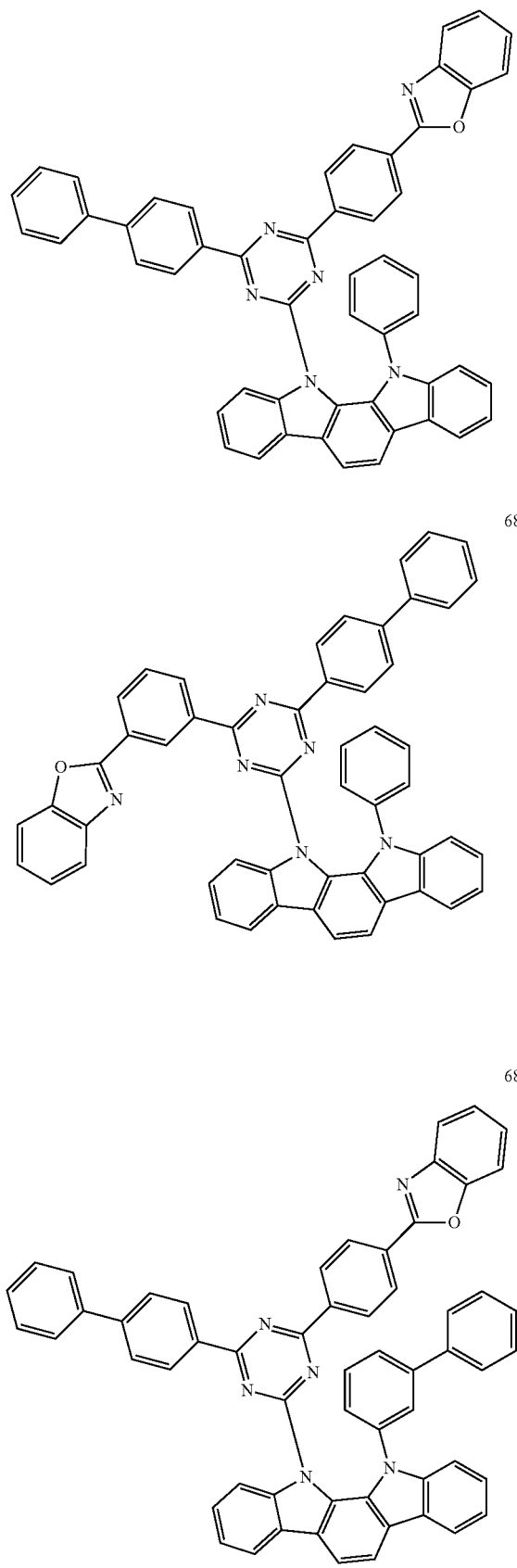
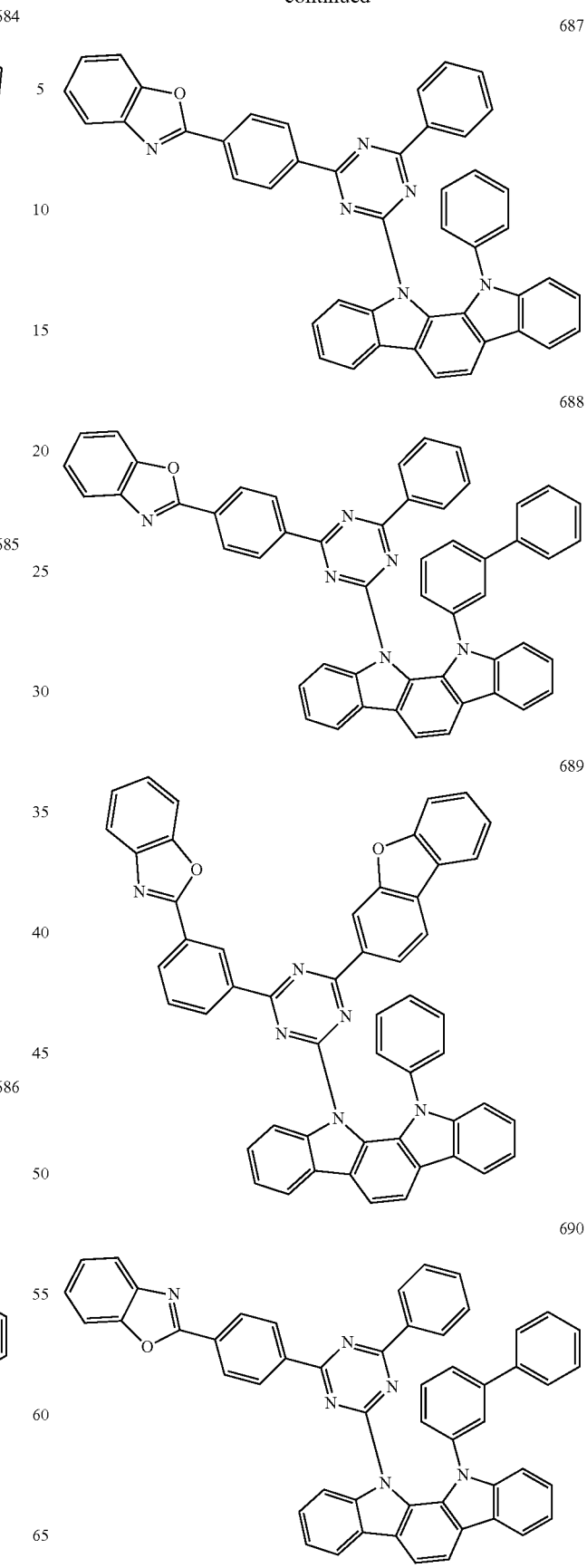

691
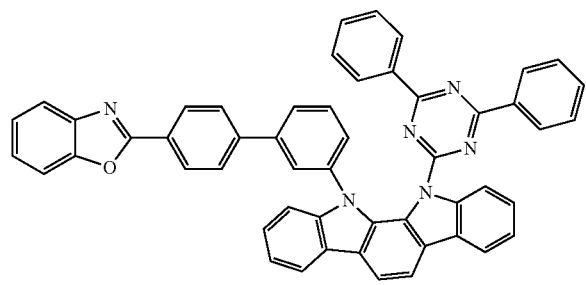
692
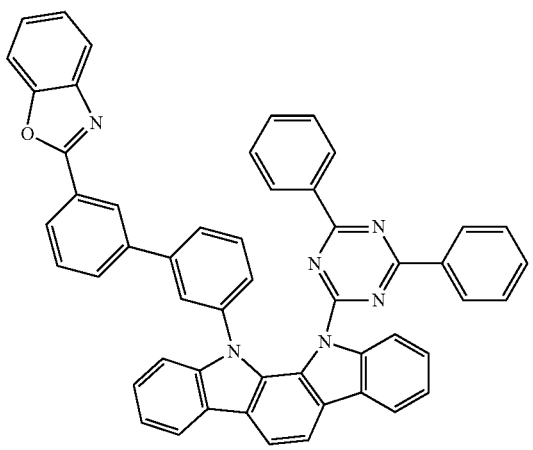
693
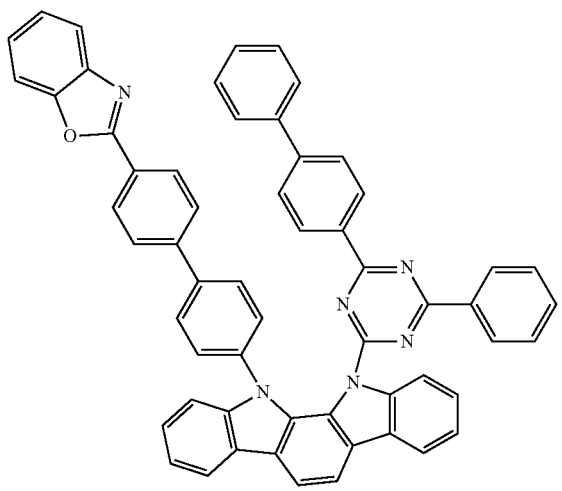
694
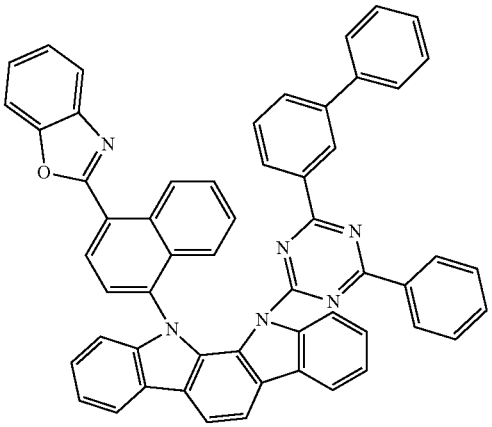
695
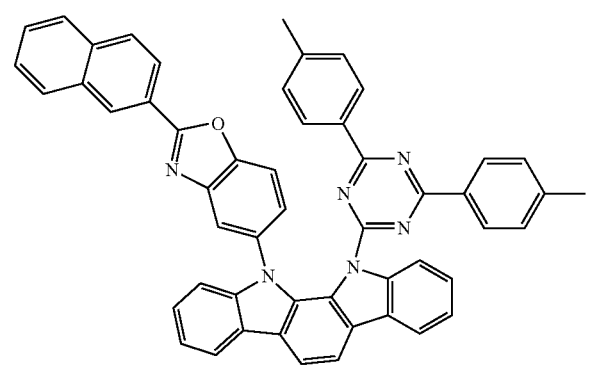
696

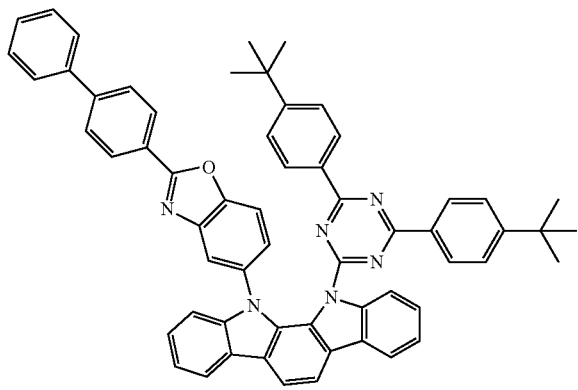

697

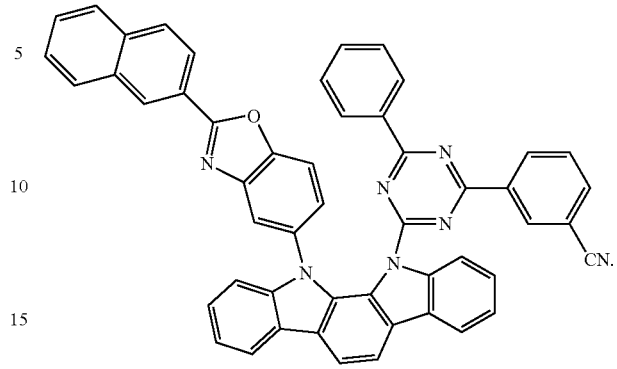

699

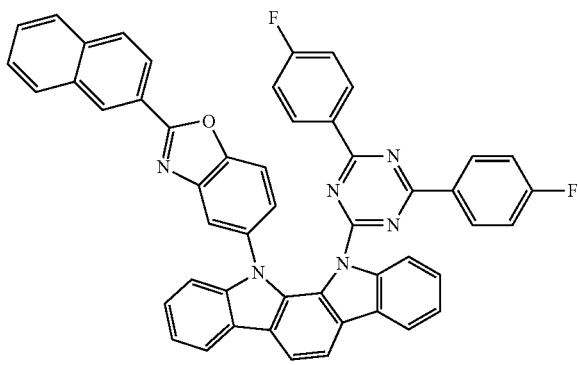

698

12. An electronic component, comprising an anode, a cathode and at least one functional layer between the anode and the cathode, and the functional layer comprises the nitrogen-containing compound of claim 1.

13. The electronic component according to claim 12, wherein the electronic component is an organic electroluminescence device.

14. The electronic component according to claim 13, wherein the organic electroluminescence device is a green organic electroluminescence device.

15. An electronic device, comprising the electronic component of claim 12.

16. The electronic component according to claim 12, wherein the functional layer comprises an organic electroluminescence layer, and the electroluminescence layer comprises the nitrogen-containing compound.

17. The nitrogen-containing compound according to claim 1, wherein the substituents in the A and B are each independently selected from deuterium, fluorine, cyano, methyl, ethyl, n-propyl, isopropyl, tert-butyl, phenyl, naphthyl, biphenyl, pyridyl, carbazolyl, dibenzofuranyl, dibenzothienyl, cyclopentyl, and cyclohexyl.

\* \* \* \* \*